(12) United States Patent
Krasnoperov et al.

(10) Patent No.: US 7,862,816 B2
(45) Date of Patent: Jan. 4, 2011

(54) POLYPEPTIDE COMPOUNDS FOR INHIBITING ANGIOGENESIS AND TUMOR GROWTH

(75) Inventors: Valery Krasnoperov, South Pasadena, CA (US); Nathalie Kertesz, Calabasas, CA (US); Ramachandra Reddy, Los Angeles, CA (US); Parkash Gill, Los Angeles, CA (US); Sergey Zozulya, San Diego, CA (US)

(73) Assignee: Vasgene Therapeutics, Inc., Los Angeles, CA (US)

( * ) Notice: Subject to any disclaimer, the term of this patent is extended or adjusted under 35 U.S.C. 154(b) by 0 days.

(21) Appl. No.: 10/800,350

(22) Filed: Mar. 12, 2004

(65) Prior Publication Data

US 2005/0084873 A1    Apr. 21, 2005

Related U.S. Application Data

(60) Provisional application No. 60/454,300, filed on Mar. 12, 2003, provisional application No. 60/454,432, filed on Mar. 12, 2003.

(51) Int. Cl.
*A61K 39/395* (2006.01)
(52) U.S. Cl. .................................... 424/141.1
(58) Field of Classification Search ............... 530/387.1
See application file for complete search history.

(56) References Cited

U.S. PATENT DOCUMENTS

| | | | |
|---|---|---|---|
| 5,512,591 A | 4/1996 | Halperin et al. | |
| 5,624,899 A | 4/1997 | Bennett | |
| 5,635,177 A | 6/1997 | Bennett | |
| 5,693,762 A * | 12/1997 | Queen et al. ............. | 530/387.3 |
| 5,770,599 A | 6/1998 | Gibson | |
| 5,795,734 A | 8/1998 | Flanagan et al. | |
| 5,824,303 A | 10/1998 | Bartley et al. | |
| 5,864,020 A | 1/1999 | Bennett | |
| 6,015,711 A | 1/2000 | Olson et al. | |
| 6,303,769 B1 | 10/2001 | Cerretti | |
| 6,413,730 B1 | 7/2002 | Holland | |
| 6,440,954 B1 | 8/2002 | Haber et al. | |
| 6,479,459 B1 | 11/2002 | Cerretti | |
| 6,492,140 B2 | 12/2002 | Cerretti | |
| 6,514,497 B1 | 2/2003 | Briskin et al. | |
| 6,579,683 B2 | 6/2003 | Wang et al. | |
| 6,864,227 B1 | 3/2005 | Wang et al. | |
| 6,887,674 B1 | 5/2005 | Wang et al. | |
| 6,916,625 B2 | 7/2005 | Wang et al. | |
| 2002/0086819 A1 | 7/2002 | Drummond et al. | |
| 2002/0136726 A1 | 9/2002 | Anderson et al. | |
| 2002/0146420 A1 | 10/2002 | Bennett | |
| 2004/0110150 A1 | 6/2004 | Koller et al. | |
| 2004/0234520 A1 | 11/2004 | Aguet et al. | |
| 2004/0247592 A1 | 12/2004 | Roifman et al. | |
| 2005/0049176 A1 | 3/2005 | Kiener et al. | |
| 2005/0084873 A1 | 4/2005 | Krasnoperov et al. | |
| 2005/0164965 A1 | 7/2005 | Reddy et al. | |
| 2005/0187154 A1 | 8/2005 | Kahn et al. | |
| 2005/0204412 A1 | 9/2005 | Wang et al. | |
| 2006/0035328 A1 | 2/2006 | Wang et al. | |
| 2006/0204512 A1 | 9/2006 | Krasnoperov et al. | |
| 2006/0241027 A1 | 10/2006 | Hauser et al. | |
| 2007/0207952 A1 | 9/2007 | Silva et al. | |

FOREIGN PATENT DOCUMENTS

| | | |
|---|---|---|
| EP | 0 442 724 | 8/1991 |
| EP | 633 315 A2 | 1/1995 |
| EP | 0999 278 | 5/2000 |
| WO | WO 93/00425 | 1/1993 |
| WO | WO-93/15201 | 8/1993 |
| WO | WO 94/10202 | 5/1994 |
| WO | WO 94/11020 | 5/1994 |
| WO | WO-95/27061 | 10/1995 |
| WO | WO-96/01839 | 1/1996 |
| WO | WO-96/02645 | 2/1996 |
| WO | WO 96/03043 | 2/1996 |
| WO | WO 96/09384 | 3/1996 |
| WO | WO 96/13518 | 5/1996 |
| WO | WO 96/23000 | 8/1996 |
| WO | WO-96/26958 | 9/1996 |
| WO | WO 96/26958 * | 9/1996 |
| WO | WO 96/36713 | 11/1996 |
| WO | WO 97/09427 | 3/1997 |
| WO | WO 97/23629 | 7/1997 |
| WO | WO 97/44453 | 11/1997 |
| WO | WO-98/01548 | 1/1998 |
| WO | WO 98/43960 | 10/1998 |
| WO | WO 98/45331 | 10/1998 |
| WO | WO-98/45708 | 10/1998 |

(Continued)

OTHER PUBLICATIONS

Stephenson et al (BMC Molecular Biology, Dec. 21, 2001, 2(15): 1-9).*

(Continued)

*Primary Examiner*—Sean E Aeder
(74) *Attorney, Agent, or Firm*—Ropes & Gray LLP

(57) ABSTRACT

In certain embodiments, this present invention provides polypeptide compositions, and methods for inhibiting Ephrin B2 or EphB4 activity. In other embodiments, the present invention provides methods and compositions for treating cancer or for treating angiogenesis-associated diseases.

13 Claims, 105 Drawing Sheets

FOREIGN PATENT DOCUMENTS

| WO | WO-99/08696 | | 2/1999 |
|---|---|---|---|
| WO | WO 99/17796 | | 4/1999 |
| WO | WO 99/52541 | | 10/1999 |
| WO | WO-00/24413 | | 5/2000 |
| WO | WO 00/30673 | * | 6/2000 |
| WO | WO-00/30673 | | 6/2000 |
| WO | WO-01/49743 A2 | | 7/2001 |
| WO | WO 01/81377 | | 11/2001 |
| WO | WO-02/11785 | | 2/2002 |
| WO | WO-02/26827 | | 4/2002 |
| WO | WO-02/058538 | | 8/2002 |
| WO | WO-02/061055 | | 8/2002 |
| WO | WO-02/079382 | | 10/2002 |
| WO | WO-02/102854 | | 12/2002 |
| WO | WO-02/102972 | | 12/2002 |
| WO | WO-02/102973 | | 12/2002 |
| WO | WO 03/000113 | | 1/2003 |
| WO | WO-03/004057 | | 1/2003 |
| WO | WO 03/094859 | | 11/2003 |
| WO | WO 2004/014292 | | 2/2004 |
| WO | WO 2004/020468 | | 3/2004 |
| WO | WO 2004/024773 | | 3/2004 |
| WO | WO 2004/024773 A | | 3/2004 |
| WO | WO 2004/080425 | | 9/2004 |
| WO | WO 2004/080425 A | | 9/2004 |
| WO | WO 2004/091375 | | 10/2004 |
| WO | WO 2005/048917 | | 6/2005 |
| WO | WO 2005/051307 | | 6/2005 |
| WO | WO 2005/090406 | | 9/2005 |

OTHER PUBLICATIONS

Inada et al (Blood, 1997, 89(8): 2757-2765).*
Santa Cruz Biotechnology Inc EphB4 (H-200) datasheet.*
Santa Cruz Biotechnology Inc datasheet for EphB4 (H-200).*
Xi et al (Clinical Cancer Research, Jun. 2005, 11(12):4305-4315).*
Sola et al (Journal of Virology, May 1998, 3762-3772).*
Adams, R.H., et al., "Roles of ephrinB ligands and EphB receptors in cardiovascular development: demarcation of arterial/venous domains, vascular morphogenesis, and sprouting angiogenesis," Genes Dev., 13:295-306 (1999).
Berclaz, G., et al., "Activation of the receptor protein tyrosine kinase EphB4 in endometrial hyperplasia and endometrial carcinoma," Ann Oncol., 14:220-226 (2003).
Berclaz, G., et al., "Expression of the receptor protein tyrosine kinase myk-1/htk in normal and malignant mammary epithelium," Biochem Biophys Res Commun., 24;226:869-875 (1996).
Brambilla, R., et al., "Membrane-bound LERK2 ligand can signal through three different Eph-related receptor tyrosine kinases," EMBO J., 14:3116-3126 (1995).
Bruhl, T., et al., "Homeobox A9 Transcriptionally Regulates the EphB4 Receptor to Modulate Endothelial Cell Migration and Tube Formation," Circ. Res., 743-751 (2004) [Epub ahead of print] DOI 10.1161/01res0000120861.27064.09.
Carbone, M., et al., "The pathogenesis of mesothelioma," Semin. Oncol., 29(1):2-17 (2002).
Cheng, N., et al., "The ephrins and Eph receptors in angiogenesis," Cytokine & Growth Factor Reviews, 13:75-85 (2002).
Cowan, C.A., et al., "Ephrins in reverse, park and drive," Trends in Cell Biology, 12(7):339-346 (2002).
Davis, S., et al., "Ligands for EPH-related receptor tyrosine kinases that require membrane attachment or clustering for activity," Science, 266(5186):816-819 (1994).
Fuller, T., et al., "Forward EphB4 signaling in endothelial cells controls cellular repulsion and segregation from ephrinB2 positive cells" J. Cell Sci., 116:2461-2470 (2003).
Gerety, S.S., et al., "Symmetrical mutant phenotypes of the receptor EphB4 and its specific transmembrane ligand ephrin-B2 in cardiovascular development," Mol. Cell, 4:403-414 (1999).

Hamada, K., et al., "Distinct roles of ephrin-B2 forward and EphB4 reverse signaling in endothelial cells," Arterioscler. Thromb. Vasc. Biol., 23:190-197 (2003).
Himanen, J.P., et al., "Eph receptors and ephrins," Intl. J. Biochem. & Cell Bio., 35:130-134 (2003).
Himanen, J.P., et al., "Eph signaling: a structural view," Trends in Neurosciences, 26(1):46-51 (2003).
Hirai, H., "A novel putative tyrosine kinase receptor encoded by the eph gene," Science, 238:1717-1720(1987).
Kiyokawa, E., et al., "Overexpression of ERK, an EPH family receptor protein tyrosine kinase, in various human tumors," Cancer Res., 54:3645-3650 (1994).
Kullander, K., et al., "Mechanisms and functions of eph and ephrin signalling," Nature Reviews, Molecular Cell Biology, 3:475-486 (2002).
Mellitzer, G., et al., "Control of cell behavior by signalling through Eph receptors and ephrins," Neurobiology, 10:400-408 (2000).
Munarini, N., et al., "Altered mammary epithelial development, pattern formation and involution in transgenic mice expressing the EphB4 receptor tyrosine kinase," J. Cell Sci., 115(Pt 1):25-37 (2002).
Nomura, A.M., et al., "Prostate cancer: a current perspective," Epidemiol Rev., 13:200-227 (1991).
Pasquale, E.B., "The Eph family of receptors," Curr. Opin. Cell Biol., 9:608-615 (1997).
Sakano, S., et al., "Characterization of a ligand for receptor protein-tyrosine kinase HTK expressed in immature hematopoietic cells," Oncogene., 13:813-822 (1996).
Schmucker, D., et al., "Signaling Downstream of Eph Receptors and Ephrin Ligands," Cell, 105:701-704 (2001).
Shin, D., et al., "Expression of ephrinB2 identifies a stable genetic difference between arterial and venous vascular smooth muscle as well as endothelial cells, and marks subsets of microvessels at sites of adult neovascularization," Dev. Biol. 230:139-150 (2001).
Sinha, U.K., et al., "Expression of EphB4 in head and neck squamous cell carcinoma," ENT J 82:721-723 (2003).
Steinle, J.J., et al., "Eph B4 receptor signaling mediates endothelial cell migration and proliferation via the phosphatidylinositol 3-kinase pathway," J. Biol. Chem., 277(46):43830-5 (Nov. 15, 2002) (Epub Sep. 13, 2002).
Stephenson, S.A., et al., "Receptor protein tyrosine kinase EphB4 is up-regulated in colon cancer," BMC Mol. Biol., 2:15 (2001).
Takai N., et al., "Expression of receptor tyrosine kinase EphB4 and its ligand ephrin-B2 is associated with malignant potential in endometrial cancer," Oncol Rep., 8:567-573 (2001).
Tang, X.X., et al., "Coexpression of transcripts encoding EphB receptor protein tyrosine kinases and their ephrin-B ligands in human small cell lung carcinoma," Clin. Cancer Res., 5:455-460 (1999).
Wang, H.U., et al., "Molecular distinction and angiogenic interaction between embryonic arteries and veins revealed by ephrin-B2 and its receptor Eph-B4," Cell 93:741-753 (1998).
Santa Cruz Biotechnology, Inc., "EphB4 (N-19): sc-7285", retrieved from the Internet: URL:http://www.genetimes.com.cn/support/pdf-ds/7200-7299/sc-7285.pdf (1999).
Sinha, et al., "Expression of EphB4 in head and neck squamous cell carcinoma" Ear, Nose and Throat Journal, 82(11), pp. 866-870 & 887 (2003).
Adams, R.H., et al., "Eph Receptors and Ephrin Ligands: Essential Mediators of Vascular Development," Trends. Cardiovasc. Med., 10:183-188 (2000).
Andres, A. C. et al., "Expression of two novel eph-related receptor protein tyrosine kinases in mammary gland development and carcinogenesis," Oncogene, 9:1461-1467 (1994).
Asahara, T. et al., "Isolation of Putative Progenitor Endothelial Cells for Angiogenesis," Science, 275:964-967 (1997).
Batlle, E., et al., "EphB receptor activity suppresses colorectal cancer progression," Nature, 435(23):1126-1130 (2005).
Bennett, B. D. et al., "Molecular cloning of a ligand for the EPH-related receptor protein-tyrosine kinase Htk," Proc. Natl. Acad. Sci. USA, 92:1866-1870 (1995).
Bennett, B.D., et al., "Cloning and Characterization of HTK, a Novel Transmembrane Tyrosine Kinase of the EPH Subfamily," The Journal of Biological Chemistry, 269(19):.14211-14218 (1994).

Bergemann, A. D. et al., "ELF-2, a New Member of the Eph Ligand Family Is Segmentally Expressed in Mouse Embryos in the Region of the Hindbrain and Newly Forming Somites," *Molecular and Cellular Biology*, 15(9):4921-4929 (1995).

Bos et al., "PD153035, a Tyrosine Kinase Inhibitor, Prevents Epidermal Growth Factor Receptor Activation and Inhibitors Growth of Cancer Cells in a Receptor Number-dependent Manner," *Clinical Cancer Research*, 3:2099-2106 (1997).

Boyd, W.A., et al., "Isolation and Characterization of a Novel Receptor-type Protein Tyrosine Kinase (hek) from a Human Pre-B Cell Line," *The Journal of Biological Chemistry*, 267(5):3262-3267 (1992).

Brehmer et al., "Cellular Targets of Gefitinib," *Cancer Research*, 65(2):379-382 (2005).

Bruckner et al., "Tyrosine Phosphorylaton of Transmembrane Ligands for Eph Receptors," *Science*, 275:1640-1643 (1997).

Chang, M.W., et al., "Adenovirus-Mediated Over-Expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty," *J. Clin. Invest.*, 96:2260-2268 (1995).

Coffman, K.T., et al., "Differential EphA2 Epitope Display on Normal versus Malignant Cells," *Cancer Research*, 63:7907-7912 (2003).

Dodelet, V.C. et al., "Eph Receptors and Ephrin Ligands: Embryogenesis to Tumorigenesis," *Oncogene*, 19(49): 5614-19 (2000).

Durbin, L., et al., "Eph signaling is required for segmentation and differentiation of the somites," *Genes & Development*, 12:3096-3109 (1998).

Easty et al., "Abnormal Protein Tyrosine Kinase Gene Expression During Melanoma Progression and Metastasis," *Int. J. Cancer*, 60:129-136 (1995).

Easty et al., "Cytokine B61 as a growth factor for metastatic melanomas and increasing expression of its receptor ECK during melanoma progression," *Proceedings of the American Asociation for Cancer Research*, 35(356) (1994) abstract only.

Easty, et al., "Expression of Eck and Lerk-1 During Melanoma Progression," P137 St. George's Hospital Medical School, London, JK and Western Infirmary, Glasgow, UK, *Collection of the National Library of Medicine by a third party*.

Feldman, L.J., et al., "Perspectives of Arterial Gene Therapy for the Prevention of Restenosis," *Cardiovasc. Res.*, 32:194-207 (1996).

Folkman et al., "Angiogenic Factors," *Science*, 235:442-447 (1987).

"Angiogenesis in cancer, vascular, rheumatoid and other disease," *Nature Medicine*, 1: 27-31, (1995).

Folkman, J. et al., "Blood Vessel Formation: What Is Its Molecular Basis?" *Cell*, 87:1153-1155 (1996).

Folkman, J., "Angiogenic Therapy of the Human Heart," *Circulation*, 97(7): 628-29 (1998).

Folkman, J., "Antiangiogenic Gene Therapy," *Proc. Natl. Acad. Sci. USA.*, 95:9064-66 (1998).

Folkman, J., "Fighting Cancer by Attacking Its Blood Supply," *Sci. Am.*, 275(3): 150-54 (1996).

Gale, N.W. et al., "Growth Factors Acting Via Endothelial Cell-Specific Receptor Tyrosine Kinases: VEGFs, Angiopoietins, and Ephrins in Vascular Development," *Genes Dev.*, 13:1055-66 (1999).

Gale, N.W., et al., "Ephrin-B2 Selectively Marks Arterial Vessels and Neovascularization Sites in the Adult, with Expression in Both Endothelial and Smooth-Muscle Cells," *Dev. Biol.*, 230: 151-160 (2001).

GenBank Acceisson No. P52803.

Genetech's Response to Final Office Action on U.S. Appl. No. 09/442,898, filed Mar. 29, 2002.

Glassberg et al., "Cultured endothelial cells derived from the human iliac arteries," In Vitro, 18:859-866 (1982).

Goetz et al., "Long-term serial cultivation of arterial and capillary endothelium from adult bovine brain," *In Vitro Cellular and Developmental Biology*, 21:172-180 (1985).

Guzman, R.J., et al., "In Vivo Suppression of Injury-Induced Vascular Smooth Muscle Cell Accumulation Using Adenovirus-Mediated Transfer of the Herpes Simplex Virus Thymidine Kinase Gene," *Proc. Natl. Acad. Sci. USA*, 91:10732-10736 (1994).

Hafner et al., "Differential Gene Expression of Eph Receptors and Ephrins in Benign Human Tissues and Cancers," *Clinical Chemistry*, 50(3):490-499 (2004).

Hafner, et al., "Loss of Eph B6 expression in metastatic melanoma," *International Journal of Oncology*, 23:1553-1559 (2003).

Hausner, C., "Organogenesis Vascular Graft Becomes Physiologically-Responsive Living Tissue After Implantation [online]," *Nature Biotechnol.*, (1999).

Henkemeyer, M., et al., "Nuk Controls Pathfinding of Commissural Axons in the Mammalian Central Nervous System," *Cell*, 86:35-46 (1996).

Indolfi, C., et al., "Inhibition of Cellular ras Prevents Smooth Muscle Cell Proliferation After Vascular Injury In Vivo," *Nature Med.*, 1(6):541-545 (1995).

Kenyon, B.M., et al., "A Model of Angiogenesis in the Mouse Cornea," *Invest Ophthalmol. Vis. Sci.*, 37:1625-1632 (1996).

Keogh, M-C, et al., "Design of a Muscle Cell-Specific Expression Vector Utilising Human Vascular Smooth Muscle ?—Actin Regulatory elements," *Gene Therapy*, 6:616-628 (1999).

Lackmann, et al., "Distinct Subdomains of the EphA3 Receptor Mediate Ligand Binding and Receptor Dimerization," *The Journal of Biological Chemistry*, 273 (32):20228-20237 (1998).

Li, J., et al., "Expression of the SM22x Promoter in Transgenic Mice Provides Evidence for Distinct Transcriptional Regulatory Programs in Vascular and Visceral Smooth Muscle Cells," *J. Cell Biol.*, 132:849-59 (1996).

Lin, P., et al., "Antiangiogenic Gene Therapy Targeting the Endothelium-Specific Receptor Tyrosine Kinase Tie2," *Proc. Natl. Acad. Sci.*, USA, 95:8829-8834 (1998).

Magal, et al., "B61, a Ligand for the Eck Receptor Protein-Tyrosine Kinase, Exhibits Neurotrophic Activity in Cultures of Rat Spinal Cord Neurons," *Journal of Neuroscience Research*, 43:735-744 (1996).

Maru, et al., "Evolution, Expression, and Chromosomal Location of a Novel Receptor Tyrosine Kinase Gene, eph," *Molecular and Cellular Biology*, 8(9):3770-3776 (1998).

Maru, et al., "Overexpression confers an oncogenic potential upon the eph gene," *Oncogene*, 5:445-447 (1990).

Mellitzer, G., et al., "Eph Receptors and Ephrins Restrict Cell Intermingling and Communication," *Nature*, 400:77-82 (1999).

Nakanuma, Y. et al., "Succinylated Wheat Germ Agglutinin Lectin Binding in Intrahepatic Vessels: A New Histochemical Tool," *Arch. Pathol. Lab. Med.*, 117:809-811 (1993).

Niklason, L.E., et al., "Functional Arteries Grown In Vitro," *Science*, 284:489-493 (1999).

Niklason, L.E., et al., "Morphologic and Mechanical Characteristics of Engineered Bovine Arteries," *J. Vasc. Surg.*, 33:628-638 (2001).

Nikolova, et al., "Cell-type specific and estrogen dependent expression of the receptor tyrosine kinase EphB4 and its ligand ephrin-B2 during mammary gland morphogenesis," *Journal of Cell Science*, 111:2741-2751 (1998).

Ogle et al., "The Role of Vascular Smooth Muscle Cell Integrins in the Compaction and Mechanical Strengthening of a Tissue-Engineered Blood Vessel," *Tissue Engineering*, 5(4):387-402 (1999).

Orioli, D., et al., "Sek4 and Nuk Receptors Cooperate in Guidance of Commissural Axons and in Palate Formation," *Embo J.*, 15(22):6035-6049.

Pandey et al., "Role of B61, the ligand for the eck receptor tyrosine kinase, in TNF-a-induced angiogenisis" *Science*, 268:567-569 (1996).

Parangi et al., "Antiangiogenic therapy of transgenic mice impairs de novo tumor growth," *Proc. Natl. Acad. Sci. USA*, 93:2002-2007 (1996).

Peng et al., "Regulation of Ca2+-activated K+ channels in pulmonary vascular smooth muscle cells: role of nitric oxide," *J. Applied Physiol.*, 81:1264-1272 (1996).

Presta et al., "Humanization of an Anti-Vascular Endothelial Growth Factor Monoclonal Antibody for the Therapy of Solid Tumors and Other Disorders," *Cancer Research*, 57:4593-4599 (1997).

Ramchandran et al., Mettaloprotease-mediated cleavage secretion of pulmonary ACE by vascular endothelial and kidney epithelial cells,: *Am. J. Physiology*, 271:H744-751 (1996).

Risau, W., "Mechanisms of angiogenesis," *Nature*, 386:671-674 (1997).

Shepard, et al., "Monoclonal Antibody Therapy of Human Cancer: Taking the HER2 Protooncogene to the Clinic," *Journal of Clinical Immunology*, 11(3):117-127 (1991).

Simonet, S., et al., "Venous and Arterial Endothelial Cells Respond Differently to Thrombin and its Endogenous Receptor Agonist," *European Journal of Pharmacology*, 216:135-137 (1992).

Simons, M., et al., "Antisense c-myb Oligonucleotides Inhibit Intimal Arterial Smooth Muscle Cell Accumulation In Vivo," *Nature*, 359(6390):67-70 (1992).

Stein, E. et al., "Eph receptors discriminate specific ligand oligomers to determine alternative signaling complexes, attachment, and assembly responses," *Genes & Development*, 12:667-678 (1998).

Stein, E. et al., "Nck Recruitment to Eph Receptor, EphB1/ELK, Couples Ligand Activation to c-Jun Kinase," *The Journal of Biological Chemistry*, 273(3):1303-1308 (1998).

Sturz, et al., "EphB4 signaling is capable of mediating ephrinB2-induced inhibition of cell migration," *Biochemical and Biophysical Research Communications*, 313:80-88 (2004).

Sunassee, et al., "Tumour angiogenesis: Hitting cancer where it hurts," *Current Biology*, 7(5):R282-R285 (1997).

Tallquist, M.D., et al., "Growth Factor Signaling Pathways in Vascular Development," *Oncogene*, 18(55):7917-7932 (1999).

The Eph Nomenclature Committee, "Unified Nomenclature for Eph Family Receptors and Their Ligands, the Ephrins," *Cell*, 90:403-404 (1997).

Thurston et al., "Permeability-related changes revealed at endothelial cell borders in inflamed venules by lectin binding," *American Journal of Physiology*, 271:H2547-H2562 (1996).

Tsui, L.V., et al., "p27-p16 Fusion Gene Inhibits Angioplasty-Induced Neointimal Hyperplasia and Coronary Artery Occlusion," *Circ. Res.*, 89:323-328 (2001).

Twardowski et al., "Clinical trials of-antiangiogenic agents," *Current Opinion in Oncology*, 9:584-589 (1997).

van de Wiel et al., "Factors that define the susceptibility of endothelial cells to tumor necrosis factor and lipid A," *Immunopharmacology*, 23:49-56 (1992).

Vasgene Therapeutics, Inc., "Statement of Grounds of Opposition," In the Matter of European Patent No. 1135153 (EP-B-1135153), (2006).

Vector Laboratories, "Wheat Germ Agglutinin (WGA)," [online].

von der Leyen, H.E., et al., "Gene Therapy Inhibiting Neointimal Vascular Lesion: In Vivo Transfer of Endothelial Cell Nitric Oxide Synthase Gene," *Proc. Natl. Acad. Sci.*, 92:1137-1141 (1995).

Wang et al., "Molecular Distinction and Angiogenic Interactions Between Embryonic Arteries and Veins Revealed by EphrinB2 and Its Receptor EphB4," *Circulation: Melvin L. Marcus Young Investigator Award*, Abstract 341.

Wang, H. U. et al., "Eph Family Transmembrane Ligands Can Mediate Repulsive Guidance of Trunk Neural Crest Migration and Motor Axon Outgrowth," *Neuron*, 18:383-396 (1997).

Waugh, J.M., et al., "Thrombomodulin Overexpression to Limit Neointima Formation," *Circulation*, 102:332-337 (2000).

Winlaw, "Angiogenesis in the Pathobiology and Treatment of Vascular and Malignant Diseases," *Ann. Thorac. Surg.*, 64:1204-1211 (1997).

Xu, et al., "Function of the Eph-related kinase rtk1 in patterning of the zebrafish forebrain," *Nature*, 381:19-322 (1996).

Yamamoto et al., "Differences in Cellular Responses to Mitogens in Arterial Smooth Muscle Cells Derived From Patients With Moyamoya Disease," *Stroke*, 29:1188-1193 (1998).

Yancopoulos, G. D. et al., "Vasculogenesis, Angiogenesis, and Growth Factors: Ephrins Enter the Fray at the Border," *Cell*, 93:661-664 (1998).

Yuan, et al., "Syndecan-1 up-regulated by ephrinB2/EphB4 plays dual roles in inflammatory angiogenesis," *Blood*, 104(4):1025-1033 (2004).

Zetter, "Angiogenesis and Tumor Metastasis," *Annu. Rev. Med*, 49:407-424, (1998).

Zhang, X-Q, et al., "Stromal Cells Expressing ephrin-B2 Promote the Growth and Sprouting of Ephrin-B2+ Endothelial Cells," *Blood*, 98:1028-37 (2001).

Zhou, "The Eph Family Receptor and Ligands," *Pharmacol. Ther.*, 77(3) 151-181 (1998).

Dermer, G., "Another Anniversary for the War on Cancer," *Bio/Technology*, 12:320 (1994).

Freshney, R. Ian, *Culture of Animal Cells: A Manual of Basic Technique*, Alan R. Liss, Inc. (1983).

Gura, T., "Systems for Identifying New Drugs Are Often Faulty," *Science*, 278:1041-1042 (1997).

Fabes et al., "Accumulation of the Inhibitory Receptor EphA4 May Prevent Regeneration of Corticospinal Tract Axons Following Lesion," *Eur. J. Neurosci.*, 23(7):1721-1730 (2006) (Abstract).

Kitamura et al., "Chemical Engineering of the Monoclonal Antibody A7 by Polyethylene Glycol for Targeting Cancer Chemotherapy," *Cancer Research*, 51:4310-4315 (1991).

Miki et al., "Association of Ash/Grb-2 with Dynamin through the Src Homology 3 Domain", The Journal of Biological Chemistry, vol. 269(8); pp. 5489-5492 (1994).

Bennett et al., "Extracellular Domain-IgG Fusion Proteins for Three Human Natriuretic Peptide Receptors," The Journal of Biological Chemistry, vol. 266(34), pp. 23060-23067 (1991).

Kiessig et al., "Application of a green fluorescent fusion protein to study protein-protein interactions by electrophoretic methods," Electrophoresis, vol. 22, pp. 1428-1435 (2001).

Perrin et al., "Expression, Purification, and Characterization of a Soluble Form of the First Extracellular Domain of the Human Type 1 Corticotropin Releasing Factor Receptor*," The Journal of Biological Chemistry, vol. 276(34), pp. 31528-31534 (2001).

Bowie et al., "Deciphering the message in protein sequences: tolerance to amino acid substitutions," Science, vol. 247(4948), pp. 1306-1310 (1990).

Burgess et al., "Possible dissociation of the heparin-binding and mitogenic activities of heparin-binding (acid fibroblast) growth factor-1 from its receptor-binding activities by site-directed mutagenesis of a single lysine residue," Journal of Cell Biology, vol. 111, pp. 2129-2138 (1990).

He et al., "The Effect of Soluble EphrinB4 Receptor on Laser-Induced Choroidal Neovascularization," *IOVS*, 45:U804 (2004).

Noren et al., The EphB4 receptor suppresses breast cancer cell tumorigenicity through an Abl-Crk pathway, Nature Cell Bio. 8:815-825 (2006).

Noren et al., "Interplay Between EphB4 on Tumor Cells and Vascular Ephrin-B2 Regulates Tumor Growth," *Proceedings of the National Academy of Sciences of USA, National Academy of Science*, 101(15):5583-5588 (2004).

R&D systems. Recombinant Mouse EphB4/Fc chimera. Nov. 14, 2000. p. 1.

Seffernick et al., "Melamine Deaminase and Atrazine Chlorohydrolase: 98 Percent Identical but Functionally Different", Journal of Bacteriology, vol. 183(8), pp. 2405-2410 (2001).

Wang, H., "Transmembrane Ephrin Ligands in Neural and Vascular Development," DAI, 59(11): 5721 (1999).

Berclaz Gilles et al., "Loss of EphB4 receptor tyrosine kinase protein expression during carcinogenesis of the human breast," *Oncology Reports*, 9(5):985-989 (2002).

Caplen, N.J., "RNAI as a Gene Therapy Approach," *Expert Opin. on Biol. Therapy*, 3(4):575-586 (2003).

Cromer et al., "Identification of genes associated with tumorigenesis and metastatic potential of hypopharyngeal cancer by microarray analysis " *Oncogene*, Basingstoke, Hants, GB, 23(14):2484-2498 (2004).

Santa Cruz, "EphB4 (N-19): sc-7285," *Product Catalog of Santa Cruz Biotechnology* (1999).

Sinha et al., "Expression of EphB4 in head and neck squamous cell carcinoma," *Bar, Nose, and Throat Journal*, 82(11):866, 869-870, 887 (2003).

Takai et al., "Expression of receptor tyrosine kinase EphB4 and its ligand Ephrin-B2 is associated with malignant potential in endometrial cancer," *Oncology Reports, National Hellenic Research Foundation*, 8(3):567-573 (2001).

Yang et al., "Gene Targets of Antisense Therapies in Breast Cancer " *Expert Opin. on Therapeutic Targets*, 6(3):375-385 (2002).

* cited by examiner

Amino acid sequence of the B4ECv3 protein

MELRVLLCWASLAAALEETLLNTKLETADLKWVTFPQVDGQWEELSG
LDEEQHSVRTYEVCEVQRAPGQAHWLRTGWVPRRGAVHVYATLRFTM
LECLSLPRAGRSCKETFTVFYYESDADTATALTPAWMENPYIKVDTV
AAEHLTRKRPGAEATGKVNVKTLRLGPLSKAGFYLAFQDQGACMALL
SLHLFYKKCAQLTVNLTRFPETVPRELVVPVAGSCVVDAVPAPGPSP
SLYCREDGQWAEQPVTGCSAPGFEAAEGNTKCRACAQGTFKPLSGE
GSCQPCPANSHSNTIGSAVCQCRVGYFRARTDPRGAPCTTPPSAPRS
VVSRLNGSSLHLEWSAPLESGGREDLTYALRCRECRPGGSCAPCGGD
LTFDPGPRDLVEPWVVVRGLRPDFTYTFEVTALNGVSSLATGPVPFE
PVNVTTDREVPPAVSDIRVTRSSPSSLSLAWAVPRAPSGAWLDYEVK
YHEKGAEGPSSVRFLKTSENRAELRGLKRGASYLVQVRARSEAGYGP
FGQEHHSQTQLDESEGWREQGSKRAILQIEGKPIPNPLLGLDSTRTG
HHHHHH

Fig. 1

Amino acid sequence of the B4ECv3NT protein

MELRVLLCWASLAAALEETLLNTKLETADLKWVTFPQVDGQWEELSGL
DEEQHSVRTYEVCEVQRAPGQAHWLRTGWVPRRGAVHVYATLRFTMLE
CLSLPRAGRSCKETFTVFYYESDADTATALTPAWMENPYIKVDTVAAE
HLTRKRPGAEATGKVNVKTLRLGPLSKAGFYLAFQDQGACMALLSLHL
FYKKCAQLTVNLTRFPETVPRELVVPVAGSCVVDAVPAPGPSPSLYCR
EDGQWAEQPVTGCSCAPGFEAAEGNTKCRACAQGTFKPLSGEGSCQPC
PANSHSNTIGSAVCQCRVGYFRARTDPRGAPCTTPPSAPRSVVSRLNG
SSLHLEWSAPLESGGREDLTYALRCRECRPGGSCAPCGGDLTFDPGPR
DLVEPWVVVRGLRPDFTYTFEVTALNGVSSLATGPVPFEPVNVTTDRE
VPPAVSDIRVTRSSPSSLSLAWAVPRAPSGAWLDYEVKYHEKGAEGPS
SVRFLKTSENRAELRGLKRGASYLVQVRARSEAGYGPFGQEHHSQTQL
DESEGWREQGSKRAILQISSTVAAARV

Fig. 2

Amino acid sequence of the B2EC protein

MAVRRDSVWKYCWGVLMVLCRTAISKSIVLEPIYWNSSNSKFLPGQGL
VLYPQIGDKLDIICPKVDSKTVGQYEYYKVYMVDKDQADRCTIKKENT
PLLNCAKPDQDIKFTIKFQEFSPNLWGLEFQKNKDYYIISTSNGSLEG
LDNQEGGVCQTRAMKILMKVGQDASSAGSTRNKDPTRRPELEAGTNGR
SSTTSPFVKPNGSSTDGNSAGHSGNNILGSEVGSHHHHHH

Fig. 3

Amino acid sequence of the B4ECv3-FC protein

MELRVLLCWASLAAALEETLLNTKLETADLKWVTFPQVDGQWEEL
SGLDEEQHSVRTYEVCEVQRAPGQAHWLRTGWVPRRGAVHVYATL
RFTMLECLSLPRAGRSCKETFTVFYYESDADTATALTPAWMENPY
IKVDTVAAEHLTRKRPGAEATGKVNVKTLRLGPLSKAGFYLAFQD
QGACMALLSLHLFYKKCAQLTVNLTRFPETVPRELVVPVAGSCVV
DAVPAPGPSPSLYCREDGQWAEQPVTGCSCAPGFEAAEGNTKCRA
CAQGTFKPLSGEGSCQPCPANSHSNTIGSAVCQCRVGYFRARTDP
RGAPCTTPPSAPRSVVSRLNGSSLHLEWSAPLESGGREDLTYALR
CRECRPGGSCAPCGGDLTFDPGPRDLVEPWVVVRGLRPDFTYTFE
VTALNGVSSLATGPVPFEPVNVTTDREVPPAVSDIRVTRSSPSSL
SLAWAVPRAPSGAWLDYEVKYHEKGAEGPSSVRFLKTSENRAELR
GLKRGASYLVQVRARSEAGYGPFGQEHHSQTQLDESEGWREQDPE
PKSCDKTHTCPPCPAPELLGGPSVFLFPPKPKDTLMISRTPEVTC
VVVDVSHEDPEVKFNWYVDGVEVHNAKTKPREEQYNSTYRVVSVL
TVLHQDWLNGKEYKCKVSNKALPAPIEKTISKAKGQPREPQVYTL
PPSRDELTKNQVSLTCLVKGFYPSDIAVEWESNGQPENNYKTTPP
VLDSDGSFFLYSKLTVDKSRWQQGNVFSCSVMHEALHNHYTQKSL
SLSPGK

Fig. 4

Amino acid sequence of the B2EC-FC protein

MAVRRDSVWKYCWGVLMVLCRTAISKSIVLEPIYWNSSNSKFLPGQ
GLVLYPQIGDKLDIICPKVDSKTVGQYEYYKVYMVDKDQADRCTIK
KENTPLLNCAKPDQDIKFTIKFQEFSPNLWGLEFQKNKDYYIISTS
NGSLEGLDNQEGGVCQTRAMKILMKVGQDASSAGSTRNKDPTRRPE
LEAGTNGRSSTTSPFVKPNPGSSTDGNSAGHSGNNILGSEVDPEPK
SCDKTHTCPPCPAPELLGGPSVFLFPPKPKDTLMISRTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELTKNQVSLTCLVKGFYPSDIAVEWESNGQPENNYKTTPPVLDSDG
SFFLYSKLTVDKSRWQQGNVFSCSVMHEALHNHYTQKSLSLSPGK

Fig. 5

B4v3 inhibitis neovascular response in a murine
corneal hydron micropocket assay

+GF        B4+GF        -GF

Migration Study of H28 with siRNA472(Boyden Chamber)

Ephrin B2 AS
Ephrin B2 S
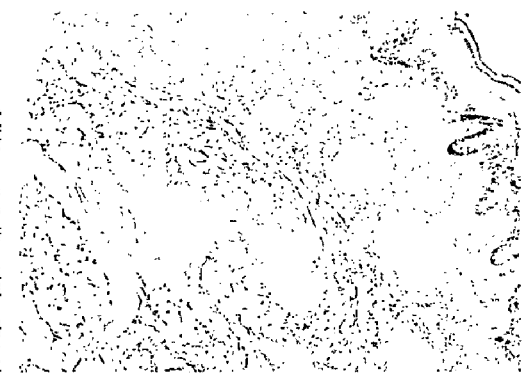
EphB4 AS
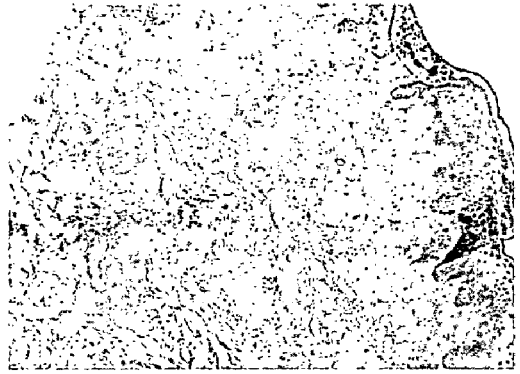
H&E
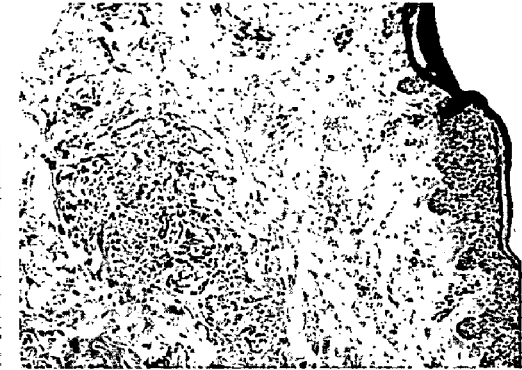
squamous cell carcinoma
EphB4 AS    H&E
Fig. 45A Expression of EPHB4 in bladder cancer cell lines
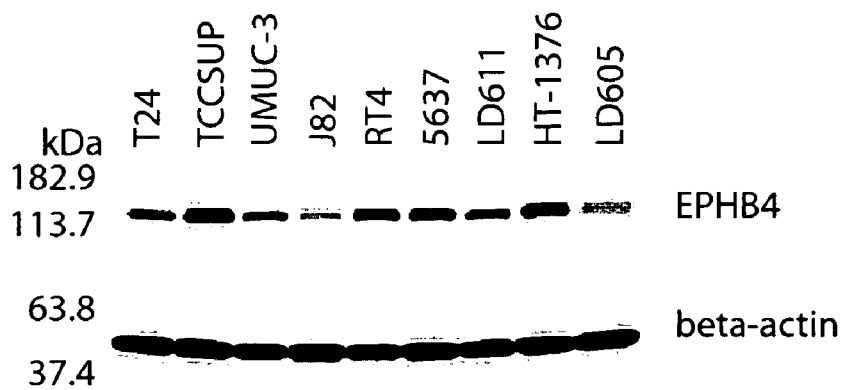
Regulation of EPHB4 expression by EGFR signaling pathway
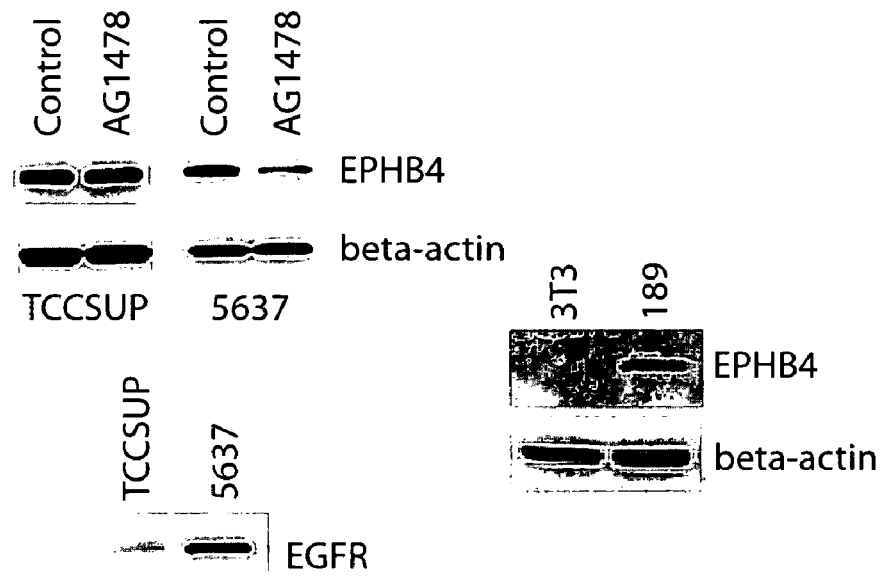
Fig. 51

Invasion study of 5637 cell transfected
with siRNA 472 or control siRNA
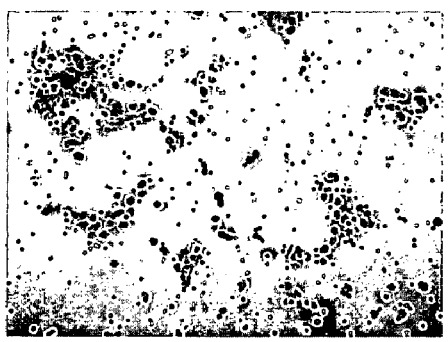 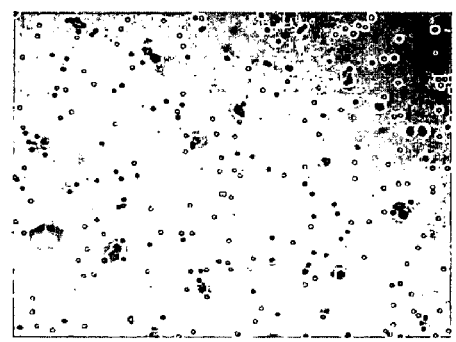
Control                                siRNA472
Fig. 56

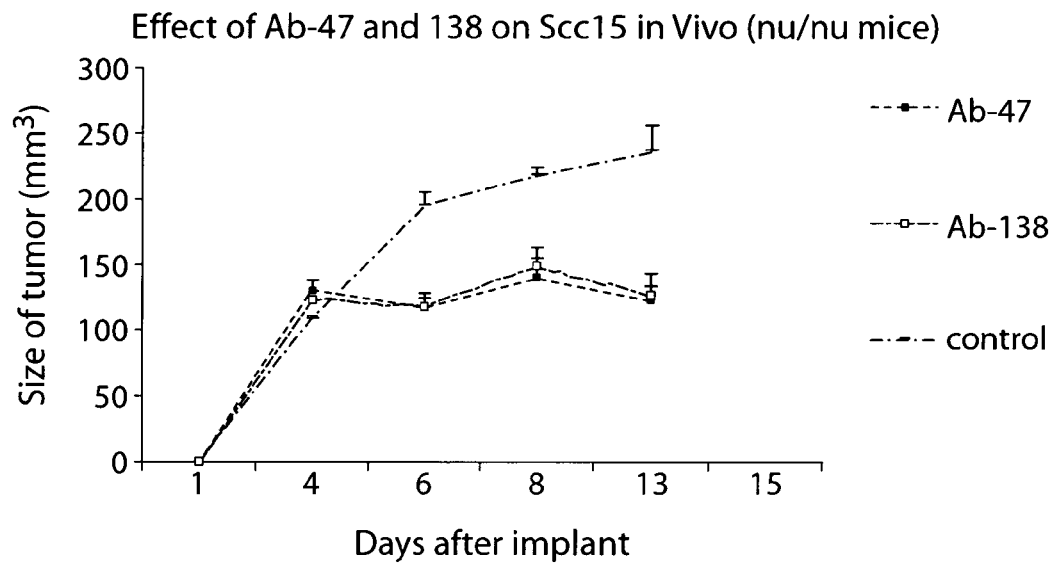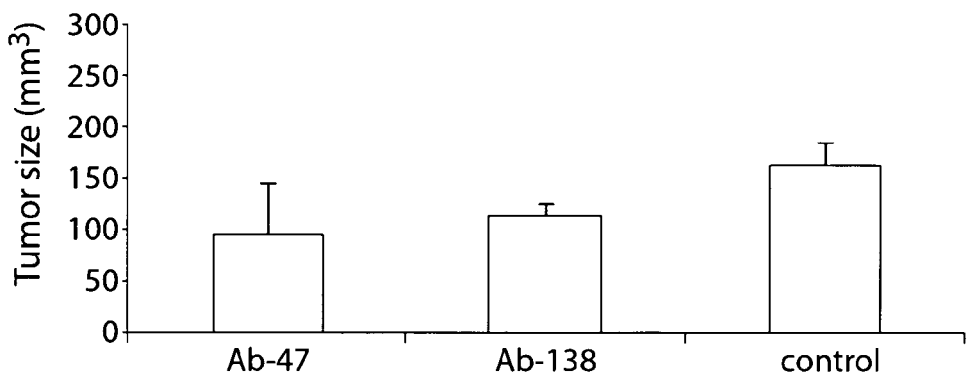
Fig. 60

EphB4 gene

```
   1 ggggtttcat catgttggcc aggctggtct tgaactcctg acctcaaatg atccgcctgc
  61 ctctgcctcc caaaatgctg ggactacagg cgtgagccac cgcgcccgcc acacccacct
 121 tttctttacc gttgtttcct cgattttct ctactcccta gcgcagctta gtgcgcgcct
 181 cctctggaca tttttcaggg cttggttgcg cgcacagtag gtccccaaca ctgaatgttt
 241 atggggtgac tgtgtgaacg ttcgctgcaa ggctatccaa actgggattg ctccttgagg
 301 ccccctgggc ggccgtcaat tctccaaagc ttctactccc ttttccttcc ttttccccca
 361 aaacgcagtc cctgcgccca ctagagggtg gtgggcgcat ccaagagcgg catctagagt
 421 ccgcagcaag gtcagagcgg gctttgtgtg cgcggtgaac atttacgtgc acgcctgggc
 481 ggccctccgt gttgctgctg ggtgtgtgtt ttctctgctc cctggtgcca gccgggttcg
 541 ggcctgtccc gggggtccct gggccccagc ccgacatgc tcggtcctgg acagcgcgca
 601 ccgccacggc gcacatctgg gcggtcccgg ggttcctcac ccgccgcccc tccccttct
 661 ccaaactttc tctcaacttc ccgacctgct ccactcggtg ccctctccg cttccctcat
 721 gaattattca gtagcgtgag ctccaatcag cgcgcccggg gctcactcgc ggagcccccg
 781 cgttgggaga gctgcccccg ccccccgcgc gcccctccct cccgggcccg gcgccgcccg
 841 gcccagttcc agcgcagctc agccctgcc cggccggcc cgccggctc cgcgccgcag
 901 tctccctccc tcccgctccg tccccgctcg ggctcccacc atccccgccc gcgaggagag
 961 cactcggccc ggcggcgcga gcagagccac tccagggagg ggggagacc gcgagcggcc
1021 ggctcagccc ccgccacccg gggcgggacc ccgaggcccc ggagggaccc caactccagc
1081 cacgtcttgc tgcgcgcccg cccggcgcgg ccactgccag cacgctccgg gcccgccgcc
1141 cgcgcgcgcg gcacagacgc ggggccacac ttggcgccgc cgcccggtgc cccgcacgct
1201 cgcatgggcc cgcgctgagg gccccgacga ggagtcccgc gcggagtatc ggcgtccacc
1261 cgcccaggga gagtcagacc tgggggggcg agggcccccc aaactcagtt cggatcctac
1321 ccgagtgagg cggcgccatg gagctccggg tgctgctctg ctgggcttcg ttggccgcag
1381 ctttggaagg tgagtttcct tgcgggggg gcgcacccc gtcactcctg gacctccc
1441 cccaacatct gggcctcgga gtgggggc cggcctctga ctacccctac ccgggcactg
1501 cagtcccaaa cacttcggac cgatagtgct ggaacgggag ggggcgggg aagaggcgcc
1561 cgacgggtag tggagttttc ttttgtttgg aaagagatg gagtctggct acgacccggg
1621 acattcccct gcccgggctc ccgaactct cactgctgat tacatacgcc cctggctgcc
1681 tttcctttcc tccctacccc actattcaaa actatctgca aagtttctgt cccagtccca
1741 cctcccgccg tacatgaggg aaggttctg gagaagcaac agcagacaag gcacaacttt
1801 tcgtgctagg ccctaaaacg accccagcg ccaattcctt agcgatcaca ccttgatcct
1861 ccagttccac actcctgcaa caggatggcc tcctttgcat tcacacagca aaccccccaaa
1921 ccgctctccc gcccactgct cctgccctg gtatagggtg gctccttggt ttctacaggc
1981 tgcaccccat ccctttaaat gcggtctaga ccccggcccc aggtgagtcc cgggcttccc
2041 ttgagaccta ggagcgggta gaaactgacc tacacagccc ccaggtagaa actgacctac
2101 acagccccca catcgcccta actaacccag tctatctccc acctcctggt ctctccaagc
2161 atttctttgg ccatggatcg ctgtccctcc tggtcccta aaggggagc caagagccct
2221 agaaactctc ctgtgtccct aatgtccttt cagtgagctg ccaacacccc cctttctctg
2281 tctggtatga aagtggttat ggggcggtag gctatgaggg actcccaaag gaaggattc
2341 agcggcgtta gaaaaccct ctcccctgg ctgggcagga ctgccctggg ctggggatca
2401 aaggctaggt gtggggttgg gagtgagggg aggcttgccc agctcagaga acggagaagg
2461 gggaacaaaa accatgaacg aggggaagag gaaggccaaa ggggtggaaa accacgagg
2521 acgaggtgtg gtgagaagga aagacgcaaa gaggaaatgg tgattgtgac acctattacc
2581 tgagtgtttc caagcaccag gcctgtgctg agcgccttac aaatattaat ttcacccatc
```

Fig. 61A

```
2641 cagcaacgct aagggtggtg ctattattgc ccccattttt cagatgagga ggctggggct
2701 tagttaaggt taagtagttt atccaaggcc ctgtgccgcg aggaacagcg agaagtggag
2761 gccgaaagcg aaggagagat agtgactgtc agaaagagaa acggaggtgg acagagagtg
2821 gaggagagat aggtgagaga catgcgaact gacagatcaa agcgtggctg cagctgagct
2881 gggacgcaga aagggagcct gcgcttgctc tgggctgcgg acagcccgag gcagagacag
2941 tgtgtaaatt ggagacagga aaacactatc ccggctggaa caatggaggg tggagacggc
3001 agcctctatc caccccttc ccagaacccg ggcatcctgt ccccagtgag cagggctgtc
3061 tcttgccacc catggggacc ttgcgcctct cacctcaggc tggctggctt cccatctgac
3121 ccctagctgg aggacatcat ttggtcccca ggaagaggct gcctcaccca ccctctttct
3181 cttctctcct gcagctccca tggggtggga gccaggtgtt ctggctcccc tctccaccct
3241 tcccagcgcc caatgccccc cacattgccg gccccgagg ggattcctgt accctccctc
3301 ctccactctc cactgccagg ggctgtgcag tttttcctaa tccccccct tcctccagtg
3361 cctgtcccct ccccgatga tccgagccaa gccaggtgtg ttcacccctc ccattcatac
3421 cgcccccag aatctcctcc cctctgcctt cccataacca aatccagatg tgaggcctcg
3481 gcgggagcct gggaaccta gcatcccgac ctccagtgct tcctgatcag ggcactcgtg
3541 gggaggggagg tactgggatg ggggccaggg ctatgcccca ggcacggagc gctcccttca
3601 aggagggaag gacggggtgt ttggtctgaa agcagagagg ggtcttggac agggaatgaa
3661 attgtggggt agagaggctg attctgggac ttaggggagg aaacgtggag gctgagacaa
3721 gaggttcccc tcccacacca gcagcctctg ctcgtggggg tcaggaccag ggcgcagctc
3781 tcatttaac cctttctgag ctgccgcccc ttctccccgt acatttgat ctccctccct
3841 cctccaggga ggcctagatc tggggtatcc caagggagcc ccatgcctac cagatgttgg
3901 gggtggggtt ggcacttagc agaagaggcc agaaatcagg cgggtgcaga gggcagggct
3961 tgctcccctc ttggcccccc aactcctcta gctcagagct aagaggatcc acctgcctcg
4021 gttcccaggg atctggtctt cctgacctcc ctcccccacc ccaggcactg actctgtctc
4081 tctgtctgtc tcagagaccc tgctgaacac aaaattggaa actgctgatc tgaagtgggt
4141 gacattccct caggtggacg ggcaggtgag agctgcaccc aggagctgga gctctggagg
4201 gaaactgagg gaggagaggg cgcctgtgcc gcctgctttc tgtgtgccac tcctctcccc
4261 tgtccccccca gatgacagca gccccagcag tgtcgtctga gccttctcca gaggcgccct
4321 cctcgcagta ccagcagccc ccctttctca gtccctctca ctttatagga ttcaccccat
4381 gcagccctct ccctggcggc tccccagccc ccttgctgac ctccttctct gcacagtggg
4441 aggaactgag cggcctggat gaggaacagc acagcgtgcg cacctacgaa gtgtgtgacg
4501 tgcagcgtgc cccgggccag gccactggc ttcgcacagg ttgggtccca cggcggggcg
4561 ccgtccacgt gtacgccacg ctgcgcttca ccatgctcga gtgcctgtcc ctgcctcggg
4621 ctgggcgctc ctgcaaggag accttcaccg tcttctacta tgagagcgat gcggacacgg
4681 ccacggccct cacgccagcc tggatggaga acccctacat caaggtacct gggtgcccc
4741 agggctcagc cacagccaag gtgggattcc agccagcagg cccgtggcct ggagggcagc
4801 cgatgtagtt gcgaggcctc tggcccgcgc gctgggggct ggaagcagga ggcttaggtc
4861 tggggaggga aggggtgat cttctgggcg gaggagcaga atatacgggg gctgcctggc
4921 ccggccccca gggaggccca agggtcaggc ttctcctcca gtcacctcaa ccaccctacc
4981 ccactgtgct ccagccacac tgagtttctc ccattccctg actgcacctg gctggtttcc
5041 agctcaagac tttgcagcgg tgatgtctcc acctgggggc ctctctgcct ctcacacccc
5101 tacttgtctt cggagttcca gctccgaga tcttgcctgt gccaccttgg ctgactctct
5161 cctccctaca atcctgcata cctctgtcca cctgcctgtc tcggcactca ttttactta
5221 tttattttc ttttatatct atatttttaa agcggggtct tctacgttac ccaggctggt
```

Fig. 61B

```
5281 ctctaactcc tgggctcaag agatttctcc cacctcggcc tcctaaagtg ctgggattat
5341 aggcatgagg cactacgccc ggcctcatgg tactttataa cttccccagg attcattcat
5401 cgctgtctcc ttgactctga ggtcaaggcc tggcatggcg tcagtgtcag taaatgtttg
5461 tagaacgagt gaataaaaag ggggagaggt gcaggccaga ggccgggcat atcgcaggag
5521 ctttgcaagg ctgaatggac agtgtggggg cctgcagaaa gtgtgcctg gggaaggtgg
5581 agggaagatt ctggaacggg aaccaaggag gtccgggagg gtgagctggg aagaacacaa
5641 cagtccgctg ggtcctcagg gagtggggac agcagcggtg tgcctccccc ccgccggcag
5701 gtggacacgg tggccgcgga gcatctcacc cggaagcgcc ctggggccga ggccaccggg
5761 aaggtgaatg tcaagacgct gcgtctggga ccgctcagca aggctggctt ctacctggcc
5821 ttccaggacc agggtgcctg catggccctg ctatccctgc acctcttcta caaaaagtgc
5881 gcccagctga ctgtgaacct gactcgattc ccggagactg tgcctcggga gctggttgtg
5941 cccgtggccg gtagctgcgt ggtggatgcc gtccccgccc ctggcccag ccccagcctc
6001 tactgccgtg aggatggcca gtgggccgaa cagccggtca cgggctgcag ctgtgctccg
6061 gggttcgagg cagctgaggg gaacaccaag tgccgaggtg agagctggag cttcccctgc
6121 gactgctgct catccggggg agagtcctga actccactca ggacccactt cttaagtttc
6181 catttgtat agttagatgt tgaaatggag gcttgctctg tcacccaggc tggagtgcag
6241 tggcacaatc tctgctcaac tgcaaccttt gcctcccggg tccctgttca agcagttctc
6301 ctgcctcagc ctcgtgagta gctgggacta caggcacacg ccaccacgcc cggctaattt
6361 ttgtatttta gtagagacgg ggtttcgcca tgttggccag gctggtctcg aactcctgac
6421 ctgaagtgat ttgcccgcct cggcctccca aagtgctggg attacaggcg tgcgtcacca
6481 cacccagctg gaaaaaaaaa gactttatt ttcacctgaa attcattaat ttccacttga
6541 aattccacct gcagttgtag caggacctga cacttgggcc ccatgaaat cacaggtatt
6601 gcctgacaca gtggttcatg cccatagtgc cagcactttg agatgccaag gtgggaggat
6661 cacttgagcc caggagttcg agatcagcct gggtgacaga gcaagacccc gtctctaaaa
6721 aaaatttttt ttttttttc aagacagagt cttgctctgt cgcccaggct ggagtgcagt
6781 ggtgcgatct cggctcactg caagctccgc ctccaagtt aacaccattc tcctgcctca
6841 gcctcccgag tagctgggac tacaggcccc gccaccacgc ccggctaatt tcttgtatt
6901 ttagtagaga tggagtttca ccgtgttagc caggatggtc tcgatctcct gacctcatga
6961 tctgcccgcc ttggcctccc aaagtgctgg gattacaggt gtgagccacc acacccggat
7021 tacaaaaact ttttagataa ttatctgggc gacctgcctg accaacatgg agaaaccctg
7081 tctctactaa aaatacaaaa ttagccggac atggtggcgc atgcctgtaa tcccagctac
7141 tgggaggct gaggcaggag aatcatttga acccaggaag cagaggttgc ggtaagccga
7201 gatcatgcca ctgcactccg gtctgggagt gcactccaac aagaaggagt ttcgctcttt
7261 ttgcccaggc tggagtgcag tggtgggatc tcagctcacc gcaacctcca cctcccgggt
7321 tcaggcgatt ctcctgcctc agcctcccaa ggagtagctg ggattatagg tatgcatcgt
7381 cacacccggc tacttttgta tttttagtag aggcaggttt ccaccatgtt ggccaggctg
7441 gtcttgaact caagtgatct gccctctttg gcctccttct caggaaaaaa aaaaaatcac
7501 aggtatttac aggccattcc aagtgccaaa agattgtttt tgctcatggt gacttcagta
7561 tcacagatgt taggagactt gctgctatat gttaagaaag aagcacaaat gttgctgtag
7621 cccaaacttt tttcctcatg tttcattgca tttcagctta attggtttcc ctggtattcc
7681 tatgtatttt gtggagtgct tttaaaatca taagttggag tagaggtctt tctgtgggct
7741 tcaccagact gccgagatca gggtcgaaac aggtgaggac cccttctctg gagagagtct
7801 ccttctcct ctaagaggaa aggttttgag atcttttgtc cattttccca ccttagcact
7861 tcatcagcct taaaagaagc tggaatttt ttttttttt ttggagatgg gatctcgata
```

Fig. 61C

```
7921  tgttgcccag gctggtcttg aacccettgg ctcaagcgat cctccagcct cagcctccca
7981  aagtgctggg attcgaggca tgagccaccg agcccaccgt gcagatggat gttttgtgc
8041  atgcttttga tgaatgcttt ctctctctca gcctgtgccc agggcacctt caagcccctg
8101  tcaggagaag ggtcctgcca gccatgccca gccaatagcc actctaacac cattggatca
8161  gccgtctgcc agtgccgcgt cgggtacttc cgggcacgca cagaccccg ggtgcaccc
8221  tgcaccagta agtgaccagc acccaggtgc agttcactgg ggaggggtca cagacctctg
8281  aggtggaccc tcacatggcc cccatcctcc ctgggcttct tcctttgtc cctggcatgc
8341  ttgtccctag cccggaggaa catgtggagc ccactgtctc caaggcaaga gtccagcatg
8401  gctgctggtg cctccattgc cctctcccca ccaccgcaga gcaggtcggc ctctgcctga
8461  ctccctggtc tcctgcagcc cctccttcgg ctccgcggag cgtggtttcc cgcctgaacg
8521  gctcctccct gcacctggaa tggagtgccc ccctggagtc tggtggccga gaggacctca
8581  cctacgccct ccgctgccgg gagtgccgac ccggaggctc ctgtgcgccc tgcggggggag
8641  acctgacttt tgaccccggc ccccgggacc tggtggagcc ctgggtggtg gttcgagggc
8701  tacgtcctga cttcacctat acctttgagg tcactgcatt gaacggggta tcctccttag
8761  ccacggggcc cgtcccattt gagcctgtca atgtcaccac tgaccgagag ggtgagactt
8821  ggggctggg gcggctggtg gtctggcggg agagatgtca ctgagggcct gaaggggaga
8881  ggcagggct gtgaagttgg gtaccccgga agtgtgaggg ctaaggctt tgggggcaag
8941  aggcagaaag agggcaatgg ctgggcgcag tggctcacgc ctgtaatccc agcactttca
9001  gaggctgaga caggcggatc acttgagccc tggagttcaa gaccagcctg ggtaacatag
9061  gaagatctct ctacaaaaaa taaaatatt agccaggcga ggtggtgcat gcctgtggtc
9121  ccagctactc aagaggctga ggcaggagga ttgcttgagc ccaggagtcg gaggctgcag
9181  tgagctatga tcgcaccgct gcatgccagc ctgggtgaca gagcagtgtg agatcctctc
9241  tcaaaataaa tgaataagaa agagagggtg aggagctcgt aaagctgggc tggagagtta
9301  agtacaggaa ggcccccagt gggactgggg ccagagagaa tcagaaggaa ttctcgaaac
9361  agccaggggg aaattgagac aagtgtagcc agcagaggaa gtgttggaaa agataaggga
9421  catggccagg ctgatcacaa ggtcaggagt tcaagactag cctggccaac gtggtgaaac
9481  cccatgtcta ctaaaaataa aaaaattagc caggcatggt ggtgggcacc tgtaatccac
9541  tgggaagcca accagaagaa ttgcttgaac ccaggaggcg gaggttgcag taagctgaga
9601  ctgcgccact gcactccagc ctgggtgata gagcacgact ccgtctcgaa aaaaaaaatt
9661  tttttaagt taagggacag agctaccatg cacaagggtt ccctgtgtct ctgcctctca
9721  cagtacctcc tgcagtgtct gacatccggg tgacgcggtc ctcacccagc agcttgagcc
9781  tggcctgggc tgttccccgg gcacccagtg gggctgtgct ggactacgag gtcaaatacc
9841  atgagaaggt aaggccatcc cccagccctg gggtgggtgg gcaatgggtt gtgctctcct
9901  ggctgggaca cctgggttgc aggcacctgg caggcatttg aattccagct ctgccatgga
9961  ttccctgggc agccttgggt aagccccttg cctgtctga gcctcagact cttcatctat
10021 aaaatagtta ctgtaatagt taccagcagc tggacacagt ggctgaggtt gggtgcggtg
10081 gctcacgcct gtaataccaa gcactttggg aggctgaggc gggcagaatg cttgagccta
10141 ggagtttgag accagcctgg gcaacatggt gaaacttcat ctctataaaa aacttaaaat
10201 gggccgggcg cggtagctta cgcctgtaat cccagcactt tgggaggccg aggtgggcgg
10261 atcacaaggt caggagtatc gagaccatcc tggctaacac ggtgaaaccc catctctact
10321 aaaatacaa aaaattagcc aggcgcggtg gcaggcgcct gtagtcccag ctactcggga
10381 ggctgaggca ggagaatggc gtgaacccag gaggcggagc ttgcagtgag ccgagatagc
10441 gccactgcag tccggcctgg gcgaagaac aagactctgt ctccaaaaaa aaaaaaaaa
10501 aaaaaaacg caaaaaatac ttaaaatgaa aaaaattaga ctgggcacag tggctcatgc
```

Fig.61D 10561 ctgtaatccc ggcactttgg gaggccgagg tgggtagaac acctggggtg aagagttcga
10621 gaccagcctg gccaacaagg tgaaatcccc gtctctacta caaatagcaa aatcagctga
10681 gtgtgttggc gggcccctgt aatcccagct actcaggagg ctgagacagg agaatcactg
10741 gaacccaagt gattctcgac ttgaggtcga ggctgcagtg agtcgtgttt gcaccattgc
10801 attccagcct gagaaagtga gaccttgtct taaaaaaaag gaatgatatt atgaatacag
10861 cacatggctt gcatgcgtaa gttctcccaa aggcctcacc agttgcaagg caggctagtg
10921 atgggagtgg agggcgaggg aaggaggcag gaagagcaac aggaacttgg gttcccgggt
10981 gacggccacc ccactacctc tcccggacag ggcgccgagg gtcccagcag cgtgcggttc
11041 ctgaagacgt cagaaaaccg ggcagagctg cgggggctga agcggggagc cagctacctg
11101 gtgcaggtac gggcgcgctc tgaggccggc tacgggccct tcggccagga acatcacagc
11161 cagacccaac tggatggtga gcctggggaa gggggtgagg gtggggggttg gaaagacccc
11221 caaagttcct gggaagaccc caggtctcca aagtcccatc atcttttttt ttttttttt
11281 ttttgagat ggagtcttgc tctgtccctc aggctggagt gcagtggcac catctccgct
11341 cactgcaacc tccgcctccc ggattcaagc cattctcctg cctcagcctc ccgagtagct
11401 gggattacag gcgcctgcca ccgcgcctgg ccgatttttt gtatttttag tagagacggg
11461 gcttcaccgc gttggccagg ctggtctcga actcctgacc ttgtgattcg cccgcctcgg
11521 cctcccgaag tgctgggatt acaggcatga gccactgcac ccggtcaaag tcctatcttc
11581 atgtccttct tcctgtggat cacatggcat gccctagaga ggagagaacg taagatgtcg
11641 aaaccaaaac caacagctga gttttgtgaa gtctggcctg cttcactctg tacccccagg
11701 ctggagcgca gttgctcgat caaagctcac tgcacagcca ggcacagtgg ctcaccctgt
11761 aaccccagca ctttgggagg ctgaagcagg aggatcactt gaggtcagga gttcgagacc
11821 agtctgacca gcatggtgaa accgcgtctc tactaaaaat atagaagtta gctgagcgtg
11881 gtggtgcaca cctgtaatcc cagctactcg ggaggctgag caggagaat cgcttgaacc
11941 tgggaggtgg aggttgcagt gagctgagat tgtgccagtg cactccagcc tgggcaacag
12001 agcaagactc tgtctcaaaa aaaaaaaagc tcaccgcagg cttgactttt agcaacaacc
12061 tgaccccctga gctccccatt ccccatccaa caaaatggga atatcatgaa gcttcctgca
12121 gggctttgag gattggaggt aacaggttat ttttaatatg ctaggccagt ggctttcttt
12181 tttctttcac atttttttt ttgagacgga gtctcactct gttgcccagg ctggagtgcg
12241 gtggcgcgat ctcagctcac cgcaagctcc acctcctggt ctcgatctgc tgacctcctg
12301 atccacccgc ctcggcttcc cgaaatgctg ggactgctgg cgtgagccac cacgcccggc
12361 ctaacttttt ctttttttta agagacacgg tcttttttat cacccaggct ggagtgcggt
12421 ggcaccatca tagctcattg cagcctacaa ctcccgagct caaccaatcc ttccaccttta
12481 gcctcccaag tagctggggc tataggcatg tgctaccgtg ctcaactaaa ttttttttta
12541 tgttttgttg agacagtttc cctatgttgc ccaggctggt ctcaaattcc tgacctcgag
12601 caatcctccc gcatcggcct cccaaagtgc tgggattaca ggcatgagcc gccacaccca
12661 gcattggacc agtggctttc taaaccttgt aattttctgt aatagcttta ctgaaataca
12721 gttcccctgc catacaattt gcctgttcaa agtgtacaat cgatgacttt tgatacattc
12781 acagaattgt gcagtcacca ccacaagtaa ttttgggaca ttttcagcac cctcaaaaga
12841 gaccctatag cccttagcca tcacccccca cccagatctt tctgttgcct tagtccctgg
12901 caagcactaa cccactttct gtcttgaaat cttccagtgt ggtcttttgt gactgttcac
12961 cgagcagaat gttttcaagg tttatgtatg ttgtagtata tatccgtggg ttttttttggt
13021 tgtggtttgt ttttgtttg tttggaaac agggtctcgc tctgtcaccc aggctggagt
13081 gcagtggttc aattacagct cactgcagcc tcaacctccc aggctcaagt gatcctccca
13141 cctcagcctc ccaagcagct gggactgtag gcatgagcca ccatgcccag ctaatttttt

Fig.61E

```
13201 ttggtatttt ttgtaaagac agggtttcac catgtttccc aggctggtct cgaactcctg
13261 agctcaggca atccacccac ctcagcctcc caaagtgctg tgattacagg catgagccac
13321 tggacctggc ctgttttttg tttttgtttt gaacacacga ttttgctttg tcacccaggc
13381 tggaatgtaa tggtctgatc atagtgcatt gcagcctcaa actcctgggc tcaagcgatc
13441 ctcctacctc agcctcctga gtatctggga ccacacgtgc tcaccaccat gcttggctaa
13501 ttattattat tttttgatag agacggggtc ttgctatgtt tcccaggctg gtcttgaaca
13561 cctggcctca cacaatcctc ccacctcagt atctcagagt gctgggatta caggcatgag
13621 ccactgctcc tggccaatat ttcatttctt tttatggaga cgtaataatc agttgtatgg
13681 aaatagctga ttttgttttt tattgtatct tttggtgaac atttcaattg tatcgacttt
13741 ttggataaaa acctgaaaat gtttcacctt tagaacgttt cattgaatgg agattttttt
13801 gtggactctg gtatttatac tagaaccaaa tcaaaaccac tctggcggct gggcatgcct
13861 aggctggttt gagactagcc tgtccaacct ggtgaaagcc catctctact aaaaatacac
13921 aaattagccg agcatggtgg tacacacctg taatcccagc tactcaggag gctgaggcag
13981 gagaatcgca gaacccggga ggcggagatt gcagtgagct gagattgcgc cactgcactc
14041 cagcctgggc gacagagtga gactgcgtct caaaaaaaca acaaaaaat tactctggca
14101 gtaagaaaag atttcgaaac ttcctccctt gccctgaggt acttcagagg agcctgctgg
14161 cccctggggg agagtttgaa acccactgtt tgttccctga ccttgcctgc ttgtgtcctc
14221 tccctccacc tgtcccctgt actgggacc tgttctcagg agatcacagt tcattgctca
14281 aagccggggc tggggcctcc tacaggacca tcagtttctc ctgatcagca gcctttcctt
14341 ccgcagagag cgagggctgg cgggagcagc tggccctgat tgcgggcacg gcagtcgtgg
14401 gtgtggtcct ggtcctggtg tcattgtgg tcgcagttct ctgcctcagg taagggctct
14461 gacacccaga ggccctgga agccctcagt tgatggccac ctgcctgggt gctacaggac
14521 aagccttcct ggctgtcccc agcctctttt tacttgaaat cttctccaat ccctgctcct
14581 tcctttggtg tgtgtgcctc ataaagatgt gtgactcagt ttacctttg ttcctttccc
14641 atcggctaca ggaagcagag caatgggaga gaagcagaat attcggacaa acacggacag
14701 tatctcatcg gacatggtgg gttgccctaa tttgatggga atagggctt ggggccgggt
14761 gtggtggctc ctatctataa tcccagcact tgggaggca gaggtgggca gatcacttga
14821 ggtcaggagt tcgagaccag cctggccaac atgttgaaac tccatctcta taaaaaatac
14881 atcagtcagc caggcatggt ggtgggcacc tgtaatccca gctactcagg aggctgaggc
14941 agaagaatca ttttaacccg ggaggcggag attgcagtga gccaagatcg cgccactgcg
15001 ctccaggcct gggtgacaga gcgagactcc atctcaggaa aaaaaaaaa aaaaaaaaa
15061 accacggaga caggggtttg gggctaaaag ctatgagccg agcctccgag tccagtggga
15121 gttaattccc agctgacggg gccctgcctg atttctcagg tactaaggtc tacatcgacc
15181 ccttcactta tgaagaccct aatgaggctg tgagggaatt tgcaaaagag atcgatgtct
15241 cctacgtcaa gattgaagag gtgattggtg caggtgagag ccgaaggctg cccgggcacc
15301 tgggaacgaa gcggggtgg gcagggccac actggagcgg gagagctgat gacctctgcg
15361 tccttgtttg aaggtgagtt tggcgaggtg tgccggggc ggctcaaggc cccagggaag
15421 aaggagagct gtgtggcaat caagaccctg aagggtggct acacggagcg gcagcggcgt
15481 gagtttctga gcgaggcctc catcatgggc cagttcgagc accccaatat catccgcctg
15541 gagggcgtgg tcaccaacag catgcccgtc atgattctca cagagttcat ggagaacggc
15601 gccctggact ccttcctgcg ggtgagcacc tccctggct ctgcggcca cccggagttc
15661 ccacttacac ccagaggcca cttgggttaa gaagccagga cagacagtgg gtcccaggtc
15721 acctcctcca gccttttcct cttgggctaa gccctggtcc tctgcctttt ctttttttta
15781 agacagagcc tcgctctgtc gcccaggctg gagtgcagtg gcgcgatctc ggctcattgc
```

Fig. 61F

```
15841 tgtctccacc tccagggttc aagcgattct cctgcctcag tctcccaagt agctggtact
15901 ataggcatgc accaccatgc tgactaattt ttgtatttttt agtagacaca gggtttcacc
15961 atgtaggcca ggctggtatc aaactcctga cctcaagtga tctccccacc tcagcctccc
16021 aaagtgctgg tattacaggt gtgaggcacc acgcctggcc agccctctgc ctttaattt
16081 ccctctggga aaggctgggc tcctgggacc ttcctttccc actgcccat acagctgaag
16141 gttgtcattc cttcttttt tttttaattt tgttttaatt gaatttttt ttttgagat
16201 ggagtttcac tcttgttgcc caggccggag tgcaatggca agatcttggc tcaccgcaac
16261 ctccgcctcc caggttcaag cgattctcct gccttagcct ccccagtagc tgggattata
16321 ggcatgtgcc accacgcttg actaattttg tatttttagt agagacgggg gtttctctgt
16381 gttggtcagg ctggtctcga actcccgacc tcaggtgatc cgcctgcctc ggcctcccaa
16441 agtgctggga ttacagacgt gagccaccgc gcccggccaa tttttttt ttttttttaa
16501 gacagagtct cactctgtcc tctaggctgg agtgcagtgg tgcattcata gctcactgta
16561 gccttgacct cctgggctca agtgatcctc ccgcctcagc ctcctgagta gctggaacta
16621 cactcatgta ccaccatgct cagcaaattt ttaaaatttt ttgtagagac aggatctcga
16681 taggttgccc aggctggtct gaactcctgg cctcaagcga gcctccctcc tcagcctccc
16741 acagcactgg gattgcaggc atgagccact gtgcctggcc tgtcattcct tcttttgaca
16801 aatatttact gagtgctttc tacgcaccgg tcatcctccc agtccccagg aataaagcta
16861 tacacacggc aaactggatt tctcctcttg gggagcagag ggtctaatgg ggcaggggga
16921 ctgaaaatta gcaagtaaat agacaggctt tttaaaaag taaacaaatc atttcaaatg
16981 tgaaaaaaag caaacggggt ccttcatgca gatgtggcta gagaggaaag agaactgctt
17041 aatttatttg gtcactttac cagatttttac tgacttttt ttttttttta actttattaa
17101 gcttttcttt tttcttgaga tggagtttcc atctgtcacc caggctggag tgcagtggtg
17161 cgttcttggc tcaccgcaac gtccacctcc tgggttcaag tgattctcct gcctcagcct
17221 cctgagtagc ttggaattgc atggcatgca ccaccatacc cagctgatgt ttgtatttt
17281 agtagagaca gggtttcatc atgttgccca ggctggtctt gaactcctgg gctcaagtga
17341 tccacccatc tcggccctc aaagtgctgg gattacaggc atgagccacc atgcctggcc
17401 taggcatctt tttaaaaaa tcaaaacatt tttctatgta gcaaaataac attgcattga
17461 acagagttat agcgattccc tagcgtcatt gaatacccag ttgattttca cgtttctcta
17521 gttgttctaa agatgtcctt cactgctgct ttattccaac caggatccag ttcaagaccg
17581 ggctttgtac ctggttatta tatatatttt atttatttat tttagaaaca aggtcttgcc
17641 ctttcgccca gtttagagtg cagtggtgca atcatagctc actgcagcct ccaaactcct
17701 tggctcaggt gatcctcctg cctcagcctc ctgggtagct ggaactacag gtgcacacca
17761 ccacacctgg ctaatttta aatttttac ggagatgggg gtctcgctat gttgcccagg
17821 ctggtctcaa actcctggac tcaagcgatc ctccctcctt aacctctcaa agtgctggga
17881 ttacaggcgt gagccaccac gctgctgat tattatattt tcgagcctct ctaaatcttg
17941 agcagttcct catgatgaca ctgacacact gaagggttag gtcccttgtc cgcctgaatg
18001 tcttgatttc tggatttatg aaattcttct tatgggatca tttagcttgt ctctctgtat
18061 ttcctgtaag agaagctcta tctgatgtgg ggttttttg gttttgtttg tttgtttttt
18121 gagatggagt cctgctgtcg cccaggctgg agtgcagtgg cacaatctcg gctcactgca
18181 acctccgcct cctgggttca agagattctt ctgcctcagc ctcctgagta gctgggacta
18241 caggcgagtg ccaccatgcc cagctaattt ttgtatttt agtagagaca gggtttcacc
18301 atattggcca ggatggtctc gaacttctga cctcgtgatc tgcccaccac ctcagcctcc
18361 cacagtgctg ggattacagg catgagccac tatgcccggc taattttgt atttttagta
```

Fig. 61G

```
18421 gagacagggc ttcgccatgt tggccaggct gatctgaaac ccctggcctc aagccatcca
18481 ccctccttgg cctcccaaag tgctgggatt aaacgcgtga gccaccgtgc ctggtcgaag
18541 agacagaaag ggtcttaaag gttcagtgac acacacctgt aatcccagca ctttgggaag
18601 ctgaggctgg tggatcactc gaggccagga gttagagatc accctgggca acatggtgaa
18661 accccgtctc tacacaaaat acaaaaatgg gcagagcatg atggtgcata tctgtagtcc
18721 cagctactcg ggaggctgag gcgggaggat cacttaagcc tgggagatcg aggctgtagt
18781 gagccatcat tgcactactg cattccagcc tgggcgatcc catctcttaa aagagagag
18841 agatgggaag accagcacag gtgaaactgg tgaacagagg agagatggta gatgctgcat
18901 tgggcagtgt gacgggaacc cgctggaggg ctttggcagg agagtagttt aagaggatcc
18961 cagctgggca cagtggctca cacttgtgat cccagcactt ggggaggccg ggcaggtgg
19021 atcacttgag gtcaggagtt cgagaccagc ctggccaaca tggtgaaacc ctgtctgtac
19081 taaaaataca aaaccagcc aggcatggtg gtgcacccct gtaatcccag ctactcagga
19141 gactaagaca ggagaatcgc ttgaactcag gaggcagagg ttgcagtgag ccaagatcac
19201 gccactttac tccagcctgg gcagtagagc gagactccat ctcaaaaaaa taaataaata
19261 aaaagacctc tttgctgggt gctagggagc aagagcagga gctgggagag gcctgcagca
19321 gaagcctgtt gccagcatcc aggccgtggg gtgaagggaa gggtttggat ttgggacatg
19381 tcttggaagc atcaccagca gaacttgctg atggattgga agtggctggt gagggagaaa
19441 agggggtcaa aggaaactct gaggtctata ccctgaccat ctggcaagtg gtggtgttgc
19501 cacaaactga gcggggagta gggcaggtgc aggtctggag gatggattca aaattcagtt
19561 tttggagtct atgtccctgg ttctgtaggg ctgcagatgg tctgccaaat cttagcggaa
19621 cccagaatac gggatttgtt tactgtctgt gacttgttgg tttccctggt gagagcaaac
19681 tctttaaagg tcaaggttgg gcttcagacc ttggtttttg caccgatcat tggtcatact
19741 gcagttcctc actcttctct tgcaaatcca tacacagcta gtccaagaga gctgaacagc
19801 tttgtggttg gatcagcacc aatgtatctc cacctgtaga cgggttgctc aggtgactca
19861 tgcctgtaat cccagcacct gggaggcca aggtgggaag attgcttgag gccaggagtt
19921 ggagacaagc ctgggaaaca cagtgagacc ccatatctac caaaaaaacc cctttgtttt
19981 aattagccag gtgcagtggt gtgcacctat agtcccagct actaaggagg ctgaggcaga
20041 aggatcattt gagcccagga gtttaaggct gcggtgaacc atgatcgtgc cactgcactc
20101 caacctgggg gaaagaaaga gaccttgtct ctaaaaaaac taaaaaacag aaaagcattt
20161 gttgagtatt tcctgggtat aaagcagtgt accaggttaa atgaaggaa agttgaaat
20221 aatttttcaa ctcataatcc gattgggaga gactgaatgc ttaccattga agcaggaacc
20281 attgtaagca atgtgttgtg atactgtagc aagagctgag aaaacttggg aaaagagaaa
20341 ggaggaaggc tcacctgagg gagttgggg gcttgcccta caggtgagtt gtgaggtggg
20401 tctggaagtg acagatgcag tttaggaagt ggacgggagg ctgggtacgg tgactcaaca
20461 tctgtaatcc cagtgctttg ggagacccag gcggaaggat cgcttcaggc caggagttaa
20521 agaccagcct gggcaacata gtgggaacct atctctacta aaaattaaaa aattatccag
20581 gcataatggc acatgcctat tgttccagct actcaggagg cttgcctgag cccaggaggt
20641 tgaggctgca gtgagctatg atggcaccac tgcactccag cctgggcgac agaacaagac
20701 cctgtctcta aaaaaaaag atgtggatgg gaggggaac ggtgggtggg ctgtcctcac
20761 caagccccca ccctatctgc tctccagcta acgacggac agttcacagt catccagctc
20821 gtggcatgc tgcgggcat cgcctcgggc atgcggtacc ttgccgagat gagctacgtc
20881 caccgagacc tggctgctcg caacatccta gtcaacagca acctcgtctg caaagtgtct
20941 gactttggcc tttcccgatt cctggaggag aactcttccg atcccaccta cacgagctcc
21001 ctggtaatgc tgggggtaat actgggtgtg agcttcttag ggccaggtgg gcagggcagg
```

Fig. 61H

```
21061 ttggaaaggt gggaggctga gggtttggca gccctgctcc agggagagga tacaggagca
21121 ggctgtgggt gggggggacag tcagctccag gaagccgact tccagatgtc taggaaaata
21181 acagttggat aacctgggca acatagcaag accccatctc tacaaaaaaa ttaaaagatt
21241 agccaggcgc agtggcatgc acctgtagtc ccagctactt gggaggttga ggcaggagga
21301 ttgcttaagc ccaggagttg gaggctgcag tgagctatga atgtgccact gtactgcaga
21361 ctgggcgaca gagcaagacc ctgtctcaaa agaacagtgg ccaggtgtgg tggctcacgc
21421 ctgtaaatcc agcactttgg gaggctgagg caggaggatc gcctgaggtc aggagttcga
21481 gaccagcctg gccaacatgg gaaaaccctg tcgctactaa aaatacaaaa ttagctgagg
21541 gtggtggtac acgcctgtaa tccagctac tcaggaggct gaggtaggag aaccagttga
21601 acccgggagg cggagtttca gtgagccaag atcgcaccac tgcactccaa cctgggcaaa
21661 cagagttgga gagtaggagg cttggggcct gagctagggg gaaaaagcag aggcaggtgg
21721 gggactgggg ggcagtgtgc tgggtctggt gagtccctca gtgagtcccc cagctcacct
21781 tttctccttt ttctgcaggg aggaaagatt cccatccgat ggactgcccc ggaggccatt
21841 gccttccgga agttcacttc cgccagtgat gcctggagtt acgggattgt gatgtgggag
21901 gtgatgtcat ttggggagag gccgtactgg gacatgagca atcaggacgt aagtgtcccg
21961 tggtcctacc aagctttcct cgagtgttct ctcacctggg atttggggtg aagggtgggt
22021 tcccagagag tcatcactgc tgggttcttg agaccatgga gatgacaaaa aggagaattg
22081 atctttgtat caaagagttg agatacaggg ccaggcctag tggctcaagc ctgtaatccc
22141 agcactttgg gaggccaagg tgggcagatc acctaaggtt aggagttcaa gaccagcctg
22201 gccaacatgg tgaaaccccg tctctaaaaa aatacaaaaa attagcccag catgatgggc
22261 gggtgcctgt aatcccagct actcaggagg ctgagacagg ataatcgctt gaacccagga
22321 acagaggttg cagtgagctg agatcacgcc attgctttcc agcctgggca actgagcgag
22381 actctgtctt aataaataaa taaaagagtt gggtacagca tatttgggtc gcagaaggat
22441 gcagagatgg agggcagggt tgagaggtaa catgtctgta tcatagccca agagctgctg
22501 gggccttcag ccacagagag cttcaactcc ggctaggagg attcctggat ctgttatttt
22561 ttggggggct gtggctccta tcctaccatc ttccaagtca ccatttcctg ggcctgttag
22621 catctttgct tttcctggac agcctcaccc agagcttctt ccctctttc caggtgatca
22681 atgccattga acaggactac cggctgcccc cgcccccaga ctgtcccacc tccctccacc
22741 agctcatgct ggactgttgg cagaaagacc ggaatgcccg gcccgcttc ccccaggtgg
22801 tcagcgccct ggacaagatg atccggaacc ccgccagcct caaaatcgtg gcccgggaga
22861 atggcgggtg aggactgcag agaatgggcc ctccttcccg ctctctgccc ccactccttg
22921 cccagaagtg tccgttcatt ggtgttgggt gggagggcct ctgtccgcct ctgcaaggct
22981 gggttccacc tcctcccccg gacctgggcc tggtactcag cattcctccc catccttgcc
23041 ccctagggcc tcacaccctc tcctggacca gcggcagcct cactactcag cttttggctc
23101 tgtgggcgag tggcttcggg ccatcaaaat gggaagatac gaagaaagtt tcgcagccgc
23161 tggctttggc tccttcgagc tggtcagcca gatctctgct gagtaagcag tggcaggagc
23221 tggagtgggg ctgggagagc ggggcagctg gagtcaggcc cacgggtct ccaggggctt
23281 tgggggtcag cttcgggtgc caatgctgtc ttcttgcact gcgctcatgc catgcctaga
23341 agggccccag aggagcagtc acagccccat ggagctgagg acccaaggac tctttggggc
23401 cagcctgccc gcctcacctc ctcctgccat cacagccctg ggccatcgcg cttccgcctc
23461 tcacttctag ctatctttgt gcatctatct gcattccagg cccggctctc acggtaacaa
23521 tgtgtcaact cgggttctct ttttccaacc ataaaggag aagattgggc taggttttgg
23581 agatcctctt cagcttttat gtgaaatggt tttatgattc cttgcctccc aaaggctgcg
23641 tatccccact tggcctttgt ctgctactcc ccctttctgc cttcccgttc ctctcccaag
23701 atctcctctc accccaggtt gaataacaga aatagaagga atagaaatct gaaggccggg
23761 catggtggct catgcctgta atgccagcac tttgggaggc cgaggtgggc agatcacttg
```

Fig. 61I

```
23821 aggttaggag ttcgagacca ttgtggacaa cttggtgaaa ccttatgtct actaaaaata
23881 caaaaattag ctgggcatgg tggtgcgtgc ctgtaatacc agctactgag gaggctgagg
23941 caggagaatc gcttgaaccc gggaggtgga ggttgcagtg agccgagatc gcaccactgc
24001 actccagcct ggatgacaga gtgaaattcc atctcaaaaa aaaaaaaaaa aaaaaaaag
24061 aaatgtgaag gccaggtggt ggctcacgcc tgtaatctca gcactttggg aggctcaggt
24121 ggaccgattg cttgagccca ggagtttgag agcagcctgg ccaaaatagc aaaacccat
24181 ctctacaaaa caaaaacaaa aaattagct gggcatggtg gtgcgtgcct gtggtcccag
24241 ctactcagga ggctagagcc agagggtctc aggccagtct gccctgccc cacggggcct
24301 gggcacatcc ctccctaatt cttcccagcc tctctgac caggggggcc tcctctccct
24361 ttttcccct tatctcagcc tccagccatc agcaacctcc tcttcctctc cacccagctc
24421 ttcctctccc acttcggcct tttctttctc acactccatt ccctctacg gcaatctgtg
24481 cagcctcttc ccccagtctc attttgcggg cttttctctc ttttcttcc ttccctggca
24541 cccaagccaa aggccctgcc tctggcctcc agccctaccc ccttctgcgg ttgcacagaa
24601 ggatggctgc ccagctctta aaaaaactgc ccgggaactg ttgacatctg ttctccctcc
24661 cccgctggct tttctgattg gcttacaatc ctgaggctag gaccgtctca ggagccaaga
24721 gaggagagcg gccacaggga acctagggtc tcaccaagct ctcctttcct tctgcaggga
24781 cctgctccga atcggagtca ctctggcggg acaccagaag aaaatcttgg ccagtgtcca
24841 gcacatgaag tcccaggcca agccgggaac cccgggtggg acaggaggac cggccccgca
24901 gtactgacct gcaggaactc cccacccccag ggacaccgcc tccccatttt ccggggcaga
24961 gtggggactc acagaggccc ccagccctgt gccccgctgg attgcacttt gagcccgtgg
25021 ggtgaggagt tggcaatttg gagagacagg atttgggggt tctgccataa taggaggga
25081 aaatcacccc ccagccacct cggggaactc cagaccaagg gtgagggcgc ctttccctca
25141 ggactgggtg tgaccagagg aaaaggaagt gcccaacatc tcccagcctc cccaggtgcc
25201 cccctcacct tgatgggtgc gttcccgcag accaaagaga gtgtgactcc cttgccagct
25261 ccagagtggg ggggctgtcc caggggggcaa gaaggggtgt cagggcccag tgacaaaatc
25321 attggggttt gtagtcccaa cttgctgctg tcaccaccaa actcaatcat tttttttcct
25381 tgtaaatgcc cctccccccag ctgctgcctt catattgaag gttttttgagt tttgttttttg
25441 gtcttaattt ttctccccgt tcccttttttg tttcttcgtt ttgtttttttct accgtccttg
25501 tcataacttt gtgttggagg gaacctgttt cactatggcc tcctttgccc aagttgaaac
25561 aggggcccat catcatgtct gtttccagaa cagtgccttg gtcatcccac atccccggac
25621 cccgcctggg accccccaagc tgtgtcctat gaaggggtgt gggggtgaggt agtgaaaagg
25681 gcggtagttg gtggtggaac ccagaaacgg acgccggtgc ttggaggggt tcttaaatta
25741 tatttaaaaa agtaactttt tgtataaata aaagaaaatg gacgtgtcc cagctccagg
25801 ggtgatgggg gtgatggact agatttctaa ggagagtggg gctgggtagg gagggctttg
25861 tggctgaccg agaggtgtca gaggtctgga ggctgcaggg ctgtagggc tggaacttgg
25921 ttatcagccc cagggtatgt ttgaggtggt ggggtggggg ccgagcgaga tgaatcattc
25981 gcagctgctt ctaacgtctc
```

Fig. 61J

EphB4, mRNA

```
   1 ctcggcccgg cggcgcgagc agagccactc cagggagggg gggagaccgc gagcggccgg
  61 ctcagccccc gccacccggg gcgggacccc gaggccccgg agggaccccca actccagcca
 121 cgtcttgctg cgcgcccgcc cggcgcggcc actgccagca cgctccgggc ccgccgcccg
 181 cgcgcgcggc acagacgcgg ggccacactt ggcgccgccg cccggtgccc cgcacgctcg
 241 catgggcccg cgctgagggc cccgacgagg agtcccgcgc ggagtatcgg cgtccacccg
 301 cccagggaga gtcagacctg ggggggcgag ggccccccaa actcagttcg gatcctaccc
 361 gagtgaggcg cgccatggag ctccgggtg ctgctctgct gggcttcgtt ggccgcagct
 421 ttggaagaga ccctgctgaa cacaaaattg aaactgctg atctgaagtg ggtgacattc
 481 cctcaggtgg acgggcagtg ggaggaactg agcggcctgg atgaggaaca gcacagcgtg
 541 cgcacctacg aagtgtgtga cgtgcagcgt gccccgggcc aggcccactg gcttcgcaca
 601 ggttgggtcc cacggcgggg cgccgtccac gtgtacgcca cgctgcgctt caccatgctc
 661 gagtgcctgt ccctgcctcg ggctgggcgc tcctgcaagg agaccttcac cgtcttctac
 721 tatgagagcg atgcggacac ggccacggcc ctcacgccag cctggatgga aaccccctac
 781 atcaaggtgg acacggtggc cgcggagcat ctcacccgga agcgcctgg ggccgaggcc
 841 accgggaagg tgaatgtcaa gacgctgcgt ctgggaccgc tcagcaaggc tggcttctac
 901 ctggccttcc aggaccaggg tgcctgcatg gccctgctat ccctgcacct cttctacaaa
 961 aagtgcgccc agctgactgt gaacctgact cgattcccgg agactgtgcc tcgggagctg
1021 gttgtgcccg tggccggtag ctgcgtggtg gatgccgtcc ccgcccctgg ccccagcccc
1081 agcctctact gccgtgagga tggccagtgg gccgaacagc cggtcacggg ctgcagctgt
1141 gctccggggt cgaggcagc tgagggggaac accaagtgcc gagcctgtgc cagggcacc
1201 ttcaagcccc tgtcaggaga agggtcctgc cagccatgcc cagccaatag ccactctaac
1261 accattggat cagccgtctg ccagtgccgc gtcgggtact cccgggcacg cacagacccc
1321 cggggtgcac cctgcaccac cctccttcg gctccgcgga gcgtggttttc ccgcctgaac
1381 ggctcctccc tgcacctgga atggagtgcc ccctggagt ctggtggccg agaggacctc
1441 acctacgccc tccgctgccg ggagtgccga cccggaggct cctgtgcgcc ctgcgggga
1501 gacctgactt tgacccccgg ccccgggac ctggtggagc cctgggtggt ggttcgaggg
1561 ctacgtcctg acttcaccta tacctttgag gtcactgcat gaacggggt atcctcctta
1621 gccacggggc ccgtcccatt tgagcctgtc aatgtcacca ctgaccgaga ggtacctcct
1681 gcagtgtctg acatccgggt gacgcggtcc tcacccagca gcttgagcct ggcctgggct
1741 gttccccggg cacccagtgg ggctgtgctg gactacgagg tcaaatacca tgagaagggc
1801 gccgagggtc ccagcagcgt gcggttcctg aagacgtcag aaaaccgggc agagctgcgg
1861 gggctgaagc ggggagccag ctacctggtc caggtacggg cgcgtctga ggccggctac
1921 gggcccttcg ccaggaaca tcacagccag acccaactgg atgagagcga gggctggcgg
1981 gagcagctgg ccctgattgc gggcacggca gtcgtgggtg tggtcctggt cctggtggtc
2041 attgtggtcg cagttctctg cctcaggaag cagagcaatg ggagagaagc agaatattcg
2101 gacaaacacg gacagtatct catcggacat ggtactaagg tctacatcga ccccttcact
2161 tatgaagacc ctaatgaggc tgtgagggaa tttgcaaaag agatcgatgt ctcctacgtc
2221 aagattgaag aggtgattgg tgcaggtgag tttggcgagg tgtgccgggg cggctcaag
2281 gccccaggga agaaggagag ctgtgtggca atcaagaccc tgaaggtgg ctacacggag
2341 cggcagcggc gtgagtttct gagcgaggcc tccatcatgg ccagttcga gcaccccaat
2401 atcatccgcc tggagggcgt ggtcaccaac agcatgcccg tcatgattct cacagagttc
2461 atggagaacg gcgccctgga ctccttcctg cggctaaacg acggacagtt cacagtcatc
2521 cagctcgtgg gcatgctgcg gggcatcgcc tcgggcatgc ggtaccttgc gagatgagc
2581 tacgtccacc gagacctggc tgctcgcaac atcctagtca acagcaacct cgtctgcaaa
```

Fig. 62A

```
2641 gtgtctgact ttggccttc ccgattcctg gaggagaact cttccgatcc cacctacacg
2701 agctccctgg gaggaaagat tcccatccga tggactgccc cggaggccat tgccttccgg
2761 aagttcactt ccgccagtga tgcctggagt tacgggattg tgatgtggga ggtgatgtca
2821 tttggggaga ggccgtactg ggacatgagc aatcaggacg tgatcaatgc cattgaacag
2881 gactaccggc tgcccccgcc cccagactgt cccacctccc tccaccagct catgctggac
2941 tgttggcaga aagaccggaa tgcccggccc cgcttccccc aggtggtcag cgccctggac
3001 aagatgatcc ggaaccccgc cagcctcaaa atcgtggccc gggagaatgg cggggcctca
3061 caccctctcc tggaccagcg gcagcctcac tactcagctt ttggctctgt gggcgagtgg
3121 cttcgggcca tcaaaatggg aagatacgaa gaaagtttcg cagccgctgg ctttggctcc
3181 ttcgagctgg tcagccagat ctctgctgag gacctgctcc gaatcggagt cactctggcg
3241 ggacaccaga agaaaatctt ggccagtgtc cagcacatga agtcccaggc caagccggga
3301 accccgggtg ggacaggagg accggccccg cagtactgac ctgcaggaac tccccacccc
3361 agggacaccg cctccccatt ttccggggca gagtggggac tcacagaggc ccccagccct
3421 gtgccccgct ggattgcact ttgagcccgt ggggtgagga gttggcaatt tggagagaca
3481 ggatttgggg gttctgccat aataggaggg gaaaatcacc cccagccac ctcggggaac
3541 tccagaccaa gggtgagggc gcctttccct caggactggg tgtgaccaga ggaaaaggaa
3601 gtgcccaaca tctcccagcc tccccaggtg ccccctcac cttgatgggt gcgttccgc
3661 agaccaaaga gagtgtgact cccttgccag ctccagagtg ggggggctgt cccaggggc
3721 aagaaggggt gtcagggccc agtgacaaaa tcattggggt ttgtagtccc aacttgctgc
3781 tgtcaccacc aaactcaatc attttttcc cttgtaaatg cccctccccc agctgctgcc
3841 ttcatattga aggtttttga gttttgtttt tggtcttaat ttctcccc gttcccttt
3901 tgtttcttcg ttttgttttt ctaccgtcct tgtcataact ttgtgttgga gggaacctgt
3961 ttcactatgg cctcctttgc ccaagttgaa acaggggccc atcatcatgt ctgtttccag
4021 aacagtgcct tggtcatccc acatccccgg accccgcctg ggaccccaa gctgtgtcct
4081 atgaagggt gtggggtgag gtagtgaaaa gggcggtagt tggtggtgga acccagaaac
4141 ggacgccggt gcttggaggg gttcttaaat tatatttaaa aaagtaactt tttgtataaa
4201 taaaagaaaa tgggacgtgt cccagctcca ggggt
```

Fig. 62B

EphrinB2 Gene

```
   1 gcgcctcgga gctgcctgcg ggcgcacgcc gtcttccccg ccagtctgcc ccggaggatt
  61 ggggggtccca gcctgcgtcc cgtcagtccc ttcttggccc ggagtgcgcg gagctgggag
 121 tggcttcgcc atggctgtga aagggactc cgtgtggaag tactgctggg gtgttttgat
 181 ggttttatgc agaactgcga tttccaaatc gatagttta gagcctatct attggaattc
 241 ctcgaactcc aagtaagtgg cgtccgcgat cccctatgt ccccgccccg gggtccgccg
 301 cgccgtccgg gcgggaggag gggtcagtcc gcggggcctc ggagcctgtt tctggaacct
 361 cggttccccg tcccccaccc ccaacccccg ccccatttca ctaggtggag actcctcgct
 421 cggctttcca acccgagccc cgctggaacg gacggtctct ccgcctttcc tcccccgaac
 481 gctcccaggc gctaaaagct actatcggct cgggtgtcaa gtccgggaag gtgtccgatg
 541 gcgatacctg accctctcct gttttcgagg acgaaggaca tggccacaat ctaggctggc
 601 cggcacgcgg ggactggtgg gctctggaga gaggcggaga tgctgcattc gcggggagcg
 661 cgggcggcgt ggtccggggc ccgcgggcgg cgaccggggg tggcaggacg ctggcagcga
 721 agcgcgttct ggagagggga gcctggagtc gctacgctgc ccgcagagcc ctggagccgg
 781 ggcgccttgg caccgcgccg ccagcccgag ggtgcgcggg gagctcgcct gcttcgcagg
 841 agaactcggg cgtcgagccc tttcctccgc gccggggaga cgggccttag gcttctccct
 901 gagggcccgc cgcacctcgg cctcccgctt cgttcataag ccggtagccc cggagtatgc
 961 ggtctcgatg gccgacctga ttgtaatgca cttcctataa aagcttaggg ccctgcccag
1021 tcgacactgc tcctgaagcc ttctccctcg ggaccctggt aggaatggga tccttaggat
1081 cagatttgct cttaccggac tctacagccg ggagcgagcc aggccttgtg gagagtaact
1141 ttcagtttgg gccaccagag tgcattcaga atttagaaaa tcccatccat ccctaaatct
1201 gtgtggtcat aactcgtagt catctgggta ttcagtactg tgtatcccct tatttcgaat
1261 cacagccaaa acatatttta cagaatcttg gaattgtagt ctcgggaaac ttggagaaga
1321 agtatgcaga cattagctgg tttctggaga aacgtttga gatcagaagc aaaatcaatg
1381 gcctaattga agttgagcaa gttgggcctg gttttaggag aaaagaaatg ggggattgat
1441 ttagaaatca cgtcttaaag gagtgtgtcc attctcttaa aagtgtcaaa tttcaaattc
1501 actaacatgt taaccaagaa tcccttcatg aaaagggcga aacgtcggt tacaaatcgg
1561 tttaaacaaa tgtttgtatg atgctagaag gcactttcaa caccgctcat acggagaagt
1621 tacttagctc tgcctccttc catgtagtct gctcttgcat ggattatatt tttaatgtaa
1681 attgttgtat ttgctgatga agtactggcg gcggcatctt tgcatcgatg ccggctcggg
1741 aggcgccagg tggtgccgga aggagccggg ctaggacctc gcgcagcagc gggtcccgga
1801 gtccgggaga ggcgggcggg cgggcgaggc ggtcgcgggg agcccgcggc gccgctgccc
1861 gcccggtgcc tccagaggtc actcttccat gcggaatcgc gcagcgccag gcctcgcccc
1921 tcccccaggc cgcctgctcc agccactctg cactttcact gaccggttct ctttgaggct
1981 gttttttttt ttcttatgag gatttaatat ttctgtttaa atctagttga aagcaattcc
2041 gttagcctct tcagcgttta gttcggtgtg tgtatcttta tctttgcgct atattaacta
2101 ttagtttgtg tgtatccggt aggagaatta gaaataccta gttgggagaa aaagaaaagt
2161 agaacaatag ttatttcaac ctaaggttta gacgttaata acttcttttt gtaatgtgtc
2221 gagatggggg gtcctggggg gaggtgacag gtactcacca ctccccccccc ccattctgat
2281 gatgaagatg agtctgtctt tccagctatg tccagacctg cgagggccct gcgtttctgg
2341 aagcctgccg tttgcgcggt tgaggttgct gctgctgtct tgtcctccac agcagcattt
2401 cttttaaaat tctcctgata acggcctgcc tggatgactg gataatgtgt gcctggaaaa
2461 ggtctccctt gcagctgaat gctagctcca gatcagaa agatttcttc ctgtaggagc
2521 cataggaaag agtcctctct aagttttga gaatgcatac aacccctga tgacagggg
2581 tcgctttcct tggggaagtt ttatatttat ttccagagga agtttgaat cggtaaatat
```

Fig. 63A

```
2641 gatgtggcag gaaggtaatc aaatgcattg aagtttcaca tcagttccta tgaactgtgg
2701 aacaattcat ttgtaatgaa gccgccatca gtaattagat ttgtttcatt cagaggtcag
2761 cttttttagc aggtggtcga cacagggagc atgcagcagc tgtttggata cagggtccag
2821 aaaacccttt gtaaattcag cgtctccgta actactttaa tcacattgtc ggctctccg
2881 tccctgactg tatgtaataa tggaagatg tcctgcgtgc tgaaacagta gctgccctgt
2941 taggttattc acattgcttt gatacgttct ggtagagttg ggtccgttgt agccattttg
3001 gttgtttaaa gttttggttt ttttttttgtt ttttttttaa ttcagcagag aacagtaatg
3061 cctagcttcc gttttaact taacacttca gtagaacatt ttcttccaag agggagattt
3121 tggcctaagt aaagtagtgg gctcttttt aaaaaaaat taattttact ttaatgtgag
3181 caaatctgta ttggtatggt gttctgcaat gcattacact gactttgaaa atttcgagta
3241 ctaatgcctt atgtctgggg ttaccattcc ctgtgcatca catactagtt agttaacata
3301 gcattttgct ttccccatgt aattttttcc ctatataata ctggattcct gatactaatt
3361 gacttgatac aaaagaatgg ctggatgata tccagataac gtataataca tgggcttcac
3421 cacaatcagg ctctgaataa atacagacct gtcagagatt gataaaataa actacaatgg
3481 atagtgctgt ttaaacagtc cattcaataa catatataag ccagcctgcc ttccattgtg
3541 tctgaaattc ttatttttgt aggtaaacaa atgcacattc agcactgatt gaatagcccc
3601 ttgaactatg ctccacagtt tgcgtttggg ttaatcttgt cggttttaat atagagagaa
3661 aaaagctcaa agcaccaggg gtggaattgt tagtgctttc acatccacat tcctcacatt
3721 ttgtcaggat gataaactgt aggtaatgga ctgtcgttgt tctgcaggac aactgagcca
3781 ggcagagcac aaagactaag ctaaagcgat acctcacaac atgcttggta gccttctttt
3841 cagatgagaa tttatttgag aatcatgtgt ctagggactg cacatcttaa cctcaacagt
3901 tacagcttca agccccagaa acaggagctg gaggttaaga tgatttgcta agcacctggt
3961 tctaaatctt ttacaaagca taagctgttg acgctggttc tgccgacgca aagacatgca
4021 gatgactcca acatttccag aggcttctga cttaagctaa agtgtgtgga caggtgaatt
4081 cgccatgggc ctggagacca gcttgctaaa aactatgtgt ttgaatggtt cctccagaca
4141 gagtcagctg aagaacaatt ggtggattta tattaaaacc tcttgtctgt aaacttactg
4201 aggtgcatcc ttcggttggt ggatcagtga gataattgcc ttcagatgga cattgcaact
4261 ggagcaacta aatccttgct gtctttcctt cctctgaaat cttccaggta gctcccgaga
4321 gcttcagtat gacaccaaac ttcgggcgac gttttagagt gcgttcacct aatgggaaac
4381 tattcgagat cccagcgtga ctgcagtaat gcgtcatagg aatgggagtg cagggggaaa
4441 aggaaataca gattgtagac cctaataaaa aaattttag gaaagatatt tctttaacgt
4501 tttatgagaa cttcattctt aaaatactta attgcaaatt agacaaatag aagtgctctt
4561 ctaaggaagg tgattaaact ggtcctccta tcagcctaat ctctgcctgc ctttgctgct
4621 gacataaaga acctgttttt caggtcactt aatatacatc tacatagatt tgcttatgag
4681 ctcaccccttt gtgtagcgga gtagagcctt aagaggagt gctcaactgt ttaaaatatt
4741 ttgattaaaa tatgcagaac ccatagaact ataagcttct agtcaggaat tagctctttc
4801 agggaacagc tccccccttc ttttaaggg gggaattaga aggaggctgg gggaggaata
4861 taagaacagc aaagaaggaa ggatagcaaa tgggacatgt tccgaacagc ttggaaaaac
4921 tcctgtggct tcattgtctc tataaagcca agaatacaa agacataagc aattcagccc
4981 ttctcccatg atggaagatg taaaccgttg acatgcctcc cctgtttaac ttgtttaatt
5041 ctcattttaa attcagcacg atactagccg tgtgaactct gaagatttct ttagtaatcc
5101 attttgtagt tccgaatcaa aaacaaagtg aaagggtctg acacaatttg cttttatttt
5161 taggcaaatc aaccctggtc atagttaata aggggattac aactcagact aggtctttac
5221 agatgtgatg taaatcaagg gcagagtata aagaaactga tcccttttga ttgaagtata
```

Fig. 63B

```
5281 gtaaaaaggc atagagaaac tagcagcagt aatctgattg tatggcaata aaaccaccat
5341 tttctgtctt tcagataaaa ataatgtggt aaatccatgc agttcataag atgtaaaggc
5401 agataaaggg tgaagccatg gcaacatata gattagcttg atgttagaaa tgacacgtct
5461 ctgaaaaggg cgcgggacga aggcccttgc ctccaggctg ttgggcatta tgtgagaacc
5521 acacagactt ggaaactggg attaggaagt atgaaagctc tacttgtggt ctgggatggc
5581 tgaggcagta aagaaaagct gctcagttct tgctcattgg tggtggataa tatggcaaag
5641 gtagatttca ttgactgcct ttttatga ttgagattgg ggctgattaa aacttcagat
5701 cactgcagtt gttagggcct gggagatttt cctttttaac tcctggccta acagcagcag
5761 ccgttctgta ggattaactg cacttcgcgg tcgttgcctt aatctatttg ggcttcaggc
5821 agggacatgc tgggaaggaa cagagaccag aggggatagg tagggctggg gttatctgaa
5881 aagaaaacag agacctttg atttcagcca tcttttcaga cccagctccc tctcccgctg
5941 catgggagaa gcaaaggtaa acaggacaca ttgtccctct ccctcagcca cagagctctt
6001 ctgtgagttt tgtctttccc accctggaaa aaagataaa atacaatttt taaaggggga
6061 gggaggaatt tagttttaat tcaaatgagt agtaatccaa tatgccaaaa gcagtgggct
6121 ctacctagat gtaattttac tcgtaaatgt gagtcttaaa ctttgagttg aatggggcag
6181 gctgttagag gtggtgtaaa ttacaggatt ataaaaatgt tagtgctgcc cagccttaaa
6241 gtcaaaaaca gaaaaatctc tgtgctgttg agtcttcccg ccctctctcc tgaacaacct
6301 tgtaagtaag ctagactttt gtttttgcct tccatacttt ccatttcagc cattaaacaa
6361 aataagccat tgaaaccacg attgggttcc atgcagagtg acatccgcaa tcgggtcaag
6421 ccagaaggaa atacttgctc gattgccccc tatttggcat tacaggaaag tctccacact
6481 ttggaagagt ctgaactctc aagacattga aaatgccaaa ggctgcaaac accctgtgtc
6541 tttcttgatg gagtgcatct tggtgtgttt tacaaagggg aattcagtgc tgtttttttg
6601 ttgttgttgt tgttttttttt tttaaagag cagcataggg cccttctaga ctcttggatt
6661 ctgtgtctga caaaaatggt cattaaatga gcaatattat aatttagacc catttcactg
6721 attttgttcc aaattctcaa ctgacttgag catctgtttg gggctgtaga tacattgccc
6781 ttgttgactg ttttttctcgt ttctatggga attactgtag ccattactat gtagctttca
6841 tagactcaaa acatttttaa agtattgcat ataggctggc catatccagt gcctgttact
6901 ttaccttctt tttctaactt aatgcagcag tctgtattaa cagatccatt tcatttgtct
6961 agcttcatca gagagaggct accccctgat ttacaggctg ctcacatcca agcaccttgc
7021 attctacact tgacagtgat tgctaatggc ccattcaact aaagtatttg cttgttaaca
7081 gggaacagaa catgataaat gtccagcaag cttgctgcct ccttcagctt ttcaaacgca
7141 gactggtgca tatttatggc aggcaaatga caaagaaaa agctgaattg ccctggcctc
7201 cagcttttcta tcagaaacag ggttaaagtg attaaagcaa tcattcaaga aagccctgcc
7261 gtttgtttac taaccttcat ccaacattta gctttgtagt ctacctgtga aagatattt
7321 cagaagtatt agagataagg aaggaggatc tagcaaacca gtgaaaagag taggtgacca
7381 gttataaaat gctttccatg cacattgaat gccaggcgaa cctatttctg ttattccagc
7441 agacaatcag cagtggctct agattattaa catatttcc tttcatgtat aaattcaaat
7501 atgtaattct agtccaaagc attctgtggc tggtaagcac atacttgctg atttcaaata
7561 agaaaacata gcaagggaaa gctccattaa acaagttgtt tctgcccta gtaattctct
7621 aaacaagata ggaagaaaaa gtggacagta gtggagtatt aatagtgtgc tcttttcatt
7681 ctctaaagca cgagtaagta agcgttcaaa ctactctgtg gtgggcatac atttagagcg
7741 ctgtgaatga accactgctg ttctgccata cttaatttat ttatattatt attttattt
7801 tattgttgtt tttatgtatt attataatta tttatttata ttactaattt attttctcaa
7861 tttaaatcct gttgcatcca atttttaatta cagttttgt atctgccttc ccatacttgc
```

Fig. 63C

```
7921  tacccacgtc cccattgcca ctgcggcctt atccatgttt tctgtgtaca ccactctcgt
7981  atcaccccag aataattatg agtgctaccc agactttga aaccactaga gtcaacatgt
8041  ttgtctttga ggaaagccaa tgatgcttta gcattttgg caggggtgga tgtgtgttta
8101  agtggggtgg gtgcagctcc ttattgtctg cctattctac tgttgttccc aatccacatt
8161  ccctgcgggg cacctaacct gtgtgcatag caaagaattt ccgaccttca gagccagaag
8221  tgtttctcaa ttgatctctt ccagcctagg gttatagctg atgaattata atccttgctc
8281  tttccacacc tttacctggg cttaccatgg ccctaaaaca tttgcccaga atcagaattg
8341  tctcatgagt gagtggggca aggcaaatcc tgttccagac cagctgagaa tgtacctagc
8401  tgcagaagaa gttagaaagt gtcatctttt acttatctac cagaactata ttcgaggtac
8461  attttagatt taaaaaaaaa gcaagttctc gtaggccttg atccccccc ttgctatggg
8521  aaaatggatc attattataa tggactgtcc agtaaagttc atgatttctc ctagacatgt
8581  tctctctctt tatgacctag atcaagagtg atctctttaa gtcttttctt cataatccca
8641  cagcactttg tacttagatg tacttagaaa gaaccatata cacggtacgt catgattgat
8701  atgcaagcct tcaccactct acctgtccta aaagtcaggg acacaccttc ttcatttcat
8761  cagtccctac ttctatccag cattggcatc cagtaagtat tagtggaatg gacagacaac
8821  ccgaatttgt gctgatggca gtttaccctg ttttaactgt catccttctg ctactagaca
8881  tggatgagac ctgagacgat gggactgctc agaggtccct ggctcttgaa ctttagggca
8941  ccagaatccc ctgcagggct tgagaaaaca ggggtttctg ggccccaccc ccagagttcc
9001  tgattcctga ggtctggggt ggggcttgaa gatggacatg tttaacaagc tcccaggtga
9061  cgctggcaac tgctgcctca gggccatgct gagaaccctc gccctacaca aacctttctg
9121  ggaaaacaac tcaacattaa agctgtttgg ggatctctga agaaatctgt agtccttgcc
9181  ttgttggggg agcatcaggg atctaaccat tgatggtgga gtatttgttg ttaattcagc
9241  aagcaactat taagtgttag gcctgttact cggctctaac aatacaaggc agagtgacct
9301  gtaccctcga gatttaaagt ctaagtcctg tagagagaag cccaggtggg agcaagcaca
9361  tttagagtta ggtgcttggt gcaaggtggg gacacagaag aagggaatgg catttgcctc
9421  tggagggtgtc cggaaacagc ctagggagga ggagcttgag tcttgaaata ctgtgggcat
9481  ctctaagcaa agtcacagta gacagctgaa ataaagaaaa tagtaagcaa gccaaagaaa
9541  cagtatttca gccaagggca gcgtgtgtct atcacgtcca cctgtgaaca cgtcccagga
9601  ttctctgcat ccggccattg ctcaagacag atccctcaca ggaacagcta agccactgat
9661  ttcagctacc tgttcacgtg agaattatca gtacctactg ctttcaaaa tgagtatgat
9721  catggatagg tgaggcaatt cagtttcgca gagacagtag ggcaagtgcc actgtagttt
9781  agttaagggc acatgcttta gagtttggct atgtgagtcc aatcccagtt tagccattta
9841  ttagctgggt agctttagga gcagtagcct tagtgtctct cagttgtccc atctctataa
9901  tagggacaat aacataatag tgctgaataa aagagtaaca aaattttggt caacatttaa
9961  tgtatttaaa gagctaagct ccgtgattgg cacaatgaac caatcaatca aacaccagtt
10021 gttattaata aaagtcagtt gaatatgtac tgtgtgcctg gcgtggttc aatttgcctt
10081 tgcatacaag gaaaaaatta aaatactctg ttaataaaga ctatagcata atactttcac
10141 cttaaacttc ttgatgttaa tttattttgt ttacctgcca aacttctact cattccttat
10201 gactttctgc tacatgaaac ccctttgta attcttttgt cctattaaat taagttctct
10261 ctcctctgct ttcctgcttt tggtgctttc taataacact tttaaccctg gactttctca
10321 ttcagctgtg caactgtgga ctgagaggag gctctttgaa ttcattttgt atattctagt
10381 agagagtact gtgagcagtt gggttgttga atgaatacat taattcaacc tggagggatg
10441 ggcagtattg cattttttac attgatatta catgatattt agaaaactgc ttaactggtg
10501 gacgttgttt tattaacagc attttgtgta tagcactcac tatgtgccag ctgctattct
```

Fig. 63D

```
10561 aactgcctga caaatactcc tgaaaccttc atggtaacca tatgagggaa gcacttttaa
10621 tatatccata ataccaacgg ggagactgtg gccaaattgg ttaattaact tagccaaagt
10681 catattgaac taataagtgg atttaaaccc agctagtctg gggccagggt ccctctttta
10741 atcttctgcc tcctgcttat gctgttgcat ggagtagtct ttatcatata actaaattaa
10801 gcatgcattt gcttaaagca gtgcatacat gatggatcaa aaagtttgtg gtataattgg
10861 tttaattctg tcattatcca ttttgattta tagtcacttt cttatgatgg tcgtgtagtt
10921 ttaaatggaa cctttgaatc tttgatataa taaggttatg tcaaatcttg ggtataataa
10981 ggttataccc aatggaaaca gaataatgat cagcccattt aaaggatgac tggagagtta
11041 ttacaataca taatagtcat gcatatattg agtagtattc ctttggtaac attttccttt
11101 taaaaattgt aacatttgat tgttccttgt tgggagaaaa ggaggtcaga ttttgaggg
11161 gagatccatt tggtgagatg ctgagtgtgt gtcaagctaa ggagatagta tgacatcttt
11221 tttagagtct agtcacaatt aaatgccatt ttattttgga ttttgggatc cgtgccagct
11281 tccagcttgt cagagctgag aagactcaaa tcaagtccag gcttatttct acagcaaact
11341 gggattctgg cttcttgccg gtggattcat tcagtacagc ccatctggct tttgatgttc
11401 tgcaagtttg gagccatttg ttgaaggaag ccaggcggtg aatattggtg gtcctggggt
11461 tctcttgact ccaagtggtg ccccttggtt tgcattttca ccatgcttag catctgctta
11521 cctggagacc atgcagccgc cggccagagg tctccaacaa ccaaatcttc atgcctttta
11581 gaactcagag tccccagcac atcctccttc ctcctccttg tccaattact ttcatgcagt
11641 tctcagtagc tgcttgtttg aatcacttat agtatttaac ttctagggtg ttttgggtt
11701 ttggtcaagg taattccagg ctgaatgtgg tgactaagca ggaaataaat gggtcgtcct
11761 caaagttaca gtggagcgct gtttctattt tcctaaggta cacagttgtg ggggcgatcc
11821 gtatggaagt caggaaccca gtctgatttt gcttcctttt gatggtagca gtacagacct
11881 ggctgttttg tagcctgctt tgttttttctt cctttcttc cctaacttca cgggctgtgg
11941 caaagccctg agacgtgcag gaaaatgtct cctgtcatac gcccacagca gacctagccc
12001 tgaccctcct ctgaagccca ggaaggaggt atctgtgaag cagcctgctt gtaaagcaat
12061 tgcacacagc cttgtaaact gtgttactgg gctgattata cttgattggc aaggtgaatc
12121 tcttatagca aaagagaact tggagagttt tatctcatct tatgccttat taatttgttc
12181 attctttaat tacacagcca cctattgagc accctattta tgcaaggtac ctggtcgggg
12241 gtcagaggga gggtcccatg gtaaacgaga cagactcaat cctggaggag caggaatggc
12301 agcccctcgc tgggctgttg gccccaccaa aagggaaagg tttcatttta ataatacatg
12361 ggtgaatcat ttttgtcaat aggcaaaatt ctttgtagtt aaaaaaaat atgatggtag
12421 gaaggaaagg gatgggcaga gggttaaaac aaaagatatg ctctccctaa ctctagattg
12481 tagtattgtt atgcttgtca ctgtagctga attccatttc tttgagtttt ttcaatgcca
12541 aggcattccc tgtatgactt acgtgagcct ttcatctccg cgatttttcc cattcaggta
12601 aatgagcaaa tggatttgaa cactcatatc taaaacaaga gagaaccagc tggaaatgcc
12661 ctttgaattt cttttctctat gtaaaccatt tttcttttctg gtgcctcacc tataaataac
12721 aggagttcca ccttccttta tagactcttg ctgaaagcat ggtttggaac aagaccgtac
12781 aggtgcacac aaattacagt tgggaaagaa gcctgcagtg catcttgtct ctgaaggtta
12841 tgaaatcctc cttttagtaa tggagctggc gtgatcaagc cagcaggatg aaatttggca
12901 tttgtgagat caccccctt ctcacttgcc cactgtacat agcatcccag ccttactctt
12961 caaatctcca cattttttct tatctagcta caaaattcat aggctgattt ttttggggtg
13021 cgtgtgtggt ttttttttg tttttttggt aaataaagac ctgcattttt attttgatat
13081 aggtggttga gttttgtctt taattcatg acagagattt aactagtctc aacttttgaa
13141 aagacaacaa tgatatttgg ggatcacaca cttaaagtta gatttctaga tgattaatac
```

Fig. 63E

```
13201 caaagtagat gattttttag cctcagccat ttataggtat gcccttctgt gaatttttta
13261 tgacagtgaa aatcatggca cagataaaaa ttaaataaat acttctgtta ttttcctgaa
13321 gaaaaaaaaa aaaagcttaa actatgagaa tactgtcttt gagcacttta aataaaatt
13381 gacttcagcc agcaggattt tgagcattac atcacaaata aaaaacaaga ttaacatcaa
13441 aaggagtcag ttttcattca attgtgcagc actgtgggct gtgaaattta atattatttt
13501 gactcatatg ctaattgtag actgacagag gaaatggat tgtgtttaaa taaaaggata
13561 cacagcatca cacgcagctg tatcaaatac aagttgaggt ctttgggcca ggaactgggg
13621 gccctctagc tctgttattg cagattcaag tttgacaaat aaaactttcc tttagactgt
13681 agtttaatta ctttttttca aaggtatgcg tgatgaagag gcacaaatac acctcacctt
13741 gaagagttgc taaactggtt tgtgtgccga tcagttcacc gtgtgtttga atttctgtgc
13801 ttctcatctt tcctttcctt gaaaagattt tgcttgtcat tggtgtgaat tgtaccccc
13861 accccaccc atctagtctt tgctctcaga tttataacac tttaatggtt ccaaattgta
13921 tagcctgctc ttagacccct tttcttttcc ttgaataaat caggttcatg ttgcagacga
13981 tatttgtttt aggaaagtgt gaaagaaggg gcacctgtga aaacacgcaa ttgttccaac
14041 acacatatac atccaaatta aagcagaaaa tgtcaaagcc tccaatcact accttatttc
14101 ttggaggttt aaagccgctg agaagatagt ggtgccctcg ctggaagttt taaggtaatt
14161 acttttact ctaagcagta gtatctggta acctaattcc gtataaacct gacacctat
14221 cgctacaccc cagtatttct ctgatttcag aataagtctg cgtagaaact tgttctgatg
14281 ttaaagtgca aaggggggca gtaaagtgct atccacaaaa aaggaaaaac attttccaag
14341 tatttcttat tactgcctgt gtctttcgta ggccctgcct ttatttattc attttataac
14401 aaaactctta tgtttggggc attcagagaa taccttatta agctgttgca gcaatctagc
14461 attaaatgga agacatgcaa gactgaagat cctgcctgtt tatgaagtgt gccatcaaat
14521 tcacatgctc atgatgcaga gtccttcttt gggagtattc gtattcccaa gtgcacagag
14581 cacttcggaa aggagccttg gtctttggtg ttaatgctct cctagctccg tatagatgtg
14641 gcaggcccaa agtacatggt ggggtgaagg gtcaagggtt tgggcttatc cagagcagcg
14701 tgcatccttt gtcaggaggt gactggaaac accagccaat tacagcagaa ctgcagactg
14761 ctcatctgca ttcggaattg cagatgaacc agtttgtact cgacttctct tcttcactgt
14821 aggctttgac atttaattaa aaattaaagc cttttatgga aaaagtacat gttttccaaa
14881 atggggtaaa ttcgaagtat acttgataca gaacactggc ttgggaataa acctgtgata
14941 ttacatgact tttggtttgc aactgctagg ctgagcctct ttgtaaagct gggatttaga
15001 atctttgaaa tgtttgtaca gttcaatgat taagcataaa ttgtatatat tccctttttt
15061 tcacttattt gagtaaacaa gtttgttact acagcttctg tggactcaga gatttatgta
15121 ttaaataggc cacaacttca actaggataa ttttatttat ctgcttgtta gggaattgca
15181 tcaaagtttt aagtctgtag gcattaaata ttttaaatgc ttatttttaa agtcaattat
15241 gaaagatagc acaagttttt tctgaaacta cattaaaaaa ataatgtttt aatcttatca
15301 caaaagcatt gactatttat tgcaagaaa acacagaaag ctaaaaatca ttctaagtcc
15361 accattcagt agcccaaagt ggtctcaggt aaaggcggtg tgtgtgacca tttgtttatg
15421 gttgtctccg tgcagtcagc aaaataaaca gaacaacatg ccatatatta ttgatgtgta
15481 tattttcaac tgaaattagc catctgctta caatgatcat atacactaat ggtataattt
15541 tgaaatgaaa agaaaaataa aataattctt tgtggagagt aatgcgaatt gacttatgaa
15601 tctcgccctg cttggcagtt tgctctagag gtagaagagc tttatgtgtg ggcctcctcc
15661 ccccccacac atttattctg ctcacacttg caccagcatc catgtcagga ctcaccttgt
15721 cctgttacat gagtaacatg gccctgattc tcaagtgcat gataactgcc ataattacac
15781 ataaatatta aatatttaaa tagatcttta cgtgtgtaat attaggtaga agtggctctg
```

Fig. 63F

```
15841 gatcgaatct gatgctttt aaatagaagc tttcccacaa catttccaag cactgtcatc
15901 gtgtctgtct cgatttgggg tttacctggc ctagttatct gtctgggtgt agaaactggt
15961 agttcctgtt tgtatctttt ttgttctgat ctctttattc tgtgtcagct aaatattctt
16021 gcagtcagtt actaacatat taactcatcc ttgtttggaa actttggcat atccttccat
16081 ggtttccttc cgtggacctg tcgcgtctct caggagagcc accaggtata ttgtcacaca
16141 tttcgcatgt attttcagag actacagcag catcaagtgg cccccagcg atttgggttt
16201 tcttctcggt taatctacac tctttggcca accgtgagaa aacttgtaag aaggcatcag
16261 atgtttgtgc taaggtgcgt gtagtatggt cagaggaaga aagaagcagg gaaaatggag
16321 tggccgtggg tgggagggga agcagggagt gcaatttcgg gttcactaca cagctctcca
16381 taaacttctc cactgctggc ttcccacgga tcctcctatt cactgggca aagtgcagaa
16441 atagatcagg cgaccactgc ctccgtccat ttcccaggca ccctgtgaga cccgataatg
16501 caatacaggt cagcagaaaa gtccagactt gacatcccaa cgtgccatgg tctggtctgt
16561 gaatgaaaat cacatgaggt gacctctgaa ctctaagtgg ctggtttatg ttttcagtgt
16621 attaggcccg tgttttaaac aagcatgtgc tcgtagtgta ggttaaaact ttctgttgtc
16681 ttcattaatt atgctgtgtt ctagtctatt aatattaaag aatattgtgt tgcataatga
16741 ctaatttttt tattttttgg agacggagtc ttgctctgtc acccaggctg gagtgcagta
16801 gtgcgatctc ggctcactgc aacctccgcc tctcggattc aagcaattct ctgtctcagc
16861 ctccgagtaa ctaggactac aggcgcccgc caccatgccc agctaagtgt tgtatttta
16921 atagagacgg gttttacca tcttggccag gctggtcttg aactcctgac ctcgtgatcc
16981 acccgcctca gcctcccaaa gtgctgggat tataggcgtg agccaccacg cctggcaaca
17041 taaggactat tttttaaagt ttttacaatt atgactgtga agttgaaatg tctaaattat
17101 tagagatcca gtttagatta ctaaatattt atgtctaatt gagatgatta gacttagcca
17161 aagtatccat gtagaagtat tagagtctag attggtgaaa aacttgaaaa agcttggctt
17221 aagttcaata ggtaatccaa gagtaaaaac agattccaat atcagatctt ttcaccatag
17281 tcatgttaag tttggaagcc ctacttgagt gttccagtt ttttccacat tatattgtgt
17341 ctatatttga ttcaaaggca gggcatctat tgtcttgctt aggactgatt cactgggaaa
17401 agccactgga gttgcctatt tccactcagt atgcctcact cttagagtag cttcccatgg
17461 ttcccaggca ggccctccag tgagaatgca ccaagccaca cgccatggcc tgggaagcag
17521 tcctgaacct ggagattgtc ttgatggaaa ggaagaggca gccttcccct cccaggaaga
17581 tagtagagag cctgctctga cttcgctcag ggatggaact ggtctggctc agttctctct
17641 cctgtgtggg acatgaatca ctcttggtgg tctttgcttt ttatttgggc ttaaaatcag
17701 cagactttat taaatgacac ctctctctaa ccactctctg tctgggcgaa gtttaacaag
17761 aacagcctcc ccccatgtgg tatgggttgt aactgtggcg gtttcctct gctgttttg
17821 gttacaagat gaacattatc tgaacacaca gaaagaaatc tgtatttggc atccataatg
17881 gaaagtcagt ttagtaattt aaacttagcc agttatcatc atcataattc ttttaacac
17941 tttcaaagtc agcataggag aagtgtattg ttgaatatta caaatatttt agggcataga
18001 tagatgtgct gtgtagtttg atttgttaat gtgtctaagc aatcaaagca acagaattca
18061 aatataaacc ccatcacttc caaaatagga actctgttta ctgacttgat tataacatat
18121 ggaactcaat tgttttccat taaaaatga tactattagg aaactcaccc catttctttt
18181 tcatatatat tctgctattt gcataattgt ctggagtcca tatgtaatat taaatgtaaa
18241 acacaaatgc catgtagctg gtctgtttct tcctcacctt ttggttcctg gcctcctggg
18301 gaagggttgc acatctgagc cgtggtctca gatgactgcc tcggaagaag cctcttccct
18361 tcaggcacca ctgatgtgtg cttggtgtgg agctagactt tccctggctc tccatgtgac
18421 gctcacatgt gcgtgtcttg atttccctta acttcatggc ttatctatga acagcttgat
```

Fig. 63G

```
18481 ttgggggaaa aaaatgtgtt tcccaatgct ggagttataa ttgaatgtgc tgcagtcaaa
18541 actgaaatgt gtgcagagaa agggggcttt tcctgtcatg ctcattgggc accagtgtgt
18601 cttcacctgt tttgtgtgtt aggtccatgc gtcatgctga aatgaagaac atgggatgta
18661 tggggctttg gacagtgctg agccaaaagc aagtgctcaa agcagctgt gtttgtatta
18721 ttagtggttc tggaggtggc tgattgcctt gcattttaag tagagaggga ttgtagaaga
18781 ctgccaatac ttagaacttt ttccagagag gaagggtcag aaactgcatc tgcagggctc
18841 cttgctctcc agaaatgcca gtgtgcctgg gagggcatct tcagaaatcc agtctctcct
18901 cctcagtgtg tcctgtaccg actcagtggt tctgtcttca gaattcctat catgtctgtg
18961 atctgcaaat agtggtattt aatttgactt caatttgtat aaatgttagc ttctatttgt
19021 tcattcctat ttttttgttca attaatacat tatttattga gcatctactc tgtgtcagcc
19081 ccttgggtgt taatactga attagtcaca tgtgggactt gcctgcctc agggagctag
19141 actataaatt cctaatgatc agtggtctcc acttttctgt cactcataat gtctggcaca
19201 acataggtta cttgagttgt tacactcaca gtactgttgt ttgctgccat ggtgctttag
19261 gaagtgtgag agttcccggg aggcagagtc aataatgcag actacacgta gtgaaaacat
19321 ggccaggaga gctgtagttc aggctctcag ctcaactgca ctctgtccac tgagaagcca
19381 taatttcttc acttaaagtg actgtgcgct atggctgttt atatatacgc ttaaaaagta
19441 aaagctgcta aaccactcaa ggattggggc cttttgtatt gatttaatta aaggaacaat
19501 cattgtttta atgagctcta gaaacaatta cttttgaaga gccgaggatc aaattcttgc
19561 ctcacgtttt gccacagtgt gttctgaaag gtgaattaat gcttttggaa tcatcaggaa
19621 tagtgagctt tgtcacgatt tacttttttac aagcgtatct aatatgcata ttgaaatgtg
19681 agcctcccca ccacacttcc gctttgataa gcatccccg gattgccgtc actgaccatt
19741 atagattttt aacaaagttg gacagtacac actgaatgaa aactttacat caaggaaggc
19801 ctggcgtgtt tgtaaaatga attaaaaggc tcattaaatg atttatatga cttacgcctt
19861 ctgaaaatat ggcctcaaac acagagatcc ccaaagccac accgacccct gcgtcccatg
19921 ttctcgacct caccgcatca gcaccagcaa gacctgtcgc tgagacggtg agtgatgaga
19981 gtcaagagga gtgacttgca tggcctggga ggaaacctcc tgtgaatctt tagttaagca
20041 ggaaaaaaaa aatcctcatg aaggaaacag gatcttggga gcattttgaa tgaagaagga
20101 gcttagtgag ccaaacttga gacataggggt gtaatgtggg agagttttaa gatttgcaga
20161 gatgtacagc ttgggagggg gtgtaatgca ttttcttaaa agagctgaat gaatggttga
20221 ggaaatgggt acatctggtt tggttaagga tcctaatctc tgaagcctgg gatgccccca
20281 gggcttgtaa tttaggaata cttcccctaa tagtagctaa cccttatata gtgctgtctg
20341 tgcaggctac aaaaggagca gattaaggat agaaaaggtt tggagtgtat gagaaaccct
20401 aggcaggaat tgactcctgg tgtttgtaaa ccttaaagat gtcctaaaaa ggtcaaggaa
20461 taagacagga gaaaaggaa atgtcaggaa gatgatcaat ttaatgttta tggaatttag
20521 tttgtactta ctgcccggca tcttgcctga ggttttaac ctcagcagca catcagaatt
20581 actgtgtgtg tgttggaggg gctggggag ataaagaaat tagcctcatc ccaaacattc
20641 tgattcagtc tgttacttga gaaactgaat tgtgttttgt ccataaagaa gatgaaattg
20701 tctacagaga acacattgcc attcacaagg ttgaggggat accacagaga ggctcccact
20761 gtgatttgca tttgtcaaaa gttctagaga attcttcaac agtacacaca tggttgtttt
20821 aaatatatca ttgttataaa aattcgtttt gagttctgtt tcacagaaag tttttttgaa
20881 tgaatgaatg tcatatatcc ttgctaaagg agctcagtta aaaaaaaagg gaccatcctt
20941 ctcttttggg ggttgtacag taacacattc ccaagaaaga ggtaacagcc acatacattt
21001 ttcttcccaa taaagagtgt gggttttaa tatgaatcca tagtatgatt tctgttatgt
21061 tttgtgctgc ttcataacca cactcatgca cttttcagaa aattaatacc attcattagc
```

Fig. 63H

```
21121 ataaatcata aactattccc ttggtatggg tttgaaattg ggggtgccct atcatccttg
21181 ctttatctct tagtgaatta tgaccctgta gtcatcatgg ctggtgggcg tctctggtta
21241 aagaaagggt tggattggaa ggattcagag gcgattcttt gttcttaggc tttaatattt
21301 taatgagcct gcaggcttgg ctgcttacga acgagctgag atttctaagt gtgttgttag
21361 tgttagcact tgtagaagga tgttcattag gaagttcttg tttcagtttt tcagagaaac
21421 tccccattaa gaaagatcat tcaggaacat ggctaccaag aaagaggaaa gggaggaggg
21481 aggctttcag ctataagcat taaggggata ttgtatcagt agtcttagtt ctaaagattt
21541 gcttctgaga attaattgga gcaaatacat ctcaagggaa gaaaaaaaaa gatttatagg
21601 gcagggacag tagttgtcct tgcaagtaga ggacacttca ttttgcagct gaatcaatac
21661 cacaactaat tatttctggt tatcttttac gcatttgtaa gacattgctt ttgttcagtg
21721 taataaaaaa cccattgttt gatcagtgac tgactaatta tgataagtaa tttgaaacat
21781 tcttgatgaa acttgtctgt taattaacat caacagcaca gggaaactaa caggacaaca
21841 aagtattagt ggatccactg ttccctccaa ttgacgagct ttctctgtgg catgcccaat
21901 aaactaaagc tgccaatggt taaaaataa caaacatgtg ggagatctga ctcaccacgg
21961 aggaagagtt atggtaaagt tacacaaagg agtactgaaa tattacaagc gaggggggtgg
22021 taaagaaatg tcagcaggta gcctgatcct acagcttaga gtaaggaaag tggtttcttt
22081 ctgtcttttcc ttttcttttt aaagcttaat tccaaaatac attcatccca tattgatctg
22141 aagtaagaga cttttgataa attaaagtgt gaatctgaaa atgtgtagtt tgggattatg
22201 ggcattgcct ggctatcttg taactgtcat taatactgtt aatttttatc aactcaatgg
22261 cttttttttc ttatgctttt aga|tttctac ctggacaagg actggtacta tacccacaga
22321 taggagacaa attggatatt atttgcccca aagtggactc taaaactgtt ggccagtatg
22381 aatattataa agtttatatg gttgataaag accaagcaga cagatgcact attaagaagg
22441 aaaataccc tctcctcaac tgtgccaaac cagaccaaga tatcaaattc accatcaagt
22501 ttcaagaatt cagccctaac ctctggggtc tagaatttca gaagaacaaa gattattaca
22561 ttatat|gtaa gtataatttt attcatttat tttatagaaa ttaagataag ctatataggt
22621 ttgtatcaat tttttgtttc cttaaaatta ttgtgacaaa taatttgatg aaaatctatg
22681 tggaaaaatt gtccccccc cctttttttt tttcaaagaa aacttcattg aatttgggac
22741 cctgtgctac cagtattcat taagtataca tacccaaaga gaaaaaaaaa cactagaatt
22801 cttaatagta ttgaaataaa tgtattatat gaatatattc agcatctcta ctgacaaaac
22861 catttttaag gaccattggt ggattttgat aggtaaatct tgtgcattgc cttttctctt
22921 cacccatcca tccattcatt cactcattca tttcgtattt attctgtgcc agagactgtg
22981 cttaagggct agggattcag cagtgaaagg tggtaaaata gcatgttttc ctcaagaagt
23041 taacagtcta gagaagatgg agctcataaa ttcgaaagat ggggatgaca ggtcacatta
23101 aaaccagatt cagaagaaaa agacgaaact tggtttgctt agtacattac tcttttttgc
23161 atacatatat ataatttgac acgctgtttc aagaagagat ggtacgtatc ccttgggtca
23221 tatctgaggc tgacttgtga ggatgtgaag tcagctgatg agcacatttg agcccacgc
23281 ctactatgtg cagatctctc gtcagcgtca ttcccagggc ccaggtggt gttaaagtct
23341 aggtgactca gacagctgtt cgcgtcattc aagcaatgaa gtcttttttc ttaatttctt
23401 tggtttaaaa ttatactcat aattaattgg gttgaatttt ccagtggctt ggttaccata
23461 gacttcagtt tattagggaa ctgctatctg ccactggttt attatttgcc ccaaggtgga
23521 ctctaaaact ttaggtagga gactcttggt gatcaaactg aaactcttgc atctcaacct
23581 atgagccgca ctttattgtt atttttatttt tttagagaca gggtctagct tgttgccga
23641 ggctggcgtg cagtggcatg atcacagctc actgtagcct tgaactccag ggctcaagtg
23701 atcctcccac ctcagcctcc aagtagctcg gactacaggc atgtgccact gcacccagct
23761 caagagctac acttcaaagc acagaatgaa aacctatttt taaagccaac ttgatacata
```

Fig. 63I

```
23821 gagtagctta ccaagaatta gtaacaacaa caacaagaaa aaaaagagag aatgtggtag
23881 agtatatact tagtaaggag taattattat aaaataaaag cattctgaaa tgaaacaggt
23941 agatggggtg gccaagtatg cagcatagta gggaaatctt tgaaaatgta aaatagttac
24001 caggtaaaat aaatggaaac tttaagcttt tggaagccta acaatgtatt tatattagta
24061 aagactttat ttttttattt tattttattt tattttttgag acggagtctc tctctttcgt
24121 caggctggag tgcagtggcg tgatctcggc tcactgcaac ctccacctcc tgggttcaag
24181 tgattctcct gcctcagcct cccaagtagc tgggactaca ggtgtgcgct aattttttgta
24241 tttttagtca agacggggtt tcaccatgtt ggccaggatc atctggatct cttgaccttg
24301 tgatccttcc gccttggcct cccaaagtac tgggattcca ggcgtgagcc accgcgcctg
24361 gccttagtaa agactttaa agtaagactt tttcagtgaa agctactgtt aggcatgaca
24421 tttacaggca actgaaactg atcagatgca tttattaaga aggttaatgc ccctaggtgg
24481 ggtgggagaa agaaggtcgt ggtacgggaa gagggacac actagagatg agatgcccta
24541 gggcagtgaa cgcatgtccc taatgcgtgg atgcagccca cgtccaccga taatgccgac
24601 acacccagag tctctcttct tactttagct tatgacttca cgaagaatgc tttgcaaatt
24661 ctaagttcgc actgggcgca agtggaattt tagtaaacat taagagttta acctttagtg
24721 tgaaataata tgcaagatat gcaaataatt gtttaccaac atctctttgc ttaatgtggt
24781 gagcatttaa taattgcttt ttattaatac atgagagatt tgtatttaga agcagtttaa
24841 tttataatta taatattaat ctacacaata acgacatcta ttattttctt tttttggaaa
24901 ctcttcatac cacactaaca ggttcattgc agttactgaa ctactctggc catcagagct
24961 ctccttagag ttacgattta ccatgcaaaa gcatatggta gcctgggata aatgaatctt
25021 tcttaataca gaattgaggg tctcaagttt gaaactacga gaggctattt gaatgttgct
25081 ttgggggact gtcataaggg ctgggtggag gactcagggc taagaagttt gccaggaagt
25141 ccagttgaga ctttcagcag agttgaaaga cttccacgat ggcgtaggca gaggaaggcg
25201 tttcagatac ttgggaaaat atagaagcca atttctcacc caccctacag caaagctcat
25261 tgatctacaa gtttccctag aaaggaaatg ggaaatgcag agaacaaatg ttaaaatagt
25321 tttagaaatt aatattgact ttgtattgct tctgcataag ttccaagaca ccaaaacaat
25381 gaatggattt taaaaagtca ctactttgca tatcagacaa atgcacacac acacacacac
25441 acacacacac acacacacac acacacagtc aagctctgta ctggcttttt tgagaaggaa
25501 agtgtttgaa gttagtaatt tttatatcag tacatttata aatagtgcta ggtagcatga
25561 cggaaagtat taaaatttac atgtatattt ttaacacttc aaatcgttgg ttcactttga
25621 gacagtaaat aatattagca tttgagttca gctttaataa attctacatg ggtttaaccc
25681 caaatctgag tgtctagttg gtaagcgcct tcagaacgag cagtgttata ataaatatgt
25741 tattgtgtgc tggtttcttt ccatggagag gaaaaagaga cctgatgctt tggaggagtg
25801 cttgactttt ccccagtgag gagtagtcca gagggactga cttgcattgg ggagtaccct
25861 acatgaacag catttcagaa gaattaaacc aggaacctag agtcctactt gctagtcctg
25921 cttcctaagc ttaatgagaa agtcaatttt atttctttga actttaattt atttccctaa
25981 aaaacgcttt tagtattgtc attgttctgg ctaatgatgg cggtctcctc cagtttcaag
26041 ccaccttagg gctgggcata caaatgcaat ataggatcac ttgttagtgt ggtttcaaat
26101 ggacatgatc ctctgtaaat tctttaaaaa catttaattt gatttgtggt gttacctgct
26161 ttaaaatata gtcatcacac ttgtgagttt cagacgtgaa atgaattttt aatttgaac
26221 tgtatttta aacacactaa gtattaacta agtccccttaa ggagatatgt ggcaaactga
26281 tatgcatcct cattcattct tctcatagat ggttatttgt ttttaacttt gtggcaaaat
26341 tatatatgaa tggtcaccga cttaaaatag ttccacttaa atttttcaac ttctgatgg
```

Fig. 63J

```
26401 gtttattgga gtattaaatg tattttcaat ttaatgatat tttcagctta ccttgtgctt
26461 atcaagtatc aagacatagc cccacctaag tcatggagca tctgtatatg ggttttatt
26521 cttgtttaga attgacttt tcaagtgacc tatttcagta attagccctg ggcctgattt
26581 gcataatgag atctcctaat cttcaagtaa tgcaaagatg gagatattat ggccatgtgg
26641 tctgaagaga cctttttcttt attatgttca gatctttaat tgccttaaaa atagagtagc
26701 taatttacct aacctctagt tattttatta ttgtctttaa agttttttt aatgttcatg
26761 aaataactgt tctgaaattg cctattttca agggaagctg tgtcttagac ttactaaatg
26821 ctccagttga tactgggaaa gccttcttgt gttcgtagcc tttatccgta gagttttctt
26881 tgcagcattt tctgtgcctg gtttagtttc ttttcagagg cgacacccag agctgaatga
26941 gtcagcaggt ttggtgtgtc gacccttgc aacagctgtc cttacgaagg ttctgtgggc
27001 tggttattct accttcgcat aaaaccttgc aaaataaccc acaaagaggt tttcgtcaca
27061 ctaccaaaat catgtgagtc agagatggat gaaaaatgaa tgccattgtg ttcatacttt
27121 tccagtgaac agtagctaca gcagagctgt tagacaaaga aaaccgtatt aatgaagcgc
27181 ctcccaattt agcttcatat ggcttttgca ttattttgct gcaaatccat agctaagaca
27241 catcttgtgg catagtccgt aagtcatctt tccgaaggac tgtttgatta aaggttgttc
27301 tgtgagatcc accctgtgtt gttcatggca tcctcttgga ggcctccctc actctccatg
27361 ccttggcaaa gtcttcctta aggaacactg aacaagtctg gagaagctgc catttcttag
27421 ggccctcatt ggttcagttg tctatagctt tttattttt atttttttt taataaagag
27481 tatgtaaaat tggaaagctt cacaaacagc tttgctattt tttagacatg tactccactt
27541 ctaagcaaaa tcacaaaata aagtaaaatg cttccacaaa tataatgaaa caatattctt
27601 aaagaatcaa agcagaagaa cttcagagtc tgttgcttat gttaagcata tatttgtttt
27661 cttctctgct tttgatttac ttatttctgg ggtgtaggtt tggcaagtag tactgaaacg
27721 tactgaatgc actgttcttt agcaagatag ttacaggagc tttcaaatgt cctcttaaca
27781 tatagatttc ttttagaata tagaataatg tgtgggctgt ataaagcgat tatgtgcttt
27841 atttgatgaa ttatttatgt acgataaatg tagcaaaagc cacatttcca tcattaaatg
27901 taatcccatt tggtgataca gcaacatcag cctgtcattt gggtcctctg attgagggt
27961 gaggatttct gtttgatacc ttgtgcataa tggctgcgtt caagcattta aactcatttt
28021 tatttctaac ctacagctgt catctttgta ataggatatt catcagaatc ttgccagaga
28081 ctgtgcattt gggatcttgg gggatacagc accaccacca ccctcccct gtccaagaga
28141 aacagatcaa catcttaggt tgagagtctg gggtctggaa gacccgagtt cctgagtgcc
28201 ctttgacaag taacttaacc cctgtctgcc tcagtctctt catctgtaaa gtggggataa
28261 tgacagcacc tgcttcacag ggttgatggg aatccagatg tggtgggata tagaaaatgc
28321 ttattacttc caccttgac accaaataca tataactaag agttaacttt ggagcagggg
28381 aggaagtgtg aggctccagg ctggaggcag acctgtgttc ggctgcaagc tggagaggat
28441 ggaccccaaa agcttggctg atttgaagtc catccataaa atggaactcc agagagttta
28501 cacgtttcag taatgctgca taacttaatt ataagatctt ctctctttgt cttctttcag
28561 tgttataaaa gctcttttgt ccttgagctt ccttaccaa gaaacatgca tttatgtatc
28621 tttttgttca tggaattgcc caagcttgtt agcagatcct ttgtaagacc caaaagagac
28681 agacagggga ggagtcttca gatacatata atcatttttc ccaatttcca tgttaccagc
28741 cttgccagga cttttctca gttccctgtt acacaatgaa aatagtgtct ctttattgat
28801 aattttagta gcatcctaat gtggtataaa tcgtcttcca gagaagaaaa tgtgtcaggg
28861 ttgcgttatc actgaggcta gctgggaaag tagatcagcc cattagtctg ataattcgaa
28921 gcgttgtttc tgttatttct gaacatcatg tgaactcctt ttctgggtgt attaaaggtt
28981 ttcccagtgt gtgtcagtga gactcctgat tgaatttaat atgaataaag ataaattctt
29041 tacatttaag gattaaagtc tcagcttctg cttaacttga gattgcactg agaaactcct
```

Fig. 63K

```
29101 ggctctcggg tatagcggag tcacgacctg gggatgtctg tcccatatgg ctctgtgtgt
29161 aagaagaaaa agctgctgtg gacggagact ctgttcacat taaatgacat cacctaagcc
29221 atcatgacag caagaattat ttaggaattg ctcagaataa aactgccttc attatttcat
29281 aaaatgtatc ttggtatctt tagcacctta tttatggctt tttaaaggtt cactgggatt
29341 tataaataat tggacaatgc tagagaccta gtacaagaat gaaagaggac aggcttcttt
29401 cttaataacc tttaaacatt catcaggaag ataaaacttt aaagcaaaat aaaacacatg
29461 aaaatagcca agatgcacag accagacaag caaatactac tttaacttat ttgtatagtt
29521 cttaagagtc acatttgttc ctgaagtttc aaaatctcgg gctgagtgtt tgatcactta
29581 gggaagtgtt gtggccttca catactcttg tctcactttg aagtctagaa acacaggtct
29641 tagagcaatt tttatcactg tgagaaagct gaaacttagt gtgagtagct tagtacaatt
29701 cagttggcca tcaaatgtca gaaacaaaac tcagtccagg ccgctggac ccttaggccg
29761 gcgttgttag tttacaacag tgcctcctgg gtccaaacat ctaagtgcac atgtagcaat
29821 agtaaagata gtatgtatgc atacataaca catatgtaga gacagcagag tatacgtaca
29881 cacatgttgc atacatagca acagcagaga agctcatgaa ctataaagga tggactgtat
29941 gcttgtatca gacattttgg tactgacgct tgtcatata ttgtgtaaca tataaccagc
30001 ttgcaatcat ctgcccccaa agttgaacta agaaaatcct acagggtact aggaaaggaa
30061 ggccattggg aaaggtggt tatagtggca atttgttagc tcttatgaat tttcttttc
30121 tttttagaca tactcttaat tccatttttt caataaatct atactatttt gtgttttat
30181 gttagcaagt actttaagcc cctcaataga aagttgctac atcatatagt gattaaaaat
30241 aaaaatctct caaacataca agtagaggtg gtatgagact tcaaattccc ttagccaagt
30301 acaagtgcag cagttttgtt ggctggctgg ctgcatagaa ggactgatgg attggcagac
30361 cctcaagctg gagtgtaatt gatctcatta cagaggagcc aggctgggtg acagttgtgc
30421 tttgcaagtg gttttttgca ttggtgaagt agcccatttt gttgttcctg atgttaaaca
30481 ggggatgaag gtattctttt attggcacaa acgcgggaaa ttgctctgga ttcttagagg
30541 atagaacatg tccctggac ggaataaggt tcatgtgtag ggcaaattta gataggggca
30601 ccttattggg gttactactg gtctctagat ggtcaaagca acaacatgt ccatctaagc
30661 tgtgatgtcc atctaagctg tgtgtgtcca tgagagtgac gcattttctc ctctgcagtg
30721 ttgttatatt ctaaactgtc agcagacatt aattcggtcg ctggtgaagt cccaccgcct
30781 agagatgaac tctgcctccg atggatgttt ccacttcag tgccactcgt ctcgcaatta
30841 ctgggtcatt aatatcattg catgcaatta gtgacagtag aaagagctag agggttgtgg
30901 gatgtgcacc ctccccacca tgaactttt actctgaccc tttcccagct agacctttc
30961 gtatcttggc aaggatattt taatgattga gactgtcaga atcttcagag caggcactgg
31021 attatgtgct ggaaataatt cactcaaaca cctgcttctc catggttcag aatattttca
31081 ttagatatta tcactatccc ttccctggga gtttcattt taaaaatct gatgcttaag
31141 tacagctaat atagacaata gggaattatg ttttatcttt agaactctta cattattctt
31201 ttctttaaaa atgtgagctg agtcattgct attgcagtgg tcatctggcc gcctattttt
31261 aaaacacaat tcctctatct tagtagattt tggcccatat taagcatatc aagaatgact
31321 ttttttttt caagacatgg ggttttattg ggggcttata tacaaggaaa gagagagtcc
31381 agtggcagtg ggctggacaa gatatccaca tggccctgtg gcagtgagct gggcaggaaa
31441 actgcaactg cttgcaaaca gcatgtagtt catctatagc attttcactt aacaccaccc
31501 agctaatgac ttccacctgg caaccttcat ttaatccaga acttaggacc tcgagtccct
31561 gtacggccca tgttccacag gatgggccga gggctcagct gttcctcata gacaaggaat
31621 gactctccac attggccact cccggattcc ctagctcagg acacatattc aggtgtgtct
31681 aaggctggct cttctatgtg aagttactta ttcttttacc attgactctc atgttcccac
31741 tatattaagt ttttctgaat tactgtggca ataagaaacg gtcccttaaa ttatactaga
```

Fig. 63L

```
31801 agaaaagctt ttttttgtt ttgtttttta ttttgaaatt atgttaaatt ttttttctta
31861 actgagagat tccacctgca taaatcgtca taacttttaa cagtaagatc ttagacttag
31921 aaagtgatgt ttttcctcaa cagaatttat taaaaatcaa gacaccaagc tgttccaaac
31981 aatagtttga gggggaaataa aataaacaac tccataaata atcttatgtt gttaaacatg
32041 tctctagcaa aacaaacaaa caaaaaagtc gggggttggg ggaggtgcag tttattgcca
32101 gtactgtctg gtctttctca gaaaagcgtc agtgtacatc actgagcctg gacggtatgt
32161 tttcttgatc tatacccct atgtgtacat gtgcttgcac gcacacacat gtagacacgc
32221 acacatgtgc acctgccatc actttctgct cttccgtctt ttcactcttg agtgtctgta
32281 gccagtagct ttccaggtct gtatagtcaa agatacctat ggccctgaat gtcttcactg
32341 attgctattt gacattcata cggttttaa tggttaaaag ctttatgcg aaagctgtga
32401 tagaatttct cctgttctag atgtggtgtt tattgcttta ttttgtgact tttctctcag
32461 tagattgacc ttctccctca gtgtccaagc ctcgcatagc atgatggcac ctgtaaactc
32521 agttctgtat cctggtatcc tttctcttcc caagtagaag caattaagta atatatgtca
32581 tcaaaacctt ttaagtgcac atacaaacaa aatcaactta ccaaactgct tcaaagttgt
32641 tccatgttta acactcttct ttctgagctc tgggtagaat gtcctattat tgttcatcat
32701 gaatatttga aattaaagaa ataaaactgt accatttttct ttaagagcat ccatttgtac
32761 tgataacat cttcagtcat atttcaatgc tggcaaagag gaggggagtt ctaaactgtg
32821 actcaatttt agaatctact ttttccaaat tattctgttt agtgcagaaa actaattaat
32881 agtgttgcat agaaaagtca ctgaagctaa gccagttatt acttcttaat gcatgattta
32941 ctgctttaag ttttcaaaac acaaccatag caatgtggta ttaattcaag tgattcttcc
33001 tatcatattg aacgatattt tcacgggtga aaaactcaca catcctacat cactgatagt
33061 ttatacagtg ttttagctgt ggctccctgc atgcaaaata agagttaatc aaatgtcagt
33121 gagaaccatc tcatcaagta gagggcttgt tttgtttaaa ttaactttgc taagtataaa
33181 tttcttcttg aaaataaatt ctgggccggg cgcggtggct cacgcctgta atcctagcac
33241 tttgggaggc cgaggcgggc ggatcacgag gtcaggagat cgagaccaaa ctggctaaca
33301 ctgtgaaacc ccgtctctac taaaaataca aaaaatgagc cgggtgtggt ggcgggctcc
33361 tgtagtccca gctactcggg aggctgaggc aggagaatgg cgtgaacctg ggaggcagag
33421 cttgtggtga gccaagatca caccactgca ctccagcctg ggtgacagag cgagactccg
33481 tctcaaaaaa aaaaaaaagg aaaataaatt cttctgtatt tttctttctt caagtgaggc
33541 catttagggg aaagtatacc ataaaacttg ctctaagata aggcaaattt ggtattatag
33601 gatgaagtgc tatgtgattt gaagtaatgc tgaatttttt aaatatatta aactaaacaa
33661 gaataatgag gccctcggaa agtcatgatt atatttctca tttttctcat tttaaagcca
33721 cagtgaaaaa cacataaaag gaagaagtta gaaaaaaaaa tgaatgaaat tcttttttttc
33781 cttttggcaa attaaataga tgtttctgtt tcagaagatt ttattaatta actttaaaga
33841 aacagtcatt tattttttggc attcagtgaa cactatcatt tccatgttta gaacttttct
33901 tctaagttag catcttaaaa gataactgtg aaactcaagg cattcaacta cattaatttg
33961 agtttcagaa attgaattct tgtttctaga gtacatagtt tgaattgatg tcagggtgtt
34021 aaatagataa atcttagctt cctaggttgt atattcacac taattatttt tttatcagcc
34081 ttcttatttt tcaacttacc ttattctttt tgttttttg acactcagat ttgatagccc
34141 tgtggtagaa gaaaacagta atacagtttg gtttgttgtt gtgtttgtgt ttattttaaa
34201 gtcacggctt tgctttccat gttgttactg gattatgctt tttttaattc ttcagtttgc
34261 caagataaca gtcttccgat cttcagaagt ctgtatcaag cttaaggaaa ctgatgtgta
34321 ggaagactcg cctaagaagt ccaaattagc aaggctagca tgtgaggaca tgctggaaaa
34381 gaatagttcc catagatatt gacagagaat gttcataaaa tgctacttgt tttgtggtta
34441 catgagagta acttgtgtcc agtgcagctg tatgtaaggg caacgttttt attctgacga
```

Fig. 63M

```
34501 ctctgtggtt tcatgaccc tggatgctta tcatgtctct ctgttggact tcttcaacgg
34561 agttgataca aatacttgct tccaagtgtc catctgccct ctcctccatc ctggccccat
34621 acaaatacgc tacattttta aataatttga ataccctca atagtattta tattcctgg
34681 tgcttcattc tttccataag aactgtgata ccattattct gtaggatttt tttgtgcttc
34741 cccgtttcac atctctgtgc cagtgagacc catatatcgg tgcaaatcca gaagtttgat
34801 tgtccatctg attagcacac tgttagcaat gtggtggact aaacacagcc aagatgtggg
34861 gctggagctt agcctcctgg gagcagagcg gtgaacatca gatgaagaca tgtgaaaatg
34921 gagtactact tcctcttcct ggggatgggc taaaaagcac agccagaaat attcttgccc
34981 ttccagtctg ctttacagtt actcactggt tctctttttt ttcctactca gataaccagt
35041 atactcttcc cagtgactaa gaactgcaga taagtatagg tgcaaataga tggcaaaccg
35101 cagatggcag ctgtgtggtt tcagatgtgc tgcagaactt ttagacgatg tgaacgcaag
35161 gaactttttt gctgagcagt aatctctacc cactggaaat taggccctgg ggggaacaat
35221 gtagtgactt ctatatactt actacatgca gttagacccc tgaagcaaaa gcttttaaaa
35281 acaggctgta aaatgcccat gtatctttat taagcctatt tccaactgg atagagaaat
35341 tttctggtaa ttttttaaatt tgtaaagtct attttttttcc tgagccaagg gaaaaaaaat
35401 atctgggccc taaaagctta gttataacaa tgttattttt tctatctctg aatgattaaa
35461 tgtgatttca tttatgtagc aatactatga ttgtggctgc attagatcac gctgatagaa
35521 agatacaaag aaaaactaag tataatgaac taacaattta ttttcactct ttctctaagt
35581 taaaaattcc cagtacattc aaatgaacaa tgaaaataat tgcagaattg tctcctgaaa
35641 tggaaataga ttttttttcc caagcattag caatttcttg ttattttca aaatcagcca
35701 ctaagccttt cagagcttct tggtgactat tgcaggagaa atcagaatat taatcttgtg
35761 gttttatttc agagttcgct gccaggaagg aggtataatt gggataggag acttttttttt
35821 tttagctgtg tcactgttca aggagggggg tttggaacct cagcataaga attacactct
35881 gtgatgagga tgtagcaggg gagaagaaag gtgatttttca ctatgggaag ctatacttac
35941 atcaagtata aaatagactg aagtcatttt gaattacgtt atacttgtaa agtttacctc
36001 ctggagtttc agttagtacc agtgtactaa ctgggttaaa acagttcatg gcaccttaga
36061 tcatttctaa ctcatggcaa aaatctttcc tggtggaacg tgtaactgta ttttaaatgc
36121 cccttatataa gcaaccaagt atttgggatg ttattttgat attagtagtg aattttttcag
36181 tatcttccag tacccctttgc aagtcacagg ttgacttaaa aggaaaagaa gcaaaatgct
36241 gaatatagca gaaaaactgt ctgcattcag actgttcagc ccacttttgc tccccacgtg
36301 gcaagcacac tcccccaaac aagcaatagc ctgtggcttc agaggaacct acaaaggcag
36361 catctgtaga ttttttccttc tcaactcta agacttgaat gtttccctct tccccacaca
36421 ctttttttttt aaaccaagaa ataaaaagt tttcactctt aaaggtgcaa agcagtttca
36481 ttcttatgca acacagcctt cctcctactg tcttatagtc tgtggatgtt aaattataga
36541 ttccaattga atttttaatac tctagagatt ttacatttgt ggttgtcaag accccgtttt
36601 ggtaaaccta gggagctccg cacaaaagca tgatattca gaaaaggcac tgacctacaa
36661 attaaaagaa aaaaaaatca aataatgtgc acctcttgtg cttccagttt gacaaagcag
36721 aagtcatcag cagtttctcc ctctgcagac gcagttctca attctattta caagtaactg
36781 ctctactgtg cctgttttttc tcttgctgat actcatttaa ttgttttttct tttggatctg
36841 aatctttgac tgtcttttcc ccctcaagat taaaataaat acatctgtat tcctccccctt
36901 tctttctgtg cactgccctt cagatctcat tttgtcattt tcagcttag tgttgaaact
36961 tttagcaaca aaaagtcagt tacttacttt gagtaagtaa ctcaaagtaa gttaactttg
37021 agtttgagtg cacttttgcg tgtaggttca tttatgtgct tgtgaattta aaacattgg
37081 gattccacct gaatgaagta aaccaaacat tttaaactat cagccagata gagacatcag
37141 cctttcactt ctttctatat gcagacatat cctaatttt tagaaaaatc aaataggaaa
```

Fig. 63N

```
37201 attctcaaca attaattgaa gattatagct ctgctctgaa atggtccaga aataggatct
37261 gctcatagaa actcatagtt tgaagcctct gggaggaaag gatactttaa aatttagtca
37321 catatttgga ggagggaaaa gggaaagagc agaatgaaga actgaaaaaa atcacacacc
37381 ggggcctgtc gtgaggtggg ggactggggg agggatagca ttaggagata tacctaatgt
37441 aaatgacgag ttaacaggcg cagcccacca acatggcaca cgtatacata tgtaacaaac
37501 ctgcacgttg tgcacatgta ccctagaact taaagtataa taaaaaaaaa ttttaatagc
37561 cccattaaat aattaaaaag atttttttta gattcacaga agtgtacaaa attttaggt
37621 tttttttttt ttaagctgtc tgctgaatag tttcttaatg gtctacaatg tttgtatcta
37681 caaacagata ctgtctgctt cttactaccc ttccaagaca agtattatta tggcaattat
37741 tgcccagttt cccgggaaaa atttatccac agttacagaa gaatgagatg caattgtgag
37801 actgtaaagt ttaagcaagc actcagagaa gcacagtgat atgtatgcac agaagaggca
37861 gtctttgttt tgaggaaaac agtgaaagta aagttaattc aagaccacaa agacaagtaa
37921 ataagtgcct tatttttgta gttaatataa tttcagtgga atgcatattt ctaccataaa
37981 tgcatataga acttgtttgc tgacctactg tttggaaaac aaacaatccc attagaagaa
38041 tgtctttggg atttatttt accagaaaat caatcctttt tcagtccct tgcaaagtac
38101 agtgttacaa gccaagactt tgataatcag gtagaaaatg gatttaaatt gcagaaatgt
38161 atatgaaaca cttttgttcc ttgcccctg aactttaggg gaatgaaaat gtctagcact
38221 ctccaccttc ttttctctcc tggaacttga actgtaattc aaagcctgtt tctcattaaa
38281 gtacctggca gcctatctct ttacagcttg agttacaaag ctattcagag acctcgctgg
38341 tctaaagaga cagaacaagg atgtgtttaa atagagcata ggctgttgaa aaaaaaatg
38401 ctgaaaatgg taaaatgatt ctgtccttcc ttccactcct cactgctgag gtggagaggg
38461 aattcagttg gtgaacacca gcaagtggct ggtaaaagtc cccactttct ctccagggct
38521 gccacaggac ccagaatgag tggtgggcat gtgtgtgaac cctctattca gccagagttt
38581 tcccgcaaca ggtagtttgg ttgaagaggt tgactaaggt tgacattggc agtaataaca
38641 cgtatgttct tctgatttac aaaacgatgg aggaaaaagg ggagatttg aagacctgat
38701 ttctggtata cttcttaagc atgcataagg ctgaaaaaag aagacaaggg ttgtgggagg
38761 ctcctggtct agtgtttaca gaacttggat gcttgacaaa cagagcgtca agctaattgt
38821 tcttgaagca ggaaatctgc agtggaggaa gcaggtgtgg ggggatgatt accacgtttg
38881 gaaatggctg cattaactat tttgctcttc tgagtttggc cccaaaagag tccatagact
38941 ttttgaagga tgccatccct tttatttata gactaacatt aaatcagtca tttgtgaagg
39001 aaggagaaag tgcctaaata aatttggagt cagatagcat acgtgcggca gtgtttccga
39061 tatccatttc tctttatttc ttttctttt tctttttggc tttcagcatc cccatacttt
39121 cagaaaactt gtgactaaga gtgaattctt attttcaaa ttgttttcag acatttcatg
39181 ttcatgtaaa cttggcttat tgatttcctg attttctttt attttttgt tttgtccatt
39241 ttatttttaa tcagctacat caaatgggtc tttggagggc ctggataacc aggagggagg
39301 ggtgtgccag acaagagcca tgaagatcct catgaaagtt ggacaaggta aagaccatct
39361 gctgcttcat gacgccactg tgacctggtg tagcccccag ctagtatggt gctaatgttg
39421 ccgatgccca ccttcattcg ctcttctttt tagttttcaa agcaaaccct tctgcacttt
39481 gagccactga cagatttcct caagtcaatg tactaagctt ttattggaga tctaagagtt
39541 aagatcagca aggtagaatg tctattgcca tagatagata gatagataga tagataatag
39601 atagatagat agatagatag atatttcttt ttaaaaagca aaacactttg gttcaaaatc
39661 aaaatatcca gaatgaaaac taaagcttg tgcagttttg ctcatttctg aatcttgact
39721 acagaagagt tttgttcatt gtgactttc caatatagat aacctattgt gcagaaagaa
39781 ataattattc ttctaattaa aaattggtat agtagtcaat caacttgctc agttaaattg
39841 aaatgtcatc tgcaatgctt tgcctgccaa atgcaagaat ccctatagtt tccacagatg
```

Fig. 63O

```
39901 gcctcacgtt ctaaacctct gaaataacta gtataaccat tttgttttaa aagaaaaatt
39961 atattcttgt atttcacagt actttgcata aagactctta tgttcattgc tattcatgcc
40021 tgttgaaata tatatgcagc tcctaaagct agatattgtc agatgtctgt gccgtaatta
40081 atcatttgtt tttcatatag atgcaagttc tgctggatca accaggaata aagatccaac
40141 aagacgtcca gaactagaag ctggtacaaa tggaagaagt cgacaacaa gtccctttgt
40201 aaaaccaaat ccaggtataa cagcatgatc tgtgtgtatg gaggtctgtg ggtaccacat
40261 tcttagtagt atcttaaaag gtagggcaga gtctaaagac ttctaaccag ttaggattag
40321 ctggaagtta cagtgatcag gaatctttgc tgtcagtgag tcattattaa ttacactcaa
40381 taagaacaaa ataactcatt ccaatgaaag tcatatattc aaaggagtag agttcatgag
40441 ctgtaagtgc cagttattag aactactctg tcaggccaaa ggtttcattg gctgacattt
40501 tatcaagctg gttgtcaact ccagcttaaa gctgatgtta atgtatatgt aattaatgtg
40561 ctaatccctc atctaattat atctaagcca cagagggttt aattgatcct cttctaaatt
40621 ttaaatggta acattttaa atattgcata atagtatttt ttcaggtggt tatcgttatt
40681 ttgtttcaca ttttccatgt aaaagaaaat attaaacagg tccctgacaa aagtgtagaa
40741 taccagataa aattgtccgt cgttgacctt cgttttctta acagtcttgg aacaaatagt
40801 tctgtatttg ttaccatgct aatgaaggtt ttatagagta gctgttgagc agacatcagc
40861 agttttgtat taggattgtt gtgtgcttgc ttggtcgttg tgcaaattta tcgtctgcag
40921 caatattcca tccctttcca agagtcaagg agggaagttg ttatttctaa ctttcaatga
40981 caagatgtgt caaattcttg tgacaaactg ataaatggat aatataatga tgccaggcag
41041 tttttagtg cttaacattt gggctggcag tctgttcggt gtgagagttt ctgctgcctt
41101 ccaaatatat tttaagtgta aatcaaataa tacagacgag ttacgagctg aacattttcc
41161 caggccccct cactccttcc gcgttcccga gctgttctgt tctgccagga ggcagggctc
41221 ttctttagaa ggcaggccct ttgaaggttt gcatgaaact ccctttctca aggaggcgg
41281 aagagcaata ccacataaac gctcaccgct gacctggaga attggccact tccctttttc
41341 ttccctgccg ctgccccagg ctggctgaca cgggttagaa gatgaagcaa gatcaagggc
41401 tggctgtcac cgacagtctg tgctcttgct ggataatgat acaaaggaaa ccctgtggct
41461 tgggagggta gggaagtccc tcctagagat acctctcatt tccttttgcg ttgagctctt
41521 agacgaggta ttggcgaggc aaagtccagc ttctagttag taataagcct ggcttatttt
41581 tcacattttt aagggtcata aaagcagtcc gtctgcactg ggacagcagt aactatctct
41641 gaccttttct gtctccgcgt ctgcaggttc tagcacagac ggcaacagcg ccggacattc
41701 ggggaacaac atcctcggtt ccgaagtggc cttatttgca gggattgctt caggatgcat
41761 catcttcatc gtcatcatca tcacgctggt ggtcctcttg ctgaagtacc ggaggagaca
41821 caggaagcac tcgccgcagc acacgaccac gctgtcgctc agcacactgg ccacacccaa
41881 gcgcagcggc aacaacaacg gctcagagcc cagtgacatt atcatcccgc taaggactgc
41941 ggacagcgtc ttctgccctc actacgagaa ggtcagcggc gactacgggc accggtgta
42001 catcgtccag gagatgcccc cgcagagccc ggcgaacatt tactacaagg tctgagaggg
42061 accctggtgg tacctgtgct ttcccagagg acacctaatg tcccgatgcc tcccttgagg
42121 gtttgagagc ccgcgtgctg gagaattgac tgaagcacag caccggggga gagggacact
42181 cctcctcgga agagcccgtc gcgctggaca gcttacctag tcttgtagca ttcggccttg
42241 gtgaacacac acgctccctg gaagctggaa gactgtgcag aagacgccca ttcggactgc
42301 tgtgccgcgt cccacgtctc ctcctcgaag ccatgtgctg cggtcactca ggcctctgca
42361 gaagccaagg gaagacagtg gtttgtggac gagagggctg tgagcatcct ggcaggtgcc
42421 ccaggatgcc acgcctggaa gggccggctt ctgcctgggg tgcatttccc ccgcagtgca
42481 taccggactt gtcacacgga cctcgggcta gttaaggtgt gcaaagatct ctagagttta
42541 gtccttactg tctcactcgt tctgttaccc agggctctgc agcacctcac ctgagacctc
```

Fig. 63P

```
42601 cactccacat ctgcatcact catggaacac tcatgtctgg agtcccctcc tccagccgct
42661 ggcaacaaca gcttcagtcc atgggtaatc cgttcataga aattgtgttt gctaacaagg
42721 tgcccttag ccagatgcta ggctgtctgc gaagaaggct aggagttcat agaagggagt
42781 ggggctgggg aaagggctgg ctgcaattgc agctcactgc tgctgcctct gaaacagaaa
42841 gttggaaagg aaaaaagaaa aaagcaatta ggtagcacag cactttggtt ttgctgagat
42901 cgaagaggcc agtaggagac acgacagcac acacagtgga ttccagtgca tggggaggca
42961 ctcgctgtta tcaaatagcg atgtgcagga agaaaagccc ctcttcattc cggggaacaa
43021 agacgggtat tgttgggaaa ggaacaggct tggagggaag ggagaaagta ggccgctgat
43081 gatatattcg ggcaggactg ttgtggtact ggcaataaga tacacagctc cgagctgtag
43141 gagagtcggt ctgctttgga tgattttta agcagactca gctgctatac ttatcacatt
43201 ttattaaaca cagggaaagc atttaggaga atagcagaga gccaaatctg acctaaaagt
43261 tgaaaagcca aaggtcaaac aggctgtaat tccatcatca tcgttgttat taaagaatcc
43321 ttatctataa aaggtaggtc agatccccct cccccaggt tcctccttcc cctcccgatt
43381 gagccttacg acactttggt ttatgcggtg ctgtccgggt gccagggctg cagggtcggt
43441 actgatggag gctgcagcgc ccggtgctct gtgtcaaggt gaagcacata cggcagacct
43501 cttagagtcc ttaagacgga agtaaattat gatgtccagg gggagaagga agataggacg
43561 tatttataat aggtatatag aacacaaggg atataaaatg aagatttttt actaatatat
43621 attttaaggt tgcacacagt acacaccaga agatgtgaaa ttcatttgtg gcaattaagt
43681 ggtcccaatg ctcagcgctt aaaaaaacaa attggacagc tacttctggg aaaaacaaca
43741 tcattccaaa aagaacaata atgagagcaa atgcaaaaat aaccaagtcc tccgaaggca
43801 tctcacggaa ccgtagacta ggaagtacga gccccacaga gcaggaagcc gatgtgactg
43861 catcatatat ttaacaatga caagatgttc cggcgtttat ttctgcgttg ggtttccct
43921 tgccttatgg gctgaagtgt tctctaga
```

Fig. 63Q

EphrinB2, mRNA

```
   1 gcgcggagct gggagtggct tcgccatggc tgtgagaagg gactccgtgt ggaagtactg
  61 ctggggtgtt ttgatggttt tatgcagaac tgcgatttcc aaatcgatag ttttagagcc
 121 tatctattgg aattcctcga actccaaatt tctacctgga caaggactgg tactataccc
 181 acagatagga gacaaattgg atattatttg ccccaaagtg gactctaaaa ctgttggcca
 241 gtatgaatat tataaagttt atatggttga taaagaccaa gcagacagat gcactattaa
 301 gaaggaaaat accctctcc tcaactgtgc caaaccagac aagatatca aattcaccat
 361 caagtttcaa gaattcagcc ctaacctctg gggtctagaa tttcagaaga caaagatta
 421 ttacattata tctacatcaa atgggtcttt ggagggcctg gataaccagg agggagggt
 481 gtgccagaca agagccatga agatcctcat gaaagttgga caagatgcaa gttctgctgg
 541 atcaaccagg aataaagatc aacaagacg tccagaacta gaagctggta caaatggaag
 601 aagttcgaca acaagtccct tgtaaaacc aaatccaggt tctagcacag acggcaacag
 661 cgccggacat tcggggaaca acatcctcgg ttccgaagtg gccttatttg cagggattgc
 721 ttcaggatgc atcatcttca tgtcatcat catcacgctg gtggtcctct tgctgaagta
 781 ccggaggaga cacaggaagc actcgccgca gcacgacc acgctgtcgc tcagcacact
 841 ggccacaccc aagcgcagcg gcaacaacaa cggctcagag cccagtgaca ttatcatccc
 901 gctaaggact gcggacagcg tcttctgccc tcactacgag aaggtcagcg ggactacgg
 961 gcacccggtg tacatcgtcc aggagatgcc cccgcagagc ccggcgaaca tttactacaa
1021 ggtctgagag ggaccctggt ggtacctgtg ctttcccaga ggacacctaa tgtcccgatg
1081 cctcccttga gggtttgaga gcccgcgtgc tggagaattg actgaagcac agcaccgggg
1141 gagagggaca ctcctcctcg gaagagcccg tcgcgctgga cagcttacct agtcttgtag
1201 cattcggcct tggtgaacac acacgctccc tggaagctgg aagactgtgc agaagacgcc
1261 cattcggact gctgtgccgc gtcccacgtc tcctcctcga agccatgtgc tgcggtcact
1321 caggcctctg cagaagccaa gggaagacag tggtttgtgg acgagagggc tgtgagcatc
1381 ctggcaggtg ccccaggatg ccacgcctgg aagggccggc ttctgcctgg ggtgcatttc
1441 ccccgcagtg cataccggac ttgtcacacg gacctcgggc tagttaaggt gtgcaaagat
1501 ctctagagtt tagtccttac tgtctcactc gttctgttac ccagggctct gcagcacctc
1561 acctgagacc tccactccac atctgcatca ctcatggaac actcatgtct ggagtccct
1621 cctccagccg ctggcaacaa cagcttcagt ccatgggtaa tccgttcata gaaattgtgt
1681 ttgctaacaa ggtgcccttt agccagatgc taggctgtct gcgaagaagg ctaggagttc
1741 atagaaggga gtggggctgg ggaaagggct ggctgcaatt gcagctcact gctgctgcct
1801 ctgaaacaga aagttggaaa ggaaaaaaga aaaagcaat taggtagcac agcactttgg
1861 ttttgctgag atcgaagagg ccagtaggag acacgacagc acacacagtg gattccagtg
1921 catggggagg cactcgctgt tatcaaatag cgatgtgcag gaagaaaagc ccctcttcat
1981 tccggggaac aaagacgggt attgttggga aggaacagg cttggaggga agggagaaag
2041 taggccgctg atgatatatt cgggcaggac tgttgtggta ctggcaataa gatacacagc
2101 tccgagctgt aggagagtcg gtctgctttg gatgattttt taagcagact cagctgctat
2161 acttatcaca ttttattaaa cacagggaaa gcatttagga gaatagcaga gagccaaatc
2221 tgacctaaaa gttgaaaagc caaaggtcaa acaggctgta attccatcat catcgttgtt
2281 attaaagaat ccttatctat aaaaggtagg tcagatcccc ctcccccag gttcctcctt
2341 cccctcccga ttgagcctta cgacactttg gtttatgcgg tgctgtccgg gtgccagggc
2401 tgcagggtcg gtactgatgg aggctgcagc gcccggtgct ctgtgtcaag gtgaagcaca
2461 tacggcagac ctcttagagt ccttaagacg gaagtaaatt atgatgtcca gggggagaag
2521 gaagatagga cgtatttata ataggtatat agaacacaag ggatataaaa tgaaagattt
2581 ttactaatat atattttaag gttgcacaca gtacacacca gaagatgtga aattcatttg
```

Fig. 64A

```
2641 tggcaattaa gtggtcccaa tgctcagcgc ttaaaaaaac aaattggaca gctacttctg
2701 ggaaaaacaa catcattcca aaaagaacaa taatgagagc aaatgcaaaa ataaccaagt
2761 cctccgaagg catctcacgg aaccgtagac taggaagtac gagccccaca gagcaggaag
2821 ccgatgtgac tgcatcatat atttaacaat gacaagatgt tccggcgttt atttctgcgt
2881 tgggttttcc cttgccttat gggctgaagt gttctctaga atccagcagg tcacactggg
2941 ggcttcaggt gacgatttag ctgtggctcc ctcctcctgt cctcccccgc accccctccc
3001 ttctgggaaa caagaagagt aaacaggaaa cctacttttt atgtgctatg caaaatagac
3061 atctttaaca tagtcctgtt actatggtaa cactttgctt tctgaattgg aagggaaaaa
3121 aaatgtagcg acagcatttt aaggttctca gacctccagt gagtacctgc aaaaatgagt
3181 tgtcacagaa attatgatcc tctatttcct gaacctggaa atgatgttgg tccaaagtgc
3241 gtgtgtgtat gtgtgagtgg gtgcgtggta tacatgtgta catatatgta taatatatat
3301 ctacaatata tattatatat atctatatca tatttctgtg gagggttgcc atggtaacca
3361 gccacagtac atatgtaatt cttttccatca ccccaacctc tcctttctgt gcattcatgc
3421 aagagtttct tgtaagccat cagaagttac ttttaggatg ggggagaggg gcgagaaggg
3481 gaaaaatggg aaatagtctg attttaatga aatcaaatgt atgtatcatc agttggctac
3541 gttttggttc tatgctaaac tgtgaaaaat cagatgaatt gataaaagag ttccctgcaa
3601 ccaattgaaa agtgttctgt gcgtctgttt tgtgtctggt gcagaatatg acaatctacc
3661 aactgtccct tgtttgaag ttggtttagc tttggaaagt tactgtaaat gccttgcttg
3721 tatgatcgtc cctggtcacc cgactttgga atttgcacca tcatgtttca gtgaagatgc
3781 tgtaaatagg ttcagatttt actgtctatg gatttggggt gttacagtag ccttattcac
3841 ctttttaata aaaatacaca tgaaaacaag aaagaaatgg cttttcttac ccagattgtg
3901 tacatagagc aatgttggtt ttttataaag tctaagcaag atgttttgta taaaatctga
3961 attttgcaat gtatttagct acagcttgtt taacggcagt gtcattcccc tttgcactgt
4021 aatgaggaaa aaatggtata aaaggttgcc aaattgctgc atatttgtgc cgtaattatg
4081 taccatgaat atttatttaa aatttcgttg tccaatttgt aagtaacaca gtattatgcc
4141 tgagttataa atattttttt ctttctttgt tttattttaa tagcctgtca taggttttaa
4201 atctgcttta gtttcacatt gcagttagcc ccagaaaatg aaatccgtga agtcacattc
4261 cacatctgtt tcaaactgaa tttgttctta aaaaaataaa atatttttttt cctatggaaa
4321 aaaaaaaaa aaaaa
```

Fig. 64B

EphB4 Precursor Protein

```
  1 melrvllcwa slaaaleetl lntkletadl kwvtfpqvdg qweelsglde eqhsvrtyev
 61 cdvqrapgqa hwlrtgwvpr rgavhvyatl rftmleclsl pragrscket ftvfyyesda
121 dtataltpaw menpyikvdt vaaehltrkr pgaeatgkvn vktlrlgpls kagfylafqd
181 qgacmallsl hlfykkcaql tvnltrfpet vprelvvpva gscvvdavpa pgpspslycr
241 edgqwaeqpv tgcscapgfe aaegntkcra caqgtfkpls gegscqpcpa nshsntigsa
301 vcqcrvgyfr artdprgapc ttppsaprsv vsrlngsslh lewsaplesg gredltyalr
361 crecrpggsc apcggdltfd pgprdlvepw vvvrglrpdf tytfevtaln gvsslatgpv
421 pfepvnvttd revppavsdi rvtrsspssl slawavprap sgavldyevk yhekgaegps
481 svrflktsen raelrglkrg asylvqvrar seagygpfgq ehhsqtqlde segwreqlal
541 iagtavvgvv lvlvvivvav lclrkqsngr eaeysdkhgq ylighgtkvy idpftyedpn
601 eavrefakei dvsyvkieev igagefgevc rgrlkapgkk escvaiktlk ggyterqrre
661 flseasimgq fehpniirle gvvtnsmpvm iltefmenga ldsflrlndg qftviqlvgm
721 lrgiasgmry laemsyvhrd laarnilvns nlvckvsdfg lsrfleenss dptytsslgg
781 kipirwtape aiafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qisaedllri gvtlaghqkk
961 ilasvqhmks qakpgtpggt ggpapqy
```

Fig. 65

EphrinB2

```
  1 mavrrdsvwk ycwgvlmvlc rtaisksivl epiywnssns kflpgqglvl ypqigdkldi
 61 icpkvdsktv gqyeyykvym vdkdqadrct ikkentplln cakpdqdikf tikfqefspn
121 lwglefqknk dyyiistsng sleglndqeg gvcqtramki lmkvgqdass agstrnkdpt
181 rrpeleagtn grssttspfv kpnpgsstdg nsaghsgnni lgsevalfag iasgciifiv
241 iiitlvvlll kyrrrhrkhs pqhtttlsls tlatpkrsgn nngsepsdii iplrtadsvf
301 cphyekvsgd yghpvyivqe mppqspaniy ykv
```

POLYPEPTIDE COMPOUNDS FOR INHIBITING ANGIOGENESIS AND TUMOR GROWTH

RELATED APPLICATIONS

This application claims the benefit of priority of U.S. Provisional Application No. 60/454,300 filed Mar. 12, 2003 and U.S. Provisional Application No. 60/454,432 filed Mar. 12, 2003. The entire teachings of the referenced Provisional Applications are incorporated herein by reference in their entirety.

BACKGROUND OF THE INVENTION

Angiogenesis, the development of new blood vessels from the endothelium of a preexisting vasculature, is a critical process in the growth, progression, and metastasis of solid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis.

It is generally thought that the development of tumor consists of sequential, and interrelated steps that lead to the generation of an autonomous clone with aggressive growth potential. These steps include sustained growth and unlimited self-renewal. Cell populations in a tumor are generally characterized by growth signal self-sufficiency, decreased sensitivity to growth suppressive signals, and resistance to apoptosis. Genetic or cytogenetic events that initiate aberrant growth sustain cells in a prolonged "ready" state by preventing apoptosis.

It is a goal of the present disclosure to provide agents and therapeutic treatments for inhibiting angiogenesis and tumor growth.

SUMMARY OF THE INVENTION

In certain aspects, the disclosure provides polypeptide agents that inhibit EphB4 or EphrinB2 mediated functions, including monomeric ligand binding portions of the EphB4 and EphrinB2 proteins and antibodies that bind to and affect EphB4 or EphrinB2 in particular ways. As demonstrated herein, EphB4 and EphrinB2 participate in various disease states, including cancers and diseases related to unwanted or excessive angiogenesis. Accordingly, certain polypeptide agents disclosed herein may be used to treat such diseases. In further aspects, the disclosure relates to the discovery that EphB4 and/or EphrinB2 are expressed, often at high levels, in a variety of tumors. Therefore, polypeptide agents that downregulate EphB4 or EphrinB2 function may affect tumors by a direct effect on the tumor cells as well as an indirect effect on the angiogenic processes recruited by the tumor. In certain embodiments, the disclosure provides the identity of tumor types particularly suited to treatment with an agent that downregulates EphB4 or EphrinB2 function.

In certain aspects, the disclosure provides soluble EphB4 polypeptides comprising an amino acid sequence of an extracellular domain of an EphB4 protein. The soluble EphB4 polypeptides bind specifically to an EphrinB2 polypeptide. The term "soluble" is used merely to indicate that these polypeptides do not contain a transmembrane domain or a portion of a transmembrane domain sufficient to compromise the solubility of the polypeptide in a physiological salt solution. Soluble polypeptides are preferably prepared as monomers that compete with EphB4 for binding to ligand such as EphrinB2 and inhibit the signaling that results from EphB4 activation. Optionally, a soluble polypeptide may be prepared in a multimeric form, by, for example, expressing as an Fc fusion protein or fusion with another multimerization domain. Such multimeric forms may have complex activities, having agonistic or antagonistic effects depending on the context. In certain embodiments the soluble EphB4 polypeptide comprises a globular domain of an EphB4 protein. A soluble EphB4 polypeptide may comprise a sequence at least 90% identical to residues 1-522 of the amino acid sequence defined by FIG. 65. A soluble EphB4 polypeptide may comprise a sequence at least 90% identical to residues 1-412 of the amino acid sequence defined by FIG. 65. A soluble EphB4 polypeptide may comprise a sequence at least 90% identical to residues 1-312 of the amino acid sequence defined by FIG. 65. A soluble EphB4 polypeptide may comprise a sequence as set forth in FIG. 1 or 2. In certain embodiments, the soluble EphB4 polypeptide may inhibit the interaction between Ephrin B2 and EphB4. The soluble EphB4 polypeptide may inhibit clustering of or phosphorylation of Ephrin B2 or EphB4. Phosphorylation of EphrinB2 or EphB4 is generally considered to be one of the initial events in triggering intracellular signaling pathways regulated by these proteins. As noted above, the soluble EphB4 polypeptide may be prepared as a monomeric or multimeric fusion protein. The soluble polypeptide may include one or more modified amino acids. Such amino acids may contribute to desirable properties, such as increased resistance to protease digestion.

In certain aspects, the disclosure provides soluble EphrinB2 polypeptides comprising an amino acid sequence of an extracellular domain of an EphrinB2 protein. The soluble EphrinB2 polypeptides bind specifically to an EphB4 polypeptide. The term "soluble" is used merely to indicate that these polypeptides do not contain a transmembrane domain or a portion of a transmembrane domain sufficient to compromise the solubility of the polypeptide in a physiological salt solution. Soluble polypeptides are preferably prepared as monomers that compete with EphrinB2 for binding to ligand such as EphB4 and inhibit the signaling that results from EphrinB2 activation. Optionally, a soluble polypeptide may be prepared in a multimeric form, by, for example, expressing as an Fc fusion protein or fusion with another multimerization domain. Such multimeric forms may have complex activities, having agonistic or antagonistic effects depending on the context. A soluble EphrinB2 polypeptide may comprise residues 1-225 of the amino acid sequence defined by FIG. 66. A soluble EphrinB2 polypeptide may comprise a sequence defined by FIG. 3. In certain embodiments, the soluble EphrinB2 polypeptide may inhibit the interaction between Ephrin B2 and EphB4. The soluble EphrinB2 polypeptide may inhibit clustering of or phosphorylation of EphrinB2 or EphB4. As noted above, the soluble EphrinB2 polypeptide may be prepared as a monomeric or multimeric fusion protein. The soluble polypeptide may include one or more modified amino acids. Such amino acids may contribute to desirable properties, such as increased resistance to protease digestion.

In certain aspects, the disclosure provides antagonist antibodies for EphB4 and EphrinB2. An antibody may be designed to bind to an extracellular domain of an EphB4 protein and inhibit an activity of the EphB4. An antibody may be designed to bind to an extracellular domain of an Ephrin B2 protein and inhibit an activity of the Ephrin B2. An antibody may be designed to inhibit the interaction between Ephrin B2 and EphB4. An antagonist antibody will generally affect Eph and/or Ephrin signaling. For example, an antibody may inhibit clustering or phosphorylation of Ephrin B2 or EphB4. An antagonist antibody may be essentially any polypeptide comprising a variable portion of an antibody, including, for example, monoclonal and polyclonal antibodies, single chain antibodies, diabodies, minibodies, etc.

In certain aspects, the disclosure provides pharmaceutical formulations comprising a polypeptide reagent and a pharmaceutically acceptable carrier. The polypeptide reagent may be any disclosed herein, including, for example, soluble EphB4 or EphrinB2 polypeptides and antagonist antibodies. Additional formulations include cosmetic compositions and diagnostic kits.

In certain aspects the disclosure provides methods of inhibiting signaling through Ephrin B2/EphB4 pathway in a cell. A method may comprise contacting the cell with an effective amount of a polypeptide agent, such as (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; or (d) an antibody which binds to an extracellular domain of an Ephrin B2 protein and inhibits an activity of the Ephrin B2.

In certain aspects the disclosure provides methods for reducing the growth rate of a tumor, comprising administering an amount of a polypeptide agent sufficient to reduce the growth rate of the tumor, wherein the polypeptide agent is selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2. Optionally, the tumor comprises cells expressing a higher level of EphB4 and/or EphrinB2 than noncancerous cells of a comparable tissue.

In certain aspects, the disclosure provides methods for treating a patient suffering from a cancer. A method may comprise administering to the patient a polypeptide agent selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2. Optionally, the cancer comprises cancer cells expressing EphrinB2 and/or EphB4 at a higher level than noncancerous cells of a comparable tissue. The cancer may be a metastatic cancer. The cancer may be selected from the group consisting of colon carcinoma, breast tumor, mesothelioma, prostate tumor, squamous cell carcinoma, Kaposi sarcoma, and leukemia. Optionally, the cancer is an angiogenesis-dependent cancer or an angiogenesis independent cancer. The polypeptide agent employed may inhibit clustering or phosphorylation of Ephrin B2 or EphB4. A polypeptide agent may be co-administered with one or more additional anti-cancer chemotherapeutic agents that inhibit cancer cells in an additive or synergistic manner with the polypeptide agent.

In certain aspects, the disclosure provides methods of inhibiting angiogenesis. A method may comprise contacting a cell with an amount of a polypeptide agent sufficient to inhibit angiogenesis, wherein the polypeptide agent is selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2.

In certain aspects, the disclosure provides methods for treating a patient suffering from an angiogenesis-associated disease, comprising administering to the patient a polypeptide agent selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2. The soluble polypeptide may be formulated with a pharmaceutically acceptable carrier. An angiogenesis related disease or unwanted angiogenesis related process may be selected from the group consisting of angiogenesis-dependent cancer, benign tumors, inflammatory disorders, chronic articular rheumatism and psoriasis, ocular angiogenic diseases, Osler-Webber Syndrome, myocardial angiogenesis, plaque neovascularization, telangiectasia, hemophiliac joints, angiofibroma, wound granulation, wound healing, telangiectasia psoriasis scleroderma, pyogenic granuloma, cororany collaterals, ischemic limb angiogenesis, rubeosis, arthritis, diabetic neovascularization, fractures, vasculogenesis, and hematopoiesis. An polypeptide agent may be co-administered with at least one additional anti-angiogenesis agent that inhibits angiogenesis in an additive or synergistic manner with the soluble polypeptide.

In certain aspects, the disclosure provides for the use of a polypeptide agent in the manufacture of medicament for the treatment of cancer or an angiogenesis related disorder, wherein the polypeptide agent is selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2.

In certain aspects, the disclosure provides methods for for treating a patient suffering from a cancer, comprising: (a) identifying in the patient a tumor having a plurality of cancer cells that express EphB4 and/or EphrinB2; and (b) administering to the patient a polypeptide agent selected from the group consisting of: (i) a soluble polypeptide comprising an amino acid sequence of an extracellular domain of an EphB4 protein, wherein the EphB4 polypeptide is a monomer and binds specifically to an Ephrin B2 polypeptide; (ii) a soluble polypeptide comprising an amino acid sequence of an extracellular domain of an Ephrin B2 protein, wherein the soluble Ephrin B2 polypeptide is a monomer and binds with high affinity to an EphB4 polypeptide; (iii) an antibody which binds to an extracellular domain of an EphB4 protein and inhibits an activity of the EphB4; and (iv) an antibody which binds to an extracellular domain of an Ephrin B2 protein and inhibits an activity of the Ephrin B2. Optionally, a method may comprise identifying in the patient a tumor having a plurality of cancer cells having a gene amplification of the EphB4 and/or EphrinB2 gene.

In certain aspects, the disclosure provides methods for identifying a tumor that is suitable for treatment with an EphrinB2 or EphB4 antagonist. A method may comprise detecting in the tumor cell one or more of the following characteristics: (a) expression of EphB4 protein and/or mRNA; (b) expression of EphrinB2 protein and/or mRNA; (c) gene amplification of the EphB4 gene; or (d) gene amplification of the EphrinB2 gene. A tumor cell having one or more of characteristics (a)-(d) may be suitable for treatment with an EphrinB2 or EphB4 antagonist, such as a polypeptide agent described herein.

BRIEF DESCRIPTION OF THE DRAWINGS

FIG. 1 shows amino acid sequence of the B4ECv3 protein (predicted sequence of the precursor including uncleaved Eph B4 leader peptide is shown), SEQ ID NO: 386.

FIG. 2 shows amino acid sequence of the B4ECv3NT protein (predicted sequence of the precursor including uncleaved Eph B4 leader peptide is shown), SEQ ID NO: 387.

FIG. 3 shows amino acid sequence of the B2EC protein (predicted sequence of the precursor including uncleaved Ephrin B2 leader peptide is shown), SEQ ID NO: 388.

FIG. 4 shows amino acid sequence of the B4ECv3-FC protein (predicted sequence of the precursor including uncleaved Eph B4 leader peptide is shown), SEQ ID NO: 389.

FIG. 5 shows amino acid sequence of the B2EC-FC protein (predicted sequence of the precursor including uncleaved Ephrin B2 leader peptide is shown), SEQ ID NO: 390.

(green), or EphB4 (red) of frozen KS biopsy material directly demonstrates co-expression of LANA1 and ephrin B2 in KS biopsy. Coexpression is seen as yellow color. Double label confocal image of biopsy with antibodies to PECAM-1 (green) in cells with nuclear propidium iodide stain (red), demonstrating the vascular nature of the tumor.

Figure 46A:
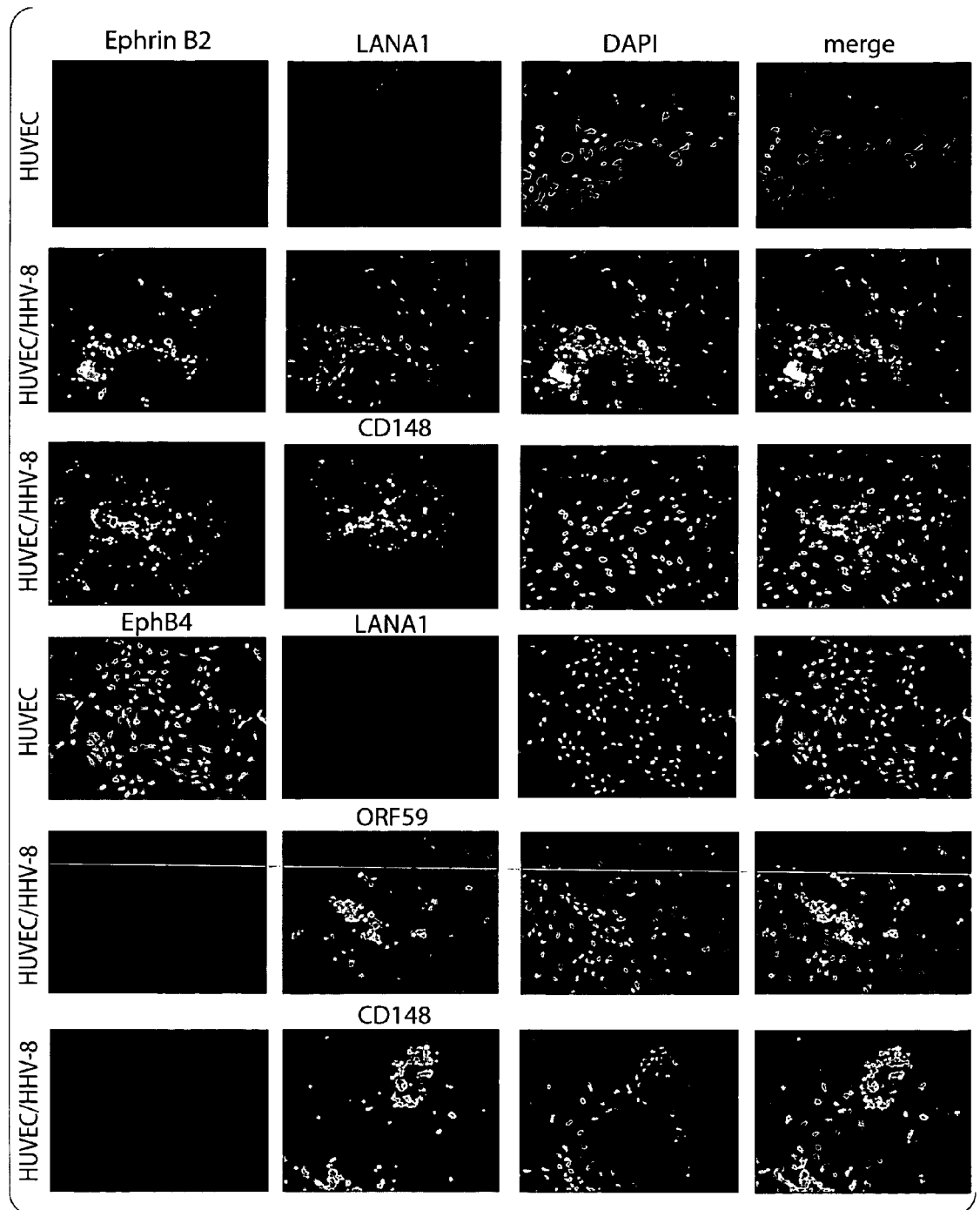

FIG. 46 shows that HHV-8 induces arterial marker expression in venous endothelial cells. (A) Immunofluorescence of cultures of HUVEC and HUVEC/BC-1 for artery/vein markers and viral proteins. Cultures were grown on chamber slides and processed for immunofluorescence detection of ephrin B2 (a, e, i), EphB4 (m, q, u), CD148 (j, v), and the HHV-8 proteins LANA1 (b, f, m) or ORF59 (r) as described in the Materials and Methods. Yellow color in the merged images of the same field demonstrate co-expression of ephrin B2 and LANA or ephrin B2 and CD148. The positions of viable cells were revealed by nuclear staining with DAPI (blue) in the third column (c, g, k, o, s, w). Photomicrographs are of representative fields. (B) RT-PCR of HUVEC and two HHV-8 infected cultures (HUVEC/BC-1 and HUVEC/BC-3) for ephrin B2 and EphB4. Ephrin B2 product (200 bp) is seen in HUVEC/BC-1, HUVEC/BC-3 and EphB4 product (400 bp) is seen in HUVEC. Shown also is β-actin RT-PCR as a control for amount and integrity of input RNA.

FIG. 47 shows that HHV-8 induces arterial marker expression in Kaposi's sarcoma cells. (A) Western blot for ephrin B2 on various cell lysates. SLK-vGPCR is a stable clone of SLK expressing the HHV-8 vGPCR, and SLK-pCEFL is control stable clone transfected with empty expression vector. SLK cells transfected with LANA or LANAΔ440 are SLK-LANA and SLK-Δ440 respectively. Quantity of protein loading and transfer was determined by reprobing the membranes with β-actin monoclonal antibody. (B) Transient transfection of KS-SLK cells with expression vector pvGPCR-CEFL resulted in the expression of ephrin B2 as shown by immunofluorescence staining with FITC (green), whereas the control vector pCEFL had no effect. KS-SLK cells (0.8×105/well) were transfected with 0.8 µg DNA using Lipofectamine 2000. 24 hr later cells were fixed and stained with ephrin B2 polyclonal antibody and FITC conjugated secondary antibody as described in the methods. (C) Transient transfection of HUVEC with vGPCR induces transcription from ephrin B2 luciferase constructs. 8×103 HUVEC in 24 well plates were transfected using Superfect with 0.8 µg/well ephrin B2 promoter constructs containing sequences from −2941 to −11 with respect to the translation start site, or two 5'-deletions as indicated, together with 80 ng/well pCEFL or pvGPCR-CEFL. Luciferase was determined 48 h post transfection and induction ratios are shown to the right of the graph. pGL3Basic is promoterless luciferase control vector. Luciferase was normalized to protein since GPCR induced expression of the cotransfected β-galactosidase. Graphed is mean ±SEM of 6 replicates. Shown is one of three similar experiments.

FIG. 48 shows that VEGF and VEGF-C regulate ephrin B2 expression. A) Inhibition of ephrin B2 by neutralizing antibodies. Cells were cultured in full growth medium and exposed to antibody (100 ng/ml) for 36 hr before collection and lysis for Western blot. B) For induction of ephrin B2 expression cells were cultured in EBM growth medium containing 5% serum lacking growth factors. Individual growth factors were added as indicated and the cells harvested after 36 h. Quantity of protein loading and transfer was determined by reprobing the membranes β-actin monoclonal antibody.

FIG. 49 shows that Ephrin B2 knock-down with specific siRNA inhibits viability in KS cells and HUVEC grown in the presence of VEGF but not IGF, EGF or bFGF. A) KS-SLK cells were transfected with various siRNA to ephrin B2 and controls. After 48 hr the cells were harvested and crude cell lysates fractionated on 4-20% SDS-PAGE. Western blot was performed with monoclonal antibody to ephrin B2 generated in-house. The membrane was stripped and reprobed with β-actin monoclonal antibody (Sigma) to illustrate equivalent loading and transfer. B) 3 day cell viability assay of KS-SLK cultures in the presence of ephrin B2 and EphB4 siRNAs. $1 \times 10^5$ cells/well in 24-well plates were treated with 0, 10 and 100 ng/ml siRNAs as indicated on the graph. Viability of cultures was determined by MTT assay as described in the methods section. Shown are the mean+standard deviation of duplicate samples. C) HUVE cells were seeded on eight wells chamber slides coated with fibronectin. The HUVE cells were grown overnight in EGM-2 media, which contains all growth supplements. On the following day, the media was replaced with media containing VEGF (10 ng/ml) or EGF, FGF and IGF as indicated. After 2 hrs of incubation at 37° C., the cells were transfected using Lipofectamine 2000 (Invitrogen) in Opti-MEM medium containing 10 nM of siRNA to ephrin B2, Eph B4 or green fluorescence protein (GFP) as control. The cells were incubated for 2 hr and then the fresh media containing growth factors or VEGF alone was added to their respective wells. After 48 hrs, the cells were stained with crystal violet and the pictures were taken immediately by digital camera at 10× magnification.

Figure 50:
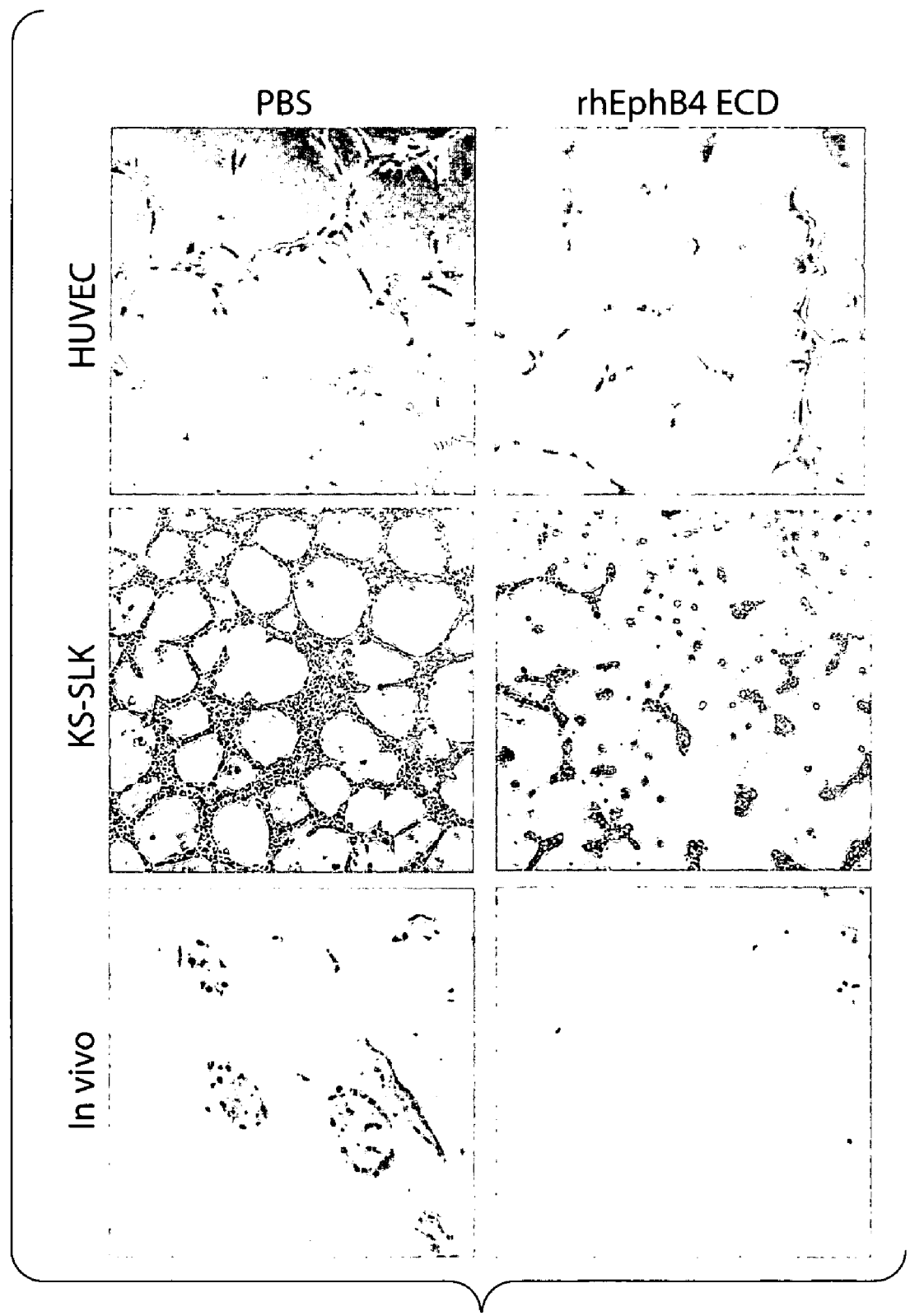

FIG. 50 shows that soluble EphB4 inhibits KS and EC cord formation and in vivo angiogenesis. Cord formation assay of HUVEC in Matrigel™ (upper row). Cells in exponential growth phase were treated overnight with the indicated concentrations of EphB4 extracellular domain (ECD) prior to plating on Matrigel™. Cells were trypsinized and plated ($1 \times 10^5$ cells/well) in a 24-well plate containing 0.5 ml Matrigel™. Shown are representative 20× phase contrast fields of cord formation after 8 hr plating on Matrigel™ in the continued presence of the test compounds as shown. Original magnification 200×. KS-SLK cells treated in a similar manner (middle row) in a cord formation assay on Matrigel™. Bottom row shows in vivo Matrigel™ assay: Matrigel™ plugs containing growth factors and EphB4 ECD or PBS were implanted subcutaneously in the mid-ventral region of mice. After 7 days the plugs were removed, sectioned and stained with H&E to visualize cells migrating into the matrix. Intact vessels with large lumens are observed in the control, whereas EphB4 ECD almost completely inhibited migration of cells into the Matrigel.

FIG. 51 shows expression of EPHB4 in bladder cancer cell lines (A), and regulation of EPHB4 expression by EGFR signaling pathway (B).

Figure 52:
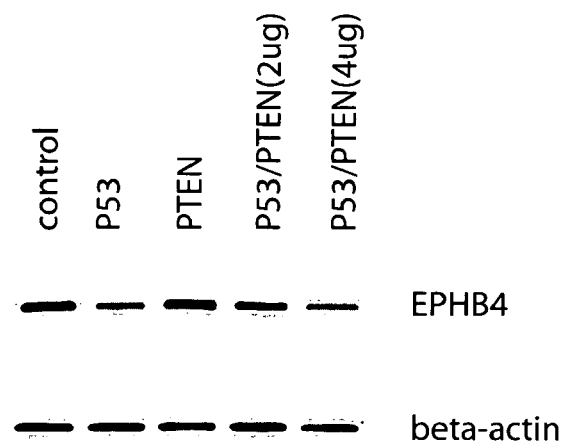

FIG. 52 shows that transfection of p53 inhibit the expression of EPHB4 in 5637 cell.

Figure 53:
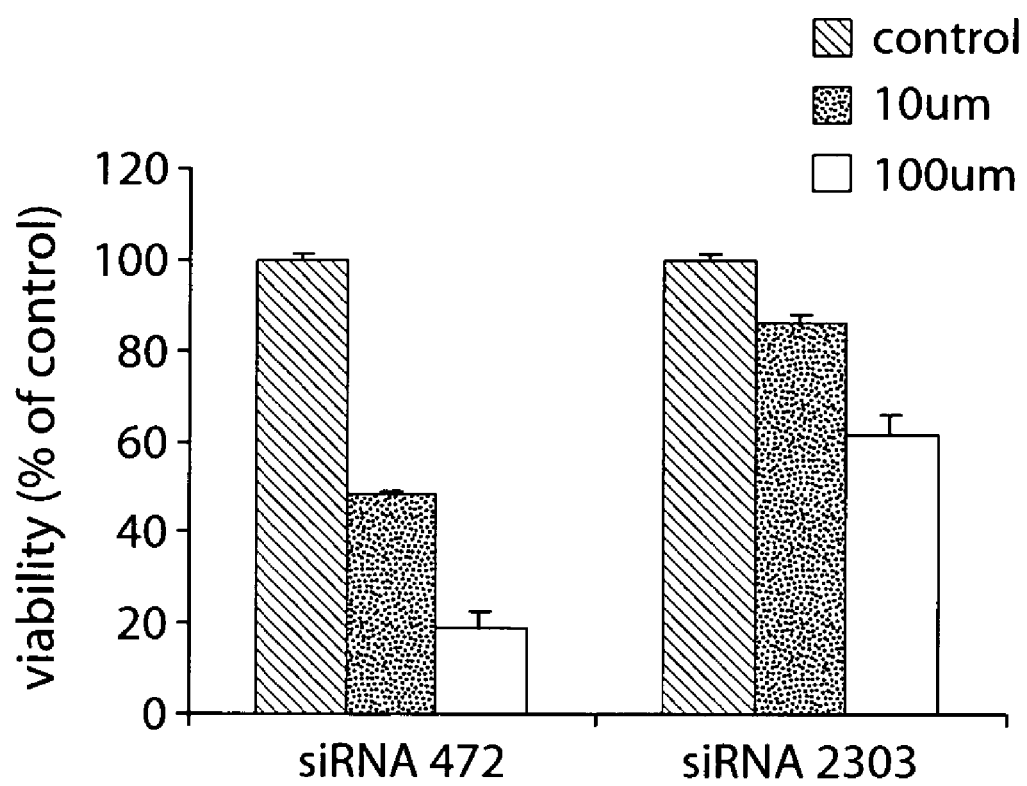

FIG. 53 shows growth inhibition of bladder cancer cell line (5637) upon treatment with EPHB4 siRNA 472.

Figure 54:
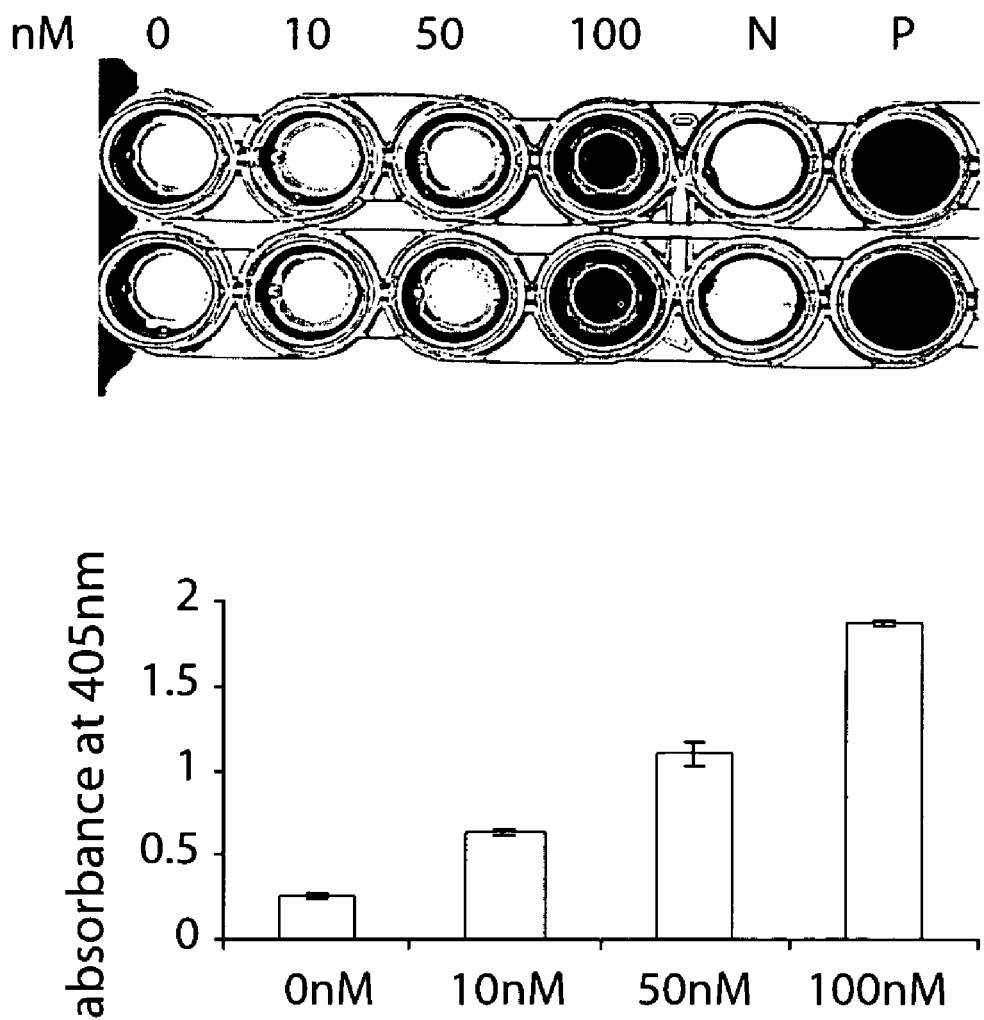

FIG. 54 shows results on apoptosis study of 5637 cells transfected with EPHB4 siRNA 472.

Figure 55:
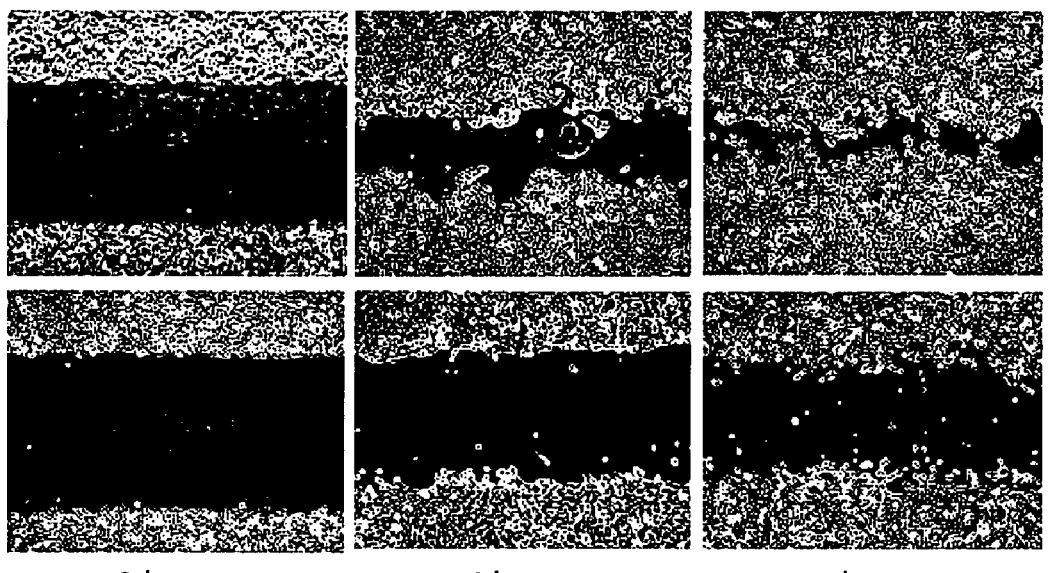

FIG. 55 shows effects of EPHB4 antisense probes on cell migration. 5637 cells were treated with EPHB4AS10 (10 µM).

FIG. 56 shows effects of EPHB4 siRNA on cell invasion. 5637 cells were transfected with siRNA 472 or control siRNA.

Figure 57:
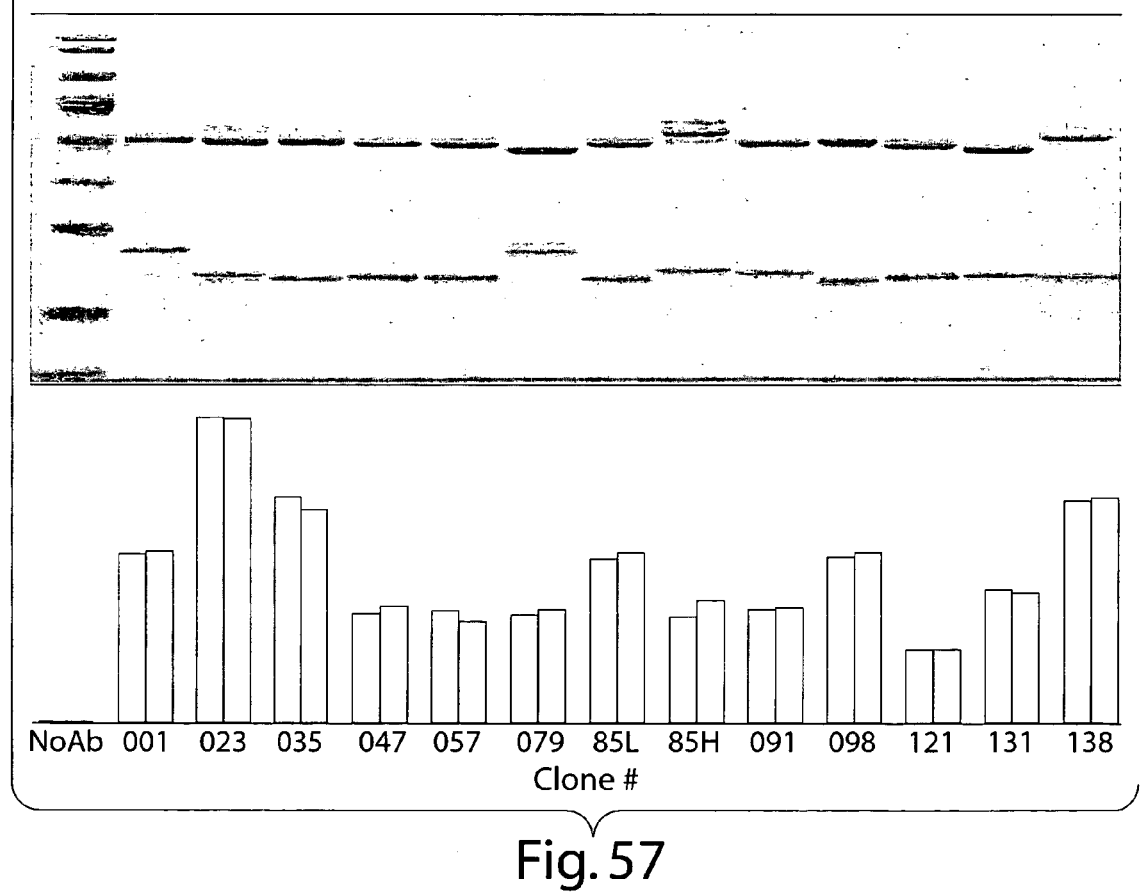

FIG. 57 shows comparison of EphB4 monoclonal antibodies by G250 and in pull-down assay. The tested EphB4 antibodies include No. 001, No. 023, No. 035, No. 047, No. 057, No. 079., No. 85L, No. 85H, No. 091, No. 098, No. 121, No. 131, and No. 138. Hybridomas producing antibody No. 098, antibody No. 091, antibody No. 023, antibody No. 131, and antibody No. 138 were deposited in the American Type Culture Collection (ATCC), 10801 University Boulevard, Manassas, VA 20110-2209 on Sep. 14 and 16, 2004. The ATCC Deposit Designation Nos. for antibody No. 023, No. 091, No. 098, No. 131, and No. 138 are PTA-6208, PTA-6209, PTA-6210, PTA-6214, and PTA-6211, respectively.

Figure 58:
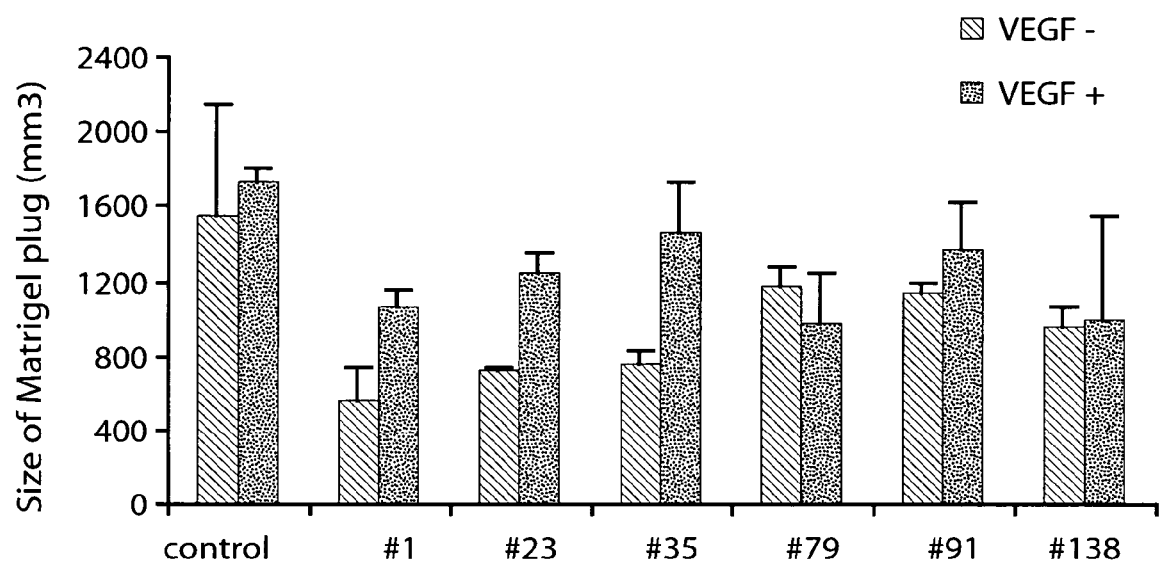

FIG. 58 shows that EphB4 antibodies inhibit the growth of SCC15 xenograft tumors.

Figure 59:
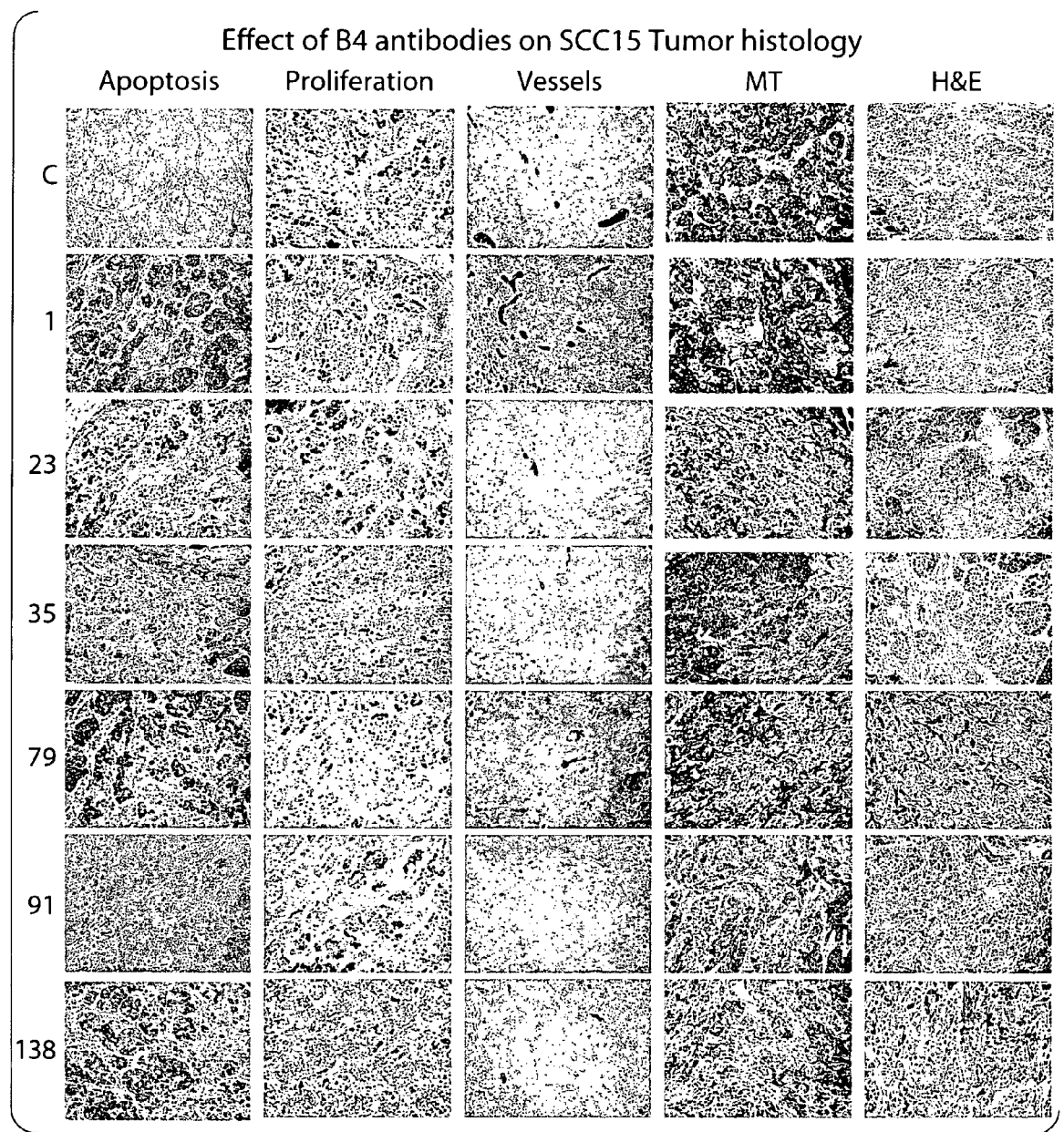

FIG. 59 shows that EphB4 antibodies cause apoptosis, necrosis and decreased angiogenesis in SCC 15, head and neck carcinoma tumor type.

FIG. 60 shows that systemic administration of EphB4 antibodies leads to tumor regression.

FIG. 61 shows a genomic nucleotide sequence of human EphB4, SEQ ID NO: 391.

FIG. 62 shows a cDNA nucleotide sequence of human EphB4, SEQ ID NO: 392.

FIG. 63 shows a genomic nucleotide sequence of human Ephrin B2, SEQ ID NO: 393.

FIG. 64 shows a cDNA nucleotide sequence of human Ephrin B2, SEQ ID NO: 394.

FIG. 65 shows an amino acid sequence of human EphB4, SEQ ID NO: 395.

FIG. 66 shows an amino acid sequence of human Ephrin B2, SEQ ID NO: 396.

DETAILED DESCRIPTION OF THE INVENTION

I. Overview

The current invention is based in part on the discovery that signaling through the ephrin/ephrin receptor pathway contributes to tumorigenesis. Applicants detected expression of ephrin B2 and EphB4 in tumor tissues and developed anti-tumor therapeutic agents for blocking signaling through the ephrin/ephrin receptor. In addition, the disclosure provides polypeptide therapeutic agents and methods for polypeptide-based inhibition of the function of EphB4 and/or Ephrin B2. Accordingly, in certain aspects, the disclosure provides numerous polypeptide compounds (agents) that may be used to treat cancer as well as angiogenesis related disorders and unwanted angiogenesis related processes.

As used herein, the terms Ephrin and Eph are used to refer, respectively, to ligands and receptors. They can be from any of a variety of animals (e.g., mammals/non-mammals, vertebrates/non-vertebrates, including humans). The nomenclature in this area has changed rapidly and the terminology used herein is that proposed as a result of work by the Eph Nomenclature Committee.

The work described herein, particularly in the examples, refers to Ephrin B2 and EphB4. However, the present invention contemplates any ephrin ligand and/or Eph receptor within their respective family, which is expressed in a tumor. The ephrins (ligands) are of two structural types, which can be further subdivided on the basis of sequence relationships and, functionally, on the basis of the preferential binding they exhibit for two corresponding receptor subgroups. Structurally, there are two types of ephrins: those which are membrane-anchored by a glycerophosphatidylinositol (GPI) linkage and those anchored through a transmembrane domain. Conventionally, the ligands are divided into the Ephrin-A subclass, which are GPI-linked proteins which bind preferentially to EphA receptors, and the Ephrin-B subclass, which are transmembrane proteins which generally bind preferentially to EphB receptors.

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to Ephrin-A proteins or Ephrin-B proteins. Receptors which interact preferentially with Ephrin-A proteins are EphA receptors and those which interact preferentially with Ephrin-B proteins are EphB receptors.

Figure 16:
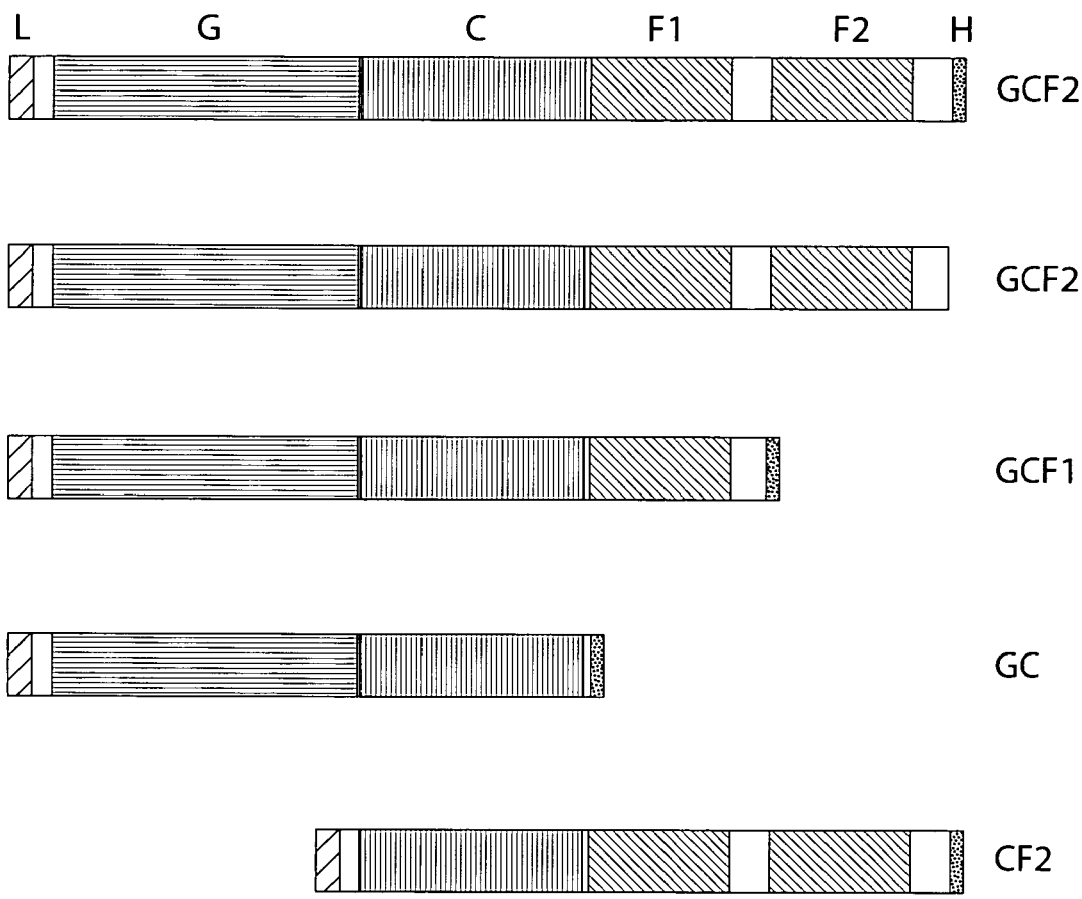
FIG. 16 shows the domain structure of the recombinant soluble EphB4EC proteins. Designation of the domains are as follows: L—leader peptide, G—globular (ligand-binding domain), C—Cys-rich domain, F1, F2—fibronectin type III repeats, H—6×His-tag.

Eph receptors have an extracellular domain composed of the ligand-binding globular domain, a cysteine rich region followed by a pair of fibronectin type III repeats (e.g., see FIG. 16). The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996; Brambilla R. et al 1995). Ephrin B2 belongs to the class of Eph ligands that have a transmembrane domain and cytoplasmic region with five conserved tyrosine residues and PDZ domain. Eph receptors are activated by binding of clustered, membrane attached ephrins (Davis S et al, 1994), indicating that contact between cells expressing the receptors and cells expressing the ligands is required for Eph activation.

Upon ligand binding, an Eph receptor dimerizes and auto-phosphorylate the juxtamembrane tyrosine residues to acquire full activation (Kalo MS et al, 1999, Binns KS, 2000). In addition to forward signaling through the Eph receptor, reverse signaling can occur through the ephrin Bs. Eph engagement of ephrins results in rapid phosphorylation of the conserved intracellular tyrosines (Bruckner K, 1997) and somewhat slower recruitment of PDZ binding proteins (Palmer A 2002). Recently, several studies have shown that high expression of Eph/ephrins may be associated with increased potentials for tumor growth, tumorigenicity, and metastasis (Easty D J, 1999; Kiyokawa E, 1994; Tang X X, 1999; Vogt T, 1998; Liu W, 2002; Stephenson S A, 2001; Steube K G 1999; Berclaz G, 1996).

In certain embodiments, the present invention provides polypeptide therapeutic agents that inhibit activity of Ephrin B2, EphB4, or both. As used herein, the term "polypeptide therapeutic agent" or "polypeptide agent" is a generic term which includes any polypeptide that blocks signaling through the Ephrin B2/EphB4 pathway. A preferred polypeptide therapeutic agent of the invention is a soluble polypeptide of Ephrin B2 or EphB4. Another preferred polypeptide therapeutic agent of the invention is an antagonist antibody that binds to Ephrin B2 or EphB4. For example, such polypeptide therapeutic agent can inhibit function of Ephrin B2 or EphB4, inhibit the interaction between Ephrin B2 and EphB4, inhibit the phosphorylation of Ephrin B2 or EphB4, or inhibit any of the downstream signaling events upon binding of Ephrin B2 to EphB4.

II. Soluble Polypeptides

Figure 14:
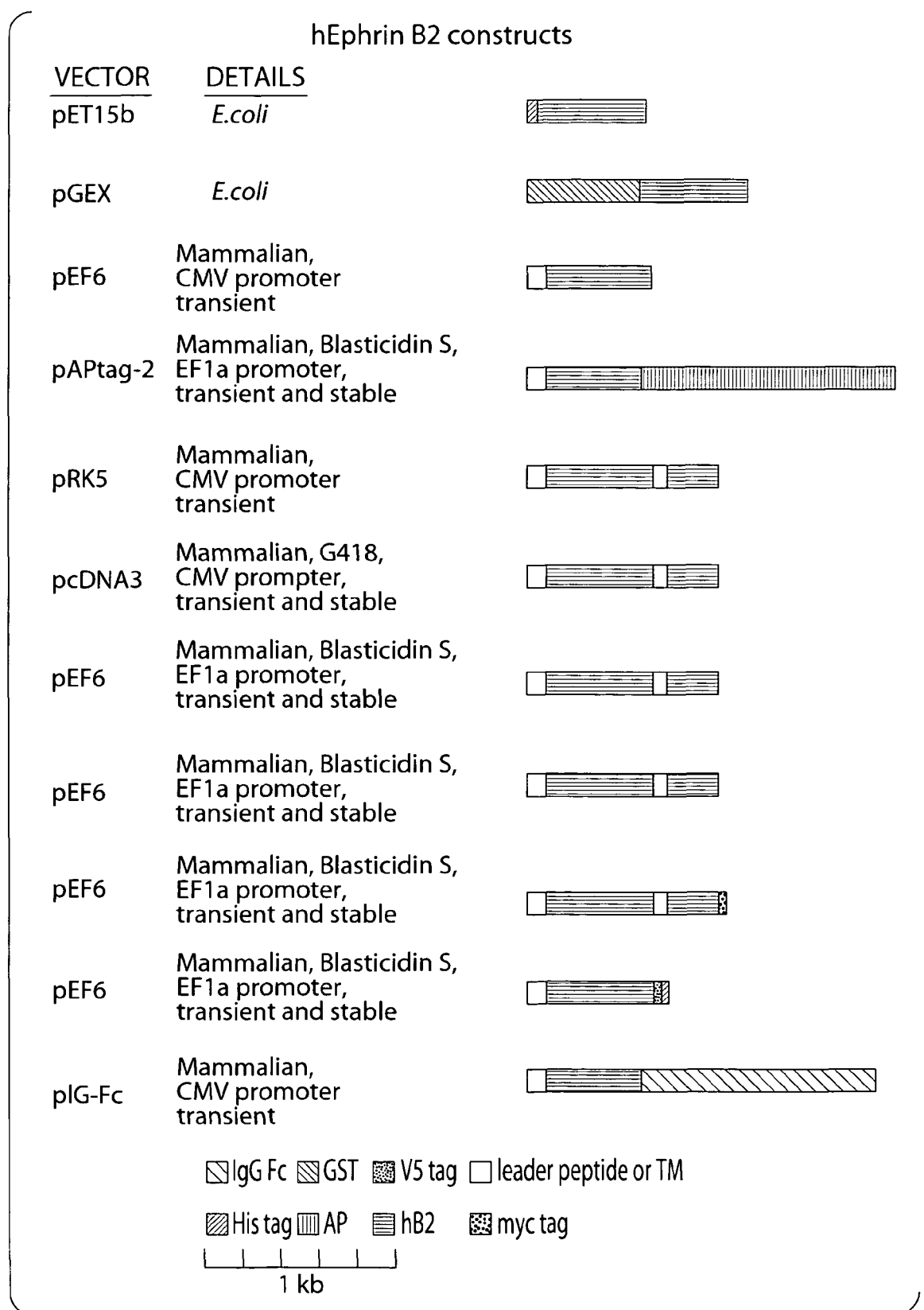
FIG. 14 is a schematic representation of human Ephrin B2 constructs.
Figure 15:
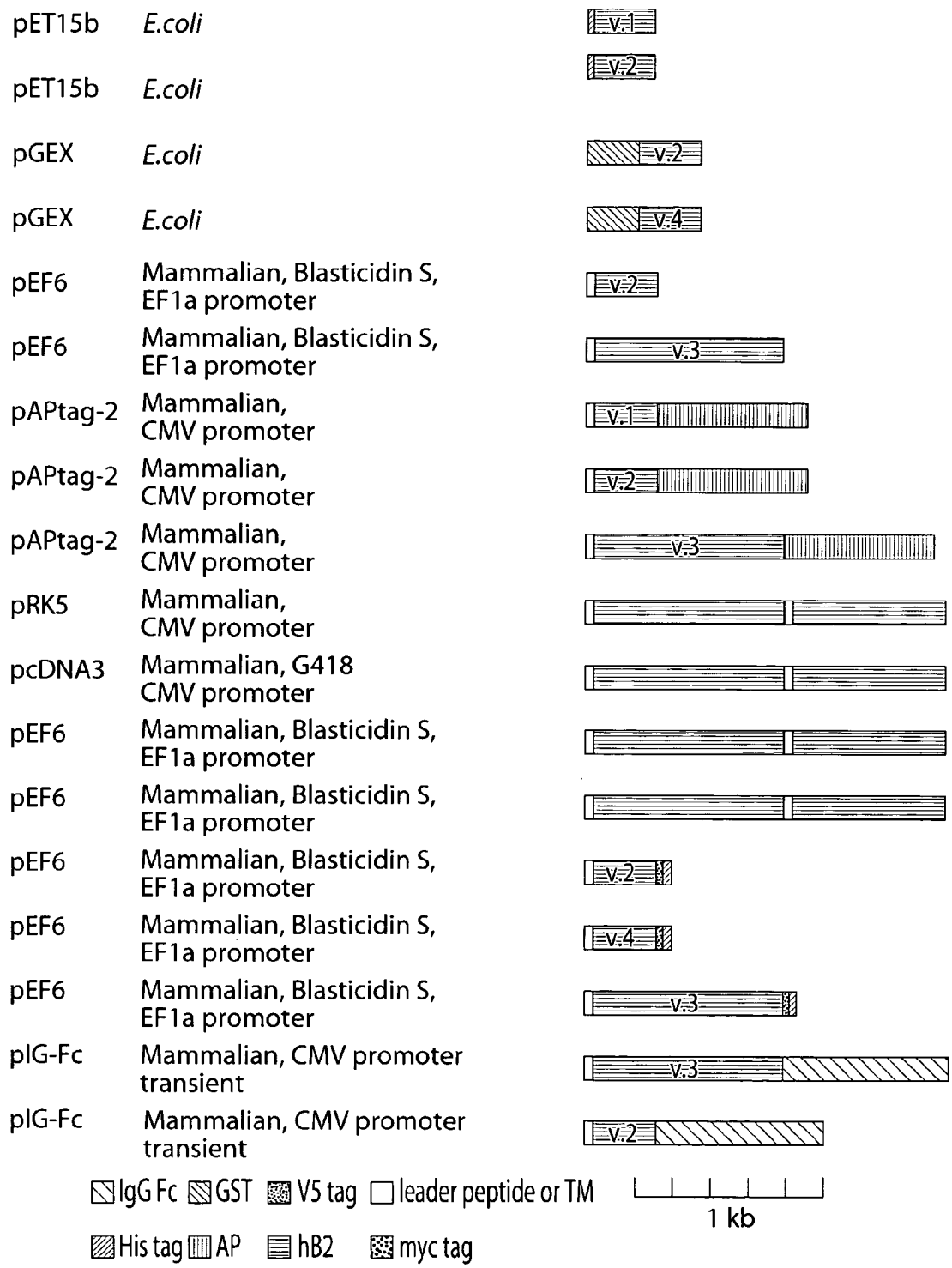
FIG. 15 is a schematic representation of human EphB4 constructs.

In certain aspects, the invention relates to a soluble polypeptide comprising an extracellular domain of an Ephrin B2 protein (referred to herein as an Ephrin B2 soluble polypeptide) or comprising an extracellular domain of an EphB4 protein (referred to herein as an EphB4 soluble polypeptide). Preferably, the subject soluble polypeptide is a monomer and is capable of binding with high affinity to Ephrin B2 or EphB4. In a specific embodiment, the EphB4 soluble polypeptide of the invention comprises a globular domain of an EphB4 protein. Specific examples EphB4 soluble polypeptides are provided in FIGS. 1, 2, and 15. Specific examples of Ephrin B2 soluble polypeptides are provided in FIGS. 3 and 14.

As used herein, the subject soluble polypeptides include fragments, functional variants, and modified forms of EphB4 soluble polypeptide or an Ephrin B2 soluble polypeptide. These fragments, functional variants, and modified forms of the subject soluble polypeptides antagonize function of EphB4, Ephrin B2 or both.

In certain embodiments, isolated fragments of the subject soluble polypeptides can be obtained by screening polypeptides recombinantly produced from the corresponding fragment of the nucleic acid encoding an EphB4 or Ephrin B2 soluble polypeptides. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function to inhibit function of EphB4 or Ephrin B2, for example, by testing the ability of the fragments to inhibit angiogenesis or tumor growth.

In certain embodiments, a functional variant of an EphB4 soluble polypeptide has an amino acid sequence that is at least 90%, 95%, 97%, 99% or 100% identical to residues 1-522, residues 1-412, or residues 1-312 of the amino acid sequence defined by FIG. 65. In other embodiments, a functional variant of an Ephrin B2 soluble polypeptide has a sequence at least 90%, 95%, 97%, 99% or 100% identical to residues 1-225 of the amino acid sequence defined by FIG. 66.

In certain embodiments, the present invention contemplates making functional variants by modifying the structure of the subject soluble polypeptide for such purposes as enhancing therapeutic or prophylactic efficacy, or stability (e.g., ex vivo shelf life and resistance to proteolytic degradation in vivo). Such modified soluble polypeptide are considered functional equivalents of the naturally-occurring EphB4 or Ephrin B2 soluble polypeptide. Modified soluble polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

This invention further contemplates a method of generating sets of combinatorial mutants of the EphB4 or Ephrin B2 soluble polypeptides, as well as truncation mutants, and is especially useful for identifying functional variant sequences. The purpose of screening such combinatorial libraries may be to generate, for example, soluble polypeptide variants which can act as antagonists of EphB4, EphB2, or both. Combinatorially-derived variants can be generated which have a selective potency relative to a naturally occurring soluble polypeptide. Such variant proteins, when expressed from recombinant DNA constructs, can be used in gene therapy protocols. Likewise, mutagenesis can give rise to variants which have intracellular half-lives dramatically different than the corresponding wild-type soluble polypeptide. For example, the altered protein can be rendered either more stable or less stable to proteolytic degradation or other cellular process which result in destruction of, or otherwise inactivation of the protein of interest (e.g., a soluble polypeptide). Such variants, and the genes which encode them, can be utilized to alter the subject soluble polypeptide levels by modulating their half-life. For instance, a short half-life can give rise to more transient biological effects and, when part of an inducible expression system, can allow tighter control of recombinant soluble polypeptide levels within the cell. As above, such proteins, and particularly their recombinant nucleic acid constructs, can be used in gene therapy protocols.

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential soluble polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, soluble polypeptide variants (e.g., the antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137: 109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193: 653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the subject soluble polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the subject soluble polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the subject soluble polypeptides of the invention include a a small molecule such as a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the EphB4 or Ephrin B2 soluble polypeptides.

To illustrate, by employing scanning mutagenesis to map the amino acid residues of a soluble polypeptide which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the soluble polypeptides of the invention may further comprise post-translational modifications. Such modifications include, but are not limited to, acetylation, carboxylation, glycosylation, phosphorylation, lipidation, and acylation. As a result, the modified soluble polypeptides may contain non-amino acid elements, such as polyethylene glycols, lipids, poly- or mono-saccharide, and phosphates. Effects of such non-amino acid elements on the functionality of a soluble polypeptide may be tested for its antagozing role in EphB4 or Ephrin B2 function, e.g, it inhibitory effect on angiogenesis or on tumor growth.

In certain aspects, functional variants or modified forms of the subject soluble polypeptides include fusion proteins having at least a portion of the soluble polypeptide and one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Another fusion domain well known in the art is green fluorescent protein (GFP). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the soluble polypeptides of the present invention contain one or more modifications that are capable of stabilizing the soluble polypeptides. For example, such modifications enhance the in vitro half life of the soluble polypeptides, enhance circulatory half life of the soluble polypeptides or reducing proteolytic degradation of the soluble polypeptides.

In certain embodiments, soluble polypeptides (unmodified or modified) of the invention can be produced by a variety of art-known techniques. For example, such soluble polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the soluble polypeptides, fragments or variants thereof may be recombinantly produced using various expression systems as is well known in the art (also see below).

III. Nucleic Acids Encoding Soluble Polypeptides

In certain aspects, the invention relates to isolated and/or recombinant nucleic acids encoding an EphB4 or Ephrin B2 soluble polypeptide. The subject nucleic acids may be single-stranded or double-stranded, DNA or RNA molecules. These nucleic acids are useful as therapeutic agents. For example, these nucleic acids are useful in making recombinant soluble polypeptides which are administered to a cell or an individual as therapeutics. Alternative, these nucleic acids can be directly administered to a cell or an individual as therapeutics such as in gene therapy.

In certain embodiments, the invention provides isolated or recombinant nucleic acid sequences that are at least 80%, 85%, 90%, 95%, 97%, 98%, 99% or 100% identical to a region of the nucleotide sequence depicted in FIG. 62 or 63. One of ordinary skill in the art will appreciate that nucleic acid sequences complementary to the subject nucleic acids, and variants of the subject nucleic acids are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence depicted in FIG. 62 or 63, or complement sequences thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×

SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the subject nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspect of the invention, the subject nucleic acid is provided in an expression vector comprising a nucleotide sequence encoding an EphB4 or Ephrin B2 soluble polypeptide and operably linked to at least one regulatory sequence. Regulatory sequences are art-recognized and are selected to direct expression of the soluble polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a soluble polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This invention also pertains to a host cell transfected with a recombinant gene including a coding sequence for one or more of the subject soluble polypeptide. The host cell may be any prokaryotic or eukaryotic cell. For example, a soluble polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject soluble polypeptides. For example, a host cell transfected with an expression vector encoding an EphB4 soluble polypeptide can be cultured under appropriate conditions to allow expression of the EphB4 soluble polypeptide to occur. The EphB4 soluble polypeptide may be secreted and isolated from a mixture of cells and medium containing the soluble polypeptides. Alternatively, the soluble polypeptides may be retained cytoplasmically or in a membrane fraction and the cells harvested, lysed and the protein isolated. A cell culture includes host cells, media and other byproducts. Suitable media for cell culture are well known in the art. The soluble polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the soluble polypeptides. In a preferred embodiment, the soluble polypeptide is a fusion protein containing a domain which facilitates its purification.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant soluble polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

IV. Antibodies

In certain aspects, the the present invention provides antagonist antibodies against Ephrin B2 or EphB4. As described herein, the term "antagonist antibody" refers to an antibody that inhibits function of Ephrin B2 or EphB4. Preferably, the antagonist antibody binds to an extracellular domain of Ephrin B2 or EphB4. It is understood that antibodies of the invention may be polyclonal or monoclonal; intact or truncated, e.g., F(ab')$_2$, Fab, Fv; xenogeneic, allogeneic, syngeneic, or modified forms thereof, e.g., humanized, chimeric, etc.

For example, by using immunogens derived from an Ephrin B2 or EphB4 polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the peptide. (e.g., a polypeptide or an antigenic fragment which is capable of eliciting an antibody response, or a fusion protein). Techniques for conferring immunogenicity on a protein or peptide include conjugation to carriers or other techniques well known in the art. An immunogenic portion of an Ephrin B2 or EphB4 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In one embodiment, antibodies of the invention are specific for the extracellular portion of the Ephrin B2 or EphB4 protein. In another embodiment, antibodies of the invention are specific for the intracellular portion or the transmembrane portion of the Ephrin B2 or EphB4 protein. In a further embodiment, antibodies of the invention are specific for the extracellular portion of the Ephrin B2 or EphB4 protein.

Following immunization of an animal with an antigenic preparation of an Ephrin B2 or EphB4 polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an Ephrin B2 or EphB4 polypeptide and monoclonal antibodies isolated from a culture comprising such hybridoma cells.

The term antibody as used herein is intended to include fragments thereof which are also specifically reactive with an Ephrin B2 or EphB4 polypeptides. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for an Ephrin B2 or EphB4 polypeptide conferred by at least one CDR region of the antibody. Techniques for the production of single chain antibodies (U.S. Pat. No. 4,946,778) can also be adapted to produce single chain antibodies. Also, transgenic mice or other organisms including other mammals, may be used to express humanized antibodies. In preferred embodiments, the antibodies further comprise a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments the invention makes available methods for generating novel antibodies. For example, a method for generating a monoclonal antibody that binds specifically to an Ephrin B2 or EphB4 polypeptide may comprise administering to a mouse an amount of an immunogenic composition comprising the Ephrin B2 or EphB4 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the Ephrin B2 or EphB4 polypeptide. Once obtained, a hybridoma can be propagated in a cell culture, optionally in culture conditions where the hybridoma-derived cells produce the monoclonal antibody that binds specifically to the Ephrin B2 or EphB4 polypeptide. The monoclonal antibody may be purified from the cell culture.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), western blots, immunoprecipitation assays and immunohistochemistry.

V. Drug Screening Assays

There are numerous approaches to screening for polypeptide therapeutic agents as antagonists of EphB4, Ephrin B2 or both. For example, high-throughput screening of compounds or molecules can be carried out to identify agents or drugs which inhibit angiogenesis or inhibit tumor growth. Test agents can be any chemical (element, molecule, compound, drug), made synthetically, made by recombinant techniques or isolated from a natural source. For example, test agents can be peptides, polypeptides, peptoids, sugars, hormones, or nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

For example, an assay can be carried out to screen for compounds that specifically inhibit binding of Ephrin B2 (ligand) to EphB4 (receptor), or vice-versa, e.g., by inhibition of binding of labeled ligand- or receptor-Fc fusion proteins to immortalized cells. Compounds identified through this screening can then be tested in animals to assess their anti-angiogenesis or anti-tumor activity in vivo.

In one embodiment of an assay to identify a substance that interferes with interaction of two cell surface molecules (e.g., Ephrin B2 and EphB4), samples of cells expressing one type of cell surface molecule (e.g., EphB4) are contacted with either labeled ligand (e.g., Ephrin B2, or a soluble portion thereof, or a fusion protein such as a fusion of the extracellular domain and the Fc domain of IgG) or labeled ligand plus a test compound (or group of test compounds). The amount of labeled ligand which has bound to the cells is determined. A lesser amount of label (where the label can be, for example, a radioactive isotope, a fluorescent or colormetric label) in the sample contacted with the test compound(s) is an indication that the test compound(s) interferes with binding. The reciprocal assay using cells expressing a ligand (e.g., an Ephrin B2 ligand or a soluble form thereof) can be used to test for a substance that interferes with the binding of an Eph receptor or soluble portion thereof.

An assay to identify a substance which interferes with interaction between an Eph receptor and an ephrin can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein (e.g., an Eph receptor or an ephrin) can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all, or a portion of, a protein (e.g., an Eph receptor or an ephrin) linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by inserting the protein (e.g., an Eph receptor or an ephrin) or a portion thereof into a suitable expression vector which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein). Immobilization can be performed prior to, simultaneous with, or after contacting the fusion protein with compound, as appropriate. Various permutations of the method are possible, depending upon factors such as the compounds tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

VI. Methods of Treatment

In certain embodiments, the present invention provides methods of inhibiting angiogenesis and methods of treating angiogenesis-associated diseases. In other embodiments, the present invention provides methods of inhibiting or reducing tumor growth and methods of treating an individual suffering from cancer. These methods involve administering to the individual a therapeutically effective amount of one or more polypeptide therapeutic agents as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

It is understood that methods and compositions of the invention are also useful for treating any angiogenesis-independent cancers (tumors). As used herein, the term "angiogenesis-independent cancer" refers to a cancer (tumor) where there is no or little neovascularization in the tumor tissue.

In particular, polypeptide therapeutic agents of the present invention are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, and leukemia.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the invention can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent is shown to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; anti secretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462, 075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the polypeptide therapeutic agents of the invention may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

VII. Methods of Administration and Pharmaceutical Compositions

In certain embodiments, the subject polypeptide therapeutic agents (e.g., soluble polypeptides or antibodies) of the present invention are formulated with a pharmaceutically acceptable carrier. Such therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject polypeptide therapeutic agents include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient.

In solid dosage forms for oral administration (capsules, tablets, pills, dragees, powders, granules, and the like), one or more polypeptide therapeutic agents of the present invention may be mixed with one or more pharmaceutically acceptable carriers, such as sodium citrate or dicalcium phosphate, and/ or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, methods of the invention can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject polypeptide therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more polypeptide therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In other embodiments, the polypeptide therapeutic agents of the instant invention can be expressed within cells from eukaryotic promoters. For example, a soluble polypeptide of EphB4 or Ephrin B2 can be expressed in eukaryotic cells from an appropriate vector. The vectors are preferably DNA plasmids or viral vectors. Viral vectors can be constructed based on, but not limited to, adeno-associated virus, retrovirus, adenovirus, or alphavirus. Preferably, the vectors stably introduced in and persist in target cells. Alternatively, viral vectors can be used that provide for transient expression. Such vectors can be repeatedly administered as necessary. Delivery of vectors encoding the subject polypeptide therapeutic agent can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

Exemplification

The invention now being generally described, it will be more readily understood by reference to the following examples, which are included merely for purposes of illustration of certain aspects and embodiments of the present invention, and are not intended to limit the invention.

EXAMPLE 1

Soluble Derivatives of the Extracellular Domains of Human Ephrin B2 and EphB4 Proteins Soluble derivatives of the extracellular domains of human Ephrin B2 and EphB4 proteins represent either truncated full-length predicted extracellular domains of Ephrin B2 (B4ECv3, B2EC) or translational fusions of the domains with constant region of human immunoglobulins (IgG1 Fc fragment), such as B2EC-FC, B4ECv2-FC and B4ECv3-FC. Representative human Ephrin B2 constructs and human EphB4 constructs are shown FIGS. 14 and 15.

Figure 7:
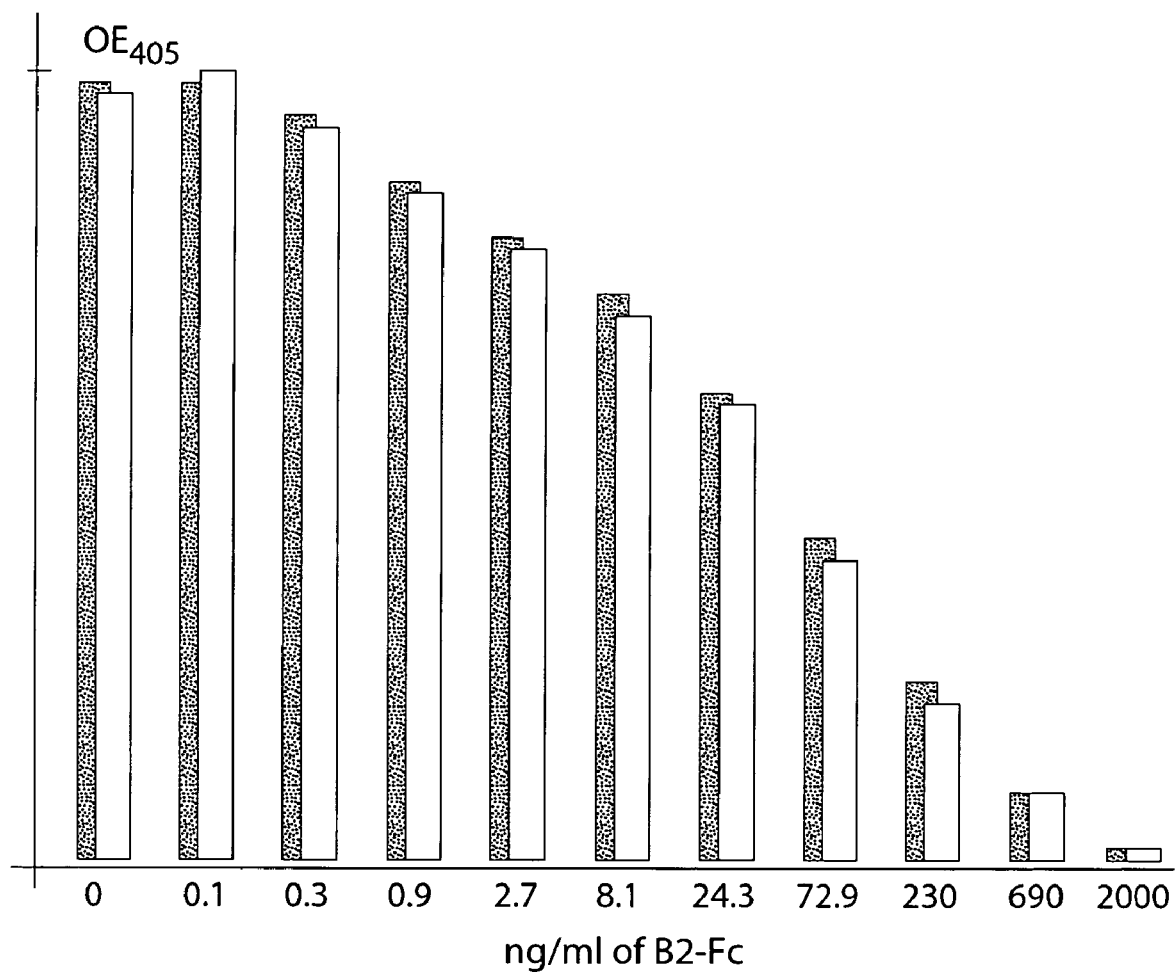
FIG. 7 shows B4EC-FC inhibition assay (Inhibition in solution).
Figure 8:
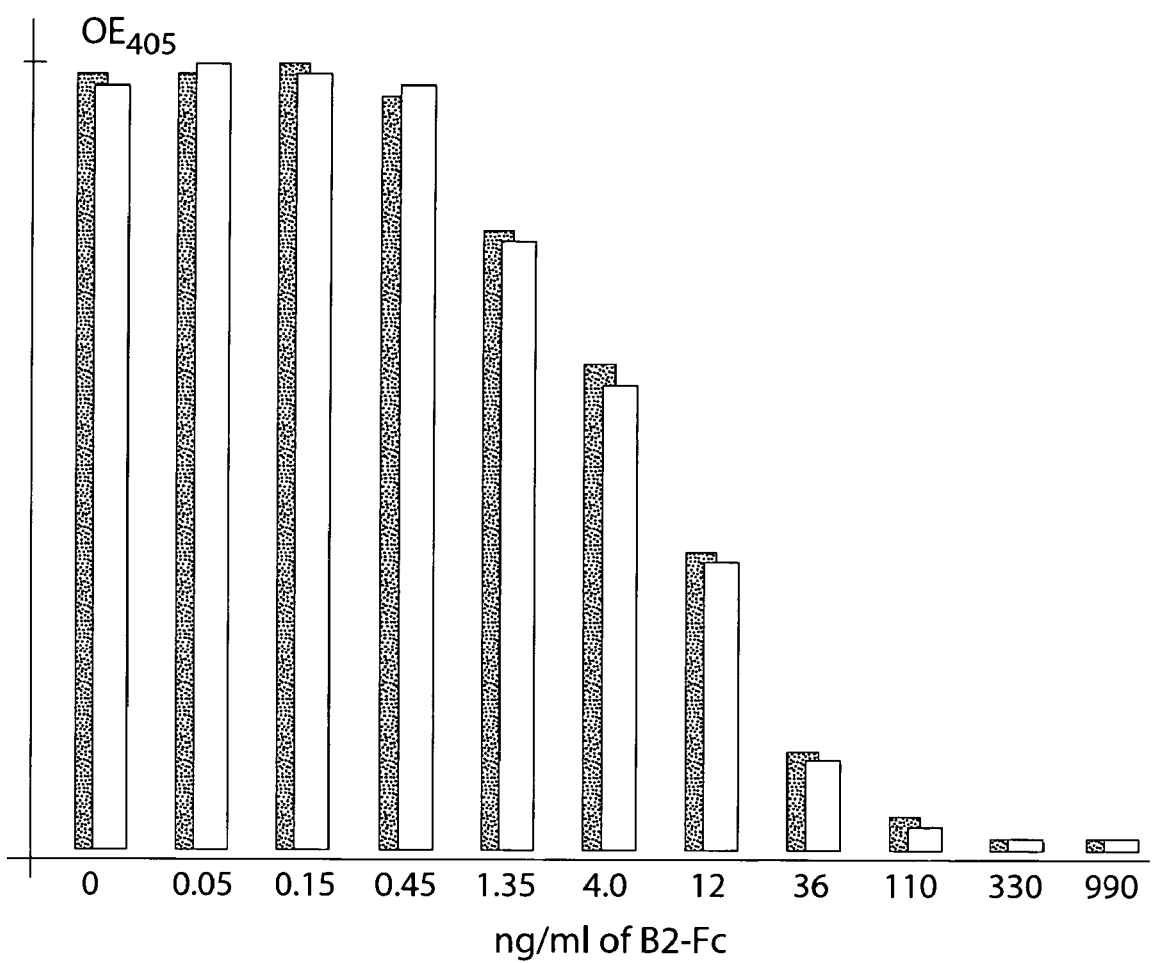
FIG. 8 shows B2EC-FC binding assay (Protein-A-agarose based assay).

The cDNA fragments encoding these recombinant proteins were subcloned into mammalian expression vectors, expressed in transiently or stably transfected mammalian cell lines and purified to homogeneity as described in detail in Materials and Methods section (see below). Predicted amino acid sequences of the proteins are shown in FIGS. 1-5. High purity of the isolated proteins and their recognition by the corresponding anti-Ephrin B2 and anti-EphB4 monoclonal or polyclonal antibodies were confirmed. The recombinant proteins exhibit the expected high-affinity binding, binding competition and specificity properties with their corresponding binding partners as corroborated by the biochemical assays (see e.g., FIGS. 6-8).

Figure 9:
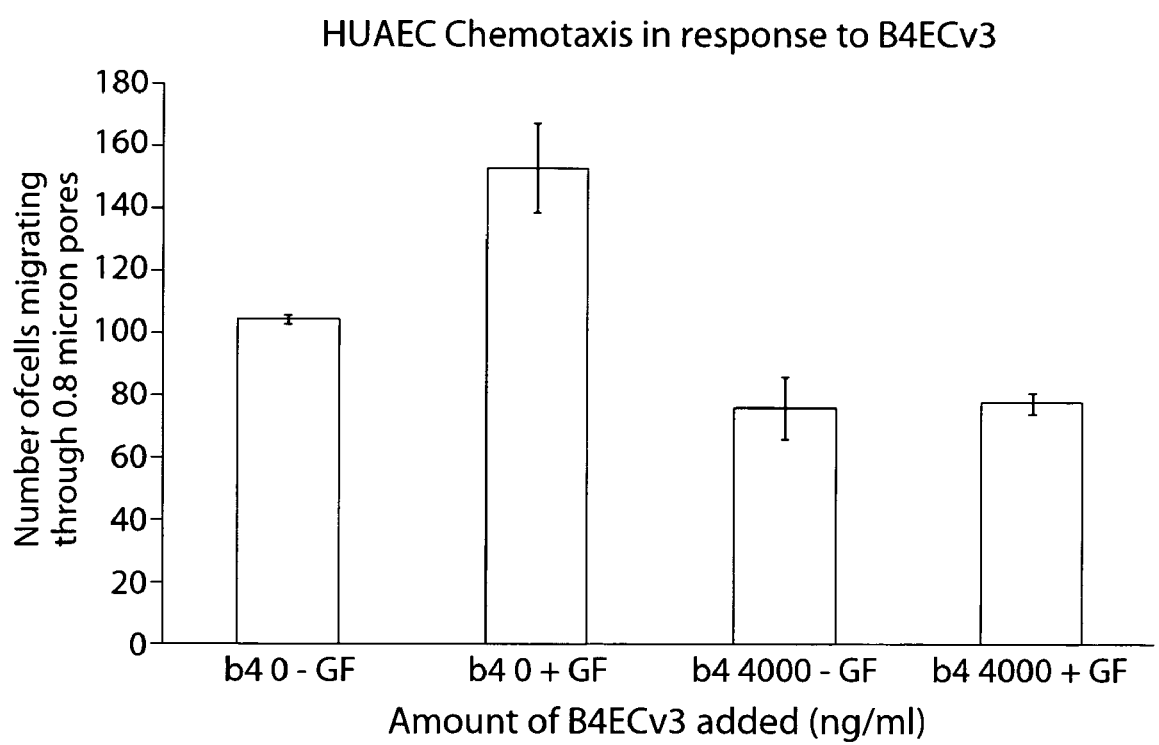
FIG. 9 shows chemotaxis of HUAEC in response to B4Ecv3.
Figure 10:
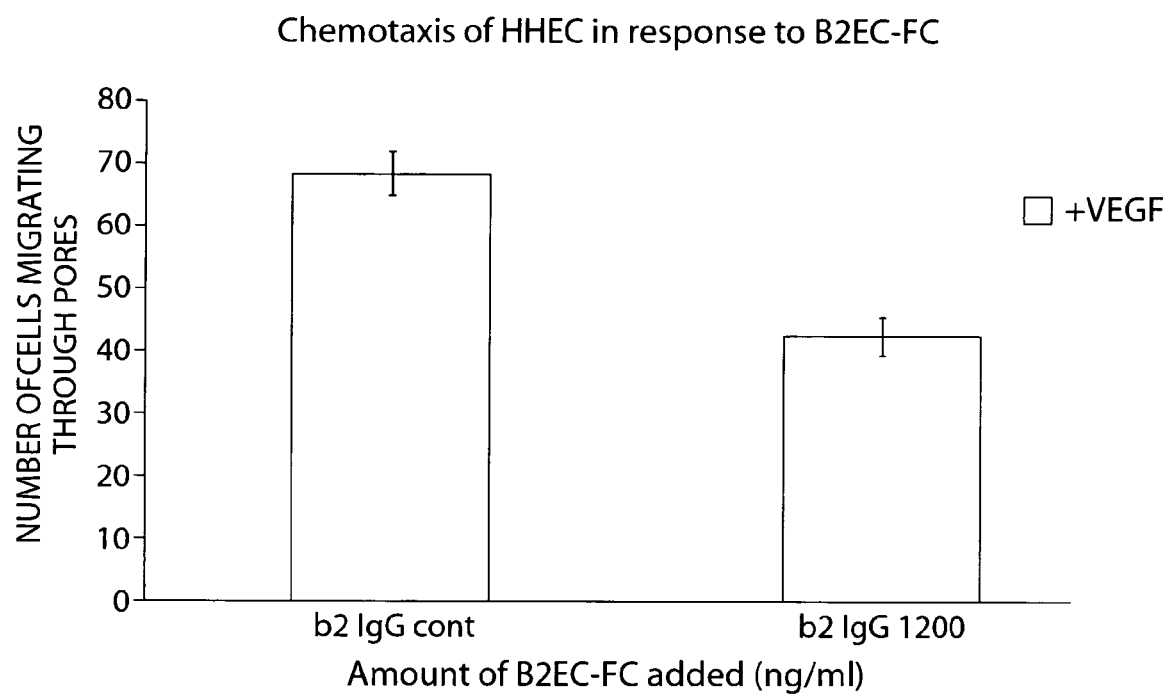
FIG. 10 shows chemotaxis of HHEC in response to B2EC-FC.
Figure 11:
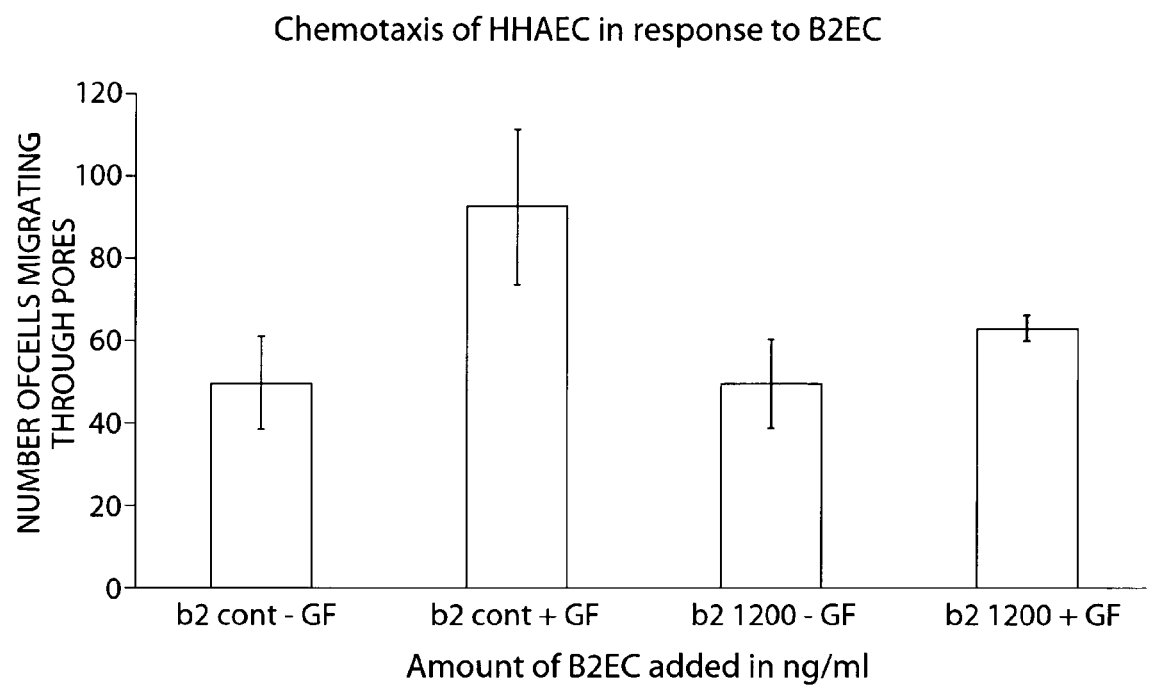
FIG. 11 shows chemotaxis of HHAEC in response to B2EC.
Figure 12:
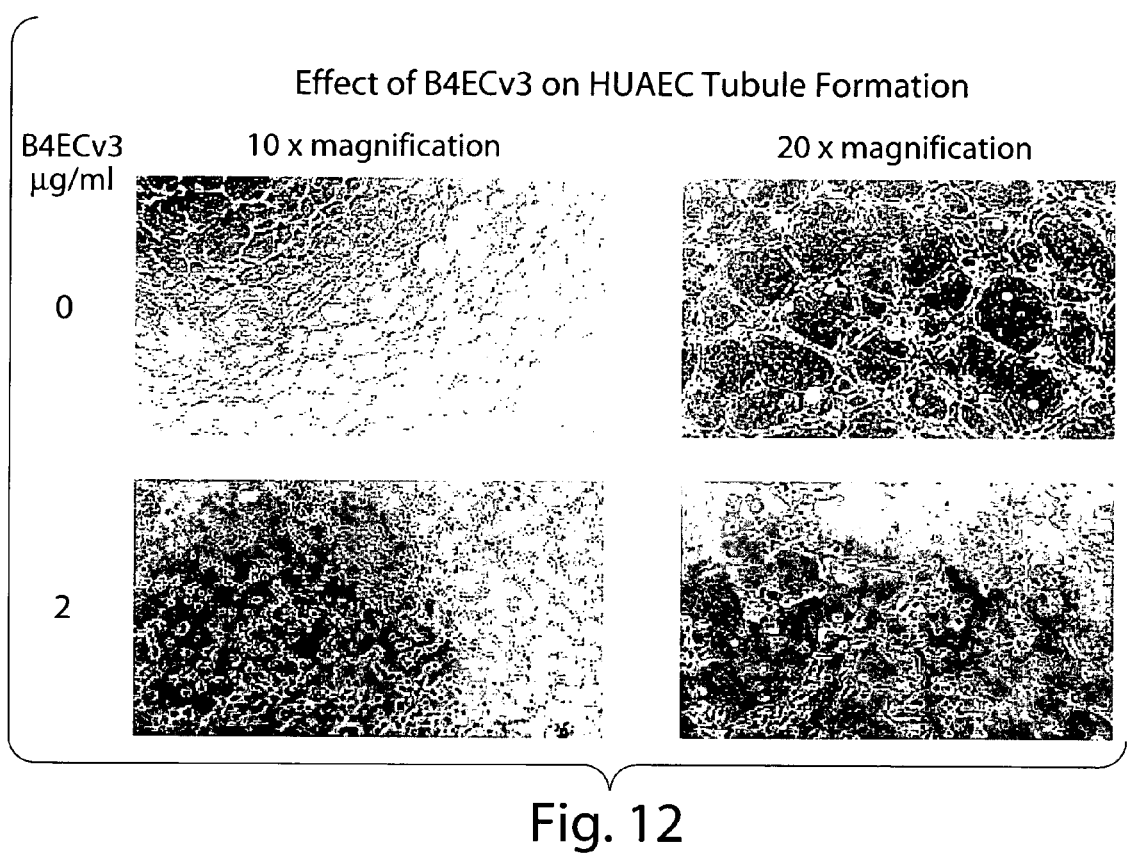
FIG. 12 shows effect of B4Ecv3 on HUAEC tubule formation.
Figure 13:
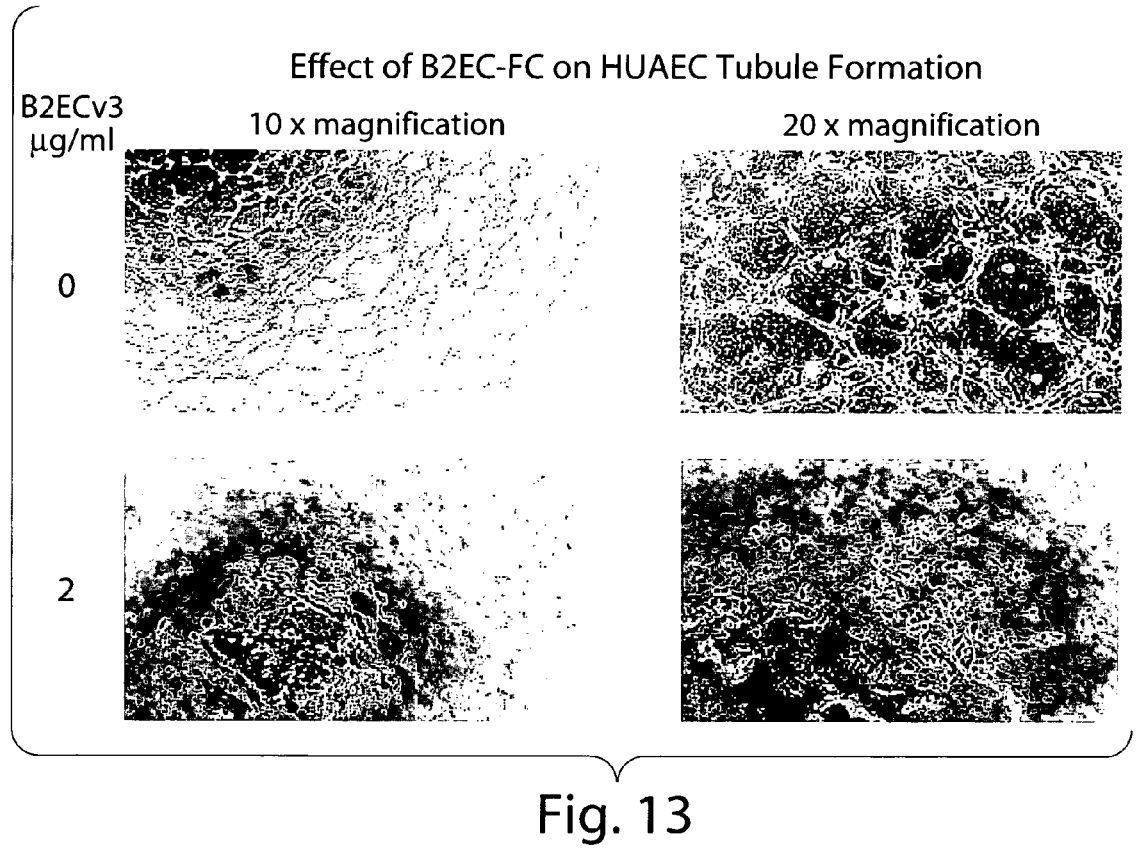
FIG. 13 shows effect of B2EC-FC on HUAEC tubule formation.

Such soluble derivative proteins human Ephrin B2 and EphB4 exhibit potent biological activity in several cell-based assays and in vivo assays which measure angiogenesis or anti-cancer activities, and are therefore perspective drug candidates for anti-angiogenic and anti-cancer therapy. B4ECv3 as well as B2EC and B2EC-FC proteins blocked chemotaxis of human endothelial cells (as tested with umbilical cord and hepatic AECs or VECs), with a decrease in degradation of the extracellular matrix, Matrigel, and a decrease in migration in response to growth factor stimuli (FIGS. 9-11). B4ECv3 and B2EC-FC proteins have potent anti-angiogenic effect as demonstrated by their inhibition of endothelial cell tube formation (FIGS. 12-13).

Materials and Methods

1) Mammalian Expression Vectors for Producing Recombinant Soluble Derivatives of Ephrin B2 and Eph B4

Plasmids vectors for expressing recombinant soluble derivatives of Ephrin B2 and EphB4 were based on pEF6/V5-His-TOPO vector (Invitrogen), pIG (Novagen) or pRK5. pEF6/V5-His-TOPO contains human elongation factor 1a enhancer/promoter and blasticidin resistance marker. pIG vector is designed for high-level expression of protein fusions with Fc portion of human IgG1 under CMV promoter control and pRK5 is a general purpose CMV promoter-containing mammalian expression vector. To generate plasmid construct pEF6-B4EC-NT, cDNA fragment of human EphB4 was amplified by PCR using oligo primers 5'-GGATCCGCC ATGGAGCTC CGGGTGCTGCT-3' (SEQ ID NO: 1)and 5'-TGGATCCCT GCTCCCGC CAGCCCTCG CTCT-CATCCA-3' (SEQ ID NO: 2), and TOPO-cloned into pEF6/V5-His-TOPO vector. pEF6-hB4ECv3 was derived from pEF6-B4ECNT by digesting the plasmid DNA with EcoRV and BstBI, filling-in the ends with Klenow enzyme and religating the vector. Recombinant EphB4 derivative encoded by pEF6-B4EC-NT does not contain epitope- or purification tags, while the similar B4ECv3 protein encoded by pEF6-hB4ECv3 contains V5 epitope tag and 6×His tag on its C-terminus to facilitate purification from conditioned media. Plasmid construct pEF6-hB2EC was created by PCR amplification of Ephrin B2 cDNA using oligo primers 5'-TG-GATCCAC CATGGCTGT GAGAAGGGAC-3' (SEQ ID NO: 3)plus 5'-ATTAATGGTGATGGT GAT GATGACTAC CCACTTCGG AACCGAGGATGTTGTTC-3' (SEQ ID NO: 4)and TOPO-cloning into pEF6/V5-His-TOPO vector. Plasmid construct pIG-hB2EC-FC was created by PCR amplification of Ephrin B2 cDNA with oligo primers 5'-TAAAGCT-TCCGCCATGG CTGTGAGAAGGGAC-3' (SEQ ID NO: 5)and 5'-TAGGATCCACTTCGGA ACCGAGGATGT-TGTT CCC-3' (SEQ ID NO: 6), followed by TOPO-cloning and sequencing the resulting PCR fragment with consecutive subcloning in pIG hIgG1 Fc fusion expression vector cut with Bam HI and Hind III. Similarly, pIG-hB2EC and pIG-hB4ECv3 were generated by PCR amplifying portions of EphB4 ECD cDNA using oligo primers 5'-ATAAGCTTCC GCCATGGAGC TCCGGGTGCTG-3' (SEQ ID NO: 7) plus 5'-TTGGATCCTGCTCCCG CCAGCCCTCGC TCT-CATC-3' (SEQ ID NO: 8)with consecutive subcloning into pIG hIgG1 Fc fusion expression vector cut with Bam HI and Hind III. Predicted sequences of the proteins encoded by the vectors described above are shown in FIGS. 1-5.

2) Mammalian Cell Culture and Transfections

HEK293T (human embryonic kidney line) cells were maintained in DMEM with 10% dialyzed fetal calf serum and 1% penicillin/streptomycin/neomycin antibiotics. Cells were maintained at 37° C. in a humidified atmosphere of 5% $CO_2$/95% air. Transfections were performed using Lipofectamine 2000 reagent (Invitrogen) according to the manufacturer's protocol. One day before transfections, 293T cells were seeded at a high density to reach 80% confluence at the time of transfection. Plasmid DNA and Lipofectamine reagent at 1:3 ratio were diluted in Opti-MEM I reduced serum medium (Invitrogen) for 5 min and mixed together to form DNA: Lipofectamine complex. For each 10 cm culture dish, 10 μg of plasmid DNA was used. After 20 min, above complex was added directly to cells in culture medium. After 16 hours of transfection, medium was aspirated, washed once with serum free DMEM and replaced with serum free DMEM. Secreted proteins were harvested after 48 hours by collecting conditional medium. Conditional medium was clarified by centrifugation at 10,000 g for 20 min, filtered through 0.2 μm filter and used for purification.

3) Generating Stable Cell Lines

To create stable cell lines producing EphB4ECv3 and EphB4ECnt HEK293 or HEK293T cells were transfected with either pEF6-B4ECv3 or pEF6-B4EC-NT plasmid constructs as described above and selected using antibiotic Blasticidin. After 24 hours of transfection, cells were seeded at low density. Next day, cells were treated with 10 μg/ml of Blasticidin. After two weeks of drug selection, surviving cells were pooled and selected further for single cell clone expansion. After establishing stable cells, they were maintained at 4 μg/ml Blasticidin. Conditioned media were tested to confirm expression and secretion of the respective recombinant proteins. Specificity of expression was confirmed by Western blot with anti-B4 mono- or polyclonal ABs and B2EC-AP reagent binding and competition assays.

4) Protein Purification

HEK293 cells were transiently transfected with a plasmid encoding secreted form of EphB4ectodomain (B4ECv3). Conditional media was harvested and supplemented with 10 mM imidazole, 0.3 M NaCl and centrifuged at 20,000 g for 30 min to remove cell debris and insoluble particles. 80 ml of obtained supernatant were applied onto the pre-equilibrated column with 1 ml of Ni-NTA-agarose (Qiagen) at the flow rate of 10 ml/h. After washing the column with 10 ml of 50 mM Tris-HCl, 0.3 M NaCl and 10 mM imidazole, pH 8, remaining proteins were eluted with 3 ml of 0.25 M imidazole. Eluted proteins were dialyzed against 20 mM Tris-HCl, 0.15 M NaCl, pH 8 overnight. Purity and identity of B4ECv3 was verified by PAGE/Coomassie G-250 and Western blot with anti-Eph.B4 antibody. Finally, the concentration of B4ECv3 was measured, and the protein was aliquoted and stored at −70° C.

B4EC-FC protein and B2EC-FC protein were similarly purified.

5) Biochemical Assays

A. Binding Assay

10 µl of Ni-NTA-Agarose were incubated in microcentrifuge tubes with 50 µl of indicated amount of B4ECv3 diluted in binding buffer BB (20 mM Tris-HCl, 0.15 M NaCl, 0.1% bovine serum albumin pH 8) After incubation for 30 min on shaking platform, Ni-NTA beads were washed twice with 1.4 ml of BB, followed by application of 50 µl of B2-AP in the final concentration of 50 nM. Binding was performed for 30 min on shaking platform, and then tubes were centrifuged and washed one time with 1.4 ml of BB. Amount of precipitated AP was measured calorimetrically after application of PNPP.

B. Iinhibition Assay

Inhibition in solution. Different amounts of B4ECv3 diluted in 50 µl of BB were pre-incubated with 50 µl of 5 nM B2EC-AP reagent (protein fusion of Ephrin B2 ectodomain with placental alkaline phosphatase). After incubation for 1 h, unbound B2EC-AP was precipitated with 5,000 HEK293 cells expressing membrane-associated full-length EphB4 for 20 min. Binding reaction was stopped by dilution with 1.2 ml of BB, followed by centrifugation for 10 min. Supernatants were discarded and alkaline phosphatase activities associated with collected cells were measured by adding para-nitrophenyl phosphate (PNPP) substrate.

Cell based inhibition. B4ECv3 was serially diluted in 20 mM Tris-HCl, 0.15 M NaCl, 0.1% BSA, pH 8 and mixed with 5,000 HEK293 cells expressing membrane-associated full-length Ephrin B2. After incubation for 1 h, 50 µl of 5 nM B4EC-AP reagent (protein fusion of EphB4 ectodomain with placental alkaline phosphatase were added into each tube for 30 min to detect unoccupied Ephrin B2 binding sites. Binding reactions were stopped by dilution with 1.2 ml of BB and centrifugation. Colorimetric reaction of cell-precipitated AP was developed with PNPP substrate.

C. B4EC-FC Binding Assay

Figure 6:
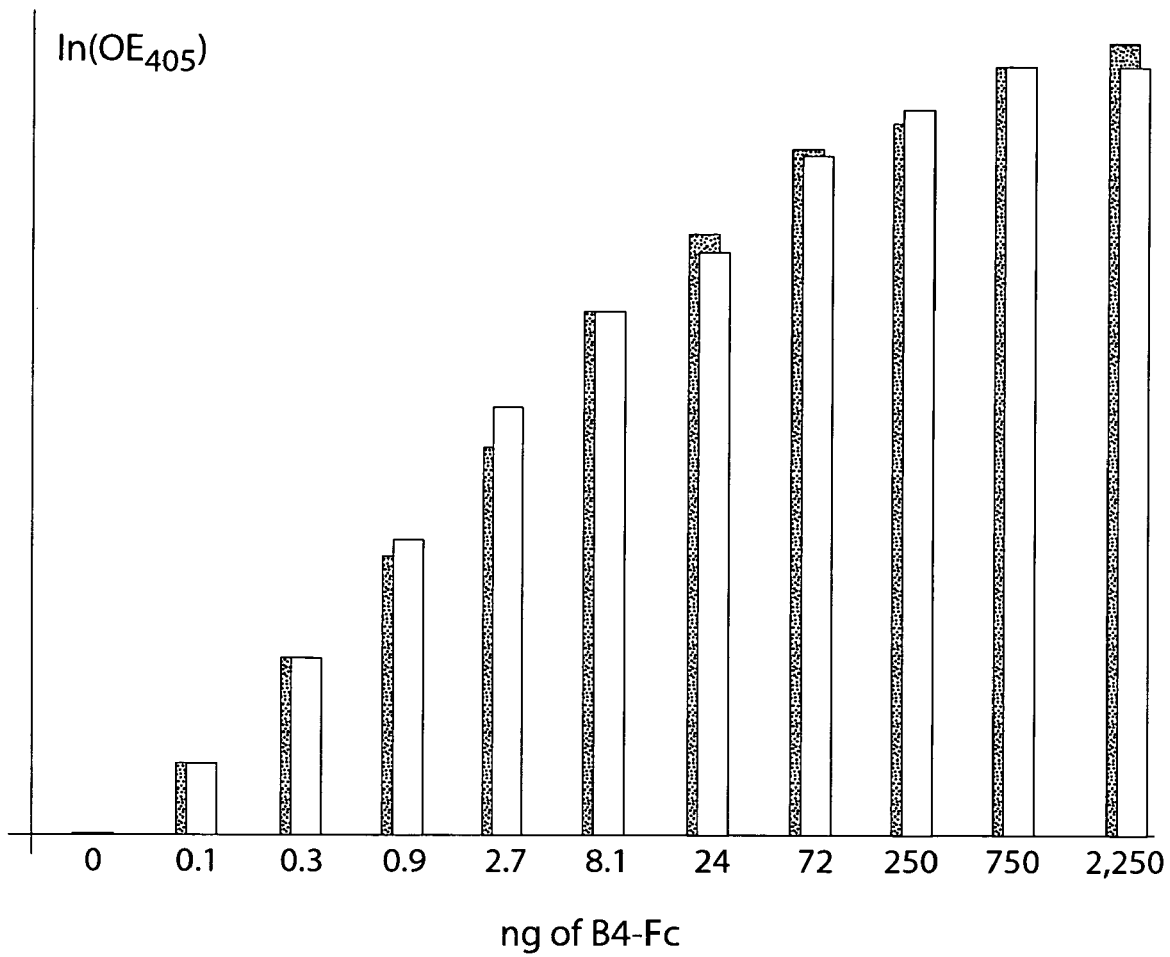
FIG. 6 shows B4EC-FC binding assay (Protein A-agarose based).

Protein A-agarose based assay. 10 µl of Protein A-agarose were incubated in Eppendorf tubes with 50 µl of indicated amount of B4EC-FC diluted in binding buffer BB (20 mM Tris-HCl, 0.15 M NaCl, 0.1% BSA pH 8). After incubation for 30 min on shaking platform, Protein AAagarose beads were washed twice with 1.4 ml of BB, followed by application of 50 µl of B2ECAP reagent at the final concentration of 50 nM. Binding was performed for 30 min on shaking platform, and then tubes were centrifuged and washed once with 1.4 ml of BB. Colorimetric reaction of precipitated AP was measured after application of PNPP (FIG. 6).

Nitrocellulose based assay. B4EC-FC was serially diluted in 20 mM Tris-HCl, 0.15 M NaCl, 50 µg/ml BSA, pH 8. 2 µl of each fraction were applied onto nitrocellulose strip and spots were dried out for 3 min. Nitrocellulose was blocked with 5% non-fat milk for 30 min, followed by incubation with 5 nM B2EC-AP reagent. After 45 min incubation for binding, nitrocellulose was washed twice with 20 mM Tris-HCl, 0.15 M NaCl, 50 µg/ml BSA, pH 8 and color was developed by application of alkaline phosphatase substrate Sigma Fast (Sigma).

D. B4EC-FC Inhibition Assay

Inhibition in solution. See above, for B4ECv3. The results were shown in FIG. 7.

Cell based inhibition. See above, for B4ECv3.

E. B2EC-FC Binding Assay

Protein-A-agarose based assay. See above, for B4EC-FC. The results were shown in FIG. 8.

Nitrocellulose based assay. See above, for B4EC-FC.

6) Cell-Based Assays

A. Growth Inhibition Assay

Human umbilical cord vein endothelial cells (HUVEC) ($1.5 \times 10^3$) are plated in a 96-well plate in 100 µl of EBM-2 (Clonetic # CC3162). After 24 hours (day 0), the test recombinant protein (100 µl) is added to each well at 2× the desired concentration (5-7 concentration levels) in EBM-2 medium. On day 0, one plate is stained with 0.5% crystal violet in 20% methanol for 10 minutes, rinsed with water, and air-dried. The remaining plates are incubated for 72 h at 37° C. After 72 h, plates are stained with 0.5% crystal violet in 20% methanol, rinsed with water and airdried. The stain is eluted with 1:1 solution of ethanol: 0.1 M sodium citrate (including day 0 plate), and absorbance is measured at 540 nm with an ELISA reader (Dynatech Laboratories). Day 0 absorbance is subtracted from the 72 h plates and data is plotted as percentage of control proliferation (vehicle treated cells). IC50 (drug concentration causing 50% inhibition) is calculated from the plotted data.

B. Cord Formation Assay (Endothelial Cell Tube Formation Assay)

Matrigel (60 µl of 10 mg/ml; Collaborative Lab # 35423) is placed in each well of an ice-cold 96-well plate. The plate is allowed to sit at room temperature for 15 minutes then incubated at 37° C. for 30 minutes to permit the matrigel to polymerize. In the mean time, HUVECs are prepared in EGM-2 (Clonetic # CC3162) at a concentration of $2 \times 10^5$ cells/ml. The test compound is prepared at 2× the desired concentration (5 concentration levels) in the same medium. Cells (500 µl) and 2× drug (500 µl) is mixed and 200 µl of this suspension are placed in duplicate on the polymerized matrigel. After 24 h incubation, triplicate pictures are taken for each concentration using a Bioquant Image Analysis system. Drug effect (IC50) is assessed compared to untreated controls by measuring the length of cords formed and number of junctions.

C. Cell Migration Assay

Migration is assessed using the 48-well Boyden chamber and 8 µm pore size collagen-coated (10 µg/ml rat tail collagen; Collaborative Laboratories) polycarbonate filters (Osmonics, Inc.). The bottom chamber wells receive 27-29 µl of DMEM medium alone (baseline) or medium containing chemo-attractant (bFGF, VEGF or Swiss 3T3 cell conditioned medium). The top chambers receive 45 µl of HUVEC cell suspension ($1 \times 10^6$ cells/ml) prepared in DMEM+1% BSA with or without test compound. After 5 h incubation at 37° C., the membrane is rinsed in PBS, fixed and stained in Diff-Quick solutions. The filter is placed on a glass slide with the migrated cells facing down and cells on top are removed using a Kimwipe. The testing is performed in 4-6 replicates and five fields are counted from each well. Negative unstimulated control values are subtracted from stimulated control and drug treated values and data is plotted as mean migrated cell ±S.D. IC50 is calculated from the plotted data.

EXAMPLE 2

Extracellular Domain Fragments of EphB4 Receptor Inhibit Angiogenesis and Tumor Growth A. Globular Domain of EphB4 is Required for EphrinB2 Binding and for the Activity of EphB4-Derived Soluble Proteins in Endothelial Tube Formation Assay.

To identify subdomain(s) of the ectopic part of EphB4 necessary and sufficient for the anti-angiogenic activity of the soluble recombinant derivatives of the receptor, four recombinant deletion variants of EphB4EC were produced and tested (FIG. 16). Extracellular part of EphB4, similarly to the other members of EphB and EphA receptor family, contains N-terminal ligand-binding globular domain followed by cysteine-rich domain and two fibronectin type III repeats (FNIII). In addition to the recombinant B4-GCF2 protein containing the complete ectopic part of EphB4, we constructed three deletion variants of EphB4EC containing globular domain and Cys-rich domain (B4-GC); globular, Cys-rich and the first FNIII domain (GCF1) as well as the ECD version with deleted globular domain (CF2). Our attempts to produce several versions of truncated EphB4EC protein containing the globular domain alone were not successful due to the lack of secretion of proteins expressed from all these constructs and absence of ligand binding by the intracellularly expressed recombinant proteins. In addition, a non-tagged version of B4-GCF2, called GCF2-F, containing complete extracellular domain of EphB4 with no additional fused amino acids was expressed, purified and used in some of the experiments described here.

Figure 17A:
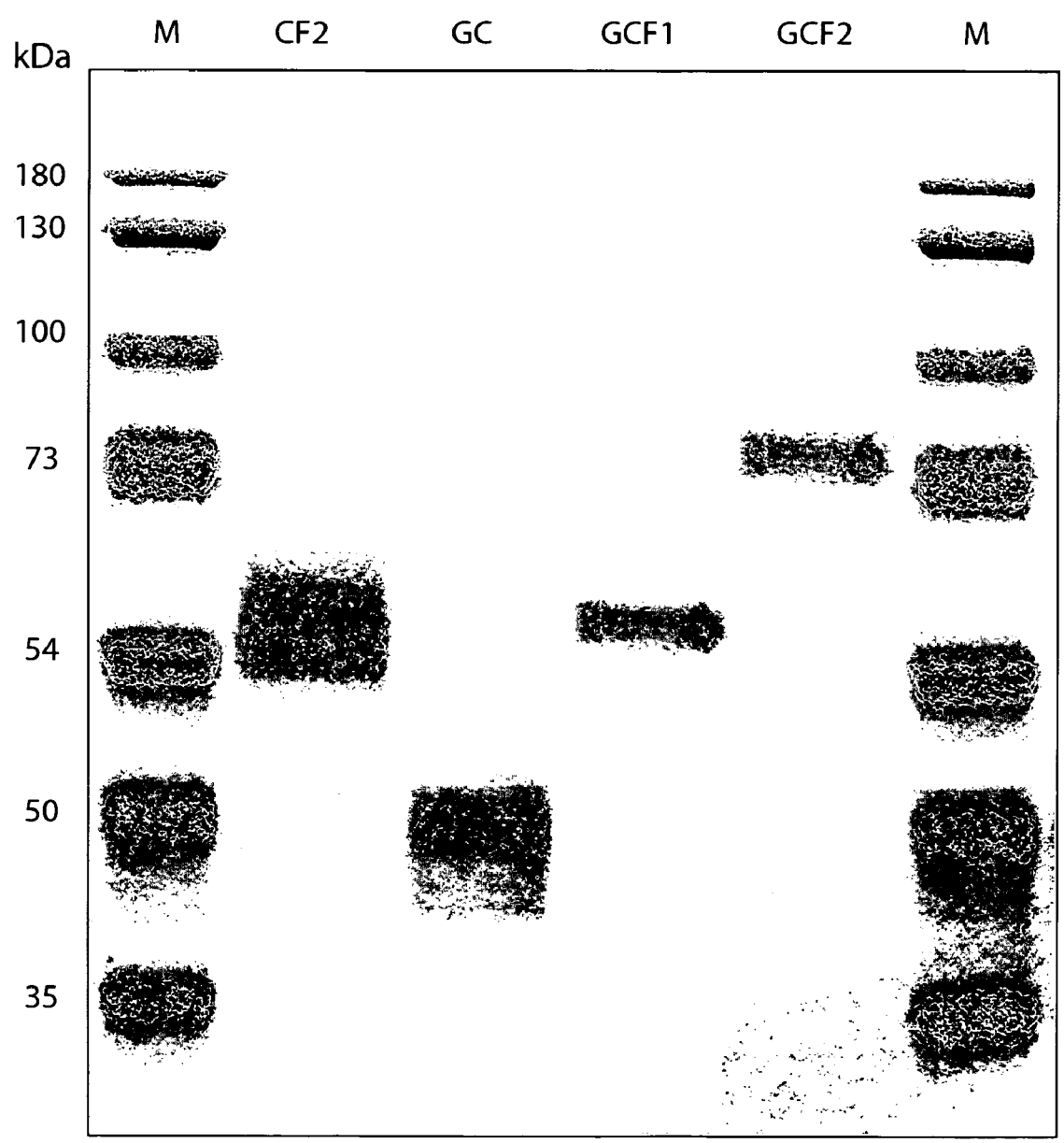
FIG. 17 shows purification and ligand binding properties of the EphB4EC proteins. A. SDS-PAAG gel electrophoresis of purified EphB4-derived recombinant soluble proteins (Coomassie-stained). B. Binding of Ephrin B2-AP fusion to EphB4-derived recombinant proteins immobilized on Ni-NTA-agarose beads. Results of three independent experiments are shown for each protein. Vertical axis—optical density at 420 nm.
Figure 17B:
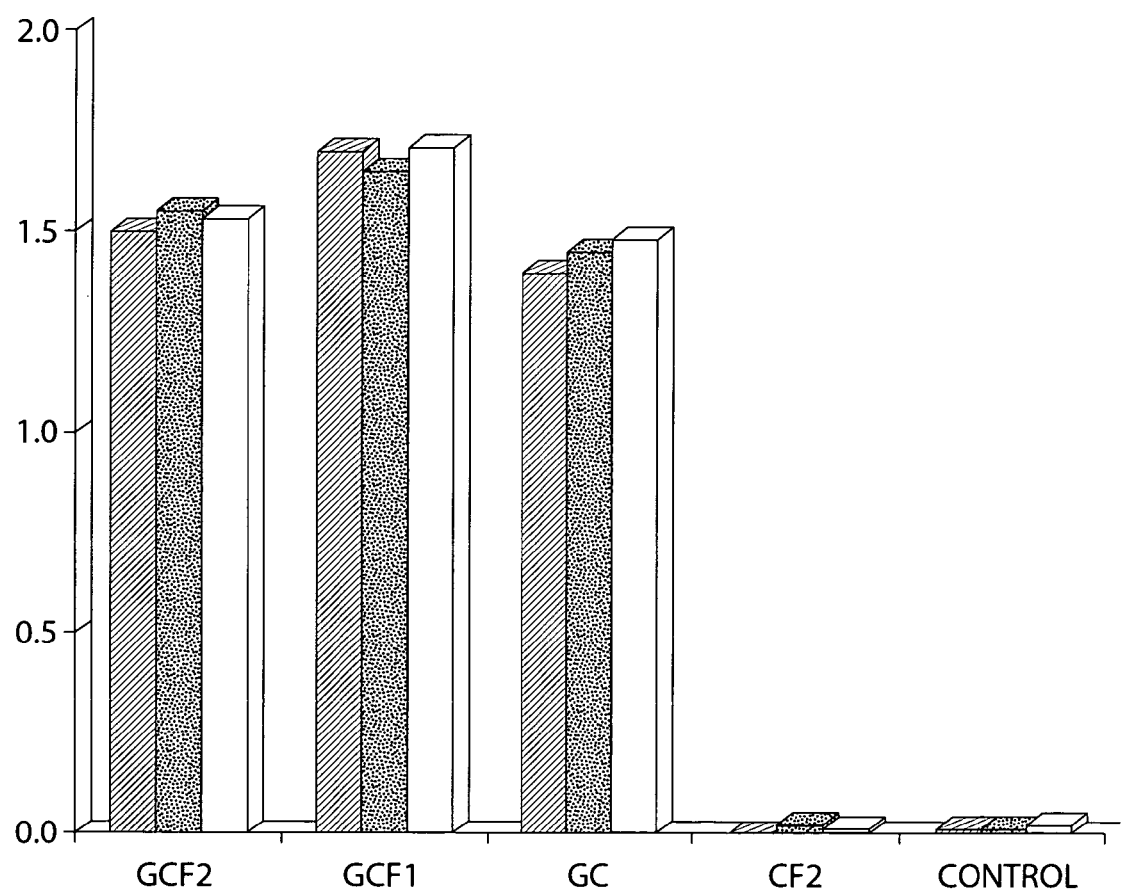

All four C-terminally 6×His tagged recombinant proteins were preparatively expressed in transiently transfected cultured mammalian cells and affinity purified to homogeneity from the conditioned growth media using chromatography on $Ni^{2+}$-chelate resin (FIG. 17). Apparently due to their glycosylation, the proteins migrate on SDS-PAAG somewhat higher than suggested by their predicted molecular weights of 34.7 kDa (GC), 41.5 (CF2), 45.6 kDa (GCF1) and 57.8 kDa (GCF2). Sequence of the extracellular domain of human EphB4 contains three predicted N-glycosylation sites (NXS/T) which are located in the Cys-rich domain, within the first fibronectin type III repeat and between the first and the second fibronectin repeats.

To confirm ability of the purified recombinant proteins to bind Ephrin B2, they were tested in an in vitro binding assay. As expected, GC, GCF1 and GCF2, but not CF2 are binding the cognate ligand Ephrin B2 as confirmed by interaction between Ephrin B2-alkaline phosphatase (Ephrin B2-AP) fusion protein with the B4 proteins immobilized on $Ni^{2+-}$ resin or on nitrocellulose membrane (FIG. 17).

All four proteins were also tested for their ability to block ligand-dependent dimerization and activation of Eph B4 receptor kinase in PC3 cells. The PC3 human prostate cancer cell line is known to express elevated levels of human Eph B4. Stimulation of PC3 cells with Ephrin B2 IgG Fc fusion protein leads to a rapid induction of tyrosine phosphorylation of the receptor. However, preincubation of the ligand with GCF2, GCF1 or GC, but not CF2 proteins suppresses subsequent EphB4 autophosphorylation. Addition of the proteins alone to the PC3 cells or preincubation of the cells with the proteins followed by changing media and adding the ligand does not affect EphB4 phosphorylation status.

Further, we found that globular domain of EphB4 is required for the activity of EphB4-derived soluble proteins in endothelial tube formation assay.

B. Effects of Soluble EphB4 on HUV/AEC In Vitro.

Figure 18:
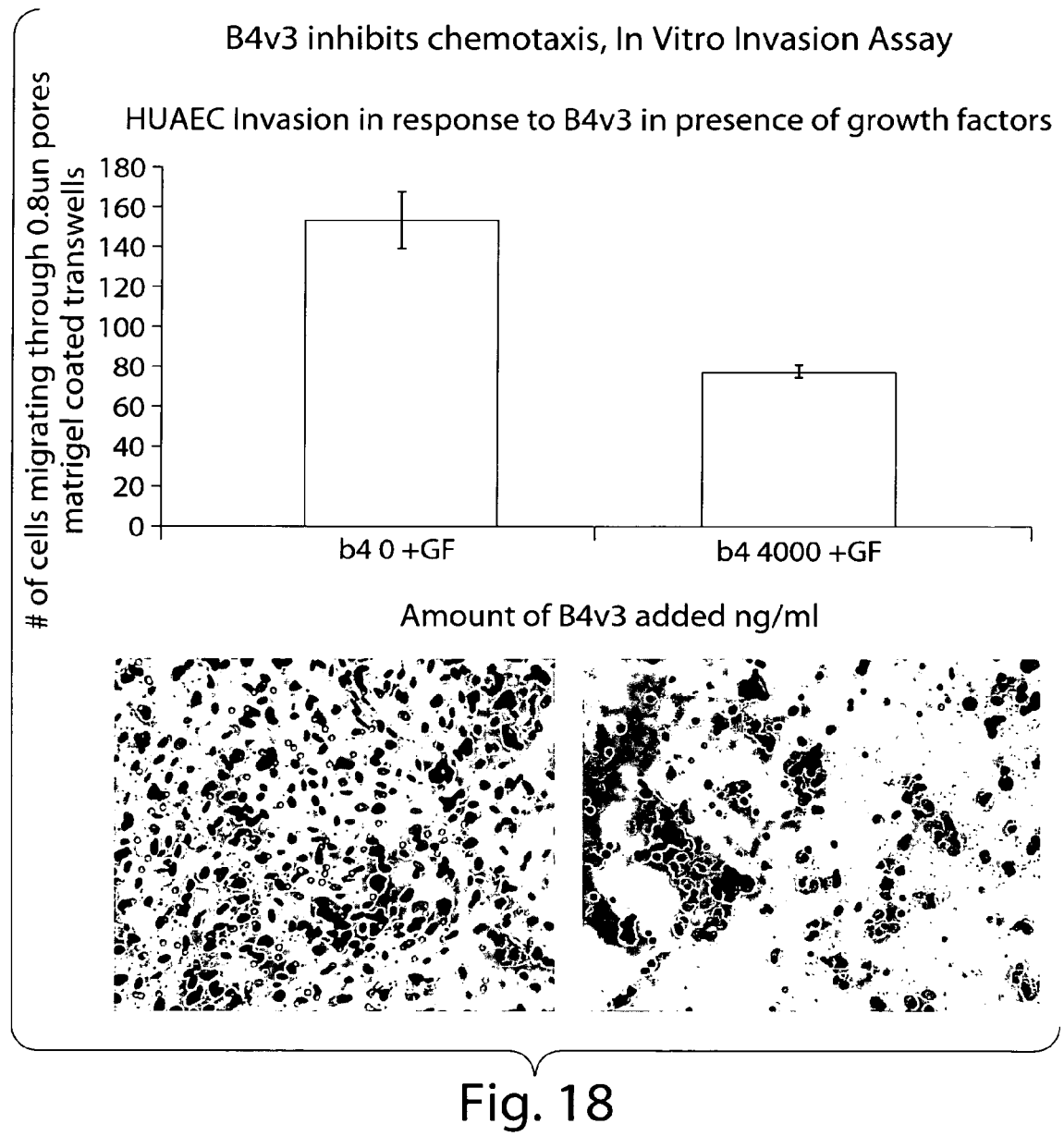
FIG. 18 shows that EphB4v3 inhibits chemotaxis.
Figure 19A:
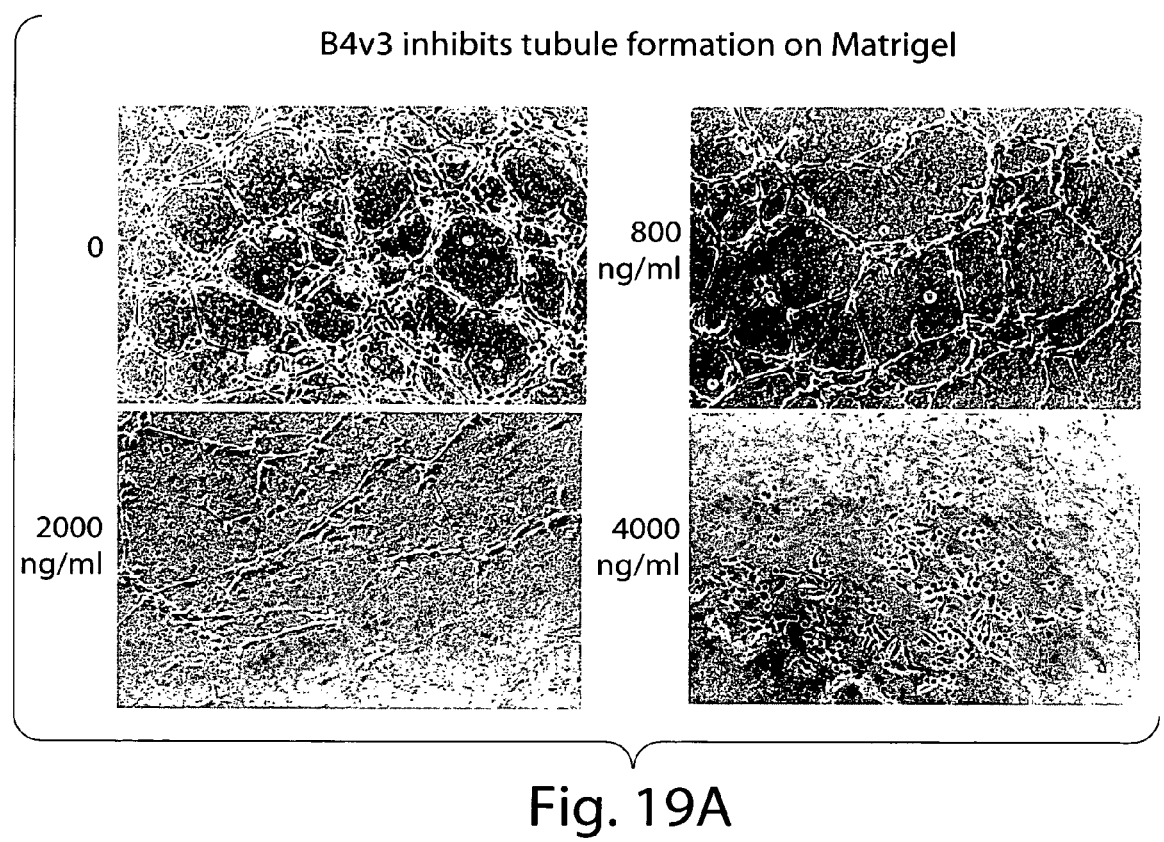
FIG. 19 shows that EphB4v3 inhibits tubule formation on Matrigel. A displays the strong inhibition of tubule formation by B4v3 in a representative experiment. B shows a quantitation of the reduction of tube-length obtained with B4v3 at increasing concentrations as well as a reduction in the number of junctions, in comparison to cells with no protein. Results are displayed as mean values_S.D. obtained from three independent experiments performed with duplicate wells.
Figure 19B:
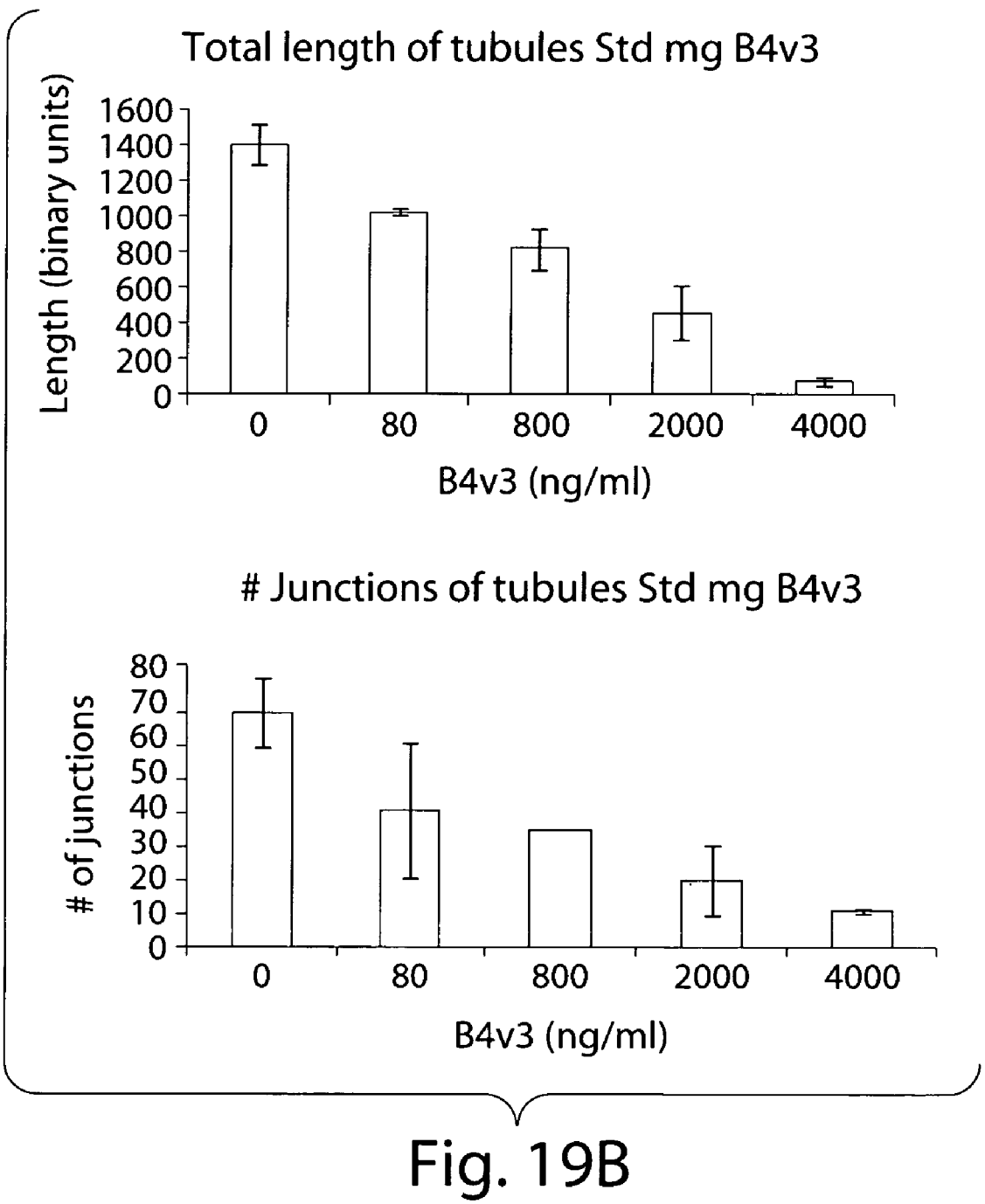
Figure 20:
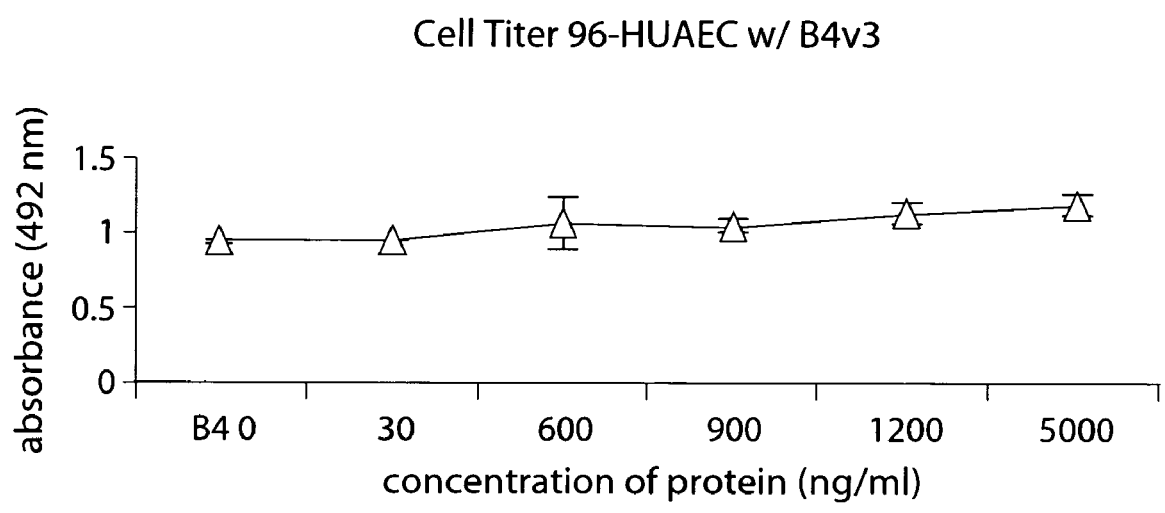
FIG. 20 shows that soluble EphB4 has no detectable cytotoxic effect as assessed by MTS assay.

Initial experiments were performed to determine whether soluble EphB4 affected the three main stages in the angiogenesis pathway. These were carried out by establishing the effects of soluble EphB4 on migration/invasion, proliferation and tubule formation by HUV/AEC in vitro. Exposure to soluble EphB4 significantly inhibited both bFGF and VEGF-induced migration in the Boyden chamber assay in a dose-dependent manner, achieving significance at nM (FIG. 18). Tubule formation by HUV/AECS on wells coated with Matrigel was significantly inhibited by soluble EphB4 in a dose-dependent manner in both the absence and presence of bFGF and VEGF (FIG. 19). We also assessed in vitro, whether nM of soluble EphB4 was cytotoxic for HUVECS. Soluble EphB4 was found to have no detectable cytotoxic effect at these doses, as assessed by MTS assay (FIG. 20).

C. Soluble EphB4 Receptor Inhibits Vascularization of Matrigel Plugs, In Vivo

Figure 21:
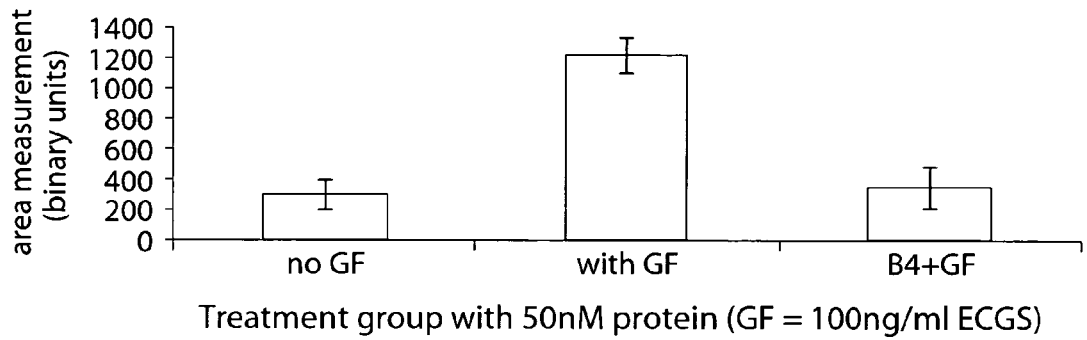
FIG. 21 shows that B4v3 inhibits invasion and tubule formation by endothelial cells in the Matrigel assay. (A) to detect total invading cells, photographed at 20× magnification or with Masson's Trichrome Top left of A B displays section of a Matrigel plug with no GF, top right of A displays section with B4IgG containing GF and lower left section contains GF, and lower right shows GF in the presence of B4v3. Significant invasion of endothelial cells is only seenin GF containing Matrigel. Top right displays an area with a high number of invaded cells induced by B4IgG, which signifies the dimeric form of B4v3. The left upper parts of the pictures correspond to the cell layers formed around the Matrigel plug from which cells invade toward the center of the plug located in the direction of the right lower corner. Total cells in sections of the Matrigel plugs were quantitated with Scion Image software. Results obtained from two experiments with duplicate plugs are displayed as mean values_S.D.

To demonstrate that soluble EphB4 can directly inhibit angiogenesis in vivo, we performed a murine matrigel plug experiment. Matrigel supplemented with bFGF and VEGF with and without soluble EphB4 was injected s.c. into Balb/C nu/nu mice, forming semi-solid plugs, for six days. Plugs without growth factors had virtually no vascularization or vessel structures after 6 days (FIG. 21). In contrast, plugs supplemented with bFGF and VEGF had extensive vascularization and vessels throughout the plug. Plugs taken from mice treated with µg of soluble EphB4 had markedly reduced vascularization of plugs, comparable to plugs without growth factor (FIG. 21). Furthermore, histological examination of plugs showed decreased vessel staining (FIG. 21). Treatment at 0 µg/dose significantly inhibited the amount of infiltration in Matrigel plugs compared to control (FIG. 21).

Figure 22:
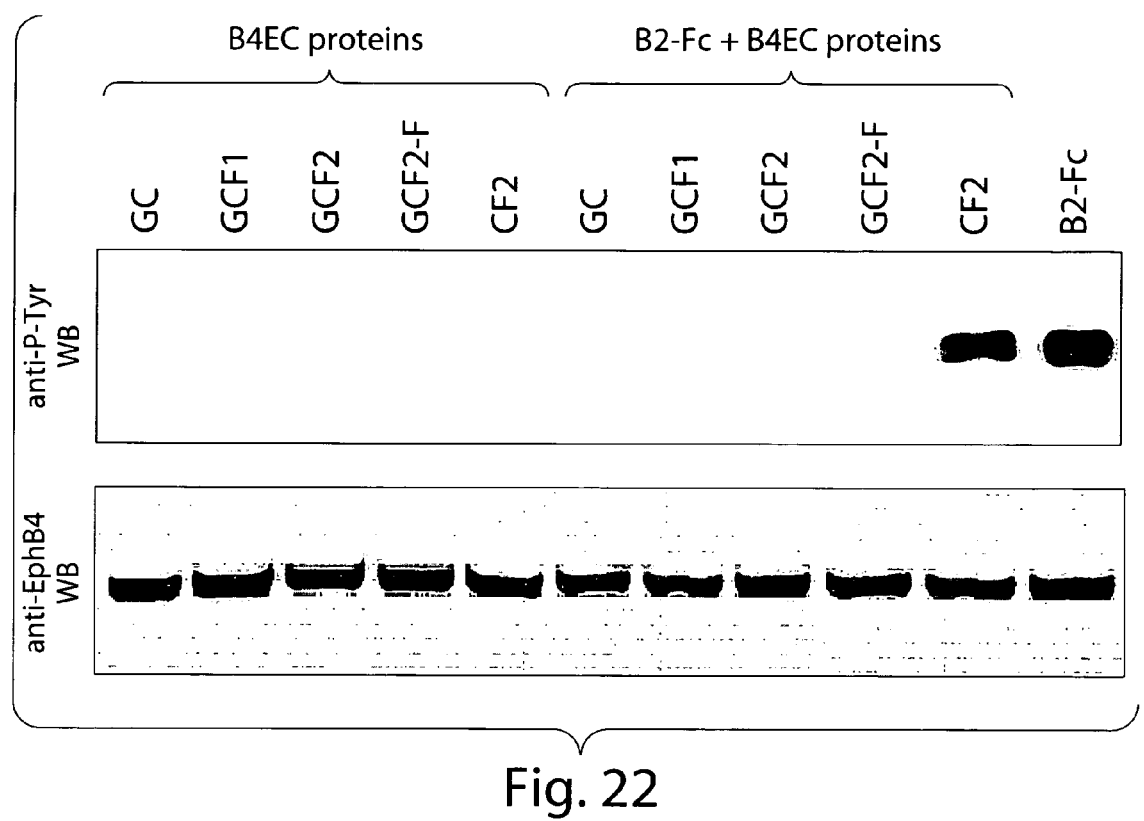
FIG. 22 shows tyrosine phosphorylation of EphB4 receptor in PC3 cells in response to stimulation with EphrinB2-Fc fusion in presence or absence of EphB4-derived recombinant soluble proteins.

We examined EphB4 receptor phosphorylation in HUVECs by performing Western blot analyses with lysates from soluble EphB4-treated cells and antibodies against phosphor-tyrosine. We found that soluble EphB4 treatment of serum-starved HUVECs stimulated a rapid and transient decrease in the level of phosphorylated EphB4, in the presence of EphrinB2Fc, EphB4 ligand dimer. Ephrin B2Fc without the soluble EphB4 protein induced phosphorylation of EphB4 receptor (FIG. 22).

D. Effects of Soluble EphB4 on Tumor Growth, In Vitro.

Figure 23A:
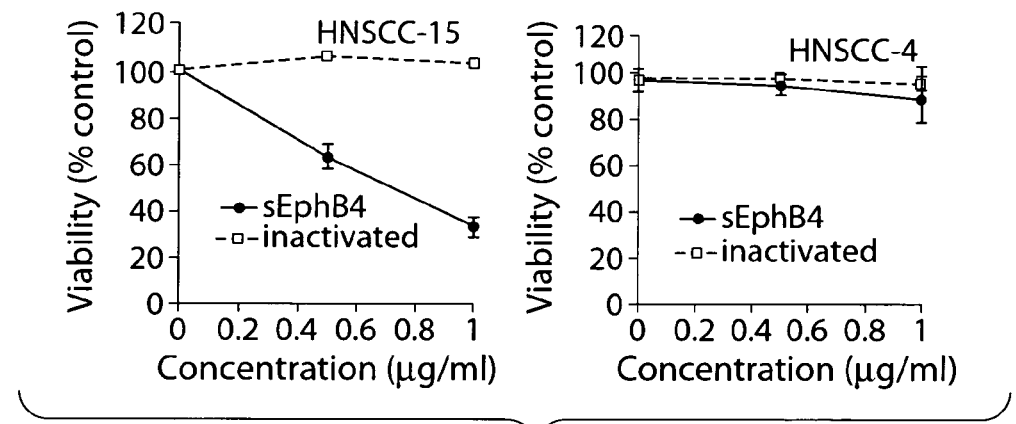
FIG. 23 shows effects of soluble EphB4ECD on viability and cell cycle. A) 3-day cell viability assay of two HNSCC cell lines. B) FACS analysis of cell cycle in HNSCC-15 cells treated as in A. Treatment of these cells resulted in accumulation in subG0/G1 and S/G2 phases as indicated by the arrows.
Figure 23B:
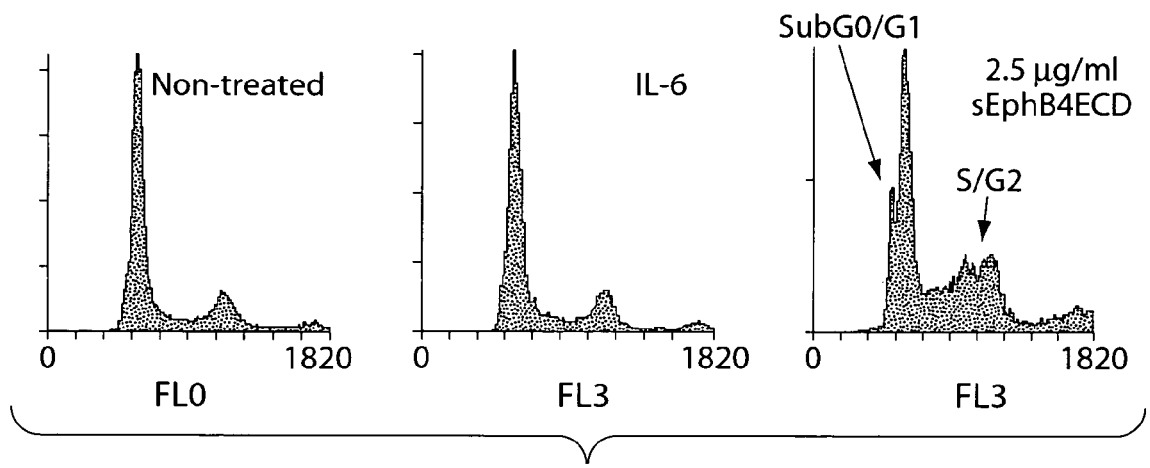

We found that soluble EphB4 inhibits the growth of SCC15 tumors grown in Balb/C Nu/Nu mice (FIG. 23).

E. Soluble EphB4 Inhibited Corneal Neovascularization

Figure 24:
FIG. 24 shows that B4v3 inhibitis neovascular response in a murine corneal hydron micropocket assay.

To further investigate the antiangiogenic activity of soluble EphB4 in vivo, we studied the inhibitory effect of administration of soluble EphB4 on neovascularization in the mouse cornea induced by bFGF. Hydron Pellets implanted into corneal micropocket could induce angiogenesis, in the presence of growth factors, in a typically avascular area. The angiogenesis response in mice cornea was moderate, the appearance of vascular buds was delayed and the new capillaries were sparse and grew slowly. Compared with the control group, on day 7 of implantation, the neovascularization induced by bFGF in mice cornea was markedly inhibited in soluble EphB4-treated group (FIG. 24).

F. Effects of Soluble EphB4 on Tumor Growth, In Vivo.

The same model was used to determine the effects of soluble EphB4 in vivo. SCC15 tumors implanted subcutaneously, pre-incubated with matrigel and with or w/o growth factors, as well as implanted sc alone, and mice treated sc or ip daily with 1-5 ug of soluble EphB4 were carried out.

Figure 25:
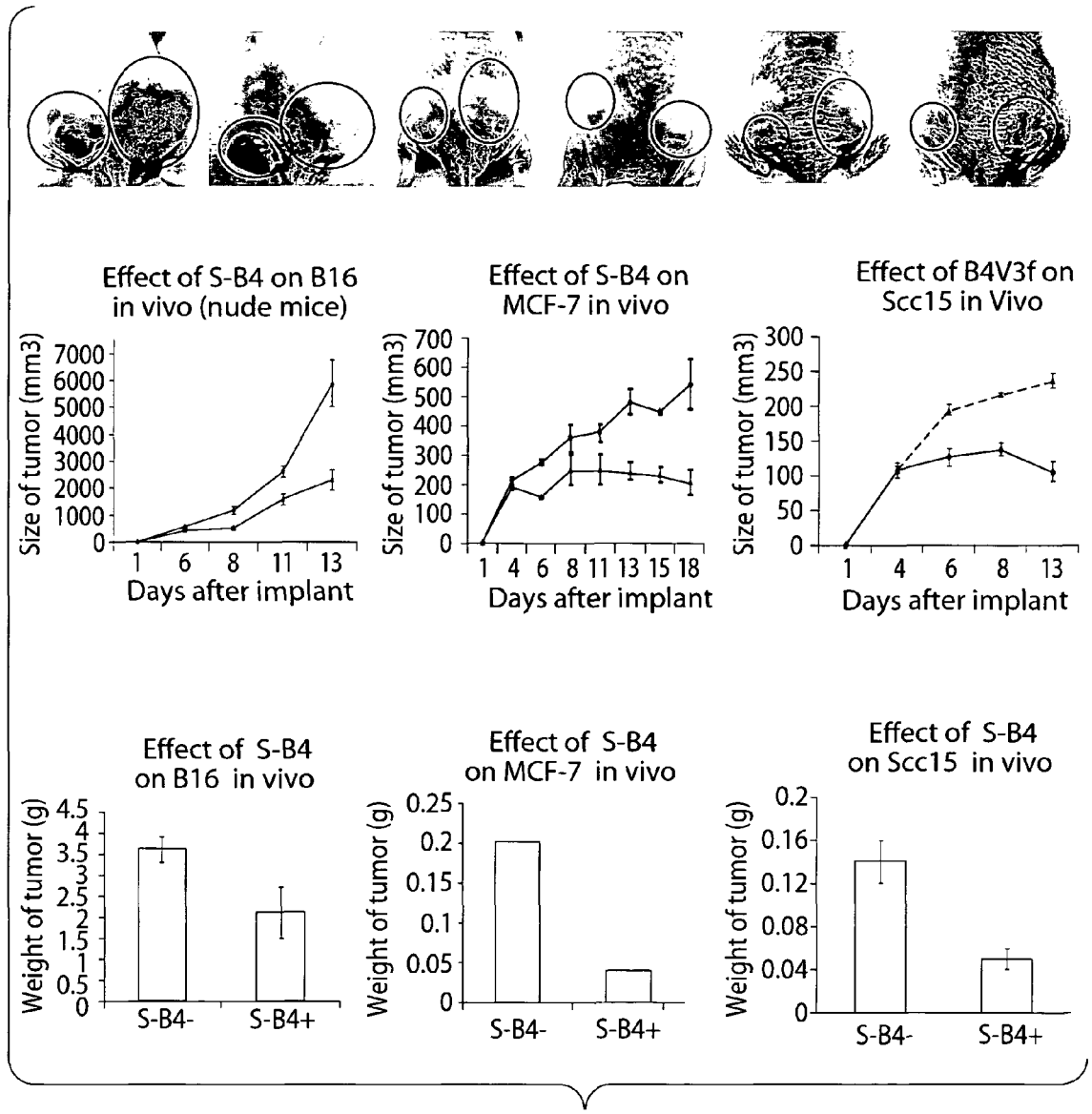
FIG. 25 shows that that SCC15, B16, and MCF-7 co-injected with sB4v3 in the presence of matrigel and growth factors, inhibits the in vivo tumor growth of these cells.

Tumors in the control group continued to grow steadily over the treatment period, reaching a final tumor volume of mm3. However, animals injected with soluble EphB4 exhibited a significantly (p<0.0/) reduced growth rate, reaching a final tumor volume of only mm3 (FIG. 25). Similar results were obtained in two further cohorts of such tumor-bearing mice. Soluble EphB4 administration appeared to be well tolerated in vivo, with no significant effect on body weight or the general well-being of the animals (as determined by the absence of lethargy, intermittent hunching, tremors or disturbed breathing patterns).

G. Effects of Soluble EphB4 on Tumor Histology.

Figure 26:
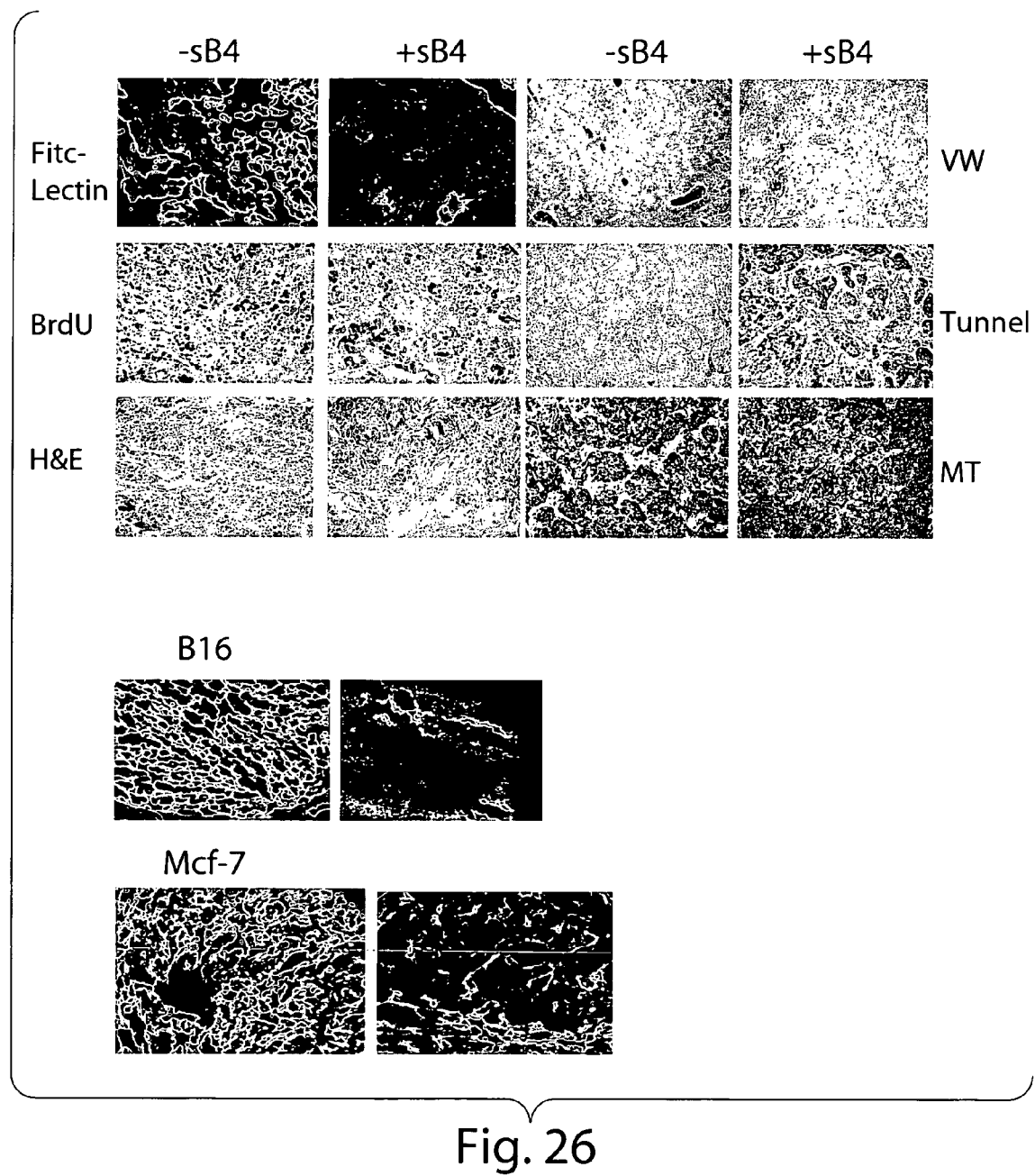
FIG. 26 shows that soluble EphB4 causes apoptosis, necrosis and decreased angiogenesis in threee tumor types, B16 melanoma, SCC15, head and neck carcinoma, and MCF-7 Breast carcinoma. Tumors were injected premixed with Matrigel plus growth factors and soluble EphB4 subcutaneously. After 10 to 14 days, the mice were injected intravenously with fitc-lectin (green) to assess blood vessel perfusion. Tumors treated with control PBS displayed abundant tumor density and a robust angiogenic response Tumors treated with sEphB4 displayed a decrease in tumor cell density and a marked inhibition of tumor angiogenesis in regions with viable tumor cells, as well as tumor necrosis and apoptosis.

Histological analysis revealed the presence of a central area of necrosis in all SCC 15 tumors, which was usually surrounded by a viable rim of tumor cells um in width. The central necrotic areas were frequently large and confluent and showed loss of cellular detail. Necrosis, assessed as a percentage of tumor section area, was significantly (p<0.02) more extensive in the soluble EphB4-treated group (% necrosis in treated vs. control). To determine whether the reduced volume of soluble EphB4 treated tumors was due to an effect of this protein on the tumor vascular supply, endothelial cells in blood vessels were identified in tumor sections using immunostaining with an anti-platelet cell adhesion molecule (PECAM-1; CD31) antibody (FIG. 26) and the density of microvessels was assessed. Microvessel density was similar in the outer viable rim of tumor cells (the uniform layer of cells adjacent to the tumor periphery with well defined nuclei) in control and soluble EphB4-treated tumors. Microvessel density was significantly in the inner, less viable region of tumor cells abutting the necrotic central areas in soluble EphB4-treated than control tumors. Fibrin deposition, as identified by Masson's Trichrome staining, was increased in and around blood vessels in the inner viable rim and the central necrotic core of soluble EphB4 treated than control tumors. In the outer viable rim of soluble EphB4 treated tumors, although the vessel lumen remained patent and contained red blood cells, fibrin deposition was evident around many vessels. Soluble EphB4 was found to have no such effects on the endothelium in the normal tissues examined (lungs, liver and kidneys).

H. Materials and Methods

1) Expression Constructs

To construct expression vectors for producing soluble, 6×His-tagged EphB4-ECD variants, cloned full-length human EphB4 cDNA was amplified by PCR using the following oligo primers: TACTAGTCCGCCATGGAGCTCCGGGTGCTGCT (SEQ ID NO: 9) (common EphB4 N-terminal primer) and GCGGCCGCTTAATGGTGATGGTGATGAGCCGAAGGA AGGAGGGGTGGTGCA (SEQ ID NO: 10) (B4-GC), AGCGGCCGCTTAATGGTGATGGTGAT GATGGACATTGA CAGGCTCAAATGGA (SEQ ID NO: 11) (B4-GCF1) or TGCGGCCGCTTAATG GTGATGGTGATGAT GCTGCTCCCGCCAGCCCTCGCTCTCAT (SEQ ID NO: 12) (B4-GCF2). The resulting PCR fragments were TA-cloned into mammalian expression vector pEF6/V5-His-TOPO (Invitrogen) under EF-1α promoter control. The expressed recombinant proteins encode the following fragments of the mature extracellular part of human EphB4: amino acid positions 1-522 (GCF2), 1-412 (GCF1) and 1-312 (GC). To generate the B4-CF2 deletion (δ amino acids 13-183) PCR fragment for pEF6 cloning, EphB4 cDNA was amplified by two-step overlap PCR using oligo primers TACTAGTCCGCCATGGA GCTCCGGGT-GCTGCT(SEQ ID NO: 13), CAGCTGAGTTTC-CAATTTTGTGTTC (SEQ ID NO: 14), GACACAAAAT-TGGAAACTCAGCTGACTGTGAACCTGAC (SEQ ID NO: 15)and GCGGCCGCCCTG CTCCCGCCAGC-CCTCGCT (SEQ ID NO: 16).

Vector for producing secreted human EphrinB2-alkaline phosphatase (B2-AP) reagent was constructed by PCR amplification of human Ephrin B2 cDNA using primers TAAAGCTTCCGCCATGGCTGTGAGAAGGGAC (SEQ ID NO: 17) and TAGGATCCTTCGGAACCG GAAC-CGAGGAGGATGTTGTTCCC (SEQ ID NO: 18)and cloning the resulting fragment, digested with Hind III and Bam HI, into Hind III-Bgl II digested pAPTag2 vector (GenHunter, Inc.). In each case, inserts in expression vectors were verified by complete sequencing.

2) Antibodies and Other Reagents

Anti-Eph B4 monoclonal antibodies mAB79 and mAB23 were raised in mice against the GCF2 protein containing amino acids 1-522 of mature human EphB4 and purified from hybridoma supernatants by Protein A chromatography. The anti-phosphotyrosine antibody 4G10 was from UBI (Lake Placid, N.Y.). Protein G-HRP conjugate was purchased from Bio-Rad.

3) Expression and Purification of EphB4-Derived Recombinant Proteins

To produce the EphB4-ECD soluble proteins, cultured human embryonic kidney cells HEK293T were transfected with the corresponding plasmid constructs using standard calcium phosphate or Lipofectamin 2000 reagent (Invitrogen) protocols. Twelve to sixteen hours post-transfection, the growth medium (DMEM+10% fetal bovine serum) was aspirated, cells washed once with serum free DMEM and replaced with serum free DMEM. Conditioned media containing the secreted proteins were harvested 72-96 hours later, clarified by centrifugation and used for purification of His-tagged proteins using Ni-NTA Agarose (Qiagen). The purity and quantity of the recombinant proteins was tested by SDS-PAAG electrophoresis with Coomassie Blue or silver staining, Western blotting and UV spectroscopy. Purified proteins were dialyzed against 20 mM Tris-HCl, 0.15 M NaCl, pH 8 and stored at −70° C.

To test ligand binding properties of the proteins, 10 µl of Ni-NTA-Agarose (Qiagen) were incubated in microcentrifuge tubes with 10-500 ng sample of a B4-ECD protein diluted in 0.5 ml of binding buffer BB (20 mM Tris-HCl, 0.15 M NaCl, 0.1% bovine serum albumin, pH 8). After incubation for 30 min on shaking platform, Ni-NTA beads were washed twice with 1.4 ml of BB, followed by addition of B2-AP fusion protein at concentration of 50 nM. Binding was performed for 30 min on a shaking platform. Tubes were centrifuged and washed once with 1.4 ml of BB. Amount of precipitated AP was measured colorimetrically at 420 nm after application of p-nitrophenyl phosphate (PNPP) and incubation for 5-30 min.

4) Immunoprecipitation

All lysates were processed at 4° C. Cells were lysed in 1 ml of buffer containing 20 mM Hepes at pH 7.4, 100 mM sodium chloride, 50 mM sodium fluoride, 2 mM EDTA, 2 mM EGTA, 1 mM sodium orthovanadate, 1%(v/v) NP-40, 0.5% (w/v) sodium deoxycholate, 1 mM phenyl methylsulphonyl fluoride (added freshly) and 100U Trasylol. Lysates were scraped into Eppendorf tubes and 50 µl of boiled, formalin-fixed *Staphylococcus aureus* was added (Calbiochem, San Diego).

After 30 min of mixing, the lysates were centrifuged for 5 min at 25,000 g in a minifuge and the supernatants transferred to new tubes containing the appropriate antibody. Lysates were mixed with antibodies for 1 h, after which time 50 µl of protein A-Sepharose beads were added and the contents of the tubes mixed for 1 h to collect the immunoprecipitates. Protein A beads were collected by centrifugation at 25,000 g for 30 s. The supernatants were discarded and the beads washed three times with 1 ml lysis buffer minus deoxycholate.

5) Cell-Based EphB4 Tyrosine Kinase Assay

The human prostate carcinoma cell line PC3 cells were maintained in RPMI medium with 10% dialyzed fetal calf serum and 1% penicillin/streptomycin/neomycin antibiotics mix. Cells were maintained at 37° C. in a humidified atmosphere of 5% $CO_2$/95% air. Typically, cells were grown in 60 mm dishes until confluency and were either treated with mouse Ephrin B2-Fc fusion at 1 µg/ml in RPMI for 10 min to activate EphB4 receptor or plain medium as a control. To study the effect of different derivatives of soluble EphB4 ECD proteins on EphB4 receptor activation, three sets of cells were used. In the first set, cells were treated with various proteins (5 proteins; GC, GCF1, GCF2, GCF2-F, CF2) at 5 µg/ml for 20 min. In the second set of cells, prior to application, proteins were premixed with ephrinB2-Fc at 1:5 (EphB4 protein: B2-Fc) molar ratio, incubated for 20 min and applied on cells for 10 min. In the third set of cells, cells were first treated with the proteins for 20 min at 5 µg/ml, media was replaced with fresh media containing 1 µg/ml of EphrinB2-Fc and incubated for another 10 min.

After the stimulation, cells were immediately harvested with protein extraction buffer containing 20 mM Tris-HCl, pH 7.4, 150 mM NaCl, 1% (v/v) Triton X100, 1 mM EDTA, 1 mM PMSF, 1 mM Sodium vanadate. Protein extracts were clarified by centrifugation at 14,000 rpm for 20 min at 4° C. Clarified protein samples were incubated overnight with protein A/G coupled agarose beads pre-coated with anti-EphB4 monoclonal antibodies. The IP complexes were washed twice with the same extraction buffer containing 0.1% Triton X100. The immunoprecipitated proteins were solubilized in 1×SDS-PAGE sample loading buffer and separated on 10% SDS-PAGE. For EphB4 receptor activation studies, electroblotted membrane was probed with anti-pTyr specific antibody 4G10 at 1:1000 dilution followed by Protein G-HRP conjugate at 1:5000 dilutions.

6) Cell Culture

Normal HUVECs were obtained from Cambrex (BioWhittaker) and maintained in EBM2 medium supplemented with 0.1 mg/ml endothelial growth supplement (crude extract from bovine brain), penicillin (50 U/ml), streptomycin (50 U/ml), 2 mmol/l glutamine and 0.1 mg/ml sodium heparin. Aliquots of cells were preserved frozen between passages 1 and 3. For all experiments, HUVECs were used at passages 4 or below and collected from a confluent dish.

7) Endothelial Cell Tube Formation Assay

Matrigel (60 µl of 10 mg/ml; Collaborative Lab, Cat. No. 35423) was placed in each well of an ice-cold 96-well plate. The plate was allowed to sit at room temperature for 15 minutes then incubated at 37° C. for 30 minutes to permit Matrigel to polymerize. In the mean time, human umbilical vein endothelial cells were prepared in EGM-2 (Clonetic, Cat. No. CC3162) at a concentration of $2\times10^5$ cells/ml. The test protein was prepared at 2× the desired concentration (5 concentration levels) in the same medium. Cells (500 µl) and 2× protein (500 µl) were mixed and 200 µl of this suspension were placed in duplicate on the polymerized Matrigel. After 24 h incubation, triplicate pictures were taken for each concentration using a Bioquant Image Analysis system. Protein addition effect ($IC_{50}$) was assessed compared to untreated controls by measuring the length of cords formed and number of junctions.

8) Cell Migration Assay

Chemotaxis of HUVECs to VEGF was assessed using a modified Boyden chamber, transwell membrane filter inserts in 24 well plates, 6.5 mm diam, 8 µm pore size, 10 µm thick matrigel coated, polycarbonate membranes (BD Biosciences). The cell suspensions of HUVECs ($2\times10^5$ cells/ml) in 200 µl of EBM were seeded in the upper chamber and the soluble EphB4 protein were added simultaneously with stimulant (VEGF or bFGF) to the lower compartment of the chamber and their migration across a polycarbonate filter in response to 10-20 ng/ml of VEGF with or without 100 nM-1 µM test compound was investigated. After incubation for 4-24 h at 37° C., the upper surface of the filter was scraped with swab and filters were fixed and stained with DiffQuick. Ten random fields at 200× mag were counted and the results expressed as mean # per field. Negative unstimulated control values were subtracted from stimulated control and protein treated sample values and the data was plotted as mean migrated cell ±S.D. $IC_{50}$ was calculated from the plotted data.

9) Growth Inhibition Assay

HUVEC ($1.5\times10^3$ cells) were plated in a 96-well plate in 100 µl of EBM-2 (Clonetic, Cat. No. CC3162). After 24 hours (day 0), the test recombinant protein (100 µl) is added to each well at 2× the desired concentration (5-7 concentration levels) in EBM-2 medium. On day 0, one plate was stained with 0.5% crystal violet in 20% methanol for 10 minutes, rinsed with water, and air-dried. The remaining plates were incubated for 72 h at 37° C. After 72 h, plates were stained with 0.5% crystal violet in 20% methanol, rinsed with water and air-dried. The stain was eluted with 1:1 solution of ethanol: 0.1 M sodium citrate (including day 0 plate), and absorbance measured at 540 nm with an ELISA reader (Dynatech Laboratories). Day 0 absorbance was subtracted from the 72 h plates and data is plotted as percentage of control proliferation (vehicle treated cells). $IC_{50}$ value was calculated from the plotted data.

10) Murine Matrigel Plug Angiogenesis Assay

In vivo angiogenesis was assayed in mice as growth of blood vessels from subcutaneous tissue into a Matrigel plug containing the test sample. Matrigel rapidly forms a solid gel at body temperature, trapping the factors to allow slow release and prolonged exposure to surrounding tissues. Matrigel (8.13 mg/ml, 0.5 ml) in liquid form at 4° C. was mixed with Endothelial Cell Growth Supplement (ECGS), test proteins plus ECGS or Matrigel plus vehicle alone (PBS containing 0.25% BSA). Matrigel (0.5 ml) was injected into the abdominal subcutaneous tissue of female nu/nu mice (6 wks old) along the peritoneal mid line. There were 3 mice in each group. The animals were cared for in accordance with institutional and NIH guidelines. At day 6, mice were sacrificed and plugs were recovered and processed for histology. Typically the overlying skin was removed, and gels were cut out by retaining the peritoneal lining for support, fixed in 10% buffered formalin in PBS and embedded in paraffin. Sections of 3 µm were cut and stained with H&E or Masson's trichrome stain and examined under light microscope.

11) Mouse Corneal Micropocket Assay

Mouse corneal micropocket assay was performed according to that detailed by Kenyon et al., 1996. Briefly, hydron pellets (polyhydroxyethylmethacrylate [polyHEMA], Interferon Sciences, New Brunswick, N.J., U.S.A.) containing either 90 ng of bFGF (R&D) or 180 ng of VEGF (R&D Systems, Minneapolis, Minn., U.S.A.) and 40 µg of sucrose aluminium sulfate (Sigma) were prepared. Using an operating microscope, a stromal linear keratotomy was made with a surgical blade (Bard-Parker no. 15) parallel to the insertion of the lateral rectus muscle in an anesthetized animal. An intrastromal micropocket was dissected using a modified von Graefe knife (2"30 mm). A single pellet was implanted and advanced toward the temporal corneal limbus (within 0±7±1±0 mm for bFGF pellets and 0±5 mm for VEGF pellets). The difference in pellet location for each growth factor was determined to be necessary given the relatively weaker angiogenic stimulation of VEGF in this model. Antibiotic ointment (erythromycin.) was then applied to the operated eye to prevent infection and to decrease surface irregularities. The subsequent vascular response was measured extending from the limbal vasculature toward the pellet and the contiguous circumferential zone of neovascularization Data and clinical photos presented here were obtained on day 6 after pellet implantation, which was found to be the day of maximal angiogenic response.

12) In Vitro Invasion Assay

"Matrigel" matrix-coated 9-mm cell culture inserts (pore size, 8 μm; Becton Dickinson, Franklin Lakes, N.J.) were set in a 24-well plate. The HUVEC cells were seeded at a density of $5 \times 10^3$ cells per well into the upper layer of the culture insert and cultured with serum-free EBM in the presence of EphB4 ECD for 24 h. The control group was cultured in the same media without EphB4. Then 0.5 ml of the human SCC15 cell line, conditioned medium was filled into the lower layer of the culture insert as a chemo-attractant. The cells were incubated for 24 h, then the remaining cells in the upper layer were swabbed with cotton and penetrating cells in the lower layer were fixed with 5% glutaraldehyde and stained with Diff Quick. The total number of cells passing through the Matrigel matrix and each 8 μm pore of the culture insert wascounted using optical microscopy and designated as an invasion index (cell number/area).

13) SCC15 Tumor Growth in Mice

Subcutaneously inject logarithmically growing SCC15, head and neck squamous cell carcinoma cell line, at $5 \times 10^6$ cell density; with or without EphB4 ECD in the presence or absence of human bFGF, into athymic Balb/c nude mice, along with Matrigel (BD Bioscience) synthetic basement membrane (1:1 v/v), and examine tumors within 2 weeks. Tumor volumes in the EphB4 ECD group, in the presence and absence of growth factor after implantation were three-fold smaller than those in the vehicle groups. There was no difference in body weight between the groups. Immunohistochemical examination of cross-sections of resected tumors and TUNEL-positive apoptosis or necrosis, CD34 immunostaining, and BrdU proliferation rate will be performed, after deparaffinized, rehydrated, and quenched for endogenous peroxidase activity, and after 10 min permeabilization with proteinase K. Quantitative assessment of vascular densities will also be performed. Local intratumoral delivery or IV delivery of EphB4 ECD will also be performed twice a week.

30 athymic nude mice, BALB/c (nu/nu), were each injected with $1 \times 10^6$ B16 melanoma cells with 0.1 ml PBS mixed with 0.1 ml matrigel or $1.5 \times 10^6$ SCC15 cells resuspended in 200 μl of DMEM serum-free medium and injected subcutaneously on day 0 on the right shoulder region of mice. Proteins were injected intravenously or subcutaneously, around the tumor beginning on day 1 at a loading dose of 4 μg/mg, with weekly injections of 2 ug/mg. (10 μg/g, 50 μg/kg/day), and at 2 weeks post-inoculation. Mice are sacrificed on Day 14. Control mice received PBS 50 μl each day.

14) Tumor Formation in Nude Mice

All animals were treated under protocols approved by the institutional animal care committees. Cancer cells ($5 \times 10^6$) were subcutaneously inoculated into the dorsal skin of nude mice. When the tumor had grown to a size of about 100 mm³ (usually it took 12 days), sEphB4 was either intraperitoneally or subcutaneously injected once/day, and tumorigenesis was monitored for 2 weeks. Tumor volume was calculated according to the formula $a^2 \times b$, where a and b are the smallest and largest diameters, respectively. A Student's t test was used to compare tumor volumes, with P<0.05 being considered significant.

15) Quantification of Microvessel Density

Tumors were fixed in 4% formaldehyde, embedded in paraffin, sectioned by 5 μm, and stained with hematoxylineosin. Vessel density was semi-quantitated using a computer-based image analyzer (five fields per section from three mice in each group).

EXAMPLE 3

EphB4 Is Upregulated and Imparts Growth Advantage in Prostate Cancer

A. Expression of EphB4 in Prostate Cancer Cell Lines

Figure 27A:
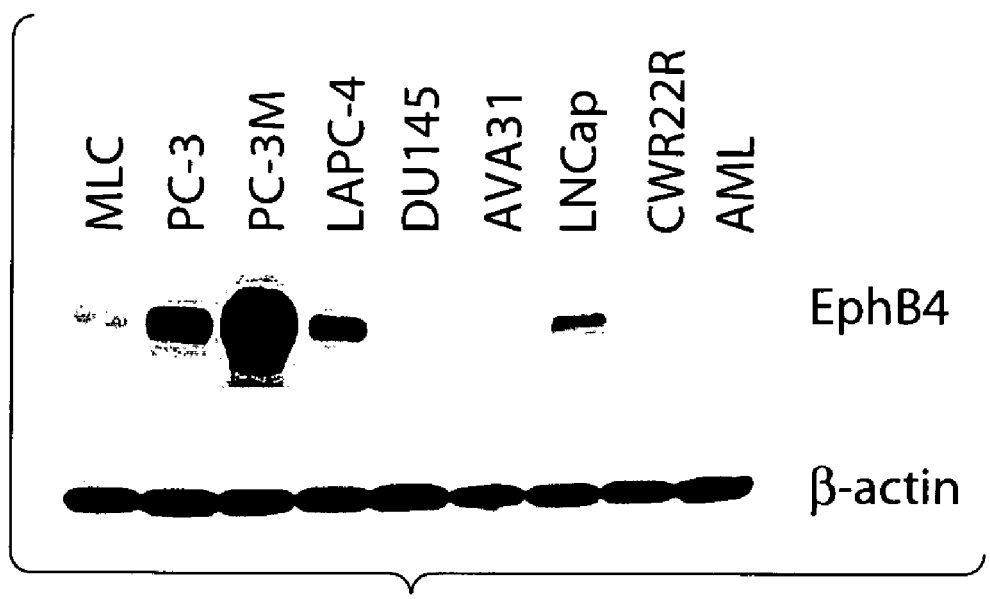
FIG. 27 shows expression of EphB4 in prostate cell lines. A) Western blot of total cell lysates of various prostate cancer cell lines, normal prostate gland derived cell line (MLC) and acute myeloblastic lymphoma cells (AML) probed with EphB4 monoclonal antibody. B) Phosphorylation of EphB4 in PC-3 cells determined by Western blot.
Figure 27B:
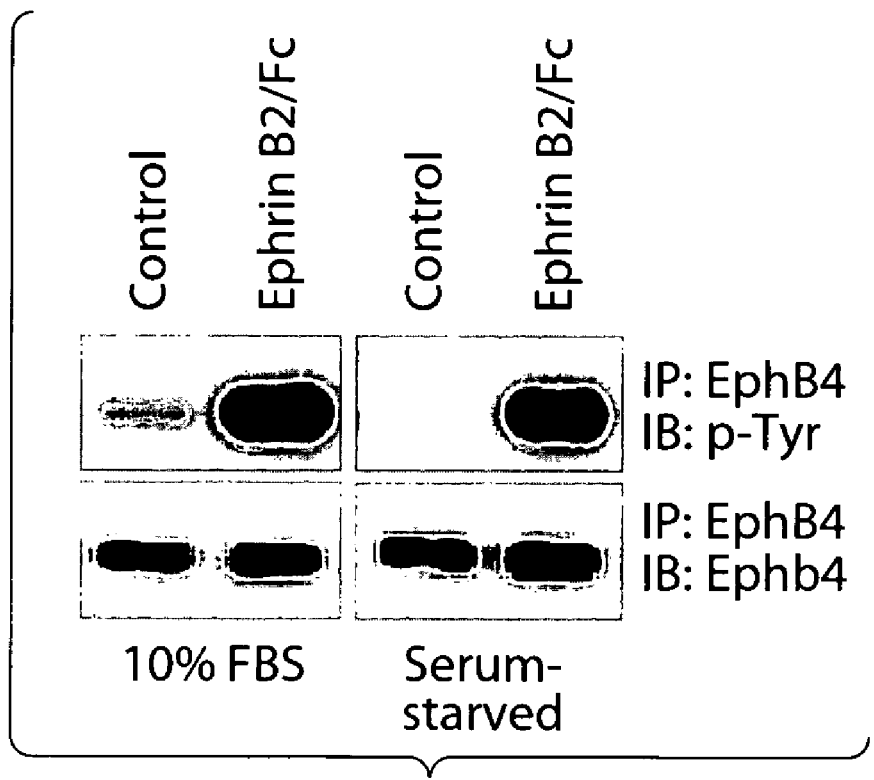

We first examined the expression of EphB4 protein in a variety of prostate cancer cell lines by Western blot. We found that prostate cancer cell lines show marked variation in the abundance of the 120 kD EphB4. The levels were relatively high in PC3 and even higher in PC3M, a metastatic clone of PC3, while normal prostate gland derived cell lines (MLC) showed low or no expression of EphB4 (FIG. 27A). We next checked the activation status of EphB4 in PC3 cells by phosphorylation study. We found that even under normal culture conditions, EphB4 is phosphorylated though it can be further induced by its ligand, ephrin B2 (FIG. 27B).

B. Expression of EphB4 in Clinical Prostate Cancer Samples

Figure 28:
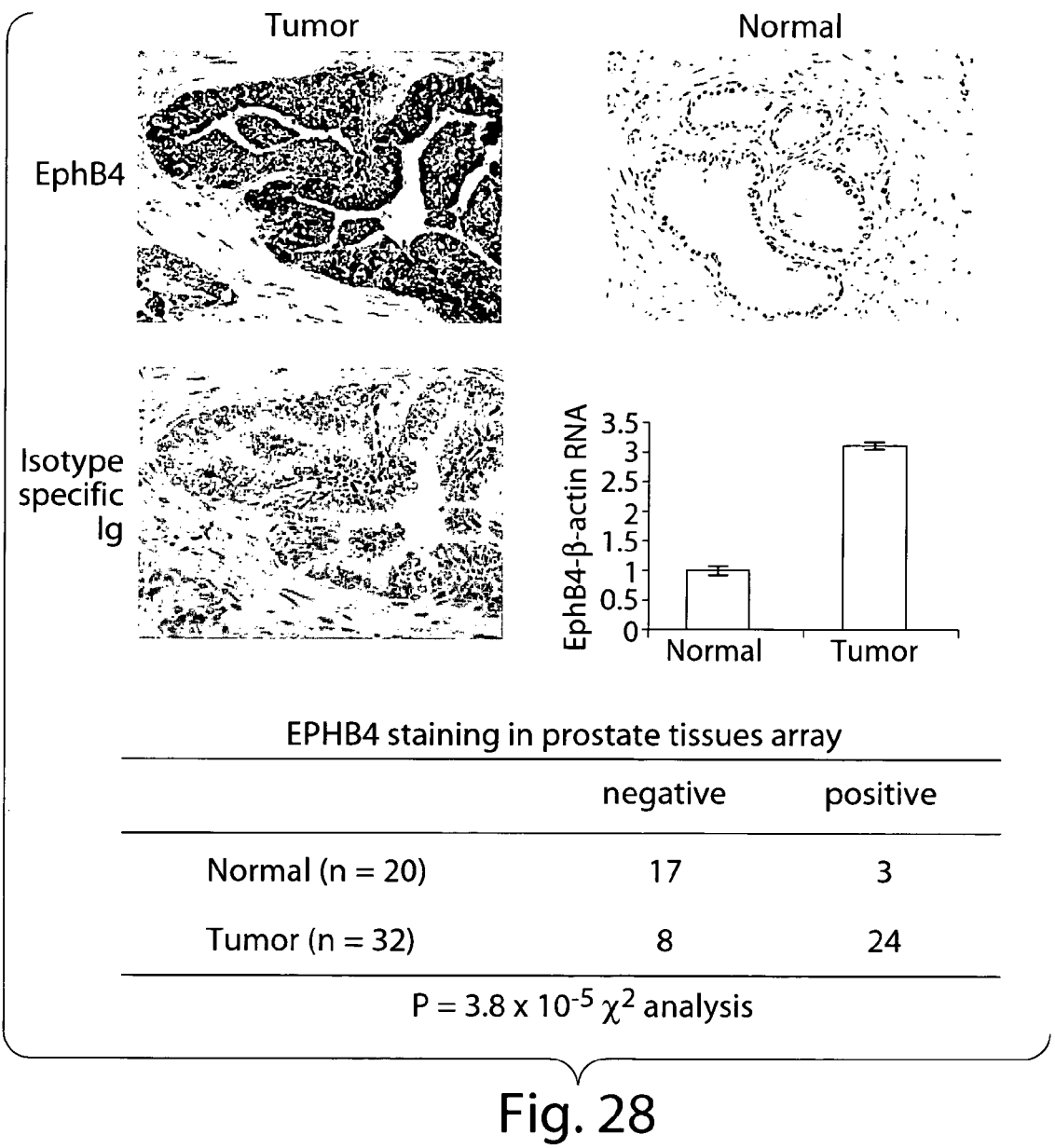
FIG. 28 shows expression of EphB4 in prostate cancer tissue. Representative prostate cancer frozen section stained with EphB4 monoclonal antibody (top left) or isotype specific control (bottom left). Adjacent BPH tissue stained with EphB4 monoclonal antibody (top right). Positive signal is brown color in the tumor cells. Stroma and the normal epithelia are negative. Note membrane localization of stain in the tumor tissue, consistent with trans-membrane localization of EphB4. Representative QRT-PCR of RNA extracted from cancer specimens and adjacent BPH tissues (lower right).

To determine whether EphB4 is expressed in clinical prostate samples, tumor tissues and adjacent normal tissue from prostate cancer surgical specimens were examined. The histological distribution of EphB4 in the prostate specimens was determined by immunohistochemistry. Clearly, EphB4 expression is confined to the neoplastic epithelium (FIG. 28, top left), and is absent in stromal and normal prostate epithelium (FIG. 28, top right). In prostate tissue array, 24 of the 32 prostate cancers examined were positive. We found EphB4 mRNA is expressed both in the normal and tumor tissues of clinical samples by quantitative RT-PCR. However, tumor EphB4 mRNA levels were at least 3 times higher than in the normal in this case (FIG. 28, lower right).

C. p53 and PTEN Inhibited the Expression of EphB4 in PC3 Cells

Figure 29A:
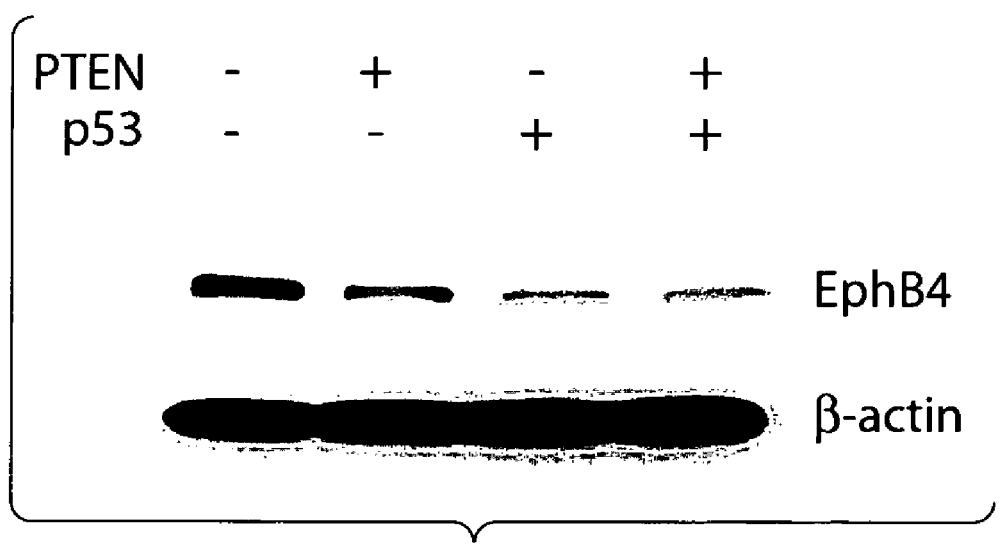
FIG. 29 shows downregulation of EphB4 in prostate cancer cells by tumor suppressors and RXR expression. A) PC3 cells were co-transfected with truncated CD4 and p53 or PTEN or vector only. 24 h later CD4-sorted cells were collected, lysed and analyzed sequentially by Western blot for the expression of EphB4 and β-actin, as a normalizer protein. B) Western blot as in (A) of various stable cell lines. LNCaP-FGF is a stable transfection clone of FGF-8, while CWR22R-RXR stably expresses the RXR receptor. BPH-1 was established from benign hypertrophic prostatic epithelium.

PC3 cells are known to lack PTEN expression (Davis, et al., 1994, Science. 266:816-819) and wild-type p53 function (Gale, et al., 1997, Cell Tissue Res. 290:227-241). We investigated whether the relatively high expression of EphB4 is related to p53 and/or PTEN by re-introducing wild-type p53 and/or PTEN into PC3 cells. To compensate for the transfection efficiency and the dilution effect, transfected cells were sorted for the cotransfected truncated CD4 marker. We found that the expression of EphB4 in PC3 cells was reduced by the re-introduction of either wild-type p53 or PTEN. The cotransfection of p53 and PTEN did not further inhibit the expression of EphB4 (FIG. 29A).

D. Retinoid X Receptor (RXR α) Regulates the Expression of EphB4

Figure 29B:
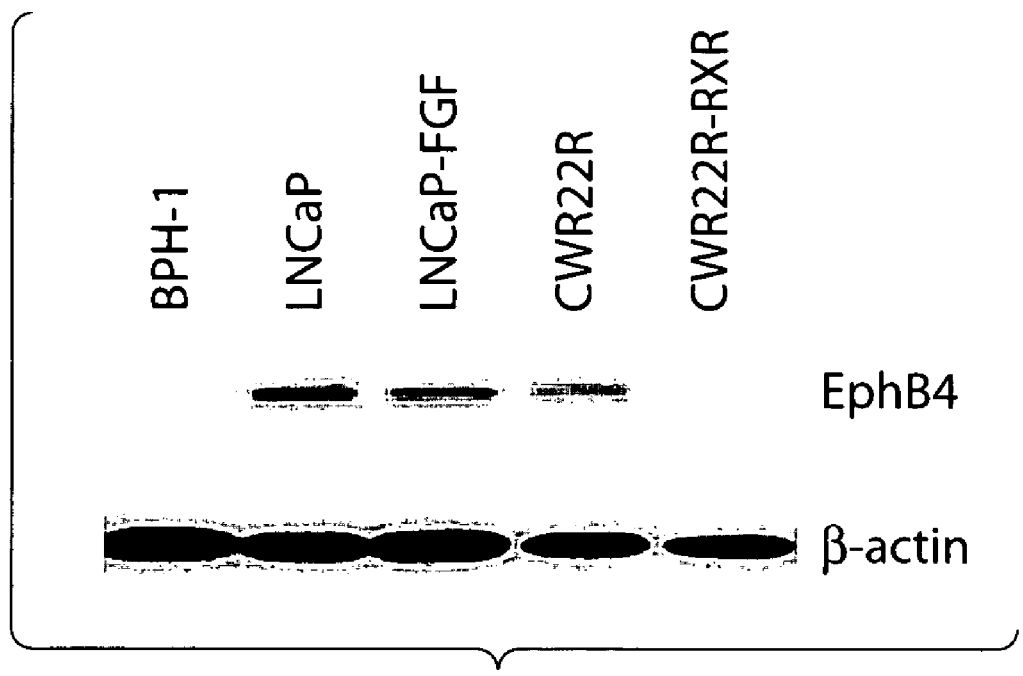

We previously found that RXRα was down-regulated in prostate cancer cell lines (Zhong, et al., 2003, Cancer Biol Ther. 2:179-184) and here we found EphB4 expression has the reverse expression pattern when we looked at "normal" prostate (MLC), prostate cancer (PC3), and metastatic prostate cancer (PC3M) (FIG. 27A), we considered whether RXRα regulates the expression of EphB4. To confirm the relationship, the expression of EphB4 was compared between CWR22R and CWR22R-RXRα, which constitutively expresses RXRα. We found a modest decrease in EphB4 expression in the RXRα overexpressing cell line, while FGF8 has no effect on EphB4 expression. Consistent with initial results, EphB4 was not found in "normal" benign prostate hypertrophic cell line BPH-1 (FIG. 29B).

Figure 30A:
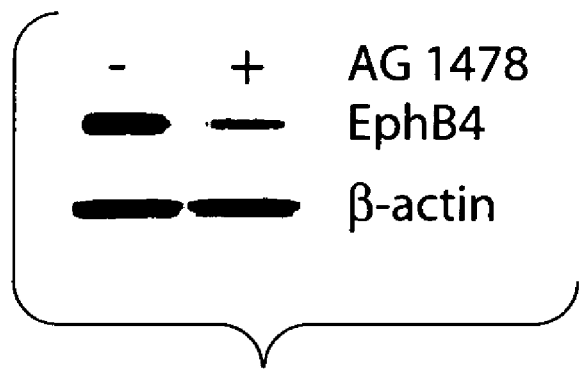
FIG. 30 shows downregulation of EphB4 in prostate cancer cells by EGFR and IGFR-1. A) Western blot of PC3 cells treated with or without EGFR specific inhibitor AG1478 (1 nM) for 36 hours. Decreased EphB4 signal is observed after AG 1478 treatment. The membrane was stripped and reprobed with β-actin, which was unaffected. B) Western Blot of triplicate samples of PC3 cells treated with or without IGFR-1 specific neutralizing antibody MAB391 (2 μg/ml; overnight). The membrane was sequentially probed with EphB4, IGFR-1 and β-actin antibodies. IGFR-1 signal shows the expected repression of signal with MAB391 treatment.
Figure 30B:
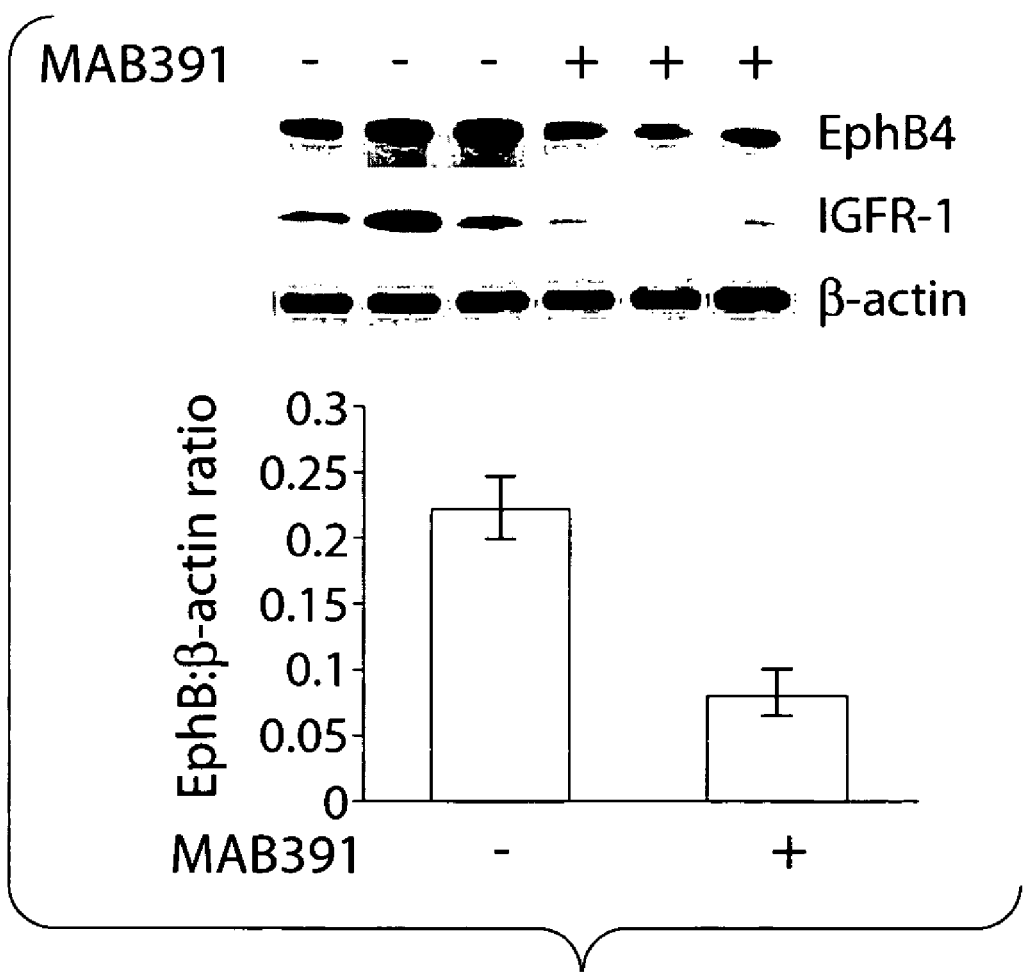

E. Growth Factor Signaling Pathway of EGFR and IGF-1R Regulates EphB4 Expression EGFR and IGF-1R have both been shown to have autocrine and paracrine action on PC3 cell growth. Because we found that EphB4 expression is higher in the more aggressive cell lines, we postulated that EphB4 expression might correlate with these pro-survival growth factors. We tested the relationship by independently blocking EGFR and IGF-1R signaling. EphB4 was down-regulated after blocking the EGFR signaling using EGFR kinase inhibitor AG 1478 (FIG. 30A) or upon blockade of the IGF-1R signaling pathway using IGF-1R neutralizing antibody (FIG. 30B).

F. EphB4 siRNA and Antisense ODNs Inhibit PC3 Cell Viability

Figure 31A:
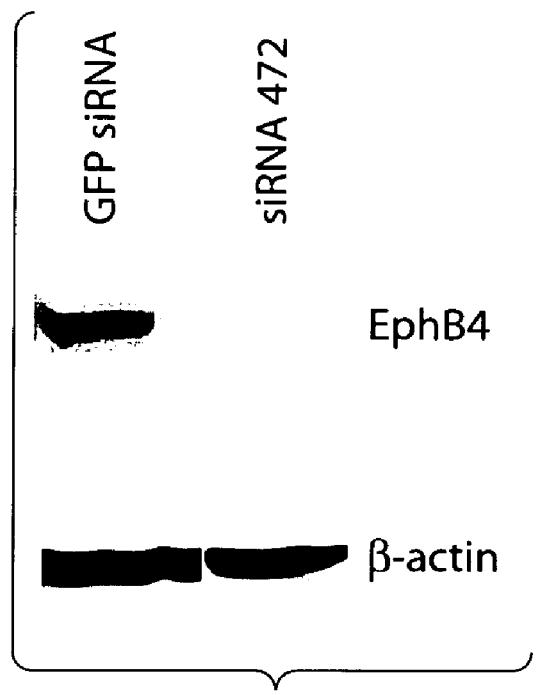
FIG. 31 shows effect of specific EphB4 AS-ODNs and siRNA on expression and prostate cell functions. A) 293 cells stably expressing full-length construct of EphB4 was used to evaluate the ability of siRNA 472 to inhibit EphB4 expression. Cells were transfected with 50 nM RNAi using Lipofectamine 2000. Western blot of cell lysates 40 h post transfection with control siRNA (green fluorescence protein; GFP siRNA) or EphB4 siRNA 472, probed with EphB4 monoclonal antibody, stripped and reprobed with β-actin monoclonal antibody. B) Effect of EphB4 AS-10 on expression in 293 transiently expressing full-length EphB4. Cells were exposed to AS-10 or sense ODN for 6 hours and analyzed by Western blot as in (A). C) 48 h viability assay of PC3 cells treated with siRNA as described in the Methods section. Shown is mean ±s.e.m. of triplicate samples. D) 5-day viability assay of PC3 cells treated with ODNs as described in the Methods. Shown is mean ±s.e.m. of triplicate samples. E) Scrape assay of migration of PC3 cells in the presence of 50 nM siRNAs transfected as in (A). Shown are photomicrographs of representative 20× fields taken immediately after the scrape was made in the monolayer (0 h) and after 20 h continued culture. A large number of cells have filled in the scrape after 20 h with control siRNA, but not with EphB4 siRNA 472. F) Shown is a similar assay for cells treated with AS-10 or sense ODN (both 10 μM). G) Matrigel invasion assay of PC3 cells transfected with siRNA or control siRNA as described in the methods. Cells migrating to the underside of the Matrigel coated insert in response to 5 mg/ml fibronectin in the lower chamber were fixed and stained with Giemsa. Shown are representative photomicrographs of control siRNA and siRNA 472 treated cells. Cell numbers were counted in 5 individual high-powered fields and the average ±s.e.m. is shown in the graph (bottom right).
Figure 31B:
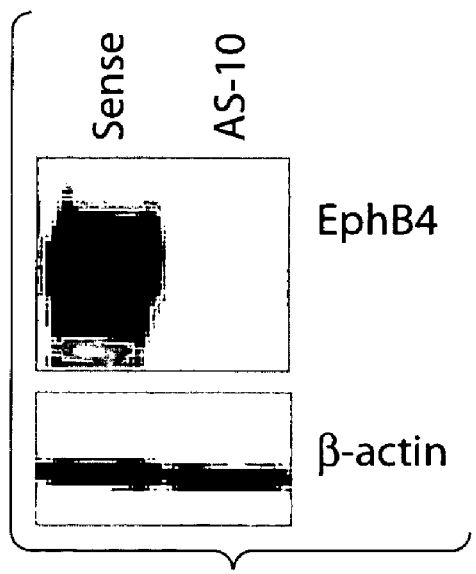
Figure 31C:
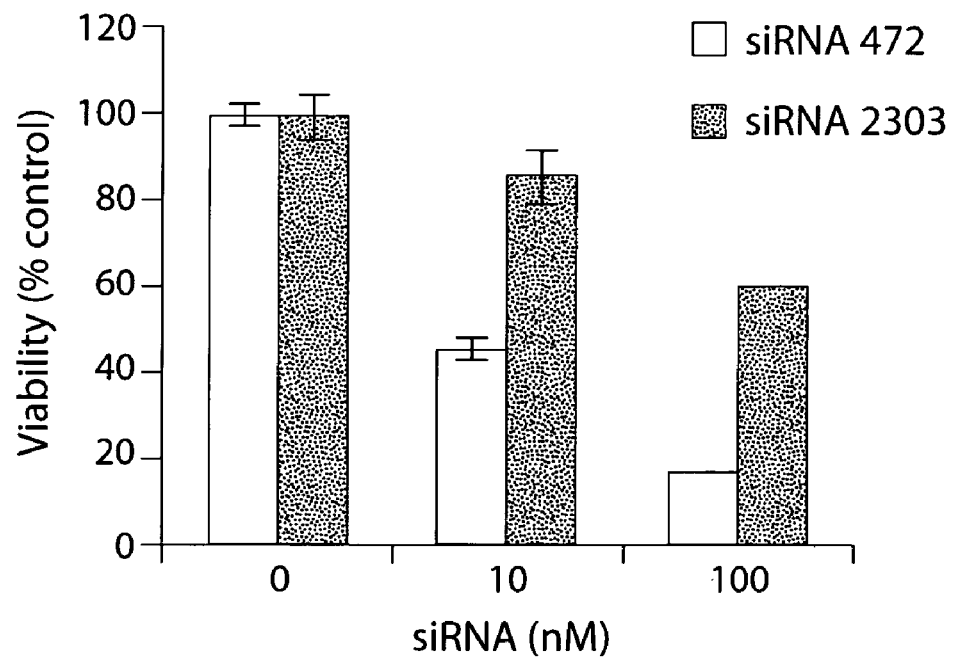
Figure 31D:
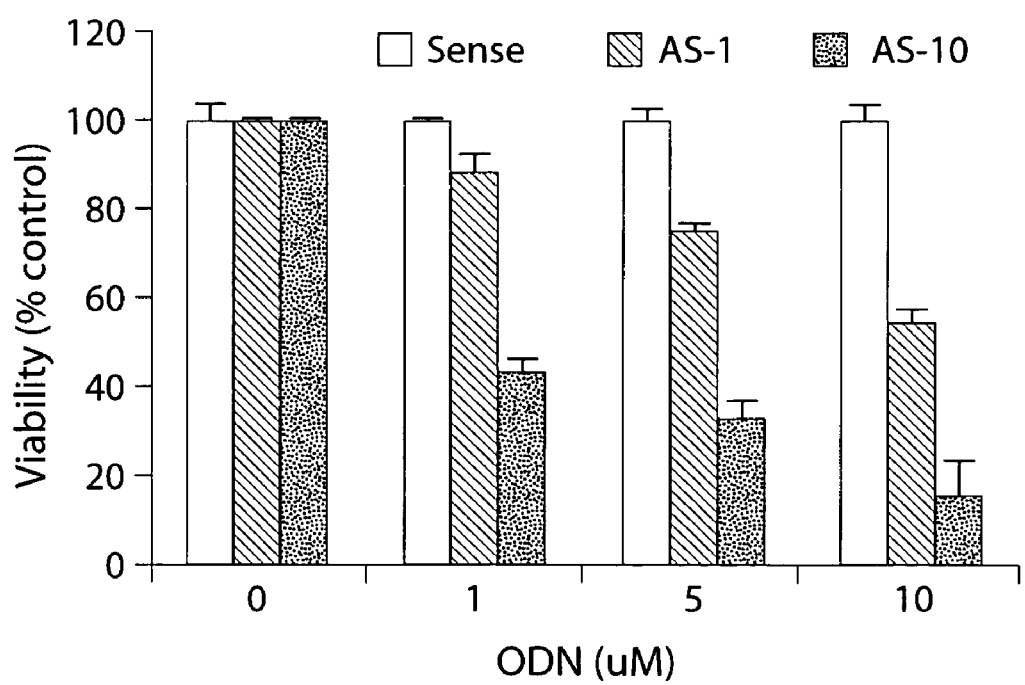

To define the significance of this EphB4 overexpression in our prostate cancer model, we concentrated our study on PC3 cells, which have a relatively high expression of EphB4. The two approaches to decreasing EphB4 expression were siRNA and AS-ODNs. A number of different phosphorothioate-modified AS-ODNs complementary to different segments of the EphB4 coding region were tested for specificity and efficacy of EphB4 inhibition. Using 293 cells transiently transfected with full-length EphB4 expression vector AS-10 was found to be the most effective (FIG. 31B). A Similar approach was applied to the selection of specific siRNA. EphB4 siRNA 472 effectively knocks down EphB4 protein expression (FIG. 31A). Both siRNA 472 and antisense AS-10 ODN reduced the viability of PC3 cells in a dose dependent manner (FIG. 31C, D). Unrelated siRNA or sense oligonucleotide had no effect on viability.

G. EphB4 siRNA and Antisense ODNs Inhibit the Mobility of PC3 Cells

Figure 31E:
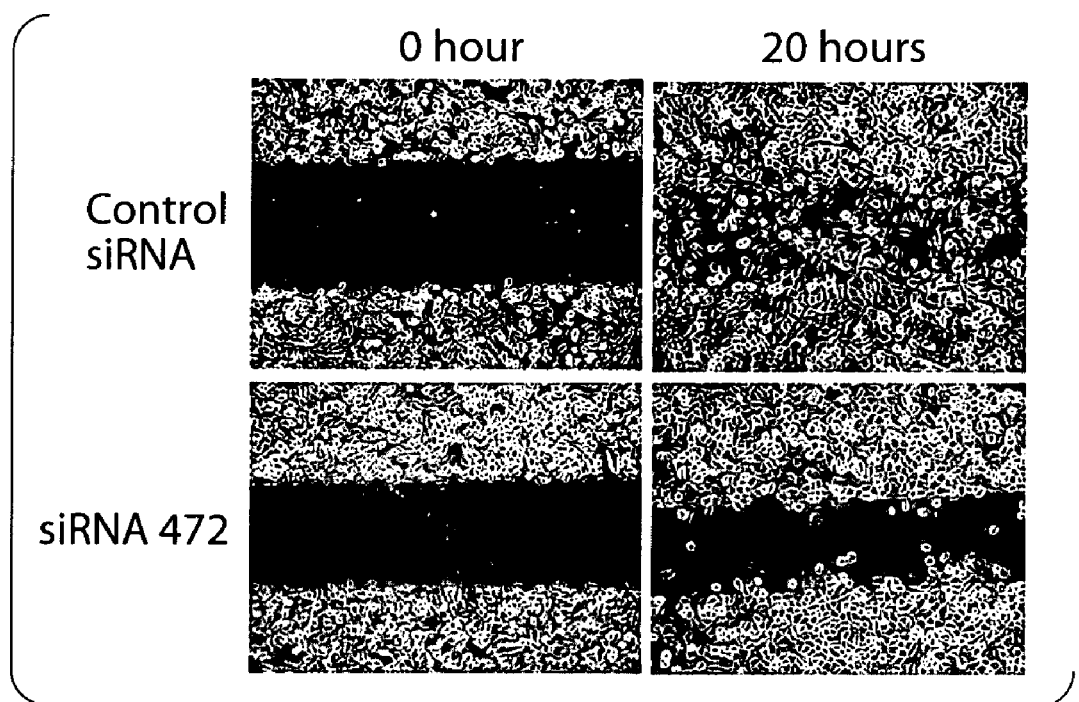
Figure 31F:
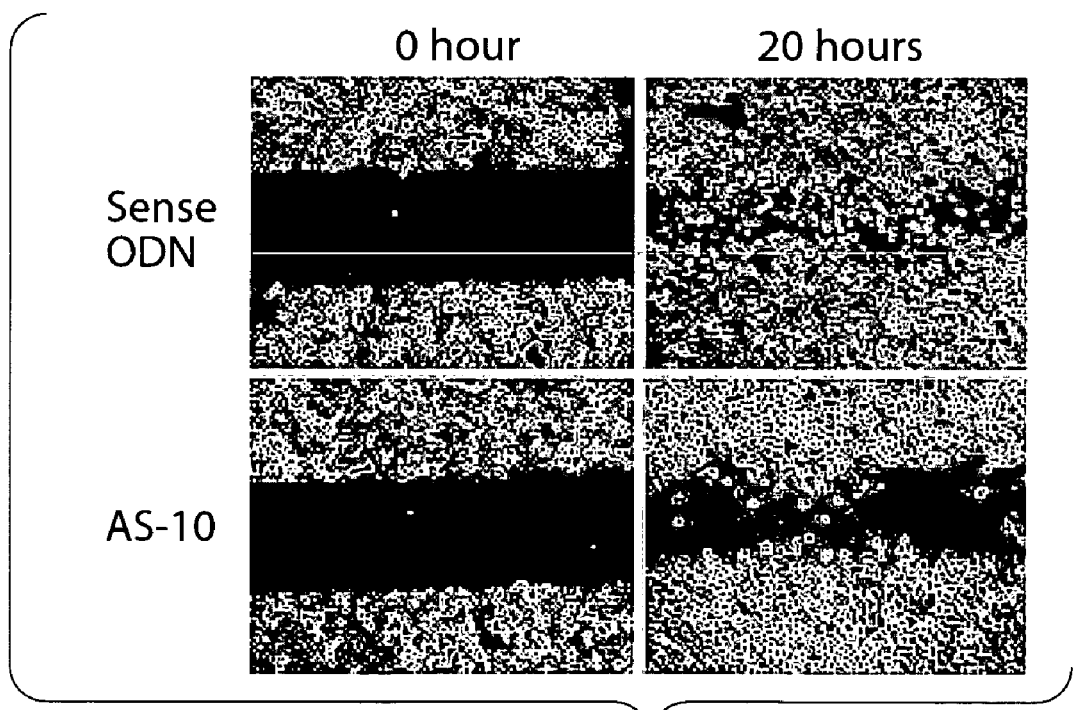
Figure 31G:
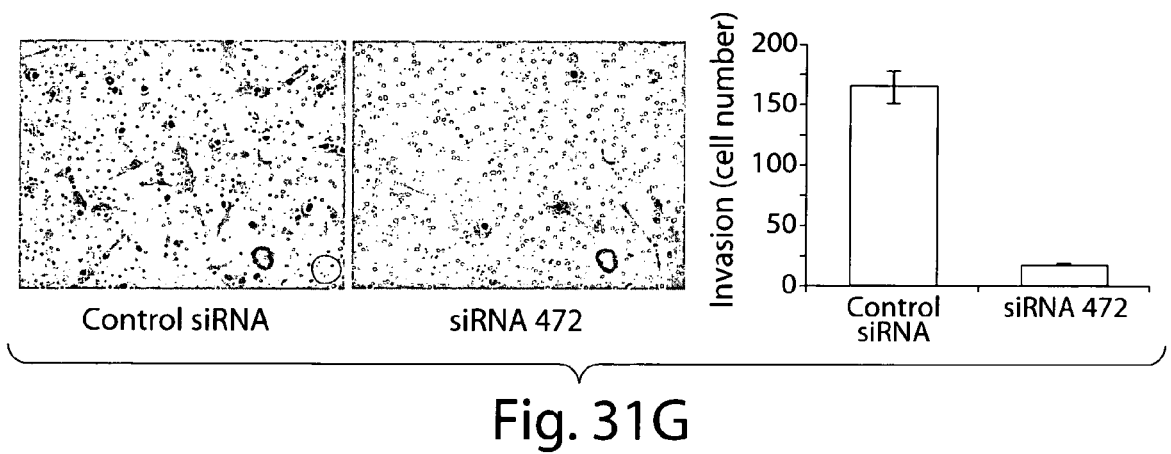

PC3 cells can grow aggressively locally and can form lymph node metastases when injected orthotopically into mice. In an effort to study the role of EphB4 on migration of PC3 cells in vitro, we performed a wound-healing assay. When a wound was introduced into a monolayer of PC3 cells, over the course of the next 20 hours cells progressively migrated into the cleared area. However, when cells were transfected with siRNA 472 and the wound was introduced, this migration was significantly inhibited (FIG. 31E). Pretreatment of PC3 cells with 10 μM EphB4 AS-10 for 12 hours generated the same effect (FIG. 31F). In addition, knock-down of EphB4 expression in PC3 cells with siRNA 472 severely reduced the ability of these cells to invade Matrigel as assessed by a double-chamber invasion assay (FIG. 31G), compared to the control siRNA.

H. EphB4 siRNA Induces Cell Cycle Arrest and Apoptosis in PC3 Cells

Figure 32A:
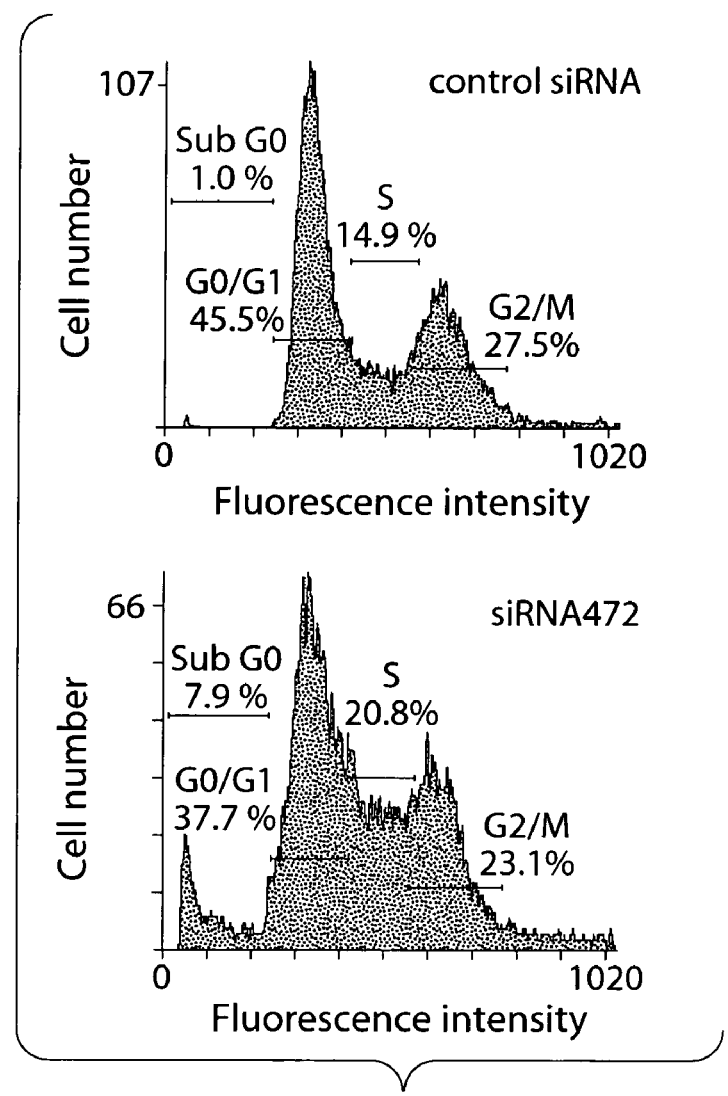
FIG. 32 shows effect of EphB4 siRNA 472 on cell cycle and apoptosis. A) PC3 cells transfected with siRNAs as indicated were analyzed 24 h post transfection for cell cycle status by flow cytometry as described in the Methods. Shown are the plots of cell number vs. propidium iodide fluorescence intensity. 7.9% of the cell population is apoptotic (in the Sub G0 peak) when treated with siRNA 472 compared to 1% with control siRNA. B) Apoptosis of PC3 cells detected by Cell Death Detection ELISA$^{plus}$ kit as described in the Methods. Absorbance at 405 nm increases in proportion to the amount of histone and DNA-POD in the nuclei-free cell fraction. Shown is the mean ±s.e.m. of triplicate samples at the indicated concentrations of siRNA 472 and GFP siRNA (control).
Figure 32B:
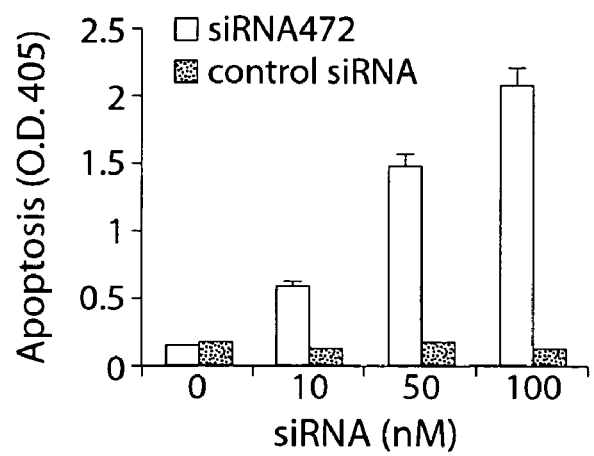

Since knock-down of EphB4 resulted in decreased cell viability (FIG. 31C) we sought to determine whether this was due to effects on the cell cycle. In comparison to control siRNA transfected cells, siRNA 472 resulted in an accumulation of cells in the sub G0 and S phase fractions compared to cells treated with control siRNA. The sub G0 fraction increased from 1% to 7.9%, and the S phase fraction from 14.9% to 20.8% in siRNA 472 treated cells compared to control siRNA treated cells (FIG. 32A). Cell cycle arrest at sub G0 and G2 is indicative of apoptosis. Apoptosis as a result of EphB4 knock-down was confirmed by ELISA assay. A dose-dependent increase in apoptosis was observed when PC3 cells were transfected with siRNA 472, but not with control siRNA (FIG. 32B). At 100 nM there was 15 times more apoptosis in siRNA 472 transfected than control siRNA transfected PC3 cells.

I. Materials and Methods

1) Reagents

Neutralizing IGF-1R antibody was from R&D Systems (Minneapolis Minn.). Anti-IGF-1R(β), -EGFR, -EphB4(C-16) were from Santa Cruz Biotech (Santa Cruz, Calif.). β-actin monoclonal antibody was purchased from Sigma Chemical Co. (St Louis, Mo.). Media and fetal bovine serum (FBS) were from Invitrogen (Carlsbad, Calif.). AG 1478(4-(3'-Chloroanilino)-6,7-dimethoxy-quinazoline) was from Calbiochem (San Diego, Calif.).

2) Antisense Oligodeoxynucleotides and EphB4 siRNAs

EphB4 specific antisense phosphorothioate-modified oligodeoxynucleotide (ODN) and Sense ODN were synthesized and purified by Qiagen (Alameda Calif.). The sequences are: Sense, 5'-TCC-TGC-AAG-GAG-ACC-TTC-AC-3' (SEQ ID NO: 19); AS1: 5'-GTG-CAG-GGA-TAG-CAG-GGC -CAT-3' (SEQ ID NO: 20); AS10: 5'-ATG-GAG-GCC-TCG-CTC-AGA-AA-3' (SEQ ID NO: 21). siRNAs were synthesized at the USC/Norris Comprehensive Cancer Center Microchemical Core laboratory. Sequences of EphB4 siRNAs are siRNA 472 5'-GGU-GAA-UGU-CAA-GAC-GCU-GUU-3' SEQ ID NO: 22) and siRNA 2303 5'-cuc-uuc-cga-ucc-cac-cua-cuu-3' (SEQ ID NO: 23). Negative control siRNA to scrambled GAPDH was from Ambion (Austin, Tex.).

3) Cell Lines and Culture

The prostate cancer cell lines, PC3, PC3M, DU145, ALVA31, LAPC-4, LNCaP, CWR22R and adult human normal prostate epithelial cell line MLC SV40, and BPH-1 were obtained and cultured as described previously (7). Stable cell line CWR22R-RXR, LNCaP-FGF8 were established and cultured as described before (7, 33).

4) Generation of EphB4 Monoclonal Antibody

The extracellular domain (ECD) of EphB4 was cloned into pGEX-4T-1 to generate GST-fused ECD (GST-ECD). EphB4ECD expressed as a GST fusion protein in BL21 *E. coli* was purified by affinity chromatography and the GST domain was cleaved by thrombin. Monoclonal antibody was generated and the sensitivity and specificity of the antibody was reconfirmed by Western blot with whole cell lysate of 293 cells stably transfected with EphB4.

5) One-Step RT-PCR and Quantitative RT-PCR

Total RNA was extracted using RNA STAT-60 (Tel-Test, Inc. Friendswood Tex.) from prostate cancer specimens and adjacent normal specimens. For quantitative RT-PCR first strand cDNA was synthesized from 5 μg of total RNA using SuperScript III (Invitrogen, Carlsbad Calif.). Quantitative RT-PCR was performed on the Stratagene MX3000P system (Stratagene, La Jolla Calif.) using SYBR Green I Brilliant Mastermix (Stragene) according to the manufacture's instructions. Optimized reactions for EphB4 and β-actin (used as the normalizer gene) were 150 nM each of the forward primer (β-actin, 5'-GGA-CCT-GAC-TGA-CTA-CCT-A-3' (SEQ ID NO: 24); EphB4,5'-AAG-GAG-ACC-TTC-ACC-GTC-TT-3' (SEQ ID NO: 25)) and reverse primer (β-actin 5'-TTG-AAG-GTA-GTT-TCG-TGG-AT-3' (SEQ ID NO: 26); EphB4,5'-TCG-AGT-CAG-GTT-CAC-AGT-CA-3' (SEQ ID NO: 27)) with DNA denaturation/activation of polymerase at 95° C. for 10 min followed by 40 cycles of 95° C. for 30 s, 60° C. for 1 min, 72° C. for 1 min. The specificity of the gene-specific amplification was confirmed by the presence of a single dissociation peak. All reactions were performed in triplicate with RT and no template negative controls.

6) Immunohistochemistry

OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody. Immunohistochemical staining on prostate array (BioMeda, Foster City, Calif.) was done using goat ABC Staining System (Santa Cruz Biotech.) according to the manufacturer's instructions.

7) Western Blot

Whole cell lysates were prepared using Cell Lysis Buffer (GeneHunter, Basgvukke Tenn.) supplemented with protease inhibitor cocktail (Pierce, Rockford Ill.), unless otherwise noted. Total protein was determined using the DC reagent system (Bio-Rad, Hercules Calif.). Typically, 20 μg whole cell lysate was run on 4-20% Tris-Glycine gradient gel. The samples were electro-transferred to PVDF membrane and the non-specific binding was blocked in TBST buffer (0.5 mM Tris-HCl, 45 mM NaCl, 0.05% Tween-20, pH 7.4) containing 5% non-fat milk. Membranes were first probed with primary antibody overnight, stripped with Restore™ Western Blot stripping buffer (Pierce, Rockford Ill.) and reprobed with β-actin to confirm equivalent loading and transfer of protein. Signal was detected using SuperSignal West Femto Maximum Sensitivity Substrate (Pierce).

8) Phosphorylation Analysis

Cells growing in 60 mm dishes were either serum starved (1% FBS supplemented RPMI 1640, 24 hours) or cultured in normal conditions (10% FBS) and then treated with or without 1 μg/ml mouse ephrin B2/$F_c$ for 10 min to activate EphB4 receptor Cleared cell lysates were incubated with EphB4 monoclonal antibody overnight at 4° C. Antigen-antibody complex was immunoprecipitated by the addition of 100 μl of Protein G-Sepharose in 20 mM sodium phosphate, pH 7.0 with incubation overnight at 4° C. Immunoprecipitates were analyzed by Western blot with pTyr specific antibody (Upstate, clone 4G10) at 1:1000 dilution followed by incubation with protein G-HRP (Bio-Rad) at 1:5000 dilution. To monitor immunoprecipitation efficiency, a duplicate membrane was probed with EphB4 specific monoclonal antibody.

9) Transient Transfection and Sorting of Transfected Cells

PC3 cells were cotransfected with pMACS 4.1 coding for CD4 and wild type p53 (pC53-SN3) or PTEN vector or both using Lipofectamine 2000 (Invitrogen) according to the manufacturer's instructions. The molar ratio of CD4 to p53 or PTEN or vector was 1:3 and total plasmid was 24 μg for a 10 $cm^2$ dish of 90% confluent cells using 60 μl of Lipofectamine 2000. 24 hours after transfection, a single cell suspension was made and sorted using truncated CD4 as a surface marker according to the manufacturer's protocol (Miltenyi Biotec, Germany). Sorted cells were lysed in 1×SDS sampling buffer and analyzed by Western blot.

10) Study of IGF and EGF Signaling Pathway on the Expression of EphB4

PC3 cells were seeded into 6-well plates and cultured until 80% confluent and treated with 2 μg/ml neutralizing IGF-1R monoclonal antibody, MAB391 (Hailey, et al., 2002, Mol Cancer Ther. 1: 1349-1353), or with 1 nM AG 1478, a strong EGFR inhibitor (Liu, et al., 1999, J Cell Sci. 112 (Pt 14): 2409-2417) for 24 h. Crude cell lysates were analyzed by Western blot. Band density was quantified with the Bio-Rad QuantityOne System software.

11) Cell Viability Assay

PC3 cells were seeded on 48-well plates at a density of approximately $1×10^4$ cells/well in a total volume of 200 ml. Media was changed after the cells were attached and the cells were treated with various concentrations (1-10 μM) of EphB4 antisense ODN or sense ODN as control. After three days media was changed and fresh ODNs added. Following a further 48 h incubation, cell viability was assessed by MTT as described previously (36). EphB4 siRNAs (10-100 nM) were introduced into $2×10^4$ PC3 cells/well of a 48-well plate using 2 μl of Lipofectamine™ 2000 according to the manufacturer's instructions. 4 h post-transfection the cells were returned to growth media (RPMI 1640 supplemented with 10% FBS). Viability was assayed by MTT 48 h following transfection.

12) Wound Healing Migration Assay

PC3 cells were seeded into 6-well plates and cultured until confluent. 10 μM AS-10 or sense ODN as control were introduced to the wells as described for the viability assay 12 hours before wounding the monolayer by scraping it with a sterile pipette tip. Medium was changed to RPMI 1640 supplemented with 5% FBS and fresh ODNs. Confluent cultures transfected with 50 nM siRNA 472 or GAPDH negative control siRNA 12 hours prior to wounding were also examined. The healing process was examined dynamically and recorded with a Nikon Coolpix 5000 digital camera with microscope adapter.

13) Invasion Assay

PC3 cells were transfected with siRNA 472 or control siRNA using Lipofectamine™ 2000 and 6 hours later 0.5× 105 cells were transferred into 8 μm Matrigel-precoated inserts (BD Bioscience, Palo Alto, Calif.). The inserts were placed in companion wells containing RPMI supplemented with 5% FBS and 5 μg/ml fibronectin as a chemoattractant. Following 22 h incubation the inserts were removed and the noninvading cells on the upper surface were removed by with a cotton swab. The cells on the lower surface of the membrane were fixed in 100% methanol for 15 min, air dried and stained with Giemsa stain for 2 min. The cells were counted in five individual high-powered fields for each membrane under a light microscope. Assays were performed in triplicate for each treatment group.

14) Cell Cycle Analysis

80% confluent cultures of PC3 cells in 6-well plates were transfected with siRNA472 (100 nM) using Lipofectamine™ 2000. 24 hours after transfection, cells were trypsinized, washed in PBS and incubated for 1 h at 4° C. in 1 ml of hypotonic solution containing 50 μg/ml propidium iodide, 0.1% sodium citrate, 0.1 Triton X-100 and 20 μg/ml Dnase-free RnaseA. Cells were analyzed in linear mode at the USC Flow cytometry facility. Results were expressed as percentages of elements detected in the different phases of the cell cycle, namely Sub G0 peak (apoptosis), G0/G1 (no DNA synthesis), S (active DNA systhesis), G2 (premitosis) and M (mitosis).

15) Apoptosis ELISA

Apoptosis was studied using the Cell Death Detection ELISAplus Kit (Roche, Piscataway, N.J.) according to the manufacturer's instructions. Briefly, PC3 80% confluent cultures in 24-well plates were transfected using Lipofectamine™ 2000 with various concentrations (0-100 nM) of siRNA 472 or 100 nM control siRNA. 16 hours later, cells were detached and $1\times10^4$ cells were incubated in 200 µl lysis buffer. Nuclei were pelleted by centrifugation and 20 µl of supernatant containing the mono- or oligonucleosomes was taken for ELISA analysis. Briefly, the supernatant was incubated with anti-histone-biotin and anti-DNA-POD in streptavidin-coated 96-well plate for 2 hours at room temperature. The color was developed with ABST and absorbance at 405 nm was read in a microplate reader (Molecular Devices, Sunnyvale, Calif.).

EXAMPLE 4

Expression of EPHB4 in Mesothelioma: a Candidate Target for Therapy

Malignant mesothelioma (MM) is a rare neoplasm that most often arises from the pleural and peritoneal cavity serous surface. The pleural cavity is by far the most frequent site affected (>90%), followed by the peritoneum (6-10%) (Carbone et al., 2002, Semin Oncol. 29:2-17). There is a strong association with asbestos exposure, about 80% of malignant mesothelioma cases occur in individuals who have ingested or inhaled asbestos. This tumor is particularly resistant to the current therapies and, up to now, the prognosis of these patients is dramatically poor (Lee et al., 2000, Curr Opin Pulm Med. 6:267-74).

Several clinical problems regarding the diagnosis and treatment of malignant mesothelioma remain unsolved. Making a diagnosis of mesothelioma from pleural or abdominal fluid is notoriously difficult and often requires a thoracoscopic or laproscopic or open biopsy and Immunohistochemical staining for certain markers such as meosthelin expressed preferentially in this tumor. Until now, no intervention has proven to be curative, despite aggressive chemotherapeutic regimens and prolonged radiotherapy. The median survival in most cases is only 12-18 months after diagnosis.

In order to identify new diagnostic markers and targets to be used for novel diagnostic and therapeutic approaches, we assessed the expression of EPHB4 and its ligand EphrinB2 in mesothelioma cell lines and clinical samples.

A. EPHB4 and EphrinB2 is Expressed in Mesothelioma Cell Lines

Figure 33A:
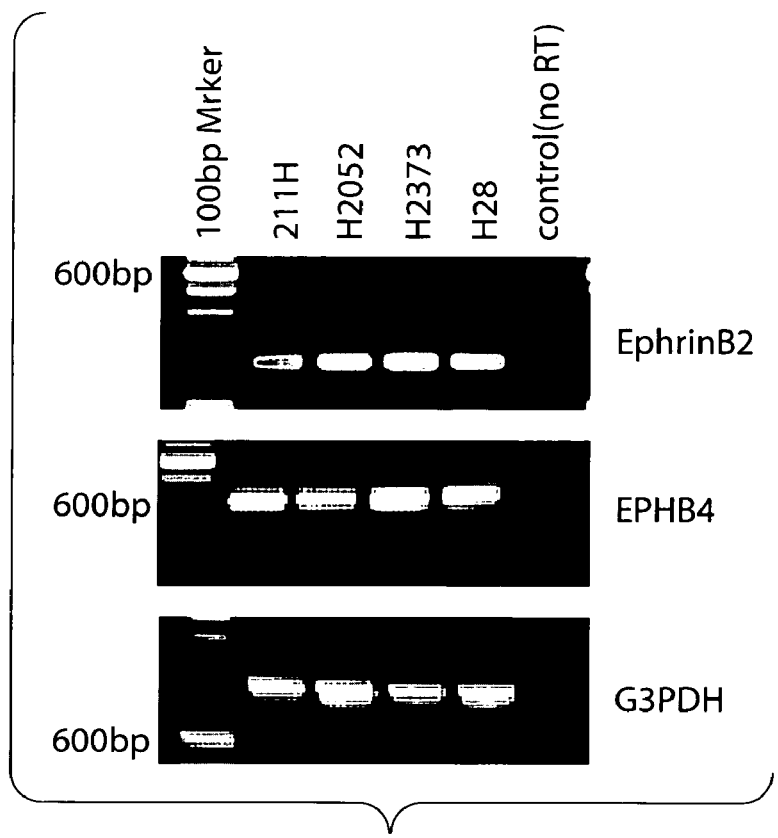
FIG. 33 shows that EphB4 and EphrinB2 are expressed in mesothelioma cell lines as shown by RT-PCR (A) and Western Blot (B).
Figure 33B:
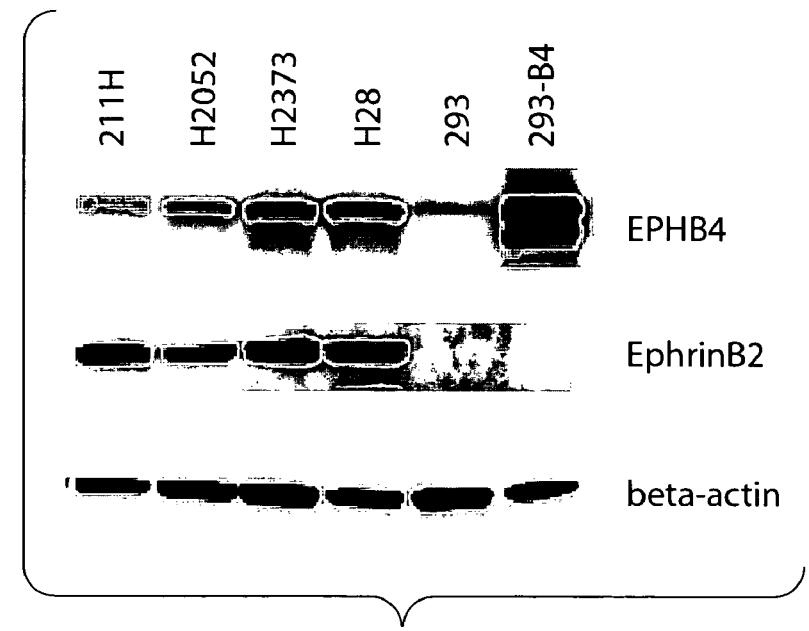

The expression of Ephrin B2 and EphB4 in malignant mesothelioma cell lines was determined at the RNA and protein level by a variety of methods. RT-PCR showed that all of the four cell lines express EphrinB2 and EPHB4 (FIG. 33A). Protein expression was determined by Western blot in these cell lines. Specific bands for EphB4 were seen at 120 kD. In addition, Ephrin B2 was detected in all cell lines tested as a 37 kD band on Western blot (FIG. 33B). No specific band for Ephrin B2 was observed in 293 human embryonic kidney cells, which were included as a negative control.

Figure 34:
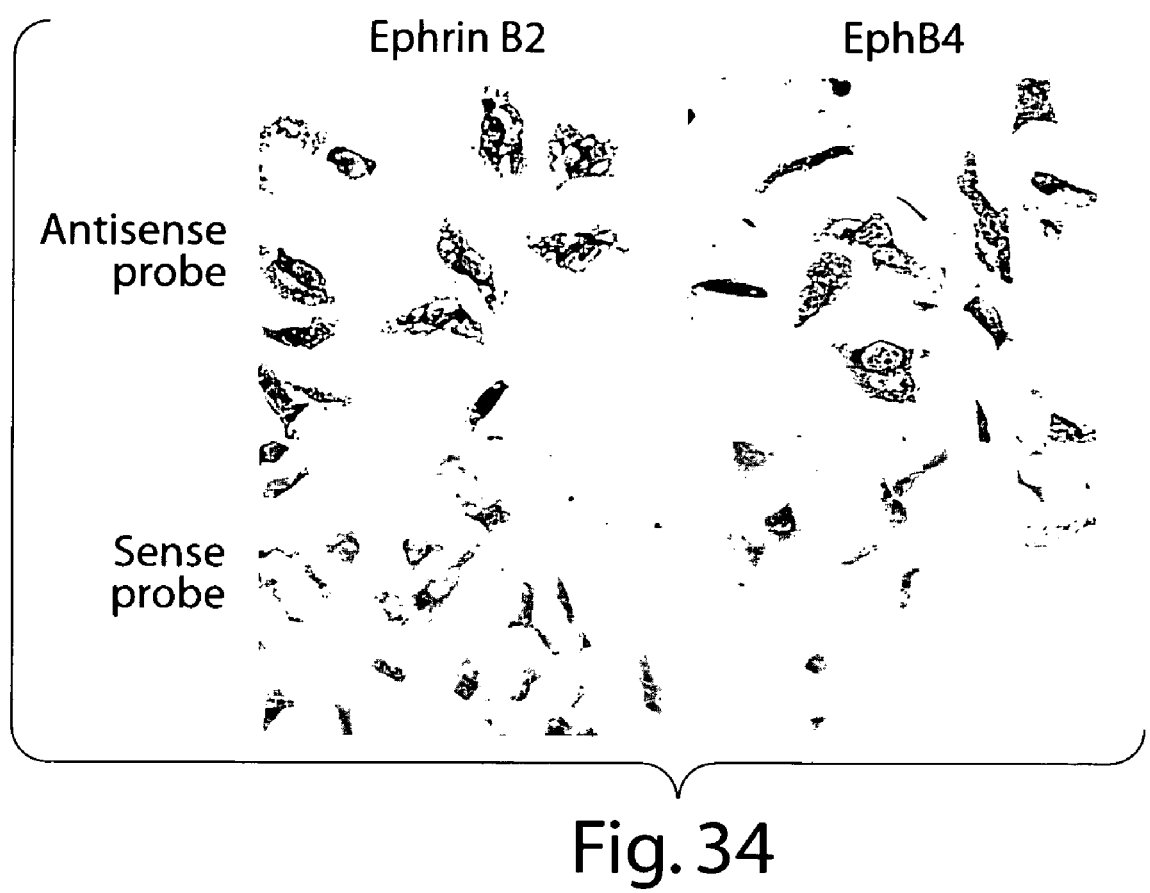
FIG. 34 shows expression of ephrin B2 and EphB4 by in situ hybridization in mesothelioma cells. NCI H28 mesothelioma cell lines cultured in chamber slides hybridized with antisense probe to ephrin B2 or EphB4 (top row). Control for each hybridization was sense (bottom row). Positive reaction is dark blue cytoplasmic stain.
Figure 35:
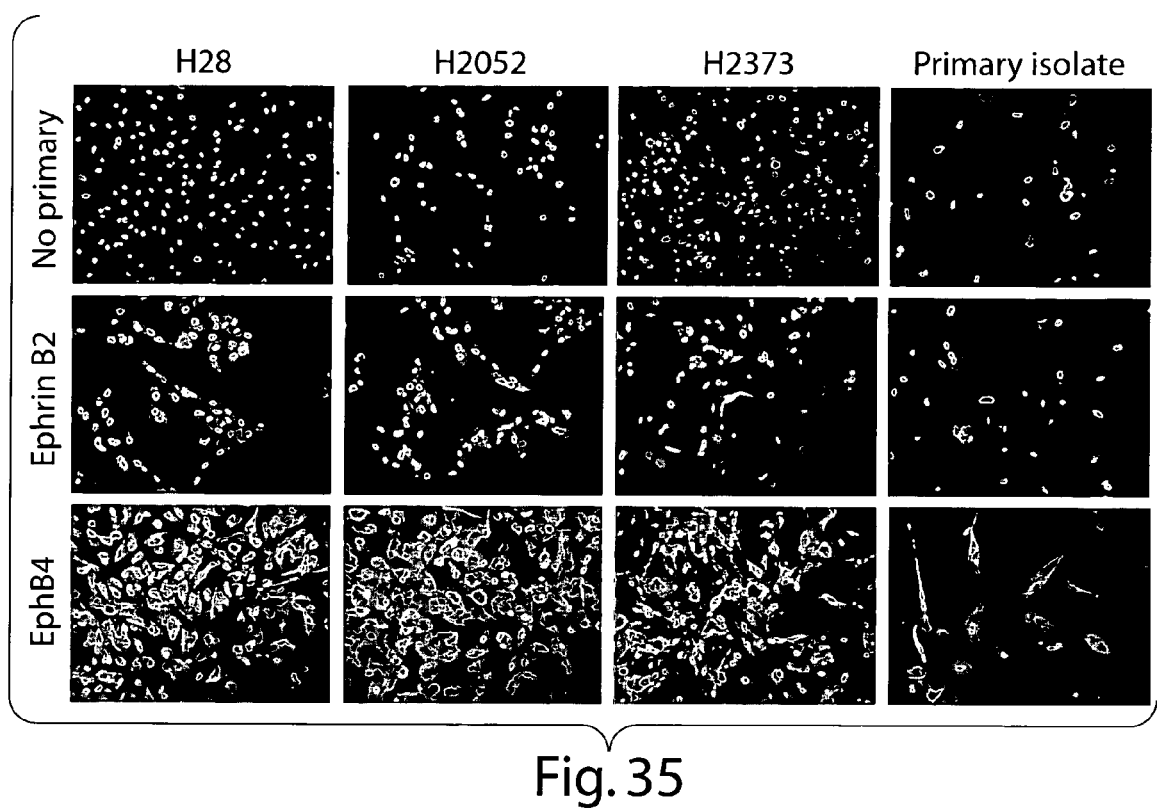
FIG. 35 shows cellular expression of EphB4 and ephrin B2 in mesothelioma cultures. Immunofluorescence staining of primary cell isolate derived from pleural effusion of a patient with malignant mesothelioma and cell lines NCI H28, NCI H2373, and NCI H2052 for ephrin B2 and EphB4. Green color is positive signal for FITC labeled secondary antibody. Specificity of immunofluorescence staining was demonstrated by lack of signal with no primary antibody (first row). Cell nuclei were counterstained with DAPI (blue color) to reveal location of all cells. Shown are merged images of DAPI and FITC fluorescence. Original magnification 200×.

To confirm the presence of EphB4 transcription in mesothelioma cells, in situ hybridization was carried out on NCI H28 cell lines cultured on chamber slides. Specific signal for EphB4 was detected using antisense probe Ephrin B2 transcripts were also detected in the same cell line. Sense probes for both EphB4 and Ephrin B2 served as negative controls and did not hybridize to the cells (FIG. 34). Expression of EphB4 and Ephrin B2 proteins was confirmed in the cell lines by immunofluorescence analysis (FIG. 35). Three cell lines showed strong expression of EphB4, whereas expression of Ephrin B2 was present in H28 and H2052, and weakly detectable in H2373.

B. Evidence of Expression of EPHB4 and EphrinB2 in Clinical Samples

Figure 36:
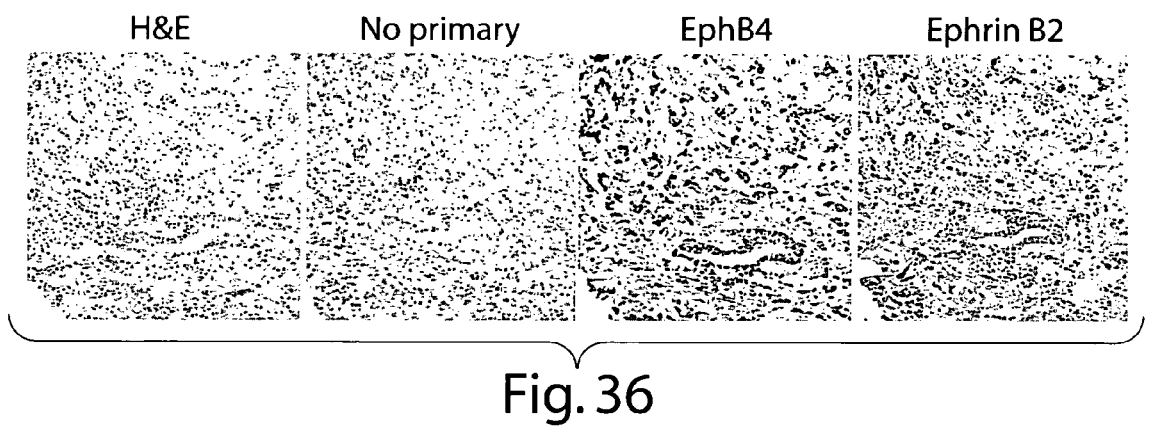
FIG. 36 shows expression of ephrin B2 and EphB4 in mesothelioma tumor. Immunohistochemistry of malignant mesothelioma biopsy. H&E stained section to reveals tumor architecture; bottom left panel is background control with no primary antibody. EphB4 and ephrin B2 specific staining is brown color. Original magnification 200×.

Tumor cells cultured from the pleural effusion of a patient diagnosed with pleural malignant mesothelioma were isolated and showed positive staining for both EphB4 and Ephrin B2 at passage 1 (FIG. 35, bottom row). These results confirm co-expression of EphB4 and Ephrin B2 in mesothelioma cell lines. To determine whether these results seen in tumor cell lines were a real reflection of expression in the disease state, tumor biopsy samples were subjected to immunohistochemical staining for EphB4 and Ephrin B2. Antibodies to both proteins revealed positive stain in the tumor cells. Representative data is shown in FIG. 36.

C. EPHB4 is Involved in the Cell Growth and Migration of Mesothelioma

Figure 37A:
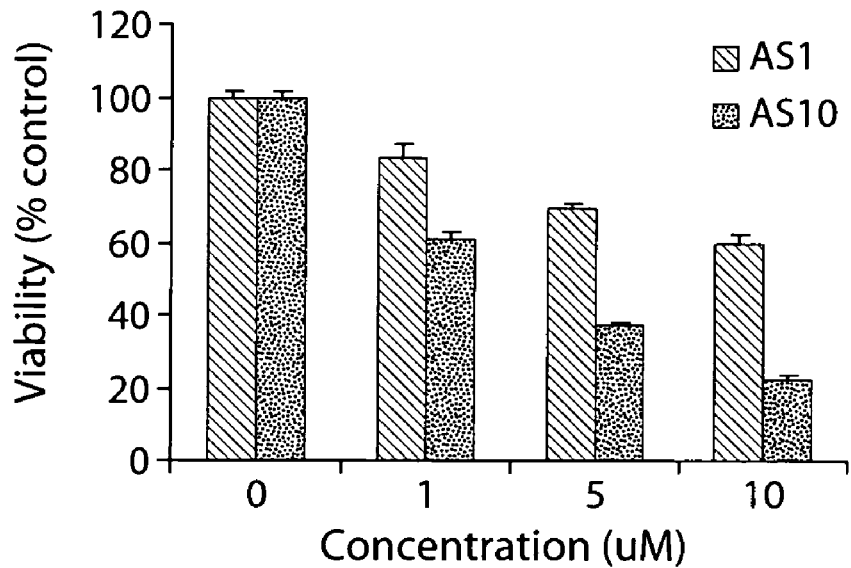
FIG. 37 shows effects of EPHB4 antisense probes (A) and EPHB4 siRNAs (B) on the growth of H28 cells.
Figure 37B:
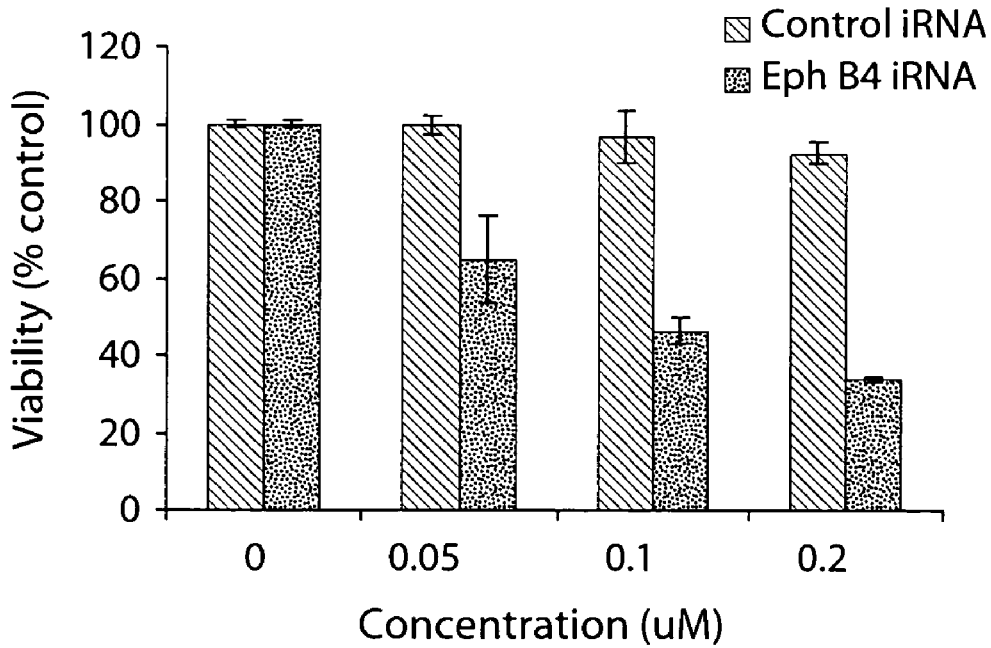

The role of EphB4 in cell proliferation was tested using EPHB4 specific antisepses oligonucleotides and siRNA. The treatment of cultured H28 with EPHB4 antisense reduced cell viability. One of the most active inhibitor of EphB4 expression is EPHB4AS-10 (FIG. 37A). Transfection of EPHB4 siRNA 472 generated the same effect (FIG. 37B).

Figure 38A:
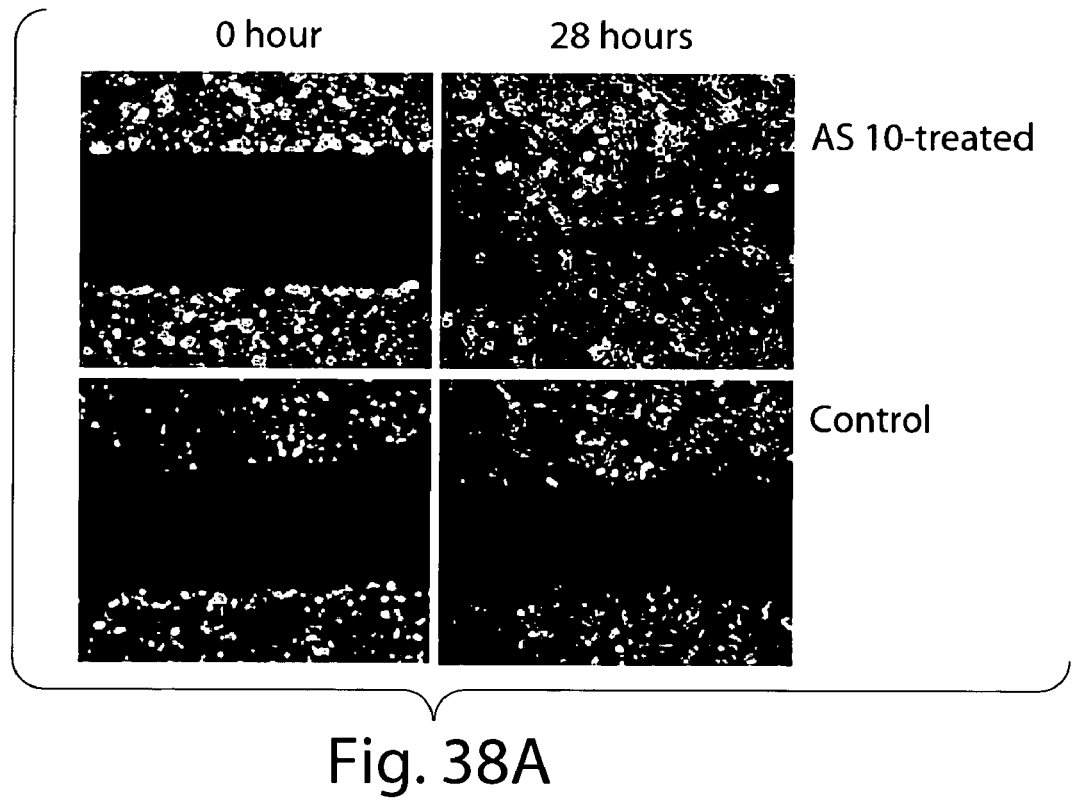
FIG. 38 shows effects of EPHB4 antisense probes (A) and EPHB4 siRNAs (B) on cell migration.
Figure 38B:
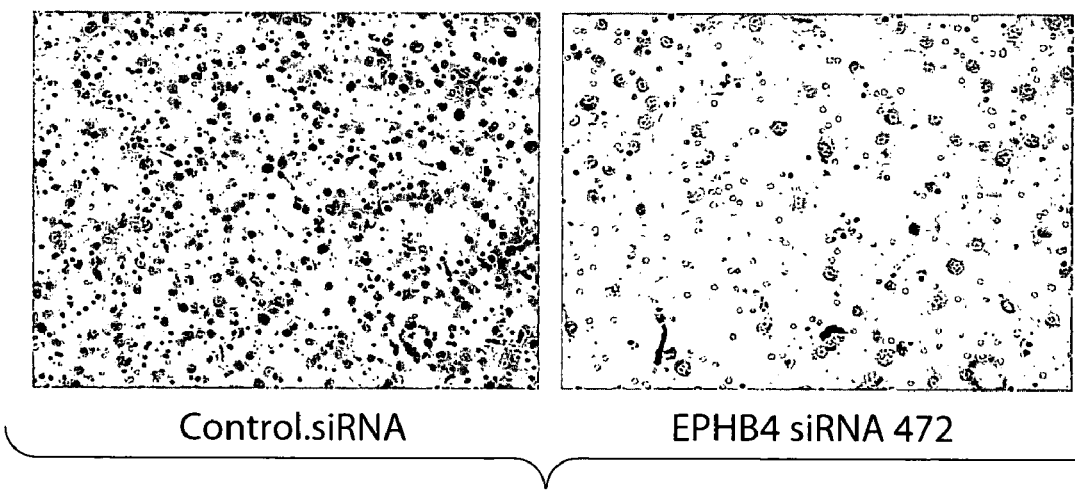

MM is a locally advancing disease with frequent extension and growth into adjacent vital structures such as the chest wall, heart, and esophagus. In an effort to study this process in vitro, we perform wound healing assay using previously described techniques (3:36). When a wound was introduced into sub confluent H28 cells, over the course of the next 28 hours cells would progressively migrate into the area of the wound. However, when cells were pretreated with EPHB4AS-10 for 24 hours, and the wound was introduced, this migration was virtually completely prevented (FIG. 38A). The migration study with Boyden Chamber assay with EPHB4 siRNA showed that cell migration was greatly inhibited with the inhibition of EPHB4 expression (FIG. 38B).

D. Materials and Methods

1) Cell Lines and Reagents

NCI H28, NCI H2052, NCI H2373, MSTO 211H mesothelioma cell lines and 293 human embryonic kidney cells were obtained from the ATCC (Manassas, Va.). Cells were maintained in RPMI 1640 media supplemented with 10% heat-inactivated fetal bovine serum (FBS; Life Technologies, Gaithersburg, Md.) and antibiotics. Primary cells were obtained from pleural effusion of patients with mesothelioma. A large number of EPHB4 phosphorothioate modified antisense oligonucleotides were synthesized. Similarly a number of EphB4 specific siRNAs were generated. Monoclonal antibody produced against EPHB4 was used for western blot. Polyclonal antibody against EphrinB2 and EPHB4 (C-16) (for immunohistochemical staining) was from Santa Cruz.

2) RT-PCR

Total RNA was reversed transcribed by use of random hexamers (Invitrogen). Primers for EphB4 and EphrinB2 were designed with Primer 3 software. The sequences for all primers are as follows: EPHB4 forward primer and EPHB4 reverse primer (see, e.g., in Example 2); EphrinB2 forward primer and EphrinB2 reverse primer (see, e.g., in Example 6);

G3PDH forward primer, 5'-GGAGCCAAAAGGGTCAT-CAT-3' (SEQ ID NO: 28); G3PDH reverse primer, 5'-GGCATTGCTGCAAAGAAAGAG-3' (SEQ ID NO: 29); Clonetics kit was used for PCR. PCRs were performed with the ABI PCR System 2700 (Applied Biosystem). The PCR conditions were 95° C. for 5 min, followed by 35 cycles of 95° C. for 30 seconds, 60° C. for 30 seconds and 72° C. for 1 min.

3) Preparation of Digoxigenin-Labeled RNA Probes

Ephrin-B2 and EphB4 PCR products were cloned using the pGEM-T Easy System (Promega, Madison Wis.) according to the manufacturer's description. The primers and PCR products were 5'-tccgtgtggaagtactgctg-3' (SEQ ID NO: 30) (forward), 5'-tctggtttggcacagttgag-3' (SEQ ID NO: 31) (reverse), for ephrin-B2 that yielded a 296-bp product and 5'-ctttggaagagaccctgctg-3' (SEQ ID NO: 32) (forward), 5'-agacggtgaaggtctccttg-3' (SEQ ID NO: 33), for EphB4 that yielded a 297-bp product. The authenticity and insert orientation were confirmed by DNA sequencing.

The pGEM-T Easy plasmids containing the PCR product of the human ephrin-B2 or EphB4 gene were linearized with Spe I or Nco I. Antisense or sense digoxigenin (DIG)-labeled RNA probes were transcribed from T7 or SP6 promoters by run-off transcription using a DIG RNA labeling kit (Roche, Indianapolis Ind.). RNA probes were quantitated by spot assay as described in the DIG RNA labeling kit instructions.

4) In Situ Hybridization

Cells were cultured in Labtech II 4-well chamber slides (Nalge Nunc International, Naperville, Ill.). Cells were washed in PBS (37° C.), then fixed for 30 min at 25° C. in a solution of 4% (w/v) formaldehyde, 5% (v/v) acetic acid, and 0.9% (w/v) NaCl. After fixation, slides were rinsed with PBS and stored in 70% ethanol at 4° C. until further use. Before in situ hybridization, cells were dehydrated, washed in 100% xylene to remove residual lipid and then rehydrated, finally in PBS. Cells were permeabilized by incubating at 37° C. with 0.1% (w/v) pepsin in 0.1N HCl for 20 min and post-fixed in 1% formaldehyde for 10 min. Prehybridization was performed for 30 min at 37° C. in a solution of 4×SSC containing 50%(v/v) deionized formamide. Slides were hybridized overnight at 42° C. with 25 ng antisense or sense RNA probes in 40% deionized formamide, 10% dextran sulfate, 1× Denhardt's solution, 4×SSC, 10 mM DTT, 1 mg/ml yeast t-RNA and 1 mg/ml denatured and sheared salmon sperm DNA in a total volume of 40 µl. Slides were then washed at 37° C. as follows: 2×15 min with 2×SSC, 2×15 min with 1×SSC, 2×15 min with 0.5×SSC and 2×30 min with 0.2×SSC. Hybridization signal was detected using alkaline-phosphatase-conjugated anti-DIG antibodies (Roche) according to the manufacturer's instructions. Color development was stopped by two washes in 0.1 M Tris-HCl, 1 mM EDTA, pH 8.0 for 10 min. Cells were visualized by counterstaining of nucleic acids with Nuclear Fast Red (Vector Laboratories, Burlingame, Calif.) and the slides were mounted with IMMU-MOUNT (Shandon, Astmoor UK).

5) Western Blot

Crude cell lysates were prepared by incubation in cell lysis buffer (10 mM Tris, pH 7.5, 1 mM EDTA, 150 mM NaCl, 1% Triton X-100, 1 mM DTT, 10% glycerol). Lysates were cleared by centrifugation at 10,000×g for 10 min. Total protein was determined by Bradford assay (Bio-Rad). Samples (20 µg protein) were fractionated on a 4-20% Tris-glycine polyacrylamide gel and transferred to polyvinylidene difluoride (PVDT) membrane (Bio-Rad) by electroblotting. Membranes were blocked with 5% non-fat milk prior to incubation with antibody to EphB4 (1:5000 dilution) at 4° C., for 16 h. Secondary antibody (1:100,000 dilution) conjugated with horseradish peroxidase was applied for 1 h at 25° C. The membranes were developed using the SuperSignal West Femto Maximum sensitivity chemiluminescent substrate (Pierce, Rockford, Ill.) according to the manufacturer's instructions.

6) Immunohistochemistry

Formalin-fixed tissue sections were deparaffinized and incubated with 10% goat serum at −70° C. for 10 minutes and incubated with the primary rabbit antibodies against either Ephrin B2 or EphB4 (Santa Cruz Biotechnologies; 1:100) at 4° C. overnight. Isotype-specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with H&E.

7) Immunofluorescence Studies

Cells were cultured on Labtech II 4-well chamber slides and fixed in 4% paraformaldehyde in Dulbecco's phosphate buffered saline pH 7.4 (PBS) for 30 min. The slides were rinsed twice in PBS and preincubated with blocking buffer (0.2% Triton-X100, 1% BSA in PBS) for 20 min. The slides were then incubated with antibodies to EphB4 or ephrin B2 (1:100 dilution in PBS) in blocking buffer at 4° C. for 16 hr. After washing three times, the slides were incubated with the appropriate fluorescein-conjugated secondary antibodies (Sigma-Aldrich, St. Louis, Mo.). Nuclei were counterstained with 4',6-diamidino-2-phenylindole dihydrochloride hydrate (DAPI), washed extensively with PBS and mounted with Vectasheild antifade mounting solution (Vector Laboratories). Images were obtained using an Olympus AX70 fluorescence microscope and Spot v2.2.2 (Diagnostic Instruments Inc., Sterling Heights, Mich.) digital imaging system.

8) Cell Viability Assay

Cells were seeded at a density of $5 \times 10^3$ per well in 48-well plates on day 0 in appropriate growth media containing 2% fetal calf serum (FCS). On the following day, the media was changed and cells were treated with various concentrations (1-10 µM) of EphB4 Antisense. On day 4, viability was assessed using 3-(4,5-dimethylthiazol-2-yl)-2,5-diphenyltetrazolium bromide (MTT) at a final concentration of 0.5 mg/ml. Cells were incubated for 2 hr, medium was aspirated, and the cells were dissolved in acidic isopropanol (90% isopropanol, 0.5% SDS and 40 mM HCl). Optical density was read in an ELISA reader at 490 nm using isopropanol as blank (Molecular Devices, Calif.).

9) Cell Migration

In vitro wound healing assay was adopted. Briefly, cells were seeded onto 6-cm plates in full culture media for 24 hours, and then switched to medium containing 5% FBS. EPHB4 antisense 10 (10 µM) was also added to treated well. 24 hours later, wounds were made using the tip of a p-200 pipette man; a line was drawn through the middle of the plates. The plate was photographed at 0, 12, 24 hours. The experiment was repeated three times.

EXAMPLE 5

EphB4 Is Expressed in Squamous Cell Carcinoma of The Head and Neck: Regulation by Epidermal Growth Factor Signaling Pathway and Growth Advantage Squamous cell carcinoma of the head and neck (HNSCC) is the sixth most frequent cancer worldwide, with estimated 900,000 cases diagnosed each year. It comprises almost 50% of all malignancies in some developing nations. In the United States, 50,000 new cases and 8,000 deaths are reported each year. Tobacco carcinogens are believed to be the primary etiologic agents of the disease, with alcohol consumption, age, gender, and ethnic background as contributing factors.

The differences between normal epithelium of the upper aerodigestive tract and cancer cells arising from that tissue are the result of mutations in specific genes and alteration of their expression. These genes control DNA repair, proliferation, immortalization, apoptosis, invasion, and angiogenesis. For head and neck cancer, alterations of three signaling pathways occur with sufficient frequency and produce such dramatic phenotypic changes as to be considered the critical transforming events of the disease. These changes include mutation of the p53 tumor suppressor, overexpression of epidermal growth factor receptor (EGFR), and inactivation of the cyclin dependent kinase inhibitor p16. Other changes such as Rb mutation, ras activation, cyclin D amplification, and myc overexpression are less frequent in HNSCC.

Although high expression of EphB4 has been reported in hematologic malignancies, breast carcinoma, endometrial carcinoma, and colon carcinoma, there is limited data on the protein levels of EphB4, and complete lack of data on the biological significance of this protein in tumor biology such as HNSCC.

A. HNSCC Tumors Express EphB4

Figure 39A:
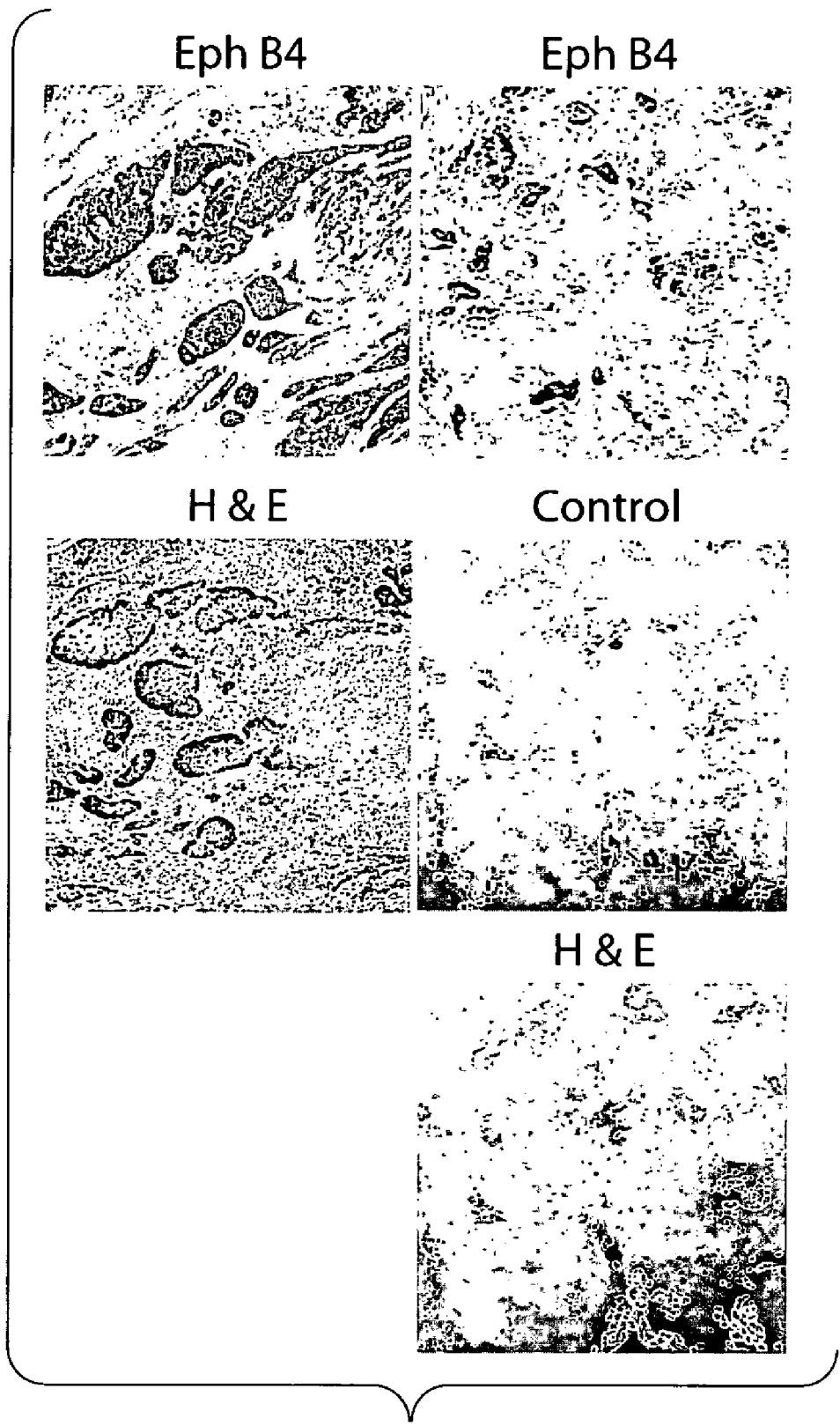
FIG. 39 shows that EphB4 is expressed in HNSCC primary tissues and metastases. A) Top: Immunohistochemistry of a representative archival section stained with EphB4 monoclonal antibody as described in the methods and visualized with DAB (brown color) localized to tumor cells. Bottom: Hematoxylin and Eosin (H&E) stain of an adjacent section. Dense purple staining indicates the presence of tumor cells. The right hand column are frozen sections of lymph node metastasis stained with EphB4 polyclonal antibody (top right) and visualized with DAB. Control (middle) was incubation with goat serum and H&E (bottom) reveals the location of the metastatic foci surrounded by stroma which does not stain. B) In situ hybridization of serial frozen sections of a HNSCC case probed with EphB4 (left column) and ephrin B2 (right column) DIG labeled antisense or sense probes generated by run-off transcription. Hybridization signal (dark blue) was detected using alkaline-phosphatase-conjugated anti-DIG antibodies and sections were counterstained with Nuclear Fast Red. A serial section stained with H&E is shown (bottom left) to illustrate tumor architecture. C) Western blot of protein extract of patient samples consisting of tumor (T), uninvolved normal tissue (N) and lymph node biopsies (LN). Samples were fractionated by polyacrylamide gel electrophoresis in 4-20% Tris-glycine gels and subsequently electroblotted onto nylon membranes. Membranes were sequentially probed with EphB4 monoclonal antibody and β-actin MoAb. Chemiluminescent signal was detected on autoradiography film. Shown is the EphB4 specific band which migrated at 120 kD and β-actin which migrated at 40 kD. The β-actin signal was used to control for loading and transfer of each sample.

We studied the expression of EphB4 in human tumor tissues by immunohistochemistry, in situ hybridization, and Western blot. Twenty prospectively collected tumor tissues following IRB approval have been evaluated with specific EphB4 monoclonal antibody that does not react with other members of the EphB and EphA family. EphB4 expression is observed in all cases, with varying intensity of staining. FIG. 39A (top left) illustrates a representative case, showing that EphB4 is expressed in the tumor regions only, as revealed by the H&E tumor architecture (FIG. 39A bottom left). Note the absence of staining for EphB4 in the stroma. Secondly, a metastatic tumor site in the lymph node shows positive staining while the remainder of the lymph node is negative (FIG. 39A, top right).

Figure 39B:
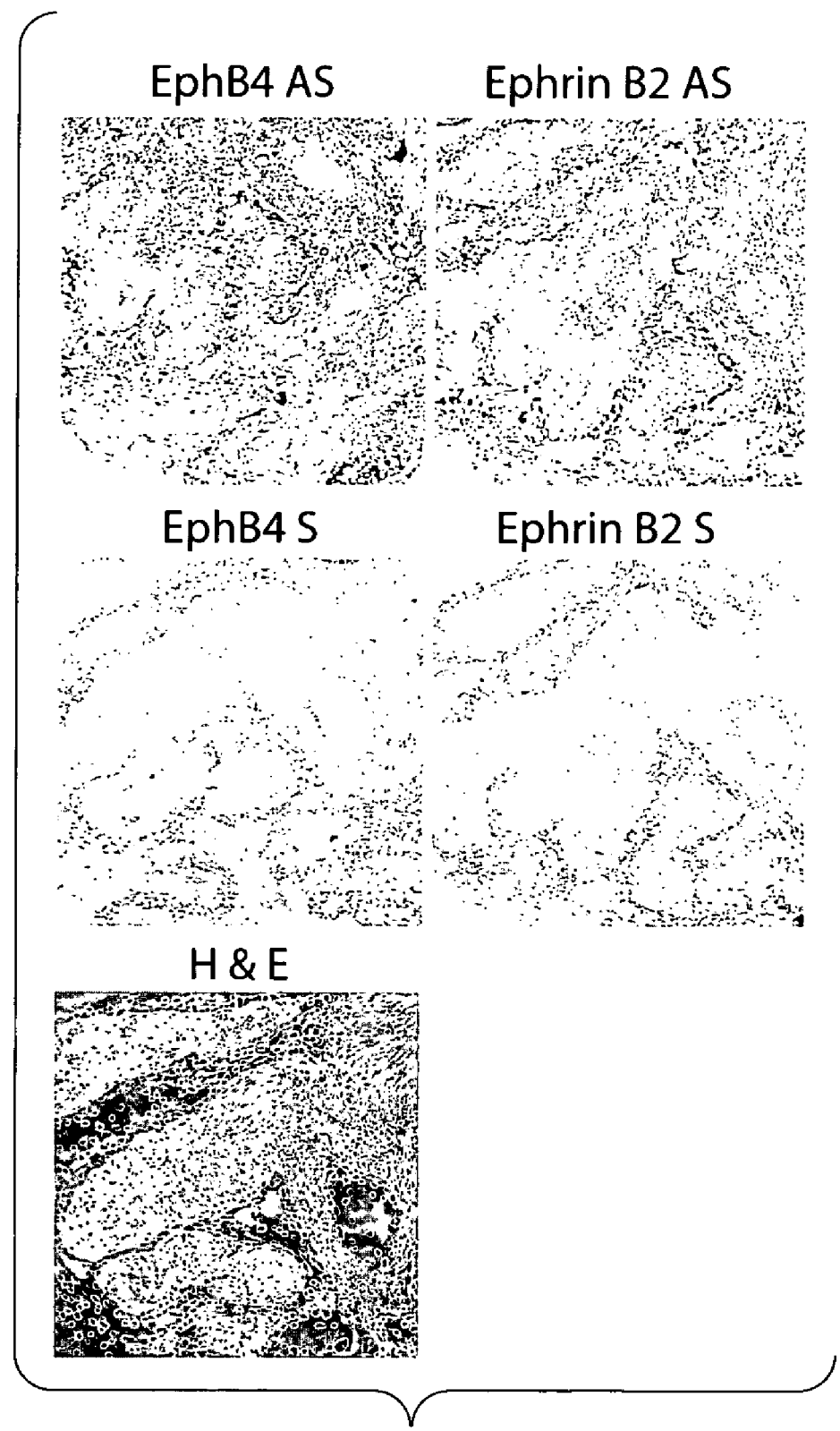

In situ hybridization was carried out to determine the presence and location of EphB4 transcripts in the tumor tissue. Strong signal for EphB4 specific antisense probe was detected indicating the presence of transcripts (FIG. 39B, top left). Comparison with the H&E stain (FIG. 39B, bottom left) to illustrate tumor architecture reveals that the signal was localized to the tumor cells, and was absent from the stromal areas. Ephrin B2 transcripts were also detected in tumor sample, and as with EphB4, the signal was localized to the tumor cells (FIG. 39B, top right). Neither EphB4 nor ephrin B2 sense probes hybridized to the sections, proving specificity of the signals.

B. High Expression of EphB4 in Primary and Metastatic Sites of HNSCC

Figure 39C:
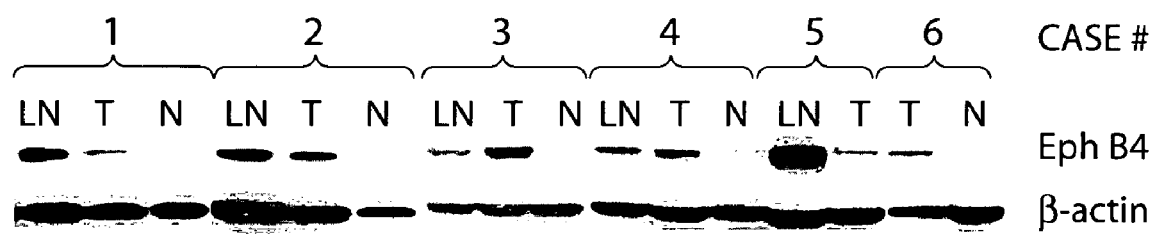

Western blots of tissue from primary tumor, lymph node metastases and uninvolved tissue were carried out to determine the relative levels of EphB4 expression in these sites. Tumor and normal adjacent tissues were collected on 20 cases, while lymph nodes positive for tumor were harvested in 9 of these 20 cases. Representative cases are shown in FIG. 39C. EphB4 expression is observed in each of the tumor samples. Similarly, all tumor positive lymph nodes show EphB4 expression that was equal to or greater than the primary tumor. No or minimal expression is observed in the normal adjacent tissue.

C. EphB4 Expression and Regulation by EGFR Activity in HNSCC Cell Lines

Figure 40A:
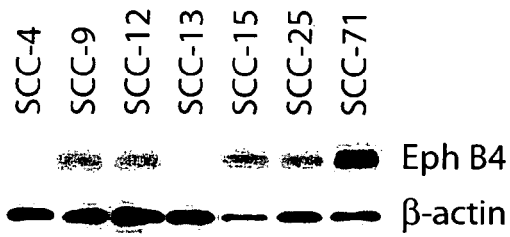
FIG. 40 shows that EphB4 is expressed in HNSCC cell lines and is regulated by EGF: A) Survey of EphB4 expression in SCC cell lines. Western blot of total cell lysates sequentially probed with EphB4 monoclonal antibody, stripped and reprobed with β-actin monoclonal antibody as described for FIG. 39C. B) Effect of the specific EGFR inhibitor AG1478 on EphB4 expression: Western blot of crude cell lysates of SCC15 treated with 0-1000 nM AG 1478 for 24 h in media supplemented with 10% FCS (left) or with 1 mM AG 1478 for 4, 8, 12 or 24 h (right). Shown are membranes sequentially probed for EphB4 and α-actin. C) Effect of inhibition of EGFR signaling on EphB4 expression in SCC cell lines: Cells maintained in growth media containing 10% FCS were treated for 24 hr with 1 μM AG 1478, after which crude cell lysates were analyzed by Western blots of cell lysates sequentially probed with for EGFR, EphB4, ephrin B2 and β-actin antibodies. Specific signal for EGFR was detected at 170 kD and ephrin B2 at 37 kD in addition to EphB4 and β-actin as described in FIG. 1C. β-actin serves as loading and transfer control.
Figure 40B:
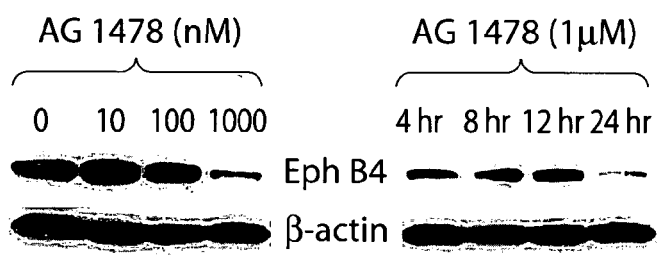
Figure 40C:
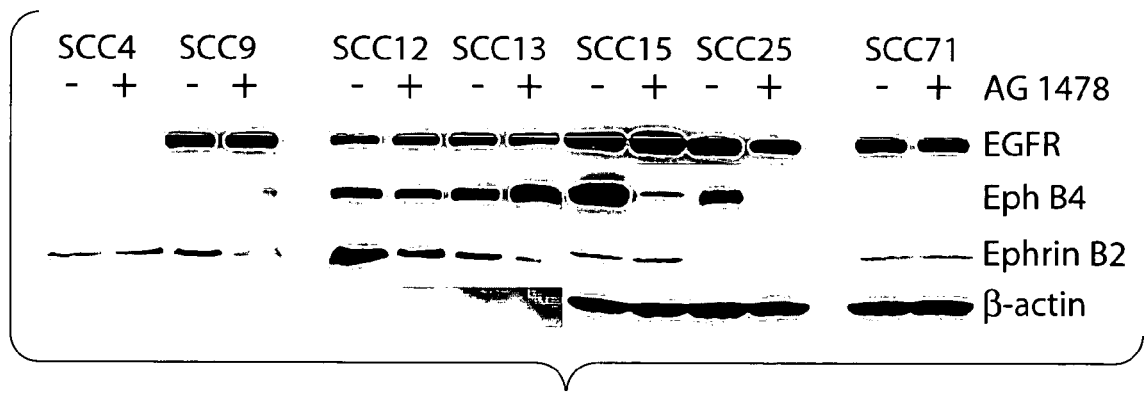

Having demonstrated the expression of EphB4 limited to tumor cells, we next sought to determine whether there was an in vitro model of EphB4 expression in HNSCC. Six HN SCC cell lines were surveyed for EphB4 protein expression by Western Blot (FIG. 40A). A majority of these showed strong EphB4 expression and thus established the basis for subsequent studies. Since EGFR is strongly implicated in HNSCC we asked whether EphB4 expression is associated with the activation of EGFR. Pilot experiments in SCC-15, which is an EGFR positive cell line, established an optimal time of 24 h and concentration of 1 mM of the specific EGFR kinase inhibitor AG 1478 (FIG. 40B) to inhibit expression of EphB4. When all the cell lines were studied, we noted robust EGFR expression in all but SCC-4, where it is detectable but not strong (FIG. 40C, top row). In response to EGFR inhibitor AG1478 marked loss in the total amount of EphB4 was observed in certain cell lines (SCC-15, and SCC-25) while no effect was observed in others (SCC-9, -12, -13 and -71). Thus SCC-15 and -25 serve as models for EphB4 being regulated by EGFR activity, while SCC-9, -12, -13 and -71 are models for regulation of EphB4 in HNSCC independent of EGFR activity, where there may be input from other factors such as p53, PTEN, IL-6 etc. We also noted expression of the ligand of EphB4, namely ephrin B2, in all of the cell lines tested. As with EphB4 in some lines ephrin B2 expression appears regulated by EGFR activity, while it is independent in other cell lines.

Figure 41A:
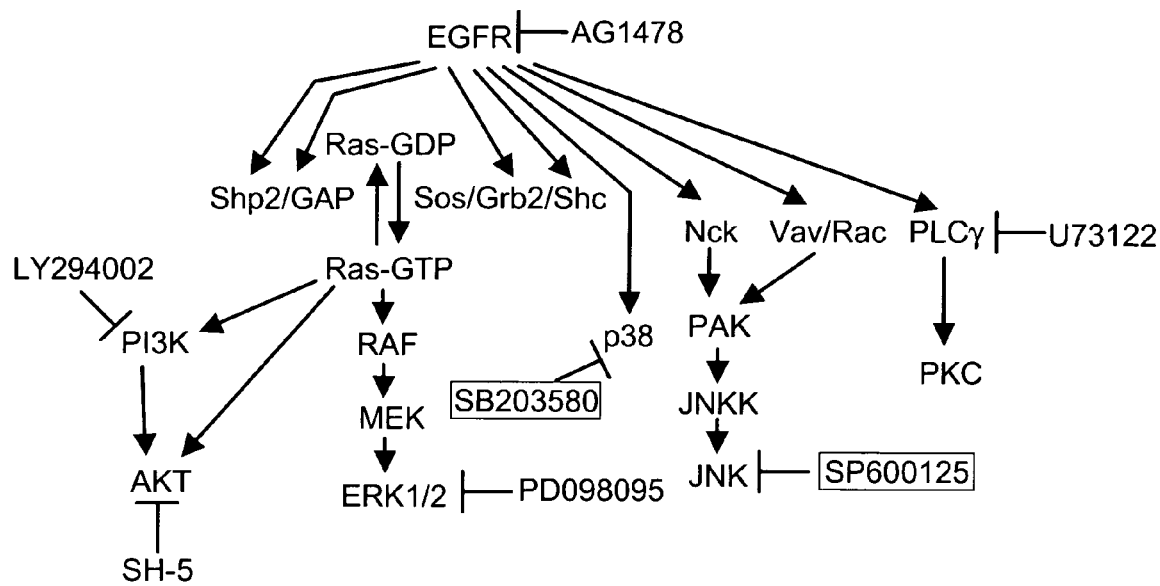
FIG. 41 shows mechanism of regulation of EphB4 by EGF: A) Schematic of the EGFR signaling pathways, showing in red the sites of action and names of specific kinase inhibitors used. B) SCC15 cells were serum-starved for 24 h prior to an additional 24 incubation as indicated with or without EGF (10 ng/ml), 3 μM U73122, or 5 μM SH-5, 5 μM SP600125, 25 nM LY294002, —μM PD098095 or 5 μM SB203580. N/A indicates cultures that received equal volume of diluent (DMSO) only. Cell lysates were subjected to Western Blot with EphB4 monoclonal antibody. β-actin signal serves as control of protein loading and transfer.
Figure 41B:
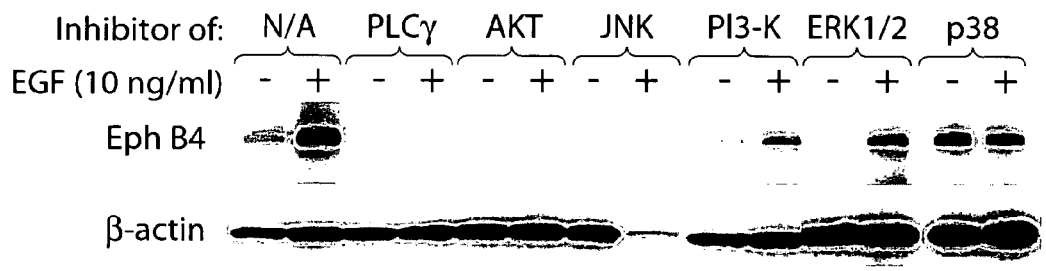

Clearly, inhibition of constitutive EGFR signaling repressed EphB4 levels in SCC15 cells. We next studied whether EGF could induce EphB4. We found that EphB4 levels were induced in SCC15 cells that had been serum starved for 24 h prior to 24 h treatment with 10 ng/ml EGF as shown in FIG. 41B (lanes 1 and 2). The downstream signaling pathways known for EGFR activation shown in FIG. 41A, (for review see Yarden & Slikowski 2001) were then investigated for their input into EGF mediated induction of EphB4. Blocking PLCg, AKT and JNK phosphorylation with the specific kinase inhibitors U73122, SH-5 and SP600125 respectively reduced basal levels and blocked EGF stimulated induction of EphB4 (FIG. 41B, lanes 3-8). In contrast, inhibition of ERK1/2 with PD098095 and P13-K with LY294002 or Wortmannin had no discernible effect on EGF induction of EphB4 levels. However, basal levels of EphB4 were reduced when ERK1/2 phosphorylation was inhibited. Interestingly, inhibition of p38 MAPK activation with SB203580 increased basal, but not EGF induced EphB4 levels. Similar results were seen in the SCC25 cell line (data not shown).

Figure 42A:
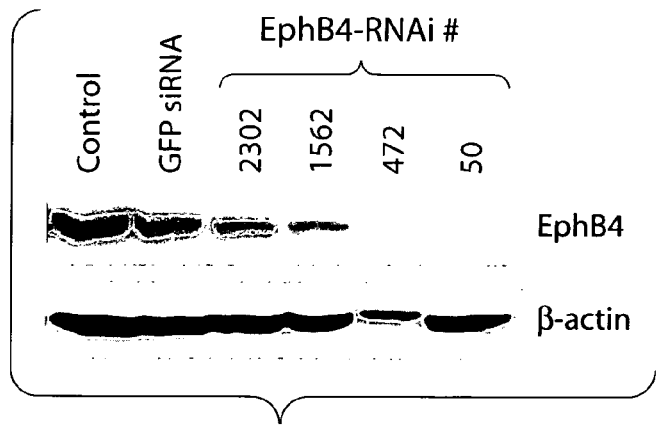
FIG. 42 shows that specific EphB4 siRNAs inhibit EphB4 expression, cell viability and cause cell cycle arrest. A) 293 cells stably expressing full length EphB4 were transfected with 50 nM RNAi using Lipofectamine™2000. 40 h post-transfection cells were harvested, lysed and processed for Western blot. Membranes were probed with EphB4 monoclonal antibody, stripped and reprobed with β-actin monoclonal antibody as control for protein loading and transfer. Negative reagent control was RNAi to scrambled green fluorescence protein (GFP) sequence and control is transfection with Lipofectamine™2000 alone. B) MTT cell viability assays of SCC cell lines treated with siRNAs for 48 h as described in the Methods section. Shown is mean +s.e.m. of triplicate samples. C)SCC15 cells transfected with siRNAs as indicated were analyzed 24 h post transfection for cell cycle status by flow cytometry as described in the Methods. Shown are the plots of cell number vs. propidium iodide fluorescence intensity. Top and middle row show plots for cells 16 h after siRNA transfection, bottom row shows plots for cells 36 h post transfection. Specific siRNA and concentration are indicated for each plot. Lipo=Lipofectamine™200 mock transfection.
Figure 42B:
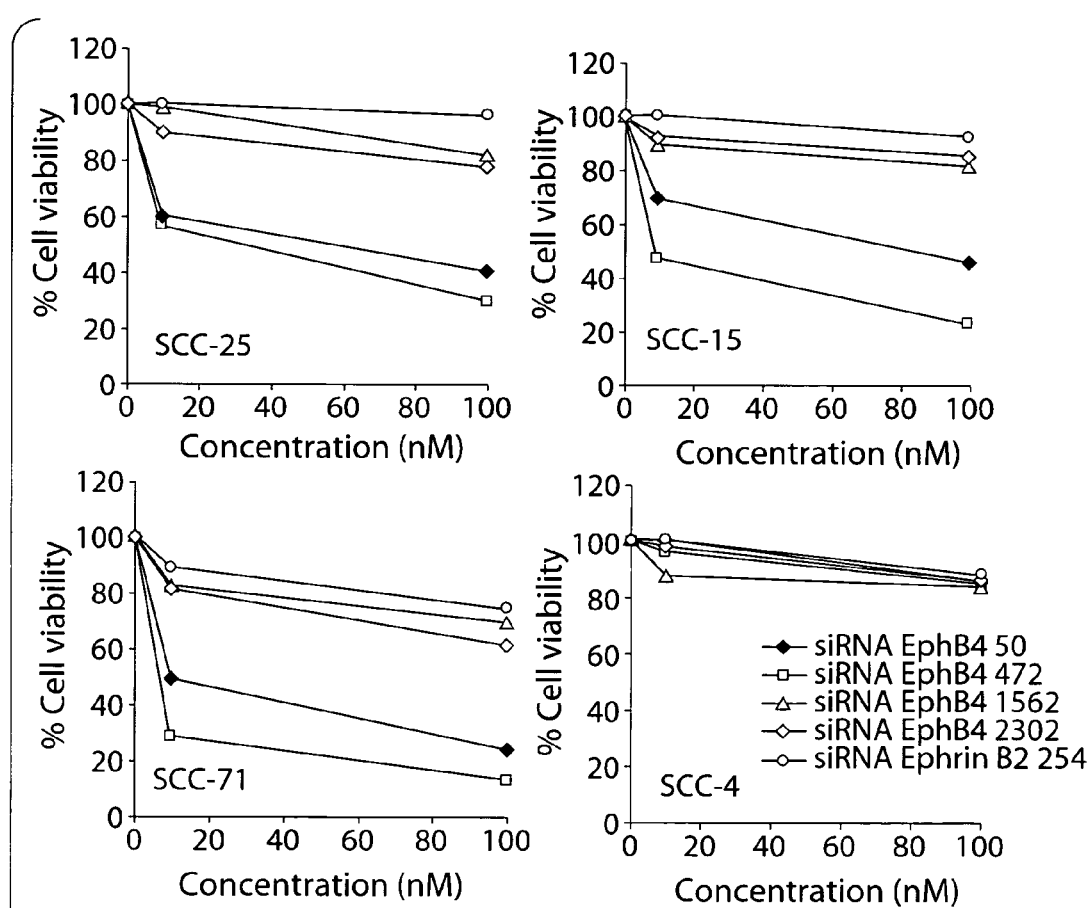
Figure 42C:
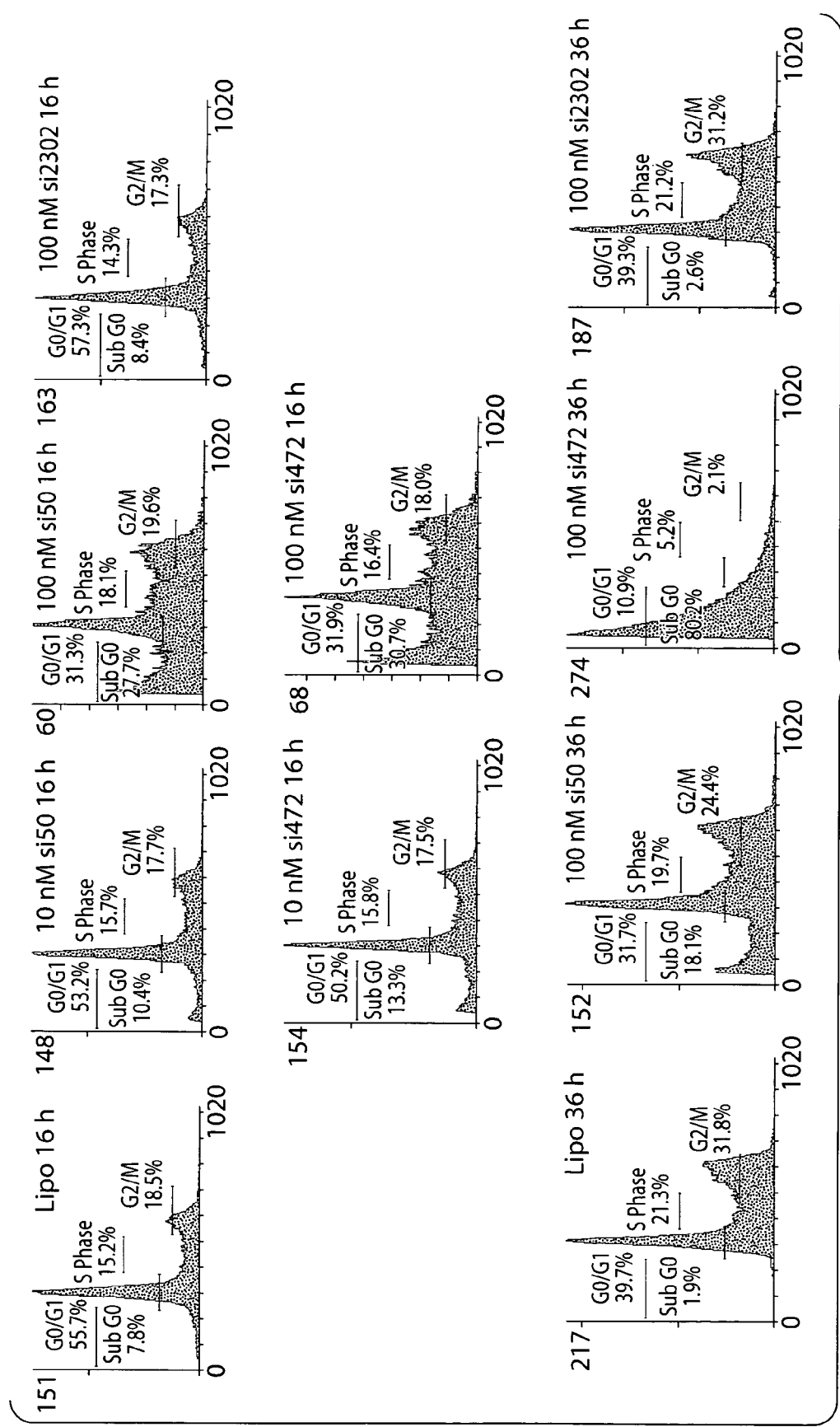

D. Inhibition of EphB4 in High Expressing Cell Lines Results in Reduced Viability and Causes Cell-Cycle Arrest We next turned to the role of EphB4 expression in HNSCC by investigating the effect of ablating expression using siRNA or AS-ODN methods. Several siRNAs to EphB4 sequence were developed (Table 1) which knocked-down EphB4 expression to varying degrees as seen in FIG. 42A. Viability was reduced in SCC-15, -25 and -71 cell lines transfected with siRNAs 50 and 472, which were most effective in blocking EphB4 expression (FIG. 42B). Little effect on viability was seen with EphB4 siRNA 1562 and 2302 or ephrin B2 siRNA 254. Note that in SCC-4, which does not express EphB4 (see FIG. 40A) there was no reduction in cell viability. The decreased cell viability seen with siRNA 50 and 472 treatment was attributable to accumulation of cells in sub G0, indicative of apoptosis. This effect was both time and dose-dependant (FIG. 42C and Table 2). In contrast, siRNA2302 that was not effective in reducing EphB4 levels and had only minor effects on viability did not produce any changes in the cell cycle when compared with the mock Lipofectamine™ 2000 transfection.

TABLE 1

EphB4 siRNAs

| Name | siRNA sequence | SEQ. ID NO: |
|---|---|---|
| Eph B4 50: | 5'-GAGACCCUGCUGAACACAAUU-3' | 34 |
| | 3'-UUCUCUGGGACGACUUGUGUU-5' | 35 |
| Eph B4 472: | 5'-GGUGAAUGUCAAGACGCUGUU-3' | 36 |
| | 3'-UUCCACUUACAGUUCUGCGAC-5' | 37 |
| Eph B4 1562: | 5'-CAUCACAGCCAGACCCAACUU-3' | 38 |
| | 3'-UUGUAGUGUCGGUCUGGGUUG-5' | 39 |
| Eph B4 2302: | 5'-CUCUUCCGAUCCCACCUACUU-3' | 40 |
| | 3'-UUGAGAAGGCUAGGGUGGAUG-5' | 41 |

TABLE 2

Effect of different EphB4 siRNA on Cell Cycle

| Treatment | Sub G0 | G1 | S | G2 |
|---|---|---|---|---|
| 36 hr | | | | |
| Lipo alone | 1.9 | 39.7 | 21.3 | 31.8 |
| 100 nM 2302 | 2.0 | 39.3 | 21.2 | 31.2 |
| 100 nM 50 | 18.1 | 31.7 | 19.7 | 24.4 |
| 100 nM 472 | 80.2 | 10.9 | 5.2 | 2.1 |
| 16 hr | | | | |
| Lipo alone | 7.8 | 55.7 | 15.2 | 18.5 |
| 100 nM 2302 | 8.4 | 57.3 | 14.3 | 17.3 |
| 10 nM 50 | 10.4 | 53.2 | 15.7 | 17.7 |
| 100 nM 50 | 27.7 | 31.3 | 18.1 | 19.6 |
| 10 nM 472 | 13.3 | 50.2 | 15.8 | 17.5 |
| 100 nM 472 | 30.7 | 31.9 | 16.4 | 18.0 |

Figure 43A:
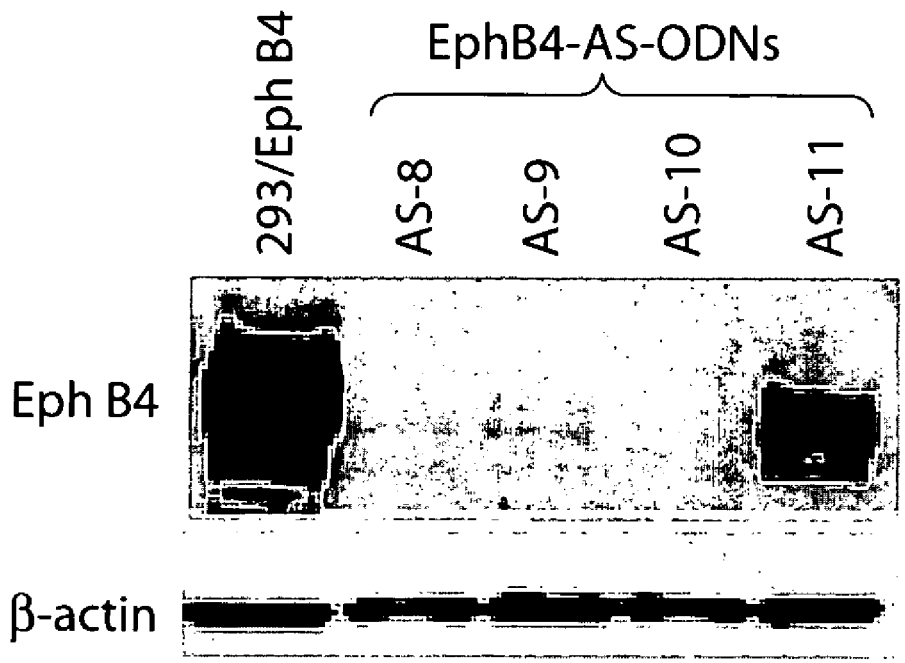
FIG. 43 shows in vitro effects of specific EphB4 AS-ODNs on SCC cells. A) 293 cells transiently transfected with EphB4 full-length expression plasmid were treated 6 h post transfection with antisense ODNs as indicated. Cell lysates were collected 24 h after AS-ODN treatment and subjected to Western Blot. B) SCC25 cells were seeded on 48 well plates at equal densities and treated with EphB4 AS-ODNs at 1, 5, and 10 μM on days 2 and 4. Cell viability was measured by MTT assay on day 5. Shown is the mean +s.e.m. of triplicate samples. Note that AS-ODNs that were active in inhibiting EphB4 protein levels were also effective inhibitors of SCC15 cell viability. C) Cell cycle analysis of SCC15 cells treated for 36 h with AS-10 (bottom) compared to cells that were not treated (top). D) Confluent cultures of SCC15 cells scraped with a plastic Pasteur pipette to produce 3 mm wide breaks in the monolayer. The ability of the cells to migrate and close the wound in the presence of inhibiting EphB4 AS-ODN (AS-10) and non-inhibiting AS-ODN (AS-1) was assessed after 48 h. Scrambled ODN is included as a negative control ODN. Culture labeled no treatment was not exposed to ODN. At initiation of the experiment, all cultures showed scrapes of equal width and similar to that seen in 1 μM EphB4 AS-10 after 48 h. The red brackets indicate the width of the original scrape. E) Migration of SCC15 cells in response to 20 mg/ml EGF in two-chamber assay as described in the Methods. Shown are representative photomicrographs of non-treated (NT), AS-6 and AS-10 treated cells and 10 ng/ml Taxol as positive control of migration inhibition. F) Cell numbers were counted in 5 individual high-powered fields and the average +s.e.m. is shown in the graph.
Figure 43B:
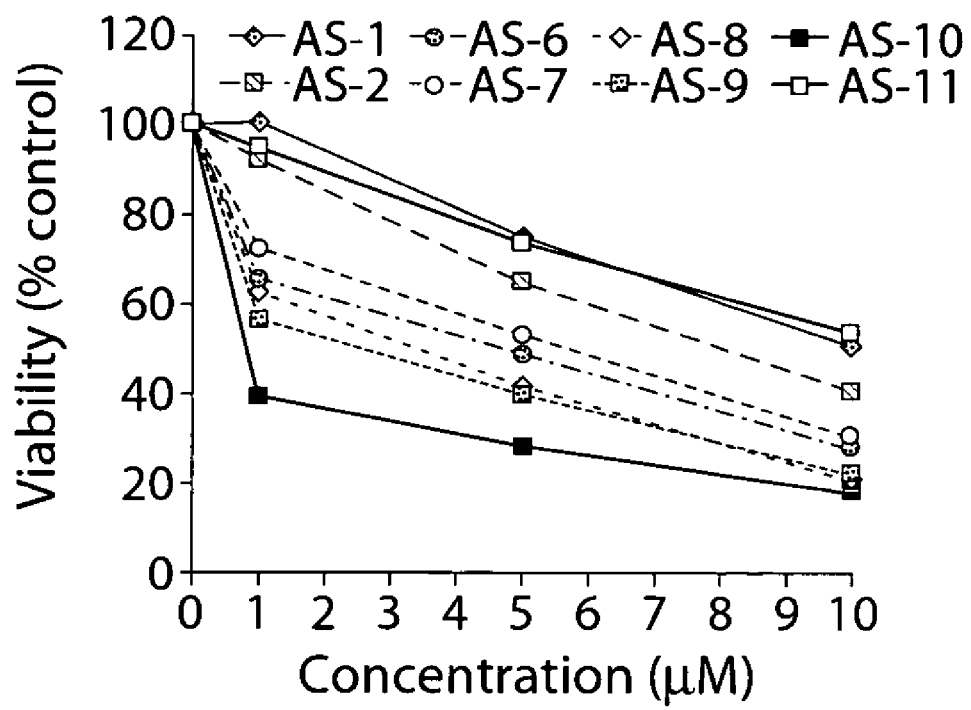
Figure 43C:
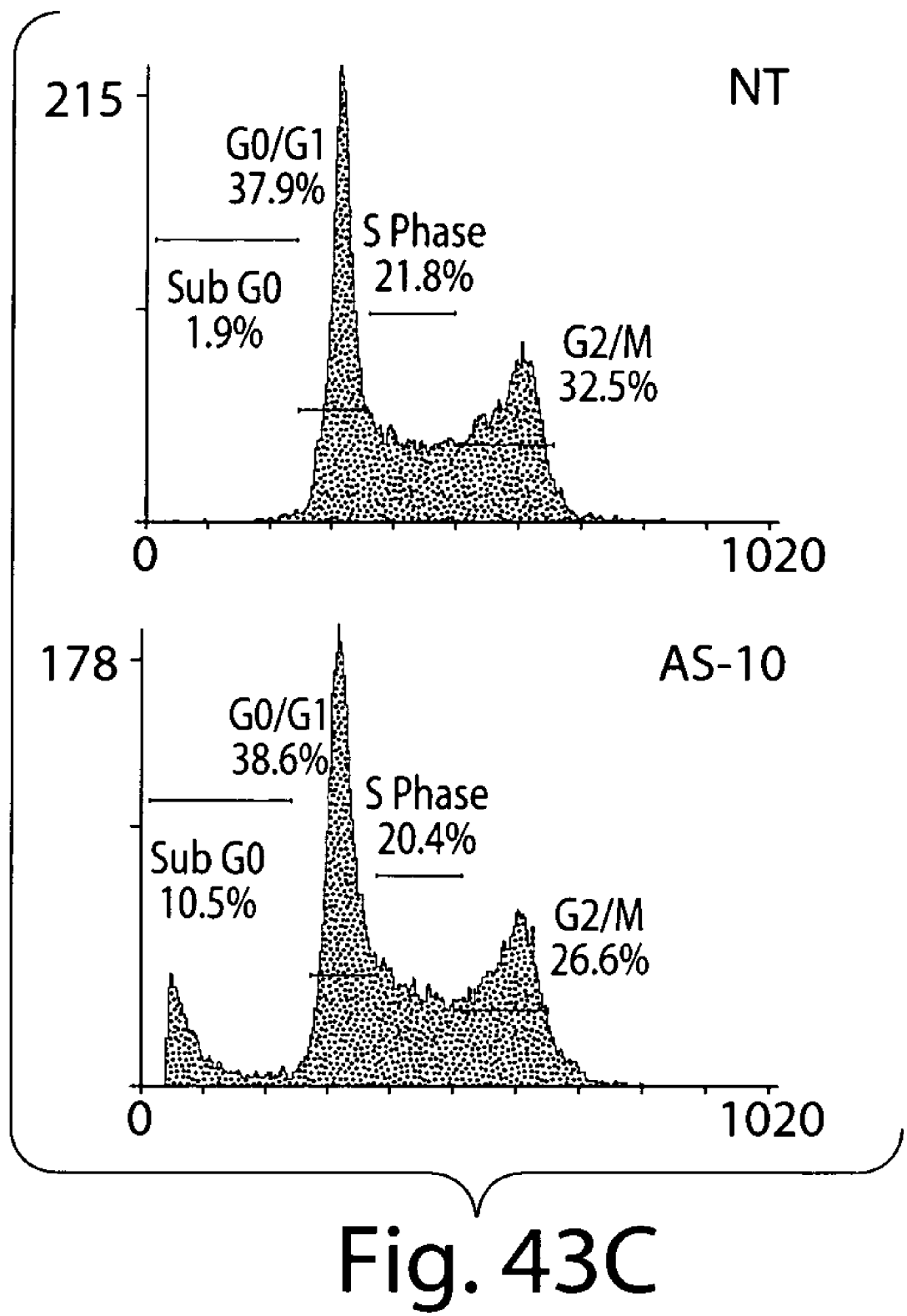

In addition, over 50 phosphorothioate AS-ODNs complementary to the human EphB4 coding sequences were synthesized and tested for their ability to inhibit EphB4 expression in 293 cells transiently transfected with full length EphB4 expression plasmid. FIG. 43A shows a representative sample of the effect of some of these AS-ODNs on EphB4 expression. Note that expression is totally abrogated with AS-10, while AS-11 has only a minor effect. The effect on cell viability in SCC15 cells was most marked with AS-ODNs that are most effective in inhibiting EphB4 expression as shown in FIG. 43B. The $IC_{50}$ for AS-10 was approximately 1 µM, while even 10 µM AS-11 was not sufficient to attain 50% reduction of viability. When the effect that AS-10 had on the cell cycle was investigated, it was found that the sub G0 fraction increased from 1.9% to 10.5% compared to non-treated cells, indicative of apoptosis (FIG. 43C).

E. EphB4 Regulates Cell Migration

Figure 43D:
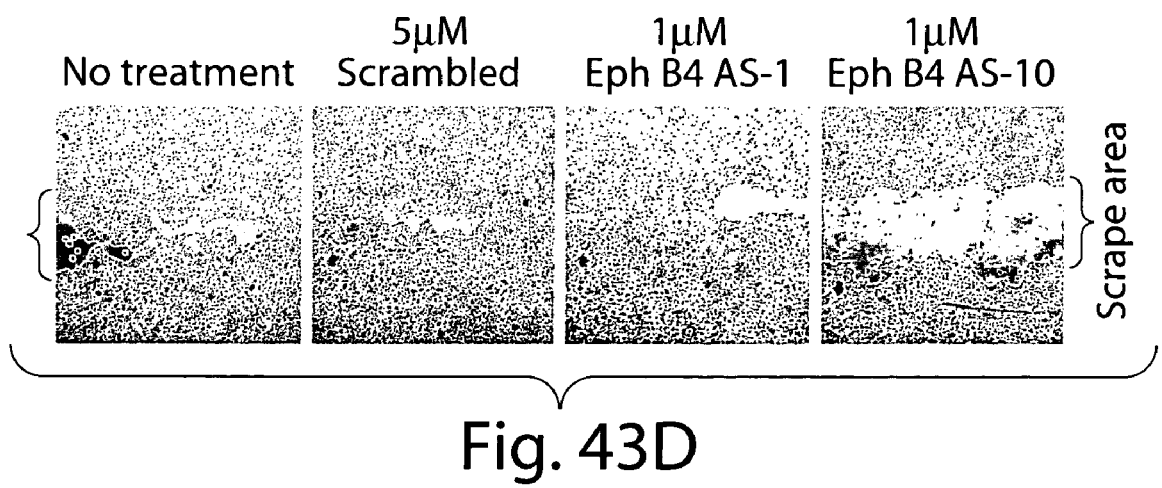
Figure 43E:
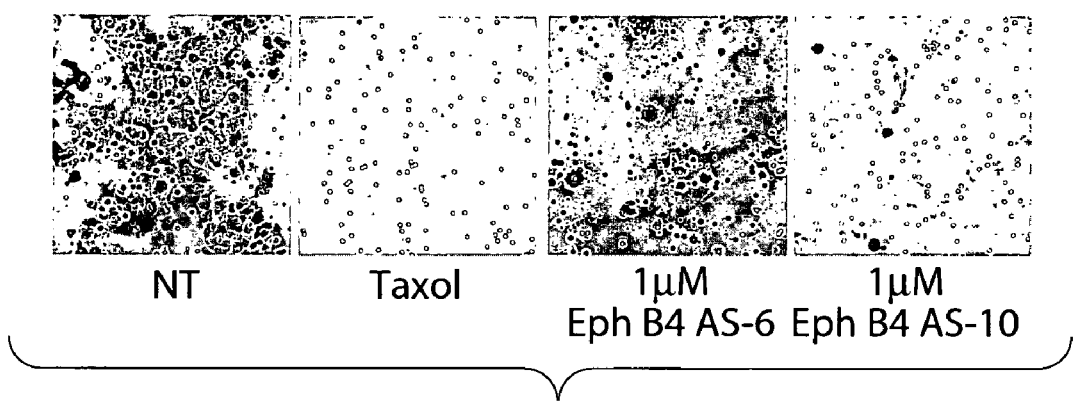
Figure 43F:
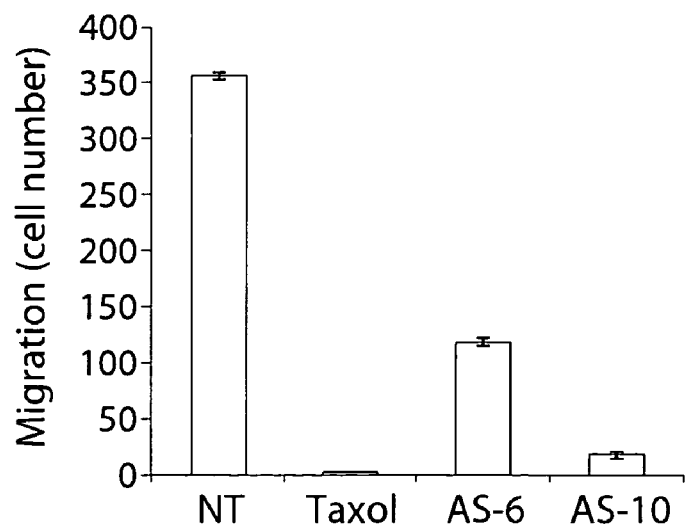

We next wished to determine if EphB4 participates in the migration of HNSCC. Involvement in migration may have implications for growth and metastasis. Migration was assessed using the wound-healing/scrape assay. Confluent SCC15 and SCC25 cultures were wounded with a single scrape with a sterile plastic Pasteur pipette, which left a 3 mm band with clearly defined borders. Migration of cells into the cleared area in the presence of test compounds was evaluated and quantitated after 24, 48 and 72 hr. Cell migration was markedly diminished in response to AS-10 that block EphB4 expression while the inactive compounds, AS-1 and scrambled ODN had little to no effect as shown in FIG. 43D. Inhibition of migration with AS-10 was also shown using the Boyden double chamber assay (FIG. 43E).

F. EphB4 AS-10 In Vivo Anti-Tumor Activity

Figure 44:
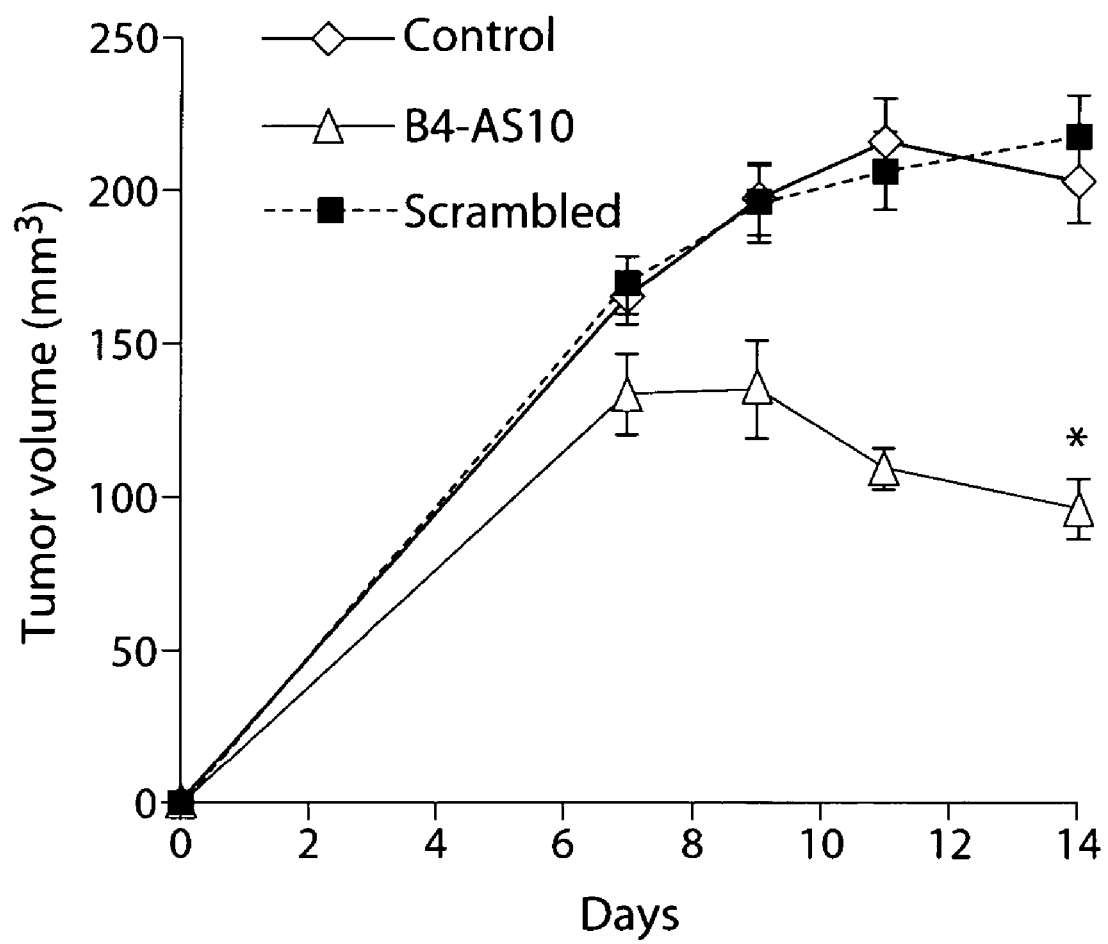
FIG. 44 shows that EphB4 AS-ODN inhibits tumor growth in vivo. Growth curves for SCC15 subcutaneous tumor xenografts in Balb/C nude mice treated with EphB4 AS-10 or scrambled ODN at 20 mg/kg/day starting the day following implantation of 5×106 cells. Control mice received and equal volume of diluent (PBS). Shown are the mean +s.e.m. of 6 mice/group. * P=0.0001 by Student's t-test compared to scrambled ODN treated group.

The effect of EphB4 AS-10, which reduces cell viability and motility, was determined in SCC 15 tumor xenografts in Balb/C nude mice. Daily treatment of mice with 20 mg/kg AS-10, sense ODN or equal volume of PBS by I.P. injection was started the day following tumor cell implantation. Growth of tumors in mice receiving AS-10 was significantly retarded compared to mice receiving either sense ODN or PBS diluent alone (FIG. 44). Non-specific effects attributable to ODN were not observed, as there was no difference between the sense ODN treated and PBS treated groups.

G. Materials and Methods

1) Cell Lines and Reagents

HNSCC-4, -9, 12, -13, -15, -25, and -71 were obtained from and 293 human embryonic kidney cells were obtained from the ATCC (Manassas, Va.). Cells were maintained in RPMI 1640 media supplemented with 10% heat-inactivated fetal bovine serum (FBS; Invitrogen, Carlsbad, Calif.) and antibiotics. EGFR, EphB4(C-16) polyclonal antibodies were from Santa Cruz Biotech (Santa Cruz, Calif.). β-actin monoclonal antibody was purchased from Sigma Chemical Co. (St Louis, Mo.). Ephrin B2 and EphB4 polyclonal antibodies and their corresponding blocking peptides were obtained from Santa Cruz Biotechnology (Santa Cruz, Calif.). AG 1478 (4-(3'-Chloroanilino)-6,7-dimethoxy-quinazoline) was from Calbiochem (San Diego, Calif.). Kinase inhibitors SH-5 and SP 600125 were from A.G. Scientific (San Diego, Calif.), PD98095, U73122, SB203580, LY294002, and Wortmannin were obtained from Sigma.

2) Preparation of Digoxigenin-Labeled RNA Probes

See above, e.g., Example 3.

3) In Situ Hybridization

See above, e.g., Example 3.

4) Immunohistochemistry

Formalin-fixed tissue sections were deparaffinized and incubated with 10% goat serum at −70° C. for 10 minutes and incubated with the EphB4 monoclonal antibody 4° C. overnight. Isotype specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with 0.12% methylene blue or H&E. For frozen sections, OCT-embedded tissues were sectioned at 5 µm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody. Immunohistochemical staining on prostate array (BioMeda, Foster City, Calif.) was done using goat ABC Staining System (Santa Cruz Biotech.) according to the manufacturer's instructions.

5) Western Blot

See above, e.g., Example 3.

6) Synthesis of EphB4 siRNA by In Vitro Transcription

The Silencer™ siRNA construction kit (Ambion, Austin Tex.) was used to synthesize siRNA to EphB4. Briefly, 21 bp target sequences containing 19 bp downstream of 5'-AA dinucleotides were identified that showed no significant homology to other sequences in the GenBank database. Sense and antisense siRNA 29-mer DNA oligonucleotide templates were synthesized at the USC Norris Microchemical Core Facility. Antisense template corresponded to the target sequence followed by 8 bp addition (5'-CCTGTCTC-3') at the 3' end complementary to the T7 promoter primer provided by the Silencer™ siRNA construction kit. Sense template comprised 5'-AA followed by the complement of the target 19 bp, then the T7 8 bp sequence as above.

In separate reactions, the two siRNA oligonucleotide templates were hybridized to a T7 promoter primer. The 3' ends of the hybridized oligonucleotides were extended by the Klenow fragment of DNA polymerase to create double-stranded siRNA transcription templates. The sense and antisense siRNA templates were transcribed by T7 RNA polymerase and the resulting RNA transcripts were hybridized to create dsRNA. The leader sequences were removed by digesting the dsRNA with a single-stranded specific ribonuclease leaving the overhanging UU dinucleotides. The DNA template was removed at the same time by treatment with RNase free deoxyribonuclease. The resulting siRNA was purified by glass fiber filter binding to remove excess nucleotides, short oligomers, proteins, and salts in the reaction. The end products (shown in Table 3) were double-stranded 21-mer siRNAs with 3' terminal uridine that can effectively reduce the expression of target mRNA when transfected into cells.

A number of phosphorothioate AS-ODNs were also synthesized (Operon, Valencia Calif.) to test for inhibition of EphB4 expression (Table 3).

TABLE 3

EphB4 Antisense ODNs

| Name | Position | Sequence (5' → 3') | SEQ. ID NO: |
|---|---|---|---|
| Eph B4 AS-1 | (552-572) | GTG CAG GGA TAG CAG GGC CAT | 42 |
| Eph B4 AS-2 | (952-972) | AAG GAG GGG TGG TGC ACG GTG | 43 |
| Eph B4 AS-3 | (1007-1027) | TTC CAG GTG CAG GGA GGA GCC | 44 |
| Eph B4 AS-4 | (1263-1285) | GTG GTG ACA TTG ACA GGC TCA | 45 |
| Eph B4 AS-5 | (1555-1575) | TCT GGC TGT GAT GTT CCT GGC | 46 |
| Eph B4 AS-6 | (123-140) | GCC GCT CAG TTC CTC CCA | 47 |
| Eph B4 AS-7 | (316-333) | TGA AGG TCT CCT TGC AGG | 48 |
| Eph B4 AS-8 | (408-428) | CGC GGC CAC CGT GTC CAC CTT | 49 |
| Eph B4 AS-9 | (1929-1949) | CTT CAG GGT CTT GAT TGC CAC | 50 |
| Eph B4 AS-10 | (1980-1999) | ATG GAG GCC TCG CTC AGA AA | 51 |
| Eph b4 AS-11 | (2138-2158) | CAT GCC CAC GAG CTG GAT GAC | 52 |

7) Cell Viability Assay

Cells were seeded at a density of $5 \times 10^3$ per well in 48-well plates on day 0 in appropriate growth media containing 2% fetal calf serum (FCS). Cells were treated with various concentrations (1-10 μg/ml) of ODNs on days 2 and 4. On day 5, viability was assessed using 3-(4,5-dimethylthiazol-2-yl)-2, 5-diphenyltetrazolium bromide (MTT) as previously described (Masood et al '03). For viability with siRNA, $2 \times 10^4$ cells/well of SCC-4, -15, -25 or -71 in a 48-well plate were transfected with siRNAs (10-100 nM) using 2 μl of Lipofectamine™ 2000 according to the manufacturer's instructions. 4 h post-transfection the cells were returned to growth media (RPMI 1640 supplemented with 10% FBS). Viability was assayed by MTT 48 h following transfection.

8) Cell Cycle Analysis

80% confluent cultures of SCC 15 cells in 6-well plates were transfected with siRNA472 (100 nM) using Lipofectamine™ 2000. Either 16 or 36 hours after transfection, cells were trypsinized, washed in PBS and incubated for 1 h at 4° C. in 1 ml of hypotonic solution containing 50 μg/ml propidium iodide, 0.1% sodium citrate, 0.1 Triton X-100 and 20 μg/ml DNase-free RNaseA. Cells were analyzed in linear mode at the USC Flow cytometry facility. Results were expressed as percentages of elements detected in the different phases of the cell cycle, namely Sub G0 peak (apoptosis), G0/G1 (no DNA synthesis), S (active DNA systhesis), G2 (premitosis) and M (mitosis). For AS-ODN experiment the cells were exposed to 5 μM ODN for 36 h prior to processing.

9) Wound Healing Migration Assay

SCC15 cells were seeded into 6-well plates and cultured until confluent. 10 μM AS-1, AS-10, or sense ODN as control were introduced to the wells as described for the viability assay 12 hours before wounding the monolayer by scraping it with a sterile pipette tip. Medium was changed to RPMI 1640 supplemented with 5% FBS and fresh ODNs. The healing process was examined dynamically and recorded with a Nikon Coolpix 5000 digital camera with microscope adapter.

10) Boyden Chamber Assay of Migration

Cell migration assays were performed as previously described (Masood ANUP paper '99) except that 1 μM AS-10 or AS-6 were added to the upper chamber. EGF (20 ng/ml) was used as chemoattractant in the lower chamber. Taxol at 10 ng/ml was used as a negative control.

11) In Vivo Studies

SCC 15 ($5 \times 10^6$ cells) were injected subcutaneously in the lower back of 5-week old male Balb/C Nu$^+$/nu$^+$ athymic mice. Treatment consisted of daily intraperitoneal injection of ODN (20 mg/kg in a total volume of 100 μl) or diluent (PBS) begun the day following tumor cell implantation and continued for two weeks. Tumor growth in mice was measured as previously described (Masood CCR '01). Mice were sacrificed at the conclusion of the study. All mice were maintained in accord with the University of Southern California Animal Care and Use Committee guidelines governing the care of laboratory mice.

EXAMPLE 6

Ephrin B2 Expression in Kaposi's Sarcoma Is Induced by Human Herpesvirus Type 8: Phenotype Switch from Venous to Arterial Endothelium Kaposi's Sarcoma (KS) manifests as a multifocal angio-proliferative disease, most commonly of the skin and mucus membranes, with subsequent spread to visceral organs (1) Hallmarks of the disease are angiogenesis, edema, infiltration of lymphomononuclear cells and growth of spindle-shaped tumor cells. Pathologically, established lesions exhibit an extensive vascular network of slit-like spaces. The KS vascular network is distinct from normal vessels in the lack of basement membranes and the abnormal spindle shaped endothelial cell (tumor cell) lining these vessels. Defective vasculature results in an accumulation of the blood components including albumin, red and mononuclear cells in the lesions (1). The KS tumor is endothelial in origin; the tumor cells express many endothelial markers, including lectin binding sites for *Ulex europeaus* agglutinin-1 (UEA-1), CD34, EN-4, PAL-E (2) and the endothelial cell specific tyrosine kinase receptors, VEGFR-1 (Flt-1), VEGFR-2 (Flk-1/KDR), VEGFR-3 (Flt-4), Tie-1 and Tie-2 (3, RM & PSG unpublished data). KS cells co-express lymphatic endothelial cell related proteins including LYVE and podoplanin (4).

The herpesvirus HHV-8 is considered the etiologic agent for the disease. In 1994 sequences of this new herpes virus were identified in KS tumor tissue (5), and subsequent molecular-epidemiology studies have shown that nearly all KS tumors contain viral genome. Sero-epidemiology studies show that HIV infected patients with KS have the highest prevalence of HHV-8 and secondly that those with HIV infection but no KS have increased risk of developement of KS over the ensuing years if they are also seropositive for HHV-8 (6). Direct evidence for the role of HHV-8 in KS is the transformation of bone marrow endothelial cells after infection with HHV-8 (7). A number of HHV-8 encoded genes could contribute to cellular transformation (reviewed in 8). However, the most evidence has accumulated for the G-protein coupled receptor (vGPCR) in this role (9).

We investigated whether KS tumor cells are derived from arterial or venous endothelium. In addition, we investigated whether HHV-8 has an effect on expression of arterial or venous markers in a model of KS. KS tumor cells were found to express the ephrin B2 arterial marker. Further, ephrin B2 expression was induced by HHV-8 vGPCR in KS and endothelial cell lines. Ephrin B2 is a potential target for treatment of KS because inhibition of ephrin B2 expression or signaling was detrimental to KS cell viability and function.

A. KS Tumors Express Ephrin B2, but not EphB4

Figure 45B:
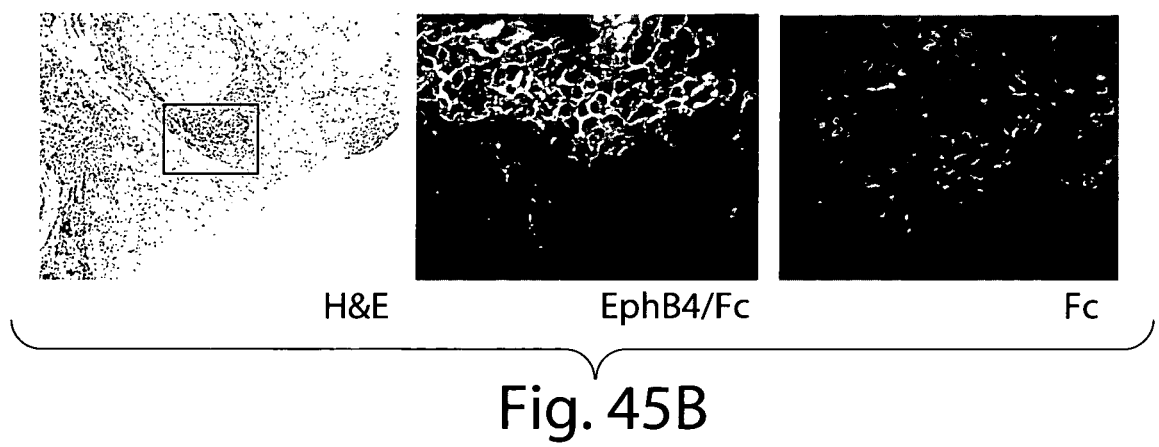
FIG. 45 shows that Ephrin B2, but not EphB4 is expressed in KS biopsy tissue. (A) In situ hybridization with antisense probes for ephrin B2 and EphB4 with corresponding H&E stained section to show tumor architecture. Dark blue color in the ISH indicates positive reaction for ephrin B2. No signal for EphB4 was detected in the Kaposi's sarcoma biopsy. For contrast, ISH signal for EphB4 is strong in squamous cell carcinoma tumor cells. Ephrin B2 was also detected in KS using EphB4-AP fusion protein (bottom left). (B) Detection of ephrin B2 with EphB4/Fc fusion protein. Adjacent sections were stained with H&E (left) to show tumor architecture, black rectangle indicates the area shown in the EphB4/Fc treated section (middle) detected with FITC-labeled anti-human Fc antibody as described in the methods section. As a control an adjacent section was treated with human Fc fragment (right). Specific signal arising from EphB4/Fc binding to the section is seen only in areas of tumor cells. (C) Co-expression of ephrin B2 and the HHV8 latency protein LANA1. Double-label confocal immunofluorescence microscopy with antibodies to ephrin B2 (red) LANA1
Figure 45C:
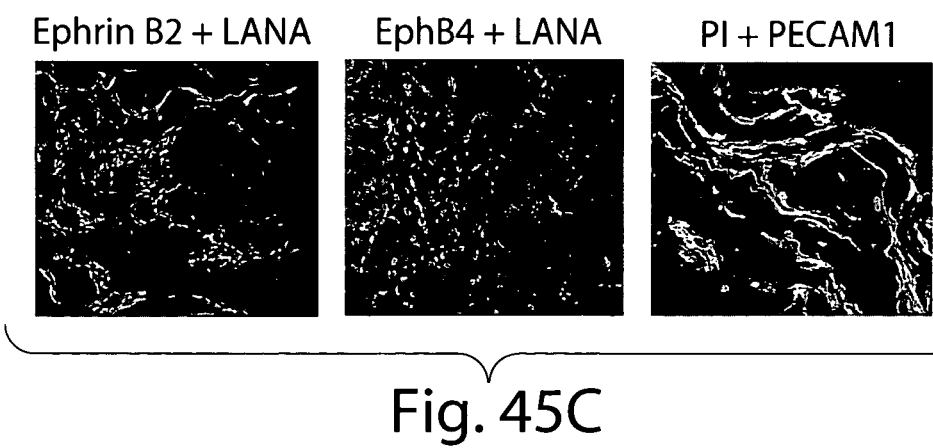

The highly vascular nature of KS lesions and the probable endothelial cell origin of the tumor cells prompted investigation of expression of EphB4 and ephrin B2 which are markers for venous and arterial endothelial cells, respectively. Ephrin B2, but not EphB4 transcripts were detected in tumor cells of KS biopsies by in situ hybridization (FIG. 45A). Comparison of the positive signal with ephrin B2 antisense probe and tumor cells as shown by H&E staining shows that ephrin B2 expression is limited to the areas of the biopsy that contain tumor cells. The lack of signal in KS with EphB4 antisense probe is not due to a defect in the probe, as it detected transcripts in squamous cell carcinoma, which we have shown expresses this protein (18). Additional evidence for the expression of ephrin B2 in KS tumor tissue is afforded by the localization of EphB4/Fc signal to tumor cells, detected by FITC conjugated anti human Fc antibody. Because ephrin B2 is the only ligand for EphB4 this reagent is specific for the expression of ephrin B2 (FIG. 45B, left). An adjacent section treated only with the secondary reagent shows no specific signal. Two-color confocal microscopy demonstrated the presence of the HHV-8 latency protein, LANA1 in the ephrin B2 positive cells (FIG. 45C, left), indicating that it is the tumor cells, not tumor vessels, which are expressing this arterial marker. Staining of tumor biopsy with PECAM-1 antibody revealed the highly vascular nature of this tumor (FIG. 45C, right). A pilot study of the prevalence of this pattern of ephrin B2 and EphB4 expression on KS biopsies was conducted by RT-PCR analysis. All six samples were positive for ephrin B2, while only 2 were weakly positive for EphB4 (data not shown).

Figure 46B:
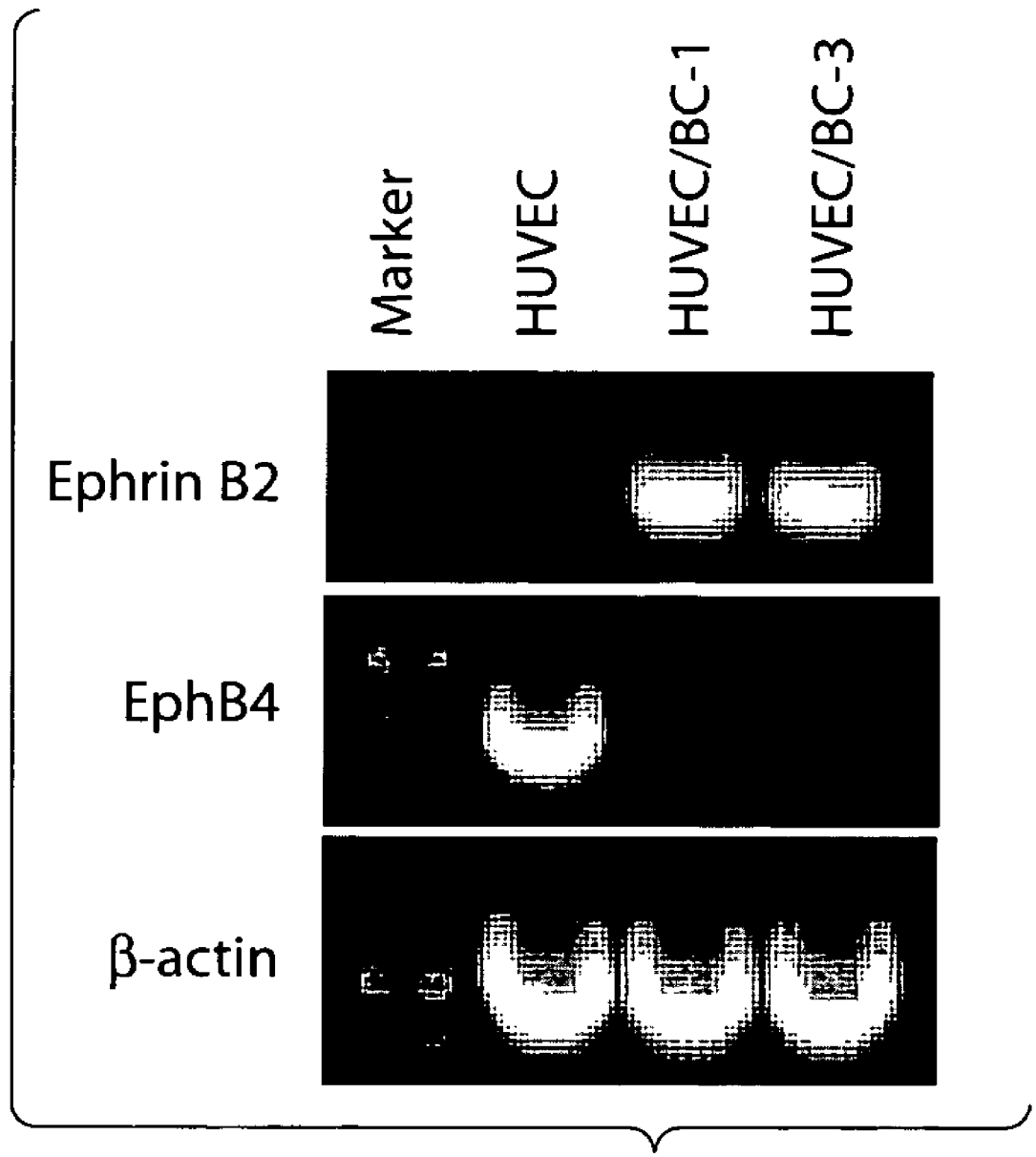

B. Infection of Venous Endothelial Cells with HHV-8 Causes a Phenotype Switch to Arterial Markers We next asked whether HHV-8, the presumed etiologic agent for KS, could itself induce expression of ephrin B2 and repress EphB4 expression in endothelial cells. Co-culture of HUVEC and BC-1 lymphoma cells, which are productively infected with HHV-8, results in effective infection of the endothelial cells (16). The attached monolayers of endothelial cells remaining after extensive washing were examined for ephrin B2 and EphB4 by RT-PCR and immunofluorescence. HUVEC express EphB4 venous marker strongly at the RNA level, but not ephrin B2 (FIG. 46B). In contrast, HHV-8 infected cultures (HUVEC/BC-1 and HUVEC/BC-3) express ephrin B2, while EphB4 transcripts are almost absent.

Immunofluorescence analysis of cultures of HUVEC and HUVEC/HHV-8 for artery/vein markers and viral proteins was undertaken to determine whether changes in protein expression mirrored that seen in the RNA. In addition, cellular localization of the proteins could be determined. Consistent with the RT-PCR data HUVEC are ephrin B2 negative and EphB4 positive (FIG. 46A(a & m)). As expected they do not express any HHV-8 latency associated nuclear antigen (LANA1) (FIG. 46A(b, n)). Co-culture of BC-1 cells, which are productively infected with HHV-8, resulted in infection of HUVEC as shown by presence of viral proteins LANA1 and ORF59 (FIG. 46A(f, r)). HHV-8 infected HUVEC now express ephrin B2 but not EphB4 (FIG. 46A(e, q, u), respectively). Expression of ephrin B2 and LANA1 co-cluster as shown by yellow signal in the merged image (FIG. 46A(h)). HHV-8 infected HUVEC positive for ephrin B2 and negative for Eph B4 also express the arterial marker CD 148 (19) (FIG. 46A (j, v)). Expression of ephrin B2 and CD 148 co-cluster as shown by yellow signal in the merged image (FIG. 46A(l)). Uninfected HUVEC expressing Eph B4 were negative for CD148 (not shown).

C. HHV-8 vGPCR Induces Ephrin B2 Expression

Figure 47A:
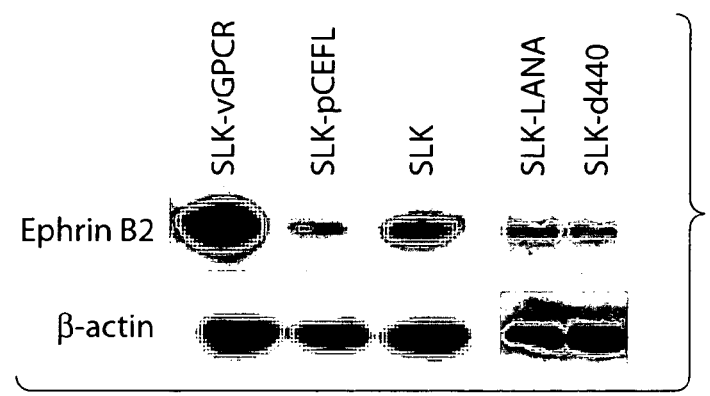
Figure 47B:
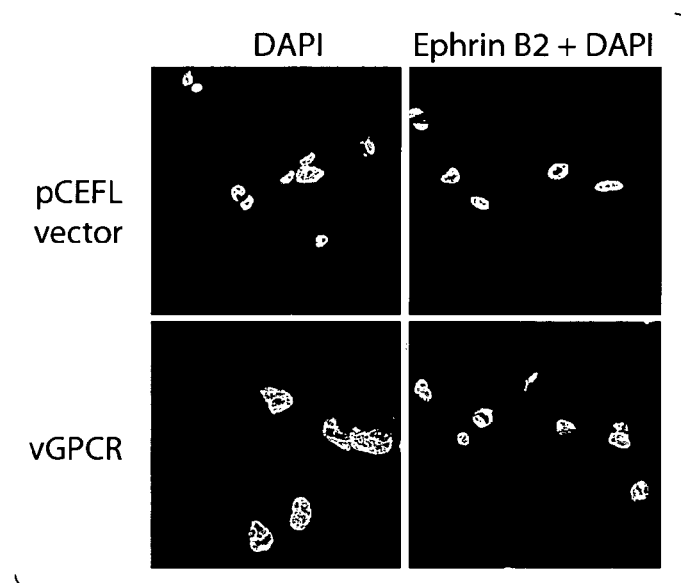
Figure 47C:
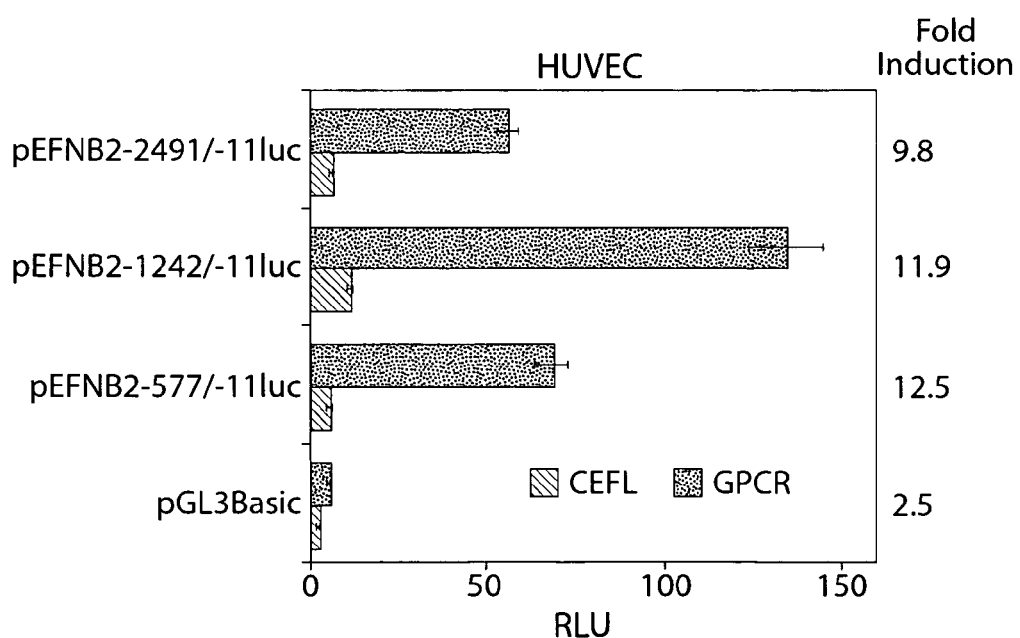

To test whether individual viral proteins could induce the expression of ephrin B2 seen with the whole virus KS-SLK cells were stably transfected with HHV-8 LANA, or LANAΔ440 or vGPCR. Western Blot of stable clones revealed a five-fold induction of ephrin B2 in KS-SLK transfected with vGPCR compared to SLK-LANA or SLK-LANAΔ440 (FIG. 47A). SLK transfected with vector alone (pCEFL) was used as a control. SLK-vGPCR and SLK-pCEFL cells were also examined for ephrin B2 and Eph B4 expression by immunofluorescence in transiently transfected KS-SLK cells. FIG. 47B shows higher expression of ephrin B2 in the SLK-vGPCR cells compared to SLK-pCEFL. No changes in Eph B4 were observed in SLK-vGPCR compared to SLK-pCEFL. This clearly demonstrates that SLK-vGPCR cells expressed high levels of ephrin B2 compared to SLK-pCEFL cells. This suggests that vGPCR of HHV-8 is directly involved in the induction of Ephrin B2 and the arterial phenotype switch in KS. Since we had shown that HHV-8 induced expression of ephrin B2 in HUVEC, we next asked if this could be mediated by a transcriptional effect. Ephrin B2 5'-flanking DNA-luciferase reporter plasmids were constructed as described in the Materials and Methods and transiently transfected into HUVECs. Ephrin B2 5'-flanking DNA sequences −2491/−11 have minimal activity in HUVEC cells (FIG. 47C). This is consistent with ephrin B2 being an arterial, not venous marker. However, we have noted that HUVEC in culture do express some ephrin B2 at the RNA level. Cotransfection of HHV-8 vGPCR induces ephrin B2 transcription approximately 10-fold compared to the control expression vector pCEFL. Roughly equal induction was seen with ephrin B2 sequences −2491/−11, −1242/−11, or −577/−11, which indicates that elements between −577 and −11 are sufficient to mediate the response to vGPCR, although maximal activity is seen with the −1242/−11 luciferase construct.

D. Expression of Ephrin B2 is Regulated by VEGF and VEGF-C

Figure 48A:
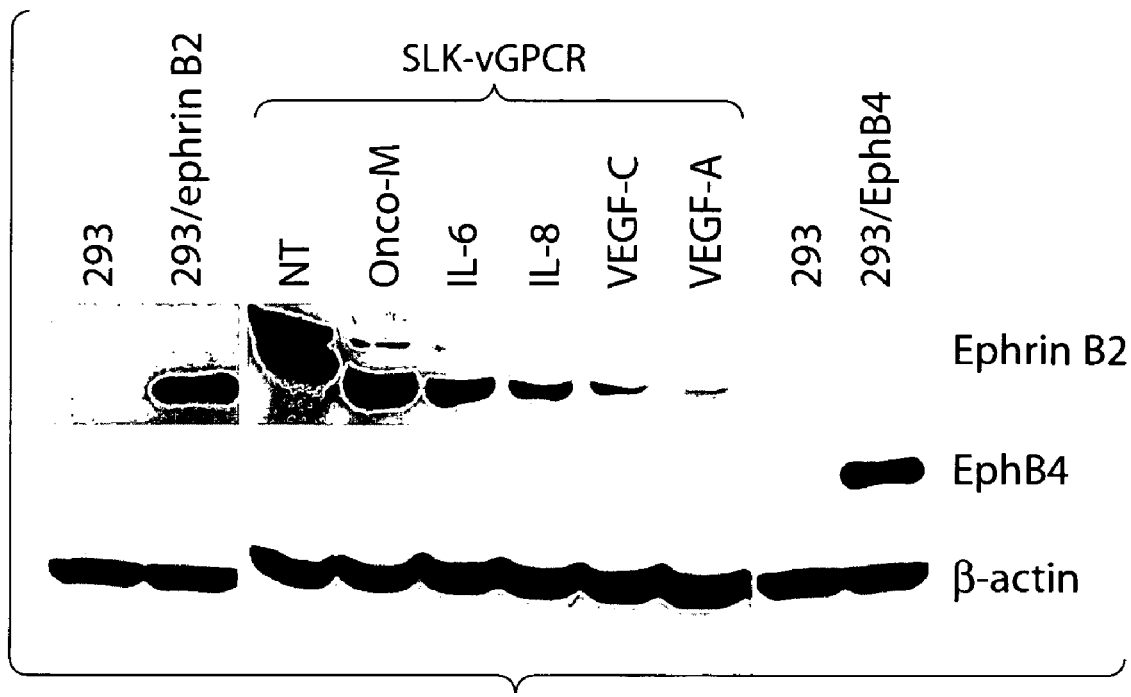
Figure 48B:

We next asked whether known KS growth factors could be involved in the vGPCR-mediated induction of ephrin B2 expression. SLK-vGPCR cells were treated with neutralizing antibodies to oncostatin-M, IL-6, IL-8, VEGF or VEGF-C for 36 hr. FIG. 48A shows that neutralization of VEGF completely blocked expression of ephrin B2 in SLK-vGPCR cells. A lesser, but significant decrease in ephrin B2 was seen neutralization of VEGF-C and IL-8. No appreciable effect was seen with neutralization of oncostatin-M or IL-6. To verify that VEGF and VEGF-C are integral to the induction of ephrin B2 expression we treated HUVEC with VEGF, VEGF-C or EGF. HUVECs were grown in EBM-2 media containing 5% FBS with two different concentration of individual growth factor (10 ng, 100 ng/ml) for 48 h. Only VEGF-A or VEGF-C induced ephrin B2 expression in a dose dependent manner (FIG. 48B). In contrast, EGF had no effect on expression of ephrin B2.

E. Ephrin B2 siRNA Inhibits the Expression of Ephrin B2 in KS

Figure 49A:
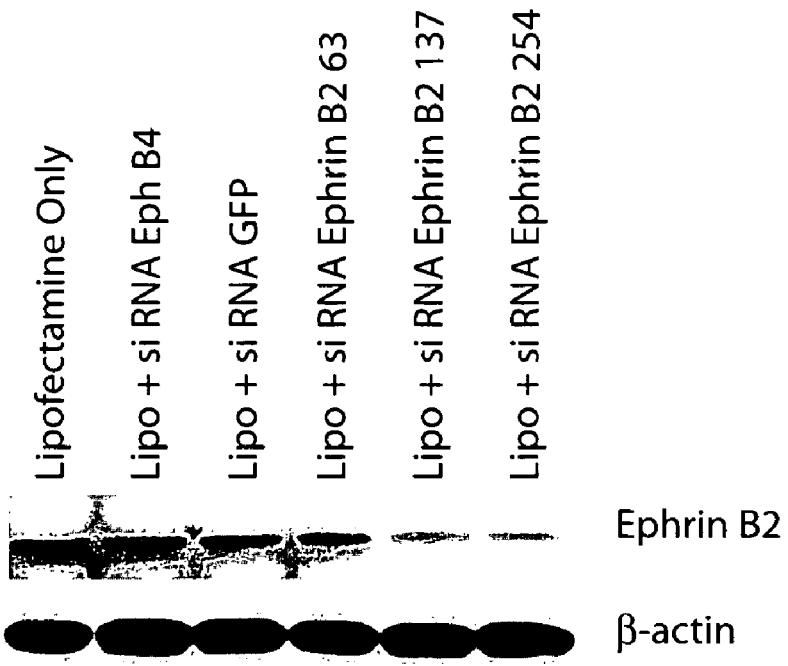

Three ephrin B2 siRNA were synthesized as described in the methods section. KS-SLK cells were transfected with siRNA and 48 h later ephrin B2 expression was determined by Western Blot. Ephrin B2 siRNAs 137 or 254 inhibited about 70% of ephrin B2 expression compared to control siRNA such as siRNA Eph B4 50 or siRNA GFP. Ephrin B2 63 siRNA was less effective than the above two siRNA Ephrin B2 (FIG. 49A).

Figure 49B:
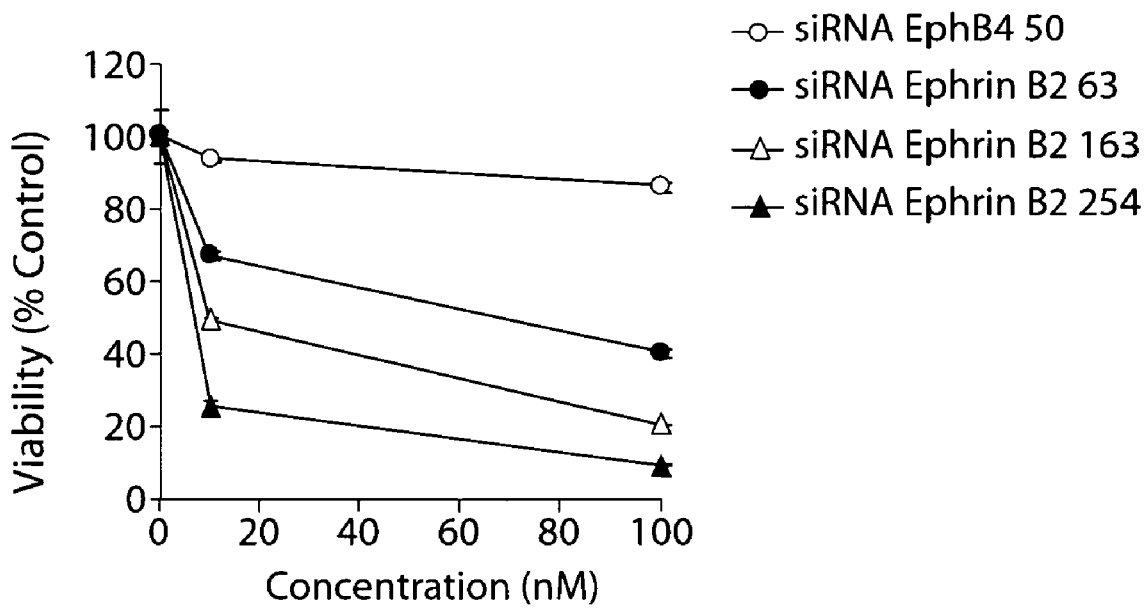
Figure 49C:
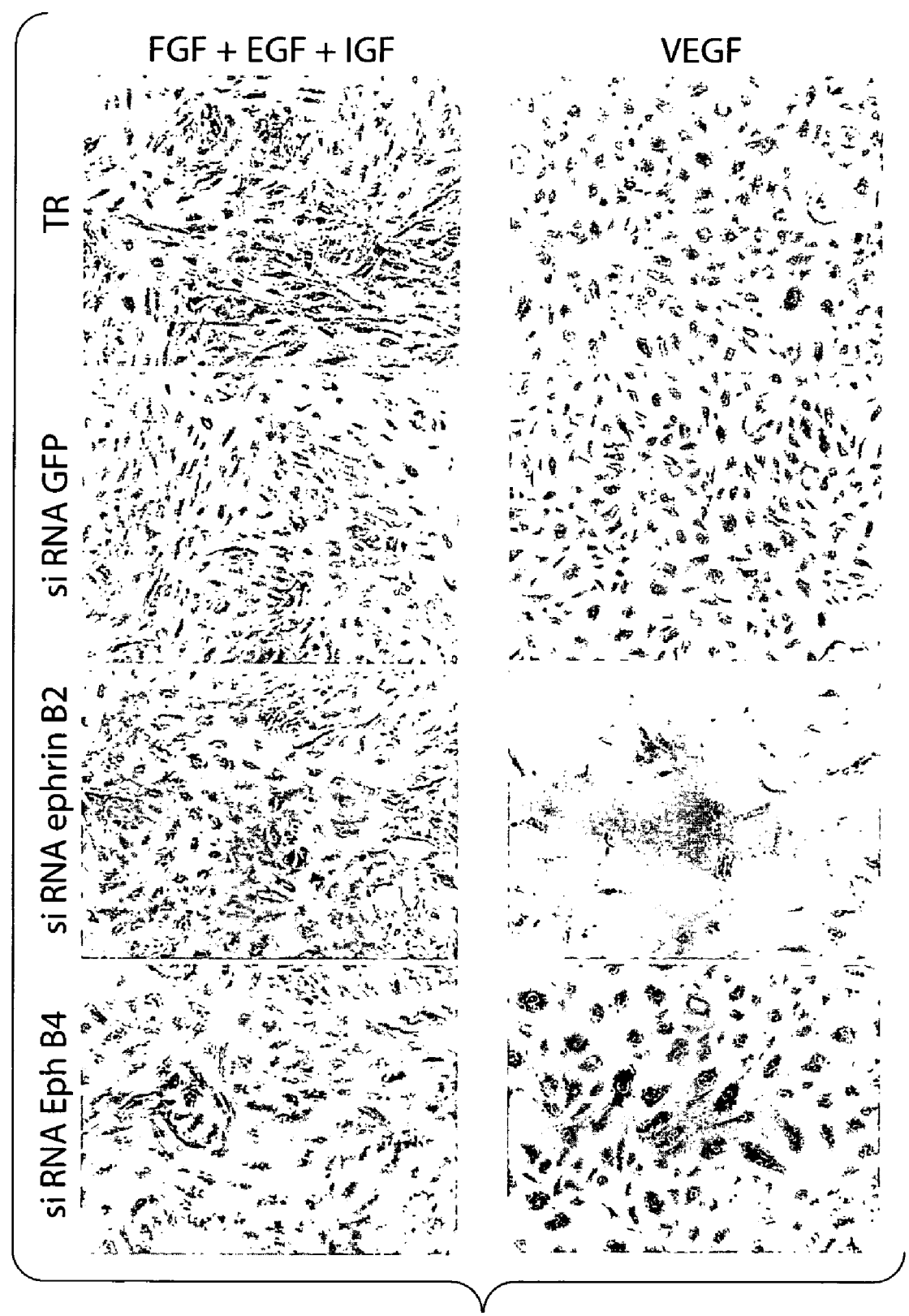

F. Ephrin B2 is Necessary for full KS and EC Viability, Cord Formation and In Vivo Angiogenesis Activities The most effective ephrin B2 siRNA (254) was then used to determine whether inhibiting expression of ephrin B2 has any effect on the growth of KS-SLK or HUVEC cells. The viability of KS-SLK cells was decreased by the same siRNAs that inhibited ephrin B2 protein levels (FIG. 49B). KS-SLK express high levels of ephrin B2 and this result shows maintenance of ephrin B2 expression is integral to cell viability in this setting. HUVECs do not express ephrin B2, except when stimulated by VEGF as shown in FIG. 48B. Ephrin B2 siRNA 264 dramatically reduced growth of HUVECs cultured with VEGF as the sole growth factor. In contrast, no significant effect was seen when HUVECs were cultured with IGF, EGF and bFGF. As a control, EphB4 siRNA 50 had no detrimental effect on HUVECs in either culture condition (FIG. 49C). In addition to inhibition of viability of KS and primary endothelial cells, EphB4-ECD inhibits cord formation in HUVEC and KS-SLK and in vivo angiogenesis in the Matrigel™ plug assay (FIG. 50).

G. Methods and Materials

1) Cell Lines and Reagents

Human vascular endothelial cells (HUVEC) were from Clonetics (San Diego, Calif.) and were maintained in EGM-2 and EGM-2MV media respectively (Clonetics). TI human fibroblast line was from Dr. Peter Jones, USC. BC-1 and BC-3 human pleural effusion lymphoma cell lines and monoclonal antibodies to LANA1 and ORF59 were the kind gift of Dr. Dharam Ablashi (Advanced Biotechnologies Inc., Columbia, Md.). KS-SLK was isolated from a Classic Kaposi's sarcoma patient (15). Polyclonal antibodies to EphB4, ephrin B2, CD 148, PECAM-I were obtained from Santa Cruz Biotechnology (Santa Cruz, Calif.). Mouse EphB4/F$_c$ and monoclonal antibodies to human vascular endothelial growth factor (VEGF), VEGF-C, interleukin-(IL)6, IL-8 and oncostatin-M were purchased from R & D Systems (Minneapolis, Minn.). Expression vectors pKSvGPCR-CEFL and pCEFL were the kind gift of Dr. Enrique Mesri (Cornell University, New York, N.Y.). Expression vectors for HHV-8 latency associated nuclear antigen (LANA) were kindly provided by Dr Matthew Rettig, Veteran's Administration Greater Los Angeles Healthcare System.

2) Collection and Preparation of Human Tissue

Human cutaneous Kaposi's sarcoma biopsy material was obtained under local anesthesia with informed consent from patients at the LAC/USC Medical Center, using an IRB approved consent form. Biopsies were processed for either total RNA, paraffin blocks or frozen tissue blocks in OCT. Total RNA was extracted by homogenization in guanidine isothiocyanate, (RNAzol: Tel-Test, Inc., Friendswoods, Tex.). cDNAs were synthesized by reverse transcriptase using a random hexamer primer (Superscript II; Invitrogen, Carlsbad, Calif.).

3) Preparation of Digoxigenin-Labeled RNA Probes

Ephrin B2 and EphB4 PCR products from the primers shown in Table 4 for in situ hybridization were cloned using the pGEM-T Easy system (Promega, Madison Wis.) according to the manufacturer's description using. The authenticity and insert orientation were confirmed by DNA sequencing. The pGEM-T Easy plasmids containing the PCR product of the human ephrin-B2 or EphB4 gene were linearized with Spe I or Nco I. Antisense or sense digoxigenin (DIG)-labeled RNA probes were transcribed from T7 or SP6 promoters by run-off transcription using a DIG RNA labeling kit (Roche, Indianapolis Ind.). RNA probes were quantitated by spot assay as described in the DIG RNA labeling kit instructions.

TABLE 4

Primers for Ephrin B2 and EphB4.

| Gene | Primer sequence | Product Size (bp) | SEQ. ID NO: |
|---|---|---|---|
| ISH Probe Primers | | | |
| ephrin B2 | 5'-TCC GTG TGG AGT ACT GCT G-3' | 296 | 53 |
|  | 5'-TCT GGT TTG GCA CAG TTG AG-3' |  | 54 |
| EphB4 | 5'-CTT TGG AAG AGA CCC TGC TG-3' | 297 | 55 |
|  | 5'-AGA CGG TGA AGG TCT CCT TG-3' |  | 56 |
| RT-PCR Primers | | | |
| ephrin B2 | 5'-AGA CAA GAG CCA TGA AGA TC-3' | 200 | 57 |
|  | 5'-GGA TCC CAC TTC GGA CCC GAG-3' |  | 58 |
| EphB4 | 5'-TCA GGT CAC TGC ATT GAA CGG G-3' | 400 | 59 |
|  | 5'-AAC TCG CTC TCA TCC AGT T-3' |  | 60 |
| β-actin | 5'-GTG GGG CGC CCC AGG CAC CA-3' | 546 | 61 |
|  | 5'-CTC CTT AAT GTC ACG CAC GAT TTC-3' |  | 62 |

4) In Situ Hybridization

See above, e.g., Example 3.

5) Co-Culture of HUVEC and BC-1

HUVEC cells were grown to 50-70% confluence in EGM-2 on gelatin-coated Labtech II 4-well chamber slides (Nalge Nunc International, Naperville, Ill.). Co-culture with BC-1 or BC-3 was essentially as described by Sakurada and coworkers (16). Briefly, BC-1 or BC-3 cells were pretreated with TPA (20 ng/ml) to induce virus for 48 hrs and then added to the HUVEC culture at a ratio of 10:1 for cocultivation for two days. The HUVECs were washed extensively with PBS to remove the attached BC-1 or BC-3 cells.

6) Preparation of cDNA and RT-PCR

The TITANIUM™ One-Step RT-PCR kit (Clontech, Palo Alto, Calif.) was used for RT-PCR from $1 \times 10^5$ cells. Primer pairs for amplification of EphB4, ephrin B2 and β-actin are shown in Table 4. Each PCR cycle consisted of denaturation at 94° C. for 30 s, primer annealing at 60° C. for 30 s and extension at 72° C. for 30 s. The samples were amplified for 30 cycles. PCR products were separated on 1.5% agarose gels and stained with ethidium bromide.

7) Cell Viability Assay

KS-SLK cells were seeded at a density of $1 \times 10^4$ per well in 48-well plates on day 0 in appropriate growth media containing 2% fetal calf serum (FCS). On the following day, the media was changed and cells were treated with 0, 10 or 100 nM siRNA. On day 3, viability was assessed using 3-(4,5-dimethylthiazol-2-yl)-2,5-diphenyltetrazolium bromide (MTT) as previously described (17).

8) Immunofluorescence Studies

Cells cultured on Labtech II 4-well chamber slides or frozen sections of KS biopsy material were fixed in 4% paraformaldehyde in Dulbecco's phosphate buffered saline pH 7.4 (PBS) for 30 min. The slides were rinsed twice in PBS and preincubated with blocking buffer (0.2% Triton-X100, 1% BSA in PBS) for 20 min, followed by incubation with antibodies to EphB4, ephrin B2, CD148, LANA1 or ORF59 (1:100 dilution in PBS) in blocking buffer at 4° C. for 16 hr. After washing three times, the slides were incubated with the appropriate fluorescein or rhodamine-conjugated secondary antibodies (Sigma-Aldrich, St. Louis, Mo.). Nuclei were counterstained with 4',6-diamidino-2-phenylindole dihydrochloride hydrate (DAPI), washed extensively with PBS and mounted with Vectasheild antifade mounting solution (Vector Laboratories, Burlingame, Calif.). Images were obtained using a Olympus AX70 fluorescence microscope and Spot v2.2.2 (Diagnostic Instruments Inc., Sterling Heights, Mich.) digital imaging system.

Immunofluorescence detection of EphrinB2 with EPHB4-Fc was done as follows. Frozen sections fixed in 4% paraformaldehyde and blocked with 20% FBS were incubated with 5 µg/ml EphB4/Fc (R&D Systems) for 1 h at RT. Sections were then incubated with 10 µg/ml rabbit anti-human IgG-FITC in PBS (Jackson ImmunoResearch Laboratories West Grove, Pa.) at RT for 1 hour. Nuclei were counterstained with DAPI and sections mounted as above. Human Fc (Jackson ImmunoResearch) was used as the negative control.

9) Western Blot

Crude cell lysates were prepared, quantitated, fractionated and transferred to membranes as described previously (17). Membranes were blocked with 5% non-fat milk prior to incubation with antibody to ephrin B2 (1:5000 dilution) at 4° C., for 16 h. Secondary antibody (1:100,000 dilution) conjugated with horseradish peroxidase was applied for 1 h at 25° C. The membranes were developed using the SuperSignal West Femto Maximum sensitivity chemiluminescent substrate (Pierce, Rockford, Ill.) according to the manufacturer's instructions. Membranes were stripped using Restore™ Western Blot Stripping Buffer (Pierce) and reprobed with EphB4 or actin.

10) Cord Formation Assay

Matrigel™ Basement Membrane Matrix (BD Biosciences Discovery Labware, Bedford, Mass.) was mixed with growth medium (3:1) on ice and 0.5 ml liquid placed in 24-well plates. Incubation of plates at 37° C. for 15 min caused Matrigel™ polymerization. HUVEC or KS-SLK in exponential phase growth were treated with 2 or 8 µg/ml EphB4-ECD or PBS as control for 16 h prior to trypsinizing and plating on the Matrigel™. Culture on Matrigel™ was continued in the presence of recombinant fusion proteins for 6 h. Cultures were fixed in 4% paraformaldehyde for 30 min and evaluated by inverted phase-contrast photomicroscopy.

11) Synthesis of Ephrin B2 and EphB4 siRNA by In Vitro Transcription

The Silencer™ siRNA construction kit (Ambion, Austin Tex.) was used to synthesize siRNA to ephrin B2 and EphB4.

Briefly, three 21 bp target sequences comprising 19 bp downstream of a 5'-AA dinucleotide were identified in the ephrin B2 cDNA (Accession number NM_004093) that showed no significant homology to other sequences in the GenBank database. Sense and antisense siRNA 29-mer DNA oligonucleotide templates were synthesized at the USC Norris Microchemical Core Facility. Antisense template corresponded to the target sequence followed by 8 bp addition (5'-CCTGTCTC-3') at the 3' end complementary to the T7 promoter primer provided with the Silencer SiRNA Construction Kit. Sense template comprised 5'-AA followed by the complement of the target 19 bp, then the T7 8 bp sequence as above. In separate reactions, the two siRNA oligonucleotide templates were hybridized to a T7 promoter primer. The 3' ends of the hybridized oligonucleotides were extended by the Klenow fragment of DNA polymerase to create double-stranded siRNA transcription templates. The sense and antisense siRNA templates were transcribed by T7 RNA polymerase and the resulting RNA transcripts were hybridized to create dsRNA. The dsRNA consisted of 5' terminal single-stranded leader sequences, a 19 nt target specific dsRNA, and 3' terminal UUs. The leader sequences were removed by digesting the dsRNA with a single-stranded specific ribonuclease. The DNA template was removed at the same time by treatment with RNAse free deoxyribonuclease.

The resulting siRNAs were purified by glass fiber filter binding to remove excess nucleotides, short oligomers, proteins, and salts in the reaction. End product double-stranded 21mer siRNAs are shown in Table 5. Similarly, an EphB4 and green fluorescence protein (GFP) siRNAs were synthesized.

TABLE 5 siRNAs of ephrin B2 and EphB4.

| | | |
|---|---|---|
| ephrin B2 264 | 5'-GCAGACAGAUGCACUAUUAUU-3'<br>3'-UUCGUCUGUCUACGUGAUAAU-5' | SEQ ID NO: 63<br>SEQ ID NO: 64 |
| ephrin B2 63: | 5'-CUGCGAUUUCCAAAUCGAUUU-3'<br>3'-UUGACGCUAAAGGUUUAGCUA-5' | SEQ ID NO: 65<br>SEQ ID NO: 66 |
| ephrin B2 137: | 5'-GGACUGGUACUAUACCCACUU-3'<br>3'-UUCCUGACCAUGAUAUGGGUG-5' | SEQ ID NO: 67<br>SEQ ID NO: 68 |
| Eph B4 50: | 5'-GAGACCCUGCUGAACACAAUU-3'<br>3'-UUCUCUGGGACGACUUGUGUU-5' | SEQ ID NO: 69<br>SEQ ID NO: 70 |
| GFP | 5'-CGCUGACCCUGAAGUUCAUUU-3'<br>3'-UUGCGACUGGGACUUCAAGUA-5' | SEQ ID NO: 71<br>SEQ ID NO: 72 |

12) Transfection of Ephrin B2 or EphB4 siRNA

HUVEC were seeded on eight-well chamber slides coated with fibronectin and grown overnight in EGM-2 (Cambrex, Walkersville, Md.). 16 h later media was replaced either with EBM-2 supplemented with 5% fetal calf serum (FCS) and EGM-2 BulletKit supplements bFGF, hEGF and $R^3$-IGF-I at the concentrations provided by the manufacturer, or EBM-2 supplemented with 5% FCS and 10 ng/ml rhVEGF (R&D Systems). After 2 h incubation at 37° C., the cells were transfected using Lipofectamine 2000 (1 µg/ml; Invitrogen) and 10 nM specific siRNAs in Opti-MEM-1 serum-free medium (Invitrogen). Following transfection for 2 hr in Opti-MEM-1, media supplemented as above was replaced in the appropriate wells. After 48 hrs, the cells were stained with crystal violet and immediately photographed at 10× magnification.

13) Construction of Ephrin B2 Reporter Plasmids

Human ephrin B2 5'-flanking DNA from −2491 to −11 with respect to the translation start site was amplified from BACPAC clone RP11-29716 (BacPac Resources, Children's Hospital, Oakland, Calif.) using the Advantage GC Genomic PCR kit (Clontech Palo Alto, Calif.) to overcome the large tracts of CG-rich sequence in the target area. Primers were designed to contain MluI sites for cloning. Amplified product was digested with MluI, gel purified and ligated into the MluI site in the multiple cloning site of pGL3Basic (Promega, Madison, Wis.). Orientation of the resulting clones was confirmed by restriction digest analysis. The correct clone was designated pEFNB2$_{-2491/-11}$luc. Digestion of this clone with either KpnI or SacI followed by recircularization yielded pEFNB2$_{-1242/-11}$luc and pEFNB2$_{-577/-11}$luc, respectively. Plasmid DNAs used for transient transfections were purified using a Mega Prep kit (QIAGEN, Valencia, Calif.).

14) Transient Transfection

HUVEC cells (0.8×10$^4$ cells/well in 24 well plates) maintained in EGM-2 media were transiently co-transfected with 0.5 µg/well ephrin B2 promoter-luciferase constructs together with 50 ng/well either pCEFL or pKSvGPCR-CEFL, using Superfect reagent (QIAGEN) according to the manufacturer's instructions. Cells were harvested 48 h post-transfection and lysed with Luciferase cell lysis buffer (Promega). Luciferase activity was assayed using the Luciferase Assay System (Promega) according to the manufacturer's instructions. Luciferase was normalized to protein, because pCEFL-vGPCR induced the expression of β-galactosidase from pCMV-Sport-βgal (Invitrogen).

15) Construction and Purification of EphB4 Extra Cellular Domain (ECD) Protein

See above, e.g., Example 1.

EXAMPLE 7

Expression of EphB4 in Bladder Cancer: a Candidate Target for Therapy

FIG. 51 shows expression of EPHB4 in bladder cancer cell lines (A), and regulation of EPHB4 expression by EGFR signaling pathway (B)

FIG. 52 shows that transfection of p53 inhibit the expression of EPHB4 in 5637 cell.

FIG. 53 shows growth inhibition of bladder cancer cell line (5637) upon treatment with EPHB4 siRNA 472.

FIG. 54 shows results on apoptosis study of 5637 cells transfected with EPHB4 siRNA 472.

FIG. 55 shows effects of EPHB4 antisense probes on cell migration. 5637 cells were treated with EPHB4AS10 (10 µM).

FIG. 56 shows effects of EPHB4 siRNA on cell invasion. 5637 cells were transfected with siRNA 472 or control siRNA.

EXAMPLE 8

Inhibition of EphB4 Gene Expression by EphB4 Antisense Probes and RNAi Probes

Cell lines expressing EphB4 were treated with the synthetic phosphorothioate modified oligonucleotides and harvested after 24 hr. Cell lysates were prepared and probed by western blot analysis for relative amounts of EphB4 compared to untreated control cells.

Studies on inhibition of cell proliferation were done in HNSCC cell lines characterized to express EphB4. Loss of cell viability was shown upon knock-down of EphB4 expression. Cells were treated in vitro and cultured in 48-well plates, seeded with 10 thousand cells per well. Test compounds were added and the cell viability was tested on day 3. The results on EphB4 antisense probes were summarized below in Table 6. The results on EphB4 RNAi probes were summarized below in Table 7.

TABLE 6

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 169 | TCA GTA CTG CGG GGC CGG TCC | (2944-2963) | ++ | 36 | 73 |
| Eph B4 168 | TCC TGT CCC ACC CGG GGT TC | (2924-2943) | ++ | 51 | 74 |
| Eph B4 167 | CCG GCT TGG CCT GGG ACT TC | (2904-2923) | +++ | 66 | 75 |
| Eph B4 166 | ATG TGC TGG ACA CTG GCC AA | (2884-2903) | ++++ | 70 | 76 |
| Eph B4 165 | GAT TTT CTT CTG GTG TCC CG | (2864-2883) | ++++ | 75 | 77 |
| Eph B4 164 | CCA GAG TGA CTC CGA TTC GG | (2844-2863) | ++ | 40 | 78 |
| Eph B4 163 | AGC AGG TCC TCA GCA GAG AT | (2824-2843) | ++++ | 66 | 79 |
| Eph B4 162 | CTG GCT GAC CAG CTC GAA GG | (2804-2823) |  | 25 | 80 |
| Eph B4 161 | AGC CAA AGC CAG CGG CTG CG | (2784-2803) | + | 33 | 81 |
| Eph B4 160 | AAA CTT TCT TCG TAT CTT CC | (2763-2783) | + | 25 | 82 |
| Eph B4 159 | CAT TTT GAT GGC CCG AAG CC | (2743-2762) | ++ | 40 | 83 |
| Eph B4 158 | ACT CGC CCA CAG AGC CAA AA | (2723-2742) |  | 30 | 84 |
| Eph B4 157 | GCT GAG TAG TGA GGC TGC CG | (2703-2722) | + | 25 | 85 |
| Eph B4 156 | CTG GTC CAG GAG AGG GTG TG | (2683-2702) | ++ | 30 | 86 |
| Eph B4 155 | AGG CCC CGC CAT TCT CCC GG | (2663-2682) |  | 25 | 87 |
| Eph B4 154 | GCC ACG ATT TTG AGG CTG GC | (2643-2662) | ++ | 40 | 88 |
| Eph B4 153 | GGG GTT CCG GAT CAT CTT GT | (2623-2642) | ++ | 35 | 89 |
| Eph B4 152 | CCA GGG CGC TGA CCA CCT GG | (2603-2622) | + | 30 | 90 |
| Eph B4 151 | GGG AAG CGG GGC CGG GCA TT | (2583-2602) | + | 25 | 91 |
| Eph B4 150 | CCG GTC TTT CTG CCA ACA GT | (2563-2582) | ++ | 25 | 92 |
| Eph B4 149 | CCA GCA TGA GCT GGT GGA GG | (2543-2562) | ++ | 20 | 93 |
| Eph B4 148 | GAG GTG GGA CAG TCT GGG GG | (2523-2542) | + | 30 | 94 |
| Eph B4 147 | CGG GGG CAG CCG GTA GTC CT | (2503-2522) | ++ | 40 | 95 |
| Eph B4 146 | GTT CAA TGG CAT TGA TCA CG | (2483-2502) | ++++ | 70 | 96 |
| Eph B4 145 | TCC TGA TTG CTC ATG TCC CA | (2463-2482) | ++++ | 80 | 97 |
| Eph B4 144 | GTA CGG CCT CTC CCC AAA TG | (2443-2462) | +++ | 60 | 98 |
| Eph B4 143 | ACA TCA CCT CCC ACA TCA CA | (2423-2442) | ++++ | 80 | 99 |
| Eph B4 142 | ATC CCG TAA CTC CAG GCA TC | (2403-2422) | ++ | 40 | 100 |
| Eph B4 141 | ACT GGC GGA AGT GAA CTT CC | (2383-2402) | +++ | 50 | 101 |
| Eph B4 140 | GGA AGG CAA TGG CCT CCG GG | (2363-2382) | ++ | 45 | 102 |
| Eph B4 139 | GCA GTC CAT CGG ATG GGA AT | (2343-2362) | ++++ | 70 | 103 |
| Eph B4 138 | CTT TCC TCC CAG GGA GCT CG | (2323-2342) | ++++ | 70 | 104 |
| Eph B4 137 | TGT AGG TGG GAT CGG AAG AG | (2303-2322) | ++ | 40 | 105 |
| Eph B4 136 | TTC TCC TCC AGG AAT CGG GA | (2283-2302) | ++ | 35 | 106 |
| Eph B4 135 | AAG GCC AAA GTC AGA CAC TT | (2263-2282) | ++++ | 60 | 107 |
| Eph B4 134 | GCA GAC GAG GTT GCT GTT GA | (2243-2262) | ++ | 50 | 108 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 133 | CTA GGA TGT TGC GAG CAG CC | (2223-2242) | ++ | 40 | 109 |
| Eph B4 132 | AGG TCT CGG TGG ACG TAG CT | (2203-2222) | ++ | 40 | 110 |
| Eph B4 131 | CAT CTC GGC AAG GTA CCG CA | (2183-2202) | +++ | 50 | 111 |
| Eph B4 130 | TGC CCG AGG CGA TGC CCC GC | (2163-2182) | ++ | 50 | 112 |
| Eph B4 129 | AGC ATG CCC ACG AGC TGG AT | (2143-2162) | ++ | 50 | 113 |
| Eph B4 128 | GAC TGT GAA CTG TCC GTC GT | (2123-2142) | ++ | 50 | 114 |
| Eph B4 127 | TTA GCC GCA GGA AGG AGT CC | (2103-2122) | +++ | 60 | 115 |
| Eph B4 126 | AGG GCG CCG TTC TCC ATG AA | (2083-2102) | ++ | 50 | 116 |
| Eph B4 125 | CTC TGT GAG AAT CAT GAC GG | (2063-2082) | ++++ | 80 | 117 |
| Eph B4 124 | GCA TGC TGT TGG TGA CCA CG | (2043-2062) | ++++ | 70 | 118 |
| Eph B4 123 | CCC TCC AGG CGG ATG ATA TT | (2023-2042) | ++ | 50 | 119 |
| Eph B4 122 | GGG GTG CTC GAA CTG GCC CA | (2003-2022) | ++++ | 80 | 120 |
| Eph B4 121 | TGA TGG AGG CCT CGC TCA GA | (1983-2002) | ++ | 50 | 121 |
| Eph B4 120 | AAC TCA CGC CGC TGC CGC TC | (1963-1982) | ++ | 40 | 122 |
| Eph B4 119 | CGT GTA GCC ACC CTT CAG GG | (1943-1962) | ++++ | 75 | 123 |
| Eph B4 118 | TCT TGA TTG CCA CAC AGC TC | (1923-1942) | ++++ | 80 | 124 |
| Eph B4 117 | TCC TTC TTC CCT GGG GCC TT | (1903-1922) | ++++ | 70 | 125 |
| Eph B4 116 | GAG CCG CCC CCG GCA CAC CT | (1883-1902) | ++ | 50 | 126 |
| Eph B4 115 | CGC CAA ACT CAC CTG CAC CA | (1863-1882) | ++++ | 60 | 127 |
| Eph B4 114 | ATC ACC TCT TCA ATC TTG AC | (1843-1862) | ++++ | 65 | 128 |
| Eph B4 113 | GTA GGA GAC ATC GAT CTC TT | (1823-1842) | ++++ | 90 | 129 |
| Eph B4 112 | TTG CAA ATT CCC TCA CAG CC | (1803-1822) | ++++ | 70 | 130 |
| Eph B4 111 | TCA TTA GGG TCT TCA TAA GT | (1783-1802) | ++++ | 70 | 131 |
| Eph B4 110 | GAA GGG GTC GAT GTA GAC CT | (1763-1782) | ++++ | 80 | 132 |
| Eph B4 109 | TAG TAC CAT GTC CGA TGA GA | (1743-1762) | ++ | 50 | 133 |
| Eph B4 108 | TAC TGT CCG TGT TTG TCC GA | (1723-1742) | ++ | 45 | 134 |
| Eph B4 107 | ATA TTC TGC TTC TCT CCC AT | (1703-1722) | ++++ | 70 | 135 |
| Eph B4 106 | TGC TCT GCT TCC TGA GGC AG | (1683-1702) | ++++ | 70 | 136 |
| Eph B4 105 | AGA ACT GCG ACC ACA ATG AC | (1663-1682) | ++ | 40 | 137 |
| Eph B4 104 | CAC CAG GAC CAG GAC CAC AC | (1643-1662) | ++++ | 70 | 138 |
| Eph B4 103 | CCA CGA CTG CCG TGC CCG CA | (1623-1642) | ++ | 40 | 139 |
| Eph B4 102 | ATC AGG GCC AGC TGC TCC CG | (1603-1622) | +++ | 50 | 140 |
| Eph B4 101 | CCA GCC CTC GCT CTC ATC CA | (1583-1602) | ++++ | 80 | 141 |
| Eph B4 100 | GTT GGG TCT GGC TGT GAT GT | (1563-1582) | ++++ | 80 | 142 |
| Eph B4 99 | TCC TGG CCG AAG GGC CCG TA | (1543-1562) | ++ | 35 | 143 |
| Eph B4 98 | GCC GGC CTC AGA GCG CGC CC | (1523-1542) | ++ | 50 | 144 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 97 | GTA CCT GCA CCA GGT AGC TG | (1503-1522) | ++++ | 80 | 145 |
| Eph B4 96 | GCT CCC CGC TTC AGC CCC CG | (1483-1502) | ++ | 50 | 146 |
| Eph B4 95 | CAG CTC TGC CCG GTT TTC TG | (1463-1482) | ++ | 50 | 147 |
| Eph B4 94 | ACG TCT TCA GGA ACC GCA CG | (1443-1462) | ++++ | 80 | 148 |
| Eph B4 93 | CTG CTG GGA CCC TCG GCG CC | (1423-1442) | ++ | 40 | 149 |
| Eph B4 92 | CTT CTC ATG GTA TTT GAC CT | (1403-1422) | ++++ | 80 | 150 |
| Eph B4 91 | CGT AGT CCA GCA CAG CCC CA | (1383-1402) | ++++ | 85 | 151 |
| Eph B4 90 | CTG GGT GCC CGG GGA ACA GC | (1363-1382) | +++ | 50 | 152 |
| Eph B4 89 | CCA GGC CAG GCT CAA GCT GC | (1343-1462) | ++++ | 70 | 153 |
| Eph B4 88 | TGG GTG AGG ACC GCG TCA CC | (1323-1342) | ++ | 40 | 154 |
| Eph B4 87 | CGG ATG TCA GAC ACT GCA GG | (1303-1322) | ++++ | 60 | 155 |
| Eph B4 86 | AGG TAC CTC TCG GTC AGT GG | (1283-1302) | ++ | 50 | 156 |
| Eph B4 85 | TGA CAT TGA CAG GCT CAA AT | (1263-1282) | ++++ | 80 | 157 |
| Eph B4 84 | GGG ACG GGC CCC GTG GCT AA | (1243-1262) | ++ | 50 | 158 |
| Eph B4 83 | GGA GGA TAC CCC GTT CAA TG | (1223-1242) | +++ | 60 | 159 |
| Eph B4 82 | CAG TGA CCT CPA AGG TAT AG | (1203-1222) | ++++ | 70 | 160 |
| Eph B4 81 | GTG AAG TCA GGA CGT AGC CC | (1183-1202) | +++ | 60 | 161 |
| Eph B4 80 | TCG AAC CAC CAC CCA GGG CT | (1163-1182) | +++ | 50 | 162 |
| Eph B4 79 | CCA CCA GGT CCC GGG GGC CG | (1143-1162) | ++ | 40 | 163 |
| Eph B4 78 | GGG TCA AAA GTC AGG TCT CC | (1123-1142) | ++++ | 70 | 164 |
| Eph B4 77 | CCC GCA GGG CGC ACA GGA GC | (1103-1122) | +++ | 60 | 165 |
| Eph B4 76 | CTC CGG TCC GGC ACT CCC GG | (1083-1102) | +++ | 60 | 166 |
| Eph B4 75 | CAG CGG AGG GCG TAG GTG AG | (1063-1082) | ++ | 40 | 167 |
| Eph B4 74 | GTC CTC TCG GCC ACC AGA CT | (1043-1062) | ++ | 50 | 168 |
| Eph B4 73 | CCA GGG GGG CAC TCC ATT CC | (1023-1042) | ++ | 50 | 169 |
| Eph B4 72 | AGG TGC AGG GAG GAG CCG TT | (1003-1022) | ++++ | 70 | 170 |
| Eph B4 71 | CAG GCG GGA AAC CAC GCT CC | (983-1002) | ++ | 40 | 171 |
| Eph B4 70 | GCG GAG CCG AAG GAG GGG TG | (963-982) | +++ | 50 | 172 |
| Eph B4 69 | GTG CAG GGT GCA CCC CGG GG | (943-962) | +++ | 50 | 173 |
| Eph B4 68 | GTC TGT GCG TGC CCG GAA GT | (923-942) | ++ | 40 | 174 |
| Eph B4 67 | ACC CGA CGC GGC ACT GGC AG | (903-922) | ++ | 40 | 175 |
| Eph B4 66 | ACG GCT GAT CCA ATG GTG TT | (883-902) | ++ | 50 | 176 |
| Eph B4 65 | AGA GTG GCT ATT GGC TGG GC | (863-882( | ++++ | 60 | 177 |
| Eph B4 64 | ATG GCT GGC AGG ACC CTT CT | (843-862) | ++++ | 80 | 178 |
| Eph B4 63 | CCT GAC AGG GGC TTG AAG GT | (823-842) | ++++ | 80 | 179 |
| Eph B4 62 | GCC CTG GGC ACA GGC TCG GC | (803-822) | +++ | 70 | 180 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 61 | ACT TGG TGT TCC CCT CAG CT | (783-802) | ++++ | 80 | 181 |
| Eph B4 60 | GCC TCG AAC CCC GGA GCA CA | (763-782) | +++ | 50 | 182 |
| Eph B4 59 | GCT GCA GCC CGT GAC CGG CT | (743-762) | +++ | 50 | 183 |
| Eph B4 58 | GTT CGG CCC ACT GGC CAT CC | (723-742) | ++ | 45 | 184 |
| Eph B4 57 | TCA CGG CAG TAG AGG CTG GG | (703-722) | +++ | 70 | 185 |
| Eph B4 56 | GCT GGG GCC AGG GGC GGG GA | (683-702) | ++ | 50 | 186 |
| Eph B4 55 | CGG CAT CCA CCA CGC AGC TA | (663-682) | ++ | 50 | 187 |
| Eph B4 54 | CCG GCC ACG GGC ACA ACC AG | (643-662) | ++ | 50 | 188 |
| Eph B4 53 | CTC CCG AGG CAC AGT CTC CG | (623-642) | +++ | 50 | 189 |
| Eph B4 52 | GGA ATC GAG TCA GGT TCA CA | (603-622) | ++++ | 90 | 190 |
| Eph B4 51 | GTC AGC TGG GCG CAC TTT TT | (583-602) | +++ | 70 | 191 |
| Eph B4 50 | GTA GAA GAG GTG CAG GGA TA | (563-582) | ++++ | 80 | 192 |
| Eph B4 49 | GCA GGG CCA TGC AGG CAC CC | (543-562) | ++++ | 80 | 193 |
| Eph B4 48 | TGG TCC TGG AAG GCC AGG TA | (523-542) | ++++ | 90 | 194 |
| Eph B4 47 | GAA GCC AGC CTT GCT GAG CG | (503-522) | ++++ | 80 | 195 |
| Eph B4 46 | GTC CCA GAC GCA GCG TCT TG | (483-502) | ++ | 40 | 196 |
| Eph B4 45 | ACA TTC ACC TTC CCG GTG GC | (463-482) | +++ | 50 | 197 |
| Eph B4 44 | CTC GGC CCC AGG GCG CTT CC | (443-462) | ++ | 50 | 198 |
| Eph B4 43 | GGG TGA GAT GCT CCG CGG CC | (423-442) | +++ | 60 | 199 |
| Eph B4 42 | ACC GTG TCC ACC TTG ATG TA | (403-422) | ++++ | 80 | 200 |
| Eph B4 41 | GGG GTT CTC CAT CCA GGC TG | (383-402) | ++++ | 80 | 201 |
| Eph B4 40 | GCG TGA GGG CCG TGG CCG TG | (363-382) | ++ | 50 | 202 |
| Eph B4 39 | TCC GCA TCG CTC TCA TAG TA | (343-362) | +++ | 60 | 203 |
| Eph B4 38 | GAA GAC GGT GAA GGT CTC CT | (323-342) | ++++ | 80 | 204 |
| Eph B4 37 | TGC AGG AGC GCC CAG CCC GA | (303-322) | +++ | 50 | 205 |
| Eph B4 36 | GGC AGG GAC AGG CAC TCG AG | (283-302) | +++ | 45 | 206 |
| Eph B4 35 | CAT GGT GAA GCG CAG CGT GG | (263-282) | ++ | 50 | 207 |
| Eph B4 34 | CGT ACA CGT GGA CGG CGC CC | (243-262) | ++ | 40 | 208 |
| Eph B4 33 | CGC CGT GGG ACC CAA CCT GT | (223-242) | +++ | 60 | 209 |
| Eph B4 32 | GCG AAG CCA GTG GGC CTG GC | (203-222) | ++++ | 70 | 210 |
| Eph B4 31 | CCG GGG CAC GCT GCA CGT CA | (183-202) | +++ | 60 | 211 |
| Eph B4 30 | CAC ACT TCG TAG GTG CGC AC | (163-182) | +++ | 70 | 212 |
| Eph B4 29 | GCT GTG CTG TTC CTC ATC CA | (143-162) | ++++ | 80 | 213 |
| Eph B4 28 | GGC CGC TCA GTT CCT CCC AC | (123-142) | ++ | 40 | 214 |
| Eph B4 27 | TGC CCG TCC ACC TGA GGG AA | (103-122) | ++ | 50 | 215 |
| Eph B4 26 | TGT CAC CCA CTT CAG ATC AG | (83-102) | ++++ | 70 | 216 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 25 | CAG TTT CCA ATT TTG TGT TC | (63-82) | ++++ | 70 | 217 |
| Eph B4 24 | AGC AGG GTC TCT TCC AAA GC | (43-62) | ++++ | 80 | 218 |
| Eph B4 23 | TGC GGC CAA CGA AGC CCA GC | (23-42) | ++ | 50 | 219 |
| Eph B4 22 | AGA GCA GCA CCC GGA GCT CC | (3-22) | +++ | 50 | 220 |
| Eph B4 21 | AGC AGC ACC CGG AGC TCC AT | (1-20) | +++ | 50 | 221 |
| Additional antisense probes described in the specification | | | | | |
| EphB4 AS-1 | GTG CAG GGA TAG CAG GGC CAT | (552-572) | | | 222 |
| EphB4 AS-2 | AAG GAG GGG TGG TGC ACG GTG | (952-972) | | | 223 |
| EphB4 AS-3 | TTC CAG GTG CAG GGA GGA GCC | (1007-1027) | | | 224 |
| EphB4 AS-4 | GTG GTG ACA TTG ACA GGC TCA | (1263-1285) | | | 225 |
| EphB4 AS-5 | TCT GGC TGT GAT GTT CCT GGC | (1555-1575) | | | 226 |
| EphB4 AS-6 | GCC GCT CAG TTC CTC CCA | (123-140) | | | 227 |
| EphB4 AS-7 | TGA AGG TCT CCT TGC AGG | (316-333) | | | 228 |
| EphB4 AS-8 | CGC GGC CAC CGT GTC CAC CTT | (408-428) | | | 229 |
| EphB4 AS-9 | CTT CAG GGT CTT GAT TGC CAC | (1929-1949) | | | 230 |
| EphB4 AS-10 | ATG GAG GCC TCG CTC AGA AA | (1980-1999) | | | 231 |
| Ephb4 AS-11 | CAT GCC CAC GAG CTG GAT GAC | (2138-2158) | | | 232 |

TABLE 7

Inhibition of EphB4 Gene Expression by EphB4 RNAi probes

| RNAi | EphB4 RNAi sequence | | Inhibition of EphB4 Expression | Percent reduction in viability | SEQ ID NO: |
|---|---|---|---|---|---|
| 1 | 446 aaattggaaactgctgatctg | 466 | | | 233 |
| 2 | 447 aattggaaactgctgatctga | 467 | +++ | 70 | 234 |
| 3 | 453 aaactgctgatctgaagtggg | 473 | ++++ | 70 | 235 |
| 4 | 454 aactgctgatctgaagtgggt | 474 | +++ | 80 | 236 |
| 5 | 854 aatgtcaagacgctgcgtctg | 874 | +++ | 65 | 237 |
| 6 | 467 aagtgggtgacattccctcag | 487 | + | 35 | 238 |
| 7 | 848 aaggtgaatgtcaagacgctg | 868 | ++ | 50 | 239 |
| 8 | 698 aaggagaccttcaccgtcttc | 718 | +++ | 75 | 240 |
| 9 | 959 aaaaagtgcgcccagctgact | 979 | + | 40 | 241 |
| 10 | 1247 aatagccactctaacaccatt | 1267 | ++ | 50 | 242 |
| 11 | 1259 aacaccattggatcagccgtc | 1279 | ++ | 50 | 243 |
| 12 | 1652 aatgtcaccactgaccgagag | 1672 | + | 35 | 244 |
| 13 | 1784 aaataccatgagaagggcgcc | 1804 | +++ | 65 | 245 |

TABLE 7-continued

Inhibition of EphB4 Gene Expression by EphB4 RNAi probes

| RNAi | EphB4 RNAi sequence | | Inhibition of EphB4 Expression | Percent reduction in viability | SEQ ID NO: |
|---|---|---|---|---|---|
| 14 | 1832 aagacgtcagaaaaccgggca | 1852 | + | 30 | 246 |
| 15 | 1938 aacatcacagccagacccaac | 19 | ++ | 50 | 247 |
| 16 | 2069 aagcagagcaatgggagagaa | 2089 | ++++ | 75 | 248 |
| 17 | 2078 aatgggagagaagcagaatat | 2098 | +++ | 65 | 249 |
| 18 | 2088 aagcagaatattcggacaaac | 2108 | +++ | 70 | 250 |
| 19 | 2094 aatattcggacaaacacggac | 2114 | ++ | 40 | 251 |
| 20 | 2105 aaacacggacagtatctcatc | 2125 | ++ | 50 | 252 |
| 21 | 2106 aacacggacagtatctcatcg | 2126 | + | 35 | 253 |
| 22 | 2197 aaaagagatcgatgtctccta | 2217 | +++ | 65 | 254 |
| 23 | 2174 aatgaggctgtgagggaattt | 2194 | ++ | 50 | 255 |
| 24 | 2166 aagaccctaatgaggctgtga | 2186 | ++ | 50 | 256 |
| 25 | 2198 aaagagatcgatgtctcctac | 2218 | +++ | 55 | 257 |
| 26 | 2199 aagagatcgatgtctcctacg | 2219 | +++ | 70 | 258 |
| 27 | 2229 aagaggtgattggtgcaggtg | 2249 | + | 33 | 259 |
| 28 | 2222 aagattgaagaggtgattggt | 2242 | + | 30 | 260 |
| 29 | 2429 aacagcatgcccgtcatgatt | 2449 | ++ | 40 | 261 |
| 30 | 2291 aagaaggagagctgtgtggca | 2311 | +++ | 50 | 262 |
| 31 | 2294 aaggagagctgtgtggcaatc | 2314 | +++ | 60 | 263 |
| 32 | 2311 aatcaagaccctgaagggtgg | 2331 | +++ | 70 | 264 |
| 33 | 2497 aaacgacggacagttcacagt | 2517 | + | 35 | 265 |
| 34 | 2498 aacgacggacagttcacagtc | 2518 | + | 40 | 266 |
| 35 | 2609 aacatcctagtcaacagcaac | 2629 | ++ | 50 | 267 |
| 36 | 2621 aacagcaacctcgtctgcaaa | 2641 | + | 35 | 268 |
| 37 | 2678 aactcttccgatcccacctac | 2698 | ++ | 50 | 269 |
| 38 | 2640 aagtgtctgactttggccttt | 2660 | +++ | 70 | 270 |
| 39 | 2627 aacctcgtctgcaaagtgtct | 2647 | ++ | 50 | 271 |
| 40 | 2639 aaagtgtctgactttggcctt | 2659 | + | 25 | 272 |
| 41 | 2852 aatcaggacgtgatcaatgcc | 2872 | +++ | 75 | 273 |
| 42 | 2716 aaagattcccatccgatggac | 2736 | ++ | 50 | 274 |
| 43 | 2717 aagattcccatccgatggact | 2737 | ++ | 60 | 275 |
| 44 | 2762 aagttcacttccgccagtgat | 2782 | +++ | 70 | 276 |
| 45 | 3142 aagatacgaagaaagtttcgc | 3162 | ++ | 50 | 277 |
| 46 | 3136 aatgggaagatacgaagaaag | 3156 | +++ | 66 | 278 |
| 47 | 2867 aatgccattgaacaggactac | 2887 | | | 279 |
| 48 | 3029 aaaatcgtggcccgggagaat | 3049 | + | 33 | 280 |
| 49 | 3254 aaaatcttggccagtgtccag | 3274 | ++ | 50 | 281 |

TABLE 7-continued

Inhibition of EphB4 Gene Expression by EphB4 RNAi probes

| RNAi | EphB4 RNAi sequence | | Inhibition of EphB4 Expression | Percent reduction in viability | SEQ ID NO: |
|---|---|---|---|---|---|
| 50 | 3255 aaatcttggccagtgtccagc | 3275 | +++ | 75 | 282 |
| 51 | 3150 aagaaagtttcgcagccgctg | 3170 | +++ | 80 | 283 |
| 52 | 3251 aagaaaatcttggccagtgtc | 3271 | ++ | 50 | 284 |
| 53 | 3256 aatcttggccagtgtccagca | 3276 | ++ | 50 | 285 |

Additional RNAi probes described in the specification

| | | | | | |
|---|---|---|---|---|---|
| Eph B4 50 | gagacccugcugaacacaauu | | | | 286 |
| Eph B4 472 | ggugaaugucaagacgcuguu | | | | 287 |
| Eph B4 1562 | caucacagccagacccaacuu | | | | 288 |
| siRNA 2303 | cucuuccgaucccaccuacuu | | | | 289 |
| Eph B4 2302 | cucuuccgaucccaccuacuu | | | | 290 |

EXAMPLE 9

Inhibition of Ephrin B2 Gene Expression by Ephrin B2 Antisense Probes and RNAi Probes KS SLK, a cell line expressing endogenous high level of ephrin B2. Cell viability was tested using fixed dose of each oligonuceotide (5 UM). Gene expression downregulation was done using cell line 293 engineered to stably express full-length ephrin B2. KS SLK expressing EphrinB2 were also used to test the viability in response to RNAi probes tested at the fixed dose of 50 nM. Protein expression levels were measured using 293 cells stably expressing full-length EphrinB2, in cell lysates after 24 hr treatment with fixed 50 nM of RNAi probes.

The results on Ephrin B2 antisense probes were summarized below in Table 8. The results on Ephrin B2 RNAi probes were summarized below in Table 9.

TABLE 8

Ephrin B2 antisense ODNs.

| | sequence | Coding region | Percent reduction in viability | Inhibition of Ephrin B2 Expression | SEQ ID NO: |
|---|---|---|---|---|---|
| Ephrin AS-51 | TCA GAC CTT GTA GTA AAT GT | (983-1002) | 35 | ++ | 291 |
| Ephrin AS-50 | TCG CCG GGC TCT GCG GGG GC | (963-982) | 50 | +++ | 292 |
| Ephrin AS-49 | ATC TCC TGG ACG ATG TAC AC | (943-962) | 45 | ++ | 293 |
| Ephrin AS-48 | CGG GTG CCC GTA GTC CCC GC | (923-942) | 35 | ++ | 294 |
| Ephrin AS-47 | TGA CCT TCT CGT AGT GAG GG | (903-922) | 40 | +++ | 295 |
| Ephrin AS-46 | CAG AAG ACG CTG TCC GCA GT | (883-902) | 40 | ++ | 296 |
| Ephrin AS-45 | CCT TAG CGG GAT GAT AAT GT | (863-882) | 35 | ++ | 297 |
| Ephrin AS-44 | CAC TGG GCT CTG AGC CGT TG | (843-862) | 60 | +++ | 298 |
| Ephrin AS-43 | TTG TTG CCG CTG CGC TTG GG | (823-842) | 40 | ++ | 299 |
| Ephrin AS-42 | TGT GGC CAG TGT GCT GAG CG | (803-822) | 40 | ++ | 300 |
| Ephrin AS-41 | ACA GCG TGG TCG TGT GCT GC | (783-802) | 70 | +++ | 301 |
| Ephrin AS-40 | GGC GAG TGC TTC CTG TGT CT | (763-782) | 80 | ++++ | 302 |
| Ephrin AS-39 | CCT CCG GTA CTT CAG CAA GA | (743-762) | 50 | +++ | 303 |
| Ephrin AS-38 | GGA CCA CCA GCG TGA TGA TG | (723-742) | 60 | +++ | 304 |
| Ephrin AS-37 | ATG ACG ATG AAG ATG ATG CA | (703-722) | 70 | +++ | 305 |

TABLE 8-continued

Ephrin B2 antisense ODNs.

| | sequence | Coding region | Percent reduction in viability | Inhibition of Ephrin B2 Expression | SEQ ID NO: |
|---|---|---|---|---|---|
| Ephrin AS-36 | TCC TGA AGC AAT CCC TGC AA | (683-702) | 60 | +++ | 306 |
| Ephrin AS-35 | ATA AGG CCA CTT CGG AAC CG | (663-682) | 45 | ++ | 307 |
| Ephrin AS-34 | AGG ATG TTG TTC CCC GAA TG | (643-662) | 50 | +++ | 308 |
| Ephrin AS-33 | TCC GGC GCT GTT GCC GTC TG | (623-642) | 75 | +++ | 309 |
| Ephrin AS-32 | TGC TAG AAC CTG GAT TTG GT | (603-622) | 60 | +++ | 310 |
| Ephrin AS-31 | TTT ACA AAG GGA CTT GTT GT | (583-602) | 66 | +++ | 311 |
| Ephrin AS-30 | CGA ACT TCT TCC ATT TGT AC | (563-582) | 50 | ++ | 312 |
| Ephrin AS-29 | CAG CTT CTA GTT CTG GAC GT | (543-562) | 50 | +++ | 313 |
| Ephrin AS-28 | CTT GTT GGA TCT TTA TTC CT | (523-542) | 70 | +++ | 314 |
| Ephrin AS-27 | GGT TGA TCC AGC AGA ACT TG | (503-522) | 65 | +++ | 315 |
| Ephrin AS-26 | CAT CTT GTC CAA CTT TCA TG | (483-502) | 75 | +++ | 316 |
| Ephrin AS-25 | AGG ATC TTC ATG GCT CTT GT | (463-482) | 60 | +++ | 317 |
| Ephrin AS-24 | CTG GCA CAC CCC TCC CTC CT | (443-462) | 45 | ++ | 318 |
| Ephrin AS-23 | GGT TAT CCA GGC CCT CCA AA | (423-442) | 50 | +++ | 319 |
| Ephrin AS-22 | GAC CCA TTT GAT GTA GAT AT | (403-422) | 50 | +++ | 320 |
| Ephrin AS-21 | AAT GTA ATA ATC TTT GTT CT | (383-402) | 60 | +++ | 321 |
| Ephrin AS-20 | TCT GAA ATT CTA GAC CCC AG | (363-382) | 60 | +++ | 322 |
| Ephrin AS-19 | AGG TTA GGG CTG AAT TCT TG | (343-362) | 75 | +++ | 323 |
| Ephrin AS-18 | AAA CTT GAT GGT GAA TTT GA | (323-342) | 60 | +++ | 324 |
| Ephrin AS-17 | TAT CTT GGT CTG GTT TGG CA | (303-322) | 50 | ++ | 325 |
| Ephrin AS-16 | CAG TTG AGG AGA GGG GTA TT | (283-302) | 40 | ++ | 326 |
| Ephrin AS-15 | TTC CTT CTT AAT AGT GCA TC | (263-282) | 66 | +++ | 327 |
| Ephrin AS-14 | TGT CTG CTT GGT CTT TAT CA | (243-262) | 70 | ++++ | 328 |
| Ephrin AS-13 | ACC ATA TAA ACT TTA TAA TA | (223-242) | 50 | +++ | 329 |
| Ephrin AS-12 | TTC ATA CTG GCC AAC AGT TT | (203-222) | 50 | +++ | 330 |
| Ephrin AS-11 | TAG AGT CCA CTT TGG GGC AA | (183-202) | 70 | ++++ | 331 |
| Ephrin AS-10 | ATA ATA TCC AAT TTG TCT CC | (163-182) | 70 | ++++ | 332 |
| Ephrin AS-9 | TAT CTG TGG GTA TAG TAC CA | (143-162) | 80 | ++++ | 333 |
| Ephrin AS-8 | GTC CTT GTC CAG GTA GAA AT | (123-142) | 60 | +++ | 334 |
| Ephrin AS-7 | TTG GAG TTC GAG GAA TTC CA | (103-122) | 80 | ++++ | 335 |
| Ephrin AS-6 | ATA GAT AGG CTC TAA AAC TA | (83-102) | 70 | +++ | 336 |
| Ephrin AS-5 | TCG ATT TGG AAA TCG CAG TT | (63-82) | 50 | +++ | 337 |
| Ephrin AS-4 | CTG CAT AAA ACC ATC AAA AC | (43-62) | 80 | ++++ | 338 |
| Ephrin AS-3 | ACC CCA GCA GTA CTT CCA CA | (23-42) | 85 | ++++ | 339 |
| Ephrin AS-2 | CGG AGT CCC TTC TCA CAG CC | (3-22) | 70 | +++ | 340 |
| Ephrin AS-1 | GAG TCC CTT CTC ACA GCC AT | (1-20) | 80 | ++++ | 341 |

TABLE 9

Ephrin B2 RNAi probes.

| RNAi Sequence and homology with other human genes. | | | Percent reduction in viability | Inhibition of Ephrin B2 Expression | RNAi no. | SEQ ID NO: |
|---|---|---|---|---|---|---|
| 89 | aactgcgatttccaaatcgat | 109 | 80 | ++++ | 1 | 342 |
| 141 | aactccaaatttctacctgga | 161 | 70 | ++++ | 2 | 343 |
| 148 | aatttctacctggacaaggac | 168 | 75 | +++ | 3 | 344 |
| 147 | aaatttctacctggacaagga | 167 | 60 | +++ | 4 | 345 |
| 163 | aaggactggtactatacccac | 183 | 40 | ++ | 5 | 346 |
| 217 | aagtggactctaaaactgttg | 237 | 80 | ++++ | 6 | 347 |
| 229 | aaactgttggccagtatgaat | 249 | 50 | +++ | 7 | 348 |
| 228 | aaaactgttggccagtatgaa | 248 | 80 | ++++ | 8 | 349 |
| 274 | aagaccaagcagacagatgca | 294 | 80 | ++++ | 11 | 350 |
| 273 | aaagaccaagcagacagatgc | 293 | 60 | +++ | 12 | 351 |
| 363 | aagtttcaagaattcagccct | 383 | 66 | +++ | 13 | 352 |
| 370 | aagaattcagccctaacctct | 390 | 50 | +++ | 14 | 353 |
| 373 | aattcagccctaacctctggg | 393 | 50 | +++ | 15 | 354 |
| 324 | aactgtgccaaaccagaccaa | 344 | 90 | ++++ | 16 | 355 |
| 440 | aaatgggtctttggagggcct | 460 | 80 | ++++ | 17 | 356 |
| 501 | aagatcctcatgaaagttgga | 521 | 50 | +++ | 18 | 357 |
| 513 | aaagttggacaagatgcaagt | 533 | 50 | +++ | 19 | 358 |
| 491 | aagagccatgaagatcctcat | 511 | 50 | +++ | 20 | 359 |
| 514 | aagttggacaagatgcaagtt | 534 | 66 | +++ | 21 | 360 |
| 523 | aagatgcaagttctgctggat | 543 | 66 | +++ | 22 | 361 |
| 530 | aagttctgctggatcaaccag | 550 | 50 | +++ | 23 | 362 |
| 545 | aaccaggaataaagatccaac | 565 | 35 | ++ | 24 | 363 |
| 555 | aaagatccaacaagacgtcca | 575 | 40 | ++ | 25 | 364 |
| 556 | aagatccaacaagacgtccag | 576 | 60 | +++ | 26 | 365 |
| 563 | aacaagacgtccagaactaga | 583 | 60 | +++ | 27 | 366 |
| 566 | aagacgtccagaactagaagc | 586 | 70 | +++ | 28 | 367 |
| 593 | aaatggaagaagttcgacaac | 613 | 75 | ++++ | 29 | 368 |
| 577 | aactagaagctggtacaaatg | 597 | 66 | +++ | 30 | 369 |
| 594 | aatggaagaagttcgacaaca | 614 | 35 | ++ | 31 | 370 |
| 583 | aagctggtacaaatggaagaa | 603 | 50 | +++ | 32 | 371 |
| 611 | aacaagtcccttgtaaaacc | 631 | 70 | ++++ | 33 | 372 |
| 599 | aagaagttcgacaacaagtcc | 619 | 70 | ++++ | 34 | 373 |
| 602 | aagttcgacaacaagtccctt | 622 | 80 | ++++ | 35 | 374 |
| 626 | aaaaccaaatccaggttctag | 646 | 50 | +++ | 36 | 375 |
| 627 | aaaccaaatccaggttctagc | 647 | 25 | + | 37 | 376 |
| 628 | aaccaaatccaggttctagca | 648 | 30 | ++ | 38 | 377 |
| 632 | aaatccaggttctagcacaga | 652 | 60 | +++ | 39 | 378 |

TABLE 9-continued

Ephrin B2 RNAi probes.

| RNAi Sequence and homology with other human genes. | | Percent reduction in viability | Inhibition of Ephrin B2 Expression | RNAi no. | SEQ ID NO: |
|---|---|---|---|---|---|
| 633 aatccaggttctagcacagac | 653 | 40 | ++ | 40 | 379 |
| 678 aacaacatcctcggttccgaa | 698 | 30 | ++ | 41 | 380 |
| 681 aacatcctcggttccgaagtg | 701 | 20 | + | 42 | 381 |
| 697 aagtggccttatttgcaggga | 717 | 30 | ++ | 43 | 382 |
| Additional Ephrin B2 RNAi probes described in the specification | | | | | |
| GCAGACAGAUGCACUAUUAUU | | | | ephrin B2 264 | 383 |
| CUGCGAUUUCCAAAUCGAUUU | | | | ephrin B2 63 | 384 |
| GGACUGGUACUAUACCCACUU | | | | ephrin B2 137 | 385 |

EXAMPLE 10

EphB4 Antibodies Inhibit Tumor Growth

FIG. 57 shows results on comparison of EphB4 monoclonal antibodies by G250 and in Pull-down assay.

FIG. 58 shows that EphB4 antibodies, in the presence of matrigel and growth factors, inhibit the in vivo tumor growth of SCC15 cells.

BalbC nude mice were injected subcutaneously with 2.5× 10$^6$ viable tumor cells SCC15 is a head and neck squamous cell carcinoma line. Tumors were initiated in nu/nu mice by injecting 2.5-5×10$^6$ cells premixed with matrigel and Growth factors, and Ab's subcutaneously to initiate tumor xenografts. Mice were opened 14 days after injections. SCC15 is a head and neck squamous cell carcinoma line, B16 is a melanoma cell line, and MCF-7 is a breast carcinoma line. The responses of tumors to these treatments were compared to control treated mice, which receive PBS injections. Animals were observed daily for tumor growth and subcutaneous tumors were measured using a caliper every 2 days. Antibodies #1 and #23 showed significant regression of SCC15 tumor size compared to control, especially with no additional growth factor added.

FIG. 59 shows that EphB4 antibodies cause apoptosis, necrosis and decreased angiogenesis in SCC15, head and neck carcinoma tumor type.

Angiogenesis was assessed by CD-31 immunohistochemistry. Tumor tissue sections from treated and untreated mice were stained for CD31. Apoptosis was assessed by immunohistochemical TUNNEL, and proliferation by BrdU assay. Following surgical removal, tumors were immediately sliced into 2 mm serial sections and embedded in paraffin using standard procedures. Paraffin embedded tissue were sectioned at 5 μm, the wax removed and the tissue rehydrated. The rehydrated tissues were microwave irradiated in antigen retreival solution. Slides were rinsed in PBS, and TUNNEL reaction mixture (Terminal deoxynucleotidyl transferase and flourescein labeled nucleotide solution), and BrdU were added in a humidity chamber completely shielded from light. The TUNNEL and BrdU reaction mixture were then removed, slides were rinsed and anti-flourescein antibody conjugated with horseradish peroxidase was added. After incubation and rinsing, 3, 3'diaminobenzidine was added. Masson's Trichrome and Hematoxylin and Eosin were also used to stain the slides to visualize morphology. Masson's Trichrome allows to visualize necrosis and fibrosis. The tumor gets blood support from tumor/skin, muscle boundary. As tumor grows, inner regions get depleted of nutrients. This leads to necrosis (cell death), preferably at the tumor center. After cells die, (tumor) tissue gets replaced with fibroblastic tissue. Slides were visualized under 20-fold magnification with digital images acquired. A different morphology was obtained on SCC tumors with each antibody administered. Ab #1 showed an increase in necrosis and fibrosis but not apoptosis. Ab #23 showed an increase in apoptosis, necrosis and fibrosis and a decrease in vessel infiltration. Ab #35 showed an increase in necrosis and fibrosis, and a small increase in apoptosis and a decrease in vessel infiltration. Ab #79 showed a large increase in apoptosis, and necrossis and fibrosis. Ab #91 showed no change in apoptosis but an increase in proliferation. And Ab #138 showed an increase in apoptosis, necrosis, fibrosis and a decrease in proliferation and vessel infiltration. Tumors treated with control PBS displayed abundant tumor density and a robust angiogenic response. Tumors treated with EphB4 antibodies displayed a decrease in tumor cell density and a marked inhibition of tumor angiogenesis in regions with viable tumor cells, as well as tumor necrosis and apoptosis.

FIG. 60 shows that systemic administration of antibodies on xenografts leads to tumor regression in SCC 15 tumor xenografts.

Alternate day treatment with EphB4 monoclonal antibody or an equal volume of PBS as control were initiated on day 4, after the tumors have established, and continued for 14 days. Systemic administration was administered either IP or SC with no significant difference. All the experiments were carried out in a double-blind manner to eliminate investigator bias. Mice were sacrificed at the conclusion of the two week treatment period. Tumors were harvested immediately post-mortem and fixed and processed for immunohistochemistry. EphB4 antibodies 40 mg per kg body weight were administered. Treatment with EphB4 antibody significantly inhibited human SCC tumor growth compared with control-treated mice ($p<0.05$). Treatment with EphB4 antibody significantly inhibited tumor weight compared with control-treated mice ($p<0.05$).

Incorporation by Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An isolated monoclonal antibody which binds to an extracellular domain of an EphB4 protein and promotes apoptosis in a tumor cell, wherein the antibody is selected from bispecific, single-chain, chimeric, human, and humanized antibodies.

2. The antibody of claim 1, wherein the antibody inhibits the interaction between Ephrin B2 and EphB4.

3. The antibody of claim 1, wherein the antibody inhibits clustering of EphB4.

4. The antibody of claim 1, wherein the antibody inhibits phosphorylation of EphB4.

5. A pharmaceutical composition comprising the antibody of claim 1, and a pharmaceutically acceptable carrier.

6. A cosmetic composition comprising the antibody of claim 1, and a pharmaceutically acceptable carrier.

7. A diagnostic kit comprising the antibody of claim 1, and a carrier.

8. An isolated cell expressing the antibody of claim 1.

9. A non-human transgenic animal expressing the antibody of claim 1.

10. The antibody of claim 1, further comprising a label attached thereto.

11. The antibody of claim 10, wherein the label is selected from a radioisotope, a fluorescent compound, an enzyme, or an enzyme co-factor.

12. The antibody of claim 1, wherein the antibody inhibits angiogenesis.

13. The antibody of claim 1, wherein the antibody promotes tumor regression.

* * * * *

SEQUENCE LISTING

```
<160> NUMBER OF SEQ ID NOS: 396

<210> SEQ ID NO 1
<211> LENGTH: 29
<212> TYPE: DNA
<213> ORGANISM: Unknown
<220> FEATURE:
<223> OTHER INFORMATION: Oligonucleotide

<400> SEQUENCE: 1
ggatccgcca tggagctccg ggtgctgct                                            29

<210> SEQ ID NO 2
<211> LENGTH: 36
<212> TYPE: DNA
<213> ORGANISM: Unknown
<220> FEATURE:
<223> OTHER INFORMATION: Oligonucleotide

<400> SEQUENCE: 2
tggatccctg ctcccgccag ccctcgctct catcca                                    36

<210> SEQ ID NO 3
<211> LENGTH: 28
<212> TYPE: DNA
<213> ORGANISM: Unknown
<220> FEATURE:
<223> OTHER INFORMATION: Oligonucleotide

<400> SEQUENCE: 3
tggatccacc atggctgtga gaagggac                                             28

<210> SEQ ID NO 4
<211> LENGTH: 53
<212> TYPE: DNA
<213> ORGANISM: Unknown
<220> FEATURE:
<223> OTHER INFORMATION: Oligonucleotide

<400> SEQUENCE: 4
attaatggtg atggtgatga tgactaccca cttcggaacc gaggatgttg ttc                 53

<210> SEQ ID NO 5
<211> LENGTH: 31
<212> TYPE: DNA
<213> ORGANISM: Unknown
<220> FEATURE:
<223> OTHER INFORMATION: Oligonucleotide

<400> SEQUENCE: 5
taaagcttcc gccatggctg tgagaaggga c                                         31
```

<210> SEQ ID NO 6
<211> LENGTH: 34
<212> TYPE: DNA
<213> ORGANISM: Unknown
<220> FEATURE:
<223> OTHER INFORMATION: Oligonucleotide

<400> SEQUENCE: 6
taggatccac ttcggaaccg aggatgttgt tccc                              34

<210> SEQ ID NO 7
<211> LENGTH: 31
<212> TYPE: DNA
<213> ORGANISM: Unknown
<220> FEATURE:
<223> OTHER INFORMATION: Oligonucleotide

<400> SEQUENCE: 7
ataagcttcc gccatggagc tccgggtgct g                                 31

<210> SEQ ID NO 8
<211> LENGTH: 34
<212> TYPE: DNA
<213> ORGANISM: Unknown
<220> FEATURE:
<223> OTHER INFORMATION: Oligonucleotide

<400> SEQUENCE: 8
ttggatcctg ctcccgccag ccctcgctct catc                              34

<210> SEQ ID NO 9
<211> LENGTH: 32
<212> TYPE: DNA
<213> ORGANISM: Unknown
<220> FEATURE:
<223> OTHER INFORMATION: Oligonucleotide

<400> SEQUENCE: 9
tactagtccg ccatggagct ccgggtgctg ct                                32

<210> SEQ ID NO 10
<211> LENGTH: 50
<212> TYPE: DNA
<213> ORGANISM: Unknown
<220> FEATURE:
<223> OTHER INFORMATION: Oligonucleotide

<400> SEQUENCE: 10
gcggccgctt aatggtgatg gtgatgatga gccgaaggag gggtggtgca              50

<210> SEQ ID NO 11
<211> LENGTH: 53
<212> TYPE: DNA
<213> ORGANISM: Unknown
<220> FEATURE:
<223> OTHER INFORMATION: Oligonucleotide

<400> SEQUENCE: 11
agcggccgct taatggtgat ggtgatgatg gacattgaca ggctcaaatg gga           53

<210> SEQ ID NO 12
<211> LENGTH: 56
<212> TYPE: DNA
<213> ORGANISM: Unknown
<220> FEATURE:
<223> OTHER INFORMATION: Oligonucleotide

```
<400> SEQUENCE: 12
tgcggccgct taatggtgat ggtgatgatg ctgctcccgc cagccctcgc tctcat        56

<210> SEQ ID NO 13
<211> LENGTH: 32
<212> TYPE: DNA
<213> ORGANISM: Unknown
<220> FEATURE:
<223> OTHER INFORMATION: Oligonucleotide

<400> SEQUENCE: 13
tactagtccg ccatggagct ccgggtgctg ct                                  32

<210> SEQ ID NO 14
<211> LENGTH: 25
<212> TYPE: DNA
<213> ORGANISM: Unknown
<220> FEATURE:
<223> OTHER INFORMATION: Oligonucleotide

<400> SEQUENCE: 14
cagctgagtt tccaattttg tgttc                                          25

<210> SEQ ID NO 15
<211> LENGTH: 39
<212> TYPE: DNA
<213> ORGANISM: Unknown
<220> FEATURE:
<223> OTHER INFORMATION: Oligonucleotide

<400> SEQUENCE: 15
gaacacaaaa ttggaaactc agctgactgt gaacctgac                           39

<210> SEQ ID NO 16
<211> LENGTH: 30
<212> TYPE: DNA
<213> ORGANISM: Unknown
<220> FEATURE:
<223> OTHER INFORMATION: Oligonucleotide

<400> SEQUENCE: 16
gcggccgccc tgctcccgcc agccctcgct                                     30

<210> SEQ ID NO 17
<211> LENGTH: 31
<212> TYPE: DNA
<213> ORGANISM: Unknown
<220> FEATURE:
<223> OTHER INFORMATION: Oligonucleotide

<400> SEQUENCE: 17
taaagcttcc gccatggctg tgagaaggga c                                   31

<210> SEQ ID NO 18
<211> LENGTH: 32
<212> TYPE: DNA
<213> ORGANISM: Unknown
<220> FEATURE:
<223> OTHER INFORMATION: Oligonucleotide

<400> SEQUENCE: 18
taggatcctt cggaaccgag gatgttgttc cc                                  32

<210> SEQ ID NO 19
```

```
<211> LENGTH: 20
<212> TYPE: DNA
<213> ORGANISM: Unknown
<220> FEATURE:
<223> OTHER INFORMATION: Oligonucleotide

<400> SEQUENCE: 19
tcctgcaagg agaccttcac                                                    20

<210> SEQ ID NO 20
<211> LENGTH: 21
<212> TYPE: DNA
<213> ORGANISM: Unknown
<220> FEATURE:
<223> OTHER INFORMATION: Oligonucleotide

<400> SEQUENCE: 20
gtgcagggat agcagggcca t                                                  21

<210> SEQ ID NO 21
<211> LENGTH: 20
<212> TYPE: DNA
<213> ORGANISM: Unknown
<220> FEATURE:
<223> OTHER INFORMATION: Oligonucleotide

<400> SEQUENCE: 21
atggaggcct cgctcagaaa                                                    20

<210> SEQ ID NO 22
<211> LENGTH: 21
<212> TYPE: RNA
<213> ORGANISM: Unknown
<220> FEATURE:
<223> OTHER INFORMATION: Oligonucleotide

<400> SEQUENCE: 22
ggugaauguc aagacgcugu u                                                  21

<210> SEQ ID NO 23
<211> LENGTH: 21
<212> TYPE: RNA
<213> ORGANISM: Unknown
<220> FEATURE:
<223> OTHER INFORMATION: Oligonucleotide

<400> SEQUENCE: 23
cucuuccgau cccaccuacu u                                                  21

<210> SEQ ID NO 24
<211> LENGTH: 19
<212> TYPE: DNA
<213> ORGANISM: Unknown
<220> FEATURE:
<223> OTHER INFORMATION: Oligonucleotide

<400> SEQUENCE: 24
ggacctgact gactaccta                                                     19

<210> SEQ ID NO 25
<211> LENGTH: 20
<212> TYPE: DNA
<213> ORGANISM: Unknown
<220> FEATURE:
<223> OTHER INFORMATION: Oligonucleotide

<400> SEQUENCE: 25
```
aaggagacct tcaccgtctt                                          20

<210> SEQ ID NO 26
<211> LENGTH: 20
<212> TYPE: DNA
<213> ORGANISM: Unknown
<220> FEATURE:
<223> OTHER INFORMATION: Oligonucleotide

<400> SEQUENCE: 26
ttgaaggtag tttcgtggat                                          20

<210> SEQ ID NO 27
<211> LENGTH: 20
<212> TYPE: DNA
<213> ORGANISM: Unknown
<220> FEATURE:
<223> OTHER INFORMATION: Oligonucleotide

<400> SEQUENCE: 27
tcgagtcagg ttcacagtca                                          20

<210> SEQ ID NO 28
<211> LENGTH: 20
<212> TYPE: DNA
<213> ORGANISM: Unknown
<220> FEATURE:
<223> OTHER INFORMATION: Oligonucleotide

<400> SEQUENCE: 28
ggagccaaaa gggtcatcat                                          20

<210> SEQ ID NO 29
<211> LENGTH: 21
<212> TYPE: DNA
<213> ORGANISM: Unknown
<220> FEATURE:
<223> OTHER INFORMATION: Oligonucleotide

<400> SEQUENCE: 29
ggcattgctg caaagaaaga g                                        21

<210> SEQ ID NO 30
<211> LENGTH: 20
<212> TYPE: DNA
<213> ORGANISM: Unknown
<220> FEATURE:
<223> OTHER INFORMATION: Oligonucleotide

<400> SEQUENCE: 30
tccgtgtgga agtactgctg                                          20

<210> SEQ ID NO 31
<211> LENGTH: 20
<212> TYPE: DNA
<213> ORGANISM: Unknown
<220> FEATURE:
<223> OTHER INFORMATION: Oligonucleotide

<400> SEQUENCE: 31
tctggtttgg cacagttgag                                          20

<210> SEQ ID NO 32
<211> LENGTH: 20
<212> TYPE: DNA

```
<213> ORGANISM: Unknown
<220> FEATURE:
<223> OTHER INFORMATION: Oligonucleotide

<400> SEQUENCE: 32
ctttggaaga gaccctgctg                                                    20

<210> SEQ ID NO 33
<211> LENGTH: 20
<212> TYPE: DNA
<213> ORGANISM: Unknown
<220> FEATURE:
<223> OTHER INFORMATION: Oligonucleotide

<400> SEQUENCE: 33
agacggtgaa ggtctccttg                                                    20

<210> SEQ ID NO 34
<211> LENGTH: 21
<212> TYPE: RNA
<213> ORGANISM: Unknown
<220> FEATURE:
<223> OTHER INFORMATION: Oligonucleotide

<400> SEQUENCE: 34
gagacccugc ugaacacaau u                                                  21

<210> SEQ ID NO 35
<211> LENGTH: 21
<212> TYPE: RNA
<213> ORGANISM: Unknown
<220> FEATURE:
<223> OTHER INFORMATION: Oligonucleotide

<400> SEQUENCE: 35
uuguguucag cagggucucu u                                                  21

<210> SEQ ID NO 36
<211> LENGTH: 21
<212> TYPE: RNA
<213> ORGANISM: Unknown
<220> FEATURE:
<223> OTHER INFORMATION: Oligonucleotide

<400> SEQUENCE: 36
ggugaauguc aagacgcugu u                                                  21

<210> SEQ ID NO 37
<211> LENGTH: 21
<212> TYPE: RNA
<213> ORGANISM: Unknown
<220> FEATURE:
<223> OTHER INFORMATION: Oligonucleotide

<400> SEQUENCE: 37
cagcgucuug acauucaccu u                                                  21

<210> SEQ ID NO 38
<211> LENGTH: 21
<212> TYPE: RNA
<213> ORGANISM: Unknown
<220> FEATURE:
<223> OTHER INFORMATION: Oligonucleotide

<400> SEQUENCE: 38
caucacagcc agacccaacu u                                                  21
```

-continued

```
<210> SEQ ID NO 39
<211> LENGTH: 21
<212> TYPE: RNA
<213> ORGANISM: Unknown
<220> FEATURE:
<223> OTHER INFORMATION: Oligonucleotide

<400> SEQUENCE: 39
guugggucug gcugugaugu u                                              21

<210> SEQ ID NO 40
<211> LENGTH: 21
<212> TYPE: RNA
<213> ORGANISM: Unknown
<220> FEATURE:
<223> OTHER INFORMATION: Oligonucleotide

<400> SEQUENCE: 40
cucuuccgau cccaccuacu u                                              21

<210> SEQ ID NO 41
<211> LENGTH: 21
<212> TYPE: RNA
<213> ORGANISM: Unknown
<220> FEATURE:
<223> OTHER INFORMATION: Oligonucleotide

<400> SEQUENCE: 41
guaggugggg a ucggaagagu u                                            21

<210> SEQ ID NO 42
<211> LENGTH: 21
<212> TYPE: DNA
<213> ORGANISM: Unknown
<220> FEATURE:
<223> OTHER INFORMATION: Oligonucleotide

<400> SEQUENCE: 42
gtgcagggat agcagggcca t                                              21

<210> SEQ ID NO 43
<211> LENGTH: 21
<212> TYPE: DNA
<213> ORGANISM: Unknown
<220> FEATURE:
<223> OTHER INFORMATION: Oligonucleotide

<400> SEQUENCE: 43
aaggaggggt ggtgcacggt g                                              21

<210> SEQ ID NO 44
<211> LENGTH: 21
<212> TYPE: DNA
<213> ORGANISM: Unknown
<220> FEATURE:
<223> OTHER INFORMATION: Oligonucleotide

<400> SEQUENCE: 44
ttccaggtgc agggaggagc c                                              21

<210> SEQ ID NO 45
<211> LENGTH: 21
<212> TYPE: DNA
<213> ORGANISM: Unknown
<220> FEATURE:
```

<223> OTHER INFORMATION: Oligonucleotide

<400> SEQUENCE: 45
gtggtgacat tgacaggctc a                                                    21

<210> SEQ ID NO 46
<211> LENGTH: 21
<212> TYPE: DNA
<213> ORGANISM: Unknown
<220> FEATURE:
<223> OTHER INFORMATION: Oligonucleotide

<400> SEQUENCE: 46
tctggctgtg atgttcctgg c                                                    21

<210> SEQ ID NO 47
<211> LENGTH: 18
<212> TYPE: DNA
<213> ORGANISM: Unknown
<220> FEATURE:
<223> OTHER INFORMATION: Oligonucleotide

<400> SEQUENCE: 47
gccgctcagt tcctccca                                                        18

<210> SEQ ID NO 48
<211> LENGTH: 18
<212> TYPE: DNA
<213> ORGANISM: Unknown
<220> FEATURE:
<223> OTHER INFORMATION: Oligonucleotide

<400> SEQUENCE: 48
tgaaggtctc cttgcagg                                                        18

<210> SEQ ID NO 49
<211> LENGTH: 21
<212> TYPE: DNA
<213> ORGANISM: Unknown
<220> FEATURE:
<223> OTHER INFORMATION: Oligonucleotide

<400> SEQUENCE: 49
cgcggccacc gtgtccacct t                                                    21

<210> SEQ ID NO 50
<211> LENGTH: 21
<212> TYPE: DNA
<213> ORGANISM: Unknown
<220> FEATURE:
<223> OTHER INFORMATION: Oligonucleotide

<400> SEQUENCE: 50
cttcagggtc ttgattgcca c                                                    21

<210> SEQ ID NO 51
<211> LENGTH: 20
<212> TYPE: DNA
<213> ORGANISM: Unknown
<220> FEATURE:
<223> OTHER INFORMATION: Oligonucleotide

<400> SEQUENCE: 51
atggaggcct cgctcagaaa                                                      20

```
<210> SEQ ID NO 52
<211> LENGTH: 21
<212> TYPE: DNA
<213> ORGANISM: Unknown
<220> FEATURE:
<223> OTHER INFORMATION: Oligonucleotide

<400> SEQUENCE: 52
catgcccacg agctggatga c                                              21

<210> SEQ ID NO 53
<211> LENGTH: 19
<212> TYPE: DNA
<213> ORGANISM: Unknown
<220> FEATURE:
<223> OTHER INFORMATION: Oligonucleotide

<400> SEQUENCE: 53
tccgtgtgga gtactgctg                                                 19

<210> SEQ ID NO 54
<211> LENGTH: 20
<212> TYPE: DNA
<213> ORGANISM: Unknown
<220> FEATURE:
<223> OTHER INFORMATION: Oligonucleotide

<400> SEQUENCE: 54
tctggtttgg cacagttgag                                                20

<210> SEQ ID NO 55
<211> LENGTH: 20
<212> TYPE: DNA
<213> ORGANISM: Unknown
<220> FEATURE:
<223> OTHER INFORMATION: Oligonucleotide

<400> SEQUENCE: 55
ctttggaaga gaccctgctg                                                20

<210> SEQ ID NO 56
<211> LENGTH: 20
<212> TYPE: DNA
<213> ORGANISM: Unknown
<220> FEATURE:
<223> OTHER INFORMATION: Oligonucleotide

<400> SEQUENCE: 56
agacggtgaa ggtctccttg                                                20

<210> SEQ ID NO 57
<211> LENGTH: 20
<212> TYPE: DNA
<213> ORGANISM: Unknown
<220> FEATURE:
<223> OTHER INFORMATION: Oligonucleotide

<400> SEQUENCE: 57
agacaagagc catgaagatc                                                20

<210> SEQ ID NO 58
<211> LENGTH: 21
<212> TYPE: DNA
<213> ORGANISM: Unknown
<220> FEATURE:
<223> OTHER INFORMATION: Oligonucleotide
```

```
<400> SEQUENCE: 58
ggatcccact tcggacccga g                                      21

<210> SEQ ID NO 59
<211> LENGTH: 22
<212> TYPE: DNA
<213> ORGANISM: Unknown
<220> FEATURE:
<223> OTHER INFORMATION: Oligonucleotide

<400> SEQUENCE: 59
tcaggtcact gcattgaacg gg                                     22

<210> SEQ ID NO 60
<211> LENGTH: 19
<212> TYPE: DNA
<213> ORGANISM: Unknown
<220> FEATURE:
<223> OTHER INFORMATION: Oligonucleotide

<400> SEQUENCE: 60
aactcgctct catccagtt                                         19

<210> SEQ ID NO 61
<211> LENGTH: 20
<212> TYPE: DNA
<213> ORGANISM: Unknown
<220> FEATURE:
<223> OTHER INFORMATION: Oligonucleotide

<400> SEQUENCE: 61
gtggggcgcc ccaggcacca                                        20

<210> SEQ ID NO 62
<211> LENGTH: 24
<212> TYPE: DNA
<213> ORGANISM: Unknown
<220> FEATURE:
<223> OTHER INFORMATION: Oligonucleotide

<400> SEQUENCE: 62
ctccttaatg tcacgcacga tttc                                   24

<210> SEQ ID NO 63
<211> LENGTH: 21
<212> TYPE: RNA
<213> ORGANISM: Unknown
<220> FEATURE:
<223> OTHER INFORMATION: Oligonucleotide

<400> SEQUENCE: 63
gcagacagau gcacuauuau u                                      21

<210> SEQ ID NO 64
<211> LENGTH: 21
<212> TYPE: RNA
<213> ORGANISM: Unknown
<220> FEATURE:
<223> OTHER INFORMATION: Oligonucleotide

<400> SEQUENCE: 64
uaauagugca ucugucugcu u                                      21

<210> SEQ ID NO 65
<211> LENGTH: 21
```

```
<212> TYPE: RNA
<213> ORGANISM: Unknown
<220> FEATURE:
<223> OTHER INFORMATION: Oligonucleotide

<400> SEQUENCE: 65
cugcgauuuc caaaucgauu u                                              21

<210> SEQ ID NO 66
<211> LENGTH: 21
<212> TYPE: RNA
<213> ORGANISM: Unknown
<220> FEATURE:
<223> OTHER INFORMATION: Oligonucleotide

<400> SEQUENCE: 66
aucgauuugg aaaucgcagu u                                              21

<210> SEQ ID NO 67
<211> LENGTH: 21
<212> TYPE: RNA
<213> ORGANISM: Unknown
<220> FEATURE:
<223> OTHER INFORMATION: Oligonucleotide

<400> SEQUENCE: 67
ggacugguac uauacccacu u                                              21

<210> SEQ ID NO 68
<211> LENGTH: 21
<212> TYPE: RNA
<213> ORGANISM: Unknown
<220> FEATURE:
<223> OTHER INFORMATION: Oligonucleotide

<400> SEQUENCE: 68
guggguauag uaccaguccu u                                              21

<210> SEQ ID NO 69
<211> LENGTH: 21
<212> TYPE: RNA
<213> ORGANISM: Unknown
<220> FEATURE:
<223> OTHER INFORMATION: Oligonucleotide

<400> SEQUENCE: 69
gagacccugc ugaacacaau u                                              21

<210> SEQ ID NO 70
<211> LENGTH: 21
<212> TYPE: RNA
<213> ORGANISM: Unknown
<220> FEATURE:
<223> OTHER INFORMATION: Oligonucleotide

<400> SEQUENCE: 70 uuuguucag cagggucucu u                                               21

<210> SEQ ID NO 71
<211> LENGTH: 21
<212> TYPE: RNA
<213> ORGANISM: Unknown
<220> FEATURE:
<223> OTHER INFORMATION: Oligonucleotide

<400> SEQUENCE: 71
```

-continued cgcugacccu gaaguucauu u                                           21

<210> SEQ ID NO 72
<211> LENGTH: 21
<212> TYPE: RNA
<213> ORGANISM: Unknown
<220> FEATURE:
<223> OTHER INFORMATION: Oligonucleotide

<400> SEQUENCE: 72
augaacuuca gggucagcgu u                                           21

<210> SEQ ID NO 73
<211> LENGTH: 21
<212> TYPE: DNA
<213> ORGANISM: Unknown
<220> FEATURE:
<223> OTHER INFORMATION: Oligonucleotide

<400> SEQUENCE: 73
tcagtactgc ggggccggtc c                                           21

<210> SEQ ID NO 74
<211> LENGTH: 20
<212> TYPE: DNA
<213> ORGANISM: Unknown
<220> FEATURE:
<223> OTHER INFORMATION: Oligonucleotide

<400> SEQUENCE: 74
tcctgtccca cccggggttc                                             20

<210> SEQ ID NO 75
<211> LENGTH: 20
<212> TYPE: DNA
<213> ORGANISM: Unknown
<220> FEATURE:
<223> OTHER INFORMATION: Oligonucleotide

<400> SEQUENCE: 75
ccggcttggc ctgggacttc                                             20

<210> SEQ ID NO 76
<211> LENGTH: 20
<212> TYPE: DNA
<213> ORGANISM: Unknown
<220> FEATURE:
<223> OTHER INFORMATION: Oligonucleotide

<400> SEQUENCE: 76
atgtgctgga cactggccaa                                             20

<210> SEQ ID NO 77
<211> LENGTH: 20
<212> TYPE: DNA
<213> ORGANISM: Unknown
<220> FEATURE:
<223> OTHER INFORMATION: Oligonucleotide

<400> SEQUENCE: 77
gattttcttc tggtgtcccg                                             20

<210> SEQ ID NO 78
<211> LENGTH: 20
<212> TYPE: DNA
<213> ORGANISM: Unknown

```
<220> FEATURE:
<223> OTHER INFORMATION: Oligonucleotide

<400> SEQUENCE: 78
ccagagtgac tccgattcgg                                              20

<210> SEQ ID NO 79
<211> LENGTH: 20
<212> TYPE: DNA
<213> ORGANISM: Unknown
<220> FEATURE:
<223> OTHER INFORMATION: Oligonucleotide

<400> SEQUENCE: 79
agcaggtcct cagcagagat                                              20

<210> SEQ ID NO 80
<211> LENGTH: 20
<212> TYPE: DNA
<213> ORGANISM: Unknown
<220> FEATURE:
<223> OTHER INFORMATION: Oligonucleotide

<400> SEQUENCE: 80
ctggctgacc agctcgaagg                                              20

<210> SEQ ID NO 81
<211> LENGTH: 20
<212> TYPE: DNA
<213> ORGANISM: Unknown
<220> FEATURE:
<223> OTHER INFORMATION: Oligonucleotide

<400> SEQUENCE: 81
agccaaagcc agcggctgcg                                              20

<210> SEQ ID NO 82
<211> LENGTH: 20
<212> TYPE: DNA
<213> ORGANISM: Unknown
<220> FEATURE:
<223> OTHER INFORMATION: Oligonucleotide

<400> SEQUENCE: 82
aaactttctt cgtatcttcc                                              20

<210> SEQ ID NO 83
<211> LENGTH: 20
<212> TYPE: DNA
<213> ORGANISM: Unknown
<220> FEATURE:
<223> OTHER INFORMATION: Oligonucleotide

<400> SEQUENCE: 83
cattttgatg gcccgaagcc                                              20

<210> SEQ ID NO 84
<211> LENGTH: 20
<212> TYPE: DNA
<213> ORGANISM: Unknown
<220> FEATURE:
<223> OTHER INFORMATION: Oligonucleotide

<400> SEQUENCE: 84
actcgcccac agagccaaaa                                              20
```

```
<210> SEQ ID NO 85
<211> LENGTH: 20
<212> TYPE: DNA
<213> ORGANISM: Unknown
<220> FEATURE:
<223> OTHER INFORMATION: Oligonucleotide

<400> SEQUENCE: 85
gctgagtagt gaggctgccg                                                    20

<210> SEQ ID NO 86
<211> LENGTH: 20
<212> TYPE: DNA
<213> ORGANISM: Unknown
<220> FEATURE:
<223> OTHER INFORMATION: Oligonucleotide

<400> SEQUENCE: 86
ctggtccagg agagggtgtg                                                    20

<210> SEQ ID NO 87
<211> LENGTH: 20
<212> TYPE: DNA
<213> ORGANISM: Unknown
<220> FEATURE:
<223> OTHER INFORMATION: Oligonucleotide

<400> SEQUENCE: 87
aggccccgcc attctcccgg                                                    20

<210> SEQ ID NO 88
<211> LENGTH: 20
<212> TYPE: DNA
<213> ORGANISM: Unknown
<220> FEATURE:
<223> OTHER INFORMATION: Oligonucleotide

<400> SEQUENCE: 88
gccacgattt tgaggctggc                                                    20

<210> SEQ ID NO 89
<211> LENGTH: 20
<212> TYPE: DNA
<213> ORGANISM: Unknown
<220> FEATURE:
<223> OTHER INFORMATION: Oligonucleotide

<400> SEQUENCE: 89
ggggttccgg atcatcttgt                                                    20

<210> SEQ ID NO 90
<211> LENGTH: 20
<212> TYPE: DNA
<213> ORGANISM: Unknown
<220> FEATURE:
<223> OTHER INFORMATION: Oligonucleotide

<400> SEQUENCE: 90
ccagggcgct gaccacctgg                                                    20

<210> SEQ ID NO 91
<211> LENGTH: 20
<212> TYPE: DNA
<213> ORGANISM: Unknown
<220> FEATURE:
<223> OTHER INFORMATION: Oligonucleotide
```

<400> SEQUENCE: 91
gggaagcggg gccgggcatt                                              20

<210> SEQ ID NO 92
<211> LENGTH: 20
<212> TYPE: DNA
<213> ORGANISM: Unknown
<220> FEATURE:
<223> OTHER INFORMATION: Oligonucleotide

<400> SEQUENCE: 92
ccggtctttc tgccaacagt                                              20

<210> SEQ ID NO 93
<211> LENGTH: 20
<212> TYPE: DNA
<213> ORGANISM: Unknown
<220> FEATURE:
<223> OTHER INFORMATION: Oligonucleotide

<400> SEQUENCE: 93
ccagcatgag ctggtggagg                                              20

<210> SEQ ID NO 94
<211> LENGTH: 20
<212> TYPE: DNA
<213> ORGANISM: Unknown
<220> FEATURE:
<223> OTHER INFORMATION: Oligonucleotide

<400> SEQUENCE: 94
gaggtgggac agtctggggg                                              20

<210> SEQ ID NO 95
<211> LENGTH: 20
<212> TYPE: DNA
<213> ORGANISM: Unknown
<220> FEATURE:
<223> OTHER INFORMATION: Oligonucleotide

<400> SEQUENCE: 95
cgggggcagc cggtagtcct                                              20

<210> SEQ ID NO 96
<211> LENGTH: 20
<212> TYPE: DNA
<213> ORGANISM: Unknown
<220> FEATURE:
<223> OTHER INFORMATION: Oligonucleotide

<400> SEQUENCE: 96
gttcaatggc attgatcacg                                              20

<210> SEQ ID NO 97
<211> LENGTH: 20
<212> TYPE: DNA
<213> ORGANISM: Unknown
<220> FEATURE:
<223> OTHER INFORMATION: Oligonucleotide

<400> SEQUENCE: 97
tcctgattgc tcatgtccca                                              20

<210> SEQ ID NO 98

```
<211> LENGTH: 20
<212> TYPE: DNA
<213> ORGANISM: Unknown
<220> FEATURE:
<223> OTHER INFORMATION: Oligonucleotide

<400> SEQUENCE: 98
gtacggcctc tccccaaatg                                              20

<210> SEQ ID NO 99
<211> LENGTH: 20
<212> TYPE: DNA
<213> ORGANISM: Unknown
<220> FEATURE:
<223> OTHER INFORMATION: Oligonucleotide

<400> SEQUENCE: 99
acatcacctc ccacatcaca                                              20

<210> SEQ ID NO 100
<211> LENGTH: 20
<212> TYPE: DNA
<213> ORGANISM: Unknown
<220> FEATURE:
<223> OTHER INFORMATION: Oligonucleotide

<400> SEQUENCE: 100
atcccgtaac tccaggcatc                                              20

<210> SEQ ID NO 101
<211> LENGTH: 20
<212> TYPE: DNA
<213> ORGANISM: Unknown
<220> FEATURE:
<223> OTHER INFORMATION: Oligonucleotide

<400> SEQUENCE: 101
actggcggaa gtgaacttcc                                              20

<210> SEQ ID NO 102
<211> LENGTH: 20
<212> TYPE: DNA
<213> ORGANISM: Unknown
<220> FEATURE:
<223> OTHER INFORMATION: Oligonucleotide

<400> SEQUENCE: 102
ggaaggcaat ggcctccggg                                              20

<210> SEQ ID NO 103
<211> LENGTH: 20
<212> TYPE: DNA
<213> ORGANISM: Unknown
<220> FEATURE:
<223> OTHER INFORMATION: Oligonucleotide

<400> SEQUENCE: 103
gcagtccatc ggatgggaat                                              20

<210> SEQ ID NO 104
<211> LENGTH: 20
<212> TYPE: DNA
<213> ORGANISM: Unknown
<220> FEATURE:
<223> OTHER INFORMATION: Oligonucleotide

<400> SEQUENCE: 104
```

-continued ctttcctccc agggagctcg    20

<210> SEQ ID NO 105
<211> LENGTH: 20
<212> TYPE: DNA
<213> ORGANISM: Unknown
<220> FEATURE:
<223> OTHER INFORMATION: Oligonucleotide

<400> SEQUENCE: 105
tgtaggtggg atcggaagag    20

<210> SEQ ID NO 106
<211> LENGTH: 20
<212> TYPE: DNA
<213> ORGANISM: Unknown
<220> FEATURE:
<223> OTHER INFORMATION: Oligonucleotide

<400> SEQUENCE: 106
ttctcctcca ggaatcggga    20

<210> SEQ ID NO 107
<211> LENGTH: 20
<212> TYPE: DNA
<213> ORGANISM: Unknown
<220> FEATURE:
<223> OTHER INFORMATION: Oligonucleotide

<400> SEQUENCE: 107
aaggccaaag tcagacactt    20

<210> SEQ ID NO 108
<211> LENGTH: 20
<212> TYPE: DNA
<213> ORGANISM: Unknown
<220> FEATURE:
<223> OTHER INFORMATION: Oligonucleotide

<400> SEQUENCE: 108
gcagacgagg ttgctgttga    20

<210> SEQ ID NO 109
<211> LENGTH: 20
<212> TYPE: DNA
<213> ORGANISM: Unknown
<220> FEATURE:
<223> OTHER INFORMATION: Oligonucleotide

<400> SEQUENCE: 109
ctaggatgtt gcgagcagcc    20

<210> SEQ ID NO 110
<211> LENGTH: 20
<212> TYPE: DNA
<213> ORGANISM: Unknown
<220> FEATURE:
<223> OTHER INFORMATION: Oligonucleotide

<400> SEQUENCE: 110
aggtctcggt ggacgtagct    20

<210> SEQ ID NO 111
<211> LENGTH: 20
<212> TYPE: DNA

```
<213> ORGANISM: Unknown
<220> FEATURE:
<223> OTHER INFORMATION: Oligonucleotide

<400> SEQUENCE: 111
catctcggca aggtaccgca                                               20

<210> SEQ ID NO 112
<211> LENGTH: 20
<212> TYPE: DNA
<213> ORGANISM: Unknown
<220> FEATURE:
<223> OTHER INFORMATION: Oligonucleotide

<400> SEQUENCE: 112
tgcccgaggc gatgccccgc                                               20

<210> SEQ ID NO 113
<211> LENGTH: 20
<212> TYPE: DNA
<213> ORGANISM: Unknown
<220> FEATURE:
<223> OTHER INFORMATION: Oligonucleotide

<400> SEQUENCE: 113
agcatgccca cgagctggat                                               20

<210> SEQ ID NO 114
<211> LENGTH: 20
<212> TYPE: DNA
<213> ORGANISM: Unknown
<220> FEATURE:
<223> OTHER INFORMATION: Oligonucleotide

<400> SEQUENCE: 114
gactgtgaac tgtccgtcgt                                               20

<210> SEQ ID NO 115
<211> LENGTH: 20
<212> TYPE: DNA
<213> ORGANISM: Unknown
<220> FEATURE:
<223> OTHER INFORMATION: Oligonucleotide

<400> SEQUENCE: 115
ttagccgcag gaaggagtcc                                               20

<210> SEQ ID NO 116
<211> LENGTH: 20
<212> TYPE: DNA
<213> ORGANISM: Unknown
<220> FEATURE:
<223> OTHER INFORMATION: Oligonucleotide

<400> SEQUENCE: 116
agggcgccgt tctccatgaa                                               20

<210> SEQ ID NO 117
<211> LENGTH: 20
<212> TYPE: DNA
<213> ORGANISM: Unknown
<220> FEATURE:
<223> OTHER INFORMATION: Oligonucleotide

<400> SEQUENCE: 117
ctctgtgaga atcatgacgg                                               20
```

-continued

<210> SEQ ID NO 118
<211> LENGTH: 20
<212> TYPE: DNA
<213> ORGANISM: Unknown
<220> FEATURE:
<223> OTHER INFORMATION: Oligonucleotide

<400> SEQUENCE: 118
gcatgctgtt ggtgaccacg                           20

<210> SEQ ID NO 119
<211> LENGTH: 20
<212> TYPE: DNA
<213> ORGANISM: Unknown
<220> FEATURE:
<223> OTHER INFORMATION: Oligonucleotide

<400> SEQUENCE: 119
ccctccaggc ggatgatatt                           20

<210> SEQ ID NO 120
<211> LENGTH: 20
<212> TYPE: DNA
<213> ORGANISM: Unknown
<220> FEATURE:
<223> OTHER INFORMATION: Oligonucleotide

<400> SEQUENCE: 120
ggggtgctcg aactggccca                           20

<210> SEQ ID NO 121
<211> LENGTH: 20
<212> TYPE: DNA
<213> ORGANISM: Unknown
<220> FEATURE:
<223> OTHER INFORMATION: Oligonucleotide

<400> SEQUENCE: 121
tgatggaggc ctcgctcaga                           20

<210> SEQ ID NO 122
<211> LENGTH: 20
<212> TYPE: DNA
<213> ORGANISM: Unknown
<220> FEATURE:
<223> OTHER INFORMATION: Oligonucleotide

<400> SEQUENCE: 122
aactcacgcc gctgccgctc                           20

<210> SEQ ID NO 123
<211> LENGTH: 20
<212> TYPE: DNA
<213> ORGANISM: Unknown
<220> FEATURE:
<223> OTHER INFORMATION: Oligonucleotide

<400> SEQUENCE: 123
cgtgtagcca cccttcaggg                           20

<210> SEQ ID NO 124
<211> LENGTH: 20
<212> TYPE: DNA
<213> ORGANISM: Unknown
<220> FEATURE:

-continued

<223> OTHER INFORMATION: Oligonucleotide

<400> SEQUENCE: 124
tcttgattgc cacacagctc                                            20

<210> SEQ ID NO 125
<211> LENGTH: 20
<212> TYPE: DNA
<213> ORGANISM: Unknown
<220> FEATURE:
<223> OTHER INFORMATION: Oligonucleotide

<400> SEQUENCE: 125
tccttcttcc ctggggcctt                                            20

<210> SEQ ID NO 126
<211> LENGTH: 20
<212> TYPE: DNA
<213> ORGANISM: Unknown
<220> FEATURE:
<223> OTHER INFORMATION: Oligonucleotide

<400> SEQUENCE: 126
gagccgcccc cggcacacct                                            20

<210> SEQ ID NO 127
<211> LENGTH: 20
<212> TYPE: DNA
<213> ORGANISM: Unknown
<220> FEATURE:
<223> OTHER INFORMATION: Oligonucleotide

<400> SEQUENCE: 127
cgccaaactc acctgcacca                                            20

<210> SEQ ID NO 128
<211> LENGTH: 20
<212> TYPE: DNA
<213> ORGANISM: Unknown
<220> FEATURE:
<223> OTHER INFORMATION: Oligonucleotide

<400> SEQUENCE: 128
atcacctctt caatcttgac                                            20

<210> SEQ ID NO 129
<211> LENGTH: 20
<212> TYPE: DNA
<213> ORGANISM: Unknown
<220> FEATURE:
<223> OTHER INFORMATION: Oligonucleotide

<400> SEQUENCE: 129
gtaggagaca tcgatctctt                                            20

<210> SEQ ID NO 130
<211> LENGTH: 20
<212> TYPE: DNA
<213> ORGANISM: Unknown
<220> FEATURE:
<223> OTHER INFORMATION: Oligonucleotide

<400> SEQUENCE: 130
ttgcaaattc cctcacagcc                                            20

```
<210> SEQ ID NO 131
<211> LENGTH: 20
<212> TYPE: DNA
<213> ORGANISM: Unknown
<220> FEATURE:
<223> OTHER INFORMATION: Oligonucleotide

<400> SEQUENCE: 131
tcattagggt cttcataagt                                               20

<210> SEQ ID NO 132
<211> LENGTH: 20
<212> TYPE: DNA
<213> ORGANISM: Unknown
<220> FEATURE:
<223> OTHER INFORMATION: Oligonucleotide

<400> SEQUENCE: 132
gaaggggtcg atgtagacct                                               20

<210> SEQ ID NO 133
<211> LENGTH: 20
<212> TYPE: DNA
<213> ORGANISM: Unknown
<220> FEATURE:
<223> OTHER INFORMATION: Oligonucleotide

<400> SEQUENCE: 133
tagtaccatg tccgatgaga                                               20

<210> SEQ ID NO 134
<211> LENGTH: 20
<212> TYPE: DNA
<213> ORGANISM: Unknown
<220> FEATURE:
<223> OTHER INFORMATION: Oligonucleotide

<400> SEQUENCE: 134
tactgtccgt gtttgtccga                                               20

<210> SEQ ID NO 135
<211> LENGTH: 20
<212> TYPE: DNA
<213> ORGANISM: Unknown
<220> FEATURE:
<223> OTHER INFORMATION: Oligonucleotide

<400> SEQUENCE: 135
atattctgct tctctcccat                                               20

<210> SEQ ID NO 136
<211> LENGTH: 20
<212> TYPE: DNA
<213> ORGANISM: Unknown
<220> FEATURE:
<223> OTHER INFORMATION: Oligonucleotide

<400> SEQUENCE: 136
tgctctgctt cctgaggcag                                               20

<210> SEQ ID NO 137
<211> LENGTH: 20
<212> TYPE: DNA
<213> ORGANISM: Unknown
<220> FEATURE:
<223> OTHER INFORMATION: Oligonucleotide
```

-continued

```
<400> SEQUENCE: 137
agaactgcga ccacaatgac                                              20

<210> SEQ ID NO 138
<211> LENGTH: 20
<212> TYPE: DNA
<213> ORGANISM: Unknown
<220> FEATURE:
<223> OTHER INFORMATION: Oligonucleotide

<400> SEQUENCE: 138
caccaggacc aggaccacac                                              20

<210> SEQ ID NO 139
<211> LENGTH: 20
<212> TYPE: DNA
<213> ORGANISM: Unknown
<220> FEATURE:
<223> OTHER INFORMATION: Oligonucleotide

<400> SEQUENCE: 139
ccacgactgc cgtgcccgca                                              20

<210> SEQ ID NO 140
<211> LENGTH: 20
<212> TYPE: DNA
<213> ORGANISM: Unknown
<220> FEATURE:
<223> OTHER INFORMATION: Oligonucleotide

<400> SEQUENCE: 140
atcagggcca gctgctcccg                                              20

<210> SEQ ID NO 141
<211> LENGTH: 20
<212> TYPE: DNA
<213> ORGANISM: Unknown
<220> FEATURE:
<223> OTHER INFORMATION: Oligonucleotide

<400> SEQUENCE: 141
ccagccctcg ctctcatcca                                              20

<210> SEQ ID NO 142
<211> LENGTH: 20
<212> TYPE: DNA
<213> ORGANISM: Unknown
<220> FEATURE:
<223> OTHER INFORMATION: Oligonucleotide

<400> SEQUENCE: 142
gttgggtctg gctgtgatgt                                              20

<210> SEQ ID NO 143
<211> LENGTH: 20
<212> TYPE: DNA
<213> ORGANISM: Unknown
<220> FEATURE:
<223> OTHER INFORMATION: Oligonucleotide

<400> SEQUENCE: 143
tcctggccga agggcccgta                                              20

<210> SEQ ID NO 144
<211> LENGTH: 20
```

```
<212> TYPE: DNA
<213> ORGANISM: Unknown
<220> FEATURE:
<223> OTHER INFORMATION: Oligonucleotide

<400> SEQUENCE: 144
gccggcctca gagcgcgccc                                              20

<210> SEQ ID NO 145
<211> LENGTH: 20
<212> TYPE: DNA
<213> ORGANISM: Unknown
<220> FEATURE:
<223> OTHER INFORMATION: Oligonucleotide

<400> SEQUENCE: 145
gtacctgcac caggtagctg                                              20

<210> SEQ ID NO 146
<211> LENGTH: 20
<212> TYPE: DNA
<213> ORGANISM: Unknown
<220> FEATURE:
<223> OTHER INFORMATION: Oligonucleotide

<400> SEQUENCE: 146
gctccccgct tcagccccccg                                             20

<210> SEQ ID NO 147
<211> LENGTH: 20
<212> TYPE: DNA
<213> ORGANISM: Unknown
<220> FEATURE:
<223> OTHER INFORMATION: Oligonucleotide

<400> SEQUENCE: 147
cagctctgcc cggttttctg                                              20

<210> SEQ ID NO 148
<211> LENGTH: 20
<212> TYPE: DNA
<213> ORGANISM: Unknown
<220> FEATURE:
<223> OTHER INFORMATION: Oligonucleotide

<400> SEQUENCE: 148
acgtcttcag gaaccgcacg                                              20

<210> SEQ ID NO 149
<211> LENGTH: 20
<212> TYPE: DNA
<213> ORGANISM: Unknown
<220> FEATURE:
<223> OTHER INFORMATION: Oligonucleotide

<400> SEQUENCE: 149
ctgctgggac cctcggcgcc                                              20

<210> SEQ ID NO 150
<211> LENGTH: 20
<212> TYPE: DNA
<213> ORGANISM: Unknown
<220> FEATURE:
<223> OTHER INFORMATION: Oligonucleotide

<400> SEQUENCE: 150
```
cttctcatgg tatttgacct                                              20

<210> SEQ ID NO 151
<211> LENGTH: 20
<212> TYPE: DNA
<213> ORGANISM: Unknown
<220> FEATURE:
<223> OTHER INFORMATION: Oligonucleotide

<400> SEQUENCE: 151
cgtagtccag cacagcccca                                              20

<210> SEQ ID NO 152
<211> LENGTH: 20
<212> TYPE: DNA
<213> ORGANISM: Unknown
<220> FEATURE:
<223> OTHER INFORMATION: Oligonucleotide

<400> SEQUENCE: 152
ctgggtgccc ggggaacagc                                              20

<210> SEQ ID NO 153
<211> LENGTH: 20
<212> TYPE: DNA
<213> ORGANISM: Unknown
<220> FEATURE:
<223> OTHER INFORMATION: Oligonucleotide

<400> SEQUENCE: 153
ccaggccagg ctcaagctgc                                              20

<210> SEQ ID NO 154
<211> LENGTH: 20
<212> TYPE: DNA
<213> ORGANISM: Unknown
<220> FEATURE:
<223> OTHER INFORMATION: Oligonucleotide

<400> SEQUENCE: 154
tgggtgagga ccgcgtcacc                                              20

<210> SEQ ID NO 155
<211> LENGTH: 20
<212> TYPE: DNA
<213> ORGANISM: Unknown
<220> FEATURE:
<223> OTHER INFORMATION: Oligonucleotide

<400> SEQUENCE: 155
cggatgtcag acactgcagg                                              20

<210> SEQ ID NO 156
<211> LENGTH: 20
<212> TYPE: DNA
<213> ORGANISM: Unknown
<220> FEATURE:
<223> OTHER INFORMATION: Oligonucleotide

<400> SEQUENCE: 156
aggtacctct cggtcagtgg                                              20

<210> SEQ ID NO 157
<211> LENGTH: 20
<212> TYPE: DNA
<213> ORGANISM: Unknown

```
<220> FEATURE:
<223> OTHER INFORMATION: Oligonucleotide

<400> SEQUENCE: 157
tgacattgac aggctcaaat                                               20

<210> SEQ ID NO 158
<211> LENGTH: 20
<212> TYPE: DNA
<213> ORGANISM: Unknown
<220> FEATURE:
<223> OTHER INFORMATION: Oligonucleotide

<400> SEQUENCE: 158
gggacgggcc ccgtggctaa                                               20

<210> SEQ ID NO 159
<211> LENGTH: 20
<212> TYPE: DNA
<213> ORGANISM: Unknown
<220> FEATURE:
<223> OTHER INFORMATION: Oligonucleotide

<400> SEQUENCE: 159
ggaggatacc ccgttcaatg                                               20

<210> SEQ ID NO 160
<211> LENGTH: 20
<212> TYPE: DNA
<213> ORGANISM: Unknown
<220> FEATURE:
<223> OTHER INFORMATION: Oligonucleotide

<400> SEQUENCE: 160
cagtgacctc aaaggtatag                                               20

<210> SEQ ID NO 161
<211> LENGTH: 20
<212> TYPE: DNA
<213> ORGANISM: Unknown
<220> FEATURE:
<223> OTHER INFORMATION: Oligonucleotide

<400> SEQUENCE: 161
gtgaagtcag gacgtagccc                                               20

<210> SEQ ID NO 162
<211> LENGTH: 20
<212> TYPE: DNA
<213> ORGANISM: Unknown
<220> FEATURE:
<223> OTHER INFORMATION: Oligonucleotide

<400> SEQUENCE: 162
tcgaaccacc acccagggct                                               20

<210> SEQ ID NO 163
<211> LENGTH: 20
<212> TYPE: DNA
<213> ORGANISM: Unknown
<220> FEATURE:
<223> OTHER INFORMATION: Oligonucleotide

<400> SEQUENCE: 163
ccaccaggtc ccgggggccg                                               20
```

<210> SEQ ID NO 164
<211> LENGTH: 20
<212> TYPE: DNA
<213> ORGANISM: Unknown
<220> FEATURE:
<223> OTHER INFORMATION: Oligonucleotide

<400> SEQUENCE: 164
gggtcaaaag tcaggtctcc                                              20

<210> SEQ ID NO 165
<211> LENGTH: 20
<212> TYPE: DNA
<213> ORGANISM: Unknown
<220> FEATURE:
<223> OTHER INFORMATION: Oligonucleotide

<400> SEQUENCE: 165
cccgcagggc gcacaggagc                                              20

<210> SEQ ID NO 166
<211> LENGTH: 20
<212> TYPE: DNA
<213> ORGANISM: Unknown
<220> FEATURE:
<223> OTHER INFORMATION: Oligonucleotide

<400> SEQUENCE: 166
ctccgggtcg gcactcccgg                                              20

<210> SEQ ID NO 167
<211> LENGTH: 20
<212> TYPE: DNA
<213> ORGANISM: Unknown
<220> FEATURE:
<223> OTHER INFORMATION: Oligonucleotide

<400> SEQUENCE: 167
cagcggaggg cgtaggtgag                                              20

<210> SEQ ID NO 168
<211> LENGTH: 20
<212> TYPE: DNA
<213> ORGANISM: Unknown
<220> FEATURE:
<223> OTHER INFORMATION: Oligonucleotide

<400> SEQUENCE: 168
gtcctctcgg ccaccagact                                              20

<210> SEQ ID NO 169
<211> LENGTH: 20
<212> TYPE: DNA
<213> ORGANISM: Unknown
<220> FEATURE:
<223> OTHER INFORMATION: Oligonucleotide

<400> SEQUENCE: 169
ccaggggggc actccattcc                                              20

<210> SEQ ID NO 170
<211> LENGTH: 20
<212> TYPE: DNA
<213> ORGANISM: Unknown
<220> FEATURE:
<223> OTHER INFORMATION: Oligonucleotide

<400> SEQUENCE: 170
aggtgcaggg aggagccgtt                                               20

<210> SEQ ID NO 171
<211> LENGTH: 20
<212> TYPE: DNA
<213> ORGANISM: Unknown
<220> FEATURE:
<223> OTHER INFORMATION: Oligonucleotide

<400> SEQUENCE: 171
caggcgggaa accacgctcc                                               20

<210> SEQ ID NO 172
<211> LENGTH: 20
<212> TYPE: DNA
<213> ORGANISM: Unknown
<220> FEATURE:
<223> OTHER INFORMATION: Oligonucleotide

<400> SEQUENCE: 172
gcggagccga aggaggggtg                                               20

<210> SEQ ID NO 173
<211> LENGTH: 20
<212> TYPE: DNA
<213> ORGANISM: Unknown
<220> FEATURE:
<223> OTHER INFORMATION: Oligonucleotide

<400> SEQUENCE: 173 gtgcaggtg cacccccgggg                                               20

<210> SEQ ID NO 174
<211> LENGTH: 20
<212> TYPE: DNA
<213> ORGANISM: Unknown
<220> FEATURE:
<223> OTHER INFORMATION: Oligonucleotide

<400> SEQUENCE: 174
gtctgtgcgt gcccggaagt                                               20

<210> SEQ ID NO 175
<211> LENGTH: 20
<212> TYPE: DNA
<213> ORGANISM: Unknown
<220> FEATURE:
<223> OTHER INFORMATION: Oligonucleotide

<400> SEQUENCE: 175
acccgacgcg gcactggcag                                               20

<210> SEQ ID NO 176
<211> LENGTH: 20
<212> TYPE: DNA
<213> ORGANISM: Unknown
<220> FEATURE:
<223> OTHER INFORMATION: Oligonucleotide

<400> SEQUENCE: 176
acggctgatc caatggtgtt                                               20

<210> SEQ ID NO 177

```
<211> LENGTH: 20
<212> TYPE: DNA
<213> ORGANISM: Unknown
<220> FEATURE:
<223> OTHER INFORMATION: Oligonucleotide

<400> SEQUENCE: 177
agagtggcta ttggctgggc                                               20

<210> SEQ ID NO 178
<211> LENGTH: 20
<212> TYPE: DNA
<213> ORGANISM: Unknown
<220> FEATURE:
<223> OTHER INFORMATION: Oligonucleotide

<400> SEQUENCE: 178
atggctggca ggaccttct                                                20

<210> SEQ ID NO 179
<211> LENGTH: 20
<212> TYPE: DNA
<213> ORGANISM: Unknown
<220> FEATURE:
<223> OTHER INFORMATION: Oligonucleotide

<400> SEQUENCE: 179
cctgacaggg gcttgaaggt                                               20

<210> SEQ ID NO 180
<211> LENGTH: 20
<212> TYPE: DNA
<213> ORGANISM: Unknown
<220> FEATURE:
<223> OTHER INFORMATION: Oligonucleotide

<400> SEQUENCE: 180
gccctgggca caggctcggc                                               20

<210> SEQ ID NO 181
<211> LENGTH: 20
<212> TYPE: DNA
<213> ORGANISM: Unknown
<220> FEATURE:
<223> OTHER INFORMATION: Oligonucleotide

<400> SEQUENCE: 181
acttggtgtt cccctcagct                                               20

<210> SEQ ID NO 182
<211> LENGTH: 20
<212> TYPE: DNA
<213> ORGANISM: Unknown
<220> FEATURE:
<223> OTHER INFORMATION: Oligonucleotide

<400> SEQUENCE: 182
gcctcgaacc ccggagcaca                                               20

<210> SEQ ID NO 183
<211> LENGTH: 20
<212> TYPE: DNA
<213> ORGANISM: Unknown
<220> FEATURE:
<223> OTHER INFORMATION: Oligonucleotide

<400> SEQUENCE: 183
```

```
gctgcagccc gtgaccggct                                         20

<210> SEQ ID NO 184
<211> LENGTH: 20
<212> TYPE: DNA
<213> ORGANISM: Unknown
<220> FEATURE:
<223> OTHER INFORMATION: Oligonucleotide

<400> SEQUENCE: 184
gttcggccca ctggccatcc                                         20

<210> SEQ ID NO 185
<211> LENGTH: 20
<212> TYPE: DNA
<213> ORGANISM: Unknown
<220> FEATURE:
<223> OTHER INFORMATION: Oligonucleotide

<400> SEQUENCE: 185
tcacggcagt agaggctggg                                         20

<210> SEQ ID NO 186
<211> LENGTH: 20
<212> TYPE: DNA
<213> ORGANISM: Unknown
<220> FEATURE:
<223> OTHER INFORMATION: Oligonucleotide

<400> SEQUENCE: 186
gctggggcca ggggcgggga                                         20

<210> SEQ ID NO 187
<211> LENGTH: 20
<212> TYPE: DNA
<213> ORGANISM: Unknown
<220> FEATURE:
<223> OTHER INFORMATION: Oligonucleotide

<400> SEQUENCE: 187
cggcatccac cacgcagcta                                         20

<210> SEQ ID NO 188
<211> LENGTH: 20
<212> TYPE: DNA
<213> ORGANISM: Unknown
<220> FEATURE:
<223> OTHER INFORMATION: Oligonucleotide

<400> SEQUENCE: 188
ccggccacgg gcacaaccag                                         20

<210> SEQ ID NO 189
<211> LENGTH: 20
<212> TYPE: DNA
<213> ORGANISM: Unknown
<220> FEATURE:
<223> OTHER INFORMATION: Oligonucleotide

<400> SEQUENCE: 189
ctcccgaggc acagtctccg                                         20

<210> SEQ ID NO 190
<211> LENGTH: 20
<212> TYPE: DNA
```

<213> ORGANISM: Unknown
<220> FEATURE:
<223> OTHER INFORMATION: Oligonucleotide

<400> SEQUENCE: 190
ggaatcgagt caggttcaca                                              20

<210> SEQ ID NO 191
<211> LENGTH: 20
<212> TYPE: DNA
<213> ORGANISM: Unknown
<220> FEATURE:
<223> OTHER INFORMATION: Oligonucleotide

<400> SEQUENCE: 191
gtcagctggg cgcactttt                                               20

<210> SEQ ID NO 192
<211> LENGTH: 20
<212> TYPE: DNA
<213> ORGANISM: Unknown
<220> FEATURE:
<223> OTHER INFORMATION: Oligonucleotide

<400> SEQUENCE: 192
gtagaagagg tgcagggata                                              20

<210> SEQ ID NO 193
<211> LENGTH: 20
<212> TYPE: DNA
<213> ORGANISM: Unknown
<220> FEATURE:
<223> OTHER INFORMATION: Oligonucleotide

<400> SEQUENCE: 193
gcagggccat gcaggcaccc                                              20

<210> SEQ ID NO 194
<211> LENGTH: 20
<212> TYPE: DNA
<213> ORGANISM: Unknown
<220> FEATURE:
<223> OTHER INFORMATION: Oligonucleotide

<400> SEQUENCE: 194
tggtcctgga aggccaggta                                              20

<210> SEQ ID NO 195
<211> LENGTH: 20
<212> TYPE: DNA
<213> ORGANISM: Unknown
<220> FEATURE:
<223> OTHER INFORMATION: Oligonucleotide

<400> SEQUENCE: 195
gaagccagcc ttgctgagcg                                              20

<210> SEQ ID NO 196
<211> LENGTH: 20
<212> TYPE: DNA
<213> ORGANISM: Unknown
<220> FEATURE:
<223> OTHER INFORMATION: Oligonucleotide

<400> SEQUENCE: 196
gtcccagacg cagcgtcttg                                              20

```
<210> SEQ ID NO 197
<211> LENGTH: 20
<212> TYPE: DNA
<213> ORGANISM: Unknown
<220> FEATURE:
<223> OTHER INFORMATION: Oligonucleotide

<400> SEQUENCE: 197
acattcacct tcccggtggc                                                   20

<210> SEQ ID NO 198
<211> LENGTH: 20
<212> TYPE: DNA
<213> ORGANISM: Unknown
<220> FEATURE:
<223> OTHER INFORMATION: Oligonucleotide

<400> SEQUENCE: 198
ctcggcccca gggcgcttcc                                                   20

<210> SEQ ID NO 199
<211> LENGTH: 20
<212> TYPE: DNA
<213> ORGANISM: Unknown
<220> FEATURE:
<223> OTHER INFORMATION: Oligonucleotide

<400> SEQUENCE: 199
gggtgagatg ctccgcggcc                                                   20

<210> SEQ ID NO 200
<211> LENGTH: 20
<212> TYPE: DNA
<213> ORGANISM: Unknown
<220> FEATURE:
<223> OTHER INFORMATION: Oligonucleotide

<400> SEQUENCE: 200
accgtgtcca ccttgatgta                                                   20

<210> SEQ ID NO 201
<211> LENGTH: 20
<212> TYPE: DNA
<213> ORGANISM: Unknown
<220> FEATURE:
<223> OTHER INFORMATION: Oligonucleotide

<400> SEQUENCE: 201
ggggttctcc atccaggctg                                                   20

<210> SEQ ID NO 202
<211> LENGTH: 20
<212> TYPE: DNA
<213> ORGANISM: Unknown
<220> FEATURE:
<223> OTHER INFORMATION: Oligonucleotide

<400> SEQUENCE: 202
gcgtgagggc cgtggccgtg                                                   20

<210> SEQ ID NO 203
<211> LENGTH: 20
<212> TYPE: DNA
<213> ORGANISM: Unknown
<220> FEATURE:
```

-continued

<223> OTHER INFORMATION: Oligonucleotide

<400> SEQUENCE: 203
tccgcatcgc tctcatagta                                              20

<210> SEQ ID NO 204
<211> LENGTH: 20
<212> TYPE: DNA
<213> ORGANISM: Unknown
<220> FEATURE:
<223> OTHER INFORMATION: Oligonucleotide

<400> SEQUENCE: 204
gaagacggtg aaggtctcct                                              20

<210> SEQ ID NO 205
<211> LENGTH: 20
<212> TYPE: DNA
<213> ORGANISM: Unknown
<220> FEATURE:
<223> OTHER INFORMATION: Oligonucleotide

<400> SEQUENCE: 205
tgcaggagcg cccagcccga                                              20

<210> SEQ ID NO 206
<211> LENGTH: 20
<212> TYPE: DNA
<213> ORGANISM: Unknown
<220> FEATURE:
<223> OTHER INFORMATION: Oligonucleotide

<400> SEQUENCE: 206
ggcagggaca ggcactcgag                                              20

<210> SEQ ID NO 207
<211> LENGTH: 20
<212> TYPE: DNA
<213> ORGANISM: Unknown
<220> FEATURE:
<223> OTHER INFORMATION: Oligonucleotide

<400> SEQUENCE: 207
catggtgaag cgcagcgtgg                                              20

<210> SEQ ID NO 208
<211> LENGTH: 20
<212> TYPE: DNA
<213> ORGANISM: Unknown
<220> FEATURE:
<223> OTHER INFORMATION: Oligonucleotide

<400> SEQUENCE: 208
cgtacacgtg gacggcgccc                                              20

<210> SEQ ID NO 209
<211> LENGTH: 20
<212> TYPE: DNA
<213> ORGANISM: Unknown
<220> FEATURE:
<223> OTHER INFORMATION: Oligonucleotide

<400> SEQUENCE: 209
cgccgtggga cccaacctgt                                              20

```
<210> SEQ ID NO 210
<211> LENGTH: 20
<212> TYPE: DNA
<213> ORGANISM: Unknown
<220> FEATURE:
<223> OTHER INFORMATION: Oligonucleotide

<400> SEQUENCE: 210
gcgaagccag tgggcctggc                                              20

<210> SEQ ID NO 211
<211> LENGTH: 20
<212> TYPE: DNA
<213> ORGANISM: Unknown
<220> FEATURE:
<223> OTHER INFORMATION: Oligonucleotide

<400> SEQUENCE: 211
ccggggcacg ctgcacgtca                                              20

<210> SEQ ID NO 212
<211> LENGTH: 20
<212> TYPE: DNA
<213> ORGANISM: Unknown
<220> FEATURE:
<223> OTHER INFORMATION: Oligonucleotide

<400> SEQUENCE: 212
cacacttcgt aggtgcgcac                                              20

<210> SEQ ID NO 213
<211> LENGTH: 20
<212> TYPE: DNA
<213> ORGANISM: Unknown
<220> FEATURE:
<223> OTHER INFORMATION: Oligonucleotide

<400> SEQUENCE: 213
gctgtgctgt tcctcatcca                                              20

<210> SEQ ID NO 214
<211> LENGTH: 20
<212> TYPE: DNA
<213> ORGANISM: Unknown
<220> FEATURE:
<223> OTHER INFORMATION: Oligonucleotide

<400> SEQUENCE: 214
ggccgctcag ttcctcccac                                              20

<210> SEQ ID NO 215
<211> LENGTH: 20
<212> TYPE: DNA
<213> ORGANISM: Unknown
<220> FEATURE:
<223> OTHER INFORMATION: Oligonucleotide

<400> SEQUENCE: 215
tgcccgtcca cctgagggaa                                              20

<210> SEQ ID NO 216
<211> LENGTH: 20
<212> TYPE: DNA
<213> ORGANISM: Unknown
<220> FEATURE:
<223> OTHER INFORMATION: Oligonucleotide
```

```
<400> SEQUENCE: 216
tgtcacccac ttcagatcag                                              20

<210> SEQ ID NO 217
<211> LENGTH: 20
<212> TYPE: DNA
<213> ORGANISM: Unknown
<220> FEATURE:
<223> OTHER INFORMATION: Oligonucleotide

<400> SEQUENCE: 217
cagtttccaa ttttgtgttc                                              20

<210> SEQ ID NO 218
<211> LENGTH: 20
<212> TYPE: DNA
<213> ORGANISM: Unknown
<220> FEATURE:
<223> OTHER INFORMATION: Oligonucleotide

<400> SEQUENCE: 218
agcagggtct cttccaaagc                                              20

<210> SEQ ID NO 219
<211> LENGTH: 20
<212> TYPE: DNA
<213> ORGANISM: Unknown
<220> FEATURE:
<223> OTHER INFORMATION: Oligonucleotide

<400> SEQUENCE: 219
tgcggccaac gaagcccagc                                              20

<210> SEQ ID NO 220
<211> LENGTH: 20
<212> TYPE: DNA
<213> ORGANISM: Unknown
<220> FEATURE:
<223> OTHER INFORMATION: Oligonucleotide

<400> SEQUENCE: 220
agagcagcac ccggagctcc                                              20

<210> SEQ ID NO 221
<211> LENGTH: 20
<212> TYPE: DNA
<213> ORGANISM: Unknown
<220> FEATURE:
<223> OTHER INFORMATION: Oligonucleotide

<400> SEQUENCE: 221
agcagcaccc ggagctccat                                              20

<210> SEQ ID NO 222
<211> LENGTH: 21
<212> TYPE: DNA
<213> ORGANISM: Unknown
<220> FEATURE:
<223> OTHER INFORMATION: Oligonucleotide

<400> SEQUENCE: 222
gtgcagggat agcagggcca t                                            21

<210> SEQ ID NO 223
<211> LENGTH: 21
```

```
<212> TYPE: DNA
<213> ORGANISM: Unknown
<220> FEATURE:
<223> OTHER INFORMATION: Oligonucleotide

<400> SEQUENCE: 223
aaggaggggt ggtgcacggt g                                              21

<210> SEQ ID NO 224
<211> LENGTH: 21
<212> TYPE: DNA
<213> ORGANISM: Unknown
<220> FEATURE:
<223> OTHER INFORMATION: Oligonucleotide

<400> SEQUENCE: 224
ttccaggtgc agggaggagc c                                              21

<210> SEQ ID NO 225
<211> LENGTH: 21
<212> TYPE: DNA
<213> ORGANISM: Unknown
<220> FEATURE:
<223> OTHER INFORMATION: Oligonucleotide

<400> SEQUENCE: 225
gtggtgacat tgacaggctc a                                              21

<210> SEQ ID NO 226
<211> LENGTH: 21
<212> TYPE: DNA
<213> ORGANISM: Unknown
<220> FEATURE:
<223> OTHER INFORMATION: Oligonucleotide

<400> SEQUENCE: 226
tctggctgtg atgttcctgg c                                              21

<210> SEQ ID NO 227
<211> LENGTH: 18
<212> TYPE: DNA
<213> ORGANISM: Unknown
<220> FEATURE:
<223> OTHER INFORMATION: Oligonucleotide

<400> SEQUENCE: 227
gccgctcagt tcctccca                                                  18

<210> SEQ ID NO 228
<211> LENGTH: 18
<212> TYPE: DNA
<213> ORGANISM: Unknown
<220> FEATURE:
<223> OTHER INFORMATION: Oligonucleotide

<400> SEQUENCE: 228
tgaaggtctc cttgcagg                                                  18

<210> SEQ ID NO 229
<211> LENGTH: 21
<212> TYPE: DNA
<213> ORGANISM: Unknown
<220> FEATURE:
<223> OTHER INFORMATION: Oligonucleotide

<400> SEQUENCE: 229
```

-continued cgcggccacc gtgtccacct t						21

<210> SEQ ID NO 230
<211> LENGTH: 21
<212> TYPE: DNA
<213> ORGANISM: Unknown
<220> FEATURE:
<223> OTHER INFORMATION: Oligonucleotide

<400> SEQUENCE: 230
cttcagggtc ttgattgcca c						21

<210> SEQ ID NO 231
<211> LENGTH: 20
<212> TYPE: DNA
<213> ORGANISM: Unknown
<220> FEATURE:
<223> OTHER INFORMATION: Oligonucleotide

<400> SEQUENCE: 231
atggaggcct cgctcagaaa						20

<210> SEQ ID NO 232
<211> LENGTH: 21
<212> TYPE: DNA
<213> ORGANISM: Unknown
<220> FEATURE:
<223> OTHER INFORMATION: Oligonucleotide

<400> SEQUENCE: 232
catgcccacg agctggatga c						21

<210> SEQ ID NO 233
<211> LENGTH: 21
<212> TYPE: DNA
<213> ORGANISM: Unknown
<220> FEATURE:
<223> OTHER INFORMATION: Oligonucleotide

<400> SEQUENCE: 233
aaattggaaa ctgctgatct g						21

<210> SEQ ID NO 234
<211> LENGTH: 21
<212> TYPE: DNA
<213> ORGANISM: Unknown
<220> FEATURE:
<223> OTHER INFORMATION: Oligonucleotide

<400> SEQUENCE: 234
aattggaaac tgctgatctg a						21

<210> SEQ ID NO 235
<211> LENGTH: 21
<212> TYPE: DNA
<213> ORGANISM: Unknown
<220> FEATURE:
<223> OTHER INFORMATION: Oligonucleotide

<400> SEQUENCE: 235
aaactgctga tctgaagtgg g						21

<210> SEQ ID NO 236
<211> LENGTH: 21
<212> TYPE: DNA
<213> ORGANISM: Unknown

-continued

```
<220> FEATURE:
<223> OTHER INFORMATION: Oligonucleotide

<400> SEQUENCE: 236
aactgctgat ctgaagtggg t                                              21

<210> SEQ ID NO 237
<211> LENGTH: 21
<212> TYPE: DNA
<213> ORGANISM: Unknown
<220> FEATURE:
<223> OTHER INFORMATION: Oligonucleotide

<400> SEQUENCE: 237
aatgtcaaga cgctgcgtct g                                              21

<210> SEQ ID NO 238
<211> LENGTH: 21
<212> TYPE: DNA
<213> ORGANISM: Unknown
<220> FEATURE:
<223> OTHER INFORMATION: Oligonucleotide

<400> SEQUENCE: 238
aagtgggtga cattccctca g                                              21

<210> SEQ ID NO 239
<211> LENGTH: 21
<212> TYPE: DNA
<213> ORGANISM: Unknown
<220> FEATURE:
<223> OTHER INFORMATION: Oligonucleotide

<400> SEQUENCE: 239
aaggtgaatg tcaagacgct g                                              21

<210> SEQ ID NO 240
<211> LENGTH: 21
<212> TYPE: DNA
<213> ORGANISM: Unknown
<220> FEATURE:
<223> OTHER INFORMATION: Oligonucleotide

<400> SEQUENCE: 240
aaggagacct tcaccgtctt c                                              21

<210> SEQ ID NO 241
<211> LENGTH: 21
<212> TYPE: DNA
<213> ORGANISM: Unknown
<220> FEATURE:
<223> OTHER INFORMATION: Oligonucleotide

<400> SEQUENCE: 241
aaaaagtgcg cccagctgac t                                              21

<210> SEQ ID NO 242
<211> LENGTH: 21
<212> TYPE: DNA
<213> ORGANISM: Unknown
<220> FEATURE:
<223> OTHER INFORMATION: Oligonucleotide

<400> SEQUENCE: 242
aatagccact ctaacaccat t                                              21
```

```
<210> SEQ ID NO 243
<211> LENGTH: 21
<212> TYPE: DNA
<213> ORGANISM: Unknown
<220> FEATURE:
<223> OTHER INFORMATION: Oligonucleotide

<400> SEQUENCE: 243
aacaccattg gatcagccgt c                                              21

<210> SEQ ID NO 244
<211> LENGTH: 21
<212> TYPE: DNA
<213> ORGANISM: Unknown
<220> FEATURE:
<223> OTHER INFORMATION: Oligonucleotide

<400> SEQUENCE: 244
aatgtcacca ctgaccgaga g                                              21

<210> SEQ ID NO 245
<211> LENGTH: 21
<212> TYPE: DNA
<213> ORGANISM: Unknown
<220> FEATURE:
<223> OTHER INFORMATION: Oligonucleotide

<400> SEQUENCE: 245
aaataccatg agaagggcgc c                                              21

<210> SEQ ID NO 246
<211> LENGTH: 21
<212> TYPE: DNA
<213> ORGANISM: Unknown
<220> FEATURE:
<223> OTHER INFORMATION: Oligonucleotide

<400> SEQUENCE: 246
aagacgtcag aaaaccgggc a                                              21

<210> SEQ ID NO 247
<211> LENGTH: 21
<212> TYPE: DNA
<213> ORGANISM: Unknown
<220> FEATURE:
<223> OTHER INFORMATION: Oligonucleotide

<400> SEQUENCE: 247
aacatcacag ccagacccaa c                                              21

<210> SEQ ID NO 248
<211> LENGTH: 21
<212> TYPE: DNA
<213> ORGANISM: Unknown
<220> FEATURE:
<223> OTHER INFORMATION: Oligonucleotide

<400> SEQUENCE: 248
aagcagagca atgggagaga a                                              21

<210> SEQ ID NO 249
<211> LENGTH: 21
<212> TYPE: DNA
<213> ORGANISM: Unknown
<220> FEATURE:
<223> OTHER INFORMATION: Oligonucleotide
```

<400> SEQUENCE: 249
aatgggagag aagcagaata t                                              21

<210> SEQ ID NO 250
<211> LENGTH: 21
<212> TYPE: DNA
<213> ORGANISM: Unknown
<220> FEATURE:
<223> OTHER INFORMATION: Oligonucleotide

<400> SEQUENCE: 250
aagcagaata ttcggacaaa c                                              21

<210> SEQ ID NO 251
<211> LENGTH: 21
<212> TYPE: DNA
<213> ORGANISM: Unknown
<220> FEATURE:
<223> OTHER INFORMATION: Oligonucleotide

<400> SEQUENCE: 251
aatattcgga caaacacgga c                                              21

<210> SEQ ID NO 252
<211> LENGTH: 21
<212> TYPE: DNA
<213> ORGANISM: Unknown
<220> FEATURE:
<223> OTHER INFORMATION: Oligonucleotide

<400> SEQUENCE: 252
aaacacggac agtatctcat c                                              21

<210> SEQ ID NO 253
<211> LENGTH: 21
<212> TYPE: DNA
<213> ORGANISM: Unknown
<220> FEATURE:
<223> OTHER INFORMATION: Oligonucleotide

<400> SEQUENCE: 253
aacacggaca gtatctcatc g                                              21

<210> SEQ ID NO 254
<211> LENGTH: 21
<212> TYPE: DNA
<213> ORGANISM: Unknown
<220> FEATURE:
<223> OTHER INFORMATION: Oligonucleotide

<400> SEQUENCE: 254
aaaagagatc gatgtctcct a                                              21

<210> SEQ ID NO 255
<211> LENGTH: 21
<212> TYPE: DNA
<213> ORGANISM: Unknown
<220> FEATURE:
<223> OTHER INFORMATION: Oligonucleotide

<400> SEQUENCE: 255
aatgaggctg tgagggaatt t                                              21

<210> SEQ ID NO 256

```
<211> LENGTH: 21
<212> TYPE: DNA
<213> ORGANISM: Unknown
<220> FEATURE:
<223> OTHER INFORMATION: Oligonucleotide

<400> SEQUENCE: 256
aagaccctaa tgaggctgtg a                                              21

<210> SEQ ID NO 257
<211> LENGTH: 21
<212> TYPE: DNA
<213> ORGANISM: Unknown
<220> FEATURE:
<223> OTHER INFORMATION: Oligonucleotide

<400> SEQUENCE: 257
aaagagatcg atgtctccta c                                              21

<210> SEQ ID NO 258
<211> LENGTH: 21
<212> TYPE: DNA
<213> ORGANISM: Unknown
<220> FEATURE:
<223> OTHER INFORMATION: Oligonucleotide

<400> SEQUENCE: 258
aagagatcga tgtctcctac g                                              21

<210> SEQ ID NO 259
<211> LENGTH: 21
<212> TYPE: DNA
<213> ORGANISM: Unknown
<220> FEATURE:
<223> OTHER INFORMATION: Oligonucleotide

<400> SEQUENCE: 259
aagaggtgat tggtgcaggt g                                              21

<210> SEQ ID NO 260
<211> LENGTH: 21
<212> TYPE: DNA
<213> ORGANISM: Unknown
<220> FEATURE:
<223> OTHER INFORMATION: Oligonucleotide

<400> SEQUENCE: 260
aagattgaag aggtgattgg t                                              21

<210> SEQ ID NO 261
<211> LENGTH: 21
<212> TYPE: DNA
<213> ORGANISM: Unknown
<220> FEATURE:
<223> OTHER INFORMATION: Oligonucleotide

<400> SEQUENCE: 261
aacagcatgc ccgtcatgat t                                              21

<210> SEQ ID NO 262
<211> LENGTH: 21
<212> TYPE: DNA
<213> ORGANISM: Unknown
<220> FEATURE:
<223> OTHER INFORMATION: Oligonucleotide

<400> SEQUENCE: 262
```

```
aagaaggaga gctgtgtggc a                                              21

<210> SEQ ID NO 263
<211> LENGTH: 21
<212> TYPE: DNA
<213> ORGANISM: Unknown
<220> FEATURE:
<223> OTHER INFORMATION: Oligonucleotide

<400> SEQUENCE: 263
aaggagagct gtgtggcaat c                                              21

<210> SEQ ID NO 264
<211> LENGTH: 21
<212> TYPE: DNA
<213> ORGANISM: Unknown
<220> FEATURE:
<223> OTHER INFORMATION: Oligonucleotide

<400> SEQUENCE: 264
aatcaagacc ctgaagggtg g                                              21

<210> SEQ ID NO 265
<211> LENGTH: 21
<212> TYPE: DNA
<213> ORGANISM: Unknown
<220> FEATURE:
<223> OTHER INFORMATION: Oligonucleotide

<400> SEQUENCE: 265
aaacgacgga cagttcacag t                                              21

<210> SEQ ID NO 266
<211> LENGTH: 21
<212> TYPE: DNA
<213> ORGANISM: Unknown
<220> FEATURE:
<223> OTHER INFORMATION: Oligonucleotide

<400> SEQUENCE: 266
aacgacggac agttcacagt c                                              21

<210> SEQ ID NO 267
<211> LENGTH: 21
<212> TYPE: DNA
<213> ORGANISM: Unknown
<220> FEATURE:
<223> OTHER INFORMATION: Oligonucleotide

<400> SEQUENCE: 267
aacatcctag tcaacagcaa c                                              21

<210> SEQ ID NO 268
<211> LENGTH: 21
<212> TYPE: DNA
<213> ORGANISM: Unknown
<220> FEATURE:
<223> OTHER INFORMATION: Oligonucleotide

<400> SEQUENCE: 268
aacagcaacc tcgtctgcaa a                                              21

<210> SEQ ID NO 269
<211> LENGTH: 21
<212> TYPE: DNA
```

```
<213> ORGANISM: Unknown
<220> FEATURE:
<223> OTHER INFORMATION: Oligonucleotide

<400> SEQUENCE: 269
aactcttccg atcccaccta c                                              21

<210> SEQ ID NO 270
<211> LENGTH: 21
<212> TYPE: DNA
<213> ORGANISM: Unknown
<220> FEATURE:
<223> OTHER INFORMATION: Oligonucleotide

<400> SEQUENCE: 270
aagtgtctga ctttggcctt t                                              21

<210> SEQ ID NO 271
<211> LENGTH: 21
<212> TYPE: DNA
<213> ORGANISM: Unknown
<220> FEATURE:
<223> OTHER INFORMATION: Oligonucleotide

<400> SEQUENCE: 271
aacctcgtct gcaaagtgtc t                                              21

<210> SEQ ID NO 272
<211> LENGTH: 21
<212> TYPE: DNA
<213> ORGANISM: Unknown
<220> FEATURE:
<223> OTHER INFORMATION: Oligonucleotide

<400> SEQUENCE: 272
aaagtgtctg actttggcct t                                              21

<210> SEQ ID NO 273
<211> LENGTH: 21
<212> TYPE: DNA
<213> ORGANISM: Unknown
<220> FEATURE:
<223> OTHER INFORMATION: Oligonucleotide

<400> SEQUENCE: 273
aatcaggacg tgatcaatgc c                                              21

<210> SEQ ID NO 274
<211> LENGTH: 21
<212> TYPE: DNA
<213> ORGANISM: Unknown
<220> FEATURE:
<223> OTHER INFORMATION: Oligonucleotide

<400> SEQUENCE: 274
aaagattccc atccgatgga c                                              21

<210> SEQ ID NO 275
<211> LENGTH: 21
<212> TYPE: DNA
<213> ORGANISM: Unknown
<220> FEATURE:
<223> OTHER INFORMATION: Oligonucleotide

<400> SEQUENCE: 275
aagattccca tccgatggac t                                              21
```

```
<210> SEQ ID NO 276
<211> LENGTH: 21
<212> TYPE: DNA
<213> ORGANISM: Unknown
<220> FEATURE:
<223> OTHER INFORMATION: Oligonucleotide

<400> SEQUENCE: 276
aagttcactt ccgccagtga t                                              21

<210> SEQ ID NO 277
<211> LENGTH: 21
<212> TYPE: DNA
<213> ORGANISM: Unknown
<220> FEATURE:
<223> OTHER INFORMATION: Oligonucleotide

<400> SEQUENCE: 277
aagatacgaa gaaagtttcg c                                              21

<210> SEQ ID NO 278
<211> LENGTH: 21
<212> TYPE: DNA
<213> ORGANISM: Unknown
<220> FEATURE:
<223> OTHER INFORMATION: Oligonucleotide

<400> SEQUENCE: 278
aatgggaaga tacgaagaaa g                                              21

<210> SEQ ID NO 279
<211> LENGTH: 21
<212> TYPE: DNA
<213> ORGANISM: Unknown
<220> FEATURE:
<223> OTHER INFORMATION: Oligonucleotide

<400> SEQUENCE: 279
aatgccattg aacaggacta c                                              21

<210> SEQ ID NO 280
<211> LENGTH: 21
<212> TYPE: DNA
<213> ORGANISM: Unknown
<220> FEATURE:
<223> OTHER INFORMATION: Oligonucleotide

<400> SEQUENCE: 280
aaaatcgtgg cccgggagaa t                                              21

<210> SEQ ID NO 281
<211> LENGTH: 21
<212> TYPE: DNA
<213> ORGANISM: Unknown
<220> FEATURE:
<223> OTHER INFORMATION: Oligonucleotide

<400> SEQUENCE: 281
aaaatcttgg ccagtgtcca g                                              21

<210> SEQ ID NO 282
<211> LENGTH: 21
<212> TYPE: DNA
<213> ORGANISM: Unknown
<220> FEATURE:
```

-continued

<223> OTHER INFORMATION: Oligonucleotide

<400> SEQUENCE: 282
aaatcttggc cagtgtccag c                                              21

<210> SEQ ID NO 283
<211> LENGTH: 21
<212> TYPE: DNA
<213> ORGANISM: Unknown
<220> FEATURE:
<223> OTHER INFORMATION: Oligonucleotide

<400> SEQUENCE: 283
aagaaagttt cgcagccgct g                                              21

<210> SEQ ID NO 284
<211> LENGTH: 21
<212> TYPE: DNA
<213> ORGANISM: Unknown
<220> FEATURE:
<223> OTHER INFORMATION: Oligonucleotide

<400> SEQUENCE: 284
aagaaaatct tggccagtgt c                                              21

<210> SEQ ID NO 285
<211> LENGTH: 21
<212> TYPE: DNA
<213> ORGANISM: Unknown
<220> FEATURE:
<223> OTHER INFORMATION: Oligonucleotide

<400> SEQUENCE: 285
aatcttggcc agtgtccagc a                                              21

<210> SEQ ID NO 286
<211> LENGTH: 21
<212> TYPE: RNA
<213> ORGANISM: Unknown
<220> FEATURE:
<223> OTHER INFORMATION: Oligonucleotide

<400> SEQUENCE: 286
gagacccugc ugaacacaau u                                              21

<210> SEQ ID NO 287
<211> LENGTH: 21
<212> TYPE: RNA
<213> ORGANISM: Unknown
<220> FEATURE:
<223> OTHER INFORMATION: Oligonucleotide

<400> SEQUENCE: 287
ggugaauguc aagacgcugu u                                              21

<210> SEQ ID NO 288
<211> LENGTH: 21
<212> TYPE: RNA
<213> ORGANISM: Unknown
<220> FEATURE:
<223> OTHER INFORMATION: Oligonucleotide

<400> SEQUENCE: 288
caucacagcc agacccaacu u                                              21

```
<210> SEQ ID NO 289
<211> LENGTH: 21
<212> TYPE: RNA
<213> ORGANISM: Unknown
<220> FEATURE:
<223> OTHER INFORMATION: Oligonucleotide

<400> SEQUENCE: 289
cucuuccgau cccaccuacu u                                              21

<210> SEQ ID NO 290
<211> LENGTH: 21
<212> TYPE: RNA
<213> ORGANISM: Unknown
<220> FEATURE:
<223> OTHER INFORMATION: Oligonucleotide

<400> SEQUENCE: 290
cucuuccgau cccaccuacu u                                              21

<210> SEQ ID NO 291
<211> LENGTH: 20
<212> TYPE: DNA
<213> ORGANISM: Unknown
<220> FEATURE:
<223> OTHER INFORMATION: Oligonucleotide

<400> SEQUENCE: 291
tcagaccttg tagtaaatgt                                                20

<210> SEQ ID NO 292
<211> LENGTH: 20
<212> TYPE: DNA
<213> ORGANISM: Unknown
<220> FEATURE:
<223> OTHER INFORMATION: Oligonucleotide

<400> SEQUENCE: 292
tcgccgggct ctgcgggggc                                                20

<210> SEQ ID NO 293
<211> LENGTH: 20
<212> TYPE: DNA
<213> ORGANISM: Unknown
<220> FEATURE:
<223> OTHER INFORMATION: Oligonucleotide

<400> SEQUENCE: 293
atctcctgga cgatgtacac                                                20

<210> SEQ ID NO 294
<211> LENGTH: 20
<212> TYPE: DNA
<213> ORGANISM: Unknown
<220> FEATURE:
<223> OTHER INFORMATION: Oligonucleotide

<400> SEQUENCE: 294
cgggtgcccg tagtccccgc                                                20

<210> SEQ ID NO 295
<211> LENGTH: 20
<212> TYPE: DNA
<213> ORGANISM: Unknown
<220> FEATURE:
<223> OTHER INFORMATION: Oligonucleotide
```

```
<400> SEQUENCE: 295
tgaccttctc gtagtgaggg                                               20

<210> SEQ ID NO 296
<211> LENGTH: 20
<212> TYPE: DNA
<213> ORGANISM: Unknown
<220> FEATURE:
<223> OTHER INFORMATION: Oligonucleotide

<400> SEQUENCE: 296
cagaagacgc tgtccgcagt                                               20

<210> SEQ ID NO 297
<211> LENGTH: 20
<212> TYPE: DNA
<213> ORGANISM: Unknown
<220> FEATURE:
<223> OTHER INFORMATION: Oligonucleotide

<400> SEQUENCE: 297
ccttagcggg atgataatgt                                               20

<210> SEQ ID NO 298
<211> LENGTH: 20
<212> TYPE: DNA
<213> ORGANISM: Unknown
<220> FEATURE:
<223> OTHER INFORMATION: Oligonucleotide

<400> SEQUENCE: 298
cactgggctc tgagccgttg                                               20

<210> SEQ ID NO 299
<211> LENGTH: 20
<212> TYPE: DNA
<213> ORGANISM: Unknown
<220> FEATURE:
<223> OTHER INFORMATION: Oligonucleotide

<400> SEQUENCE: 299
ttgttgccgc tgcgcttggg                                               20

<210> SEQ ID NO 300
<211> LENGTH: 20
<212> TYPE: DNA
<213> ORGANISM: Unknown
<220> FEATURE:
<223> OTHER INFORMATION: Oligonucleotide

<400> SEQUENCE: 300
tgtggccagt gtgctgagcg                                               20

<210> SEQ ID NO 301
<211> LENGTH: 20
<212> TYPE: DNA
<213> ORGANISM: Unknown
<220> FEATURE:
<223> OTHER INFORMATION: Oligonucleotide

<400> SEQUENCE: 301
acagcgtggt cgtgtgctgc                                               20

<210> SEQ ID NO 302
<211> LENGTH: 20
```

```
<212> TYPE: DNA
<213> ORGANISM: Unknown
<220> FEATURE:
<223> OTHER INFORMATION: Oligonucleotide

<400> SEQUENCE: 302
ggcgagtgct tcctgtgtct                                             20

<210> SEQ ID NO 303
<211> LENGTH: 20
<212> TYPE: DNA
<213> ORGANISM: Unknown
<220> FEATURE:
<223> OTHER INFORMATION: Oligonucleotide

<400> SEQUENCE: 303
cctccggtac ttcagcaaga                                             20

<210> SEQ ID NO 304
<211> LENGTH: 20
<212> TYPE: DNA
<213> ORGANISM: Unknown
<220> FEATURE:
<223> OTHER INFORMATION: Oligonucleotide

<400> SEQUENCE: 304
ggaccaccag cgtgatgatg                                             20

<210> SEQ ID NO 305
<211> LENGTH: 20
<212> TYPE: DNA
<213> ORGANISM: Unknown
<220> FEATURE:
<223> OTHER INFORMATION: Oligonucleotide

<400> SEQUENCE: 305
atgacgatga agatgatgca                                             20

<210> SEQ ID NO 306
<211> LENGTH: 20
<212> TYPE: DNA
<213> ORGANISM: Unknown
<220> FEATURE:
<223> OTHER INFORMATION: Oligonucleotide

<400> SEQUENCE: 306
tcctgaagca atccctgcaa                                             20

<210> SEQ ID NO 307
<211> LENGTH: 20
<212> TYPE: DNA
<213> ORGANISM: Unknown
<220> FEATURE:
<223> OTHER INFORMATION: Oligonucleotide

<400> SEQUENCE: 307
ataaggccac ttcggaaccg                                             20

<210> SEQ ID NO 308
<211> LENGTH: 20
<212> TYPE: DNA
<213> ORGANISM: Unknown
<220> FEATURE:
<223> OTHER INFORMATION: Oligonucleotide

<400> SEQUENCE: 308
```

-continued aggatgttgt tccccgaatg                                                    20

<210> SEQ ID NO 309
<211> LENGTH: 20
<212> TYPE: DNA
<213> ORGANISM: Unknown
<220> FEATURE:
<223> OTHER INFORMATION: Oligonucleotide

<400> SEQUENCE: 309
tccggcgctg ttgccgtctg                                                    20

<210> SEQ ID NO 310
<211> LENGTH: 20
<212> TYPE: DNA
<213> ORGANISM: Unknown
<220> FEATURE:
<223> OTHER INFORMATION: Oligonucleotide

<400> SEQUENCE: 310
tgctagaacc tggatttggt                                                    20

<210> SEQ ID NO 311
<211> LENGTH: 20
<212> TYPE: DNA
<213> ORGANISM: Unknown
<220> FEATURE:
<223> OTHER INFORMATION: Oligonucleotide

<400> SEQUENCE: 311
tttacaaagg gacttgttgt                                                    20

<210> SEQ ID NO 312
<211> LENGTH: 20
<212> TYPE: DNA
<213> ORGANISM: Unknown
<220> FEATURE:
<223> OTHER INFORMATION: Oligonucleotide

<400> SEQUENCE: 312
cgaacttctt ccatttgtac                                                    20

<210> SEQ ID NO 313
<211> LENGTH: 20
<212> TYPE: DNA
<213> ORGANISM: Unknown
<220> FEATURE:
<223> OTHER INFORMATION: Oligonucleotide

<400> SEQUENCE: 313
cagcttctag ttctggacgt                                                    20

<210> SEQ ID NO 314
<211> LENGTH: 20
<212> TYPE: DNA
<213> ORGANISM: Unknown
<220> FEATURE:
<223> OTHER INFORMATION: Oligonucleotide

<400> SEQUENCE: 314
cttgttggat ctttattcct                                                    20

<210> SEQ ID NO 315
<211> LENGTH: 20
<212> TYPE: DNA
<213> ORGANISM: Unknown

```
<220> FEATURE:
<223> OTHER INFORMATION: Oligonucleotide

<400> SEQUENCE: 315
ggttgatcca gcagaacttg                                               20

<210> SEQ ID NO 316
<211> LENGTH: 20
<212> TYPE: DNA
<213> ORGANISM: Unknown
<220> FEATURE:
<223> OTHER INFORMATION: Oligonucleotide

<400> SEQUENCE: 316
catcttgtcc aactttcatg                                               20

<210> SEQ ID NO 317
<211> LENGTH: 20
<212> TYPE: DNA
<213> ORGANISM: Unknown
<220> FEATURE:
<223> OTHER INFORMATION: Oligonucleotide

<400> SEQUENCE: 317
aggatcttca tggctcttgt                                               20

<210> SEQ ID NO 318
<211> LENGTH: 20
<212> TYPE: DNA
<213> ORGANISM: Unknown
<220> FEATURE:
<223> OTHER INFORMATION: Oligonucleotide

<400> SEQUENCE: 318
ctggcacacc cctccctcct                                               20

<210> SEQ ID NO 319
<211> LENGTH: 20
<212> TYPE: DNA
<213> ORGANISM: Unknown
<220> FEATURE:
<223> OTHER INFORMATION: Oligonucleotide

<400> SEQUENCE: 319
ggttatccag gccctccaaa                                               20

<210> SEQ ID NO 320
<211> LENGTH: 20
<212> TYPE: DNA
<213> ORGANISM: Unknown
<220> FEATURE:
<223> OTHER INFORMATION: Oligonucleotide

<400> SEQUENCE: 320
gacccatttg atgtagatat                                               20

<210> SEQ ID NO 321
<211> LENGTH: 20
<212> TYPE: DNA
<213> ORGANISM: Unknown
<220> FEATURE:
<223> OTHER INFORMATION: Oligonucleotide

<400> SEQUENCE: 321
aatgtaataa tctttgttct                                               20
```

```
<210> SEQ ID NO 322
<211> LENGTH: 20
<212> TYPE: DNA
<213> ORGANISM: Unknown
<220> FEATURE:
<223> OTHER INFORMATION: Oligonucleotide

<400> SEQUENCE: 322
tctgaaattc tagaccccag                                                 20

<210> SEQ ID NO 323
<211> LENGTH: 20
<212> TYPE: DNA
<213> ORGANISM: Unknown
<220> FEATURE:
<223> OTHER INFORMATION: Oligonucleotide

<400> SEQUENCE: 323
aggttagggc tgaattcttg                                                 20

<210> SEQ ID NO 324
<211> LENGTH: 20
<212> TYPE: DNA
<213> ORGANISM: Unknown
<220> FEATURE:
<223> OTHER INFORMATION: Oligonucleotide

<400> SEQUENCE: 324
aaacttgatg gtgaatttga                                                 20

<210> SEQ ID NO 325
<211> LENGTH: 20
<212> TYPE: DNA
<213> ORGANISM: Unknown
<220> FEATURE:
<223> OTHER INFORMATION: Oligonucleotide

<400> SEQUENCE: 325
tatcttggtc tggtttggca                                                 20

<210> SEQ ID NO 326
<211> LENGTH: 20
<212> TYPE: DNA
<213> ORGANISM: Unknown
<220> FEATURE:
<223> OTHER INFORMATION: Oligonucleotide

<400> SEQUENCE: 326
cagttgagga gagggtatt                                                  20

<210> SEQ ID NO 327
<211> LENGTH: 20
<212> TYPE: DNA
<213> ORGANISM: Unknown
<220> FEATURE:
<223> OTHER INFORMATION: Oligonucleotide

<400> SEQUENCE: 327
ttccttctta atagtgcatc                                                 20

<210> SEQ ID NO 328
<211> LENGTH: 20
<212> TYPE: DNA
<213> ORGANISM: Unknown
<220> FEATURE:
<223> OTHER INFORMATION: Oligonucleotide
```

```
<400> SEQUENCE: 328
tgtctgcttg gtctttatca                                              20

<210> SEQ ID NO 329
<211> LENGTH: 20
<212> TYPE: DNA
<213> ORGANISM: Unknown
<220> FEATURE:
<223> OTHER INFORMATION: Oligonucleotide

<400> SEQUENCE: 329
accatataaa ctttataata                                              20

<210> SEQ ID NO 330
<211> LENGTH: 20
<212> TYPE: DNA
<213> ORGANISM: Unknown
<220> FEATURE:
<223> OTHER INFORMATION: Oligonucleotide

<400> SEQUENCE: 330
ttcatactgg ccaacagttt                                              20

<210> SEQ ID NO 331
<211> LENGTH: 20
<212> TYPE: DNA
<213> ORGANISM: Unknown
<220> FEATURE:
<223> OTHER INFORMATION: Oligonucleotide

<400> SEQUENCE: 331
tagagtccac tttggggcaa                                              20

<210> SEQ ID NO 332
<211> LENGTH: 20
<212> TYPE: DNA
<213> ORGANISM: Unknown
<220> FEATURE:
<223> OTHER INFORMATION: Oligonucleotide

<400> SEQUENCE: 332
ataatatcca atttgtctcc                                              20

<210> SEQ ID NO 333
<211> LENGTH: 20
<212> TYPE: DNA
<213> ORGANISM: Unknown
<220> FEATURE:
<223> OTHER INFORMATION: Oligonucleotide

<400> SEQUENCE: 333
tatctgtggg tatagtacca                                              20

<210> SEQ ID NO 334
<211> LENGTH: 20
<212> TYPE: DNA
<213> ORGANISM: Unknown
<220> FEATURE:
<223> OTHER INFORMATION: Oligonucleotide

<400> SEQUENCE: 334
gtccttgtcc aggtagaaat                                              20

<210> SEQ ID NO 335
```

```
<211> LENGTH: 20
<212> TYPE: DNA
<213> ORGANISM: Unknown
<220> FEATURE:
<223> OTHER INFORMATION: Oligonucleotide

<400> SEQUENCE: 335
ttggagttcg aggaattcca                                                   20

<210> SEQ ID NO 336
<211> LENGTH: 20
<212> TYPE: DNA
<213> ORGANISM: Unknown
<220> FEATURE:
<223> OTHER INFORMATION: Oligonucleotide

<400> SEQUENCE: 336
atagataggc tctaaaacta                                                   20

<210> SEQ ID NO 337
<211> LENGTH: 20
<212> TYPE: DNA
<213> ORGANISM: Unknown
<220> FEATURE:
<223> OTHER INFORMATION: Oligonucleotide

<400> SEQUENCE: 337
tcgatttgga aatcgcagtt                                                   20

<210> SEQ ID NO 338
<211> LENGTH: 20
<212> TYPE: DNA
<213> ORGANISM: Unknown
<220> FEATURE:
<223> OTHER INFORMATION: Oligonucleotide

<400> SEQUENCE: 338
ctgcataaaa ccatcaaaac                                                   20

<210> SEQ ID NO 339
<211> LENGTH: 20
<212> TYPE: DNA
<213> ORGANISM: Unknown
<220> FEATURE:
<223> OTHER INFORMATION: Oligonucleotide

<400> SEQUENCE: 339
accccagcag tacttccaca                                                   20

<210> SEQ ID NO 340
<211> LENGTH: 20
<212> TYPE: DNA
<213> ORGANISM: Unknown
<220> FEATURE:
<223> OTHER INFORMATION: Oligonucleotide

<400> SEQUENCE: 340
cggagtccct tctcacagcc                                                   20

<210> SEQ ID NO 341
<211> LENGTH: 20
<212> TYPE: DNA
<213> ORGANISM: Unknown
<220> FEATURE:
<223> OTHER INFORMATION: Oligonucleotide

<400> SEQUENCE: 341
```

```
gagtcccttc tcacagccat                                              20

<210> SEQ ID NO 342
<211> LENGTH: 21
<212> TYPE: DNA
<213> ORGANISM: Unknown
<220> FEATURE:
<223> OTHER INFORMATION: Oligonucleotide

<400> SEQUENCE: 342
aactgcgatt ccaaatcga t                                             21

<210> SEQ ID NO 343
<211> LENGTH: 21
<212> TYPE: DNA
<213> ORGANISM: Unknown
<220> FEATURE:
<223> OTHER INFORMATION: Oligonucleotide

<400> SEQUENCE: 343
aactccaaat ttctacctgg a                                            21

<210> SEQ ID NO 344
<211> LENGTH: 21
<212> TYPE: DNA
<213> ORGANISM: Unknown
<220> FEATURE:
<223> OTHER INFORMATION: Oligonucleotide

<400> SEQUENCE: 344
aatttctacc tggacaagga c                                            21

<210> SEQ ID NO 345
<211> LENGTH: 21
<212> TYPE: DNA
<213> ORGANISM: Unknown
<220> FEATURE:
<223> OTHER INFORMATION: Oligonucleotide

<400> SEQUENCE: 345
aaatttctac ctggacaagg a                                            21

<210> SEQ ID NO 346
<211> LENGTH: 21
<212> TYPE: DNA
<213> ORGANISM: Unknown
<220> FEATURE:
<223> OTHER INFORMATION: Oligonucleotide

<400> SEQUENCE: 346
aaggactggt actataccca c                                            21

<210> SEQ ID NO 347
<211> LENGTH: 21
<212> TYPE: DNA
<213> ORGANISM: Unknown
<220> FEATURE:
<223> OTHER INFORMATION: Oligonucleotide

<400> SEQUENCE: 347
aagtggactc taaaactgtt g                                            21

<210> SEQ ID NO 348
<211> LENGTH: 21
<212> TYPE: DNA
```

```
<213> ORGANISM: Unknown
<220> FEATURE:
<223> OTHER INFORMATION: Oligonucleotide

<400> SEQUENCE: 348
aaactgttgg ccagtatgaa t                                              21

<210> SEQ ID NO 349
<211> LENGTH: 21
<212> TYPE: DNA
<213> ORGANISM: Unknown
<220> FEATURE:
<223> OTHER INFORMATION: Oligonucleotide

<400> SEQUENCE: 349
aaaactgttg gccagtatga a                                              21

<210> SEQ ID NO 350
<211> LENGTH: 21
<212> TYPE: DNA
<213> ORGANISM: Unknown
<220> FEATURE:
<223> OTHER INFORMATION: Oligonucleotide

<400> SEQUENCE: 350
aagaccaagc agacagatgc a                                              21

<210> SEQ ID NO 351
<211> LENGTH: 21
<212> TYPE: DNA
<213> ORGANISM: Unknown
<220> FEATURE:
<223> OTHER INFORMATION: Oligonucleotide

<400> SEQUENCE: 351
aaagaccaag cagacagatg c                                              21

<210> SEQ ID NO 352
<211> LENGTH: 21
<212> TYPE: DNA
<213> ORGANISM: Unknown
<220> FEATURE:
<223> OTHER INFORMATION: Oligonucleotide

<400> SEQUENCE: 352
aagtttcaag aattcagccc t                                              21

<210> SEQ ID NO 353
<211> LENGTH: 21
<212> TYPE: DNA
<213> ORGANISM: Unknown
<220> FEATURE:
<223> OTHER INFORMATION: Oligonucleotide

<400> SEQUENCE: 353
aagaattcag ccctaacctc t                                              21

<210> SEQ ID NO 354
<211> LENGTH: 21
<212> TYPE: DNA
<213> ORGANISM: Unknown
<220> FEATURE:
<223> OTHER INFORMATION: Oligonucleotide

<400> SEQUENCE: 354
aattcagccc taacctctgg g                                              21
```

```
<210> SEQ ID NO 355
<211> LENGTH: 21
<212> TYPE: DNA
<213> ORGANISM: Unknown
<220> FEATURE:
<223> OTHER INFORMATION: Oligonucleotide

<400> SEQUENCE: 355
aactgtgcca aaccagacca a                                              21

<210> SEQ ID NO 356
<211> LENGTH: 21
<212> TYPE: DNA
<213> ORGANISM: Unknown
<220> FEATURE:
<223> OTHER INFORMATION: Oligonucleotide

<400> SEQUENCE: 356
aaatgggtct tggagggcc t                                               21

<210> SEQ ID NO 357
<211> LENGTH: 21
<212> TYPE: DNA
<213> ORGANISM: Unknown
<220> FEATURE:
<223> OTHER INFORMATION: Oligonucleotide

<400> SEQUENCE: 357
aagatcctca tgaaagttgg a                                              21

<210> SEQ ID NO 358
<211> LENGTH: 21
<212> TYPE: DNA
<213> ORGANISM: Unknown
<220> FEATURE:
<223> OTHER INFORMATION: Oligonucleotide

<400> SEQUENCE: 358
aaagttggac aagatgcaag t                                              21

<210> SEQ ID NO 359
<211> LENGTH: 21
<212> TYPE: DNA
<213> ORGANISM: Unknown
<220> FEATURE:
<223> OTHER INFORMATION: Oligonucleotide

<400> SEQUENCE: 359
aagagccatg aagatcctca t                                              21

<210> SEQ ID NO 360
<211> LENGTH: 21
<212> TYPE: DNA
<213> ORGANISM: Unknown
<220> FEATURE:
<223> OTHER INFORMATION: Oligonucleotide

<400> SEQUENCE: 360
aagttggaca agatgcaagt t                                              21

<210> SEQ ID NO 361
<211> LENGTH: 21
<212> TYPE: DNA
<213> ORGANISM: Unknown
<220> FEATURE:
```

```
<223> OTHER INFORMATION: Oligonucleotide

<400> SEQUENCE: 361
aagatgcaag ttctgctgga t                                              21

<210> SEQ ID NO 362
<211> LENGTH: 21
<212> TYPE: DNA
<213> ORGANISM: Unknown
<220> FEATURE:
<223> OTHER INFORMATION: Oligonucleotide

<400> SEQUENCE: 362
aagttctgct ggatcaacca g                                              21

<210> SEQ ID NO 363
<211> LENGTH: 21
<212> TYPE: DNA
<213> ORGANISM: Unknown
<220> FEATURE:
<223> OTHER INFORMATION: Oligonucleotide

<400> SEQUENCE: 363
aaccaggaat aaagatccaa c                                              21

<210> SEQ ID NO 364
<211> LENGTH: 21
<212> TYPE: DNA
<213> ORGANISM: Unknown
<220> FEATURE:
<223> OTHER INFORMATION: Oligonucleotide

<400> SEQUENCE: 364
aaagatccaa caagacgtcc a                                              21

<210> SEQ ID NO 365
<211> LENGTH: 21
<212> TYPE: DNA
<213> ORGANISM: Unknown
<220> FEATURE:
<223> OTHER INFORMATION: Oligonucleotide

<400> SEQUENCE: 365
aagatccaac aagacgtcca g                                              21

<210> SEQ ID NO 366
<211> LENGTH: 21
<212> TYPE: DNA
<213> ORGANISM: Unknown
<220> FEATURE:
<223> OTHER INFORMATION: Oligonucleotide

<400> SEQUENCE: 366
aacaagacgt ccagaactag a                                              21

<210> SEQ ID NO 367
<211> LENGTH: 21
<212> TYPE: DNA
<213> ORGANISM: Unknown
<220> FEATURE:
<223> OTHER INFORMATION: Oligonucleotide

<400> SEQUENCE: 367
aagacgtcca gaactagaag c                                              21
```

```
<210> SEQ ID NO 368
<211> LENGTH: 21
<212> TYPE: DNA
<213> ORGANISM: Unknown
<220> FEATURE:
<223> OTHER INFORMATION: Oligonucleotide

<400> SEQUENCE: 368
aaatggaaga agttcgacaa c                                              21

<210> SEQ ID NO 369
<211> LENGTH: 21
<212> TYPE: DNA
<213> ORGANISM: Unknown
<220> FEATURE:
<223> OTHER INFORMATION: Oligonucleotide

<400> SEQUENCE: 369
aactagaagc tggtacaaat g                                              21

<210> SEQ ID NO 370
<211> LENGTH: 21
<212> TYPE: DNA
<213> ORGANISM: Unknown
<220> FEATURE:
<223> OTHER INFORMATION: Oligonucleotide

<400> SEQUENCE: 370
aatggaagaa gttcgacaac a                                              21

<210> SEQ ID NO 371
<211> LENGTH: 21
<212> TYPE: DNA
<213> ORGANISM: Unknown
<220> FEATURE:
<223> OTHER INFORMATION: Oligonucleotide

<400> SEQUENCE: 371
aagctggtac aaatggaaga a                                              21

<210> SEQ ID NO 372
<211> LENGTH: 21
<212> TYPE: DNA
<213> ORGANISM: Unknown
<220> FEATURE:
<223> OTHER INFORMATION: Oligonucleotide

<400> SEQUENCE: 372
aacaagtccc tttgtaaaac c                                              21

<210> SEQ ID NO 373
<211> LENGTH: 21
<212> TYPE: DNA
<213> ORGANISM: Unknown
<220> FEATURE:
<223> OTHER INFORMATION: Oligonucleotide

<400> SEQUENCE: 373
aagaagttcg acaacaagtc c                                              21

<210> SEQ ID NO 374
<211> LENGTH: 21
<212> TYPE: DNA
<213> ORGANISM: Unknown
<220> FEATURE:
<223> OTHER INFORMATION: Oligonucleotide
```

```
<400> SEQUENCE: 374
aagttcgaca acaagtccct t                                              21

<210> SEQ ID NO 375
<211> LENGTH: 21
<212> TYPE: DNA
<213> ORGANISM: Unknown
<220> FEATURE:
<223> OTHER INFORMATION: Oligonucleotide

<400> SEQUENCE: 375
aaaaccaaat ccaggttcta g                                              21

<210> SEQ ID NO 376
<211> LENGTH: 21
<212> TYPE: DNA
<213> ORGANISM: Unknown
<220> FEATURE:
<223> OTHER INFORMATION: Oligonucleotide

<400> SEQUENCE: 376
aaaccaaatc caggttctag c                                              21

<210> SEQ ID NO 377
<211> LENGTH: 21
<212> TYPE: DNA
<213> ORGANISM: Unknown
<220> FEATURE:
<223> OTHER INFORMATION: Oligonucleotide

<400> SEQUENCE: 377
aaccaaatcc aggttctagc a                                              21

<210> SEQ ID NO 378
<211> LENGTH: 21
<212> TYPE: DNA
<213> ORGANISM: Unknown
<220> FEATURE:
<223> OTHER INFORMATION: Oligonucleotide

<400> SEQUENCE: 378
aaatccaggt tctagcacag a                                              21

<210> SEQ ID NO 379
<211> LENGTH: 21
<212> TYPE: DNA
<213> ORGANISM: Unknown
<220> FEATURE:
<223> OTHER INFORMATION: Oligonucleotide

<400> SEQUENCE: 379
aatccaggtt ctagcacaga c                                              21

<210> SEQ ID NO 380
<211> LENGTH: 21
<212> TYPE: DNA
<213> ORGANISM: Unknown
<220> FEATURE:
<223> OTHER INFORMATION: Oligonucleotide

<400> SEQUENCE: 380
aacaacatcc tcggttccga a                                              21

<210> SEQ ID NO 381
<211> LENGTH: 21
```

```
<212> TYPE: DNA
<213> ORGANISM: Unknown
<220> FEATURE:
<223> OTHER INFORMATION: Oligonucleotide

<400> SEQUENCE: 381
aacatcctcg gttccgaagt g                                                  21

<210> SEQ ID NO 382
<211> LENGTH: 21
<212> TYPE: DNA
<213> ORGANISM: Unknown
<220> FEATURE:
<223> OTHER INFORMATION: Oligonucleotide

<400> SEQUENCE: 382
aagtggcctt atttgcaggg a                                                  21

<210> SEQ ID NO 383
<211> LENGTH: 21
<212> TYPE: RNA
<213> ORGANISM: Unknown
<220> FEATURE:
<223> OTHER INFORMATION: Oligonucleotide

<400> SEQUENCE: 383
gcagacagau gcacuauuau u                                                  21

<210> SEQ ID NO 384
<211> LENGTH: 21
<212> TYPE: RNA
<213> ORGANISM: Unknown
<220> FEATURE:
<223> OTHER INFORMATION: Oligonucleotide

<400> SEQUENCE: 384
cugcgauuuc caaaucgauu u                                                  21

<210> SEQ ID NO 385
<211> LENGTH: 21
<212> TYPE: RNA
<213> ORGANISM: Unknown
<220> FEATURE:
<223> OTHER INFORMATION: Oligonucleotide

<400> SEQUENCE: 385
ggacugguac uauacccacu u                                                  21

<210> SEQ ID NO 386
<211> LENGTH: 570
<212> TYPE: PRT
<213> ORGANISM: Unknown
<220> FEATURE:
<223> OTHER INFORMATION: Recombinant B4ECv3 protein

<400> SEQUENCE: 386
```

Met Glu Leu Arg Val Leu Leu Cys Trp Ala Ser Leu Ala Ala Ala Leu
1 5 10 15

Glu Glu Thr Leu Leu Asn Thr Lys Leu Glu Thr Ala Asp Leu Lys Trp
20 25 30

Val Thr Phe Pro Gln Val Asp Gly Gln Trp Glu Glu Leu Ser Gly Leu
35 40 45

Asp Glu Glu Gln His Ser Val Arg Thr Tyr Glu Val Cys Glu Val Gln
50 55 60

-continued

```
Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                 85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
```

```
                485                 490                 495
Leu Lys Arg Gly Ala Ser Tyr Leu Val Gln Val Arg Ala Arg Ser Glu
            500                 505                 510
Ala Gly Tyr Gly Pro Phe Gly Gln Glu His His Ser Gln Thr Gln Leu
        515                 520                 525
Asp Glu Ser Glu Gly Trp Arg Glu Gln Gly Ser Lys Arg Ala Ile Leu
    530                 535                 540
Gln Ile Glu Gly Lys Pro Ile Pro Asn Pro Leu Leu Gly Leu Asp Ser
545                 550                 555                 560
Thr Arg Thr Gly His His His His His His
                565                 570

<210> SEQ ID NO 387
<211> LENGTH: 555
<212> TYPE: PRT
<213> ORGANISM: Unknown
<220> FEATURE:
<223> OTHER INFORMATION: Recombinant B4ECv3NT protein

<400> SEQUENCE: 387

Met Glu Leu Arg Val Leu Leu Cys Trp Ala Ser Leu Ala Ala Ala Leu
1               5                   10                  15
Glu Glu Thr Leu Leu Asn Thr Lys Leu Glu Thr Ala Asp Leu Lys Trp
            20                  25                  30
Val Thr Phe Pro Gln Val Asp Gly Gln Trp Glu Glu Leu Ser Gly Leu
        35                  40                  45
Asp Glu Glu Gln His Ser Val Arg Thr Tyr Glu Val Cys Glu Val Gln
    50                  55                  60
Arg Ala Pro Gly Gln Ala His Trp Leu Arg Thr Gly Trp Val Pro Arg
65                  70                  75                  80
Arg Gly Ala Val His Val Tyr Ala Thr Leu Arg Phe Thr Met Leu Glu
                85                  90                  95
Cys Leu Ser Leu Pro Arg Ala Gly Arg Ser Cys Lys Glu Thr Phe Thr
            100                 105                 110
Val Phe Tyr Tyr Glu Ser Asp Ala Asp Thr Ala Thr Ala Leu Thr Pro
        115                 120                 125
Ala Trp Met Glu Asn Pro Tyr Ile Lys Val Asp Thr Val Ala Ala Glu
    130                 135                 140
His Leu Thr Arg Lys Arg Pro Gly Ala Glu Ala Thr Gly Lys Val Asn
145                 150                 155                 160
Val Lys Thr Leu Arg Leu Gly Pro Leu Ser Lys Ala Gly Phe Tyr Leu
                165                 170                 175
Ala Phe Gln Asp Gln Gly Ala Cys Met Ala Leu Leu Ser Leu His Leu
            180                 185                 190
Phe Tyr Lys Lys Cys Ala Gln Leu Thr Val Asn Leu Thr Arg Phe Pro
        195                 200                 205
Glu Thr Val Pro Arg Glu Leu Val Val Pro Val Ala Gly Ser Cys Val
    210                 215                 220
Val Asp Ala Val Pro Ala Pro Gly Pro Ser Pro Ser Leu Tyr Cys Arg
225                 230                 235                 240
Glu Asp Gly Gln Trp Ala Glu Gln Pro Val Thr Gly Cys Ser Cys Ala
                245                 250                 255
Pro Gly Phe Glu Ala Ala Glu Gly Asn Thr Lys Cys Arg Ala Cys Ala
            260                 265                 270
Gln Gly Thr Phe Lys Pro Leu Ser Gly Glu Gly Ser Cys Gln Pro Cys
```

```
                275                 280                 285
Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Ser Ser Thr Val Ala Ala Ala Arg Val
545                 550                 555

<210> SEQ ID NO 388
<211> LENGTH: 233
<212> TYPE: PRT
<213> ORGANISM: Unknown
<220> FEATURE:
<223> OTHER INFORMATION: Recombinant B2EC protein

<400> SEQUENCE: 388

Met Ala Val Arg Arg Asp Ser Val Trp Lys Tyr Cys Trp Gly Val Leu
1               5                   10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
```

```
                85                  90                  95
Pro Leu Leu Asn Cys Ala Lys Pro Asp Gln Asp Ile Lys Phe Thr Ile
            100                 105                 110
Lys Phe Gln Glu Phe Ser Pro Asn Leu Trp Gly Leu Glu Phe Gln Lys
            115                 120                 125
Asn Lys Asp Tyr Tyr Ile Ile Ser Thr Ser Asn Gly Ser Leu Glu Gly
            130                 135                 140
Leu Asp Asn Gln Glu Gly Gly Val Cys Gln Thr Arg Ala Met Lys Ile
145                 150                 155                 160
Leu Met Lys Val Gly Gln Asp Ala Ser Ser Ala Gly Ser Thr Arg Asn
                165                 170                 175
Lys Asp Pro Thr Arg Arg Pro Glu Leu Glu Ala Gly Thr Asn Gly Arg
            180                 185                 190
Ser Ser Thr Thr Ser Pro Phe Val Lys Pro Asn Pro Gly Ser Ser Thr
            195                 200                 205
Asp Gly Asn Ser Ala Gly His Ser Gly Asn Asn Ile Leu Gly Ser Glu
            210                 215                 220
Val Gly Ser His His His His His His
225                 230

<210> SEQ ID NO 389
<211> LENGTH: 771
<212> TYPE: PRT
<213> ORGANISM: Unknown
<220> FEATURE:
<223> OTHER INFORMATION: Recombinant B4ECv3-FC protein

<400> SEQUENCE: 389

Met Glu Leu Arg Val Leu Leu Cys Trp Ala Ser Leu Ala Ala Ala Leu
1               5                   10                  15
Glu Glu Thr Leu Leu Asn Thr Lys Leu Glu Thr Ala Asp Leu Lys Trp
            20                  25                  30
Val Thr Phe Pro Gln Val Asp Gly Gln Trp Glu Glu Leu Ser Gly Leu
            35                  40                  45
Asp Glu Glu Gln His Ser Val Arg Thr Tyr Glu Val Cys Glu Val Gln
50                  55                  60
Arg Ala Pro Gly Gln Ala His Trp Leu Arg Thr Gly Trp Val Pro Arg
65                  70                  75                  80
Arg Gly Ala Val His Val Tyr Ala Thr Leu Arg Phe Thr Met Leu Glu
                85                  90                  95
Cys Leu Ser Leu Pro Arg Ala Gly Arg Ser Cys Lys Glu Thr Phe Thr
            100                 105                 110
Val Phe Tyr Tyr Glu Ser Asp Ala Asp Thr Ala Thr Ala Leu Thr Pro
            115                 120                 125
Ala Trp Met Glu Asn Pro Tyr Ile Lys Val Asp Thr Val Ala Ala Glu
            130                 135                 140
His Leu Thr Arg Lys Arg Pro Gly Ala Glu Ala Thr Gly Lys Val Asn
145                 150                 155                 160
Val Lys Thr Leu Arg Leu Gly Pro Leu Ser Lys Ala Gly Phe Tyr Leu
                165                 170                 175
Ala Phe Gln Asp Gln Gly Ala Cys Met Ala Leu Leu Ser Leu His Leu
            180                 185                 190
Phe Tyr Lys Lys Cys Ala Gln Leu Thr Val Asn Leu Thr Arg Phe Pro
            195                 200                 205
Glu Thr Val Pro Arg Glu Leu Val Val Pro Val Ala Gly Ser Cys Val
```

-continued

```
                210                 215                 220
Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
                260                 265                 270

Gln Gly Thr Phe Lys Pro Leu Ser Gly Glu Gly Ser Cys Gln Pro Cys
                275                 280                 285

Pro Ala Asn Ser His Ser Asn Thr Ile Gly Ser Ala Val Cys Gln Cys
                290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
                340                 345                 350

Glu Asp Leu Thr Tyr Ala Leu Arg Cys Arg Glu Cys Arg Pro Gly Gly
                355                 360                 365

Ser Cys Ala Pro Cys Gly Gly Asp Leu Thr Phe Asp Pro Gly Pro Arg
370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
                420                 425                 430

Val Pro Pro Ala Val Ser Asp Ile Arg Val Thr Arg Ser Ser Pro Ser
                435                 440                 445

Ser Leu Ser Leu Ala Trp Ala Val Pro Arg Ala Pro Ser Gly Ala Trp
                450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
                500                 505                 510

Ala Gly Tyr Gly Pro Phe Gly Gln Glu His His Ser Gln Thr Gln Leu
                515                 520                 525

Asp Glu Ser Glu Gly Trp Arg Glu Gln Asp Pro Glu Pro Lys Ser Cys
                530                 535                 540

Asp Lys Thr His Thr Cys Pro Pro Cys Pro Ala Pro Glu Leu Leu Gly
545                 550                 555                 560

Gly Pro Ser Val Phe Leu Phe Pro Pro Lys Pro Lys Asp Thr Leu Met
                565                 570                 575

Ile Ser Arg Thr Pro Glu Val Thr Cys Val Val Val Asp Val Ser His
                580                 585                 590

Glu Asp Pro Glu Val Lys Phe Asn Trp Tyr Val Asp Gly Val Glu Val
                595                 600                 605

His Asn Ala Lys Thr Lys Pro Arg Glu Glu Gln Tyr Asn Ser Thr Tyr
                610                 615                 620

Arg Val Val Ser Val Leu Thr Val Leu His Gln Asp Trp Leu Asn Gly
625                 630                 635                 640
```

```
Lys Glu Tyr Lys Cys Lys Val Ser Asn Lys Ala Leu Pro Ala Pro Ile
                645                 650                 655
Glu Lys Thr Ile Ser Lys Ala Lys Gly Gln Pro Arg Glu Pro Gln Val
            660                 665                 670
Tyr Thr Leu Pro Pro Ser Arg Asp Glu Leu Thr Lys Asn Gln Val Ser
        675                 680                 685
Leu Thr Cys Leu Val Lys Gly Phe Tyr Pro Ser Asp Ile Ala Val Glu
    690                 695                 700
Trp Glu Ser Asn Gly Gln Pro Glu Asn Asn Tyr Lys Thr Thr Pro Pro
705                 710                 715                 720
Val Leu Asp Ser Asp Gly Ser Phe Phe Leu Tyr Ser Lys Leu Thr Val
                725                 730                 735
Asp Lys Ser Arg Trp Gln Gln Gly Asn Val Phe Ser Cys Ser Val Met
            740                 745                 750
His Glu Ala Leu His Asn His Tyr Thr Gln Lys Ser Leu Ser Leu Ser
        755                 760                 765
Pro Gly Lys
    770

<210> SEQ ID NO 390
<211> LENGTH: 459
<212> TYPE: PRT
<213> ORGANISM: Unknown
<220> FEATURE:
<223> OTHER INFORMATION: Recombinant B2EC-FC protein

<400> SEQUENCE: 390

Met Ala Val Arg Arg Asp Ser Val Trp Lys Tyr Cys Trp Gly Val Leu
 1               5                  10                  15
Met Val Leu Cys Arg Thr Ala Ile Ser Lys Ser Ile Val Leu Glu Pro
            20                  25                  30
Ile Tyr Trp Asn Ser Ser Asn Ser Lys Phe Leu Pro Gly Gln Gly Leu
        35                  40                  45
Val Leu Tyr Pro Gln Ile Gly Asp Lys Leu Asp Ile Ile Cys Pro Lys
50                  55                  60
Val Asp Ser Lys Thr Val Gly Gln Tyr Glu Tyr Tyr Lys Val Tyr Met
65                  70                  75                  80
Val Asp Lys Asp Gln Ala Asp Arg Cys Thr Ile Lys Lys Glu Asn Thr
                85                  90                  95
Pro Leu Leu Asn Cys Ala Lys Pro Asp Gln Asp Ile Lys Phe Thr Ile
            100                 105                 110
Lys Phe Gln Glu Phe Ser Pro Asn Leu Trp Gly Leu Glu Phe Gln Lys
        115                 120                 125
Asn Lys Asp Tyr Tyr Ile Ile Ser Thr Ser Asn Gly Ser Leu Glu Gly
    130                 135                 140
Leu Asp Asn Gln Glu Gly Gly Val Cys Gln Thr Arg Ala Met Lys Ile
145                 150                 155                 160
Leu Met Lys Val Gly Gln Asp Ala Ser Ser Ala Gly Ser Thr Arg Asn
                165                 170                 175
Lys Asp Pro Thr Arg Arg Pro Glu Leu Glu Ala Gly Thr Asn Gly Arg
            180                 185                 190
Ser Ser Thr Thr Ser Pro Phe Val Lys Pro Asn Pro Gly Ser Ser Thr
        195                 200                 205
Asp Gly Asn Ser Ala Gly His Ser Gly Asn Asn Ile Leu Gly Ser Glu
    210                 215                 220
```

Val Asp Pro Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
            245                 250                 255

Pro Lys Pro Lys Asp Thr Leu Met Ile Ser Arg Thr Pro Glu Val Thr
        260                 265                 270

Cys Val Val Val Asp Val Ser His Glu Asp Pro Glu Val Lys Phe Asn
    275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 391
<211> LENGTH: 26000
<212> TYPE: DNA
<213> ORGANISM: Homo sapiens

<400> SEQUENCE: 391 gggg tttcat catgttggcc aggctggtct tgaactcctg acctcaaatg atccgcctgc    60
ctctgcctcc caaaatgctg ggactacagg cgtgagccac cgcgcccgcc acacccacct   120
tttctttacc gttgtttcct cgattttct ctactcccta gcgcagctta gtgcgcgcct    180
cctctggaca ttttcaggg cttggttgcg cgcacagtag gtccccaaca ctgaatgttt    240
atggggtgac tgtgtgaacg ttcgctgcaa ggctatccaa actgggattg ctccttgagg   300
ccccctgggc ggccgtcaat tctccaaagc ttctactccc ttttccttcc ttttccccca   360
aaacgcagtc cctgcgccca ctagagggtg gtgggcgcat ccaagagcgg catctagagt   420
ccgcagcaag gtcagagcgg gctttgtgtg cgcggtgaac atttacgtgc acgcctgggc   480
ggccctccgt gttgctgctg ggtgtgtgtt ttctctgctc cctggtgcca gccgggttcg   540
ggcctgtccc gggggtccct gggccccagc ccgacatgc tcggtcctgg acagcgcgca    600
ccgccacggc gcacatctgg gcggtcccgg ggttcctcac ccgccgcccc tccccttct    660 ccaaactttc tctcaacttc ccgacctgct ccactcggtg cccctctccg cttccctcat   720
gaattattca gtagcgtgag ctccaatcag cgcgcccggg gctcactcgc ggagcccccg   780

-continued

```
cgttgggaga gctgcccccg ccccccgcgc gccccctccct cccgggcccg gcgccgcccg    840
gcccagttcc agcgcagctc agcccctgcc cggcccggcc cgcccggctc cgcgccgcag    900
tctccctccc tcccgctccg tcccgctcg ggctccacc atcccgccc gcgaggagag    960
cactcggccc ggcggcgcga gcagagccac tccagggagg gggggagacc gcgagcggcc   1020
ggctcagccc ccgccacccg gggcgggacc ccgaggcccc ggagggaccc caactccagc   1080
cacgtcttgc tgcgcgcccg cccggcgcgg ccactgccag cacgctccgg gcccgccgcc   1140
cgcgcgcgcg gcacagacgc ggggccacac ttggcgccgc cgcccggtgc cccgcacgct   1200
cgcatgggcc cgcgctgagg gccccgacga ggagtcccgc gcggagtatc ggcgtccacc   1260
cgcccaggga gagtcagacc tgggggggcg agggccccc aaactcagtt cggatcctac   1320
ccgagtgagg cggcgccatg gagctccggg tgctgctctg ctgggcttcg ttggccgcag   1380
ctttggaagg tgagtttcct tgcggggggg ggcgcacccc gtcactcctg gacctcccc   1440
cccaacatct gggcctcgga gtggaggggc cggcctctga ctacccctac ccgggcactg   1500
cagtcccaaa cacttcggac cgatagtgct ggaacgggag gggggcgggg aagaggcgcc   1560
cgacgggtag tggagttttc ttttgtttgg gaaagagatg gagtctggct acgacccggg   1620
acattcccct gcccgggctc cccgaactct cactgctgat tacatacgcc cctggctgcc   1680
tttcctttcc tccctacccc actattcaaa actatctgca aagtttctgt cccagtccca   1740
cctcccgccg tacatgaggg aaggtttctg gagaagcaac agcagacaag gcacaacttt   1800
tcgtgctagg ccctaaaacg accccgcg ccaattcctt agcgatcaca ccttgatcct   1860
ccagttccac actcctgcaa caggatggcc tcctttgcat tcacacagca aaccccaaa   1920
ccgctctccc gcccactgct cctgcccctg gtataggtg gctccttggt ttctacaggc   1980
tgcaccccat ccctttaaat gcggtctaga ccccggcccc aggtgagtcc cgggcttccc   2040
ttgagaccta ggagcgggta gaaactgacc tacacagccc ccaggtagaa actgacctac   2100
acagccccca catcgcccta actaacccag tctatctccc acctcctggt ctctccaagc   2160
atttctttgg ccatggatcg ctgtccctcc tggtcccta aagggggagc caagagccct   2220
agaaactctc ctgtgtccct aatgtccttt cagtgagctg ccaacacccc cctttctctg   2280
tctggtatga aagtggttat ggggcggtag gctatgaggg actcccaaag gaaggattc    2340
agcggcgtta gaaaaaccct ctcccccctgg ctgggcagga ctgccctggg ctggggatca   2400
aaggctaggt gtggggttgg gagtgagggg aggcttgccc agctcagaga acggagaagg   2460
gggaacaaaa accatgaacg agggagag gaaggccaaa ggggtggaaa aaccacgagg   2520
acgaggtgtg gtgagaagga aagacgcaaa gaggaaatgg tgattgtgac acctattacc   2580
tgagtgtttc caagcaccag gcctgtgctg agcgccttac aaatattaat ttcacccatc   2640
cagcaacgct aagggtggtg ctattattgc ccccattttt cagatgagga ggctggggct   2700
tagttaaggt taagtagttt atccaaggcc ctgtgccgcg aggaacagcg agaagtggag   2760
gccgaaagcg aaggagagat agtgactgtc agaaagagaa acggaggtgg acagagagtg   2820
gaggagagat aggtgagaga catgcgaact gacagatcaa agcgtggctg cagctgagct   2880
gggacgcaga aagggagcct gcgcttgctc tgggctgcgg acagcccgag gcagagacag   2940
tgtgtaaatt ggagacagga aaacactatc ccggctggaa caatggaggg tggagacggc   3000
agcctctatc caccccttc ccagaacccg ggcatcctgt ccccagtgag cagggctgtc   3060
tcttgccacc catggggacc ttgcgcctct cacctcaggc tggctggctt ccatctgac    3120
```

```
ccctagctgg aggacatcat ttggtcccca ggaagaggct gcctcaccca ccctctttct   3180
cttctctcct gcagctccca tggggtggga gccaggtgtt ctggctcccc tctccaccct   3240
tcccagcgcc caatgccccc cacattgccg gcccccgagg ggattcctgt accctccctc   3300
ctccactctc cactgccagg ggctgtgcag ttttcctaa tcccccccct tcctccagtg    3360
cctgtcccct cccccgatga tccgagccaa gccaggtgtg ttcacccctc ccattcatac   3420
cgccccccag aatctcctcc cctctgcctt cccataacca aatccagatg tgaggcctcg   3480
gcgggagcct gggaaccta gcatcccgac ctccagtgct tcctgatcag ggcactcgtg    3540
gggagggagg tactgggatg ggggccaggg ctatgcccca ggcacggagc gctcccttca   3600
aggagggaag gacgggtgt ttggtctgaa agcagagagg ggtcttggac agggaatgaa    3660
attgtggggt agagaggctg attctgggac ttaggggagg aaacgtggag gctgagacaa   3720
gaggttcccc tcccacacca gcagcctctg ctcgtggggg tcaggaccag ggcgcagctc   3780
tcattttaac cctttctgag ctgccgcccc ttctccccgt acattttgat ctccctccct   3840
cctccaggga ggcctagatc tggggtatcc caagggagcc ccatgcctac cagatgttgg   3900
gggtgggtt ggcacttagc agaagaggcc agaaatcagg cgggtgcaga gggcagggct    3960
tgctcccctc ttggcccccc aactcctcta gctcagagct aagaggatcc acctgcctcg   4020
gttcccaggg atctggtctt cctgacctcc ctccccacc ccaggcactg actctgtctc    4080
tctgtctgtc tcagagaccc tgctgaacac aaaattggaa actgctgatc tgaagtgggt   4140
gacattccct caggtggacg ggcaggtgag agctgcaccc aggagctgga gctctggagg   4200
gaaactgagg gaggagaggg cgcctgtgcc gcctgctttc tgtgtgccac tcctctcccc   4260
tgtccccca gatgacagca gccccagcag tgtcgtctga gcccttctca gaggcgccct    4320
cctcgcagta ccagcagccc cccttctca gtccctctca ctttatagga ttcacccat    4380
gcagccctct ccctggcggc tccccagccc ccttgctgac ctccttctct gcacagtggg   4440
aggaactgag cggcctggat gaggaacagc acagcgtgcg cacctacgaa gtgtgtgacg   4500
tgcagcgtgc cccgggccag gcccactggc ttcgcacagg ttgggtccca cggcggggcg   4560
ccgtccacgt gtacgccacg ctgcgcttca ccatgctcga gtgcctgtcc ctgcctcggg   4620
ctgggcgctc ctgcaaggag accttcaccg tcttctacta tgagagcgat gcggacacgg   4680
ccacggccct cacgccagcc tggatggaga acccctacat caaggtacct gggtgccccc   4740
agggctcagc cacagccaag gtgggattcc agccagcagg cccgtggcct ggagggcagc   4800
cgatgtagtt gcgaggcctc tggcccgcgc gctgggggct ggaagcagga ggcttaggtc   4860
tggggaggga agggggtgat cttctgggcg gaggagcaga atatacgggg gctgcctggc   4920
ccggcccca gggaggccca agggtcaggc ttctcctcca gtcacctcaa ccaccctacc    4980
ccactgtgct ccagccacac tgagtttctc ccattccctg actgcacctg gctggtttcc   5040
agctcaagac tttgcagcgg tgatgtctcc acctgggggc ctctctgcct ctcacacccc   5100
tacttgtctt cggagttcca gctcccgaga tcttgcctgt gccaccttgg ctgactctct   5160
cctcccctaca atcctgcata cctctgtcca cctgcctgtc tcggcactca tttactttta   5220
tttatttttc ttttatatct atattttaa agcggggtct tctacgttac ccaggctggt   5280
ctctaactcc tgggctcaag agattctccc cacctcggcc tcctaaagtg ctgggattat   5340
aggcatgagg cactacgccc ggcctcatgg tactttataa cttccccagg attcattcat   5400
cgctgtctcc ttgactctga ggtcaaggcc tggcatggcg tcagtgtcag taaatgtttg   5460
tagaacgagt gaataaaaag ggggagaggt gcaggccaga ggccgggcat atcgcaggag   5520
```

```
ctttgcaagg ctgaatggac agtgtggggg cctgcagaaa gtgtgccctg ggaaggtgg    5580
agggaagatt ctggaacggg aaccaaggag gtccgggagg gtgagctggg aagaacacaa   5640
cagtccgctg ggtcctcagg gagtggggac agcagcggtg tgcctccccc ccgccggcag   5700
gtggacacgg tggccgcgga gcatctcacc cggaagcgcc ctgggccga ggccaccggg    5760
aaggtgaatg tcaagacgct gcgtctggga ccgctcagca aggctggctt ctacctggcc   5820
ttccaggacc agggtgcctg catggccctg ctatccctgc acctcttcta caaaaagtgc   5880
gcccagctga ctgtgaacct gactcgattc ccggagactg tgcctcggga gctggttgtg   5940
cccgtggccg gtagctgcgt ggtggatgcc gtccccgccc ctggcccag ccccagcctc    6000
tactgccgtg aggatggcca gtgggccgaa cagccggtca cgggctgcag ctgtgctccg   6060
gggttcgagg cagctgaggg gaacaccaag tgccgaggtg agagctggag cttcccctgc   6120
gactgctgct catccggggg agagtcctga actccactca ggacccactt cttaagtttc   6180
cattttgtat agttagatgt tgaaatggag gcttgctctg tcacccaggc tggagtgcag   6240
tggcacaatc tctgctcaac tgcaaccttt gcctcccggg tccctgttca agcagttctc   6300
ctgcctcagc ctcgtgagta gctgggacta caggcacacg ccaccacgcc cggctaattt   6360
ttgtatttta gtagagacgg ggtttcgcca tgttggccag gctggtctcg aactcctgac   6420
ctgaagtgat ttgcccgcct cggcctccca aagtgctggg attacaggcg tgcgtcacca   6480
cacccagctg gaaaaaaaaa agactttatt ttcacctgaa attcattaat ttccacttga   6540
aattccacct gcagttgtag caggacctga cacttgggcc ccatggaaat cacaggtatt   6600
gcctgacaca gtggttcatg cccatagtgc cagcactttg agatgccaag gtgggaggat   6660
cacttgagcc caggagttcg agatcagcct gggtgacaga gcaagacccc gtctctaaaa   6720
aaaattttt tttttttttc aagacagagt cttgctctgt cgcccaggct ggagtgcagt   6780
ggtgcgatct cggctcactg caagctccgc ctcccaagtt aacaccattc tcctgcctca   6840
gcctcccgag tagctgggac tacaggcccc gccaccacgc ccggctaatt tcttgtattt   6900
ttagtagaga tggagtttca ccgtgttagc caggatggtc tcgatctcct gacctcatga   6960
tctgcccgcc ttggcctccc aaagtgctgg gattacaggt gtgagccacc acacccggat   7020
tacaaaaact ttttagataa ttatctgggc gacctgcctg accaacatgg agaaccctg    7080
tctctactaa aaatacaaaa ttagccggac atggtggcgc atgcctgtaa tcccagctac   7140
ttgggaggct gaggcaggag aatcatttga acccaggaag cagaggttgc ggtaagccga   7200
gatcatgcca ctgcactccg gtctgggagt gcactccaac aagaaggagt tcgctctttt   7260
ttgcccaggc tggagtgcag tggtgggatc tcagctcacc gcaacctcca cctcccgggt   7320
tcaggcgatt ctcctgcctc agcctcccaa ggagtagctg ggattatagg tatgcatcgt   7380
cacacccggc tactttttgta tttttttagtag aggcaggttt ccaccatgtt ggccaggctg   7440
gtcttgaact caagtgatct gccctctttg gcctccttct caggaaaaaa aaaaaatcac   7500
aggtatttac aggccattcc aagtgccaaa agattgtttt tgctcatggt gacttcagta   7560
tcacagatgt taggagactt gctgctatat gttaagaaag aagcacaaat gttgctgtag   7620
cccaaacttt tttcctcatg tttcattgca tttcagctta attggtttcc ctggtattcc   7680
tatgtatttt gtggagtgct tttaaaatca taagttggag tagaggtctt tctgtgggct   7740
tcaccagact gccgagatca gggtcgaaac aggtgaggac cccttctctg gagagagtct   7800
cctttctcct ctaagaggaa aggttttgag atcttttgtc catttttccca ccttagcact   7860
```

-continued

```
tcatcagcct taaaagaagc tggaatttttt tttttttttt ttggagatgg gatctcgata      7920
tgttgcccag gctggtcttg aacccctttgg ctcaagcgat cctccagcct cagcctccca      7980
aagtgctggg attcgaggca tgagccaccg agcccaccgt gcagatggat gtttttgtgc      8040
atgcttttga tgaatgcttt ctctctctca gcctgtgccc agggcacctt caagcccctg      8100
tcaggagaag gtcctgcca gccatgccca gccaatagcc actctaacac cattggatca       8160
gccgtctgcc agtgccgcgt cgggtacttc cgggcacgca cagacccccg gggtgcaccc      8220
tgcaccagta agtgaccagc acccaggtgc agttcactgg ggaggggtca cagacctctg      8280
aggtggaccc tcacatggcc cccatcctcc ctgggcttct tcccttttgtc cctggcatgc     8340 ttgtccctag cccggaggaa catgtggagc ccactgtctc caaggcaaga gtccagcatg      8400
gctgctggtg cctccattgc cctctcccca ccaccgcaga gcaggtcggc ctctgcctga      8460
ctccctggtc tcctgcagcc cctccttcgg ctccgcggag cgtggtttcc cgcctgaacg      8520
gctcctccct gcacctggaa tggagtgccc cctggagtc tggtggccga gaggacctca       8580
cctacgccct ccgctgccgg gagtgccgac ccggaggctc ctgtgcgccc tgcggggag       8640 acctgacttt tgacccccggc cccccgggacc tggtggagcc ctgggtggtg gttcgagggc    8700
tacgtcctga cttcacctat accttttgagg tcactgcatt gaacgggta tcctccttag      8760 ccacggggcc cgtcccattt gagcctgtca atgtcaccac tgaccgagag ggtgagactt      8820
gggggctggg gcggctggtg gtctggcggg agagatgtca ctgagggcct gaaggggaga      8880 ggcagggggct gtgaagttgg gtaccccgga agtgtgaggg gctaaggctt tggggggcaag    8940 aggcagaaag agggcaatgg ctgggcgcag tggctcacgc ctgtaatccc agcactttca      9000
gaggctgaga caggcggatc acttgagccc tggagttcaa gaccagcctg gtaacatag       9060 gaagatctct ctacaaaaaa taaaaatatt agccaggcga ggtggtgcat gcctgtggtc      9120
ccagctactc aagaggctga ggcaggagga ttgcttgagc ccaggagtcg gaggctgcag      9180
tgagctatga tcgcaccgct gcatgccagc ctgggtgaca gagcagtgtg agatcctctc      9240
tcaaaataaa tgaataagaa agagagggtg aggagctcgt aaagctgggc tggagagtta     9300
agtacaggaa ggcccccagt gggactgggg ccagagagaa tcagaaggaa ttctcgaaac     9360
agccaggggg aaattgagac aagtgtagcc agcagaggaa gtgttggaaa agataaggga     9420
catggccagg ctgatcacaa ggtcaggagt tcaagactag cctggccaac gtggtgaaac     9480
cccatgtcta ctaaaaataa aaaaattagc caggcatggt ggtgggcacc tgtaatccac     9540
ttgggaagca accagaagaa ttgcttgaac ccaggaggcg gaggttgcag taagctgaga     9600
ctgcgccact gcactccagc ctgggtgata gagcacgact ccgtctcgaa aaaaaaaatt     9660
ttttttaagt taagggacag agctaccatg cacaagggtt ccctgtgtct ctgcctctca     9720
cagtacctcc tgcagtgtct gacatccggg tgacgcggtc ctcacccagc agcttgagcc     9780
tggcctgggc tgttccccgg gcacccagtg gggctgtgct ggactacgag gtcaaatacc     9840
atgagaaggt aaggccatcc cccagccctg gggtgggtgg gcaatgggtt gtgctctcct     9900
ggctgggaca cctgggttgc aggcacctgg caggcatttg aattccagct ctgccatgga     9960
ttccctgggc agccttgggt aagccccttg gcctgtctga gcctcagact cttcatctat    10020
aaaatagtta ctgtaatagt taccagcagc tggacacagt ggctgaggtt gggtgcggtg    10080
gctcacgcct gtaataccaa gcactttggg aggctgaggc gggcagaatg cttgagccta    10140
ggagtttgag accagcctgg gcaacatggt gaaacttcat ctctataaaa aacttaaaat    10200
gggccgggcg cggtagctta cgcctgtaat cccagcactt tgggaggccg aggtgggcgg    10260
```

```
atcacaaggt caggagtatc gagaccatcc tggctaacac ggtgaaaccc catctctact   10320
aaaaatacaa aaaattagcc aggcgcggtg gcaggcgcct gtagtcccag ctactcggga   10380
ggctgaggca ggagaatggc gtgaacccag gaggcggagc ttgcagtgag ccgagatagc   10440
gccactgcag tccggcctgg gcgaaagaac aagactctgt ctccaaaaaa aaaaaaaaa   10500
aaaaaaacg caaaaaatac ttaaaatgaa aaaaattaga ctgggcacag tggctcatgc   10560
ctgtaatccc ggcactttgg gaggccgagg tgggtagaac acctggggtg aagagttcga   10620
gaccagcctg gccaacaagg tgaaatcccc gtctctacta caaatagcaa aatcagctga   10680
gtgtgttggc gggcccctgt aatcccagct actcaggagg ctgagacagg agaatcactg   10740
gaacccaagt gattctcgac ttgaggtcga ggctgcagtg agtcgtgttt gcaccattgc   10800
attccagcct gagaaagtga gaccttgtct taaaaaaaag gaatgatatt atgaatacag   10860
cacatggctt gcatgcgtaa gttctcccaa aggcctcacc agttgcaagg caggctagtg   10920
atgggagtgg agggcgaggg aaggaggcag gaagagcaac aggaacttgg gttcccgggt   10980
gacggccacc ccactacctc tcccggacag ggcgccgagg gtcccagcag cgtgcggttc   11040
ctgaagacgt cagaaaaccg ggcagagctg cgggggctga agcggggagc cagctacctg   11100
gtgcaggtac gggcgcgctc tgaggccggc tacgggccct tcggccagga acatcacagc   11160
cagacccaac tggatggtga gcctggggaa ggggtgaggg tgggggttg gaaagacccc   11220
caaagttcct gggaagaccc caggtctcca aagtcccatc atcttttttt tttttttttt   11280
ttttgagat ggagtcttgc tctgtccctc aggctggagt gcagtggcac catctccgct   11340
cactgcaacc tccgcctccc ggattcaagc cattctcctg cctcagcctc ccgagtagct   11400
gggattacag gcgcctgcca ccgcgcctgg ccgattttt gtattttag tagagacggg   11460
gcttcaccgc gttggccagg ctggtctcga actcctgacc ttgtgattcg cccgcctcgg   11520
cctcccgaag tgctgggatt acaggcatga gccactgcac ccggtcaaag tcctatcttc   11580
atgtccttct tcctgtggat cacatggcat gccctagaga ggagagaacg taagatgtcg   11640
aaaccaaaac caacagctga gttttgtgaa gtctggcctg cttcactctg tacccccagg   11700
ctggagcgca gttgctcgat caaagctcac tgcacagcca ggcacagtgg ctcaccctgt   11760
aaccccagca ctttgggagg ctgaagcagg aggatcactt gaggtcagga gttcgagacc   11820
agtctgacca gcatggtgaa accgcgtctc tactaaaaat atagaagtta gctgagcgtg   11880
gtggtgcaca cctgtaatcc cagctactcg ggaggctgag gcaggagaat cgcttgaacc   11940
tgggaggtgg aggttgcagt gagctgagat tgtgccagtg cactccagcc tgggcaacag   12000
agcaagactc tgtctcaaaa aaaaaaaagc tcaccgcagg cttgactttt agcaacaacc   12060
tgacccctga gctccccatt ccccatccaa caaaatggga atatcatgaa gcttcctgca   12120
gggctttgag gattggaggt aacaggttat ttttaatatg ctaggccagt ggctttcttt   12180
tttctttcac atttttttttt ttgagacgga gtctcactct gttgcccagg ctggagtgcg   12240
gtggcgcgat ctcagctcac cgcaagctcc acctcctggt ctcgatctgc tgacctcctg   12300
atccacccgc ctcggcttcc cgaaatgctg ggactgctgg cgtgagccac cacgcccggc   12360
ctaactttt cttttttta agagacacgt ctttttttat cacccaggct ggagtgcggt   12420
ggcaccatca tagctcattg cagcctacaa ctcccgagct caaccaatcc ttccaccta   12480
gcctcccaag tagctgggc tataggcatg tgctaccgtg ctcaactaaa tttttttta   12540
tgttttgttg agacagtttc cctatgttgc ccaggctggt ctcaaattcc tgacctcgag   12600
```

```
caatcctccc gcatcggcct cccaaagtgc tgggattaca ggcatgagcc gccacaccca   12660
gcattggacc agtggctttc taaaccttgt aattttctgt aatagcttta ctgaaataca   12720
gttcccctgc catacaattt gcctgttcaa agtgtacaat cgatgacttt tgatacattc   12780
acagaattgt gcagtcacca ccacaagtaa ttttgggaca ttttcagcac cctcaaaaga   12840
gaccctatag cccttagcca tcaccccca cccagatctt tctgttgcct tagtccctgg   12900
caagcactaa cccactttct gtcttgaaat cttccagtgt ggtctttgt gactgttcac   12960 cgagcagaat gttttcaagg tttatgtatg ttgtagtata tatccgtggg ttttttggt   13020 tgtggtttgt tttttgttg ttttggaaac agggtctcgc tctgtcaccc aggctggagt   13080
gcagtggttc aattacagct cactgcagcc tcaacctccc aggctcaagt gatcctccca   13140
cctcagcctc ccaagcagct gggactgtag gcatgagcca ccatgcccag ctaatttttt   13200
ttggtatttt ttgtaaagac agggtttcac catgtttccc aggctggtct cgaactcctg   13260
agctcaggca atccacccac ctcagcctcc caaagtgctg tgattacagg catgagccac   13320
tggacctggc ctgttttttg tttttgtttt gaacacacga ttttgctttg tcacccaggc   13380
tggaatgtaa tggtctgatc atagtgcatt gcagcctcaa actcctgggc tcaagcgatc   13440
ctcctacctc agcctcctga gtatctggga ccacacgtgc tcaccaccat gcttggctaa   13500
ttattattat ttttgatag agacggggtc ttgctatgtt tcccaggctg gtcttgaaca   13560
cctggcctca cacaatcctc ccacctcagt atctcagagt gctgggatta caggcatgag   13620
ccactgctcc tggccaatat ttcatttctt tttatggaga cgtaataatc agttgtatgg   13680
aaatagctga ttttgttttt tattgtatct tttggtgaac atttcaattg tatcgacttt   13740
ttggataaaa acctgaaaat gtttcacctt tagaacgttt cattgaatgg agattttttt   13800
gtggactctg gtatttatac tagaaccaaa tcaaaaccac tctggcggct gggcatgcct   13860
aggctggttt gagactagcc tgtccaacct ggtgaaagcc catctctact aaaaatacac   13920
aaattagccg agcatggtgg tacacacctg taatcccagc tactcaggag gctgaggcag   13980
gagaatcgca gaacccggga ggcggagatt gcagtgagct gagattgcgc cactgcactc   14040
cagcctgggc gacagagtga gactgcgtct caaaaaaaca aacaaaaaat tactctggca   14100
gtaagaaaag atttcgaaac ttcctcccctt gccctgaggt acttcagagg agcctgctgg   14160
cccctggggg agagtttgaa acccactgtt tgttccctga ccttgcctgc ttgtgtcctc   14220
tccctccacc tgtcccctgt actggggacc tgttctcagg agatcacagt tcattgctca   14280
aagccggggc tggggcctcc tacaggacca tcagtttctc ctgatcagca gcctttcctt   14340
ccgcagagag cgagggctgg cgggagcagc tggccctgat tgcgggcacg gcagtcgtgg   14400
gtgtggtcct ggtcctggtg gtcattgtgg tcgcagttct ctgcctcagg taagggctct   14460
gacacccaga ggcccctgga agccctcagt tgatggccac ctgcctgggt gctacaggac   14520
aagcctttct ggctgtcccc agcctctttt tacttgaaat cttctccaat ccctgctcct   14580
tcctttggtg tgtgtgcctc ataaagatgt gtgactcagt ttaccttttg ttcctttccc   14640
atcggctaca ggaagcagag caatgggaga gaagcagaat attcggacaa acacggacag   14700
tatctcatcg gacatggtgg gttgccctaa tttgatggga ataggggctt ggggccgggt   14760
gtggtggctc ctatctataa tcccagcact tgggaggca gaggtgggca gatcacttga   14820
ggtcaggagt tcgagaccag cctggccaac atgttgaaac tccatctcta taaaaatac   14880 atcagtcagc caggcatggt ggtgggcacc tgtaatccca gctactcagg aggctgaggc   14940
agaagaatca ttttaacccg ggaggcggag attgcagtga gccaagatcg cgccactgcg   15000
```

```
ctccaggcct gggtgacaga gcgagactcc atctcaggaa aaaaaaaaaa aaaaaaaaaa    15060
accacggaga caggggtttg gggctaaaag ctatgagccg agcctccgag tccagtggga    15120
gttaattccc agctgacggg gccctgcctg atttctcagg tactaaggtc tacatcgacc    15180
ccttcactta tgaagaccct aatgaggctg tgagggaatt tgcaaaagag atcgatgtct    15240
cctacgtcaa gattgaagag gtgattggtg caggtgagag ccgaaggctg cccgggcacc    15300
tgggaacgaa gcggggtgg gcagggccac actggagcgg gagagctgat gacctctgcg    15360
tccttgtttg aaggtgagtt tggcgaggtg tgccggggc ggctcaaggc cccagggaag    15420
aaggagagct gtgtggcaat caagaccctg aagggtggct acacggagcg gcagcggcgt    15480
gagtttctga gcgaggcctc catcatgggc cagttcgagc accccaatat catccgcctg    15540
gagggcgtgg tcaccaacag catgcccgtc atgattctca cagagttcat ggagaacggc    15600
gccctggact ccttcctgcg ggtgagcacc ctccctggct tctgcggcca cccggagttc    15660
ccacttacac ccagaggcca cttgggttaa gaagccagga cagacagtgg gtcccaggtc    15720
acctcctcca gccttttcct cttgggctaa gccctggtcc tctgcctttt cttttttta    15780 agacagagcc tcgctctgtc gcccaggctg gagtgcagtg gcgcgatctc ggctcattgc    15840
tgtctccacc tccagggttc aagcgattct cctgcctcag tctcccaagt agctggtact    15900
ataggcatgc accaccatgc tgactaattt ttgtatttt agtagacaca gggtttcacc    15960
atgtaggcca ggctggtatc aaactcctga cctcaagtga tctccccacc tcagcctccc    16020
aaagtgctgg tattacaggt gtgaggcacc acgcctggcc agccctctgc ctttaatttt    16080
ccctctggga aaggctgggc tcctgggacc ttcctttccc actgcccat acagctgaag    16140 gttgtcattc cttctttttt tttttaattt tgttttaatt gaattttttt ttttgagat    16200 ggagtttcac tcttgttgcc caggccggag tgcaatggca agatcttggc tcaccgcaac    16260
ctccgcctcc caggttcaag cgattctcct gccttagcct ccccagtagc tgggattata    16320
ggcatgtgcc accacgcttg actaatttg tattttagt agagacgggg gtttctctgt    16380
gttggtcagg ctggtctcga actcccgacc tcaggtgatc cgcctgcctc ggcctcccaa    16440
agtgctggga ttacagacgt gagccaccgc gcccggccaa tttttttttt tttttttaa    16500 gacagagtct cactctgtcc tctaggctgg agtgcagtgg tgcattcata gctcactgta    16560
gccttgacct cctgggctca agtgatcctc ccgcctcagc ctcctgagta gctggaacta    16620
cactcatgta ccaccatgct cagcaaattt ttaaaatttt ttgtagagac aggatctcga    16680
taggttgccc aggctggtct gaactcctgg cctcaagcga gcctccctcc tcagcctccc    16740
acagcactgg gattgcaggc atgagccact gtgcctggcc tgtcattcct tcttttgaca    16800
aatatttact gagtgctttc tacgcaccgg tcatcctccc agtccccagg aataaagcta    16860
tacacacggc aaactggatt tctcctcttg gggagcagag ggtctaatgg ggcagggga    16920 ctgaaaatta gcaagtaaat agacaggctt tttaaaaaag taaacaaatc atttcaaatg    16980
tgaaaaaaag caaacggggt ccttcatgca gatgtggcta gagaggaaag agaactgctt    17040
aatttatttg gtcactttac cagatttac tgactttttt ttttttttta actttattaa    17100
gcttttcttt ttcttgaga tggagtttcc atctgtcacc caggctggag tgcagtggtg    17160
cgttcttggc tcaccgcaac gtccacctcc tgggttcaag tgattctcct gcctcagcct    17220
cctgagtagc ttggaattgc atggcatgca ccaccatacc cagctgatgt ttgtattttt    17280
agtagagaca gggtttcatc atgttgccca ggctggtctt gaactcctgg gctcaagtga    17340
```

```
tccacccatc tcggcccctc aaagtgctgg gattacaggc atgagccacc atgcctggcc    17400
taggcatctt tttaaaaaaa tcaaaacatt tttctatgta gcaaataaac attgcattga    17460
acagagttat agcgattccc tagcgtcatt gaatacccag ttgattttca cgtttctcta    17520
gttgttctaa agatgtcctt cactgctgct ttattccaac caggatccag ttcaagaccg    17580
ggctttgtac ctggttatta tatatatttt atttatttat tttagaaaca aggtcttgcc    17640
ctttcgccca gtttagagtg cagtggtgca atcatagctc actgcagcct ccaaactcct    17700
tggctcaggt gatcctcctg cctcagcctc ctgggtagct ggaactacag gtgcacacca    17760
ccacacctgg ctaattttta aattttttac ggagatgggg gtctcgctat gttgcccagg    17820
ctggtctcaa actcctggac tcaagcgatc ctccctcctt aacctctcaa agtgctggga    17880
ttacaggcgt gagccaccac gcctgctgat tattatattt tcgagcctct ctaaatcttg    17940
agcagttcct catgatgaca ctgacacact gaagggttag gtcccttgtc cgcctgaatg    18000
tcttgatttc tggatttatg aaattcttct tatgggatca tttagcttgt ctctctgtat    18060
ttcctgtaag agaagctcta tctgatgtgg ggttttttg gttttgtttg tttgtttttt    18120
gagatggagt cctgctgtcg cccaggctgg agtgcagtgg cacaatctcg gctcactgca    18180
acctccgcct cctgggttca agagattctt ctgcctcagc ctcctgagta gctgggacta    18240
caggcgagtg ccaccatgcc cagctaattt ttgtatttt agtagagaca gggtttcacc    18300
atattggcca ggatggtctc gaacttctga cctcgtgatc tgcccaccac ctcagcctcc    18360
cacagtgctg ggattacagg catgagccac tatgcccggc taattttgt attttagta    18420 gagacagggc ttcgccatgt tggccaggct gatctgaaac ccctggcctc aagccatcca    18480
ccctccttgg cctcccaaag tgctgggatt aaacgcgtga ccaccgtgc ctggtcgaag    18540 agacagaaag ggtcttaaag gttcagtgac acacacctgt aatcccagca ctttgggaag    18600
ctgaggctgg tggatcactc gaggccagga gttagagatc accctgggca acatggtgaa    18660
accccgtctc tacacaaaat acaaaaatgg gcagagcatg atggtgcata tctgtagtcc    18720
cagctactcg ggaggctgag gcgggaggat cacttaagcc tgggagatcg aggctgtagt    18780
gagccatcat tgcactactg cattccagcc tgggcgatcc catctcttaa aaagagagag    18840
agatgggaag accagcacag gtgaaactgg tgaacagagg agagatggta gatgctgcat    18900
tgggcagtgt gacgggaacc cgctggaggg ctttggcagg agagtagttt aagaggatcc    18960
cagctgggca cagtggctca cacttgtgat cccagcactt ggggaggccg ggcaggtgg    19020 atcacttgag gtcaggagtt cgagaccagc ctggccaaca tggtgaaacc ctgtctgtac    19080
taaaaataca aaaccagcc aggcatggtg gtgcacccct gtaatcccag ctactcagga    19140
gactaagaca ggagaatcgc ttgaactcag gaggcagagg ttgcagtgag ccaagatcac    19200
gccactttac tccagcctgg gcagtagagc gagactccat ctcaaaaaaa taaataaata    19260 aaagacctc tttgctgggt gctagggagc aagagcagga gctgggagag gcctgcagca    19320
gaagcctgtt gccagcatcc aggccgtggg gtgaagggaa gggtttggat ttgggacatg    19380
tcttggaagc atcaccagca gaacttgctg atggattgga agtggctggt gagggagaaa    19440 aggggtcaa aggaaactct gaggtctata ccctgaccat ctggcaagtg gtggtgttgc    19500
cacaaactga gcgggagta gggcaggtgc aggtctggag gatggattca aaattcagtt    19560
tttggagtct atgtccctgg ttctgtaggg ctgcagatgg tctgccaaat cttagcggaa    19620
cccagaatac gggatttgtt tactgtctgt gacttgttgg tttccctggt gagagcaaac    19680
tctttaaagg tcaaggttgg gcttcagacc ttggttttg caccgatcat tggtcatact    19740
```

```
gcagttcctc actcttctct tgcaaatcca tacacagcta gtccaagaga gctgaacagc   19800
tttgtggttg gatcagcacc aatgtatctc cacctgtaga cgggttgctc aggtgactca   19860
tgcctgtaat cccagcacct tgggaggcca aggtgggaag attgcttgag gccaggagtt   19920
ggagacaagc ctgggaaaca cagtgagacc ccatatctac caaaaaaacc cctttgtttt   19980
aattagccag gtgcagtggt gtgcacctat agtcccagct actaaggagg ctgaggcaga   20040
aggatcattt gagcccagga gtttaaggct gcggtgaacc atgatcgtgc cactgcactc   20100
caacctgggg gaaagaaaga gaccttgtct ctaaaaaaac taaaaaacag aaaagcattt   20160
gttgagtatt tcctgggtat aaagcagtgt accaggttaa atggaaggaa agttgaaat   20220 aatttttcaa ctcataatcc gattgggaga gactgaatgc ttaccattga agcaggaacc   20280
attgtaagca atgtgttgtg atactgtagc aagagctgag aaaacttggg aaaagagaaa   20340
ggaggaaggc tcacctgagg gagttggggg gcttgcccta caggtgagtt gtgaggtggg   20400
tctggaagtg acagatgcag tttaggaagt ggacgggagg ctgggtacgg tgactcaaca   20460
tctgtaatcc cagtgctttg ggagacccag gcggaaggat cgcttcaggc caggagttaa   20520
agaccagcct gggcaacata gtgggaacct atctctacta aaaattaaaa aattatccag   20580
gcataatggc acatgcctat tgttccagct actcaggagg cttgcctgag cccaggaggt   20640
tgaggctgca gtgagctatg atggcaccac tgcactccag cctgggcgac agaacaagac   20700
cctgtctcta aaaaaaaaag atgtggatgg gaggggaac ggtgggtggg ctgtcctcac   20760
caagccccca ccctatctgc tctccagcta aacgacggac agttcacagt catccagctc   20820
gtgggcatgc tgcggggcat cgcctcgggc atgcggtacc ttgccgagat gagctacgtc   20880
caccgagacc tggctgctcg caacatccta gtcaacagca acctcgtctg caaagtgtct   20940
gactttggcc tttcccgatt cctggaggag aactcttccg atcccaccta cacgagctcc   21000
ctggtaatgc tggggtaat actgggtgtg agcttcttag gccaggtgg gcagggcagg   21060 ttggaaaggt gggaggctga gggtttggca gccctgctcc agggagagga tacaggagca   21120
ggctgtgggt gggggacag tcagctccag gaagccgact tccagatgtc taggaaaata   21180
acagttggat aacctgggca acatagcaag accccatctc tacaaaaaaa ttaaaagatt   21240
agccaggcgc agtggcatgc acctgtagtc ccagctactt gggaggttga ggcaggagga   21300
ttgcttaagc ccaggagttg gaggctgcag tgagctatga atgtgccact gtactgcaga   21360
ctgggcgaca gagcaagacc ctgtctcaaa agaacagtgg ccaggtgtgg tggctcacgc   21420
ctgtaaatcc agcactttgg gaggctgagg caggaggatc gcctgaggtc aggagttcga   21480
gaccagcctg gccaacatgg gaaaaccctg tcgctactaa aaatacaaaa ttagctgagg   21540
gtggtggtac acgcctgtaa tccgagctac tcaggaggct gaggtaggag aaccagttga   21600
acccgggagg cggagtttca gtgagccaag atcgcaccac tgcactccaa cctgggcaaa   21660
cagagttgga gagtaggagg cttggggcct gagctagggg gaaaaagcag aggcaggtgg   21720
gggactgggg ggcagtgtgc tgggtctggt gagtccctca gtgagtcccc cagctcacct   21780
tttctccttt ttctgcaggg aggaaagatt cccatccgat ggactgcccc ggaggccatt   21840
gccttccgga agttcacttc cgccagtgat gcctggagtt acgggattgt gatgtgggag   21900
gtgatgtcat ttgggagag gccgtactgg gacatgagca atcaggacgt aagtgtcccg   21960
tggtcctacc aagctttcct cgagtgttct ctcacctggg attgggtg aagggtgggt   22020 tcccagagag tcatcactgc tgggttcttg agaccatgga gatgacaaaa aggagaattg   22080
```

```
atctttgtat caaagagttg agatacaggg ccaggcctag tggctcaagc ctgtaatccc   22140
agcactttgg gaggccaagg tgggcagatc acctaaggtt aggagttcaa gaccagcctg   22200
gccaacatgg tgaaacccg tctctaaaaa aatacaaaaa attagcccag catgatgggc    22260
gggtgcctgt aatcccagct actcaggagg ctgagacagg ataatcgctt gaacccagga   22320
acagaggttg cagtgagctg agatcacgcc attgctttcc agcctgggca actgagcgag   22380
actctgtctt aataaataaa taaaagagtt gggtacagca tatttgggtc gcagaaggat   22440
gcagagatgg agggcagggt tgagaggtaa catgtctgta tcatagccca agagctgctg   22500
gggccttcag ccacagagag cttcaactcc ggctaggagg attcctggat ctgttatttt   22560 ttgggggct gtggctccta tcctaccatc ttccaagtca ccatttcctg ggcctgttag    22620
catctttgct tttcctggac agcctcaccc agagcttctt ccctctttc caggtgatca    22680 atgccattga acaggactac cggctgcccc cgccccaga ctgtcccacc tccctccacc    22740
agctcatgct ggactgttgg cagaaagacc ggaatgcccg gccccgcttc ccccaggtgg   22800
tcagcgccct ggacaagatg atccggaacc ccgccagcct caaaatcgtg gcccgggaga   22860
atggcgggtg aggactgcag agaatgggcc ctccttcccg ctctctgccc ccactccttg   22920
cccagaagtg tccgttcatt ggtgttgggt gggagggcct ctgtccgcct ctgcaaggct   22980
gggttccacc tcctcccccg gacctgggcc tggtactcag cattcctccc catccttgcc   23040
ccctagggcc tcacaccctc tcctggacca gcggcagcct cactactcag cttttggctc   23100
tgtgggcgag tggcttcggg ccatcaaaat gggaagatac gaagaaagtt tcgcagccgc   23160
tggctttggc tccttcgagc tggtcagcca gatctctgct gagtaagcag tggcaggagc   23220
tggagtgggg ctgggagagc ggggcagctg gagtcaggcc cacggggtct ccagggcctt   23280
ttggggtcag cttcgggtgc caatgctgtc ttcttgcact gcgctcatgc catgcctaga   23340
agggccccag aggagcagtc acagcccat ggagctgagg acccaaggac tctttggggc    23400
cagcctgccc gcctcacctc tcctgccat cacagccctg ggccatcgcg cttccgcctc    23460
tcacttctag ctatctttgt gcatctatct gcattccagg cccggctctc acggtaacaa   23520
tgtgtcaact cgggttctct ttttccaacc ataaaggag aagattgggc taggttttgg    23580
agatcctctt cagcttttat gtgaaatggt tttatgattc cttgcctccc aaaggctgcg   23640
tatccccact tggcctttgt ctgctactcc ccctttctgc cttcccgttc ctctcccaag   23700
atctcctctc accccaggtt gaataacaga aatagaagga atagaaatct gaaggccggg   23760
catggtggct catgcctgta atgccagcac tttgggaggc cgaggtgggc agatcacttg   23820
aggttaggag ttcgagacca ttgtggacaa cttggtgaaa ccttatgtct actaaaaata   23880
caaaaattag ctgggcatgg tggtgcgtgc ctgtaatacc agctactgag gaggctgagg   23940
caggagaatc gcttgaaccc gggaggtgga ggttgcagtg agccgagatc gcaccactgc   24000
actccagcct ggatgacaga gtgaaattcc atctcaaaaa aaaaaaaaa aaaaaaaag    24060 aaatgtgaag gccaggtggt ggctcacgcc tgtaatctca gcactttggg aggctcaggt   24120
ggaccgattg cttgagccca ggagtttgag agcagcctgg ccaaaatagc aaaaccccat   24180
ctctacaaaa caaaaacaaa aaattagct gggcatggtg gtgcgtgcct gtggtcccag    24240
ctactcagga ggctagagcc agagggtctc aggccagtct gccccctgccc cacggggcct   24300 gggcacatcc ctccctaatt cttccagcc tctctctgac ccaggggcc tcctctccct    24360 tttttcccct tatctcagcc tccagccatc agcaacctcc tcttcctctc cacccagctc   24420
ttcctctccc acttcggcct tttctttctc acactccatt tccctctacg gcaatctgtg   24480
```

```
cagcctcttc ccccagtctc attttgcggg cttttctctc ttttctttcc ttccctggca    24540
cccaagccaa aggccctgcc tctggcctcc agccctaccc ccttctgcgg ttgcacagaa    24600
ggatggctgc ccagctctta aaaaaactgc ccgggaactg ttgacatctg ttctccctcc    24660
cccgctggct tttctgattg cttacaatc ctgaggctag gaccgtctca ggagccaaga     24720
gaggagagcg gccacaggga acctagggtc tcaccaagct ctcctttcct tctgcaggga    24780
cctgctccga atcggagtca ctctggcggg acaccagaag aaaatcttgg ccagtgtcca    24840
gcacatgaag tcccaggcca agccgggaac cccgggtggg acaggaggac cggccccgca    24900
gtactgacct gcaggaactc cccaccccag ggacaccgcc tccccatttt ccggggcaga    24960
gtggggactc acagaggccc ccagcccgtg ccccgctgg attgcactt gagcccgtgg      25020
ggtgaggagt tggcaatttg gagagacagg atttgggggt tctgccataa taggagggga    25080
aaatcacccc ccagccacct cggggaactc cagaccaagg gtgagggcgc ctttccctca    25140
ggactgggtg tgaccagagg aaaaggaagt gcccaacatc tcccagcctc cccaggtgcc    25200
cccctcacct tgatgggtgc gttcccgcag accaaagaga gtgtgactcc cttgccagct    25260
ccagagtggg ggggctgtcc caggggggcaa gaagggtgt cagggcccag tgacaaaatc    25320
attgggtttt gtagtcccaa cttgctgctg tcaccaccaa actcaatcat ttttttccct    25380
tgtaaatgcc cctcccccag ctgctgcctt catattgaag gtttttgagt tttgtttttg    25440
gtcttaattt ttctccccgt tcccttttg tttcttcgtt ttgttttct accgtccttg      25500
tcataacttt gtgttggagg gaacctgttt cactatggcc tcctttgccc aagttgaaac    25560
agggggcccat catcatgtct gtttccagaa cagtgccttg gtcatccac atccccggac    25620
cccgcctggg accccaagc tgtgtcctat gaaggggtgt gggtgaggt agtgaaaagg      25680
gcggtagttg gtggtggaac ccagaaacgg acgccggtgc ttggaggggt tcttaaatta    25740
tatttaaaaa agtaacttt tgtataaata aagaaaatg ggacgtgtcc cagctccagg      25800
ggtgatgggg gtgatggact agatttctaa ggagagtggg gctgggtagg gagggctttg    25860
tggctgaccg agaggtgtca gaggtctgga ggctgcaggg ctgtagggggc tggaacttgg    25920
ttatcagccc cagggtatgt ttgaggtggt ggggtgggg ccgagcgaga tgaatcattc     25980
gcagctgctt ctaacgtctc                                                26000

<210> SEQ ID NO 392
<211> LENGTH: 4235
<212> TYPE: DNA
<213> ORGANISM: Homo sapiens

<400> SEQUENCE: 392
ctcggcccgg cggcgcgagc agagccactc cagggagggg gggagaccgc gagcggccgg       60
ctcagccccc gccacccggg gcgggacccc gaggccccgg agggaccccca actccagcca     120
cgtcttgctg cgcgcccgcc cggcgcggcc actgccagca cgctccgggc ccgccgcccg      180
cgcgcgcggc acagacgcgg ggccacactt ggcgccgccg cccggtgccc cgcacgctcg      240
catgggcccg cgctgagggc cccgacgagg agtcccgcgc ggagtatcgg cgtccacccg      300
cccaggggaga gtcagacctg gggggcgag ggccccccaa actcagttcg gatcctaccc      360
gagtgaggcg gcgccatgga gctccggggtg ctgctctgct gggcttcgtt ggccgcagct     420
ttggaagaga ccctgctgaa cacaaaattg gaaactgctg atctgaagtg ggtgacattc      480
cctcaggtgg acgggcagtg ggaggaactg agcggcctgg atgaggaaca gcacagcgtg      540
```

```
cgcacctacg aagtgtgtga cgtgcagcgt gccccgggcc aggcccactg gcttcgcaca    600
ggttgggtcc cacggcgggg cgccgtccac gtgtacgcca cgctgcgctt caccatgctc    660
gagtgcctgt ccctgcctcg ggctgggcgc tcctgcaagg agaccttcac cgtcttctac    720
tatgagagcg atgcggacac ggccacggcc ctcacgccag cctggatgga gaacccctac    780
atcaaggtgg acacggtggc cgcggagcat ctcacccgga agcgcctggg gccgaggcc     840
accgggaagg tgaatgtcaa gacgctgcgt ctgggaccgc tcagcaaggc tggcttctac    900
ctggccttcc aggaccaggg tgcctgcatg gccctgctat ccctgcacct cttctacaaa    960
aagtgcgccc agctgactgt gaacctgact cgattcccgg agactgtgcc tcgggagctg   1020
gttgtgcccg tggccggtag ctgcgtggtg gatgccgtcc ccgcccctgg ccccagcccc   1080
agcctctact gccgtgagga tggccagtgg gccgaacagc cggtcacggg ctgcagctgt   1140
gctccggggt tcgaggcagc tgaggggaac accaagtgcc gagcctgtgc ccagggcacc   1200
ttcaagcccc tgtcaggaga agggtcctgc cagccatgcc cagccaatag ccactctaac   1260
accattggat cagccgtctg ccagtgccgc gtcgggtact ccgggcacg cacagacccc    1320
cggggtgcac cctgcaccac ccctccttcg gctccgcgga gcgtggtttc ccgcctgaac   1380
ggctcctccc tgcacctgga atggagtgcc ccctggagt ctggtggccg agaggacctc    1440
acctacgccc tccgctgccg ggagtgccga cccggaggct cctgtgcgcc ctgcggggga   1500
gacctgactt ttgaccccgg ccccgggac ctggtggagc cctgggtggt ggttcgaggg    1560
ctacgtcctg acttcaccta ccctttgag gtcactgcat tgaacggggt atcctcctta    1620
gccacggggc ccgtcccatt tgagcctgtc aatgtcacca ctgaccgaga ggtacctcct   1680
gcagtgtctg acatccgggt gacgcggtcc tcacccagca gcttgagcct ggcctgggct   1740
gttccccggg cacccagtgg ggctgtgctg gactacgagg tcaaatacca tgagaagggc   1800
gccgagggtc ccagcagcgt gcggttcctg aagacgtcag aaaaccgggc agagctgcgg   1860
gggctgaagc ggggagccag ctacctggtg caggtacggg cgcgctctga ggccggctac   1920
gggcccttcg gccaggaaca tcacagccag acccaactgg atgagagcga gggctggcgg   1980
gagcagctgg ccctgattgc gggcacggca gtcgtgggtg tggtcctggt cctggtggtc   2040
attgtggtcg cagttctctg cctcaggaag cagagcaatg ggagagaagc agaatattcg   2100
gacaaacacg gacagtatct catcggacat ggtactaagg tctacatcga cccttcact    2160
tatgaagacc ctaatgaggc tgtgagggaa tttgcaaaag agatcgatgt ctcctacgtc   2220
aagattgaag aggtgattgg tgcaggtgag tttggcgagg tgtgccgggg gcggctcaag   2280
gccccaggga agaaggagag ctgtgtggca atcaagaccc tgaagggtgg ctacacggag   2340
cggcagcggc gtgagtttct gagcgaggcc tccatcatgg ccagttcga gcaccccaat    2400
atcatccgcc tggagggcgt ggtcaccaac agcatgcccg tcatgattct cacagagttc   2460
atggagaacg gcgccctgga ctccttcctg cggctaaacg acggacagtt cacagtcatc   2520
cagctcgtgg gcatgctgcg gggcatcgcc tcggcatgc ggtaccttgc cgagatgagc    2580
tacgtccacc gagacctggc tgctcgcaac atcctagtca acagcaacct cgtctgcaaa   2640
gtgtctgact ttggcctttc ccgattcctg gaggagaact cttccgatcc cacctacacg   2700
agctccctgg aggaaagat tcccatccga tggactgccc cggaggccat tgccttccgg   2760
aagttcactt ccgccagtga tgcctggagt tacgggattg tgatgtggga ggtgatgtca   2820
tttgggagga ggccgtactg ggacatgagc aatcaggacg tgatcaatgc cattgaacag   2880
gactaccggc tgccccccgc cccagactgt cccacctccc tccaccagct catgctggac   2940
```

```
tgttggcaga aagaccggaa tgcccggccc cgcttccccc aggtggtcag cgccctggac   3000
aagatgatcc ggaaccccgc cagcctcaaa atcgtggccc gggagaatgg cggggcctca   3060
caccctctcc tggaccagcg gcagcctcac tactcagctt ttggctctgt gggcgagtgg   3120
cttcgggcca tcaaaatggg aagatacgaa gaaagtttcg cagccgctgg ctttggctcc   3180
ttcgagctgg tcagccagat ctctgctgag gacctgctcc gaatcggagt cactctggcg   3240
ggacaccaga agaaaatctt ggccagtgtc cagcacatga agtcccaggc caagccggga   3300
accccgggtg ggacaggagg accggccccg cagtactgac ctgcaggaac tccccacccc   3360
agggacaccg cctccccatt ttccggggca gagtggggac tcacagaggc ccccagccct   3420 gtgcccgct ggattgcact ttgagcccgt ggggtgagga gttggcaatt tggagagaca   3480
ggatttgggg gttctgccat aataggaggg gaaaatcacc ccccagccac ctcggggaac   3540
tccagaccaa gggtgagggc gcctttccct caggactggg tgtgaccaga ggaaaaggaa   3600
gtgcccaaca tctcccagcc tccccaggtg ccccctcac cttgatgggt gcgttcccgc   3660
agaccaaaga gagtgtgact cccttgccag ctccagagtg ggggggctgt cccagggggc   3720
aagaaggggt gtcagggccc agtgacaaaa tcattggggt ttgtagtccc aacttgctgc   3780
tgtcaccacc aaactcaatc attttttttcc cttgtaaatg cccctccccc agctgctgcc   3840
ttcatattga aggttttgt gttttgtttt tggtcttaat ttttctcccc gttccctttt   3900
tgtttcttcg ttttgttttt ctaccgtcct tgtcataact ttgtgttgga gggaacctgt   3960
ttcactatgg cctcctttgc ccaagttgaa acagggggccc atcatcatgt ctgtttccag   4020
aacagtgcct tggtcatccc acatccccgg acccgcctg gaccccaa gctgtgtcct   4080 atgaaggggg gtggggtgag gtagtgaaaa gggcggtagt tggtggtgga acccagaaac   4140
ggacgccggt gcttggaggg gttcttaaat tatatttaaa aaagtaactt tttgtataaa   4200
taaaagaaaa tgggacgtgt cccagctcca ggggt                              4235
```

<210> SEQ ID NO 393
<211> LENGTH: 43948
<212> TYPE: DNA
<213> ORGANISM: Homo sapiens

<400> SEQUENCE: 393

```
gcgcctcgga gctgctgcg ggcgcacgcc gtcttccccg ccagtctgcc ccggaggatt      60
gggggtccca gcctgcgtcc cgtcagtccc ttcttggccc ggagtgcgcg gagctgggag    120
tggcttcgcc atggctgtga aagggactcc cgtgtggaag tactgctggg gtgttttgat    180
ggttttatgc agaactgcga tttccaaatc gatagtttta gagcctatct attggaattc    240
ctcgaactcc aagtaagtgg cgtccgcgat ccccctatgt ccccgccccg gggtccgccg    300
cgccgtccgg gcgggaggag gggtcagtcc gcggggcctc ggagcctgtt tctgaacct    360 cggttccccg tcccccaccc ccaacccccg ccccatttca ctaggtggag actcctcgct    420
cggctttcca acccgagccc cgctggaacg gacggtctct ccgcctttcc tcccccgaac    480
gctcccaggc gctaaaagct actatcggct cgggtgtcaa gtccgggaag gtgtccgatg    540
gcgatacctg accctctcct gttttcgagg acgaaggaca tggccacaat ctaggctggc    600
cggcacgcgg ggactggtgg gctctggaga gaggcggaga tgctgcattc gcgggagcg    660 cgggcggcgt ggtccgggc ccgcgggcgg gcgaccgggg tggcaggacg ctggcagcga    720
agcgcgttct ggagagggga gcctggagtc gctacgctgc ccgcagagcc ctggagccgg    780
```

-continued

```
ggcgccttgg caccgcgccg ccagcccgag ggtgcgcggg gagctcgcct gcttcgcagg     840
agaactcggg cgtcgagccc tttcctccgc gccgggagga cgggccttag gcttctccct     900
gagggcccgc cgcacctcgg cctcccgctt cgttcataag ccggtagccc cggagtatgc     960
ggtctcgatg gccgacctga ttgtaatgca cttcctataa aagcttaggg ccctgcccag    1020
tcgacactgc tcctgaagcc ttctccctcg ggaccctggt aggaatggga tccttaggat    1080
cagatttgct cttaccggac tctacagccg ggagcgagcc aggccttgtg gagagtaact    1140
ttcagtttgg gccaccagag tgcattcaga atttagaaaa tcccatccat ccctaaatct    1200
gtgtggtcat aactcgtagt catctgggta ttcagtactg tgtatcccct tatttcgaat    1260
cacagccaaa acatatttta cagaatcttg gaattgtagt ctcgggaaac ttggagaaga    1320
agtatgcaga cattagctgg tttctggaga aaacgtttga gatcagaagc aaaatcaatg    1380
gcctaattga agttgagcaa gttgggcctg gttttaggag aaaagaaatg ggggattgat    1440
ttagaaatca cgtcttaaag gagtgtgtcc attctcttaa aagtgtcaaa tttcaaattc    1500
actaacatgt taaccaagaa tcccttcatg aaaagggcga aaacgtcggt tacaaatcgg    1560
tttaaacaaa tgtttgtatg atgctagaag gcactttcaa caccgctcat acggagaagt    1620
tacttagctc tgcctccttc catgtagtct gctcttgcat ggattatatt tttaatgtaa    1680
attgttgtat ttgctgatga agtactggcg gcggcatctt tgcatcgatg ccggctcggg    1740
aggcgccagg tggtgccgga aggagccggg ctaggacctc gcgcagcagc gggtcccgga    1800
gtccgggaga ggcgggcggg cgggcgaggc ggtcgcgggg agcccgcggc gccgctgccc    1860
gcccggtgcc tccagaggtc actcttccat gcggaatcgc gcagcgccag gcctcgcccc    1920
tcccccaggc cgcctgctcc agccactctg cactttcact gaccggttct ctttgaggct    1980
gttttttttt ttcttatgag gatttaatat ttctgtttaa atctagttga aagcaattcc    2040
gttagcctct tcagcgttta gttcggtgtg tgtatcttta tctttgcgct atattaacta    2100
ttagtttgtg tgtatccggt aggagaatta gaaatacctc gttgggagaa aaagaaaagt    2160
agaacaatag ttatttcaac ctaaggttta gacgttaata acttcttttt gtaatgtgtc    2220 gagatgggggg gtcctggggg gaggtgacag gtactcacca ctccccccccc ccattctgat    2280 gatgaagatg agtctgtctt tccagctatg tccagacctg cgagggccct gcgtttctgg    2340
aagcctgccg tttgcgcggt tgaggttgct gctgctgtct tgtcctccac agcagcattt    2400
cttttaaaat tctcctgata acggcctgcc tggatgactg gataatgtgt gcctggaaaa    2460
ggtctcccct tgcagctgaat gctagctcca gagatcagaa agatttcttc ctgtaggagc    2520
cataggaaag agtcctctct aagttttttga gaatgcatac aaccccctga tgacagggggg    2580 tcgctttcct tgggggaagtt ttatatttat ttccagagga agtttgaat cggtaaaatat    2640 gatgtggcag gaaggtaatc aaatgcattg aagtttcaca tcagttccta tgaactgtgg    2700
aacaattcat ttgtaatgaa gccgccatca gtaattagat ttgtttcatt cagaggtcag    2760 ctttttttagc aggtggtcga cacagggagc atgcagcagc tgtttggata cagggtccag    2820 aaaaccctttt gtaaattcag cgtctccgta actactttaa tcacattgtc ggctctcccg    2880
tccctgactg tatgtaataa tggaaagatg tcctgcgtgc tgaaacagta gctgccctgt    2940
taggttattc acattgcttt gatacgttct ggtagagttg ggtccgttgt agccattttg    3000
gttgtttaaa gttttggttt ttttttttgtt ttttttttaa ttcagcagag aacagtaatg    3060
cctagcttcc gttttttaact taacacttca gtagaacatt ttcttccaag agggagattt    3120
tggcctaagt aaagtagtgg gctctttttt aaaaaaaaat taatttttact ttaatgtgag    3180
```

```
caaatctgta ttggtatggt gttctgcaat gcattacact gactttgaaa atttcgagta    3240
ctaatgcctt atgtctgggg ttaccattcc ctgtgcatca catactagtt agttaacata    3300
gcattttgct tttcccatgt aattttttcc ctatataata ctggattcct gatactaatt    3360
gacttgatac aaaagaatgg ctggatgata ccagataacg tataatacac tgggcttcac    3420
cacaatcagg ctctgaataa atacagacct gtcagagatt gataaaataa actacaatgg    3480
atagtgctgt ttaaacagtc cattcaataa catatataag ccagcctgcc ttccattgtg    3540
tctgaaattc ttattttgt aggtaaacaa atgcacattc agcactgatt gaatagcccc    3600
ttgaactatg ctccacagtt tgcgtttggg ttaatcttgt cggttttaat atagagagaa    3660
aaaagctcaa agcaccaggg gtggaattgt tagtgctttc acatccacat tcctcacatt    3720
ttgtcaggat gataaactgt aggtaatgga ctgtcgttgt tctgcaggac aactgagcca    3780
ggcagagcac aaagactaag ctaaagcgat acctcacaac atgcttggta gccttctttt    3840
cagatgagaa tttatttgag aatcatgtgt ctagggactg cacatcttaa cctcaacagt    3900
tacagcttca agcccagaa acaggagctg gaggttaaga tgatttgcta agcacctggt    3960
tctaaatctt ttacaaagca taagctgttg acgctggttc tgccgacgca aagacatgca    4020
gatgactcca acatttccag aggcttctga cttaagctaa agtgtgtgga caggtgaatt    4080
cgccatgggc ctggagacca gctgctaaa aactatgtgt ttgaatggtt cctccagaca    4140
gagtcagctg aagaacaatt ggtggattta tattaaaacc tcttgtctgt aaacttactg    4200
aggtgcatcc ttcggttggt ggatcagtga gataattgcc ttcagatgga cattgcaact    4260
ggagcaacta aatccttgct gtctttcctt cctctgaaat cttccaggta gctcccgaga    4320
gcttcagtat gacaccaaac ttcgggcgac gttttagagt gcgttcacct aatgggaaac    4380
tattcgagat cccagcgtga ctgcagtaat gcgtcatagg aatgggagtg cagggaaa    4440
aggaaataca gattgtagac cctaataaaa aaattttag gaaagatatt tctttaacgt    4500
tttatgagaa cttcattctt aaaatactta attgcaaatt agacaaatag aagtgctctt    4560
ctaaggaagg tgattaaact ggtcctccta tcagcctaat ctctgcctgc ctttgctgct    4620
gacataaaga acctgttttt caggtcactt aatatacatc tacatagatt tgcttatgag    4680
ctcaccctt gtgtagcgga gtagagcctt aagaggagt gctcaactgt ttaaaatatt    4740
ttgattaaaa tatgcagaac ccatagaact ataagcttct agtcaggaat tagctctttc    4800
agggaacagc tccccccttc tttttaaggg gggaattaga aggaggctgg gggaggaata    4860
taagaacagc aaagaaggaa ggatagcaaa tgggacatgt tccgaacagc ttggaaaaac    4920
tcctgtggct tcattgtctc tataaagcca aagaatacaa agacataagc aattcagccc    4980
ttctcccatg atggaagatg taaaccgttg acatgcctcc cctgtttaac ttgtttaatt    5040
ctcattttaa attcagcacg atactagccg tgtgaactct gaagatttct ttagtaatcc    5100
attttgtagt tccgaatcaa aaacaaagtg aaagggtctg acacaatttg cttttatttt    5160
taggcaaatc aaccctggtc atagttaata aggggattac aactcagact aggtctttac    5220
agatgtgatg taaatcaagg gcagagtata aagaaactga tcccttttga ttgaagtata    5280
gtaaaaaggc atagagaaac tagcagcagt aatctgattg tatggcaata aaaccaccat    5340
tttctgtctt tcagataaaa ataatgtggt aaatccatgc agttcataag atgtaaaggc    5400
agataaaggg tgaagccatg gcaacatata gattagcttg atgttagaaa tgacacgtct    5460
ctgaaaaggg cgcgggacga aggcccttgc ctccaggctg ttgggcatta tgtgagaacc    5520
```

```
acacagactt ggaaactggg attaggaagt atgaaagctc tacttgtggt ctgggatggc    5580
tgaggcagta aagaaaagct gctcagttct tgctcattgg tggtggataa tatggcaaag    5640
gtagatttca ttgactgcct tttttataga ttgagattgg ggctgattaa aacttcagat    5700
cactgcagtt gttagggcct gggagatttt cctttttaac tcctggccta acagcagcag    5760
ccgttctgta ggattaactg cacttcgcgg tcgttgcctt aatctatttg ggcttcaggc    5820
agggacatgc tgggaaggaa cagagaccag aggggatagg tagggctggg gttatctgaa    5880
aagaaaacag agacctttg atttcagcca tcttttcaga cccagctccc tctcccgctg     5940
catgggagaa gcaaaggtaa acaggacaca ttgtccctct ccctcagcca cagagctctt    6000
ctgtgagttt tgtctttccc accctggaaa aaagataaa atacaatttt taaaagggga    6060
gggaggaatt tagtttaat tcaaatgagt agtaatccaa tatgccaaaa gcagtgggct      6120
ctacctagat gtaattttac tcgtaaatgt gagtcttaaa ctttgagttg aatggggcag    6180
gctgttagag gtggtgtaaa ttacaggatt ataaaaatgt tagtgctgcc cagccttaaa    6240
gtcaaaaaca gaaaaatctc tgtgctgttg agtcttcccg ccctctctcc tgaacaacct    6300
tgtaagtaag ctagcttttt gttttgcct tccatacttt ccatttcagc cattaaacaa      6360
aataagccat tgaaaccacg attgggttcc atgcagagtg acatccgcaa tcgggtcaag    6420
ccagaaggaa atacttgctc gattgccccc tatttggcat tacaggaaag tctccacact    6480
ttggaagagt ctgaactctc aagacattga aaatgccaaa ggctgcaaac accctgtgtc    6540
tttcttgatg gagtgcatct tggtgtgttt tacaaagggg aattcagtgc tgttttttg     6600 ttgttgttgt tgttttttt ttttaaagag cagcataggg cccttctaga ctcttggatt     6660
ctgtgtctga caaaaatggt cattaaatga gcaatattat aatttagacc catttcactg    6720
attttgttcc aaattctcaa ctgacttgag catctgtttg gggctgtaga tacattgccc    6780
ttgttgactg ttttttctcgt ttctatggga attactgtag ccattactat gtagcttttca   6840 tagactcaaa acatttttaa agtattgcat ataggctggc catatccagt gcctgttact    6900
ttaccttctt tttctaactt aatgcagcag tctgtattaa cagatccatt tcatttgtct    6960
agcttcatca gagagaggct accccctgat ttacaggctg ctcacatcca agcaccttgc    7020
attctacact tgacagtgat tgctaatggc ccattcaact aaagtatttg cttgttaaca    7080
gggaacagaa catgataaat gtccagcaag cttgctgcct ccttcagctt ttcaaacgca    7140
gactggtgca tatttatggc aggcaaatga caaaagaaaa agctgaattg ccctggcctc    7200
cagctttcta tcagaaacag ggttaaagtg attaaagcaa tcattcaaga aagccctgcc    7260
gtttgtttac taaccttcat ccaacattta gctttgtagt ctacctgtga gaagatattt    7320
cagaagtatt agagataagg aaggaggatc tagcaaacca gtgaaaagag taggtgacca    7380
gttataaaat gctttccatg cacattgaat gccaggcgaa cctatttctg ttattccagc    7440
agacaatcag cagtggctct agattattaa catattttcc tttcatgtat aaattcaaat    7500
atgtaattct agtccaaagc attctgtggc tggtaagcac atacttgctg atttcaaata    7560
agaaaacata gcaagggaaa gctccattaa acaagttgtt tctgcccttaa gtaattctct    7620 aaacaagata ggaagaaaaa gtggacagta gtggagtatt aatagtgtgc tcttttcatt    7680
ctctaaagca cgagtaagta agcgttcaaa ctactctgtg gtgggcatac atttagagcg    7740
ctgtgaatga accactgctg ttctgccata cttaatttat ttatattatt attttatttt    7800
tattgttgtt tttatgtatt attataatta tttatttata ttactaattt attttctcaa    7860
tttaaatcct gttgcatcca attttaatta cagttttgt atctgccttc ccatacttgc     7920
```

```
tacccacgtc cccattgcca ctgcggcctt atccatgttt tctgtgtaca ccactctcgt   7980
atcaccccag aataattatg agtgctaccc agacttttga aaccactaga gtcaacatgt   8040
ttgtctttga ggaaagccaa tgatgcttta gcattttttgg caggggtgga tgtgtgttta   8100
agtggggtgg gtgcagctcc ttattgtctg cctattctac tgttgttccc aatccacatt   8160
ccctgcgggg cacctaacct gtgtgcatag caaagaattt ccgaccttca gagccagaag   8220
tgtttctcaa ttgatctctt ccagcctagg gttatagctg atgaattata atccttgctc   8280
tttccacacc tttacctggg cttaccatgg ccctaaaaca tttgcccaga atcagaattg   8340
tctcatgagt gagtggggca aggcaaatcc tgttccagac cagctgagaa tgtacctagc   8400
tgcagaagaa gttagaaagt gtcatctttt acttatctac cagaactata ttcgaggtac   8460
attttagatt taaaaaaaaa gcaagttctc gtaggccttg aatccccccc ttgctatggg   8520
aaaatggatc attattataa tggactgtcc agtaaagttc atgatttctc ctagacatgt   8580
tctctctctt tatgacctag atcaagagtg atctctttaa gtcttttctt cataatccca   8640
cagcactttg tacttagatg tacttagaaa gaaccatata cacggtacgt catgattgat   8700
atgcaagcct tcaccactct acctgtccta aaagtcaggg acacaccttc ttcatttcat   8760
cagtccctac ttctatccag cattggcatc cagtaagtat tagtggaatg acagacaac   8820
ccgaatttgt gctgatggca gtttaccctg ttttaactgt catccttctg ctactagaca   8880
tggatgagac ctgagacgat gggactgctc agaggtccct ggctcttgaa ctttagggca   8940
ccagaatccc ctgcagggct tgagaaaaca ggggtttctg gccccacccc cagagttcc    9000
tgattcctga ggtctggggt ggggcttgaa gatggacatg tttaacaagc tcccaggtga   9060
cgctggcaac tgctgcctca gggccatgct gagaaccctc gccctacaca aacctttctg   9120
ggaaaacaac tcaacattaa agctgtttgg ggatctctga agaaatctgt agtccttgcc   9180
ttgttggggg agcatcaggg atctaaccat tgatggtgga gtatttgttg ttaattcagc   9240
aagcaactat taagtgttag gcctgttact cggctctaac aatacaaggc agagtgacct   9300
gtaccctcga gatttaaagt ctaagtcctg tagagagaag cccaggtggg agcaagcaca   9360
tttagagtta ggtgcttggt gcaaggtggg gacacagaag aagggaatgg catttgcctc   9420
tggagggggtc cggaaacagc ctagggagga ggagcttgag tcttgaaata ctgtgggcat   9480
ctctaagcaa agtcacagta gacagctgaa ataaagaaaa tagtaagcaa gccaaagaaa   9540
cagtatttca gccaagggca gcgtgtgtct atcacgtcca cctgtgaaca cgtcccagga   9600
ttctctgcat ccggccattg ctcaagacag atccctcaca ggaacagcta agccactgat   9660
ttcagctacc tgttcacgtg agaattatca gtacctactg ctttttcaaaa tgagtatgat   9720
catggatagg tgaggcaatt cagtttcgca gagacagtag ggcaagtgcc actgtagttt   9780
agttaagggc acatgcttta gagtttggct atgtgagtcc aatcccagtt tagccattta   9840
ttagctgggt agctttagga gcagtagcct tagtgtctct cagttgtccc atctctataa   9900
tagggacaat aacataatag tgctgaataa aagagtaaca aaattttggt caacatttaa   9960
tgtatttaaa gagctaagct ccgtgattgg cacaatgaac caatcaatca aacaccagtt   10020
gttattaata aaagtcagtt gaatatgtac tgtgtgcctg gccgtggttc aatttgcctt   10080
tgcatacaag gaaaaaatta aaatactctg ttaataaga ctatagcata atactttcac   10140
cttaaacttc ttgatgttaa tttattttgt ttacctgcca aacttctact cattccttat   10200
gactttctgc tacatgaaac acccttttgta attcttttgt cctattaaat taagttctct   10260
```

```
ctcctctgct ttcctgcttt tggtgctttc taataacact tttaaccctg gactttctca   10320
ttcagctgtg caactgtgga ctgagaggag gctctttgaa ttcattttgt atattctagt   10380
agagagtact gtgagcagtt gggttgttga atgaatacat taattcaacc tggagggatg   10440
ggcagtattg cattttttac attgatatta catgatattt agaaaactgc ttaactggtg   10500
gacgttgttt tattaacagc attttgtgta tagcactcac tatgtgccag ctgctattct   10560
aactgcctga caaatactcc tgaaaccttc atggtaacca tgagggaa  gcacttttaa   10620
tatatccata ataccaacgg ggagactgtg gccaaattgg ttaattaact tagccaaagt   10680
catattgaac taataagtgg atttaaaccc agctagtctg gggccagggt ccctctttta   10740
atcttctgcc tcctgcttat gctgttgcat ggagtagtct ttatcatata actaaattaa   10800
gcatgcattt gcttaaagca gtgcatacat gatggatcaa aaagtttgtg gtataattgg   10860
tttaattctg tcattatcca ttttgattta tagtcacttt cttatgatgg tcgtgtagtt   10920
ttaaatggaa ccttttgaatc tttgatataa taaggttatg tcaaatcttg ggtataataa   10980
ggttataccc aatggaaaca gaataatgat cagcccattt aaaggatgac tggagagtta   11040
ttacaataca taatagtcat gcatatattg agtagtattc ctttggtaac attttccttt   11100
taaaaattgt aacatttgat tgttccttgt tgggagaaaa ggaggtcaga tttttgaggg   11160
gagatccatt tggtgagatg ctgagtgtgt gtcaagctaa ggagatagta tgacatcttt   11220
tttagagtct agtcacaatt aaatgccatt ttattttgga ttttgggatc cgtgccagct   11280
tccagcttgt cagagctgag aagactcaaa tcaagtccag gcttatttct acagcaaact   11340
gggattctgg cttcttgccg gtggattcat tcagtacagc ccatctggct tttgatgttc   11400
tgcaagtttg gagccatttg ttgaaggaag ccaggcggtg aatattggtg gtcctggggt   11460
tctcttgact ccaagtggtg ccccttggtt tgcatttttca ccatgcttag catctgctta   11520
cctggagacc atgcagccgc cggccagagg tctccaacaa ccaaatcttc atgccttta   11580
gaactcagag tccccagcac atcctccttc ctcctccttg tccaattact ttcatgcagt   11640
tctcagtagc tgcttgtttg aatcacttat agtatttaac ttctagggtg ttttggggtt   11700
ttggtcaagg taattccagg ctgaatgtgg tgactaagca ggaaataaat gggtcgtcct   11760
caaagttaca gtggagcgct gtttctattt tcctaaggta cacagttgtg ggggcgatcc   11820
gtatggaagt caggaaccca gtctgatttt gcttcctttt gatggtagca gtacagacct   11880
ggctgttttg tagcctgctt tgttttttctt cctttcttc cctaacttca cgggctgtgg   11940
caaagccctg agacgtgcag gaaaatgtct cctgtcatac gcccacagca gacctagccc   12000
tgaccctcct ctgaagccca ggaaggaggt atctgtgaag cagcctgctt gtaaagcaat   12060
tgcacacagc cttgtaaact gtgttactgg gctgattata cttgattggc aaggtgaatc   12120
tcttatagca aaagagaact tggagagttt tatctcatct tatgccttat taatttgttc   12180
attctttaat tacacagcca ccctattgagc accctattta tgcaaggtac ctggtcgggg   12240
gtcagaggga gggtcccatg gtaaacgaga cagactcaat cctggaggag caggaatggc   12300
agcccctcgc tgggctgttg gccccaccaa aagggaaagg tttcatttta ataatacatg   12360
ggtgaatcat ttttgtcaat aggcaaaatt ctttgtagtt aaaaaaaaat atgatggtag   12420
gaaggaaagg gatgggcaga gggttaaaac aaaagatatg ctctccctaa ctctagattg   12480
tagtattgtt atgcttgtca ctgtagctga attccatttc tttgagtttt ttcaatgcca   12540
aggcattccc tgtatgactt acgtgagcct ttcatctccg cgattttttcc cattcaggta   12600
aatgagcaaa tggatttgaa cactcatatc taaaacaaga gagaaccagc tggaaatgcc   12660
```

```
ctttgaattt ctttctctat gtaaaccatt tttctttctg gtgcctcacc tataaataac   12720
aggagttcca ccttccttta tagactcttg ctgaaagcat ggtttggaac aagaccgtac   12780
aggtgcacac aaattacagt tgggaaagaa gcctgcagtg catcttgtct ctgaaggtta   12840
tgaaatcctc cttttagtaa tggagctggc gtgatcaagc cagcaggatg aaatttggca   12900
tttgtgagat caccccccct ctcacttgcc cactgtacat agcatcccag ccttactctt   12960
caaatctcca cattttttct tatctagcta caaaattcat aggctgattt ttttggggtg   13020
cgtgtgtggt ttttttttg ttttttggt aaataaagac ctgcattttt attttgatat    13080
aggtggttga gttttgtctt taatttcatg acagagattt aactagtctc aacttttgaa   13140
aagacaacaa tgatatttgg ggatcacaca cttaaagtta gatttctaga tgattaatac   13200
caaagtagat gattttttag cctcagccat ttataggtat gcccttctgt gaattttta    13260
tgacagtgaa aatcatggca cagataaaaa ttaaataaat acttctgtta ttttcctgaa   13320
gaaaaaaaa aaaagcttaa actatgagaa tactgtcttt gagcactta aaataaaatt     13380
gacttcagcc agcaggattt tgagcattac atcacaaata aaaacaaga ttaacatcaa    13440
aaggagtcag ttttcattca attgtgcagc actgtgggct gtgaaattta atattatttt   13500
gactcatatg ctaattgtag actgacagag gaaaatggat tgtgtttaaa taaaaggata   13560
cacagcatca cacgcagctg tatcaaatac aagttgaggt ctttgggcca ggaactgggg   13620
gccctctagc tctgttattg cagattcaag tttgacaaat aaaactttcc tttagactgt   13680
agtttaatta ctttttttca aaggtatgcg tgatgaagag gcacaaatac acctcacctt   13740
gaagagttgc taaactggtt tgtgtgccga tcagttcacc gtgtgtttga atttctgtgc   13800
ttctcatctt tccttttctt gaaaagattt tgcttgtcat tggtgtgaat tgtaccccc    13860
acccccaccc atctagtctt tgctctcaga tttataacac tttaatggtt ccaaattgta   13920
tagcctgctc ttagaccccct tttcttttcc ttgaataaat caggttcatg ttgcagacga   13980
tatttgtttt aggaaagtgt gaagaaggg gcacctgtga aaacacgcaa ttgttccaac    14040
acacatatac atccaaatta aagcagaaaa tgtcaaagcc tccaatcact accttatttc   14100
ttggaggttt aaagccgctg agaagatagt ggtgccctcg ctggaagttt taaggtaatt   14160
acttttact ctaagcagta gtatctggta acctaattcc gtataaacct gacaccctat     14220
cgctacaccc cagtatttct ctgatttcag aataagtctg cgtagaaact tgttctgatg   14280
ttaaagtgca aaaggggca gtaaagtgct atccacaaaa aaggaaaaac attttccaag    14340
tatttcttat tactgcctgt gtctttcgta ggccctgcct ttatttattc attttataac   14400
aaaactctta tgtttggggc attcagagaa taccttatta agctgttgca gcaatctagc   14460
attaaatgga agacatgcaa gactgaagat cctgcctgtt tatgaagtgt gccatcaaat   14520
tcacatgctc atgatgcaga gtccttcttt gggagtattc gtattcccaa gtgcacagag   14580
cacttcggaa aggagccttg gtctttggtg ttaatgctct cctagctccg tatagatgtg   14640
gcaggcccaa agtacatggt ggggtgaagg gtcaagggtt tggcttatc cagagcagcg    14700
tgcatccttt gtcaggaggt gactggaaac accagccaat tacagcagaa ctgcagactg   14760
ctcatctgca ttcggaattg cagatgaacc agtttgtact cgacttctct tcttcactgt   14820
aggctttgac atttaattaa aaattaaagc cttttatgga aaaagtacat gttttccaaa   14880
atggggtaaa ttcgaagtat acttgataca gaacactggc ttgggaataa acctgtgata   14940
ttacatgact tttggtttgc aactgctagg ctgagcctct ttgtaaagct gggatttaga   15000
```

```
atctttgaaa tgtttgtaca gttcaatgat taagcataaa ttgtatatat tcccttttt   15060
tcacttattt gagtaaacaa gtttgttact acagcttctg tggactcaga gatttatgta   15120
ttaaataggc cacaacttca actaggataa ttttatttat ctgcttgtta gggaattgca   15180
tcaaaagttt aagtctgtag gcattaaata ttttaaatgc ttattttaa agtcaattat    15240
gaaagatagc acaaagtttt tctgaaacta cattaaaaaa ataatgtttt aatcttatca   15300
caaaagcatt gactatttat tgcaaagaaa acacagaaag ctaaaatca ttctaagtcc    15360
accattcagt agcccaaagt ggtctcaggt aaaggcggtg tgtgtgacca tttgtttatg   15420
gttgtctccg tgcagtcagc aaaataaaca gaacaacatg ccatatatta ttgatgtgta   15480
tattttcaac tgaaattagc catctgctta caatgatcat atacactaat ggtataattt   15540
tgaaatgaaa agaaaaataa aataattctt tgtggagagt aatgcgaatt gacttatgaa   15600
tctcgccctg cttggcagtt tgctctagag gtagaagagc tttatgtgtg ggcctcctcc   15660
ccccccacac atttattctg ctcacacttg caccagcatc catgtcagga ctcaccttgt   15720
cctgttacat gagtaacatg gccctgattc tcaagtgcat gataactgcc ataattacac   15780
ataaatatta aatatttaaa tagatcttta cgtgtgtaat attaggtaga agtggctctg   15840
gatcgaatct gatgcttttt aaatagaagc tttcccacaa catttccaag cactgtcatc   15900
gtgtctgtct cgatttgggg tttacctggc ctagttatct gtctgggtgt agaaactggt   15960
agttcctgtt tgtatctttt ttgttctgat ctctttattc tgtgtcagct aaatattctt   16020
gcagtcagtt actaacatat taactcatcc ttgtttggaa actttggcat atccttccat   16080
ggtttccttc cgtggacctg tcgcgtctct caggagagcc accaggtata ttgtcacaca   16140
tttcgcatgt atttcagag actacagcag catcaagtgg cccccagcg atttgggttt     16200
tcttctcggt taatctacac tctttggcca accgtgagaa aacttgtaag aaggcatcag   16260
atgtttgtgc taaggtgcgt gtagtatggt cagaggaaga aagaagcagg gaaaatggag   16320
tggccgtggg tgggagggga agcagggagt gcaatttcgg gttcactaca cagctctcca   16380
taaacttctc cactgctggc ttcccacgga tcctcctatt acactgggca aagtgcagaa   16440
atagatcagg cgaccactgc ctccgtccat ttcccaggca ccctgtgaga cccgataatg   16500
caatacaggt cagcagaaaa gtccagactt gacatcccaa cgtgccatgg tctggtctgt   16560
gaatgaaaat cacatgaggt gacctctgaa ctctaagtgg ctggtttatg ttttcagtgt   16620
attaggcccg tgttttaaac aagcatgtgc tcgtagtgta ggttaaaact ttctgttgtc   16680
ttcattaatt atgctgtgtt ctagtctatt aatattaaag aatattgtgt tgcataatga   16740
ctaattttt tatttttgg agacggagtc ttgctctgtc acccaggctg gagtgcagta    16800
gtgcgatctc ggctcactgc aacctccgcc tctcggattc aagcaattct ctgtctcagc   16860
ctccgagtaa ctaggactac aggcgcccgc caccatgccc agctaagtgt tgtattttta  16920
atagagacgg ggttttacca tcttggccag gctggtcttg aactcctgac ctcgtgatcc   16980
acccgcctca gcctcccaaa gtgctgggat tataggcgtg agccaccacg cctggcaaca   17040
taaggactat tttttaaagt ttttacaatt atgactgtga agttgaaatg tctaaattat   17100
tagagatcca gtttagatta ctaaatattt atgtctaatt gagatgatta gacttagcca   17160
aagtatccat gtgaagtat tagagtctag attggtgaaa aacttgaaaa agcttggctt    17220
aagttcaata ggtaatccaa gagtaaaaac agattccaat atcagatctt ttcaccatag   17280
tcatgttaag tttggaagcc ctacttgagt gttttccagtt ttttccacat tatattgtgt   17340
ctatatttga ttcaaaggca gggcatctat tgtcttgctt aggactgatt cactgggaaa   17400
```

```
agccactgga gttgcctatt tccactcagt atgcctcact cttagagtag cttcccatgg    17460
ttcccaggca ggccctccag tgagaatgca ccaagccaca cgccatggcc tgggaagcag    17520
tcctgaacct ggagattgtc ttgatggaaa ggaagaggca gccttcccct cccaggaaga    17580
tagtagagag cctgctctga cttcgctcag ggatggaact ggtctggctc agttctctct    17640
cctgtgtggg acatgaatca ctcttggtgg tctttgcttt ttatttgggc ttaaaatcag    17700
cagactttat aaatgacac  ctctctctaa ccactctctg tctgggcgaa gtttaacaag    17760
aacagcctcc ccccatgtgg tatgggttgt aactgtggcg gtttccctct gctgtttttg    17820
gttacaagat gaacattatc tgaacacaca gaaagaaatc tgtatttggc atccataatg    17880
gaaagtcagt ttagtaattt aaacttagcc agttatcatc atcataattc ttttttaacac   17940 tttcaaagtc agcataggag aagtgtattg ttgaatatta caaaatattt agggcataga    18000
tagatgtgct gtgtagtttg atttgttaat gtgtctaagc aatcaaagca acagaattca    18060
aatataaacc ccatcacttc caaaatagga actctgttta ctgacttgat tataacatat    18120
ggaactcaat tgttttccat taaaaaatga tactattagg aaactcaccc catttctttt    18180
tcatatatat tctgctatt  gcataattgt ctggagtcca tatgtaatat taaatgtaaa    18240
acacaaatgc catgtagctg gtctgttct  cctcacctt  ttggttcctg gcctcctggg    18300
gaagggttgc acatctgagc cgtggtctca gatgactgcc tcggaagaag cctcttccct    18360
tcaggcacca ctgatgtgtg cttggtgtgg agctagactt tccctggctc tccatgtgac    18420
gctcacatgt gcgtgtcttg atttcccta  acttcatggc ttatctatga acagcttgat    18480
ttgggggaaa aaaatgtgtt tcccaatgct ggagttataa ttgaatgtgc tgcagtcaaa    18540
actgaaatgt gtgcagagaa aggggctttt tcctgtcatg ctcattgggc accagtgtgt    18600
cttcacctgt tttgtgtgtt aggtccatgc gtcatgctga aatgaagaac atgggatgta    18660
tggggctttg gacagtgctg agccaaaagc aagtgctcaa aagcagctgt gtttgtatta    18720
ttagtggttc tggaggtggc tgattgcctt gcattttaag tagagaggga ttgtagaaga    18780
ctgccaatac ttagaacttt ttccagagag gaaggggcag aaactgcatc tgcagggctc    18840
cttgctctcc agaaatgcca gtgtgcctgg gagggcatct tcagaaatcc agtctctcct    18900
cctcagtgtg tcctgtaccg actcagtggt tctgtcttca gaattcctat catgtctgtg    18960
atctgcaaat agtggtattt aatttgactt caatttgtat aaatgttagc ttctatttgt    19020
tcattcctat ttttttgttca attaatacat tattattga gcatctactc tgtgtcagcc    19080
ccttgggtgt ttaatactga attagtcaca tgtgggactt gcctgccctc agggagctag    19140
actataaatt cctaatgatc agtggtctcc acttttctgt cactcataat gtctggcaca    19200
acataggtta cttgagttgt tacactcaca gtactgttgt ttgctgccat ggtgctttag    19260
gaagtgtgag agttcccggg aggcagagtc aataatgcag actacacgta gtgaaaacat    19320
ggccaggaga gctgtagttc aggctctcag ctcaactgca ctctgtccac tgagaagcca    19380
taatttcttc acttaaagtg actgtgcgct atggctgttt atatatacgc ttaaaaagta    19440
aaagctgcta aaccactcaa ggattggggc cttttgtatt gatttaatta aaggaacaat    19500
cattgtttta atgagctcta gaaacaatta cttttgaaga gccgaggatc aaattcttgc    19560
ctcacgtttt gccacagtgt gttctgaaag gtgaattaat gcttttggaa tcatcaggaa    19620
tagtgagctt tgtcacgatt tacttttttac aagcgtatct aatatgcata ttgaatgtg    19680 agcctcccca ccacacttcc gctttgataa gcatccccg  gattgccgtc actgaccatt    19740
```

```
atagattttt aacaaagttg gacagtacac actgaatgaa aactttacat caaggaaggc    19800
ctggcgtgtt tgtaaaatga attaaaaggc tcattaaatg atttatatga cttacgcctt    19860
ctgaaaatat ggcctcaaac acagagatcc ccaaagccac accgacccct gcgtcccatg    19920
ttctcgacct caccgcatca gcaccagcaa gacctgtcgc tgagacggtg agtgatgaga    19980
gtcaagagga gtgacttgca tggcctggga ggaaacctcc tgtgaatctt tagttaagca    20040
ggaaaaaaaa aatcctcatg aaggaaacag gatcttggga gcattttgaa tgaagaagga    20100
gcttagtgag ccaaacttga gacatagggt gtaatgtggg agagttttaa gatttgcaga    20160
gatgtacagc ttgggagggg gtgtaatgca ttttcttaaa agagctgaat gaatggttga    20220
ggaaatgggt acatctggtt tggttaagga tcctaatctc tgaagcctgg gatgccccca    20280
gggcttgtaa tttaggaata cttcccctaa tagtagctaa ccttatata gtgctgtctg    20340
tgcaggctac aaaaggagca gattaaggat agaaaggtt tggagtgtat gagaaaccct    20400
aggcaggaat tgactcctgg tgtttgtaaa ccttaaagat gtcctaaaaa ggtcaaggaa    20460
taagacagga gaaaaggaa atgtcaggaa gatgatcaat ttaatgttta tggaatttag    20520
tttgtactta ctgcccggca tcttgcctga ggttttttaac ctcagcagca catcagaatt    20580
actgtgtgtg tgttggaggg gctggggag ataaagaaat tagcctcatc ccaaacattc    20640
tgattcagtc tgttacttga gaaactgaat tgtgttttgt ccataaagaa gatgaaattg    20700
tctacagaga acacattgcc attcacaagg ttgaggggat accacagaga ggctcccact    20760
gtgatttgca tttgtcaaaa gttctagaga attcttcaac agtacacaca tggttgtttt    20820
aaatatatca ttgttataaa aattcgtttt gagttctgtt tcacagaaag ttttttttgaa    20880
tgaatgaatg tcatatatcc ttgctaaagg agctcagtta aaaaaaaagg gaccatcctt    20940
ctcttttggg ggttgtacag taacacattc ccaagaaaga ggtaacagcc acatacattt    21000
ttcttcccaa taaagagtgt gggttttttaa tatgaatcca tagtatgatt tctgttatgt    21060
tttgtgctgc ttcataacca cactcatgca cttttcagaa aattaatacc attcattagc    21120
ataaatcata aactattccc ttggtatggg tttgaaattg ggggtgccct atcatccttg    21180
ctttatctct tagtgaatta tgaccctgta gtcatcatgg ctggtgggcg tctctggtta    21240
aagaaagggt tggattggaa ggattcagag gcgattcttt gttcttaggc tttaatattt    21300
taatgagcct gcaggcttgg ctgcttacga acagctgag atttctaagt gtgttgttag    21360
tgttagcact tgtagaagga tgttcattag gaagttcttg tttcagtttt tcagagaaac    21420
tccccattaa gaaagatcat tcaggaacat ggctaccaag aaagaggaaa gggaggaggg    21480
aggctttcag ctataagcat taaggggata ttgtatcagt agtcttagtt ctaaagattt    21540
gcttctgaga attaattgga gcaaatacat ctcaaggaga gaaaaaaaaa gatttatagg    21600
gcagggacag tagttgtcct tgcaagtaga ggacacttca ttttgcagct gaatcaatac    21660
cacaactaat tatttctggt tatctttttac gcatttgtaa gacattgctt ttgttcagtg    21720
taataaaaaa cccattgttt gatcagtgac tgactaatta tgataagtaa tttgaaacat    21780
tcttgatgaa acttgtctgt taattaacat caacagcaca gggaaactaa caggacaaca    21840
aagtattagt ggatccactg ttccctccaa ttgacgagct ttctctgtgg catgcccaat    21900
aaactaaagc tgccaatggt taaaaataaa caaacatgtg ggagatctga ctcaccacgg    21960
aggaagagtt atggtaaagt tacacaaagg agtactgaaa tattacaagc gaggggtgg    22020
taaagaaatg tcagcaggta gcctgatcct acagcttaga gtaaggaaag tggtttcttt    22080
ctgtcttttcc tttttctttt aaagcttaat tccaaaatac attcatccca tattgatctg    22140
```

```
aagtaagaga cttttgataa attaaagtgt gaatctgaaa atgtgtagtt tgggattatg    22200
ggcattgcct ggctatcttg taactgtcat taatactgtt aattttttatc aactcaatgg   22260 ctttttttttc ttatgctttt agatttctac ctggacaagg actggtacta tcccacaga   22320 taggagacaa attggatatt atttgcccca aagtggactc taaaactgtt ggccagtatg    22380
aatattataa agtttatatg gttgataaag accaagcaga cagatgcact attaagaagg    22440
aaaatacccc tctcctcaac tgtgccaaac cagaccaaga tatcaaattc accatcaagt    22500
ttcaagaatt cagccctaac ctctggggtc tagaatttca gaagaacaaa gattattaca    22560
ttatatgtaa gtataatttt attcatttat tttatagaaa ttaagataag ctatataggt    22620
ttgtatcaat ttttttgtttc cttaaaatta ttgtgacaaa taatttgatg aaaatctatg    22680
tggaaaaatt gtcccccccc cctttttttt tttcaaagaa aacttcattg aatttgggac    22740
cctgtgctac cagtattcat taagtataca tacccaaaga gaaaaaaaaa cactagaatt    22800
cttaatagta ttgaaataaa tgtattatat gaatatattc agcatctcta ctgacaaaac    22860 cattttttaag gaccattggt ggattttgat aggtaaatct tgtgcattgc ctttttctctt   22920 cacccatcca tccattcatt cactcattca tttcgtattt attctgtgcc agagactgtg    22980
cttaagggct agggattcag cagtgaaagg tggtaaaata gcatgttttc ctcaagaagt    23040
taacagtcta gagaagatgg agctcataaa ttcgaaagat ggggatgaca ggtcacatta    23100
aaaccagatt cagaagaaaa agacgaaact tggtttgctt agtacattac tctttttttgc   23160 atacatatat ataatttgac acgctgtttc aagaagagat ggtacgtatc ccttgggtca    23220
tatctgaggc tgacttgtga ggatgtgaag tcagctgatg agcacatttg gagcccacgc    23280
ctactatgtg cagatctctc gtcagcgtca ttcccagggc cccaggtggt gttaaagtct    23340
aggtgactca gacagctgtt cgcgtcattc aagcaatgaa gtctttttttc ttaatttctt    23400 tggttttaaaa ttatactcat aattaattgg gttgaatttt ccagtggctt ggttaccata    23460
gacttcagtt tattagggaa ctgctatctg ccactggttt attatttgcc ccaaggtgga    23520
ctctaaaact ttaggtagga gactcttggt gatcaaactg aaactcttgc atctcaacct    23580
atgagccgca ctttattgtt atttttatttt tttagagaca gggtctagct ttgttgccga    23640
ggctggcgtg cagtggcatg atcacagctc actgtagcct tgaactccag ggctcaagtg    23700
atcctcccac ctcagcctcc aagtagctcg gactacaggc atgtgccact gcacccagct    23760
caagagctac acttcaaagc acagaatgaa aacctatttt taaagccaac ttgatacata    23820
gagtagctta ccaagaatta gtaacaacaa caacaagaaa aaaagagag aatgtggtag    23880 agtatatact tagtaaggag taattattat aaaaataaaag cattctgaaa tgaaacaggt    23940
agatggggtg gccaagtatg cagcatagta gggaaatctt tgaaaatgta aaatagttac    24000
caggtaaaat aaatgaaac tttaagctttt tggaagccta acaatgtatt tatattagta    24060
aagactttat tttttttattt tattttattt tattttttgag acggagtctc tctctttcgt    24120
caggctggag tgcagtggcg tgatctcggc tcactgcaac ctccacctcc tgggttcaag    24180
tgattctcct gcctcagcct cccaagtagc tgggactaca ggtgtgcgct aattttttgta    24240 tttttagtca agacggggtt tcaccatgtt ggccaggatc atctggatct cttgaccttg    24300
tgatccttcc gccttggcct cccaaagtac tgggattcca ggcgtgagcc accgcgcctg    24360
gccttagtaa agacttttaa agtaagactt tttcagtgaa agctactgtt aggcatgaca    24420
tttacaggca actgaaactg atcagatgca tttattaaga aggttaatgc ccctaggtgg    24480
```

```
ggtgggagaa agaaggtcgt ggtacgggaa gaggggacac actagagatg agatgcccta    24540
gggcagtgaa cgcatgtccc taatgcgtgg atgcagccca cgtccaccga taatgccgac    24600
acacccagag tctctcttct tactttagct tatgacttca cgaagaatgc tttgcaaatt    24660
ctaagttcgc actgggcgca agtggaattt tagtaaacat taagagttta acctttagtg    24720
tgaaataata tgcaagatat gcaaataatt gtttaccaac atctcttgc ttaatgtggt     24780
gagcatttaa taattgcttt ttattaatac atgagagatt tgtatttaga agcagtttaa    24840
tttataatta taatattaat ctacacaata acgacatcta ttattttctt tttttggaaa    24900
ctcttcatac cacactaaca ggttcattgc agttactgaa ctactctggc catcagagct    24960
ctccttagag ttacgattta ccatgcaaaa gcatatggta gcctgggata aatgaatctt    25020
tcttaataca gaattgaggg tctcaagttt gaaactacga gaggctattt gaatgttgct    25080
ttgggggact gtcataaggg ctgggtggag gactcagggc taagaagttt gccaggaagt    25140
ccagttgaga ctttcagcag agttgaaaga cttccacgat ggcgtaggca gaggaaggcg    25200
tttcagatac ttgggaaaat atagaagcca atttctcacc caccctacag caaagctcat    25260
tgatctacaa gtttccctag aaaggaaatg ggaaatgcag agaacaaatg ttaaaatagt    25320
tttagaaatt aatattgact ttgtattgct tctgcataag ttccaagaca ccaaaacaat    25380
gaatggattt taaaaagtca ctactttgca tatcagacaa atgcacacac acacacacac    25440
acacacacac acacacacac acacacagtc aagctctgta ctggcttttt tgagaaggaa    25500
agtgtttgaa gttagtaatt tttatatcag tacatttata aatagtgcta ggtagcatga    25560
cggaaagtat taaaatttac atgtatattt ttaacacttc aaatcgttgg ttcactttga    25620
gacagtaaat aatattagca tttgagttca gctttaataa attctacatg ggtttaaccc    25680
caaatctgag tgtctagttg gtaagcgcct tcagaacgag cagtgttata ataaatatgt    25740
tattgtgtgc tggtttcttt ccatggagag gaaaaagaga cctgatgctt tggaggagtg    25800
cttgactttt ccccagtgag gagtagtcca gagggactga cttgcattgg ggagtaccct    25860
acatgaacag catttcagaa gaattaaacc aggaacctag agtcctactt gctagtcctg    25920
cttcctaagc ttaatgagaa agtcaatttt atttctttga actttaattt atttccctaa    25980
aaaacgcttt tagtattgtc attgttctgg ctaatgatgg cggtctcctc cagtttcaag    26040
ccaccttagg gctgggcata caaatgcaat ataggatcac ttgttagtgt ggtttcaaat    26100
ggacatgatc ctctgtaaat tctttaaaaa catttaattt gatttgtggt gttacctgct    26160
ttaaaatata gtcatcacac ttgtgagttt cagacgtgaa tatgaatttt taatttgaac    26220
tgtatttta aacacactaa gtattaacta agtcccctta ggagatatgt ggcaaactga    26280
tatgcatcct cattcattct tctcatagat ggttatttgt ttttaacttt gtggcaaaat    26340
tatatatgaa tggtcaccga cttaaaatag ttccacttaa attttcaac tttctgatgg     26400
gtttattgga gtattaaatg tattttcaat ttaatgatat tttcagctta ccttgtgctt    26460
atcaagtatc aagacatagc cccacctaag tcatggagca tctgtatatg ggttttatt     26520
cttgtttaga attgactttt tcaagtgacc tatttcagta attagccctg ggcctgattt    26580
gcataatgag atctcctaat cttcaagtaa tgcaaagatg gagatattat ggccatgtgg    26640
tctgaagaga cctttctttt attatgttca gatcttaat tgccttaaaa atagagtagc      26700
taatttacct aacctctagt tattttatta ttgtctttaa agttttttt aatgttcatg      26760
aaataactgt tctgaaattg cctatttca agggaagctg tgtcttagac ttactaaatg      26820
ctccagttga tactgggaaa gccttcttgt gttcgtagcc tttatccgta gagttttctt    26880
```

```
tgcagcattt tctgtgcctg gtttagtttc ttttcagagg cgacacccag agctgaatga   26940
gtcagcaggt ttggtgtgtc gacccttttgc aacagctgtc cttacgaagg ttctgtgggc   27000
tggttattct accttcgcat aaaaccttgc aaaataaccc acaaagaggt tttcgtcaca   27060
ctaccaaaat catgtgagtc agagatggat gaaaaatgaa tgccattgtg ttcatacttt   27120
tccagtgaac agtagctaca gcagagctgt tagacaaaga aaaccgtatt aatgaagcgc   27180
ctcccaattt agcttcatat ggcttttgca ttattttgct gcaaatccat agctaagaca   27240
catcttgtgg catagtccgt aagtcatctt tccgaaggac tgtttgatta aaggttgttc   27300
tgtgagatcc accctgtgtt gttcatggca tcctcttgga ggcctccctc actctccatg   27360
ccttggcaaa gtcttcctta aggaacactg aacaagtctg gagaagctgc catttcttag   27420
ggccctcatt ggttcagttg tctatagctt tttatttttt attttttttt taataaagag   27480
tatgtaaaat tggaaagctt cacaaacagc tttgctattt tttagacatg tactccactt   27540
ctaagcaaaa tcacaaaata aagtaaaatg cttccacaaa tataatgaaa caatattctt   27600
aaagaatcaa agcagaagaa cttcagagtc tgttgcttat gttaagcata tatttgtttt   27660
cttctctgct tttgatttac ttattctctgg ggtgtaggtt tggcaagtag tactgaaacg   27720
tactgaatgc actgttcttt agcaagatag ttacaggagc tttcaaatgt cctcttaaca   27780
tatagatttc ttttagaata tagaataatg tgtgggctgt ataaagcgat tatgtgctttt   27840 atttgatgaa ttatttatgt acgataaatg tagcaaaagc cacatttcca tcattaaatg   27900
taatcccatt tggtgataca gcaacatcag cctgtcattt gggtcctctg attgaggggt   27960
gaggatttct gtttgatacc ttgtgcataa tggctgcgtt caagcattta aactcatttt   28020
tatttctaac ctacagctgt catctttgta ataggatatt catcagaatc ttgccagaga   28080
ctgtgcattt gggatcttgg gggatacagc accaccacca ccctccccct gtccaagaga   28140
aacagatcaa catcttaggt tgagagtctg gggtctggaa gacccgagtt cctgagtgcc   28200
ctttgacaag taacttaacc cctgtctgcc tcagtctctt catctgtaaa gtggggataa   28260
tgacagcacc tgcttcacag ggttgatggg aatccagatg tggtgggata tagaaaatgc   28320
ttattacttc cacctttgac accaaataca tataactaag agttaacttt ggagcagggg   28380
aggaagtgtg aggctccagg ctggaggcag acctgtgttc ggctgcaagc tggagaggat   28440 ggacccccaaa agcttggctg atttgaagtc catccataaa atggaactcc agagagttta   28500
cacgtttcag taatgctgca taacttaatt ataagatctt ctctctttgt cttcttcag    28560 tgttataaaa gctctttttgt ccttgagctt cctttaccaa gaaacatgca tttatgtatc   28620
tttttgttca tggaattgcc caagcttgtt agcagatcct ttgtaagacc caaaagagac   28680
agacagggga ggagtcttca gatacatata atcattttc ccaatttcca tgttaccagc    28740
cttgccagga ctttttctca gttccctgtt acacaatgaa aatagtgtct ctttattgat   28800
aattttagta gcatcctaat gtggtataaa tcgtcttcca gagaagaaaa tgtgtcaggg   28860
ttgcgttatc actgaggcta gctgggaaag tagatcagcc cattagtctg ataattcgaa   28920
gcgttgtttc tgttatttct gaacatcatg tgaactcctt ttctgggtgt attaaaggtt   28980 ttccagtgt gtgtcagtga gactcctgat tgaatttaat atgaataaag ataaattctt    29040
tacatttaag gattaaagtc tcagcttctg cttaacttga gattgcactg agaaactcct   29100
ggctctcggg tatagcggag tcacgacctg gggatgtctg tcccatatgg ctctgtgtgt   29160
aagaagaaaa agctgctgtg gacggagact ctgttcacat taaatgacat cacctaagcc   29220
```

```
atcatgacag caagaattat ttaggaattg ctcagaataa aactgccttc attatttcat   29280
aaaatgtatc ttggtatctt tagcacctta tttatggctt tttaaaggtt cactgggatt   29340
tataaataat tggacaatgc tagagaccta gtacaagaat gaaagaggac aggcttcttt   29400
cttaataacc tttaaacatt catcaggaag ataaaacttt aaagcaaaat aaaacacatg   29460
aaaatagcca agatgcacag accagacaag caaatactac tttaacttat ttgtatagtt   29520
cttaagagtc acatttgttc ctgaagtttc aaaatctcgg gctgagtgtt tgatcactta   29580
gggaagtgtt gtggccttca catactcttg tctcactttg aagtctagaa acacaggtct   29640
tagagcaatt tttatcactg tgagaaagct gaaacttagt gtgagtagct tagtacaatt   29700
cagttggcca tcaaatgtca gaaacaaaac tcagtccagg gccgctggac ccttaggccg   29760
gcgttgttag tttacaacag tgcctcctgg gtccaaacat ctaagtgcac atgtagcaat   29820
agtaaagata gtatgtatgc atacataaca catatgtaga gacagcagag tatacgtaca   29880
cacatgttgc atacatagca acagcagaga agctcatgaa ctataaagga tggactgtat   29940
gcttgtatca gacattttgg tactgacgct ttgtcatata ttgtgtaaca tataaccagc   30000
ttgcaatcat ctgcccccaa agttgaacta agaaaatcct acagggtact aggaaaggaa   30060
ggccattggg aaaaggtggt tatagtggca atttgttagc tcttatgaat tttcttttc   30120 tttttagaca tactcttaat tccatttttt caataaatct atactatttt gtgttttat    30180 gttagcaagt actttaagcc cctcaataga aagttgctac atcatatagt gattaaaaat   30240
aaaaatctct caaacataca agtagaggtg gtatgagact tcaaattccc ttagccaagt   30300
acaagtgcag cagttttgtt ggctggctgg ctgcatagaa ggactgatgg attggcagac   30360
cctcaagctg gagtgtaatt gatctcatta cagaggagcc aggctgggtg acagttgtgc   30420
tttgcaagtg gttttttgca ttggtgaagt agcccatttt gttgttcctg atgttaaaca   30480
ggggatgaag gtattctttt attggcacaa acgcgggaaa ttgctctgga ttcttagagg   30540
atagaacatg tccctggac ggaataaggt tcatgtgtag ggcaaattta gatagggca    30600 ccttattggg gttactactg gtctctagat ggtcaaagca acaacatgt ccatctaagc    30660 tgtgatgtcc atctaagctg tgtgtgtcca tgagagtgac gcattttctc ctctgcagtg   30720
ttgttatatt ctaaactgtc agcagacatt aattcggtcg ctggtgaagt cccaccgcct   30780
agagatgaac tctgcctccg atggatgttt tccacttcag tgccactcgt ctcgcaatta   30840
ctgggtcatt aatatcattg catgcaatta gtgacagtag aaagagctag agggttgtgg   30900
gatgtgcacc ctccccacca tgaacttttt actctgaccc tttcccagct agacctttc    30960 gtatcttggc aaggatattt taatgattga gactgtcaga atcttcagag caggcactgg   31020
attatgtgct ggaaataatt cactcaaaca cctgcttctc catggttcag aatatttca    31080 ttagatatta tcactatccc ttccctggga agtttcattt ttaaaaatct gatgcttaag   31140
tacagctaat atagacaata gggaattatg ttttatcttt agaactctta cattattctt   31200
ttctttaaaa atgtgagctg agtcattgct attgcagtgg tcatctggcc gcctattttt   31260
aaaacacaat tcctctatct tagtagattt tggcccatat taagcatatc aagaatgact   31320 ttttttttt caagacatgg ggttttattg ggggcttata tacaaggaaa gagagagtcc    31380
agtggcagtg ggctggacaa gatatccaca tggccctgtg gcagtgagct gggcaggaaa   31440
actgcaactg cttgcaaaca gcatgtagtt catctatagc attttcactt aacaccaccc   31500
agctaatgac ttccacctgg caaccttcat ttaatccaga acttaggacc tcgagtccct   31560
gtacggccca tgttccacag gatgggccga gggctcagct gttcctcata gacaaggaat   31620
```

```
gactctccac attggccact cccggattcc ctagctcagg acacatattc aggtgtgtct    31680
aaggctggct cttctatgtg aagttactta ttcttttacc attgactctc atgttcccac    31740
tatattaagt ttttctgaat tactgtggca ataagaaacg gtcccttaaa ttatactaga    31800
agaaaagctt ttttttttgtt ttgttttta ttttgaaatt atgttaaatt tttttctta    31860 actgagagat tccacctgca taaatcgtca taacttttaa cagtaagatc ttagacttag    31920
aaagtgatgt ttttcctcaa cagaatttat taaaaatcaa gacaccaagc tgttccaaac    31980
aatagtttga ggggaaataa aataaacaac tccataaata atcttatgtt gttaaacatg    32040
tctctagcaa aacaaacaaa caaaaaagtc gggggttggg ggaggtgcag tttattgcca    32100
gtactgtctg gtcttttctca gaaaagcgtc agtgtacatc actgagcctg acggtatgt    32160 tttcttgatc tatacccccct atgtgtacat gtgcttgcac gcacacacat gtagacacgc    32220
acacatgtgc acctgccatc actttctgct cttccgtctt ttcactcttg agtgtctgta    32280
gccagtagct ttccaggtct gtatagtcaa agatacctat ggccctgaat gtcttcactg    32340
attgctattt gacattcata cggtttttaa tggttaaaag ctttatgcg aaagctgtga    32400 tagaatttct cctgttctag atgtggtgtt tattgcttta ttttgtgact tttctctcag    32460
tagattgacc ttctccctca gtgtccaagc ctcgcatagc atgatggcac ctgtaaactc    32520
agttctgtat cctggtatcc tttctcttcc caagtagaag caattaagta atatatgtca    32580
tcaaaacctt ttaagtgcac atacaaacaa aatcaactta ccaaactgct tcaaagttgt    32640
tccatgttta acactcttct ttctgagctc tgggtagaat gtcctattat tgttcatcat    32700
gaatatttga aattaaagaa ataaaactgt accattttct ttaagagcat ccatttgtac    32760
ttgataacat cttcagtcat atttcaatgc tggcaaagag gaggggagtt ctaaactgtg    32820
actcaatttt agaatctact ttttccaaat tattctgttt agtgcagaaa actaattaat    32880
agtgttgcat agaaaagtca ctgaagctaa gccagttatt acttcttaat gcatgattta    32940
ctgctttaag ttttcaaaac acaaccatag caatgtggta ttaattcaag tgattcttcc    33000
tatcatattg aacgatattt tcacgggtga aaaactcaca catcctacat cactgatagt    33060
ttatacagtg ttttagctgt ggctccctgc atgcaaaata agagttaatc aaatgtcagt    33120
gagaaccatc tcatcaagta gagggcttgt tttgtttaaa ttaactttgc taagtataaa    33180
tttcttcttg aaaataaatt ctgggccggg cgcggtggct cacgcctgta atcctagcac    33240
tttgggaggc cgaggcgggc ggatcacgag gtcaggagat cgagaccaaa ctggctaaca    33300
ctgtgaaacc ccgtctctac taaaaataca aaaaatgagc cgggtgtggt ggcgggctcc    33360
tgtagtccca gctactcggg aggctgaggc aggagaatgg cgtgaacctg ggaggcagag    33420
cttgtggtga gccaagatca caccactgca ctccagcctg ggtgacagag cgagactccg    33480
tctcaaaaaa aaaaaaaagg aaaataaatt cttctgtatt tttctttctt caagtgaggc    33540
catttagggg aaagtatacc ataaaacttg ctctaagata aggcaaattt ggtattatag    33600
gatgaagtgc tatgtgattt gaagtaatgc tgaattttt aaatatatta aactaaacaa    33660
gaataatgag gccctcggaa agtcatgatt atatttctca tttttctcat tttaaagcca    33720
cagtgaaaaa cacataaaag gaagaagtta gaaaaaaaaa tgaatgaaat tctttttttc    33780
cttttggcaa attaaataga tgtttctgtt tcagaagatt ttattaatta actttaaaga    33840
aacagtcatt tattttttggc attcagtgaa cactatcatt tccatgttta gaacttttct    33900
tctaagttag catcttaaaa gataactgtg aaactcaagg cattcaacta cattaatttg    33960
```

```
agtttcagaa attgaattct tgtttctaga gtacatagtt tgaattgatg tcagggtgtt    34020
aaatagataa atcttagctt cctaggttgt atattcacac taattatttt tttatcagcc    34080
ttcttatttt tcaacttacc ttattctttt tgttttttg acactcagat ttgatagccc     34140
tgtggtagaa gaaaacagta atacagtttg gtttgttgtt gtgtttgtgt ttattttaaa    34200
gtcacggctt tgctttccat gttgttactg gattatgctt tttttaattc ttcagtttgc    34260
caagataaca gtcttccgat cttcagaagt ctgtatcaag cttaaggaaa ctgatgtgta    34320
ggaagactcg cctaagaagt ccaaattagc aaggctagca tgtgaggaca tgctggaaaa    34380
gaatagttcc catagatatt gacagagaat gttcataaaa tgctacttgt tttgtggtta    34440
catgagagta acttgtgtcc agtgcagctg tatgtaaggg caacgttttt attctgacga    34500
ctctgtggtt ttcatgaccc tggatgctta tcatgtctct ctgttggact tcttcaacgg    34560
agttgataca aatacttgct tccaagtgtc catctgccct ctcctccatc ctggccccat    34620
acaaatacgc tacatttta aataatttga aataccctca atagtattta tatttcctgg     34680
tgcttcattc tttccataag aactgtgata ccattattct gtaggatttt tttgtgcttc    34740
cccgtttcac atctctgtgc cagtgagacc catatatcgg tgcaaatcca gaagtttgat    34800
tgtccatctg attagcacac tgttagcaat gtggtggact aaacacagcc aagatgtggg    34860
gctggagctt agcctcctgg gagcagagcg gtgaacatca gatgaagaca tgtgaaaatg    34920
gagtactact tcctcttcct ggggatgggc taaaaagcac agccagaaat attcttgccc    34980
ttccagtctg ctttacagtt actcactggt tctcttttt ttcctactca gataaccagt      35040
atactcttcc cagtgactaa gaactgcaga taagtatagg tgcaaataga tggcaaaccg    35100
cagatggcag ctgtgtggtt tcagatgtgc tgcagaactt ttagacgatg tgaacgcaag    35160 gaacttttt gctgagcagt aatctctacc cactggaaat taggccctgg ggggaacaat     35220
gtagtgactt ctatatactt actacatgca gttagacccc tgaagcaaaa gcttttaaaa    35280
acaggctgta aaatgcccat gtatctttat taagcctatt ttccaactgg atagagaaat    35340
tttctggtaa tttttaaatt tgtaaagtct attttttcc tgagccaagg gaaaaaaaat      35400
atctgggccc taaaagctta gttataacaa tgttattttt tctatctctg aatgattaaa    35460
tgtgatttca tttatgtagc aatactatga ttgtggctgc attagatcac gctgatagaa    35520
agatacaaag aaaaactaag tataatgaac taacaattta ttttcactct ttctctaagt    35580
taaaaattcc cagtacattc aaatgaacaa tgaaaataat tgcagaattg tctcctgaaa    35640
tggaaataga ttttttttcc caagcattag caatttcttg ttattttca aaatcagcca      35700 ctaagccttt cagagcttct tggtgactat tgcaggagaa atcagaatat taatcttgtg    35760
gttttatttc agagttcgct gccaggaagg aggtataatt gggataggag acttttttt     35820 tttagctgtg tcactgttca aggagggggg tttggaacct cagcataaga attacactct    35880
gtgatgagga tgtagcaggg gagaagaaag gtgattttca ctatgggaag ctatacttac    35940
atcaagtata aaatagactg aagtcatttt gaattacgtt atacttgtaa agtttacctc    36000
ctggagtttc agttagtacc agtgtactaa ctgggttaaa acagttcatg gcaccttaga    36060
tcatttctaa ctcatggcaa aaatctttcc tggtggaacg tgtaactgta ttttaaatgc    36120
ccctttataa gcaaccaagt atttgggatg ttattttgat attagtagtg aattttcag     36180 tatcttccag tacccttgc aagtcacagg ttgacttaaa aggaaaagaa gcaaaatgct      36240
gaatatagca gaaaaactgt ctgcattcag actgttcagc ccactttgc tccccacgtg      36300 gcaagcacac tcccccaaac aagcaatagc ctgtggcttc agaggaacct acaaaggcag    36360
```

```
catctgtaga ttttccttc ttcaactcta agacttgaat gtttccctct tccccacaca    36420
cttttttttt aaaccaagaa ataaaaaagt tttcactctt aaaggtgcaa agcagtttca    36480
ttcttatgca acacagcctt cctcctactg tcttatagtc tgtggatgtt aaattataga    36540
ttccaattga atttttaatac tctagagatt ttacatttgt ggttgtcaag accccgtttt   36600
ggtaaaccta gggagctccg cacaaaagca ttgatattca gaaaaggcac tgacctacaa    36660
attaaaagaa aaaaaaatca ataatgtgc acctcttgtg cttccagttt gacaaagcag     36720
aagtcatcag cagtttctcc ctctgcagac gcagttctca attctattta caagtaactg    36780
ctctactgtg cctgtttttc tcttgctgat actcatttaa ttgttttct tttggatctg     36840
aatctttgac tgtcttttcc ccctcaagat taaaataaat acatctgtat tcctccctt    36900
tctttctgtg cactgcccctt cagatctcat tttgtcattt ttcagcttag tgttgaaact   36960
tttagcaaca aaaagtcagt tacttacttt gagtaagtaa ctcaaagtaa gttaactttg    37020
agtttgagtg cacttttgcg tgtaggttca tttatgtgct tgtgaattta aaaacattgg    37080
gattccacct gaatgaagta aaccaaacat tttaaactat cagccagata gagacatcag    37140
cctttcactt ctttctatat gcagacatat cctaattttt tagaaaaatc aaataggaaa    37200
attctcaaca attaattgaa gattatagct ctgctctgaa atggtccaga ataggatct    37260
gctcatagaa actcatagtt tgaagcctct gggaggaaag gatactttaa aatttagtca    37320
catatttgga ggagggaaaa gggaaagagc agaatgaaga actgaaaaaa atcacacacc    37380
ggggcctgtc gtgaggtggg ggactggggg agggatagca ttaggagata tacctaatgt    37440
aaatgacgag ttaacaggcg cagcccacca acatggcaca cgtatacata tgtaacaaac    37500
ctgcacgttg tgcacatgta ccctagaact taaagtataa taaaaaaaaa ttttaatagc    37560
cccattaaat aattaaaaag atttttttta gattcacaga agtgtacaaa attttaggt    37620
ttttttttt ttaagctgtc tgctgaatag tttcttaatg gtctacaatg tttgtatcta    37680
caaacagata ctgtctgctt cttactaccc ttccaagaca agtattatta tggcaattat    37740
tgcccagttt cccgggaaaa atttatccac agttacagaa gaatgagatg caattgtgag    37800
actgtaaagt ttaagcaagc actcagagaa gcacagtgat atgtatgcac agaagaggca    37860
gtctttgttt tgaggaaaac agtgaaagta aagttaattc aagaccacaa agacaagtaa    37920
ataagtgcct tattttgta gttaatataa tttcagtgga atgcatattt ctaccataaa    37980
tgcatataga acttgtttgc tgacctactg tttggaaaac aaacaatccc attagaagaa    38040
tgtctttggg atttatttttt accagaaaat caatcctttt ttcagtccct tgcaaagtac    38100
agtgttacaa gccaagactt tgataatcag gtagaaaatg gatttaaatt gcagaaatgt    38160
atatgaaaca cttttgttcc ttgccccttg aactttaggg gaatgaaaat gtctagcact    38220
ctccaccttc ttttctctcc tggaacttga actgtaattc aaagcctgtt tctcattaaa    38280
gtacctggca gccatctct ttacagcttg agttacaaag ctattcagag acctcgctgg     38340
tctaaagaga cagaacaagg atgtgtttaa atagagcata ggctgttgaa aaaaaaatg     38400
ctgaaaatgg taaaatgatt ctgtccttcc ttccactcct cactgctgag gtggagaggg    38460
aattcagttg gtgaacacca gcaagtggct ggtaaaagtc cccactttct ctccagggct    38520
gccacaggac ccagaatgag tggtgggcat gtgtgtgaac cctctattca gccagagttt    38580
tcccgcaaca ggtagtttgg ttgaagaggt tgactaaggt tgacattggc agtaataaca    38640
cgtatgttct tctgatttac aaaacgatgg aggaaaaagg ggagattttg aagacctgat    38700
```

```
ttctggtata cttcttaagc atgcataagg ctgaaaaaag aagacaaggg ttgtgggagg    38760
ctcctggtct agtgtttaca gaacttggat gcttgacaaa cagagcgtca agctaattgt    38820
tcttgaagca ggaaatctgc agtggaggaa gcaggtgtgg ggggatgatt accacgtttg    38880
gaaatggctg cattaactat tttgctcttc tgagtttggc cccaaaagag tccatagact    38940
ttttgaagga tgccatccct tttatttata gactaacatt aaatcagtca tttgtgaagg    39000
aaggagaaag tgcctaaata aatttggagt cagatagcat acgtgcggca gtgtttccga    39060
tatccatttc tctttatttc ttttttcttt tcttttggc tttcagcatc cccatacttt     39120
cagaaaactt gtgactaaga gtgaattctt attttcaaa ttgttttcag acatttcatg      39180
ttcatgtaaa cttggcttat tgatttcctg attttctttt atttttttgt tttgtccatt    39240
ttatttttaa tcagctacat caaatgggtc tttggagggc ctggataacc aggagggagg    39300
ggtgtgccag acaagagcca tgaagatcct catgaaagtt ggacaaggta agaccatct    39360 gctgcttcat gacgccactg tgacctggtg tagcccccag ctagtatggt gctaatgttg     39420
ccgatgccca ccttcattcg ctcttctttt tagttttcaa agcaaaccct tctgcacttt    39480
gagccactga cagatttcct caagtcaatg tactaagctt ttattggaga tctaagagtt    39540
aagatcagca aggtagaatg tctattgcca tagatagata gatagataga tagataatag    39600
atagatagat agatagatag atatttcttt ttaaaaagca aaacactttg gttcaaaatc    39660
aaaatatcca gaatgaaaac taaaagcttg tgcagttttg ctcatttctg aatcttgact    39720
acagaagagt tttgttcatt gtgacttttc caatatagat aacctattgt gcagaaagaa    39780
ataattattc ttctaattaa aaattggtat agtagtcaat caacttgctc agttaaattg    39840
aaatgtcatc tgcaatgctt tgcctgccaa atgcaagaat ccctatagtt tccacagatg    39900
gcctcacgtt ctaaacctct gaaataacta gtataaccat tttgttttaa aagaaaaatt    39960
atattcttgt atttcacagt actttgcata aagactctta tgttcattgc tattcatgcc    40020
tgttgaaata tatatgcagc tcctaaagct agatattgtc agatgtctgt gccgtaatta    40080
atcatttgtt tttcatatag atgcaagttc tgctggatca accaggaata aagatccaac    40140
aagacgtcca gaactagaag ctggtacaaa tggaagaagt tcgacaacaa gtcccttgt     40200 aaaaccaaat ccaggtataa cagcatgatc tgtgtgtatg gaggtctgtg ggtaccacat    40260
tcttagtagt atcttaaaag gtagggcaga gtctaaagac ttctaaccag ttaggattag    40320
ctggaagtta cagtgatcag gaatctttgc tgtcagtgag tcattattaa ttacactcaa    40380
taagaacaaa ataactcatt ccaatgaaag tcatatattc aaaggagtag agttcatgag    40440
ctgtaagtgc cagttattag aactactctg tcaggccaaa ggtttcattg gctgacattt    40500
tatcaagctg gttgtcaact ccagcttaaa gctgatgtta atgtatatgt aattaatgtg    40560
ctaatccctc atctaattat atctaagcca cagagggttt aattgatcct cttctaaatt    40620
ttaaatggta acattttta  atattgcata atagtatttt ttcaggtggt tatcgttatt    40680
ttgtttcaca ttttccatgt aaaagaaaat attaaacagg tccctgacaa aagtgtagaa    40740
taccagataa aattgtccgt cgttgacctt cgttttctta acagtcttgg aacaaatagt    40800
tctgtatttg ttaccatgct aatgaaggtt ttatagagta gctgttgagc agacatcagc    40860
agttttgtat taggattgtt gtgtgcttgc ttggtcgttg tgcaaattta tcgtctgcag    40920
caatattcca tccctttcca agagtcaagg agggaagttg ttatttctaa cttctcaatga   40980 caagatgtgt caaattcttg tgacaaactg ataaatggat aatataatga tgccaggcag    41040
ttttttagtg cttaacattt gggctggcag tctgttcggt gtgagagttt ctgctgcctt    41100
```

```
ccaaatatat tttaagtgta aatcaaataa tacagacgag ttacgagctg aacatttcc   41160
caggccccct cactccttcc gcgttcccga gctgttctgt tctgccagga ggcagggctc  41220
ttctttagaa ggcaggccct ttgaaggttt gcatgaaact ccctttctca aaggaggcgg  41280
aagagcaata ccacataaac gctcaccgct gacctggaga attggccact tcccttttc   41340
ttccctgccg ctgccccagg ctggctgaca cgggttagaa gatgaagcaa gatcaagggc  41400
tggctgtcac cgacagtctg tgctcttgct ggataatgat acaaaggaaa ccctgtggct  41460
tgggagggta gggaagtccc tcctagagat acctctcatt tccttttgcg ttgagctctt  41520
agacgaggta ttggcgaggc aaagtccagc ttctagttag taataagcct ggcttatttt  41580
tcacatttt  aagggtcata aaagcagtcc gtctgcactg ggacagcagt aactatctct  41640
gaccttttct gtctccgcgt ctgcaggttc tagcacagac ggcaacagcg ccggacattc  41700
ggggaacaac atcctcggtt ccgaagtggc cttatttgca gggattgctt caggatgcat  41760
catcttcatc gtcatcatca tcacgctggt ggtcctcttg ctgaagtacc ggaggagaca  41820
caggaagcac tcgccgcagc acacgaccac gctgtcgctc agcacactgg ccacacccaa  41880
gcgcagcggc aacaacaacg gctcagagcc cagtgacatt atcatcccgc taaggactgc  41940
ggacagcgtt ttctgccctc actacgagaa ggtcagcggc gactacgggc acccggtgta  42000
catcgtccag gagatgcccc cgcagagccc ggcgaacatt tactacaagg tctgagaggg  42060
accctggtgg tacctgtgct ttcccagagg acacctaatg tcccgatgcc tcccttgagg  42120
gtttgagagc ccgcgtgctg gagaattgac tgaagcacag caccggggga gagggacact  42180
cctcctcgga agagcccgtc gcgctggaca gcttacctag tcttgtagca ttcggccttg  42240
gtgaacacac acgctccctg gaagctggaa gactgtgcag aagacgccca ttcggactgc  42300
tgtgccgcgt cccacgtctc ctcctcgaag ccatgtgctg cggtcactca ggcctctgca  42360
gaagccaagg gaagacagtg gtttgtggac gagagggctg tgagcatcct ggcaggtgcc  42420
ccaggatgcc acgcctggaa gggccggctt ctgcctgggg tgcatttccc ccgcagtgca  42480
taccggactt gtcacacgga cctcgggcta gttaaggtgt gcaaagatct ctagagttta  42540
gtccttactg tctcactcgt tctgttaccc agggctctgc agcacctcac ctgagacctc  42600
cactccacat ctgcatcact catggaacac tcatgtctgg agtcccctcc tccagccgct  42660
ggcaacaaca gcttcagtcc atgggtaatc cgttcataga aattgtgttt gctaacaagg  42720
tgcccttag ccagatgcta ggctgtctgc gaagaaggct aggagttcat agaagggagt   42780
ggggctgggg aaagggctgg ctgcaattgc agctcactgc tgctgcctct gaaacagaaa  42840
gttgaaaagg aaaaaagaaa aaagcaatta ggtagcacag cactttggtt ttgctgagat  42900
cgaagaggcc agtaggagac acgacagcac acacagtgga ttccagtgca tggggaggca  42960
ctcgctgtta tcaaatagcg atgtgcagga agaaaagccc ctcttcattc cggggaacaa  43020
agacgggtat tgttgggaaa ggaacaggct tggagggaag ggagaaagta ggccgctgat  43080
gatatattcg ggcaggactg ttgtggtact ggcaataaga tacacagctc cgagctgtag  43140
gagagtcggt ctgctttgga tgattttta agcagactca gctgctatac ttatcacatt   43200
ttattaaaca cagggaaagc atttaggaga atagcagaga gccaaatctg acctaaaagt  43260
tgaaaagcca aaggtcaaac aggctgtaat tccatcatca tcgttgttat taagaatcc   43320
ttatctataa aaggtaggtc agatcccct cccccaggt tcctccttcc cctcccgatt    43380
gagccttacg acactttggt ttatgcggtg ctgtccgggt gccagggctg cagggtcggt  43440
```

| | |
|---|---|
| actgatggag gctgcagcgc ccggtgctct gtgtcaaggt gaagcacata cggcagacct | 43500 |
| cttagagtcc ttaagacgga agtaaattat gatgtccagg gggagaagga agataggacg | 43560 |
| tatttataat aggtatatag aacacaaggg atataaaatg aaagattttt actaatatat | 43620 |
| attttaaggt tgcacacagt acacaccaga agatgtgaaa ttcatttgtg gcaattaagt | 43680 |
| ggtcccaatg ctcagcgctt aaaaaaacaa attggacagc tacttctggg aaaaacaaca | 43740 |
| tcattccaaa aagaacaata atgagagcaa atgcaaaaat aaccaagtcc tccgaaggca | 43800 |
| tctcacggaa ccgtagacta ggaagtacga gccccacaga gcaggaagcc gatgtgactg | 43860 |
| catcatatat ttaacaatga caagatgttc cggcgtttat ttctgcgttg ggttttccct | 43920 |
| tgccttatgg gctgaagtgt tctctaga | 43948 |

<210> SEQ ID NO 394
<211> LENGTH: 4335
<212> TYPE: DNA
<213> ORGANISM: Homo sapiens

<400> SEQUENCE: 394

| | |
|---|---|
| gcgcggagct gggagtggct tcgccatggc tgtgagaagg gactccgtgt ggaagtactg | 60 |
| ctggggtgtt ttgatggttt tatgcagaac tgcgatttcc aaatcgatag ttttagagcc | 120 |
| tatctattgg aattcctcga actccaaatt tctacctgga caaggactgg tactataccc | 180 |
| acagatagga gacaaattgg atattatttg ccccaaagtg gactctaaaa ctgttggcca | 240 |
| gtatgaatat tataaagttt atatggttga taaagaccaa gcagacagat gcactattaa | 300 |
| gaaggaaaat accccctctcc tcaactgtgc caaaccagac caagatatca aattcaccat | 360 |
| caagtttcaa gaattcagcc ctaacctctg gggtctagaa tttcagaaga acaaagatta | 420 |
| ttacattata tctacatcaa atgggtcttt ggagggcctg gataaccagg agggaggggt | 480 |
| gtgccagaca agagccatga agatcctcat gaaagttgga caagatgcaa gttctgctgg | 540 |
| atcaaccagg aataaagatc caacaagacg tccagaacta gaagctggta caaatggaag | 600 |
| aagttcgaca caagtccct ttgtaaaaacc aaatccaggt tctagcacag acggcaacag | 660 |
| cgccggacat tcggggaaca acatcctcgg ttccgaagtg gccttatttg cagggattgc | 720 |
| ttcaggatgc atcatcttca tcgtcatcat catcacgctg gtggtcctct tgctgaagta | 780 |
| ccggaggaga cacaggaagc actcgccgca gcacacgacc acgctgtcgc tcagcacact | 840 |
| ggccacaccc aagcgcagcg gcaacaacaa cggctcagag cccagtgaca ttatcatccc | 900 |
| gctaaggact gcggacagcg tcttctgccc tcactacgag aaggtcagcg gggactacgg | 960 |
| gcacccggtg tacatcgtcc aggagatgcc cccgcagagc ccggcgaaca tttactacaa | 1020 |
| ggtctgagag ggaccctggt ggtacctgtg ctttcccaga ggacacctaa tgtcccgatg | 1080 |
| cctcccttga gggtttgaga gcccgcgtgc tggagaattg actgaagcac agcaccgggg | 1140 |
| gagagggaca ctcctcctcg gaagagcccg tcgcgctgga cagcttacct agtcttgtag | 1200 |
| cattcggcct tggtgaacac acacgctccc tggaagctgg aagactgtgc agaagacgcc | 1260 |
| cattcggact gctgtgccgc gtcccacgtc tcctcctcga agccatgtgc tgcggtcact | 1320 |
| caggcctctg cagaagccaa gggaagacag tggtttgtgg acgagagggc tgtgagcatc | 1380 |
| ctggcaggtg ccccaggatg ccacgcctgg aagggccggc ttctgcctgg ggtgcatttc | 1440 |
| ccccgcagtg cataccggac ttgtcacacg gacctcgggc tagttaaggt gtgcaaagat | 1500 |
| ctctagagtt tagtccttac tgtctcactc gttctgttac ccaggggctct gcagcacctc | 1560 |
| acctgagacc tccactccac atctgcatca ctcatggaac actcatgtct ggagtcccct | 1620 |

```
cctccagccg ctggcaacaa cagcttcagt ccatgggtaa tccgttcata gaaattgtgt   1680
ttgctaacaa ggtgccctttt agccagatgc taggctgtct gcgaagaagg ctaggagttc   1740
atagaaggga gtggggctgg ggaaagggct ggctgcaatt gcagctcact gctgctgcct   1800
ctgaaacaga aagttggaaa ggaaaaaaga aaaagcaat taggtagcac agcactttgg   1860
tttgctgag atcgaagagg ccagtaggag acacgacagc acacacagtg gattccagtg   1920
catggggagg cactcgctgt tatcaaatag cgatgtgcag gaagaaaagc ccctcttcat   1980
tccggggaac aaagacgggt attgttggga aggaacagg cttggaggga agggagaaag   2040
taggccgctg atgatatatt cgggcaggac tgttgtggta ctggcaataa gatacacagc   2100
tccgagctgt aggagagtcg gtctgctttg gatgatttttt taagcagact cagctgctat   2160
acttatcaca ttttattaaa cacagggaaa gcatttagga gaatagcaga gagccaaatc   2220
tgacctaaaa gttgaaaagc caaaggtcaa acaggctgta attccatcat catcgttgtt   2280
attaaagaat ccttatctat aaaaggtagg tcagatcccc ctccccccag gttcctcctt   2340
cccctcccga ttgagcctta cgacactttg gtttatgcgg tgctgtccgg gtgccagggc   2400
tgcagggtcg gtactgatgg aggctgcagc gcccggtgct ctgtgtcaag gtgaagcaca   2460
tacggcagac ctcttagagt ccttaagacg gaagtaaatt atgatgtcca gggggagaag   2520
gaagatagga cgtatttata ataggtatat agaacacaag ggatataaaa tgaaagattt   2580
ttactaatat atatttttaag gttgcacaca gtacacacca gaagatgtga aattcatttg   2640
tggcaattaa gtggtcccaa tgctcagcgc ttaaaaaaac aaattggaca gctacttctg   2700
ggaaaaacaa catcattcca aaaagaacaa taatgagagc aaatgcaaaa ataaccaagt   2760
cctccgaagg catctcacgg aaccgtagac taggaagtac gagccccaca gagcaggaag   2820
ccgatgtgac tgcatcatat atttaacaat gacaagatgt tccggcgttt atttctgcgt   2880
tgggtttttcc cttgccttat gggctgaagt gttctctaga atccagcagg tcacactggg   2940
ggcttcaggt gacgatttag ctgtggctcc ctcctcctgt cctcccccgc acccccctccc   3000
ttctgggaaa caagaagagt aaacaggaaa cctacttttt atgtgctatg caaaatagac   3060
atctttaaca tagtcctgtt actatggtaa cactttgctt tctgaattgg aagggaaaaa   3120
aaatgtagcg acagcatttt aaggttctca gacctccagt gagtacctgc aaaaatgagt   3180
tgtcacagaa attatgatcc tctatttcct gaacctggaa atgatgttgg tccaaagtgc   3240
gtgtgtgtat gtgtgagtgg gtgcgtggta tacatgtgta catatatgta taatatatat   3300
ctacaatata tattatatat atctatatca tatttctgtg gagggttgcc atggtaacca   3360
gccacagtac atatgtaatt cttttccatca ccccaacctc tcctttctgt gcattcatgc   3420
aagagtttct tgtaagccat cagaagttac ttttaggatg ggggagaggg gcgagaaggg   3480
gaaaaatggg aaatagtctg attttaatga aatcaaatgt atgtatcatc agttggctac   3540
gttttggttc tatgctaaac tgtgaaaaat cagatgaatt gataaaagag ttccctgcaa   3600
ccaattgaaa agtgttctgt gcgtctgttt tgtgtctggt gcagaatatg acaatctacc   3660
aactgtccct ttgtttgaag ttggtttagc tttggaaagt tactgtaaat gccttgcttg   3720
tatgatcgtc cctggtcacc cgactttgga atttgcacca tcatgtttca gtgaagatgc   3780
tgtaaatagg ttcagatttt actgtctatg gatttggggt gttacagtag ccttattcac   3840
cttttttaata aaaatacaca tgaaaacaag aaagaaatgg cttttcttac ccagattgtg   3900
tacatagagc aatgttggtt ttttataaag tctaagcaag atgttttgta taaaatctga   3960
```

-continued

```
attttgcaat gtatttagct acagcttgtt taacggcagt gtcattcccc tttgcactgt    4020
aatgaggaaa aaatggtata aaaggttgcc aaattgctgc atatttgtgc cgtaattatg    4080
taccatgaat atttatttaa aatttcgttg tccaatttgt aagtaacaca gtattatgcc    4140
tgagttataa atatttttt ctttctttgt tttatttaa tagcctgtca taggttttaa     4200
atctgcttta gtttcacatt gcagttagcc ccagaaaatg aaatccgtga agtcacattc   4260
cacatctgtt tcaaactgaa tttgttctta aaaaaataaa atatttttt cctatggaaa    4320 aaaaaaaaaa aaaaa                                                     4335
```

<210> SEQ ID NO 395
<211> LENGTH: 987
<212> TYPE: PRT
<213> ORGANISM: Homo sapiens

<400> SEQUENCE: 395

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Asp Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300
```

-continued

```
Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
    610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
        675                 680                 685

Val Met Ile Leu Thr Glu Phe Met Glu Asn Gly Ala Leu Asp Ser Phe
    690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
```

-continued

```
                725                 730                 735
Val His Arg Asp Leu Ala Ala Arg Asn Ile Leu Val Asn Ser Asn Leu
            740                 745                 750
Val Cys Lys Val Ser Asp Phe Gly Leu Ser Arg Phe Leu Glu Glu Asn
        755                 760                 765
Ser Ser Asp Pro Thr Tyr Thr Ser Ser Leu Gly Gly Lys Ile Pro Ile
    770                 775                 780
Arg Trp Thr Ala Pro Glu Ala Ile Ala Phe Arg Lys Phe Thr Ser Ala
785                 790                 795                 800
Ser Asp Ala Trp Ser Tyr Gly Ile Val Met Trp Glu Val Met Ser Phe
                805                 810                 815
Gly Glu Arg Pro Tyr Trp Asp Met Ser Asn Gln Asp Val Ile Asn Ala
            820                 825                 830
Ile Glu Gln Asp Tyr Arg Leu Pro Pro Pro Asp Cys Pro Thr Ser
        835                 840                 845
Leu His Gln Leu Met Leu Asp Cys Trp Gln Lys Asp Arg Asn Ala Arg
    850                 855                 860
Pro Arg Phe Pro Gln Val Val Ser Ala Leu Asp Lys Met Ile Arg Asn
865                 870                 875                 880
Pro Ala Ser Leu Lys Ile Val Ala Arg Glu Asn Gly Gly Ala Ser His
                885                 890                 895
Pro Leu Leu Asp Gln Arg Gln Pro His Tyr Ser Ala Phe Gly Ser Val
            900                 905                 910
Gly Glu Trp Leu Arg Ala Ile Lys Met Gly Arg Tyr Glu Glu Ser Phe
        915                 920                 925
Ala Ala Ala Gly Phe Gly Ser Phe Glu Leu Val Ser Gln Ile Ser Ala
    930                 935                 940
Glu Asp Leu Leu Arg Ile Gly Val Thr Leu Ala Gly His Gln Lys Lys
945                 950                 955                 960
Ile Leu Ala Ser Val Gln His Met Lys Ser Gln Ala Lys Pro Gly Thr
                965                 970                 975
Pro Gly Gly Thr Gly Gly Pro Ala Pro Gln Tyr
            980                 985
```

<210> SEQ ID NO 396
<211> LENGTH: 333
<212> TYPE: PRT
<213> ORGANISM: Homo sapiens

<400> SEQUENCE: 396

```
Met Ala Val Arg Arg Asp Ser Val Trp Lys Tyr Cys Trp Gly Val Leu
1               5                   10                  15
Met Val Leu Cys Arg Thr Ala Ile Ser Lys Ser Ile Val Leu Glu Pro
            20                  25                  30
Ile Tyr Trp Asn Ser Ser Asn Ser Lys Phe Leu Pro Gly Gln Gly Leu
        35                  40                  45
Val Leu Tyr Pro Gln Ile Gly Asp Lys Leu Asp Ile Ile Cys Pro Lys
50                  55                  60
Val Asp Ser Lys Thr Val Gly Gln Tyr Glu Tyr Tyr Lys Val Tyr Met
65                  70                  75                  80
Val Asp Lys Asp Gln Ala Asp Arg Cys Thr Ile Lys Lys Glu Asn Thr
                85                  90                  95
Pro Leu Leu Asn Cys Ala Lys Pro Asp Gln Asp Ile Lys Phe Thr Ile
            100                 105                 110
```

```
-continued

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
        130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
        210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Leu Lys Tyr Arg Arg Arg His
            245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
        275                 280                 285

Ile Ile Ile Pro Leu Arg Thr Ala Asp Ser Val Phe Cys Pro His Tyr
        290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330
```